(12) United States Patent
Fisher et al.

(10) Patent No.: US 11,008,325 B2
(45) Date of Patent: May 18, 2021

(54) INHIBITORS OF CANCER INVASION, ATTACHMENT, AND/OR METASTASIS

(71) Applicants: VIRGINIA COMMONWEALTH UNIVERSITY, Richmond, VA (US); SANFORD BURNHAM PREBYS MEDICAL DISCOVERY INSTITUTE, La Jolla, CA (US)

(72) Inventors: Paul B. Fisher, Henrico, VA (US); Maurizio Pellecchia, Riverside, CA (US); Swadesh K. Das, Richmond, VA (US); Timothy P. Kegelman, Richmond, VA (US); Bainan Wu, Richmond, VA (US); Surya K. De, Richmond, VA (US); Jun Wei, La Jolla, CA (US); Mitchell E. Menezes, Richmond, VA (US); Luni Emdad, Richmond, VA (US)

(73) Assignees: VIRGINIA COMMONWEALTH UNIVERSITY, Richmond, VA (US); SANFORD BURNHAM PREBYS MEDICAL DISCOVERY INSTITUTE, La Jolla, CA (US)

(*) Notice: Subject to any disclaimer, the term of this patent is extended or adjusted under 35 U.S.C. 154(b) by 0 days.

(21) Appl. No.: 16/349,467

(22) PCT Filed: Nov. 14, 2017

(86) PCT No.: PCT/US2017/061443
§ 371 (c)(1),
(2) Date: May 13, 2019

(87) PCT Pub. No.: WO2018/089967
PCT Pub. Date: May 17, 2018

(65) Prior Publication Data
US 2019/0263824 A1    Aug. 29, 2019

Related U.S. Application Data

(60) Provisional application No. 62/421,468, filed on Nov. 14, 2016, provisional application No. 62/424,571, filed on Nov. 21, 2016.

(51) Int. Cl.
| | | |
|---|---|---|
| *C07D 487/04* | (2006.01) |
| *C07D 495/14* | (2006.01) |
| *A61P 35/04* | (2006.01) |
| *A61K 31/519* | (2006.01) |
| *A61K 45/06* | (2006.01) |

(52) U.S. Cl.
CPC ......... *C07D 487/04* (2013.01); *A61K 31/519* (2013.01); *A61K 45/06* (2013.01); *A61P 35/04* (2018.01); *C07D 495/14* (2013.01)

(58) Field of Classification Search
CPC .. A61K 31/519; A61K 2300/00; A61K 45/06; A61P 35/00; A61P 35/04; C07D 487/04; C07D 495/14
See application file for complete search history.

(56) References Cited

U.S. PATENT DOCUMENTS

| | | |
|---|---|---|
| 8,642,668 B2 | 2/2014 | Goldfarb |
| 9,216,180 B2 | 12/2015 | Gardner et al. |
| 2011/0105477 A1* | 5/2011 | Carlson .................. A61K 31/41 514/221 |
| 2011/0224155 A1 | 9/2011 | Tachdjian et al. |

FOREIGN PATENT DOCUMENTS

| | | |
|---|---|---|
| WO | 2002/014311 A2 | 2/2002 |
| WO | 2002/064211 A1 | 8/2002 |
| WO | 2004/014370 A2 | 2/2004 |
| WO | 2011/147199 A1 | 1/2011 |
| WO | 2012/080729 A2 | 6/2012 |
| WO | 2013/178816 A1 | 12/2013 |
| WO | 2014/197586 A1 | 12/2014 |
| WO | 2015/116968 A1 | 8/2015 |
| WO | 2017/161028 A1 | 9/2017 |
| WO | 2018/161033 A1 | 9/2018 |

OTHER PUBLICATIONS

Kleschick et al: "regioselection in the reaction of 3-amino-5-benzylthio-1,2,4-triazole with unsymmetrical 1,3,-diketones", Journal of Heterocyclic Chemistry, vol. 26, pp. 1489-1493, Nov. 1, 1979.
Ram et al: "Functionalized azoles and triazolo[1,5-a]pyrimidines as latent leishmanicides", Bioorganic & Medicinal Chemistry Letters, vol. 7, No. 8, pp. 1087-1090, Apr. 22, 1997.
Kegelman et al.; "Inhibition of radiation-induced glioblastoma invasion by genetic and pharmacological targeting of MDA-9/Syntenin"; Proceedings of the National Academy of Sciences, vol. 114, No. 2, Jan. 20, 2017, pp. 370-375.

* cited by examiner

*Primary Examiner* — Erich A Leeser
(74) *Attorney, Agent, or Firm* — W&C IP

(57) ABSTRACT

Provided herein are, inter alia, compositions that bind to a PDZ1 domain of MDA-9/Syntenin (syndecan binding protein: SDCBP), thereby inhibiting MDA-9/Syntenin activity, and methods of use of same. The compositions and methods provided herein are useful for treating cancer and preventing cancer metastasis, particularly in cancers that have increased MDA-9/Syntenin expression.

50 Claims, 103 Drawing Sheets
Specification includes a Sequence Listing.

FIG. 4E
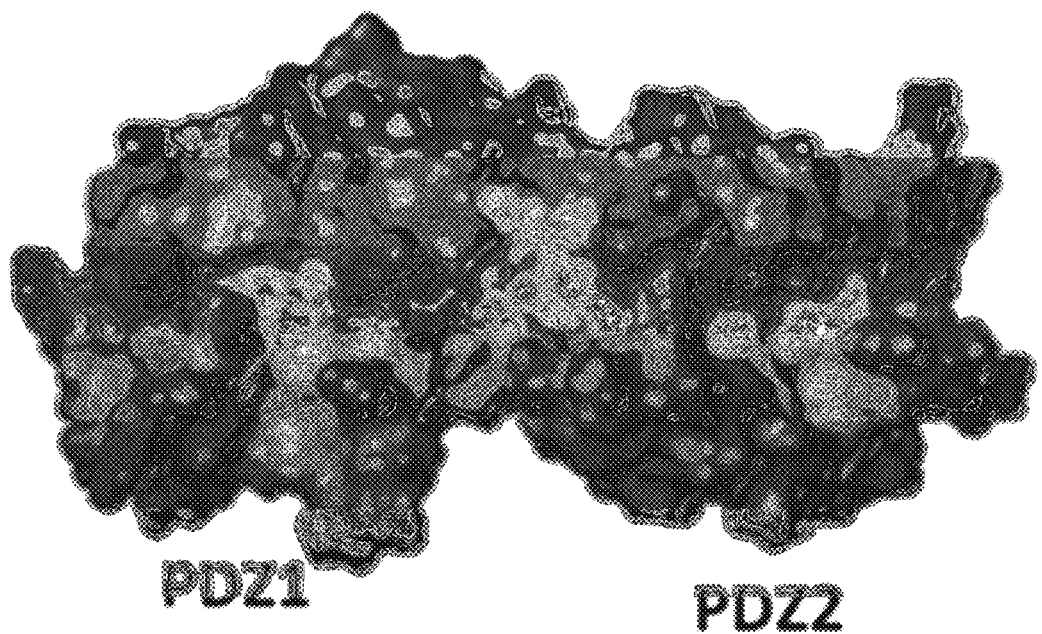
FIG. 5
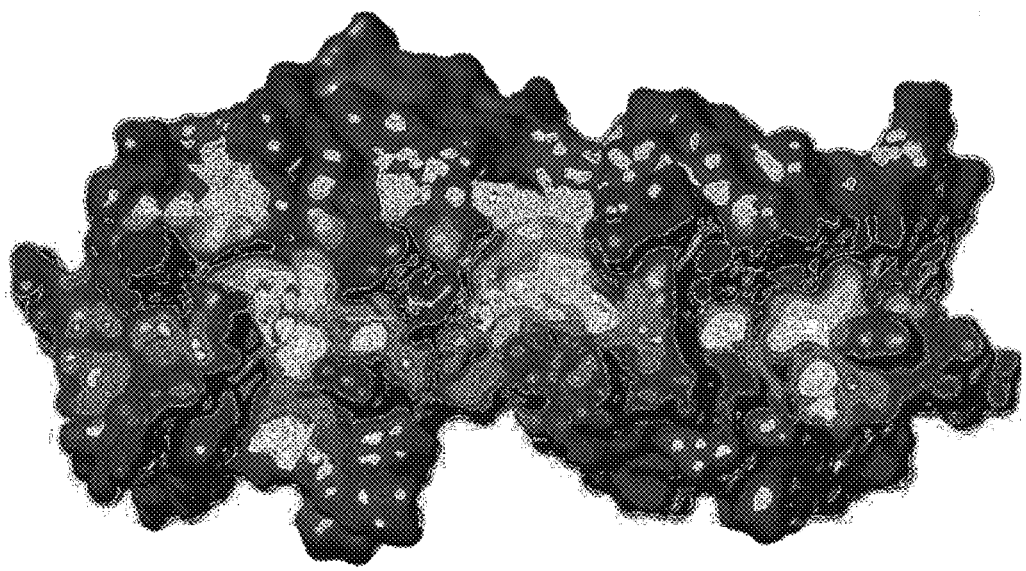
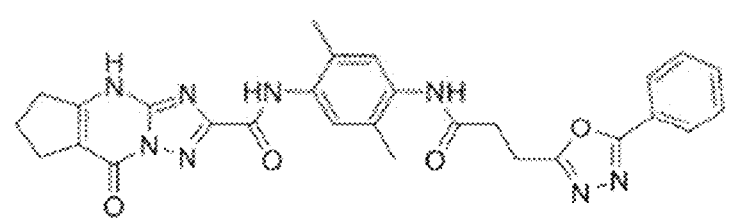

GBM6 -pretreated
7 d Post Injection

DMSO

FIG. 21A
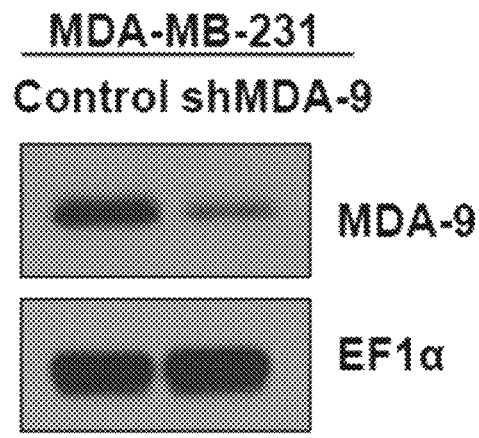
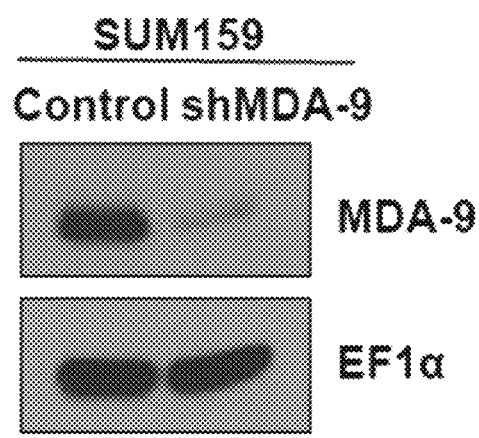
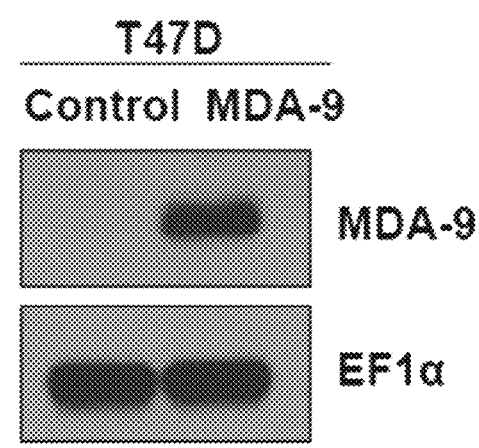

FIG. 22A
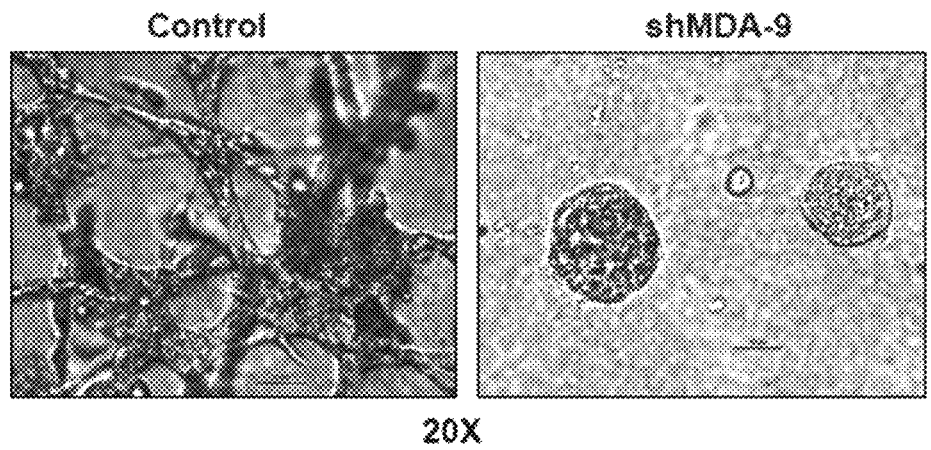
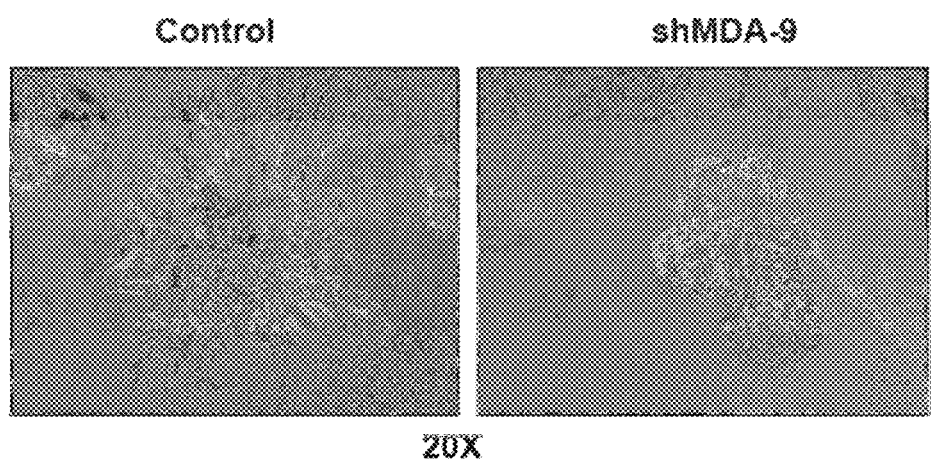
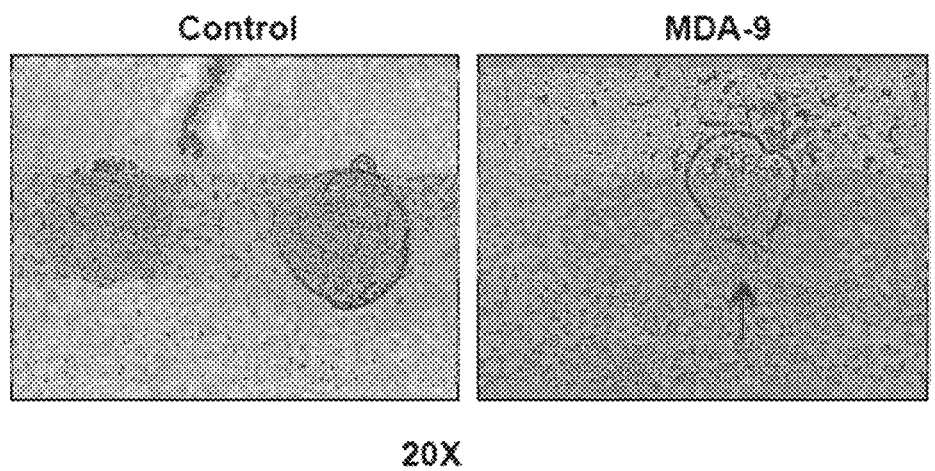

FIG. 23A
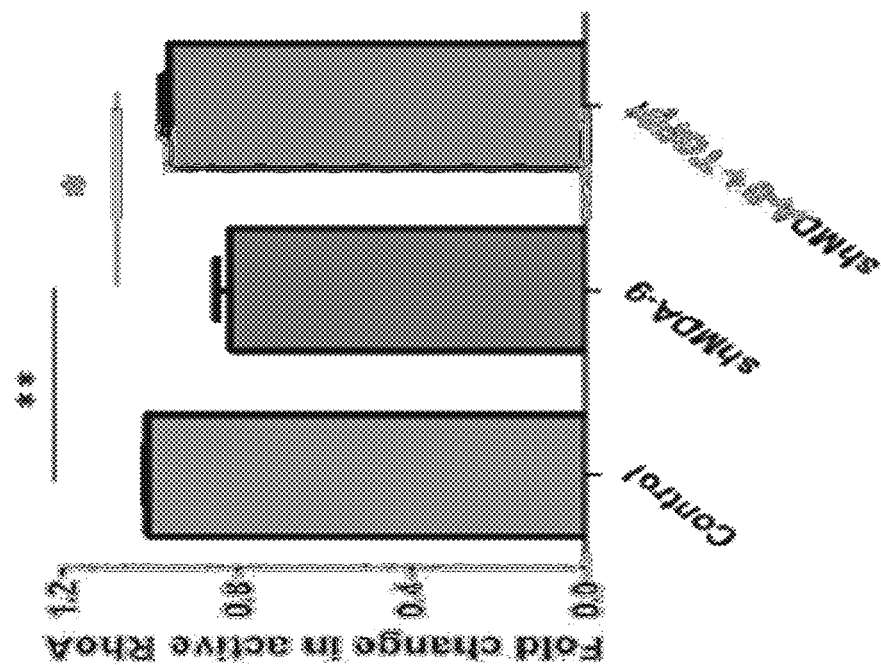
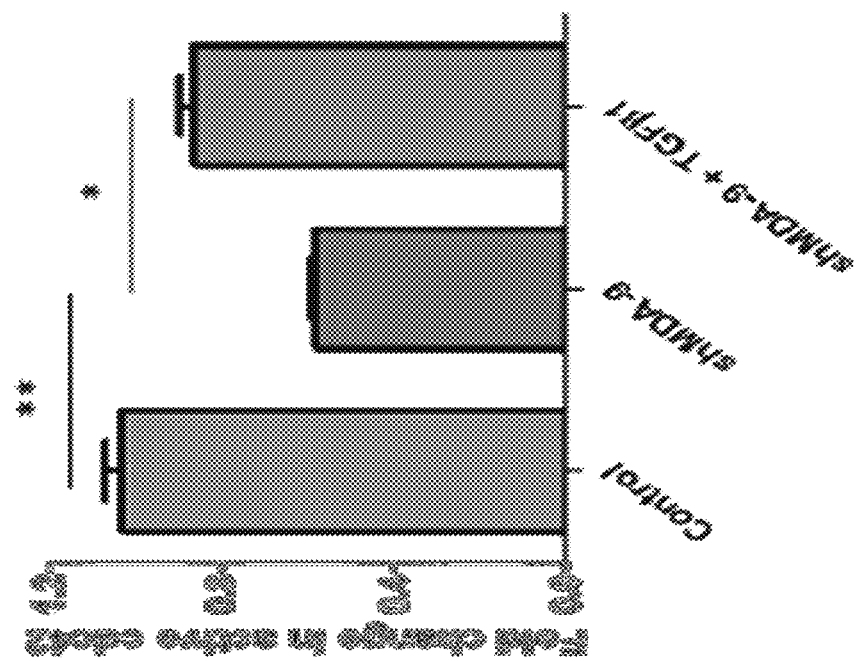

FIG. 23B
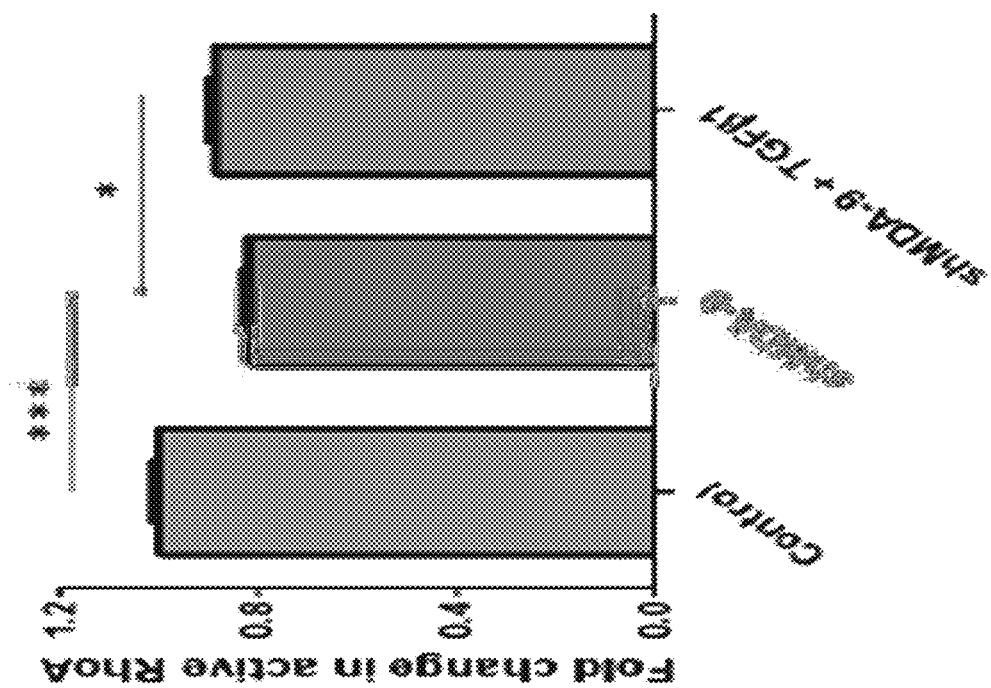
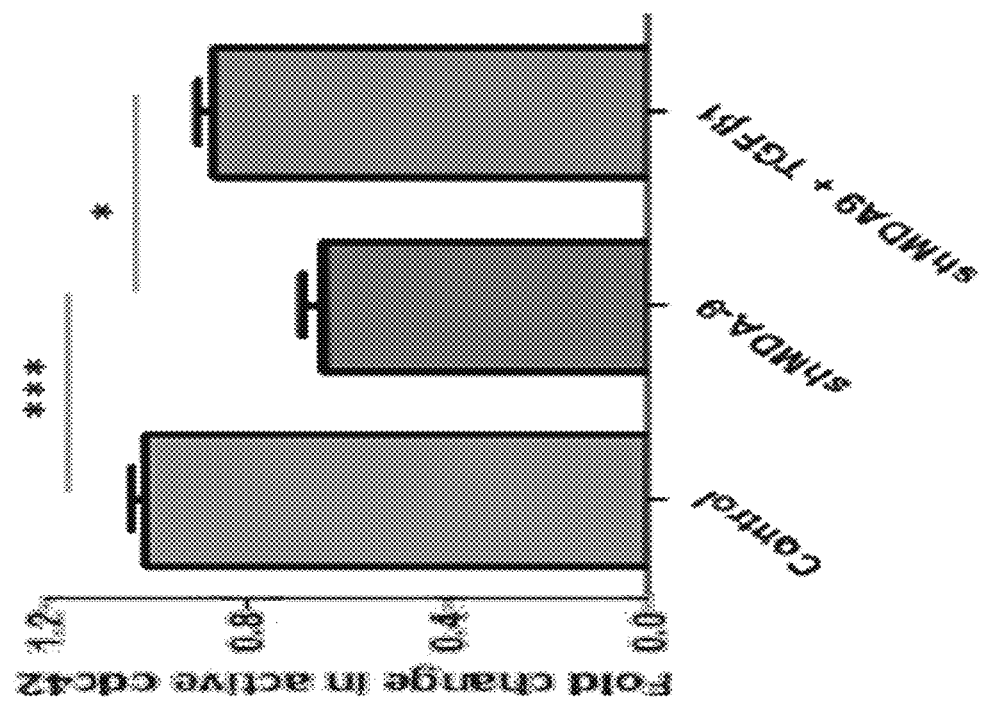

FIG. 23C
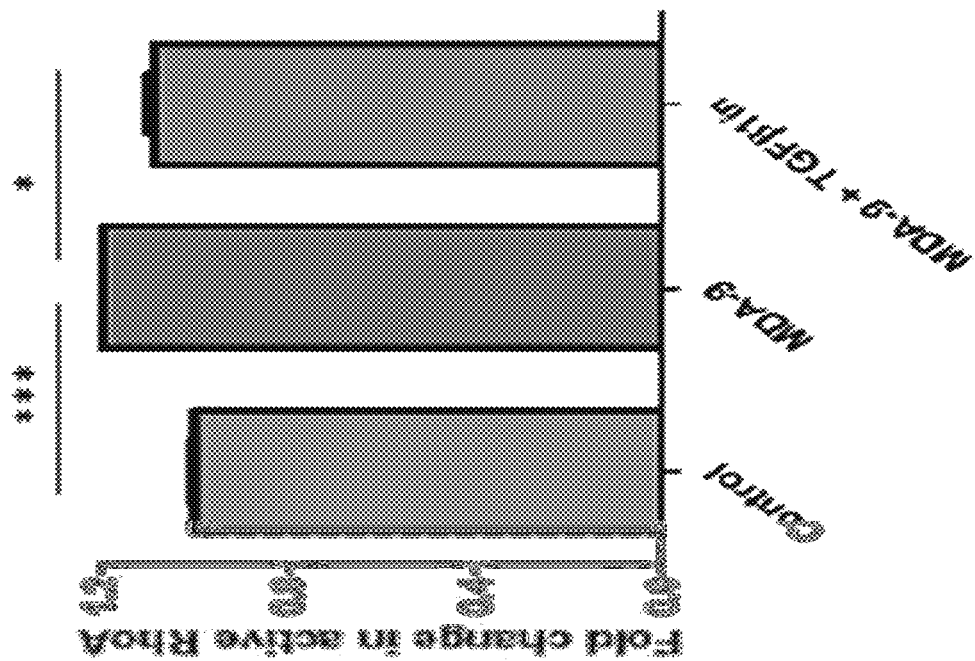
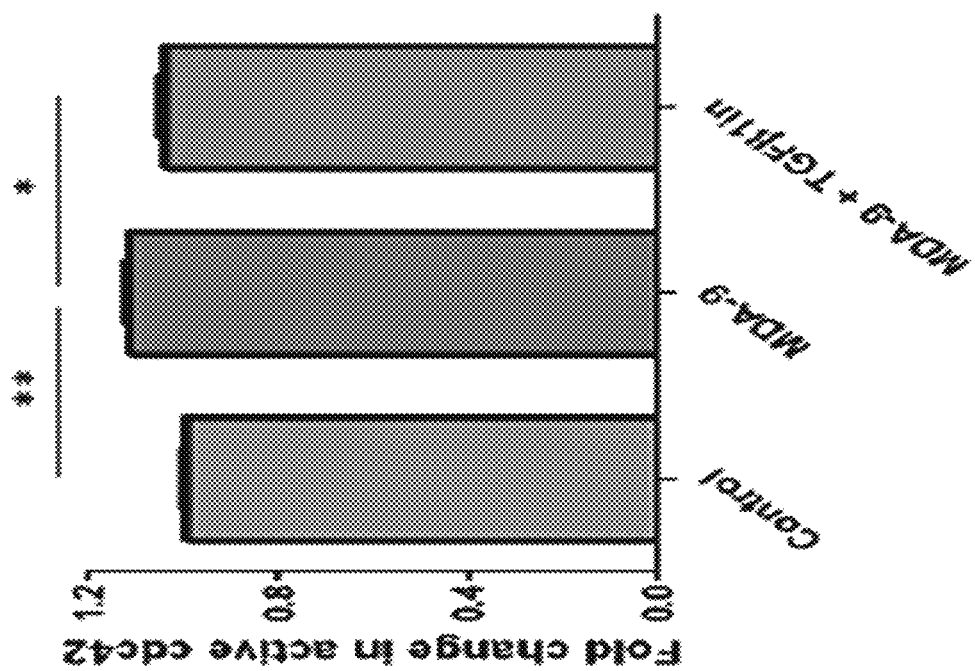

FIG. 27

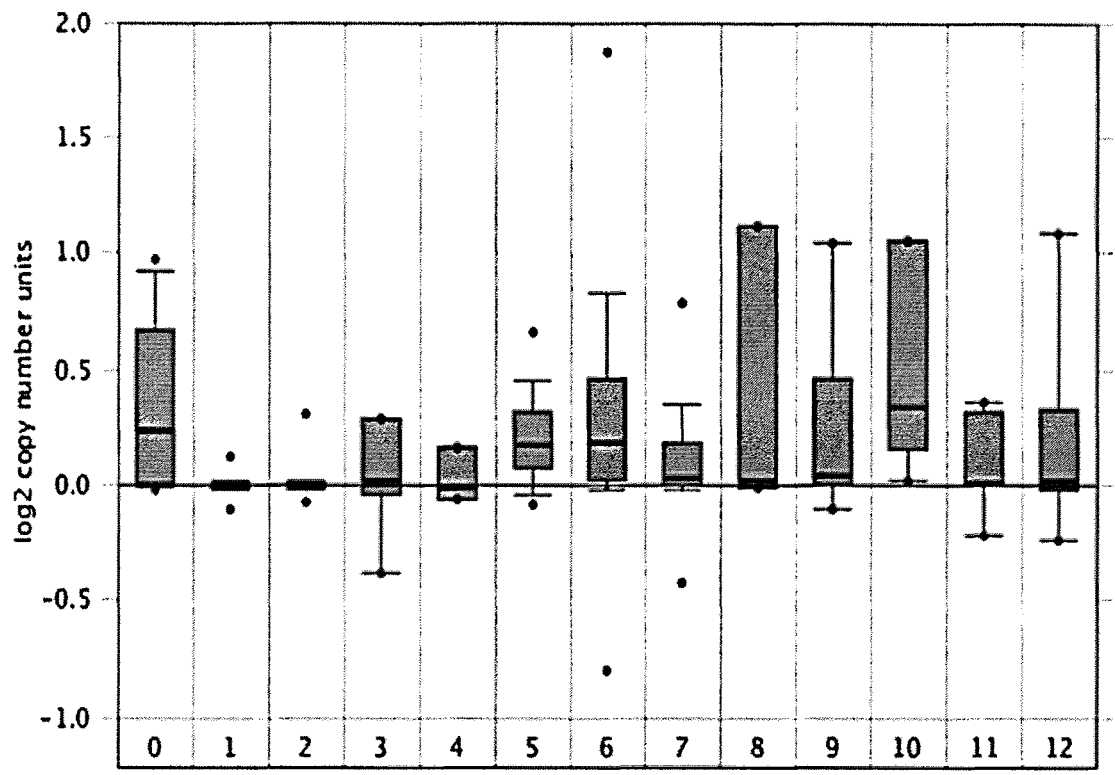

Legend

0. No value (23)
1. Blood (702)
2. Breast (111)
3. Ductal Breast Carcinoma (5)
4. Invasive Ductal and Invasive Lobular Breast Carcinoma (3)
5. Invasive Ductal and Lobular Carcinoma (14)
6. Invasive Ductal Breast Carcinoma (639)
7. Invasive Lobular Breast Carcinoma (71)
8. Invasive Papillary Breast Carcinoma (3)
9. Male Breast Carcinoma (9)
10. Medullary Breast Carcinoma (4)
11. Mixed Lobular and Ductal Breast Carcinoma (9)
12. Mucinous Breast Carcinoma (9)

TCGA Breast 2

| | | |
|---|---|---|
| No Associated Paper 2012/02/29 | 1,602 samples | SDCBP Information |
| DNA | 18,823 measured genes | Reporter Information |
| RefSeq Genes (UCSC refGene, July 2009, hg18, NCBI 36.1, March 2006) | | |

FIG. 30

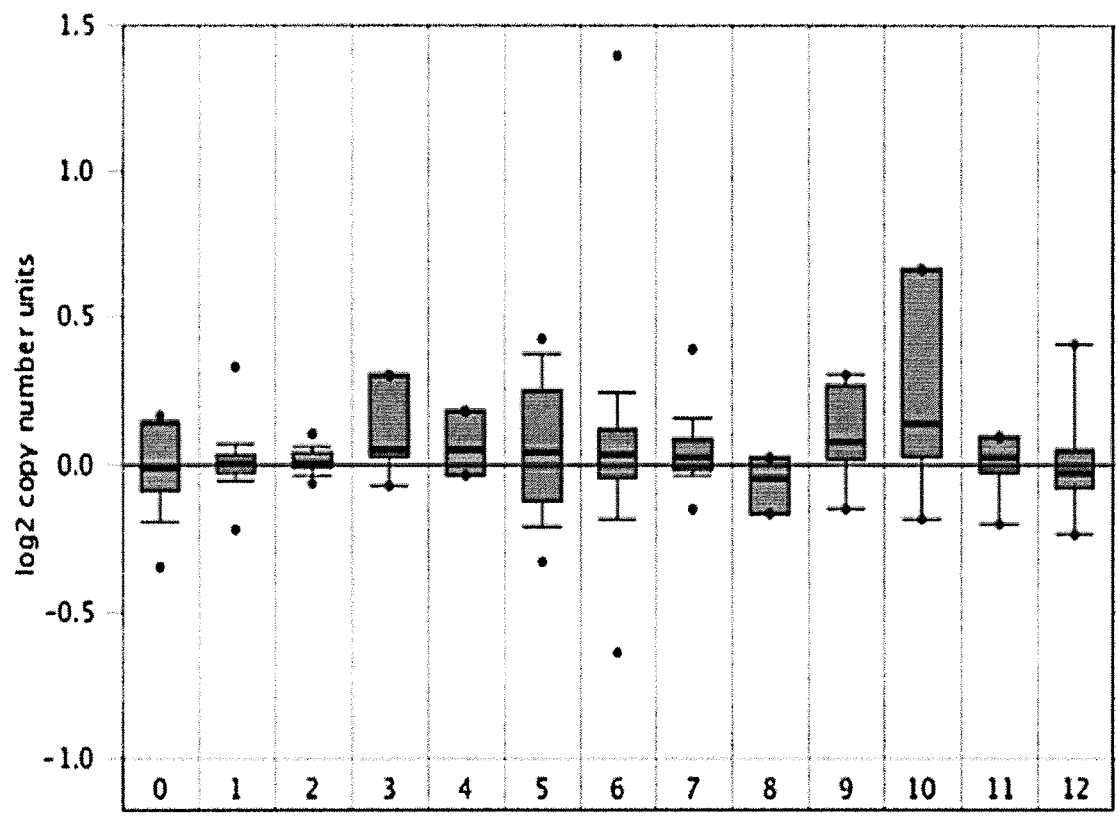

TGFB1 Copy Number in TCGA Breast 2
Grouped by Cancer and Normal Type

Legend

0. No value (23)
1. Blood (702)
2. Breast (111)
3. Ductal Breast Carcinoma (5)
4. Invasive Ductal and Invasive Lobular Breast Carcinoma (3)
5. Invasive Ductal and Lobular Carcinoma (14)
6. Invasive Ductal Breast Carcinoma (639)
7. Invasive Lobular Breast Carcinoma (71)
8. Invasive Papillary Breast Carcinoma (3)
9. Male Breast Carcinoma (9)
10. Medullary Breast Carcinoma (4)
11. Mixed Lobular and Ductal Breast Carcinoma (9)
12. Mucinous Breast Carcinoma (9)

TCGA Breast 2

| | | |
|---|---|---|
| No Associated Paper 2012/02/29 | 1,602 samples | TGFB1 Information |
| DNA | 18,823 measured genes | Reporter Information |
| RefSeq Genes (UCSC refGene, July 2009, hg18, NCBI 36.1, March 2006) | | |

63X oil

113B7 (PDZ1in)

FIG. 52
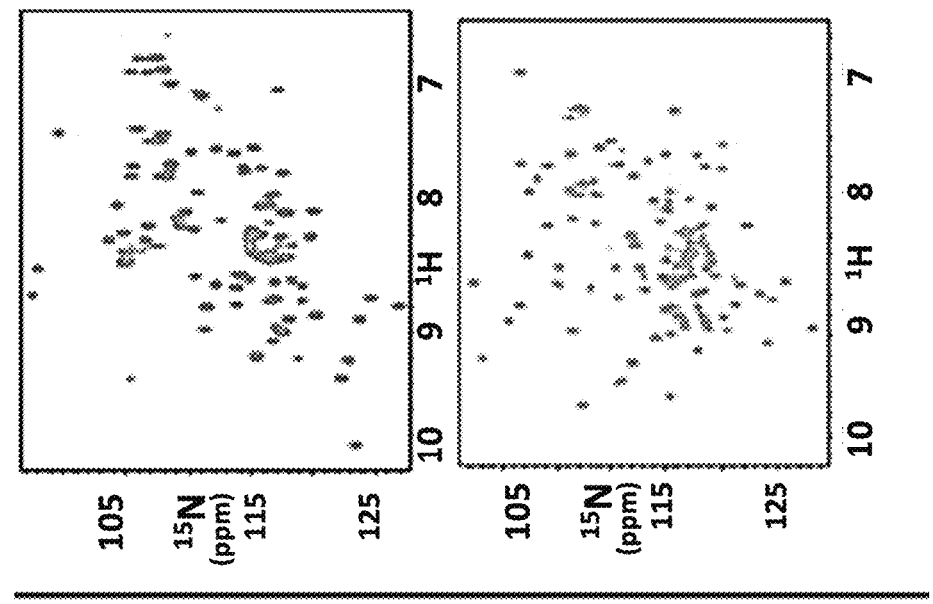
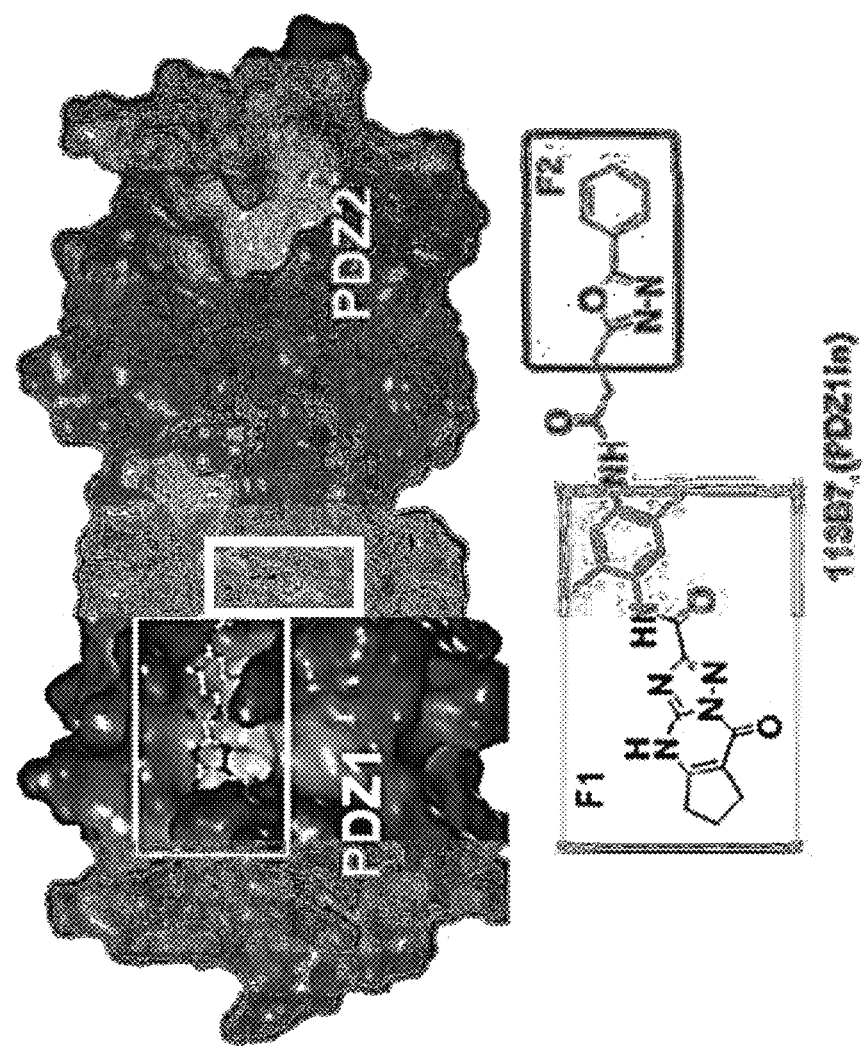

INHIBITORS OF CANCER INVASION, ATTACHMENT, AND/OR METASTASIS

CROSS-REFERENCES TO RELATED APPLICATIONS

This application claims to the benefit of U.S. Provisional Application No. 62/421,468, filed Nov. 14, 2016, and U.S. Provisional Application No. 62/424,571, filed Nov. 21, 2016, which are incorporated herein in their entirety and for all purposes.

STATEMENT AS TO RIGHTS TO INVENTIONS MADE UNDER FEDERALLY SPONSORED RESEARCH AND DEVELOPMENT

This invention was made with government support under grant nos. CA097318, CA168517, and CA016059, awarded by the National Institutes of Health. The government has certain rights in the invention.

REFERENCE TO A "SEQUENCE LISTING," A TABLE, OR A COMPUTER PROGRAM LISTING APPENDIX SUBMITTED ON A COMPACT DISK

The Sequence Listing written in file 052893-502001WO Sequence Listing_ST25.TXT, created Nov. 13, 2017, 1,360 bytes, machine format IBM-PC, MS-Windows operating system, is hereby incorporated by reference.

BACKGROUND

Described herein, inter alia, are small molecule inhibitors for the treatment of cancer, including small molecule inhibitors capable of treating or preventing cancer invasion, attachment and/or metastasis, for example difficult to treat tumors such as glioblastoma.

Cancer (malignant neoplasia) is a disease involving unregulated cell growth. In cancer, cells divide and grow uncontrollably, forming malignant tumors, which may invade nearby parts of the body. The cancer may also spread to more distant parts of the body through the lymphatic system or bloodstream (metastasis). Metastasis is a complex series of steps in which cancer cells leave the primary tumor site, migrate and colonize to distant sites or organs of the body via the bloodstream or the lymphatic system. Cancer is usually treated with one or a combination of chemotherapy, radiation therapy and/or surgery. While treatment methods have advanced significantly, the outcomes for particular cancers are still not optimal, current treatments often have very harsh side effects, and if the cancer is not detected early, the chances of survival are greatly reduced. Invasive, metastatic cancer is particularly difficult to treat.

Glioblastoma multiforme (GBM) is an especially intractable tumor despite therapeutic advances principally because of its invasive properties. Radiation is a staple in modern therapeutic regimens. However, when glioblastoma multiforme (GBM) cells are irradiated (a common mode of therapy after tumor debulking) the invasive ability of GBM is increased, and cells surviving radiation become even more aggressive and invasive.

There is a need in the art for additional agents to treat cancer. In particular, there is a need for additional agents that prevent cancer invasion, attachment and/or metastasis, and that prevent or attenuate the increase in invasive ability of cancer cells after exposure to irradiation. Described herein are solutions to these and other problems in the art.

BRIEF SUMMARY

In an aspect is provided a compound, or pharmaceutically acceptable salt thereof, having the formula:

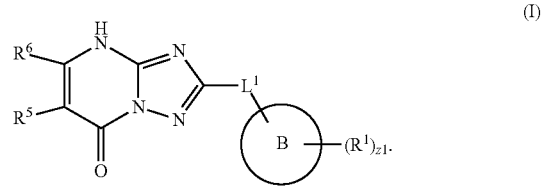

(I)

Ring B is a cycloalkyl, heterocycloalkyl, aryl, or heteroaryl.

$R^1$ is independently halogen, $-CX^1_3$, $-CHX^1_2$, $-CH_2X^1$, $-OCX^1_3$, $-OCH_2X^1$, $-OCHX^1_2$, $-CN$, $-SO_{n1}R^{1D}$, $-SO_{v1}NR^{1A}R^{1B}$, $-NHC(O)NR^{1A}R^{1B}$, $-N(O)_{m1}$, $-NR^{1A}R^{1B}$, $-C(O)R^{1C}$, $-C(O)-OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl;

$L^1$ is a bond, $-S(O)_2-$, $-N(R^3)-$, $-O-$, $-S-$, $-C(O)-$, $-C(O)N(R^3)-$, $-N(R^3)C(O)-$, $-N(R^3)C(O)NH-$, $-NHC(O)N(R^3)-$, $-S(O)_2N(R^3)-$, $-N(R^3)S(O)_2-$, $-C(O)S(O)_2N(R^3)-$, $-N(R^3)S(O)_2C(O)-$, $-C(O)O-$, $-OC(O)-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^3$ is independently hydrogen, $-CX^3_3$, $-CHX^3_2$, $-CH_2X^3$, $-CN$, $-C(O)R^{3C}$, $-C(O)OR^{3C}$, $-C(O)NR^{3A}R^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^5$ is independently hydrogen, halogen, $-CX^5_3$, $-CHX^5_2$, $-CH_2X^5$, $-OCX^5_3$, $-OCH_2X^5$, $-OCHX^5_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^6$ is independently hydrogen, halogen, $-CX^6_3$, $-CHX^6_2$, $-CH_2X^6$, $-OCX^6_3$, $-OCH_2X^6$, $-OCHX^6_2$, $-CN$, $-OH$, $-NH_2$, $-COOH$, $-CONH_2$, $-NO_2$, $-SH$, $-SO_3H$, $-SO_4H$, $-SO_2NH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^5$ and $R^6$ substituents may optionally be joined to form a substituted or unsubstituted cycloalkyl, substituted or unsubstituted heterocycloalkyl, substituted or unsubstituted aryl, or substituted or unsubstituted heteroaryl;

$R^{1A}$, $R^{1B}$, $R^{1C}$, $R^{1D}$, $R^{3A}$, $R^{3B}$, and $R^{3C}$ are independently hydrogen, $-CX_3$, $-CN$, $-COOH$, $-CONH_2$, $-CHX_2$, $-CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl;

X, $X^1$, $X^3$, $X^5$, and $X^6$ are independently $-F$, $-Cl$, $-Br$, or $-I$; n1 is independently an integer from 0 to 4; m1 and v1 are independently 1 or 2; and z1 is an integer from 0 to 5.

In an aspect is provided a compound, or pharmaceutically acceptable salt thereof, having the formula:

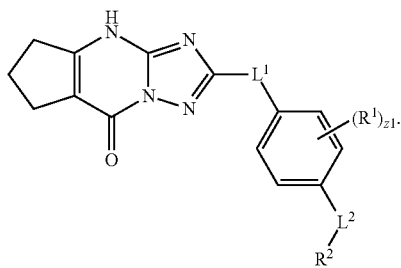

$R^1$ is independently halogen, $-CX^1_3$, $-CX^1_2$, $-CH_2X^1$, $-OCX^1_3$, $-OCH_2X^1$, $-OCHX^1_2$, $-CN$, $-SO_{n1}R^{1D}$, $-SO_{v1}NR^{1A}R^{1B}$, $-NHC(O)NR^{1A}R^{1B}$, $-N(O)_{m1}$, $-NR^{1A}R^{1B}$, $-C(O)R^{1C}$, $-C(O)-OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl;

$R^2$ is independently hydrogen, halogen, $-CX^2_3$, $-CHX^2_2$, $-CH_2X^2$, $-OCX^2_3$, $-OCH_2X^2$, $-OCHX^2_2$, $-CN$, $-SO_{n2}R^{2D}$, $-SO_{v2}NR^{2A}R^{2B}$, $-NHC(O)NR^{2A}R^{2B}$, $-N(O)_{m2}$, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}R^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^1$ is a bond, $-S(O)_2-$, $-N(R^3)-$, $-O-$, $-S-$, $-C(O)-$, $-C(O)N(R^3)-$, $-N(R^3)C(O)-$, $-N(R^3)C(O)NH-$, $-NHC(O)N(R^3)-$, $-S(O)_2N(R^3)-$, $-N(R^3)S(O)_2-$, $-C(O)S(O)_2N(R^3)-$, $-N(R^3)S(O)_2C(O)-$, $-C(O)O-$, $-OC(O)-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^3$ is independently hydrogen, $-CX^3_3$, $-CHX^3_2$, $-CH_2X^3$, $-CN$, $-C(O)R^{3C}$, $-C(O)OR^{3C}$, $-C(O)NR^{3A}R^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$L^2$ is a bond, $-S(O)_2-$, $-N(R^4)-$, $-O-$, $-S-$, $-C(O)-$, $-C(O)N(R^4)-$, $-N(R^4)C(O)-$, $-N(R^4)C(O)NH-$, $-NHC(O)N(R^4)-$, $-S(O)_2N(R^4)-$, $-N(R^4)S(O)_2-$, $-C(O)S(O)_2N(R^4)-$, $-N(R^4)S(O)_2C(O)-$, $-C(O)O-$, $-OC(O)-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^4$ is independently hydrogen, $-CX^4_3$, $-CHX^4_2$, $-CH_2X^4$, $-CN$, $-C(O)R^{4C}$, $-C(O)OR^{4C}$, $-C(O)NR^{4A}R^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{4A}$, $R^{4B}$, and $R^{4C}$ are independently hydrogen, $-CX_3$, $-CN$, $-COOH$, $-CONH_2$, $-CHX_2$, $-CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; $R^{4A}$ and $R^{4B}$ substituents bonded to the same nitrogen atom may optionally be joined to form a substituted or unsubstituted heterocycloalkyl or substituted or unsubstituted heteroaryl; X, $X^1$, $X^2$, $X^3$, and $X^4$ are independently $-F$, $-Cl$, $-Br$, or $-I$; n1 and n2 are independently an integer from 0 to 4; m1, m2, v1, and v2 are independently 1 or 2; and z1 is an integer from 0 to 4.

In another aspect is provided a method of preventing or treating cancer in a subject in need thereof, including administering to the subject a therapeutically effective amount of a compound described herein, including embodiments thereof, wherein the therapeutically effective amount is sufficient to prevent or treat the cancer.

In another aspect is provided a method of sensitizing cancer cells to killing by radiation, including contacting the cancer cells with an effective (e.g., therapeutically effective) amount of a compound described herein, including embodiments thereof, wherein the therapeutically effective amount is sufficient to sensitize the cancer cells to killing by radiation.

In another aspect is provided a method of slowing or preventing metastasis of cancer cells in a subject in need thereof, including administering to the subject an effective (e.g., therapeutically effective) amount of a compound described herein, including embodiments thereof, wherein the therapeutically effective amount is sufficient to slow or prevent the metastasis.

In another aspect is provided s a method of treating a glioblastoma multiforme brain tumor in a subject in need thereof, including performing surgery on the subject to debulk the glioblastoma multiform brain tumor; radiosensitizing remaining tumor cells by administering to the subject a therapeutically effective amount of at least one of the compounds of any of the invention, wherein the therapeutically effective amount is sufficient to sensitize the remaining tumor cells to killing by radiation; and providing radiation therapy to the subject.

In an aspect is provided a pharmaceutical composition including a compound as described herein, including embodiments thereof, and a pharmaceutically acceptable excipient.

In an aspect is provided a method of inhibiting MDA-9 protein activity, the method including contacting the MDA-9 protein with an effective amount of a PDZ1 domain binder, thereby inhibiting MDA-9 activity.

In an aspect is provided a method of treating cancer in a subject in need thereof, the method including administering to the subject an effective amount of a PDZ1 domain binder.

In an aspect is provided a method of preventing metastasis of cancer cells in a subject in need thereof, the method including administering to the subject an effective amount of a PDZ1 domain binder.

In an aspect is provided a method of inhibiting cancer associated angiogenesis in a subject in need thereof, the method including administering to the subject an effective amount of a PDZ1 domain binder.

In an aspect is provided a method of treating an inflammatory disease in a subject in need thereof, the method including administering to the subject an effective amount of a PDZ1 domain binder.

In an aspect is provided a method of treating a neurodegenerative disease in a subject in need thereof, the method including administering to the subject an effective amount of a PDZ1 domain binder.

In an aspect is provided a method of treating an infectious disease in a subject in need thereof, the method including administering to the subject an effective amount of a PDZ1 domain binder.

BRIEF DESCRIPTION OF THE DRAWINGS

FIG. 1A. The REMBRANDT database was mined for glioma patients with no previous radiation treatment, who then underwent radiation therapy. These were stratified by SDCBP (mda-9/syntenin) expression (High was set >1.5-fold overexpression). High tumor MDA-9/Syntenin led to a worse prognosis in those undergoing radiotherapy. FIG. 1B. U1242-shcon and U1242-shmda-9 cells were analyzed for colony formation 14 d post radiation treatment. FIG. 1C. U1242 cells treated with either Ad.5/3-shcon or Ad.5/3-shmda-9 were analyzed for viability at the indicated time points via MTT assay. Error bars=±s.d. *$p<0.05$, **$p<0.01$.

FIGS. 3A-3C. Immunoblot analysis of GBM cells treated with either Ad.5/3-shcon or Ad.5/3-shmda-9 and irradiated 48 hrs later. Cell lysates were collected 24 hr post-radiation. Changes in protein levels were quantified in FIGS. 3D-3F. β-actin used as protein loading control.

FIGS. 4A-4E. FIG. 4A. Chemical structures of the two initial fragment hits (top) and the structure of the resulting molecule 113B7 (PDZ1i). FIG. 4B. Superposition of 2D [$^{15}$N, $^{1}$H]-HSQC spectra of 50 μM MDA-9 PDZ12 tandem domain in the absence and presence of 350 μM 113B7. FIG. 4C. Binding curve and representative spectra for the titration of 113B7 against MDA-9 PDZ12 tandem domain. Top: Zoom of box region in FIG. 4B after titrating 113B7 into Mda9 PDZ, tandem domain. The cross peak corresponding to the backbone amide of residue A147 experiences a gradual shift upon the addition of 113B7. Bottom: Titration curve of 113B7 for residue A147. The dissociation constant for the binding of 113B7 to MDA-9 was calculated to be 21.37±8.62 μM. FIG. 4D. Superposition of 2D [$^{15}$N, $^{1}$H]-HSQC spectra of 50 μM PDZ domain from X11/mint scaffold protein (20 mM; 33% identity with PDZ1) are shown in absence and in presence of 100 mM 113B7. No appreciable binding is detected. FIG. 4E. Docked structure of 113B7 in complex with MDA-9 PDZ tandem domain (PDB: 1W9E). The pose was obtained with GOLD. Two PDZ domains of MDA-9 are labeled. The surface of MDA-9 PDZ tandem domain is displayed. The structure of 113B7 is displayed in balls and sticks.

FIG. 5. Docked structure of PDZ1i (113B7) in complex with MDA-9 PDZ tandem domain (PDB: 1W9E) and chemical structure of PDZ (113B7). The pose was obtained with GOLD. Two PDZ domains of MDA-9 are labeled. The surface of MDA-9 PDZ tandem domain is displayed. The structure of 113B7 is displayed in balls and sticks.

FIG. 7A. Im-PHFA, primary immortal human fetal astrocyte cells were infected with an MDA-9/Syntenin expression plasmid carrying adenovirus. 48 hrs post-infection both the control and MDA-9/Syntenin over-expressing cells were treated with DMSO or PDZ1i followed by seeding in a trans-well Matrigel invasion assay and stained after 24 hrs. FIG. 7B. T98G and U87 were treated with DMSO or PDZ1i and seeding in a trans-well Matrigel invasion assay and stained after 24 hrs. Invasion was quantified from 4 random fields. Data represents fold changes and average±S.D.

FIG. 8A. ImPHFA and U87 cells were treated with 50 μM PDZ1i 2 h prior to radiation and analyzed for colony formation after 14 d. FIG. 8B. U87 cells were treated with 50 μM PDZ1i 2 h prior to radiation and analyzed via MTT assay after 24 h. FIG. 8C. U87 cells were pretreated with 50 μM PDZ1i 2 h prior to radiation and subsequently seeded in a trans-well Matrigel invasion assay and stained after 24 h. Invasion was quantified from 5 random fields in FIG. 8D. Error bars=±s.d. *$p<0.05$, **$p<0.01$.

FIG. 9A. Immunoblot analysis showing expression of mutated EGFR in U87 or U87EGFRvIII cells. FIG. 9B. Cells were treated with either DMSO or PDZ1i 2 hrs prior to radiation. These cells were subsequently seeded on fibronectin-coated plates and cell lysates were collected after 1 hr and analyzed for protein expression. FIG. 9C. Lysates from cells treated with and without radiation or PDZ1i as indicated were analyzed via immunoprecipitation. Anti-MDA-9, top, and anti-EGFR, bottom, were used to pull down associated complexes, and western blotting was performed with the indicated antibodies. Left lanes include IgG and control input samples.

FIG. 10A, MMP1; FIG. 10B, MMP2; FIG. 10C, MMP3; FIG. 10D, MMP8; FIG. 10E, MMP9; FIG. 10F, MMP13; FIG. 10G. Cathepsin A; FIG. 10H, Cathepsin B; FIG. 10I, Cathepsin C; FIG. 10J, Cathepsin S; FIG. 10K, Cathepsin V; FIG. 10L, ASAM9.

FIG. 13A, brain tissue at site of injection of DMSO treated cells; FIG. 13B, brain tissue are site of injection of PDZ1i treated cells. 7 days after tumor implantation, mice received either vehicle or PDZ1i (30 mg/kg) three times per week for 3 weeks. Brain tissue was isolated and analyzed via H&E stain, FIG. 13C, brain tissue from mice treated with vehicle; FIG. 13D, brain tissue from mice treated with PDZ1i. FIG. 13E, Kaplan-Myer curves of these groups based on animal survival. **p<0.01.

FIG. 14A. U1242-luc cells were injected intracranially into nude mice. After 7 days mice were randomized to 4 groups, and mice receiving therapy were treated on days 11-14 as pictured. FIG. 14B. Kaplan-Meier survival curves for each treatment group. Median survival as listed. Two brain tissue samples were isolated for each group, sectioned, and H and E staining is shown. FIG. 14C, DMSO treated mice, FIG. 14D, PDZ1i treated mice, FIG. 14E, mice treated with radiation and DMSO; FIG. 14F, mice treated with radiation and PDZ1i.

FIG. 15A) mda-9 expression level in primary immortal normal prostate epithelial (RWPE-1) and different PC cells. FIG. 15B) Knockdown of mda-9 by shRNA reduces in vitro invasive properties of different PC cells. FIG. 15C) over expression of mda-9/syntenin in RWPE-1 cells enhances invasiveness. FIG. 15D) Lucifearase expressing ARCaPM cells either carrying control shRNA or shmda-9 were inoculated i.v. into athymic nude mice by tail vein injections. Mice were maintained until tumors reached maximally permitted size, then animals were euthanized. Kalpan-Meier survival graph was constructed using Graph Pad software.

FIG. 16A) Western blot analysis was performed for the indicated cells for both phospho-STAT3 (Tyr705) and total STAT3. FIG. 16N) Model of MDA-9/syntenin-mediated PC progression.

FIG. 17A) Different cancer cells (25,000 cells/well) from various anatomic origins were pre-treated with either DMSO (vehicle) or PDZ1i (dose as indicated) and invasion ability was assayed using modified Boyden Chamber according to the manufacturer's instructions. Photomicrographs were taken at 10× magnification and quantification of the results of three independent experiments is provided in the graphs. The data presents mean±S.D. B) The designated cells were treated with DMSO or PDZ1i and invasion properties were determined using a modified Boyden Chamber assay (BD bioscience). RWPE-1 mda-9: mda-9 transiently overexpressing cell line. FIG. 17C) and FIG. 17D) cell lysates prepared from DU145 cells, treated or not with PDZ1i, were subjected to IP using anti-MDA-9 antibody and IB was performed using anti-IGF-1R antibody. FIG. 17E) Cells were growth starved for 24 h and treated with either DMSO or PDZ1i (dose indicated in µM) for 6 h. Cells were treated with human recombinant IGFBP-2 (hIGFBP-2, 10 ng/ml) for 2 h, lysates were prepared and western blot analysis was conducted with specific antibodies. FIG. 17F) Cells were serum-starved for 24 h and treated with either DMSO or PDZ1i (20 μM) for 6 h. Cells were treated with human recombinant IGFBP-2 (hIGFBP-2, 10 ng/ml) for different times (30 to 120 min), cell lysates were prepared and subjected to western blotting. FIG. 17G) Cells were serum-starved for 24 h and treated with either DMSO or PDZ1i (20 μM) for 6 h. Cells were treated with human recombinant IL-6 (hIGFBP-2, 1 ng/ml) for 2 h, cell lysates were prepared and analyzed by western blotting. FIG. 17H) the indicated cells were treated with DMSO or PDZ1i (50 μM) for 24 h. Tumor-derived conditioned media were subjected to western blotting analysis (left panel) for the expression of MMP-2 and MMP-9 and Zymography (right panel) for enzymatic activity.

FIG. 18A) The strategy for qPCR based array is shown schematically. Briefly, ARCaPM cells were pre-treated with either DMSO or PDZ1i (50 μM) for 24 h followed by RNA extraction. cDNA was prepared and angiogenesis-related gene expression arrays were analyzed. FIG. 18B) Cell lines were treated with DMSO or PDZ1i for 24 h and qPCR was performed for the specific indicated genes using Taqman probes. FIG. 18C) Cells were treated with DMSO or PDZ1i for 24 h and expression of VEGF-A mRNA was analyzed.

FIG. 19A) Survival data for athymic nude mice in which DMSO or PDZ1i pre-treated ARCaPM cells were injected. FIG. 19B) Survival data for athymic nude mice which were injected with (n=5, each group) ARCaPM-Luc ($1 \times 10^6$ cells in 100 μl saline) through an intracardiac route. Mice received either vehicle or PDZ1i every alternative day (9 injections during the first three months) and maintained until they needed to be euthanized. FIG. 19C) Survival data for C57BL/6 mice injected through the intracardiac route with RM1-Luc. Vehicle or PDZ1i was administered through intraperitoneal injection every alternate day (total 3 injections during the first week). Survival curves were generated using 6 control vehicle-treated and 5 PDZ1i-treated. Kaplan—Meier survival curves were prepared using Graph Pad software. FIG. 19D) PDZ1i can efficiently inhibit tumor progression in Hi-Myc mice. Graphical representation of the average prostate weights from control and treated groups. FIG. 19E and FIG. 19F) Photomicrographs representing the histological changes in prostate sections obtained from 6-month old Hi-Myc mice receiving either vehicle (FIG. 19E) or PDZ1i (FIG. 19F).

(FIG. 20A) Immunohistochemistry of breast cancer patient samples showing overexpression of MDA-9 in breast cancer. (FIG. 20B) MDA-9 protein expression is increased in invasive and metastatic cell lines. (FIG. 20C) MDA-9 transcript expression is increased in invasive and metastatic breast cancer cell lines.

FIGS. 21A-21C. MDA-9 enhances invasion and cytoskeletal rearrangement. (FIG. 21A) Western blots showing efficient silencing of MDA-9 in MDA-MB-231 cells, efficient silencing of MDA-9 in SUM159 cells and efficient overexpression of MDA-9 in T47D cells. (FIG. 21B) Graphical representation of the invasion assay results in MDA-9 silenced MDA-MB-231 and SUM159 cells and MDA-9 overexpressing T47D cells. (FIG. 21C) Representative images showing change in cytoskeletal reorganization following silencing of MDA-9 expression in MDA-MB-231 and SUM159 cells and overexpressing MDA-9 in T47D cells. *, $p<0.05$; ***, $p<0.0001$.

FIGS. 22A-22B. Silencing or overexpressing MDA-9 regulates EMT. (FIG. 22A) Representative images showing change in morphology in 3D culture following silencing MDA-9 expression in MDA-MB-231 and SUM159 cells and overexpressing MDA-9 in T47D cells. (FIG. 22B) Western blots showing changes in key epithelial and mesenchymal markers following modulation of MDA-9 expression.

FIGS. 23A-23D. MDA-9 modulates small GTPases RhoA and Cdc42 via TGFβ1. Fold change in active cdc42 and RhoA levels in (FIG. 23A) MDA-MB-231 cells and (FIG. 23B) SUM159 cells after silencing MDA-9 expression and after re-introduction of TGFβ1. (FIG. 23C) Fold change in active cdc42 and RhoA levels in T47D cells after overexpression of MDA-9 and after addition of mot inhibitor (FIG. 23D) Western blots showing changes in TGFβ1 expression following modulation of MDA-9 expression. *, $p<0.05$; , $p<0.01$; *, $p<0.0001$.

(FIG. 24C) Graphical representation of the invasion assay results and representative images showing cytoskeletal rearrangement upon TGFβ1 inhibition in T47D cells overexpressing MDA-9. Inset: western blot showing efficient overexpression of MDA-9. ***, $p<0.0001$.

(FIG. 25A) Immunoprecipitation with MDA-9 antibody and immunoblotting using TGFβ1 antibody showed that MDA-9 interacts with TGFβ1. (FIG. 25B) Immunoprecipitation with TGFβ1 tag antibody and immunoblotting with MDA-9 antibody showed that TGFβ1 interacts with MDA-9 and this interaction was decreased when MDA-9 expression was silenced. (FIG. 25C) Schematic representation of full length MDA-9 constructs and PDZ1 deleted constructs (with FLAG tag). (FIG. 25D) Immunoprecipitation with FLAG antibody and immunoblotting with TGFβ1 antibody shows that PDZ1 domain of MDA-9 interacts with TGFβ1.

(FIG. 26A) Western blot images showing stable expression of TGFβ1 in MDA-MB-231 control TGFβ1 luciferase cells and MDA-MB-231 shMDA-9 TGFβ1 luciferase cells. (FIG. 26B) Bioluminescence imaging showing reduction of lung metastasis in mice injected with MDA-MB-231 shMDA-9 luciferase cells and rescue following re-expression of TGFβ1. (FIG. 26C) Bioluminescence imaging showing rescue of lung metastasis in mice injected with MDA-MB-231 shMDA-9 TGFβ1 luciferase cells compared to mice injected with MDA-MB-231 shMDA-9 luciferase cells. (FIG. 26D) Bioluminescent images of the lungs showing metastasis. (FIG. 26E) Western blot images of cells isolated from the respective lungs and probed for MDA-9 and TGFβ1 tag expression. (FIG. 26F) H&E images of the lung sections showing presence of lung metastases. MDA-MB-231 control luciferase and MDA-MB-231 control TGFβ1 luciferase cells efficiently colonized the entire lungs. MDA-MB-231 shMDA-9 luciferase cells formed a few small lung metastases while MDA-MB-231 shMDA-9 TGFβ1 luciferase cells showed partial restoration of metastatic capabilities and formed multiple larger lung metastatic lesions. (FIG. 26G) Schematic representation of the signaling mechanism mediated by MDA-9 to regulate cytoskeletal rearrangement, EMT and invasion. MDA-9 has previously been shown to regulate the formation of various integrin β1 signaling complexes. Integrin β1, in turn, functions to enhance TGFβ1-mediated non-canonical signaling and EMT and blocking integrin β1 function inhibited TGFβ-mediated non-canonical signaling and EMT. In breast cancer cells, MDA-9 interacts with TGFβ1 and regulates the small GTPases RhoA and cdc42 via TGFβ1. Further, MDA-9 regulates EMT and invasion via TGFβ1.

FIG. 27. DNA copy number of MDA-9 is elevated in human breast cancer patients. Histogram from TCGA database in Oncomine demonstrating MDA-9 copy number elevation in breast tumors compared to normal breast.

FIG. 30. DNA copy number of TGFβ1 is elevated in human breast cancer patients. Histogram from TCGA database in Oncomine demonstrating TGFβ1 copy number elevation in breast tumors compared to normal breast in the same sample set assessed for MDA-9 expression in FIG. 27.

(FIG. 31A) Representative images showing change in cytoskeletal reorganization following addition of Integrin pi blocking antibody in SUM159 cells. (FIG. 31B) Representative images showing change in cytoskeletal reorganization following overexpression of MDA-9 that was restored upon addition of Integrin β1 blocking antibody.

FIG. 48A) Compounds were administered I.P. 6 times within first two weeks following inoculation (I.V. injection) of B16 cells in C57BL/6 mice to evaluate the anti-metastatic efficacy. FIG. 48B) HCC-driven tumor xenograft was established in athymic nude mice. Compound alone or in combination with Sorafenib were given through I.P. Tumor volumes were considered as an end point of this study. FIG. 48C) Hi-Myc, a mouse model for spontaneous prostate cancer either received the compound or vehicle at the age of 8 weeks (immediate after onset of disease) for total 9 injections (3/week). After 16 weeks from the first injection, prostate were collected and pathologically evaluated. Representative photomicrographs (Left panel) and H and E stained slides (Right panel) from prostate were presented.

FIG. 49A) C8161.9 cells were pre-treated with either DMSO or PDZ1in and cell lysates were immunoprecipitated and immunoblotted with the indicated antibodies. FIG. 49B) 200 μg total protein from PC-3 (Prostate Cancer) cells were immunoprecipitated and immunoblotted with the antibody as indicated. FIG. 49C) Left Panel, Coimmunoprecipitation studies were done in different conditions to document AEG-1 and MDA-9/Syntenin interaction in the membrane. Right panel, co-IP studies to document AEG-1 and EGFR interaction in the membrane fraction. FIG. 49D), immunofluorescence studies in non-permeabilized cells to document co-localization of AEG-1, MDA-9/Syntenin and EGFR in the membrane.

FIG. 52. Left panel, Docked structure of compound 113B7 on the surface of MDA-9/Syntenin. The docked structure is supported by NMR chemical shift mapping data. The titration (see later in FIG. 55 for chemical shift mapping and titration) allows for the calculation of an upper limit for the dissociation constant of the complex, Kd<10 µM. Of note is that 113B7 does not bind appreciably to PDZ2 from MDA-9/Syntenin or other PDZs used as counter screens as can be seen in the right panel spectra. The [$^{15}$N,$^1$FI]-HSQC spectra of MDA-9/Syntenin PDZ2 only domain are reported in the top right panel (apo at 20 µM; in presence of 100 µM 113B7). In the bottom right panel can be seen the spectra of the PDZ domain from X11/mint scaffold protein (33% identity with PDZ1) are reported in absence (20 µM protein) and in presence of 100 µM 113B7. No appreciable binding is detected in both cases.

FIG. 55A. Schematic illustration of the proposed approach to derive a PDZ focused library against PDZs. After identification of an initial binding element, a diversity element scaffold will be identified by the second-site screening using the SAR by ILOEs approach. Elements of the resulting hi-dentate libraries will be tested against the given target. FIG. 55B. Application of the approach to targeting the PDZ1 domain of MDA-9/Syntenin, led to compounds 112G4 ($K_d$~300 µM) and 3D11 ($K_d$~500 µM). Chemical shift mapping studies. ILOE based second site screening revealed compound 3D11 ($K_d$ in the millimolar range). Chemical shift mapping data and docked structure for 3D11 are reported. The bi-dentate compound and its docked geometry (note that the structure is rotated by 90 degrees around the horizontal axis) are shown on the right panel. FIG. 55C. Overlays of HSQC spectra of PDZ12 of MDA-9/Syntenin in presence of the increasing amounts bi-dentate 113B7 ($K_d$ in low micromolar range). FIG. 55D. Synthetic scheme for the generation of the PDZ focused library based on the identified scaffolds. The structure of hit compound 113B7 and titration data are reported ($K_d$ in low micromolar range).

DETAILED DESCRIPTION

Figure 1A:
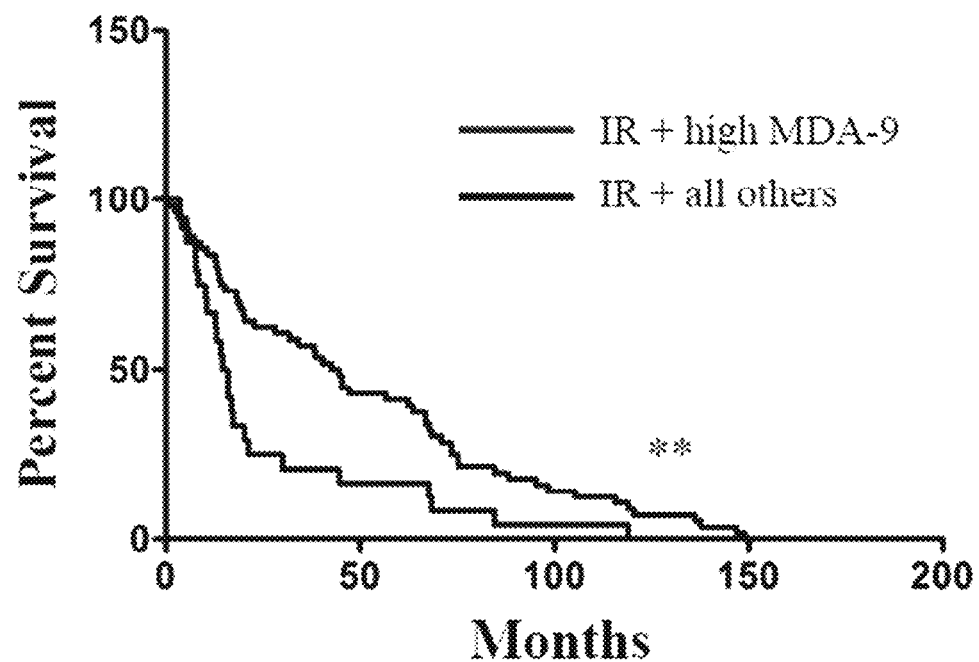
FIGS. 1A-1C. MDA-9/Syntenin is involved in radiosensitivity.

MDA-9 is a scaffold protein that plays a key role in tumor progression and metastasis in cancer. MDA-9 can effect tumor progression and metastasis through protein-protein interactions. For example, in breast cancer MDA-9 interacts with TGFβ1 to facilitate epithelial mesenchymal transition (EMT), a key step in the processes of metastatsis. MDA-9 protein-protein interactions can occur through binding of a MDA-9 PDZ domain (i.e., PDZ1 domain) to a downstream target (e.g., TGFβ1, c-Src, FAK, STAT3, IGF-R1, etc.) in the MDA-9 signaling pathway.

There are an estimated 150 PDZ domain-containing proteins that are involved in cancer and associated with important physiological processes in transformed cells. Targeting the PDZ domain to develop specific and effective small molecule inhibitors has historically proven difficult. However, as described herein, specific and effective PDZ1 domain binders which target the PDZ1 domain of MDA-9/Syntenin, thereby inhibiting MDA-9 protein-protein interactions, have been developed for use in cancer treatment.

I. Definitions

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., C$_1$-C$_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form (CH$_2$)v, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. In embodiments, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkyl is attached to the parent molecular moiety through any carbon atom contained within the monocyclic cycloalkyl ring. In embodiments, cycloalkyl groups are optionally substituted with one or two groups which are independently oxo or thia. In embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkyl is attached to the parent molecular moiety through any carbon atom contained within the base ring. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic cycloalkenyls include, but are not limited to, norbornenyl and bicyclo[2.2.2]oct 2 enyl. In embodiments, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkenyl is attached to the parent molecular moiety through any carbon atom contained within the monocyclic cycloalkenyl ring. In embodiments, cycloalkenyl groups are optionally substituted with one or two groups which are independently oxo or thia. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3 dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. In embodiments, heterocyclyl groups are optionally substituted with one or two groups which are independently oxo or thia. In certain embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring.

In embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl.

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$. A heteroalkyl moiety may include one heteroatom (e.g., O, N, S, Si, or P).

A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring.

The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "⟿" denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

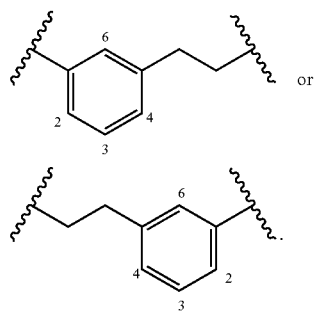

An alkylarylene moiety may be substituted (e.g. with a substituent group) on the alkylene moiety or the arylene linker (e.g. at carbons 2, 3, 4, or 6) with halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$CH$_3$— SO$_3$H, —OSO$_3$H, —SO$_2$NH$_2$, —NHNH$_2$, —ONH$_2$, —NHC(O)NHNH$_2$, substituted or unsubstituted C$_1$-C$_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$-U-, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$-B-, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo,
halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl, heteroalkyl, cycloalkyl, heterocycloalkyl, aryl, heteroaryl, substituted with at least one substituent selected from:
(i) oxo,
halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and
(ii) alkyl, heteroalkyl, cycloalkyl, heterocycloalkyl, aryl, heteroaryl, substituted with at least one substituent selected from:
(a) oxo,
halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, ☐NHNH$_2$, ☐ONH$_2$, ☐NHC(O)NHNH$_2$, ☐NHC(O)NH$_2$, —NHSO$_2$H, —NHC(O)H, —NHC(O)OH, —NHOH, —OCCl$_3$, —OCF$_3$, —OCBr$_3$, —OCI$_3$, —O CHCl$_2$, —OCHBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl, heteroalkyl, cycloalkyl, heterocycloalkyl, aryl, heteroaryl, substituted with at least one substituent selected from: oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OC HBr$_2$, —OCHI$_2$, —OCHF$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or"size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted C$_1$-C$_{20}$ alkylene, each substituted or unsubstituted heteroalkylene is a substituted or unsubstituted 2 to 20 membered heteroalkylene, each substituted or unsubstituted cycloalkylene is a substituted or unsubstituted C$_3$-C$_8$ cycloalkylene, each substituted or unsubstituted heterocycloalkylene is a substituted or unsubstituted 3 to 8 membered heterocycloalkylene, each substituted or unsubstituted arylene is a substituted or unsubstituted C$_6$-C$_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted C$_1$-C$_8$ alkylene, each substituted or unsubstituted heteroalkylene is a substituted or unsubstituted 2 to 8 membered heteroalkylene, each substituted or unsubstituted cycloalkylene is a substituted or unsubstituted C$_3$-C$_7$ cycloalkylene, each substituted or unsubstituted heterocycloalkylene is a substituted or unsubstituted 3 to 7 membered heterocycloalkylene, each substituted or unsubstituted arylene is a substituted or unsubstituted C$_6$-C$_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another. For example, formula I may be written as

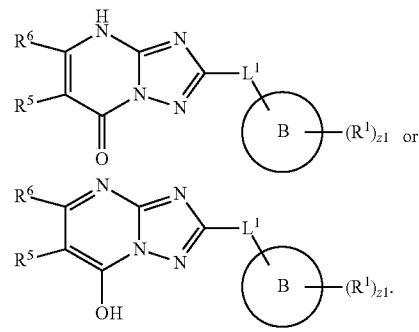

Additionally, any formula or compound described herein may be written as either isomeric (e.g. tautomeric) form.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{s3}$ and optionally differently.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, N.Y. 1989). Any methods, devices and materials similar or equivalent to those described herein can be used in the practice of this invention. The following definitions are provided to facilitate understanding of certain terms used frequently herein and are not meant to limit the scope of the present disclosure.

As may be used herein, the terms "nucleic acid," "nucleic acid molecule," "nucleic acid oligomer," "oligonucleotide," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

The term "phosphorothioate nucleic acid" refers to a nucleic acid in which one or more internucleotide linkages are through a phosphorothioate moiety (thiophosphate) moiety. The phosphorothioate moiety may be a monothiophosphate (—P(O)₃(S)³⁻—) or a dithiophosphate (—P(O)₂(S)₂³⁻—). In embodiments of all the aspects provided herein, the phosphorothioate moiety is a monothiophosphate (—P(O)₃(S)³⁻—). That is, in embodiments of all the aspects provided herein, the phosphorothioate nucleic acid is a monothiophosphate nucleic acid. In embodiments, one or more of the nucleosides of a phosphorothioate nucleic acid are linked through a phosphorothioate moiety (e.g. monothiophosphate) moiety, and the remaining nucleosides are linked through a phosphodiester moiety (—P(O)₄³⁻—). In embodiments, one or more of the nucleosides of a phosphorothioate nucleic acid are linked through a phosphorothioate moiety (e.g. monothiophosphate) moiety, and the remaining nucleosides are linked through a methylphosphonate linkage. In embodiments, all the nucleosides of a phosphorothioate nucleic acid are linked through a phosphorothioate moiety (e.g. a monothiophosphate) moiety.

Phosphorothioate oligonucleotides (phosphorothioate nucleic acids) are typically from about 5, 6, 7, 8, 9, 10, 12, 15, 25, 30, 40, 50 or more nucleotides in length, up to about 100 nucleotides in length. Phosphorothioate nucleic acids may also be longer in lengths, e.g., 200, 300, 500, 1000, 2000, 3000, 5000, 7000, 10,000, etc. As described above, in certain embodiments, the phosphorothioate nucleic acids herein contain one or more phosphodiester bonds. In other embodiments, the phosphorothioate nucleic acids include alternate backbones (e.g., mimics or analogs of phosphodiesters as known in the art, such as, boranophosphate, methylphosphonate, phosphoramidate, or O-methylphosphoroamidite linkages (see Eckstein, Oligonucleotides and Analogues: A Practical Approach, Oxford University Press). The phosphorothioate nucleic acids may also include one or more nucleic acid analog monomers known in the art, such as, peptide nucleic acid monomer or polymer, locked nucleic acid monomer or polymer, morpholino monomer or polymer, glycol nucleic acid monomer or polymer, or threose nucleic acid monomer or polymer. Other analog nucleic acids include those with positive backbones; non-ionic backbones, and nonribose backbones, including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. Phosphorothioate nucleic acids and phosphorothioate polymer backbones can be linear or branched. For example, the branched nucleic acids are repetitively branched to form higher ordered structures such as dendrimers and the like.

As used herein, a "phosphorothioate polymer backbone" is a chemical polymer with at least two phosphorothioate linkages (e.g. monothiophosphate) (e.g. linking together sugar subunits, cyclic subunits or alkyl subunits). The phosphorothioate polymer backbone may be a phosphorothioate sugar polymer, which is a phosphorothioate nucleic acid in which one or more (or all) of the chain of pentose sugars lack the bases (nucleobases) normally present in a nucleic acid. The phosphorothioate polymer backbone can include two or more phosphorothioate linkages. The phosphorothioate polymer backbone can include 5, 6, 7, 8, 9, 10, 12, 15, 25, 30, 40, 50 or more linkages and can contain up to about 100 phosphorothioate linkages. Phosphorothioate polymer backbones may also contain a larger number of linkages, e.g., 200, 300, 500, 1000, 2000, 3000, 5000, 7000, 10,000, and the like.

The phosphorothioate nucleic acids and phophorothioate polymer backbones may be partially or completely phosphorothioated. For example, 50% or more of the interneucleotide linkages of a phosphorothioate nucleic acid can be phosphorothioate linkages. Optionally, 5%, 10%, 15%, 20%, 25%, 30%, 35%, 40%/0, 45%, 50%, 55%, 60%, 65%, 70%, 75%, 80%, 85%, 90%, 95%, or 99% of the internucleotide linkages of a phosphorothioate nucleic acid are phosphorothioate linkages. Optionally, 50%, 55%, 60%, 65%, 70%, 75%, 80%, 85%, 90%, 95%, or 99% of the internucleotide linkages of a phosphorothioate nucleic acid are phosphorothioate linkages. Optionally, 75%, 80%, 85%, 90%, 95%, or 99% of the internucleotide linkages of a phosphorothioate nucleic acid are phosphorothioate linkages. Optionally, 90%, 95%, or 99% of the internucleotide linkages of a phosphorothioate nucleic acid are phosphorothioate linkages. In embodiments, the remaining internucleotide linkages are phosphodiester linkages. In embodiments, the remaining internucleotide linkages are methylphosphonate linkages. Optionally, 100% of the internucleotide linkages of the phosphorothioate nucleic acids are phosphorothioate linkages. Similarly, 5%, 10%, 15%, 20%, 25%, 30%, 35%, 40%, 45%, 50%, 55%, 60%, 65%, 70%, 75%, 80%, 85%, 90%, 95%, or 99%, of the intersugar linkages in a phosphorothioate polymer backbone can be phosphorothioate linkages. Optionally, 50%, 55%, 60%, 65%, 70%, 75%, 80%, 85%, 90%, 95%, or 99%, of the intersugar linkages in a phosphorothioate polymer backbone can be phosphorothioate linkages. Optionally, 75%, 80%, 85%, 90%, 95%, or 99%, of the intersugar linkages in a phosphorothioate polymer backbone can be phosphorothioate linkages. Optionally, 90%, 95%, or 99%, of the intersugar linkages in a phosphorothioate polymer backbone can be phosphorothioate linkages. In embodiments, the remaining internucleotide linkages are phosphodiester linkages. In embodiments, the remaining internucleotide linkages are methylphosphonate linkages. Optionally, 100% of the intersugar linkages of the phosphorothioate polymer backbone are phosphorothioate linkages.

Optionally, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 99% of the internucleotide linkages of a phosphorothioate nucleic acid are phosphorothioate linkages. Optionally, about 50%, about 55%, about 60%, about 65%, about 70%, about 75%, about 80%, about 85%, about 90%, about 95%, or about 99% of the internucleotide linkages of a phosphorothioate nucleic acid are phosphorothioate linkages. Optionally, about 75%, about 80%, about 85%, about 90%, about 95%, or about 99% of the internucleotide linkages of a phosphorothioate nucleic acid are phosphorothioate linkages. Optionally, about 90%, about 95%, or about 99% of the internucleotide linkages of a phosphorothioate nucleic acid are phosphorothioate linkages. In embodiments, the remaining internucleotide linkages are phosphodiester linkages. In embodiments, the remaining internucleotide linkages are methylphosphonate linkages. Optionally, about 100% of the internucleotide linkages of the phosphorothioate nucleic acids are phosphorothioate linkages. Similarly, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 99%, of the intersugar linkages in a phosphorothioate polymer backbone can be phosphorothioate linkages. Optionally, about 50%, about 55%, about 60%, about 65%, about 70%, about 75%, about 80%, about 85%, about 90%, about 95%, or about 99%, of the intersugar linkages in a phosphorothioate polymer backbone can be phosphorothioate linkages. Optionally, about 75%, about 80%, about 85%, about 90%, about 95%, or about 99%, of the intersugar linkages in a phosphorothioate polymer backbone can be phosphorothioate linkages. Optionally, about 90%, about 95%, or about 99%, of the intersugar linkages in a phosphorothioate polymer backbone can be phosphorothioate linkages. In embodiments, the remaining internucleotide linkages are phosphodiester linkages. In embodiments, the remaining internucleotide linkages are methylphosphonate linkages. Optionally, about 100% of the intersugar linkages of the phosphorothioate polymer backbone are phosphorothioate linkages.

The term "aptamer" as provided herein refers to oligonucleotides (e.g. short oligonucleotides or deoxyribonucleotides), that bind (e.g. with high affinity and specificity) to proteins, peptides, and small molecules. Aptamers may have secondary or tertiary structure and, thus, may be able to fold into diverse and intricate molecular structures. Aptamers can be selected in vitro from very large libraries of randomized sequences by the process of systemic evolution of ligands by exponential enrichment (SELEX as described in Ellington A D, Szostak J W (1990) In vitro selection of RNA molecules that bind specific ligands. Nature 346:818-822; Tuerk C, Gold L (1990) Systematic evolution of ligands by exponential enrichment: RNA ligands to bacteriophage T4 DNA polymerase. Science 249:505-510) or by developing SOMAmers (slow off-rate modified aptamers) (Gold L et al. (2010) Aptamer-based multiplexed proteomic technology for biomarker discovery. PLoS ONE 5(12):e15004). Applying the SELEX and the SOMAmer technology includes for instance adding functional groups that mimic amino acid side chains to expand the aptamer's chemical diversity. As a result high affinity aptamers for almost any protein target are enriched and identified. Aptamers exhibit many desirable properties for targeted drug delivery, such as ease of selection and synthesis, high binding affinity and specificity, low immunogenicity, and versatile synthetic accessibility. To date, a variety of anti-cancer agents (e.g. chemotherapy drugs, toxins, and siRNAs) have been successfully delivered to cancer cells in vitro using apatmers.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell. The level of expression of non-coding nucleic acid molecules (e.g., microRNA) may be detected by standard PCR or Northern blot methods well known in the art. See, Sambrook et al., 1989 *Molecular Cloning: A Laboratory Manual,* 18.1-18.88.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues, wherein the polymer may In embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure.

The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross-reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

An amino acid residue in a protein "corresponds" to a given residue when it occupies the same essential structural position within the protein as the given residue. For example, a selected residue in a selected protein corresponds to, for example, glutamine at position 110 of a human MDA-9 protein when the selected residue occupies the same essential spatial or other structural relationship as a glutamine at position 110 in human MDA-9 protein. In some embodiments, where a selected protein is aligned for maximum homology with the human MDA-9 protein, the position in the aligned selected protein aligning with glutamine 110 is said to correspond to glutamine 110. Instead of a primary sequence alignment, a three dimensional structural alignment can also be used, e.g., where the structure of the selected protein is aligned for maximum correspondence with the human MDA-9 protein and the overall structures compared. In this case, an amino acid that occupies the same essential position as glutamine 110 in the structural model is said to correspond to the glutamine 110 residue.

A "cell" as used herein, refers to a cell carrying out metabolic or other functions sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., spodoptera) and human cells. Cells may be useful when they are naturally nonadherent or have been treated not to adhere to surfaces, for example by trypsinization.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody plays a significant role in determining the specificity and affinity of binding. In some embodiments, antibodies or fragments of antibodies may be derived from different organisms, including humans, mice, rats, hamsters, camels, etc. Antibodies of the invention may include antibodies that have been modified or mutated at one or more amino acid positions to improve or modulate a desired function of the antibody (e.g. glycosylation, expression, antigen recognition, effector functions, antigen binding, specificity, etc.).

Antibodies are large, complex molecules (molecular weight of ~150,000 or about 1320 amino acids) with intricate internal structure. A natural antibody molecule contains two identical pairs of polypeptide chains, each pair having one light chain and one heavy chain. Each light chain and heavy chain in turn consists of two regions: a variable ("V") region involved in binding the target antigen, and a constant ("C") region that interacts with other components of the immune system. The light and heavy chain variable regions come together in 3-dimensional space to form a variable region that binds the antigen (for example, a receptor on the surface of a cell). Within each light or heavy chain variable region, there are three short segments (averaging 10 amino acids in length) called the complementarity determining regions ("CDRs"). The six CDRs in an antibody variable domain (three from the light chain and three from the heavy chain) fold up together in 3-dimensional space to form the actual antibody binding site which docks onto the target antigen. The position and length of the CDRs have been precisely defined by Kabat, E. et al., Sequences of Proteins of Immunological Interest, U.S. Department of Health and Human Services, 1983, 1987. The part of a variable region not contained in the CDRs is called the framework ("FR"), which forms the environment for the CDRs.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) or light chain variable region and variable heavy chain (VH) or heavy chain variable region refer to these light and heavy chain regions, respectively. The terms variable light chain (VL) and light chain variable region as referred to herein may be used interchangeably. The terms variable heavy chain (VH) and heavy chain variable region as referred to herein may be used interchangeably. The Fc (i.e. fragment crystallizable region) is the "base" or "tail" of an immunoglobulin and is typically composed of two heavy chains that contribute two or three constant domains depending on the class of the antibody. By binding to specific proteins the Fc region ensures that each antibody generates an appropriate immune response for a given antigen. The Fc region also binds to various cell receptors, such as Fc receptors, and other immune molecules, such as complement proteins.

The term "antigen" as provided herein refers to molecules capable of binding to the antibody region provided herein, wherein the binding site is not the peptide binding site.

Antibodies exist, for example, as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region, thereby converting the F(ab)'2 dimer into an Fab' monomer. The Fab' monomer is essentially the antigen binding portion with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

A single-chain variable fragment (scFv) is typically a fusion protein of the variable regions of the heavy (VH) and light chains (VL) of immunoglobulins, connected with a short linker peptide of 10 to about 25 amino acids. The linker may usually be rich in glycine for flexibility, as well as serine or threonine for solubility. The linker can either connect the N-terminus of the VH with the C-terminus of the VL, or vice versa.

The epitope of a mAb is the region of its antigen to which the mAb binds. Two antibodies bind to the same or overlapping epitope if each competitively inhibits (blocks) binding of the other to the antigen. That is, a 1x, 5x, 10x, 20x or 100x excess of one antibody inhibits binding of the other by at least 30% but preferably 50%, 75%, 90% or even 99% as measured in a competitive binding assay (see, e.g., Junghans et al., Cancer Res. 50:1495, 1990). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

For preparation of suitable antibodies of the invention and for use according to the invention, e.g., recombinant, monoclonal, or polyclonal antibodies, many techniques known in the art can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy, Alan R. Liss, Inc. (1985); Coligan, Current Protocols in Immunology (1991); Harlow & Lane, Antibodies, A Laboratory Manual (1988); and Goding, Monoclonal Antibodies: Principles and Practice (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, Immunology (3rd ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633, 425; 5,661,016, Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); and Lonberg & Huszar, Intern. Rev. Immunol. 13:65-93 (1995)). Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)). Antibodies can also be made bispecific, i.e., able to recognize two different antigens (see, e.g., WO 93/08829, Traunecker et al., EMBO J. 10:3655-3659 (1991); and Suresh et al., Methods in Enzymology 121:210 (1986)). Antibodies can also be heteroconjugates, e.g., two covalently joined antibodies, or immunotoxins (see, e.g., U.S. Pat. No. 4,676, 980, WO 91/00360; WO 92/200373; and EP 03089).

Methods for humanizing or primatizing non-human antibodies are well known in the art (e.g., U.S. Pat. Nos. 4,816,567; 5,530,101; 5,859,205; 5,585,089; 5,693,761; 5,693,762; 5,777,085; 6,180,370; 6,210,671; and 6,329,511; WO 87/02671; EP Patent Application 0173494; Jones et al. (1986) Nature 321:522; and Verhoyen et al. (1988) Science 239:1534). Humanized antibodies are further described in, e.g., Winter and Milstein (1991) Nature 349:293. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Morrison et al., PNAS USA, 81:6851-6855 (1984), Jones et al., Nature 321:522-525 (1986); Riechmann et al., Nature 332:323-327 (1988); Morrison and Oi, Adv. Immunol., 44:65-92 (1988), Verhoeyen et al., Science 239:1534-1536 (1988) and Presta, Curr. Op. Struct. Biol. 2:593-596 (1992), Padlan, Molec. Immun., 28:489-498 (1991); Padlan, Molec. Immun., 31(3):169-217 (1994)), by substituting rodent CDRs or CDR sequences for the corresponding sequences of a human antibody. Accordingly, such humanized antibodies are chimeric antibodies (U.S. Pat. No. 4,816, 567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies. For example, polynucleotides comprising a first sequence coding for humanized immunoglobulin framework regions and a second sequence set coding for the desired immunoglobulin complementarity determining regions can be produced synthetically or by combining appropriate cDNA and genomic DNA segments. Human constant region DNA sequences can be isolated in accordance with well known procedures from a variety of human cells.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of; and for use according to the invention include humanized and/or chimeric monoclonal antibodies.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions typically requires an antibody that is selected for its specificity for a particular protein. For example, polyclonal antibodies can be selected to obtain only a subset of antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity).

A "ligand" refers to an agent, e.g., a polypeptide or other molecule, capable of binding to a receptor or target polypeptide (e.g, PDZ1 domain).

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be, for example, a PDZ1 domain binder (e.g., small molecule, antibody, aptamer, ligand, or compound as described herein and a polypeptide provided herein (e.g., MDA-9 (e.g, PDZ1 domain)). In embodiments, contacting includes, for example, allowing a PDZ1 domain binder as described herein, including embodiments thereof, to interact with a PDZ1 domain of a MDA-9 protein.

As defined herein, the term "inhibition", "inhibit", "inhibiting" and the like in reference to a protein-binder (e.g., PDZ1 domain binder) interaction means negatively affecting (e.g. decreasing) the activity or function of the protein (e.g., MDA-9) relative to the activity or function of the protein in the absence of the binder. In embodiments, inhibition means negatively affecting (e.g. decreasing) the concentration or levels of the protein relative to the concentration or level of the protein in the absence of the binder. In embodiments, inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation). A "PDZ1 domain binder" is a compound that negatively affects (e.g. decreases) the activity or function of MDA-9 relative to the activity or function of MDA-9 in the absence of the PDZ1 domain binder by binding to the PDZ1 domain of the MDA-9 protein. A decrease in MDA-9 activity may result in changes in the signaling pathway downstream of MDA-9. For example, MDA-9 inhibition by a PDZ1 domain binder may decrease activation, activity, expression, or stability of TGFβ1, p38 MAPK, NF-κB, STAT3, IGF-R1, AEG-1, JNK, EGFR, AKT, phohoinositide 3-kinase, FAK, and/or c-Src.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components. For example, binding of a MDA-9 protein with a compound as described herein (e.g., PDZ1 domain binder) may reduce the level of a product of the MDA-9 catalyzed reaction or the level of a downstream derivatives of the product or binding may reduce the interactions between MDA-9 or an MDA-9 reaction product and downstream effectors or signaling pathway components, resulting in changes in cell growth, proliferation, metastasis, or survival.

As defined herein, the term "activation", "activate", "activating" and the like in reference to a protein refers to conversion of a protein into a biologically active derivative from an initial inactive or deactivated state. The terms reference activation, or activating, sensitizing, or up-regulating signal transduction or enzymatic activity or the amount of a protein decreased in a disease.

The terms "agonist," "activator," "upregulator," etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist.

The terms "inhibitor," "repressor" or "antagonist" or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist.

The terms "MDA-9," "Syntenin," "MDA-9/Syntenin," or "SDCBP" refer to a protein (including homologs, isoforms, and functional fragments thereof) with MDA-9 activity. The term includes any recombinant or naturally-occurring form of MDA-9 variants thereof that maintain MDA-9 activity (e.g. within at least 30%, 40%, 50%, 60%, 70%, 80%, 90%, 95%, or 100% activity compared to wildtype MDA-9). In embodiments, the MDA-9 protein encoded by the SDCBP gene has the amino acid sequence set forth in or corresponding to Entrez 6386, UniProt 000560, or RefSeq (protein) NP_001007068.1. In embodiments, the SDCBP gene has the nucleic acid sequence set forth in RefSeq (mRNA) NM_001007067.1. In embodiments, the amino acid sequence or nucleic acid sequence is the sequence known at the time of filing of the present application. In embodiments, the MDA-9 protein includes the sequence of SEQ ID NO: 1.

The term "PDZ domain" as referred to herein refers to a common structural domain typically including 80-90 amino acids. PDZ domains are common to scaffold and signaling proteins and play an important role in signal transduction complexes. PDZ domains of a protein can facilitate protein-protein interactions by binding target proteins. MDA-9 proteins include two tandem PDZ domains, PDZ1 and PDZ2, respectively, separated by a sequence of amino acids linking the two domains. The amino acid sequence linking the PDZ1 and PDZ2 domains is referred to herein as an "interface region.". In embodiments, the amino acid sequence of PDZ1 includes the sequence of SEQ ID NO:1. In embodiments, the amino acid sequence of PDZ1 is the sequence of SEQ ID NO:1.

"Biological sample" or "sample" refer to materials obtained from or derived from a subject or patient. A biological sample includes sections of tissues such as biopsy and autopsy samples, and frozen sections taken for histological purposes. Such samples include bodily fluids such as blood and blood fractions or products (e.g., serum, plasma, platelets, red blood cells, and the like), sputum, tissue, cultured cells (e.g., primary cultures, explants, and transformed cells) stool, urine, synovial fluid, joint tissue, synovial tissue, synoviocytes, fibroblast-like synoviocytes, macrophage-like synoviocytes, immune cells, hematopoietic cells, fibroblasts, macrophages, T cells, etc. A biological sample is typically obtained from a eukaryotic organism, such as a mammal such as a primate e.g., chimpanzee or human; cow; dog; cat; a rodent, e.g., guinea pig, rat, mouse; rabbit; or a bird; reptile; or fish.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

"Patient" or "subject in need thereof" refers to a living organism suffering from or prone to a disease or condition that can be treated by administration of a compound, composition, or pharmaceutical composition as provided herein. Non-limiting examples include humans, other mammals, bovines, rats, mice, dogs, monkeys, goat, sheep, cows, deer, and other non-mammalian animals. In some embodiments, a patient is human.

The terms "disease" or "condition" refer to a state of being or health status of a patient or subject capable of being treated with a compound, pharmaceutical composition, or method provided herein. In embodiments, the disease is cancer (e.g. melanoma, glioblastoma, head and neck cancer, urothelial cancer, breast cancer, uveal melanoma, gastric cancer, lung adenocarcinoma, hepatocellular carcinoma, colorectal cancer, prostate cancer, pancreatic cancer, or neuroblastoma).

The terms "treating", or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, include prevention of an injury, pathology, condition, or disease. In embodiments, "treating" refers to treatment of cancer. In embodiments, "treating" refers to treatment of infectious disease. In embodiments, "treating" refers to treatment of neurodegenerative disease. In embodiments, "treating" refers to treatment of inflammatory disease.

In embodiments, treatment or treating includes (1) inhibiting a disease in a subject or patient experiencing or displaying the pathology or symptomatology of cancer (e.g., arresting further development of the pathology and/or symptomatology), (2) ameliorating a disease in a subject or patient that is experiencing or displaying the pathology or symptomatology of cancer (e.g., reversing the pathology and/or symptomatology), and/or (3) effecting any measurable decrease in a disease in a subject or patient that is experiencing or displaying the pathology or symptomatology of cancer. In embodiments, the subject treated as described herein may also fully recover from cancer and may become cancer-free as a result of the present methods.

In embodiments, treating cancer refers to at least ameliorating and/or decreasing and/or eradicating aspects of the disease such as the following: the size of a tumor may be lessened and/or the tumor may be completely destroyed; remnants of a tumor (e.g. after surgery) may be lessened and/or destroyed; the growth of a tumor may be prevented and/or the growth rate may be slowed; the metastatic potential of a tumor may be decreased or eliminated; cancer cells may be sensitized to radiation therapy, etc. For example, when cancer cells are exposed to a compound or drug described herein prior to, during or after radiation therapy, they are more susceptible to killing by radiation, e.g. at least about 25% more of the cancer cells die without dividing, and typically at least about 50, 75 or even 100% of the cells die without dividing, compared to the number that die when exposed to radiation alone. In addition, in embodiments, select changes which typically occur in cancer cells when exposed to radiation are decreased or eliminated when a compound or drug described herein is administered to a subject receiving radiotherapy. For example, cancer cells frequently exhibit an increased ability to grow, divide, and/or metastasize after radiation therapy, and administration of the present drugs (e.g., compound described herein) attenuates or eliminates this ability. In embodiments, the treatment of cancer metastasis includes the treatment of at least one of invasion, migration, and angiogenesis.

A "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." For example, for a given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control. A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist or inhibitor (e.g., PDZ1 domain binder) required to disrupt the function of an enzyme or protein (e.g., MDA-9) relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present disclosure, should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent.

"Co-administer" it is meant that a composition described herein is administered at the same time, just prior to, or just after the administration of one or more additional therapies. The compounds provided herein can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present disclosure can be delivered transdermally, by a topical route, or formulated as applicator sticks, solutions, suspensions, emulsions, gels, creams, ointments, pastes, jellies, paints, powders, and aerosols.

As used herein, the term "cancer" refers to all types of cancer, neoplasm or malignant tumors found in mammals, including leukemias, lymphomas, melanomas, neuroendocrine tumors, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, herceptin resistant, HER2 positive, doxombicin resistant, tamoxifen resistant, ductal carcinoma, lobular carcinoma, primary, metastatic), ovarian cancer, pancreatic cancer, liver cancer (e.g., hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma. Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, pre-invasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

As used herein, the terms "metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

In embodiments, a patient who is treated by the compounds described herein, including embodiments thereof (e.g., as pure drugs, salts, or prodrugs), and methods disclosed herein suffers from cancer. Examples of cancer that may be so treated include but are not limited to: adrenal cortical cancer, anal cancer, bile duct cancer (e.g. peripheral cancer, distal bile duct cancer, intrahepatic bile duct cancer), bladder cancer, bone cancer (e.g. osteoblastoma, osteochrondroma, hemangioma, chondromyxoid fibroma, osteosarcoma, chondrosarcoma, fibrosarcoma, malignant fibrous histiocytoma, giant cell tumor of the bone, chordoma, lymphoma, multiple myeloma), brain and central nervous system cancer (e.g. meningioma, astocytoma, oligodendrogliomas, ependymoma, glioma, glioblastoma, medulloblastoma, ganglioglioma, Schwannoma, germinoma, craniopharyngioma), breast cancer (e.g. ductal carcinoma in situ, infiltrating ductal carcinoma, infiltrating lobular carcinoma, lobular carcinoma in situ, gynecomastia), Castleman disease (e.g. giant lymph node hyperplasia, angiofollicular lymph node hyperplasia), cervical cancer, colorectal cancer, endometrial cancer (e.g. endometrial adenocarcinoma, adenocanthoma, papillary serous adnocarcinoma, clear cell), esophagus cancer, gallbladder cancer (mucinous adenocarcinoma, small cell carcinoma), gastrointestinal carcinoid tumors (e.g. choriocarcinoma, chorioadenoma destruens), Hodgkin's disease, non-Hodgkin's lymphoma, Kaposi's sarcoma, kidney cancer (e.g. renal cell cancer), laryngeal and hypopharyngeal cancer, liver cancer (e.g. hemangioma, hepatic adenoma, focal nodular hyperplasia, hepatocellular carcinoma), lung cancer (e.g. small cell lung cancer, non-small cell lung cancer), mesothelioma, plasmacytoma, nasal cavity and paranasal sinus cancer (e.g. esthesioneuroblastoma, midline granuloma), nasopharyngeal cancer, neuroblastoma, oral cavity and oropharyngeal cancer, ovarian cancer, pancreatic cancer, penile cancer, pituitary cancer, prostate cancer, retinoblastoma, rhabdomyosarcoma (e.g. embryonal rhabdomyosarcoma, alveolar rhabdomyosarcoma, pleomorphic rhabdomyosarcoma), salivary gland cancer, skin cancer (e.g. melanoma, nonmelanoma skin cancer), stomach cancer, testicular cancer (e.g. seminoma, nonseminoma germ cell cancer), thymus cancer, thyroid cancer (e.g. follicular carcinoma, anaplastic carcinoma, poorly differentiated carcinoma, medullary thyroid carcinoma, thyroid lymphoma), urothelial cell cancer, vaginal cancer, vulvar cancer, and uterine cancer (e.g. uterine leiomyosarcoma). Generally, the cancer is characterized by the presence of at least one solid tumor.

The term "associated" or "associated with" in the context of a substance or substance activity or function associated with a disease (e.g., cancer (e.g. melanoma, glioblastoma, head and neck cancer, urothelial cancer, breast cancer, uveal melanoma, gastric cancer, lung adenocarcinoma, hepatocellular carcinoma, colorectal cancer, prostate cancer, pancreatic cancer, or neuroblastoma) means that the disease (e.g. melanoma, glioblastoma, head and neck cancer, urothelial cancer, breast cancer, uveal melanoma, gastric cancer, lung adenocarcinoma, hepatocellular carcinoma, colorectal cancer, prostate cancer, pancreatic cancer, or neuroblastoma) is caused by (in whole or in part), or a symptom of the disease is caused by (in whole or in part) the substance or substance activity or function.

"Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. In embodiments, an anti-cancer agent is a chemotherapeutic. In embodiments, an anti-cancer agent is an agent identified herein having utility in methods of treating cancer. In embodiments, an anti-cancer agent is an agent approved by the FDA or similar regulatory agency of a country other than the USA, for treating cancer.

The compositions described herein can be used in combination with one another, with other active agents known to be useful in treating a cancer such as anti-cancer agents.

Examples of anti-cancer agents include, but are not limited to, radiation, MEK (e.g. MEK1, MEK2, or MEK1 and MEK2) inhibitors (e.g. XL518, CI-1040, PD035901, selumetinib/AZD6244, GSK 1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor, mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator, protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor, retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor, urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer, carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rIL.sub.2), interferon alfa-2a; interferon alfa-2b; interferon alfa-n1; interferon alfa-n3; interferon beta-la; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur, teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), Cryptophycin 52 (i.e. LY-355703), Vitilevuamide, Tubulysin A, Canadensol, Centaureidin (i.e. NSC-106969), Oncocidin A1 (i.e. BTO-956 and DIME), Fijianolide B, Laulimalide, Narcosine (also known as NSC-5366), Nascapine, Vanadocene acetylacetonate, T-138026 (Tularik), Monsatrol, Inanocine (i.e. NSC-698666), Eleutherobins (such as Desmethyleleutherobin, Desaetyleleutherobin, lso-eleutherobin A, and Z-Eleutherobin), Caribaeoside, Caribaeolin, Halichondrin B, Diazonamide A, Taccalonolide A, Diozostatin, (−)-Phenylahistin (i.e. NSCL-96F037), Myoseverin B, Resverastatin phosphate sodium, steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), 5-FU, MCL-1 inhibitor, sorafenib, imatinib, sunitinib, dasatinib, or the like. In embodiments, the compositions herein may be used in combination with adjunctive agents that may not be effective alone, but may contribute to the efficacy of the active agent in treating cancer.

"Chemotherapeutic" or "chemotherapeutic agent" is used in accordance with its plain ordinary meaning and refers to a chemical composition or compound having antineoplastic properties or the ability to inhibit the growth or proliferation of cells.

As used herein, the term "inflammatory disease" refers to a disease or condition characterized by aberrant inflammation (e.g. an increased level of inflammation compared to a control such as a healthy person not suffering from a disease). Examples of inflammatory diseases include traumatic brain injury, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, asthma, allergic asthma, acne vulgaris, celiac disease, chronic prostatitis, inflammatory bowel disease, pelvic inflammatory disease, reperfusion injury, sarcoidosis, transplant rejection, interstitial cystitis, atherosclerosis, and atopic dermatitis. In embodiments, the inflammatory disease is asthma. In embodiments, the disease associated with elevated expression of mda-9 is an inflammatory disease.

As used herein, the term "neurodegenerative disorder" or "neurodegenerative disease" refers to a disease or condition in which the function of a subject's nervous system becomes impaired. Examples of neurodegenerative diseases that may be treated with a compound, pharmaceutical composition, or method described herein include Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, chronic fatigue syndrome, Cockayne syndrome, Corticobasal degeneration, Creutzfeldt-Jakob disease, frontotemporal dementia, Gerstmann-Sträussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, myalgic encephalomyelitis, Narcolepsy, Neuroborreliosis, Parkinson's disease, Pelizaeus-Merzbacher Disease, Pick's disease, Primary lateral sclerosis, Prion diseases, Refsum's disease, Sandhoffs disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, progressive supranuclear palsy, or Tabes dorsalis.

The term "infection" or "infectious disease" refers to a disease or condition that can be caused by organisms such as a bacterium, virus, fungi or any other pathogenic microbial agents. In embodiments, the infectious diseases is a viral infection (e.g., HIV, SARS, HPV, influenza), or bacterial colonization in the human gastrointestinal tract (e.g., pathenogenic bacterial colonization). In embodiments, the infectious disease is associated with elevated expression of mda-9. In embodiments, the infectious disease is characterized by the presence of virus shedding (e.g., HIV viral shedding or Herpes viral shedding). In embodiments, the infectious disease is a bacterial infection. In embodiments, the infectious disease is a gram-positive bacterial infection. In embodiments, the infectious disease is a *Staphylococcus aureus* infection. In embodiments, the infectious disease is Gram-positive or Gram-negative bacterial infection. In embodiments, the infectious disease is an infection associated with *S. aureus, E. facium, E. faecalis, K. pneumonoiaea, H. influenzaea*, or *P. aeruginosa*. In embodiments, the infectious disease is a *S. aureus, E. facium, E. faecalis, K. pneumonoiaea, H. influenzaea*, or *P. aeruginosa* infection.

II. Compounds

In an aspect is provided a compound, or pharmaceutically acceptable salt thereof, having the formula:

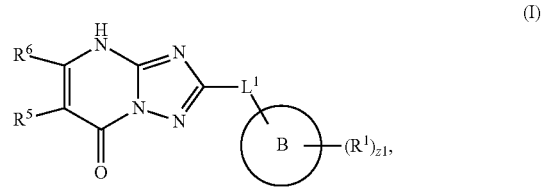

(I)

or a tautomer thereof.

Ring B is a cycloalkyl, heterocycloalkyl, aryl, or heteroaryl.

$R^1$ is independently halogen, $-CX^1_3$, $-CHX^1_2$, $-CH_2X^1$, $-OCX^1_3$, $-OCH_2X^1$, $-OCHX^1_2$, $-CN$, $-SO_{n1}R^{1D}$, $-SO_{v1}NR^{1A}R^{1B}$, $-NHC(O)NR^{1A}R^{1B}$, $-N(O)_{m1}$, $-NR^{1A}R^{1B}$, $-C(O)R^{1C}$, $-C(O)-OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl.

$L^1$ is a bond, $-S(O)_2-$, $-N(R^3)-$, $-O-$, $-S-$, $-C(O)-$, $-C(O)N(R^3)-$, $-N(R^3)C(O)-$, $-N(R^3)C(O)NH-$, $-NHC(O)N(R^3)-$, $-S(O)_2N(R^3)-$, $-N(R^3)S(O)_2-$, $-C(O)S(O)_2N(R^3)-$, $-N(R^3)S(O)_2C(O)-$, $-C(O)O-$, $-OC(O)-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

$R^3$ is independently hydrogen, $-CX^3_3$, $-CHX^3_2$, $-CH_2X^3$, $-CN$, $-C(O)R^{3C}$, $-C(O)OR^{3C}$, $-C(O)NR^{3A}R^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^5$ is independently hydrogen, halogen, $-CX^5_3$, $-CHX^5_2$, $-CH_2X^5$, $-OCX^5_3$, $-OCH_2X^5$, $-OCHX^5_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)$ $NH_2$, $-NHSO_2H$, $-NHC=(O)H$, $-NHC(O)-OH$, $-NHOH$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^6$ is independently hydrogen, halogen, $-CX^6_3$, $-CHX^6_2$, $-CH_2X^6$, $-OCX^6_3$, $-OCH_2X^6$, $-OCHX^6_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^5$ and $R^6$ substituents may optionally be joined to form a substituted or unsubstituted cycloalkyl, substituted or unsubstituted heterocycloalkyl, substituted or unsubstituted aryl, or substituted or unsubstituted heteroaryl.

$R^{1A}$, $R^{1B}$, $R^{1C}$, $R^{1D}$, $R^{3A}$, $R^{3B}$, and $R^{3C}$ are independently hydrogen, $-CX_3$, $-CN$, $-COOH$, $-CONH_2$, $-CHX_2$, $-CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{1A}$ and $R^{1B}$ substituents bonded to the same nitrogen atom may optionally be joined to form a substituted or unsubstituted heterocycloalkyl or substituted or unsubstituted heteroaryl. $R^{3A}$ and $R^{3B}$ substituents bonded to the same nitrogen atom may optionally be joined to form a substituted or unsubstituted heterocycloalkyl or substituted or unsubstituted heteroaryl.

X, $X^1$, $X^3$, $X^5$, and $X^6$ are independently $-F$, $-Cl$, $-Br$, or $-I$. The symbol n1 is an integer from 0 to 4. The symbols m1 and v1 are independently 1 or 2. The symbol z1 is an integer from 0 to 5.

In embodiments, Ring B is a ($C_3$-$C_{10}$) cycloalkyl, a 3 to 10 membered heterocycloalkyl, a ($C_6$-$C_{10}$) aryl, or a 5 to 10 membered heteroaryl. In embodiments, Ring B is a cycloalkyl (e.g., $C_3$-$C_8$ cycloalkyl, $C_3$-$C_6$ cycloalkyl, or $C_5$-$C_6$ cycloalkyl). In embodiments, Ring B is a $C_3$-$C_8$ cycloalkyl. In embodiments, Ring B is a $C_3$-$C_6$ cycloalkyl. In embodiments, Ring B is a $C_5$-$C_6$ cycloalkyl. In embodiments, Ring B is a $C_6$ cycloalkyl. In embodiments, Ring B is a $C_5$ cycloalkyl. In embodiments, Ring B is a ($C_6$-$C_{10}$) aryl. In embodiments, Ring B is phenyl. In embodiments, Ring B is naphthyl. In embodiments, Ring B is aziridinyl, oxiranyl, thiiranyl, azetidinyl, oxetanyl, thietanyl, pyrrolidinyl, pyrrolyl, imidazolyl, imidazolinyl, pyrazolinyl, tetrahydrofuranyl, thiolanyl, piperidinyl, piperazinyl, pyranyl, morpholinyl, 1,4-dioxanyl, tetrahydro-2H-pyranyl, thianyl, or dithianyl. In embodiments, Ring B is a phenyl, thiofuranyl, imidazolyl, pyrazolyl, triazolyl, tetrazolyl, furanyl, oxazolyl, isooxazolyl, oxadiazolyl, oxatriazolyl, thienyl, thiazolyl, isothiazolyl, pyridinyl, pyrazinyl, pyrimidinyl, pyridazinyl, or triazinyl (e.g., 1,3,5-triazinyl, 1,2,3-triazinyl, or 1,2,4-triazinyl). In embodiments, Ring B is indolyl, benzimidazolyl, indazolyl, benzotriazolyl, pyrrolopyrimidinyl, purinyl, indolizinyl, pyrrolopyriazinyl, pyrrolopyrimidinyl, imidazopyridazinyl, imidazopyridinyl, imidazopyrimidinyl, cinnolinyl, quinazolinyl, quinoxalinyl, phthalazinyl, pyridopyrazinyl, pteridinyl, pyrazolopyridinyl, quinolinyl, isoquinolinyl, naphthyridinyl, or carbazolyl. In embodiments, Ring B is

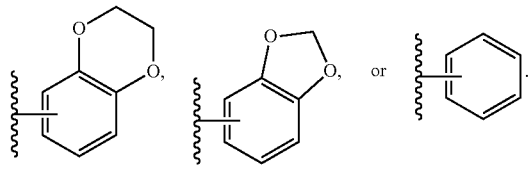

In embodiments, $R^5$ is hydrogen, halogen, unsubstituted methyl, unsubstituted ethyl, unsubstituted propyl (e.g., unsubstituted n-propyl or unsubstituted isopropyl). In embodiments, $R^5$ is a substituted or unsubstituted $C_1$-$C_6$ alkyl. In embodiments, $R^5$ is substituted (e.g., substituted with a substituent group, a size-limited substituent group, or lower substituent group) or unsubstituted alkyl. In embodiments, $R^5$ is substituted (e.g., substituted with a substituent group, a size-limited substituent group, or lower substituent group) alkyl. In embodiments, $R^5$ is unsubstituted alkyl. In embodiments, $R^5$ is substituted or unsubstituted alkyl (e.g., $C_1$-$C_8$, $C_1$-$C_6$, $C_1$-$C_4$, or $C_1$-$C_2$). In embodiments, $R^5$ is substituted alkyl (e.g., $C_1$-$C_8$, $C_1$-$C_6$, $C_1$-$C_4$, or $C_1$-$C_2$). In embodiments, $R^5$ is unsubstituted alkyl (e.g., $C_1$-$C_8$, $C_1$-$C_6$, $C_1$-$C_4$, or $C_1$-$C_2$).

In embodiments, $R^5$ is independently unsubstituted methyl, unsubstituted ethyl, unsubstituted isopropyl, or unsubstituted tert-butyl. In embodiments, $R^5$ is independently unsubstituted methyl. In embodiments, $R^5$ is independently unsubstituted ethyl. In embodiments, $R^5$ is independently unsubstituted propyl. In embodiments, $R^5$ is independently unsubstituted n-propyl. In embodiments, $R^5$ is independently unsubstituted isopropyl. In embodiments, $R^5$ is independently unsubstituted butyl. In embodiments, $R^5$ is independently unsubstituted n-butyl. In embodiments, $R^5$ is independently unsubstituted isobutyl. In embodiments, $R^5$ is independently unsubstituted tert-butyl. In embodiments, $R^5$ is independently unsubstituted pentyl. In embodiments, $R^5$ is independently unsubstituted hexyl. In embodiments, $R^5$ is independently unsubstituted heptyl. In embodiments, $R^5$ is independently unsubstituted octyl.

In embodiments, $R^5$ is substituted (e.g., substituted with a substituent group, a size-limited substituent group, or lower substituent group) or unsubstituted heteroalkyl. In embodiments, $R^5$ is substituted (e.g., substituted with a substituent group, a size-limited substituent group, or lower substituent group) heteroalkyl. In embodiments, $R^5$ is unsubstituted heteroalkyl. In embodiments, $R^5$ is substituted or unsubstituted heteroalkyl (e.g., 2 to 8 membered, 2 to 6 membered, 4 to 6 membered, 2 to 3 membered, or 4 to 5 membered). In embodiments, $R^5$ is substituted heteroalkyl (e.g., 2 to 8 membered, 2 to 6 membered, 4 to 6 membered, 2 to 3 membered, or 4 to 5 membered). In embodiments, $R^5$ is an unsubstituted heteroalkyl (e.g., 2 to 8 membered, 2 to 6 membered, 4 to 6 membered, 2 to 3 membered, or 4 to 5 membered).

In embodiments, $R^6$ is hydrogen, halogen, unsubstituted methyl, unsubstituted ethyl, unsubstituted propyl (e.g., unsubstituted n-propyl or unsubstituted isopropyl). In embodiments, $R^6$ is a substituted or unsubstituted $C_1$-$C_6$ alkyl. In embodiments, $R^6$ is substituted (e.g., substituted with a substituent group, a size-limited substituent group, or lower substituent group) or unsubstituted alkyl. In embodiments, $R^6$ is substituted (e.g., substituted with a substituent group, a size-limited substituent group, or lower substituent group) alkyl. In embodiments, $R^6$ is unsubstituted alkyl. In embodiments, $R^6$ is substituted or unsubstituted alkyl (e.g., $C_1$-$C_8$, $C_1$-$C_6$, $C_1$-$C_4$, or $C_1$-$C_2$). In embodiments, $R^6$ is substituted alkyl (e.g., $C_1$-$C_8$, $C_1$-$C_6$, $C_1$-$C_4$, or $C_1$-$C_2$). In embodiments, $R^6$ is unsubstituted alkyl (e.g., $C_1$-$C_8$, $C_1$-$C_6$, $C_1$-$C_4$, or $C_1$-$C_2$).

In embodiments, $R^6$ is substituted (e.g., substituted with a substituent group, a size-limited substituent group, or lower substituent group) or unsubstituted heteroalkyl. In embodiments, $R^6$ is substituted (e.g., substituted with a substituent group, a size-limited substituent group, or lower substituent group) heteroalkyl. In embodiments, $R^6$ is unsubstituted heteroalkyl. In embodiments, $R^6$ is substituted or unsubstituted heteroalkyl (e.g., 2 to 8 membered, 2 to 6 membered, 4 to 6 membered, 2 to 3 membered, or 4 to 5 membered). In embodiments, $R^6$ is substituted heteroalkyl (e.g., 2 to 8 membered, 2 to 6 membered, 4 to 6 membered, 2 to 3 membered, or 4 to 5 membered). In embodiments, $R^6$ is an unsubstituted heteroalkyl (e.g., 2 to 8 membered, 2 to 6 membered, 4 to 6 membered, 2 to 3 membered, or 4 to 5 membered).

In embodiments, $R^6$ is independently unsubstituted methyl, unsubstituted ethyl, unsubstituted isopropyl, or unsubstituted tert-butyl. In embodiments, $R^6$ is independently unsubstituted methyl. In embodiments, $R^6$ is independently unsubstituted ethyl. In embodiments, $R^6$ is independently unsubstituted propyl. In embodiments, $R^6$ is independently unsubstituted n-propyl. In embodiments, $R^6$ is independently unsubstituted isopropyl. In embodiments, $R^6$ is independently unsubstituted butyl. In embodiments, $R^6$ is independently unsubstituted n-butyl. In embodiments, $R^6$ is independently unsubstituted isobutyl. In embodiments, $R^6$ is independently unsubstituted tert-butyl. In embodiments, $R^6$ is independently unsubstituted pentyl. In embodiments, $R^6$ is independently unsubstituted hexyl. In embodiments, $R^6$ is independently unsubstituted heptyl. In embodiments, $R^6$ is independently unsubstituted octyl.

In embodiments, $R^5$ and $R^6$ are joined to form a substituted or unsubstituted cyclopropyl, substituted or unsubstituted cyclopentyl, or substituted or unsubstituted cyclohexyl. In embodiments, $R^5$ and $R^6$ are joined to form a substituted cyclopropyl, substituted cyclobutyl, substituted cyclopentyl, or substituted cyclohexyl. In embodiments, $R^5$ and $R^6$ are joined to form an unsubstituted cyclopropyl, unsubstituted cyclobutyl, an unsubstituted cyclopentyl, or an unsubstituted cyclohexyl. In embodiments, $R^5$ and $R^6$ are joined to form a substituted cyclopropyl, substituted cyclopentyl, or substituted cyclohexyl.

In embodiments, $R^5$ and $R^6$ are joined to form an unsubstituted cyclopropyl, an unsubstituted cyclopentyl, or an unsubstituted cyclohexyl.

In embodiments, $R^5$ and $R^6$ are joined to form a substituted or unsubstituted cycloalkyl (e.g., $C_3$-$C_8$, $C_3$-$C_6$, $C_4$-$C_6$, or $C_5$-$C_6$). In embodiments, $R^5$ and $R^6$ are joined to form a substituted (e.g., substituted with a substituent group, a size-limited substituent group, or lower substituent group) or unsubstituted cycloalkyl (e.g., $C_3$-$C_8$, $C_3$-$C_6$, $C_4$-$C_6$, or $C_5$-$C_6$). In embodiments, $R^5$ and $R^6$ are joined to form a substituted (e.g., substituted with a substituent group, a size-limited substituent group, or lower substituent group) cycloalkyl (e.g., $C_3$-$C_8$, $C_3$-$C_6$, $C_4$-$C_6$, or $C_5$-$C_6$). In embodiments, $R^5$ and $R^6$ are joined to form an unsubstituted cycloalkyl (e.g., $C_3$-$C_8$, $C_3$-$C_6$, $C_4$-$C_6$, or $C_5$-$C_6$).

In embodiments, $R^5$ and $R^6$ are joined to form a substituted (e.g., substituted with a substituent group, a size-limited substituent group, or lower substituent group) or unsubstituted heterocycloalkyl (e.g., 3 to 8 membered, 3 to 6 membered, 4 to 6 membered, 4 to 5 membered, or 5 to 6 membered). In embodiments, $R^5$ and $R^6$ are joined to form a substituted (e.g., substituted with a substituent group, a size-limited substituent group, or lower substituent group) heterocycloalkyl (e.g., 3 to 8 membered, 3 to 6 membered, 4 to 6 membered, 4 to 5 membered, or 5 to 6 membered). In embodiments, $R^5$ and $R^6$ are joined to form an unsubstituted heterocycloalkyl (e.g., 3 to 8 membered, 3 to 6 membered, 4 to 6 membered, 4 to 5 membered, or 5 to 6 membered).

In embodiments, two adjacent $R^1$ substituents are joined to form a substituted or unsubstituted ($C_3$-$C_{10}$) cycloalkyl, substituted or unsubstituted 3 to 10 membered heterocycloalkyl, substituted or unsubstituted ($C_6$-$C_{10}$) aryl, or substituted or unsubstituted 5 to 10 membered heteroaryl.

In embodiments, two adjacent $R^1$ substituents are joined to form a substituted or unsubstituted aziridinyl, substituted or unsubstituted oxiranyl, substituted or unsubstituted thiiranyl, substituted or unsubstituted azetidinyl, substituted or unsubstituted oxetanyl, substituted or unsubstituted thietanyl, substituted or unsubstituted pyrrolidinyl, substituted or unsubstituted pyrrolyl, substituted or unsubstituted imidazolyl, substituted or unsubstituted imidazolinyl, substituted or unsubstituted pyrazolinyl, substituted or unsubstituted tetrahydrofuranyl, substituted or unsubstituted thiolanyl, substituted or unsubstituted piperidinyl, substituted or unsubstituted piperazinyl, substituted or unsubstituted pyranyl, substituted or unsubstituted morpholinyl, substituted or unsubstituted 1,4-dioxanyl, substituted or unsubstituted tetrahydro-2H-pyranyl, substituted or unsubstituted thianyl, or substituted or unsubstituted dithianyl. In embodiments, two adjacent $R^1$ substituents are joined to form a substituted aziridinyl, substituted oxiranyl, substituted thiiranyl, substituted azetidinyl, substituted oxetanyl, substituted thietanyl, substituted pyrrolidinyl, substituted pyrrolyl, substituted imidazolyl, substituted imidazolinyl, substituted pyrazolinyl, substituted tetrahydrofuranyl, substituted thiolanyl, substituted piperidinyl, substituted piperazinyl, substituted pyranyl, substituted morpholinyl, substituted 1,4-dioxanyl, substituted tetrahydro-2H-pyranyl, substituted thianyl, or substituted dithianyl. In embodiments, two adjacent $R^1$ substituents are joined to form an unsubstituted aziridinyl, unsubstituted oxiranyl, unsubstituted thiiranyl, unsubstituted azetidinyl, unsubstituted oxetanyl, unsubstituted thietanyl, unsubstituted pyrrolidinyl, unsubstituted pyrrolyl, unsubstituted imidazolyl, unsubstituted imidazolinyl, unsubstituted pyrazolinyl, unsubstituted tetrahydrofuranyl, unsubstituted thiolanyl, unsubstituted piperidinyl, unsubstituted piperazinyl, unsubstituted pyranyl, unsubstituted morpholinyl, unsubstituted 1,4-dioxanyl, unsubstituted tetrahydro-2H-pyranyl, unsubstituted thianyl, or unsubstituted dithianyl.

In an aspect is provided a compound, or pharmaceutically acceptable salt thereof, having the formula:

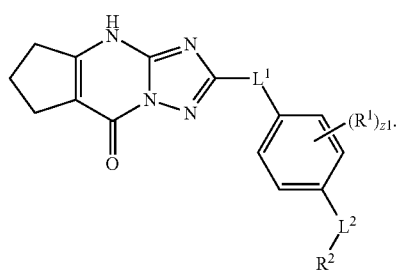

(II)

$R^1$ is independently halogen, —$CX^1_3$, —$CHX^1_2$, —$CH_2X^1$, —$OCX^1_3$, —$OCH_2X^1$, —$OCHX^1_2$, —CN, —$SO_{n1}R^{1D}$, —$SO_{v1}NR^{1A}R^{1B}$, —$NHC(O)NR^{1A}R^{1B}$, —N(O)$_{m1}$, —NR$^{1A}$R$^{1B}$, —C(O)R$^{1C}$, —C(O)—OR$^{1C}$, —C(O)NR$^{1A}$R$^{1B}$, —OR$^{1D}$, —NR$^{1A}$SO$_2$R$^{1D}$, —NR$^{1A}$C(O) R$^{1C}$, —NR$^{1A}$C(O)O R$^{1C}$, —NR$^{1A}$OR$^{1C}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent R$^1$ substituents may optionally be joined to form a substituted or unsubstituted cycloalkyl, substituted or unsubstituted heterocycloalkyl, substituted or unsubstituted aryl, or substituted or unsubstituted heteroaryl.

R$^2$ is independently hydrogen, halogen, —CX$^2_3$, —CHX$^2_2$, —CH$_2$X$^2$, —OCX$^2_3$, —OCH$_2$X$^2$, —OCHX$^2_2$, —CN, —SO$_{n2}$R$^{2D}$, —SO$_{v2}$NR$^{2A}$R$^{2B}$, —NHC(O)NR$^{2A}$R$^{2B}$, —N(O)$_{m2}$, —NR$^{2A}$R$^{2B}$, —C(O)R$^{2C}$, —C(O)—OR$^{2C}$, —C(O)NR$^{2A}$R$^{2B}$, —OR$^{2D}$, —NR$^{2A}$SO$_2$R$^{2D}$, —NR$^{2A}$C(O) R$^{2C}$, —NR$^{2A}$C(O)O R$^{2C}$, —NR$^{2A}$OR$^{2C}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

L$^1$ is a bond, —S(O)$_2$—, —N(R$^3$)—, —O—, —S—, —C(O)—, —C(O)N(R$^3$)—, —N(R$^3$)C(O)—, —N(R$^3$)C(O)NH—, —NHC(O)N(R$^3$)—, —S(O)$_2$N(R$^3$)—, N(R$^3$)S(O)$_2$—, —C(O)S(O)$_2$N(R$^3$)—, —N(R$^3$)S(O)$_2$C(O)—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

R$^3$ is independently hydrogen, —CX$^3_3$, —CHX$^3_2$, —CH$_2$X$^3$, —CN, —C(O)R$^3$, —C(O)OR$^{3C}$, —C(O)NR$^{3A}$R$^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

L$^2$ is a bond, —S(O)$_2$—, —N(R$^4$)—, —O—, —S—, —C(O)—, —C(O)N(R$^4$)—, —N(R$^4$)C(O)—, —N(R$^4$)C(O)NH—, —NHC(O)N(R$^4$)—, —S(O)$_2$N(R$^4$)—, N(R$^4$)S(O)$_2$—, —C(O)S(O)$_2$N(R$^4$)—, —N(R$^4$)S(O)$_2$C(O)—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

R$^4$ is independently hydrogen, —CX$^4_3$, —CHX$^4_2$, —CH$_2$X$^4$, —CN, —C(O)R$^{4C}$, —C(O)OR$^{4C}$, —C(O)NR$^{4A}$R$^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{4A}$, R$^{4B}$, and R$^{4C}$ are independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{1A}$ and R$^{1B}$ substituents bonded to the same nitrogen atom may optionally be joined to form a substituted or unsubstituted heterocycloalkyl or substituted or unsubstituted heteroaryl. R$^{2A}$ and R$^{2B}$ substituents bonded to the same nitrogen atom may optionally be joined to form a substituted or unsubstituted heterocycloalkyl or substituted or unsubstituted heteroaryl. R$^{3A}$ and R$^{3B}$ substituents bonded to the same nitrogen atom may optionally be joined to form a substituted or unsubstituted heterocycloalkyl or substituted or unsubstituted heteroaryl. R$^{4A}$ and R$^{4B}$ substituents bonded to the same nitrogen atom may optionally be joined to form a substituted or unsubstituted heterocycloalkyl or substituted or unsubstituted heteroaryl.

X, X$^1$, X$^2$, X$^3$, and X$^4$ are independently —F, —Cl, —Br, or —I. The symbols n1 and n2 are independently an integer from 0 to 4. The symbols m1, m2, v1, and v2 are independently 1 or 2. The symbol z1 is an integer from 0 to 4.

In embodiments, R$^1$ is independently halogen, —CX$^1_3$, —CHX$^1_2$, —CH$_2$X$^1$, —OCX$^1_3$, —OCH$_2$X$^1$, —OCHX$^1_2$, —CN, —SO$_{n1}$R$^{1D}$, —SO$_{v1}$NR$^{1A}$R$^{1B}$, —NHC(O)NR$^{1A}$R$^{1B}$, —N(O)$_{m1}$, —NR$^{1A}$R$^{1B}$, —C(O)R$^{1C}$, —C(O)—OR$^{1C}$, —C(O)NR$^{1A}$R$^{1B}$, —OR$^{1D}$, —NR$^{1A}$SO$_2$R$^{1D}$, —NR$^{1A}$C(O) R$^{1C}$, —NR$^{1A}$C(O)O R$^{1C}$, —NR$^{1A}$OR$^{1C}$, —N$_3$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{10}$ or phenyl), or substituted or unsubstituted heteroaryl (e.g., 5 to 10 membered, 5 to 9 membered, or 5 to 6 membered).

In embodiments, R$^1$ is independently halogen, —CX$^1_3$, —CN, —OH, —NH$_2$, —SH, —OCX$^1_3$, —OCHX$^1_2$, —OCH$_2$X$^1$, —CHX$^1_2$, —CH$_2$X$^1$, substituted or unsubstituted C$_1$-C$_4$ alkyl, substituted or unsubstituted 2 to 4 membered heteroalkyl, substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroaryl. In embodiments, R$^1$ is independently halogen, —CX$^1_3$, —CN, —OR$^{2D}$, —NH$_2$, —SH, —OCX$^1_3$, —OCHX$^1_2$, —OCH$_2$X$^1$, —CHX$^1_2$, —CH$_2$X$^1$, unsubstituted C$_1$-C$_4$ alkyl, or unsubstituted 2 to 4 membered heteroalkyl.

In embodiments, R$^1$ is independently halogen, —CX$^1_3$, —CHX$^1_2$, —CH$_2$X$^1$, —OCX$^1_3$, —OR$^{2D}$, —CN, —NR$^{1A}$R$^{1B}$, substituted or unsubstituted alkyl or two adjacent R$^1$ substituents may optionally be joined to form a substituted or unsubstituted cycloalkyl, substituted or unsubstituted heterocycloalkyl, substituted or unsubstituted aryl, or substituted or unsubstituted heteroaryl. In embodiments, R$^1$ is independently halogen, —CX$^1_3$, —CHX$^1_2$, —CH$_2$X$^1$, —OCX$^1_3$, —OR$^{2D}$, —CN, —NR$^{1A}$R$^{1B}$, or substituted or unsubstituted alkyl.

In embodiments, R$^1$ is independently, halogen, —CX$^1_3$, —CHX$^1_2$, —CH$_2$X$^1$, —OCX$^1_3$, —OCH$_2$X$^1$, —OCHX$^1_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC═(O)NHNH$_2$, —NHC—(O) NH$_2$, —NHSO$_2$H, —NHC═(O)H, —NHC(O)—OH, —NHOH, —N$_3$, R$^{20}$-substituted or unsubstituted alkyl (e.g., C$_1$-C$_8$, C$_1$-C$_6$, C$_1$-C$_4$, or C$_1$-C$_2$), R$^{20}$-substituted or unsubstituted heteroalkyl (e.g., 2 to 8 membered, 2 to 6 membered, 4 to 6 membered, 2 to 3 membered, or 4 to 5 membered), R$^{20}$-substituted or unsubstituted cycloalkyl (e.g., C$_3$-C$_8$, C$_3$-C$_6$, C$_4$-C$_6$, or C$_5$-C$_6$), R$^{20}$-substituted or unsubstituted heterocycloalkyl (e.g., 3 to 8 membered, 3 to 6 membered, 4 to 6 membered, 4 to 5 membered, or 5 to 6 membered), R$^{20}$-substituted or unsubstituted aryl (e.g., C$_6$-C$_0$ or phenyl), or R$^{20}$-substituted or unsubstituted heteroaryl (e.g., 5 to 10 membered, 5 to 9 membered, or 5 to 6 membered). In embodiments, $R^1$ is independently hydrogen, halogen, —$CX^1_3$, —$CHX^1_2$, —$CH_2X^1$, —$OCX^1_3$, —$OCH_2X^1$, —$OCHX^1_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^1$ is independently —F, —Cl, —Br, or —I.

In embodiments, $R^1$ is independently hydrogen, halogen, —$NR^{1A}R^{1B}$, —$OR^{1D}$, or substituted or unsubstituted heteroaryl. In embodiments, $R^1$ is substituted or unsubstituted aryl. In embodiments, $R^1$ is substituted or unsubstituted phenyl. In embodiments, $R^1$ is hydrogen. In embodiments, $R^1$ is halogen. In embodiments, $R^1$ is —$NR^{1A}R^{1B}$. In embodiments, $R^1$ is —$OR^{1D}$. In embodiments, $R^1$ is substituted or unsubstituted heteroaryl. In embodiments, $R^1$ is substituted heteroaryl. In embodiments, $R^1$ is substituted 5 to 6 membered heteroaryl. In embodiments, $R^1$ is —$NH_2$. In embodiments, $R^1$ is —OH. In embodiments, $R^1$ is —Cl. In embodiments, $R^1$ is —F. In embodiments, $R^1$ is halogen.

In embodiments, $R^1$ is $R^{20}$-substituted or unsubstituted alkyl or $R^{20}$-substituted or unsubstituted heteroalkyl. In embodiments, $R^1$ is independently $R^{20}$-substituted methyl. In embodiments, $R^1$ is independently $R^{20}$-substituted ethyl. In embodiments, $R^1$ is independently unsubstituted methyl. In embodiments, $R^1$ is independently unsubstituted ethyl. In embodiments, $R^1$ is independently halogen, —$OR^{2D}$, or —$CH_3$. In embodiments, $R^1$ is halogen. In embodiments, $R^1$ is —$CH_3$. In embodiments, $R^1$ is —$OR^{2D}$. In embodiments, $R^1$ is —OH.

In embodiments, $R^1$ is $R^{20}$-substituted or unsubstituted alkyl (e.g., $C_1$-$C_8$ alkyl, $C_1$-$C_6$ alkyl, or $C_1$-$C_4$ alkyl). In embodiments, $R^1$ is $R^{20}$-substituted alkyl (e.g., $C_1$-$C_8$ alkyl, $C_1$-$C_6$ alkyl, or $C_1$-$C_4$ alkyl). In embodiments, $R^1$ is an unsubstituted alkyl (e.g., $C_1$-$C_8$ alkyl, $C_1$-$C_6$ alkyl, or $C_1$-$C_4$ alkyl). In embodiments, $R^1$ is $R^{20}$-substituted or unsubstituted heteroalkyl (e.g., 2 to 8 membered heteroalkyl, 2 to 6 membered heteroalkyl, or 2 to 4 membered heteroalkyl). In embodiments, $R^1$ is $R^{20}$-substituted heteroalkyl (e.g., 2 to 8 membered heteroalkyl, 2 to 6 membered heteroalkyl, or 2 to 4 membered heteroalkyl). In embodiments, $R^1$ is an unsubstituted heteroalkyl (e.g., 2 to 8 membered heteroalkyl, 2 to 6 membered heteroalkyl, or 2 to 4 membered heteroalkyl). In embodiments, $R^1$ is $R^{20}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^1$ is $R^{20}$-substituted cycloalkyl (e.g., $C_3$-$C_8$ cycloalkyl, $C_3$-$C_6$ cycloalkyl, or $C_5$-$C_6$ cycloalkyl). In embodiments, $R^1$ is an unsubstituted cycloalkyl (e.g., $C_3$-$C_8$ cycloalkyl, $C_3$-$C_6$ cycloalkyl, or $C_5$-$C_6$ cycloalkyl). In embodiments, $R^1$ is $R^{20}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^1$ is $R^{20}$-substituted heterocycloalkyl (e.g., 3 to 8 membered heterocycloalkyl, 3 to 6 membered heterocycloalkyl, or 5 to 6 membered heterocycloalkyl). In embodiments, $R^1$ is an unsubstituted heterocycloalkyl (e.g., 3 to 8 membered heterocycloalkyl, 3 to 6 membered heterocycloalkyl, or 5 to 6 membered heterocycloalkyl). In embodiments, $R^1$ is $R^{20}$-substituted or unsubstituted aryl (e.g., $C_6$-$C_{10}$ aryl, $C_{10}$ aryl, or phenyl). In embodiments, $R^1$ is $R^{20}$-substituted aryl (e.g., $C_6$-$C_{10}$ aryl, $C_{10}$ aryl, or phenyl). In embodiments, $R^1$ is an unsubstituted aryl (e.g., $C_6$-$C_{10}$ aryl, $C_{10}$ aryl, or phenyl). In embodiments, $R^1$ is $R^{20}$-substituted or unsubstituted heteroaryl (e.g., 5 to 10 membered heteroaryl, 5 to 9 membered heteroaryl, or 5 to 6 membered heteroaryl). In embodiments, $R^1$ is $R^{20}$-substituted heteroaryl (e.g., 5 to 10 membered heteroaryl, 5 to 9 membered heteroaryl, or 5 to 6 membered heteroaryl). In embodiments, $R^1$ is an unsubstituted heteroaryl (e.g., 5 to 10 membered heteroaryl, 5 to 9 membered heteroaryl, or 5 to 6 membered heteroaryl).

In embodiments, $R^1$ is $R^{20}$-substituted or unsubstituted methyl. In embodiments, $R^1$ is $R^{20}$-substituted or unsubstituted $C_2$ alkyl. In embodiments, $R^1$ is $R^{20}$-substituted or unsubstituted $C_3$ alkyl. In embodiments, $R^1$ is $R^{20}$-substituted or unsubstituted $C_4$ alkyl. In embodiments, $R^1$ is $R^{20}$-substituted or unsubstituted $C_5$ alkyl. In embodiments, $R^1$ is $R^{20}$-substituted or unsubstituted $C_6$ alkyl. In embodiments, $R^1$ is $R^{20}$-substituted or unsubstituted $C_7$ alkyl. In embodiments, $R^1$ is $R^{20}$-substituted or unsubstituted $C_6$ alkyl. In embodiments, $R^1$ is $R^{20}$-substituted methyl. In embodiments, $R^1$ is $R^{20}$-substituted $C_2$ alkyl. In embodiments, $R^1$ is $R^{20}$-substituted $C_3$ alkyl. In embodiments, $R^1$ is $R^{20}$-substituted $C_4$ alkyl. In embodiments, $R^1$ is $R^{20}$-substituted $C_5$ alkyl. In embodiments, $R^1$ is $R^{20}$-substituted $C_6$ alkyl. In embodiments, $R^1$ is $R^{20}$-substituted $C_7$ alkyl. In embodiments, $R^1$ is $R^{20}$-substituted $C_6$ alkyl. In embodiments, $R^1$ is an unsubstituted methyl. In embodiments, $R^1$ is an unsubstituted $C_2$ alkyl. In embodiments, $R^1$ is an unsubstituted $C_3$ alkyl. In embodiments, $R^1$ is an unsubstituted $C_4$ alkyl. In embodiments, $R^1$ is an unsubstituted $C_5$ alkyl. In embodiments, $R^1$ is an unsubstituted $C_6$ alkyl. In embodiments, $R^1$ is an unsubstituted $C_7$ alkyl. In embodiments, $R^1$ is an unsubstituted $C_8$ alkyl.

$R^{20}$ is independently oxo, halogen, —$CX^{20}_3$, —$CHX^{20}_2$, —$CH_2X^{20}$, —$OCX^{20}_3$, —$OCH_2X^{20}$, —$OCHX^{20}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, $R^{21}$-substituted or unsubstituted alkyl (e.g., $C_1$-$C_8$, $C_1$-$C_6$, $C_1$-$C_4$, or $C_1$-$C_2$), $R^{21}$-substituted or unsubstituted heteroalkyl (e.g., 2 to 8 membered, 2 to 6 membered, 4 to 6 membered, 2 to 3 membered, or 4 to 5 membered), $R^{21}$-substituted or unsubstituted cycloalkyl (e.g., $C_3$-$C_8$, $C_3$-$C_6$, $C_4$-$C_6$, or $C_5$-$C_6$), $R^{21}$-substituted or unsubstituted heterocycloalkyl (e.g., 3 to 8 membered, 3 to 6 membered, 4 to 6 membered, 4 to 5 membered, or 5 to 6 membered), $R^{21}$-substituted or unsubstituted aryl (e.g., $C_6$-$C_0$ or phenyl), or $R^{21}$-substituted or unsubstituted heteroaryl (e.g., 5 to 10 membered, 5 to 9 membered, or 5 to 6 membered). In embodiments, $R^{20}$ is independently oxo, halogen, —$CX^{20}_3$, —$CHX^{20}_2$, —$CH_2X^{20}$, —$OCX^{20}_3$, —$OCH_2X^{20}$, —$OCHX^{20}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{20}$ is independently —F, —Cl, —Br, or —I.

In embodiments, $R^{20}$ is $R^{21}$-substituted or unsubstituted alkyl or $R^{21}$-substituted or unsubstituted heteroalkyl. In embodiments, $R^{20}$ is independently $R^{21}$-substituted methyl. In embodiments, $R^{20}$ is $R^{21}$-substituted ethyl. In embodiments, $R^{20}$ is independently unsubstituted methyl. In embodiments, $R^{20}$ is independently unsubstituted ethyl.

$R^{21}$ is independently oxo, halogen, —$CX^{21}_3$, —$CHX^{21}_2$, —$CH_2X^{21}$, —$OCX^{21}_3$, —$OCH_2X^{21}$, —$OCHX^{21}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, $R^{22}$-substituted or unsubstituted alkyl (e.g., $C_1$-$C_8$, $C_1$-$C_6$, $C_1$-$C_4$, or $C_1$-$C_2$), $R^{22}$-substituted or unsubstituted heteroalkyl (e.g., 2 to 8 membered, 2 to 6 membered, 4 to 6 membered, 2 to 3 membered, or 4 to 5 membered), $R^{22}$-substituted or unsubstituted cycloalkyl (e.g., $C_3$-$C_8$, $C_3$-$C_6$, $C_4$-$C_6$, or $C_5$-$C_6$), $R^{22}$-substituted or unsubstituted heterocycloalkyl (e.g., 3 to 8 membered, 3 to 6 membered, 4 to 6 membered, 4 to 5 membered, or 5 to 6 membered), $R^{22}$-substituted or unsubstituted aryl (e.g., $C_6$-$C_{10}$ or phenyl), or $R^{22}$-substituted or unsubstituted heteroaryl (e.g., 5 to 10 membered, 5 to 9 membered, or 5 to 6 membered). In embodiments, $R^{2'}$ is independently oxo, halogen, —$CX^{21}_3$, —$CHX^{21}_2$, —$CH_2X^{21}$, —$OCX^{21}_3$, —$OCH_2X^{21}$, —$OCHX^{21}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_0$ or phenyl), or unsubstituted heteroaryl (e.g., 5 to 10 membered, 5 to 9 membered, or 5 to 6 membered). $X^{21}$ is independently —F, —Cl, —Br, or —I.

In embodiments, $R^{21}$ is $R^{22}$-substituted or unsubstituted alkyl or $R^{22}$-substituted or unsubstituted heteroalkyl. In embodiments, $R^{21}$ is independently $R^{22}$-substituted methyl. In embodiments, $R^{21}$ is $R^{22}$-substituted ethyl. In embodiments, $R^{21}$ is independently unsubstituted methyl. In embodiments, $R^{21}$ is independently unsubstituted ethyl.

$R^{22}$ is independently oxo, halogen, —$CX^{22}_3$, —$CHX^{22}_2$, —$CH_2X^{22}$, —$OCX^{22}_3$, —$OCH_2X^{22}$, —$OCHX^{22}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_0$ or phenyl), or unsubstituted heteroaryl (e.g., 5 to 10 membered, 5 to 9 membered, or 5 to 6 membered). $X^{22}$ is independently —F, —Cl, —Br, or —I.

In embodiments, $R^{1A}$ is independently substituted or unsubstituted alkyl (e.g., $C_1$-$C_8$, $C_1$-$C_6$, $C_1$-$C_4$, or $C_1$-$C_2$). In embodiments, $R^{1A}$ is independently substituted alkyl (e.g., $C_1$-$C_8$, $C_1$-$C_6$, $C_1$-$C_4$, or $C_1$-$C_2$). In embodiments, $R^{1A}$ is independently unsubstituted alkyl (e.g., $C_1$-$C_8$, $C_1$-$C_6$, $C_1$-$C_4$, or $C_1$-$C_2$). In embodiments, $R^{1A}$ is independently unsubstituted methyl. In embodiments, $R^{1A}$ is independently unsubstituted ethyl. In embodiments, $R^{1A}$ is independently unsubstituted propyl. In embodiments, $R^{1A}$ is independently unsubstituted isopropyl. In embodiments, $R^{1A}$ is independently unsubstituted tert-butyl. In embodiments, $R^{1A}$ is independently substituted or unsubstituted heteroalkyl (e.g., 2 to 8 membered, 2 to 6 membered, 4 to 6 membered, 2 to 3 membered, or 4 to 5 membered). In embodiments, $R^{1A}$ is independently substituted heteroalkyl (e.g., 2 to 8 membered, 2 to 6 membered, 4 to 6 membered, 2 to 3 membered, or 4 to 5 membered). In embodiments, $R^{1A}$ is independently unsubstituted heteroalkyl (e.g., 2 to 8 membered, 2 to 6 membered, 4 to 6 membered, 2 to 3 membered, or 4 to 5 membered). In embodiments, $R^{1A}$ is independently substituted or unsubstituted cycloalkyl (e.g., $C_3$-$C_8$, $C_3$-$C_6$, $C_4$-$C_6$, or $C_5$-$C_6$). In embodiments, $R^{1A}$ is independently substituted cycloalkyl (e.g., $C_3$-$C_8$, $C_3$-$C_6$, $C_4$-$C_6$, or $C_5$-$C_6$). In embodiments, $R^{1A}$ is independently unsubstituted cycloalkyl (e.g., $C_3$-$C_8$, $C_3$-$C_6$, $C_4$-$C_6$, or $C_5$-$C_6$). In embodiments, $R^{1A}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{1A}$ is independently substituted heterocycloalkyl (e.g., 3 to 8 membered, 3 to 6 membered, 4 to 6 membered, 4 to 5 membered, or 5 to 6 membered). In embodiments, $R^{1A}$ is independently unsubstituted heterocycloalkyl (e.g., 3 to 8 membered, 3 to 6 membered, 4 to 6 membered, 4 to 5 membered, or 5 to 6 membered). In embodiments, $R^{1A}$ is independently substituted or unsubstituted aryl (e.g., $C_6$-$C_{10}$ or phenyl). In embodiments, $R^{1A}$ is independently substituted aryl (e.g., $C_6$-$C_{10}$ or phenyl). In embodiments, $R^{1A}$ is independently unsubstituted aryl (e.g., $C_6$-$C_{10}$ or phenyl). In embodiments, $R^{1A}$ is independently substituted or unsubstituted heteroaryl (e.g., 5 to 10 membered, 5 to 9 membered, or 5 to 6 membered). In embodiments, $R^{1A}$ is independently substituted heteroaryl (e.g., 5 to 10 membered, 5 to 9 membered, or 5 to 6 membered). In embodiments, $R^{1A}$ is independently unsubstituted heteroaryl (e.g., 5 to 10 membered, 5 to 9 membered, or 5 to 6 membered).

In embodiments, $R^{1B}$ is independently substituted or unsubstituted alkyl (e.g., $C_1$-$C_8$, $C_1$-$C_6$, $C_1$-$C_4$, or $C_1$-$C_2$). In embodiments, $R^{1B}$ is independently substituted alkyl (e.g., $C_1$-$C_8$, $C_1$-$C_6$, $C_1$-$C_4$, or $C_1$-$C_2$). In embodiments, $R^{1B}$ is independently unsubstituted alkyl (e.g., $C_1$-$C_8$, $C_1$-$C_6$, $C_1$-$C_4$, or $C_1$-$C_2$). In embodiments, $R^{1B}$ is independently unsubstituted methyl. In embodiments, $R^{1B}$ is independently unsubstituted ethyl. In embodiments, $R^{1B}$ is independently unsubstituted propyl. In embodiments, $R^{1B}$ is independently unsubstituted isopropyl. In embodiments, $R^{1B}$ is independently unsubstituted tert-butyl. In embodiments, $R^{1B}$ is independently substituted or unsubstituted heteroalkyl (e.g., 2 to 8 membered, 2 to 6 membered, 4 to 6 membered, 2 to 3 membered, or 4 to 5 membered). In embodiments, $R^{1B}$ is independently substituted heteroalkyl (e.g., 2 to 8 membered, 2 to 6 membered, 4 to 6 membered, 2 to 3 membered, or 4 to 5 membered). In embodiments, $R^{1B}$ is independently unsubstituted heteroalkyl (e.g., 2 to 8 membered, 2 to 6 membered, 4 to 6 membered, 2 to 3 membered, or 4 to 5 membered). In embodiments, $R^{1B}$ is independently substituted or unsubstituted cycloalkyl (e.g., $C_3$-$C_8$, $C_3$-$C_6$, $C_4$-$C_6$, or $C_5$-$C_6$). In embodiments, $R^{1B}$ is independently substituted cycloalkyl (e.g., $C_3$-$C_8$, $C_3$-$C_6$, $C_4$-$C_6$, or $C_5$-$C_6$). In embodiments, $R^{1B}$ is independently unsubstituted cycloalkyl (e.g., $C_3$-$C_8$, $C_3$-$C_6$, $C_4$-$C_6$, or $C_5$-$C_6$). In embodiments, $R^{1B}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{1B}$ is independently substituted heterocycloalkyl (e.g., 3 to 8 membered, 3 to 6 membered, 4 to 6 membered, 4 to 5 membered, or 5 to 6 membered). In embodiments, $R^{1B}$ is independently unsubstituted heterocycloalkyl (e.g., 3 to 8 membered, 3 to 6 membered, 4 to 6 membered, 4 to 5 membered, or 5 to 6 membered). In embodiments, $R^{1B}$ is independently substituted or unsubstituted aryl (e.g., $C_6$-$C_0$ or phenyl). In embodiments, $R^{1B}$ is independently substituted aryl (e.g., $C_6$-$C_{10}$ or phenyl). In embodiments, $R^{1B}$ is independently unsubstituted aryl (e.g., $C_6$-$C_{10}$ or phenyl). In embodiments, $R^T$ is independently substituted or unsubstituted heteroaryl (e.g., 5 to 10 membered, 5 to 9 membered, or 5 to 6 membered). In embodiments, $R^{1B}$ is independently substituted heteroaryl (e.g., 5 to 10 membered, 5 to 9 membered, or 5 to 6 membered). In embodiments, $R^{1B}$ is independently unsubstituted heteroaryl (e.g., 5 to 10 membered, 5 to 9 membered, or 5 to 6 membered).

In embodiments, $R^{1A}$ and $R^{1B}$ substituents bonded to the same nitrogen atom may be joined to form a substituted or unsubstituted heterocycloalkyl (e.g., 3 to 8 membered, 3 to 6 membered, 4 to 6 membered, 4 to 5 membered, or 5 to 6 membered). In embodiments, $R^{1A}$ and $R^{1B}$ substituents bonded to the same nitrogen atom may be joined to form a substituted heterocycloalkyl (e.g., 3 to 8 membered, 3 to 6 membered, 4 to 6 membered, 4 to 5 membered, or 5 to 6 membered). In embodiments, $R^{1A}$ and $R^{1B}$ substituents bonded to the same nitrogen atom may be joined to form an unsubstituted heterocycloalkyl (e.g., 3 to 8 membered, 3 to 6 membered, 4 to 6 membered, 4 to 5 membered, or 5 to 6 membered).

In embodiments, $R^{1A}$ and $R^{1B}$ substituents bonded to the same nitrogen atom may be joined to form a substituted or unsubstituted heteroaryl (e.g., 5 to 10 membered, 5 to 9 membered, or 5 to 6 membered). In embodiments, $R^{1A}$ and $R^{1B}$ substituents bonded to the same nitrogen atom may be joined to form a substituted heteroaryl (e.g., 5 to 10 membered, 5 to 9 membered, or 5 to 6 membered). In embodiments, $R^{1A}$ and $R^{1B}$ substituents bonded to the same nitrogen atom may be joined to form an unsubstituted heteroaryl (e.g., 5 to 10 membered, 5 to 9 membered, or 5 to 6 membered).

In embodiments, $R^{1C}$ is independently substituted or unsubstituted alkyl (e.g., $C_1$-$C_8$, $C_1$-$C_6$, $C_1$-$C_4$, or $C_1$-$C_2$). In embodiments, $R^{1C}$ is independently substituted alkyl (e.g., $C_1$-$C_8$, $C_1$-$C_6$, $C_1$-$C_4$, or $C_1$-$C_2$). In embodiments, $R^{1C}$ is independently unsubstituted alkyl (e.g., $C_1$-$C_8$, $C_1$-$C_6$, $C_1$-$C_4$, or $C_1$-$C_2$). In embodiments, $R^{1C}$ is independently unsubstituted methyl. In embodiments, $R^{1C}$ is independently unsubstituted ethyl. In embodiments, $R^{1C}$ is independently unsubstituted propyl. In embodiments, $R^{1C}$ is independently unsubstituted isopropyl. In embodiments, $R^{1C}$ is independently unsubstituted tert-butyl. In embodiments, $R^{1C}$ is independently substituted or unsubstituted heteroalkyl (e.g., 2 to 8 membered, 2 to 6 membered, 4 to 6 membered, 2 to 3 membered, or 4 to 5 membered). In embodiments, $R^{1C}$ is independently substituted heteroalkyl (e.g., 2 to 8 membered, 2 to 6 membered, 4 to 6 membered, 2 to 3 membered, or 4 to 5 membered). In embodiments, $R^{1C}$ is independently unsubstituted heteroalkyl (e.g., 2 to 8 membered, 2 to 6 membered, 4 to 6 membered, 2 to 3 membered, or 4 to 5 membered). In embodiments, $R^{1C}$ is independently substituted or unsubstituted cycloalkyl (e.g., $C_3$-$C_8$, $C_3$-$C_6$, $C_4$-$C_6$, or $C_5$-$C_6$). In embodiments, $R^{1C}$ is independently substituted cycloalkyl (e.g., $C_3$-$C_8$, $C_3$-$C_6$, $C_4$-$C_6$, or $C_5$-$C_6$). In embodiments, $R^{1C}$ is independently unsubstituted cycloalkyl (e.g., $C_3$-$C_8$, $C_3$-$C_6$, $C_4$-$C_6$, or $C_5$-$C_6$). In embodiments, $R^{1C}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{1C}$ is independently substituted heterocycloalkyl (e.g., 3 to 8 membered, 3 to 6 membered, 4 to 6 membered, 4 to 5 membered, or 5 to 6 membered). In embodiments, $R^{1C}$ is independently unsubstituted heterocycloalkyl (e.g., 3 to 8 membered, 3 to 6 membered, 4 to 6 membered, 4 to 5 membered, or 5 to 6 membered). In embodiments, $R^{1C}$ is independently substituted or unsubstituted aryl (e.g., $C_6$-$C_{10}$ or phenyl). In embodiments, $R^{1C}$ is independently substituted aryl (e.g., $C_6$-$C_{10}$ or phenyl). In embodiments, $R^{1C}$ is independently unsubstituted aryl (e.g., $C_6$-$C_{10}$ or phenyl). In embodiments, $R^{1C}$ is independently substituted or unsubstituted heteroaryl (e.g., 5 to 10 membered, 5 to 9 membered, or 5 to 6 membered). In embodiments, $R^{1C}$ is independently substituted heteroaryl (e.g., 5 to 10 membered, 5 to 9 membered, or 5 to 6 membered). In embodiments, $R^{1C}$ is independently unsubstituted heteroaryl (e.g., 5 to 10 membered, 5 to 9 membered, or 5 to 6 membered).

In embodiments, $R^{1D}$ is independently substituted or unsubstituted alkyl (e.g., $C_1$-$C_8$, $C_1$-$C_6$, $C_1$-$C_4$, or $C_1$-$C_2$). In embodiments, $R^{1D}$ is independently substituted alkyl (e.g., $C_1$-$C_8$, $C_1$-$C_6$, $C_1$-$C_4$, or $C_1$-$C_2$). In embodiments, $R^{1D}$ is independently unsubstituted alkyl (e.g., $C_1$-$C_8$, $C_1$-$C_6$, $C_1$-$C_4$, or $C_1$-$C_2$). In embodiments, $R^{1D}$ is independently unsubstituted methyl. In embodiments, $R^{1D}$ is independently unsubstituted ethyl. In embodiments, $R^{1D}$ is independently unsubstituted propyl. In embodiments, $R^{1D}$ is independently unsubstituted isopropyl. In embodiments, $R^{1D}$ is independently unsubstituted tert-butyl. In embodiments, $R^{1D}$ is independently substituted or unsubstituted heteroalkyl (e.g., 2 to 8 membered, 2 to 6 membered, 4 to 6 membered, 2 to 3 membered, or 4 to 5 membered). In embodiments, $R^{1D}$ is independently substituted heteroalkyl (e.g., 2 to 8 membered, 2 to 6 membered, 4 to 6 membered, 2 to 3 membered, or 4 to 5 membered). In embodiments, $R^{1D}$ is independently unsubstituted heteroalkyl (e.g., 2 to 8 membered, 2 to 6 membered, 4 to 6 membered, 2 to 3 membered, or 4 to 5 membered). In embodiments, $R^{1D}$ is independently substituted or unsubstituted cycloalkyl (e.g., $C_3$-$C_8$, $C_3$-$C_6$, $C_4$-$C_6$, or $C_5$-$C_6$). In embodiments, $R^{1D}$ is independently substituted cycloalkyl (e.g., $C_3$-$C_8$, $C_3$-$C_6$, $C_4$-$C_6$, or $C_5$-$C_6$). In embodiments, $R^{1D}$ is independently unsubstituted cycloalkyl (e.g., $C_3$-$C_8$, $C_3$-$C_6$, $C_4$-$C_6$, or $C_5$-$C_6$). In embodiments, $R^{1D}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{1D}$ is independently substituted heterocycloalkyl (e.g., 3 to 8 membered, 3 to 6 membered, 4 to 6 membered, 4 to 5 membered, or 5 to 6 membered). In embodiments, $R^{1D}$ is independently unsubstituted heterocycloalkyl (e.g., 3 to 8 membered, 3 to 6 membered, 4 to 6 membered, 4 to 5 membered, or 5 to 6 membered). In embodiments, $R^{1D}$ is independently substituted or unsubstituted aryl (e.g., $C_6$-$C_{10}$ or phenyl). In embodiments, $R^{1D}$ is independently substituted aryl (e.g., $C_6$-$C_{10}$ or phenyl). In embodiments, $R^{1D}$ is independently unsubstituted aryl (e.g., $C_6$-$C_{10}$ or phenyl). In embodiments, $R^{1D}$ is independently substituted or unsubstituted heteroaryl (e.g., 5 to 10 membered, 5 to 9 membered, or 5 to 6 membered). In embodiments, $R^{1D}$ is independently substituted heteroaryl (e.g., 5 to 10 membered, 5 to 9 membered, or 5 to 6 membered). In embodiments, $R^{1D}$ is independently unsubstituted heteroaryl (e.g., 5 to 10 membered, 5 to 9 membered, or 5 to 6 membered).

In embodiments, $R^{1A}$ is independently hydrogen, $-CX^{1A}{}_3$, $-CHX^{1A}{}_2$, $-CH_2X^{1A}$, $-CN$, $-COOH$, $-CONH_2$, $R^{20A}$-substituted or unsubstituted alkyl (e.g., $C_1$-$C_8$, $C_1$-$C_6$, $C_1$-$C_4$, or $C_1$-$C_2$), $R^{20A}$-substituted or unsubstituted heteroalkyl (e.g., 2 to 8 membered, 2 to 6 membered, 4 to 6 membered, 2 to 3 membered, or 4 to 5 membered), $R^{20A}$-substituted or unsubstituted cycloalkyl (e.g., $C_3$-$C_8$, $C_3$-$C_6$, $C_4$-$C_6$, or $C_5$-$C_6$), $R^{20A}$-substituted or unsubstituted heterocycloalkyl (e.g., 3 to 8 membered, 3 to 6 membered, 4 to 6 membered, 4 to 5 membered, or 5 to 6 membered), $R^{20A}$-substituted or unsubstituted aryl (e.g., $C_6$-$C_0$ or phenyl), or $R^{20A}$-substituted or unsubstituted heteroaryl (e.g., 5 to 10 membered, 5 to 9 membered, or 5 to 6 membered). In embodiments, $R^{1A}$ is independently hydrogen, $-CX^{1A}{}_3$, $-CHX^{1A}{}_2$, $-CH_2X^{1A}$, $-CN$, $-COOH$, $-CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_0$ or phenyl), or unsubstituted heteroaryl (e.g., 5 to 10 membered, 5 to 9 membered, or 5 to 6 membered). $X^{1A}$ is independently $-F$, $-Cl$, $-Br$, or $-I$.

In embodiments, $R^{1A}$ is independently hydrogen. In embodiments, $R^{1A}$ is independently unsubstituted methyl. In embodiments, $R^{1A}$ is independently unsubstituted ethyl.

In embodiments, $R^{1A}$ and $R^{1B}$ substituents bonded to the same nitrogen atom may optionally be joined to form a $R^{20A}$-substituted or unsubstituted heterocycloalkyl (e.g., 3 to 8 membered, 3 to 6 membered, 4 to 6 membered, 4 to 5 membered, or 5 to 6 membered) or $R^{20A}$-substituted or unsubstituted heteroaryl (e.g., 5 to 10 membered, 5 to 9 membered, or 5 to 6 membered). In embodiments, $R^{1A}$ and $R^{1B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 10 membered, 5 to 9 membered, or 5 to 6 membered). In embodiments, $R^{1A}$ and $R^{1B}$ substituents bonded to the same nitrogen atom may optionally be joined to form a $R^{20A}$-substituted or unsubstituted heterocycloalkyl (e.g., 3 to 8 membered, 3 to 6 membered, 4 to 6 membered, 4 to 5 membered, or 5 to 6 membered). In embodiments, $R^{1A}$ and $R^{1B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

$R^{20A}$ is independently oxo, halogen, $-CX^{20A}{}_3$, $-CHX^{20A}{}_3$, $-CH_2X^{20A}$, $-OCX^{20A}{}_3$, $-OCH_2X^{20A}$, $-OCHX^{20A}{}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, $R^{21A}$-substituted or unsubstituted alkyl (e.g., $C_1$-$C_8$, $C_1$-$C_6$, $C_1$-$C_4$, or $C_1$-$C_2$), $R^{21A}$-substituted or unsubstituted heteroalkyl (e.g., 2 to 8 membered, 2 to 6 membered, 4 to 6 membered, 2 to 3 membered, or 4 to 5 membered), $R^{21A}$-substituted or unsubstituted cycloalkyl (e.g., $C_3$-$C_8$, $C_3$-$C_6$, $C_4$-$C_6$, or $C_5$-$C_6$), $R^{21A}$-substituted or unsubstituted heterocycloalkyl (e.g., 3 to 8 membered, 3 to 6 membered, 4 to 6 membered, 4 to 5 membered, or 5 to 6 membered), $R^{21A}$-substituted or unsubstituted aryl (e.g., $C_6$-$C_{10}$ or phenyl), or $R^{21A}$-substituted or unsubstituted heteroaryl (e.g., 5 to 10 membered, 5 to 9 membered, or 5 to 6 membered). In embodiments, $R^{20A}$ is independently oxo, halogen, $-CX^{20A}{}_3$, $-CHX^{20A}{}_2$, $-CH_2X^{20A}$, $-OCX^{20A}{}_3$, $-OCH_2X^{20A}$, $-OCHX^{20A}{}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC-(O)NHNH_2$, $-NHC=(O)NH_2$, $-NHSO_2H$, $-NHC=(O)H$, $-NHC(O)-OH$, $-NHOH$, $-N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_0$ or phenyl), or unsubstituted heteroaryl (e.g., 5 to 10 membered, 5 to 9 membered, or 5 to 6 membered). $X^{20A}$ is independently $-F$, $-Cl$, $-Br$, or $-I$.

In embodiments, $R^{20A}$ is independently unsubstituted methyl. In embodiments, $R^{20A}$ is independently unsubstituted ethyl.

$R^{21A}$ is independently oxo, halogen, $-CX^{21A}{}_3$, $-CHX^{21A}{}_2$, $-CH_2X^{21A}$, $-OCX^{21A}{}_3$, $-OCH_2X^{21A}$, $-OCHX^{21A}{}_2$-CN, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, $R^2$-substituted or unsubstituted alkyl (e.g., $C_1$-$C_8$, $C_1$-$C_6$, $C_1$-$C_4$, or $C_1$-$C_2$), $R^{22A}$-substituted or unsubstituted heteroalkyl (e.g., 2 to 8 membered, 2 to 6 membered, 4 to 6 membered, 2 to 3 membered, or 4 to 5 membered), $R^{22A}$-substituted or unsubstituted cycloalkyl (e.g., $C_3$-$C_8$, $C_3$-$C_6$, $C_4$-$C_6$, or $C_5$-$C_6$), $R^{22A}$-substituted or unsubstituted heterocycloalkyl (e.g., 3 to 8 membered, 3 to 6 membered, 4 to 6 membered, 4 to 5 membered, or 5 to 6 membered), $R^{22A}$-substituted or unsubstituted aryl (e.g., $C_6$-$C_0$ or phenyl), or $R^{22A}$-substituted or unsubstituted heteroaryl (e.g., 5 to 10 membered, 5 to 9 membered, or 5 to 6 membered). In embodiments, $R^{21A}$ is independently oxo, halogen, $-CX^{21A}{}_3$, $-CHX^{21A}{}_2$, $-CH_2X^{21A}$, $-OCX^{21A}{}_3$, $-OCH_2X^{21A}$, $-OCHX^{21A}{}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{21A}$ is independently $-F$, $-Cl$, $-Br$, or $-I$.

In embodiments, $R^{21A}$ is independently unsubstituted methyl. In embodiments, $R^{21A}$ is independently unsubstituted ethyl.

$R^{22}$ is independently oxo, halogen, $-CX^{22A}{}_3$, $-CHX^{22A}{}_2$, $-CH_2X^{22A}$, $-OCX^{22A}{}_3$, $-OCH_2X^{22A}$, $-OCHX^{22A}{}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{22A}$ is independently —F, —Cl, —Br, or —I.

In embodiments, $R^{22A}$ is independently unsubstituted methyl. In embodiments, $R^{22A}$ is independently unsubstituted ethyl.

In embodiments, $R^{1B}$ is independently hydrogen, —$CX^{1B}_3$, —$CHX^{1B}_2$, —$CH_2X^{1B}$, —CN, —COOH, —$CONH_2$, $R^{20B}$-substituted or unsubstituted alkyl (e.g., $C_1$-$C_8$, $C_1$-$C_6$, $C_1$-$C_4$, or $C_1$-$C_2$), $R^{20B}$-substituted or unsubstituted heteroalkyl (e.g., 2 to 8 membered, 2 to 6 membered, 4 to 6 membered, 2 to 3 membered, or 4 to 5 membered), $R^{20B}$-substituted or unsubstituted cycloalkyl (e.g., $C_3$-$C_8$, $C_3$-$C_6$, $C_4$-$C_6$, or $C_5$-$C_6$), $R^{20B}$-substituted or unsubstituted heterocycloalkyl (e.g., 3 to 8 membered, 3 to 6 membered, 4 to 6 membered, 4 to 5 membered, or 5 to 6 membered), $R^{20B}$-substituted or unsubstituted aryl (e.g., $C_6$-$C_{10}$ or phenyl), or $R^{20B}$-substituted or unsubstituted heteroaryl (e.g., 5 to 10 membered, 5 to 9 membered, or 5 to 6 membered). In embodiments, $R^{1B}$ is independently hydrogen, —$CX^{1B}_3$, —$CHX^{1B}_2$, —$CH_2X^{1B}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{1B}$ is independently —F, —Cl, —Br, or —I.

In embodiments, $R^{1B}$ is independently hydrogen. In embodiments, $R^{1B}$ is independently unsubstituted methyl. In embodiments, $R^{1B}$ is independently unsubstituted ethyl.

In embodiments, $R^{1A}$ and $R^{1B}$ substituents bonded to the same nitrogen atom may optionally be joined to form a $R^{20B}$-substituted or unsubstituted heterocycloalkyl (e.g., 3 to 8 membered, 3 to 6 membered, 4 to 6 membered, 4 to 5 membered, or 5 to 6 membered) or $R^{20B}$-substituted or unsubstituted heteroaryl (e.g., 5 to 10 membered, 5 to 9 membered, or 5 to 6 membered). In embodiments, $R^{1A}$ and $R^{1B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 10 membered, 5 to 9 membered, or 5 to 6 membered). In embodiments, $R^{1A}$ and $R^{1B}$ substituents bonded to the same nitrogen atom may optionally be joined to form a $R^{20B}$-substituted or unsubstituted heterocycloalkyl (e.g., 3 to 8 membered, 3 to 6 membered, 4 to 6 membered, 4 to 5 membered, or 5 to 6 membered). In embodiments, $R^{1A}$ and $R^{1B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

$R^{20B}$ is independently oxo, halogen, —$CX^{20B}_3$, —$CHX^{20B}_2$, —$CH_2X^{20B}$, —$OCX^{20B}_3$, —$OCH_2X^{20B}$, —$OCHX^{20B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC=(O)NHNH_2$, —$NHC=(O)NH_2$, —$NHSO_2H$, —$NHC=(O)H$, —$NHC(O)$—OH, —NHOH, —$N_3$, $R^{21B}$-substituted or unsubstituted alkyl (e.g., $C_1$-$C_8$, $C_1$-$C_6$, $C_1$-$C_4$, or $C_1$-$C_2$), $R^{21B}$-substituted or unsubstituted heteroalkyl (e.g., 2 to 8 membered, 2 to 6 membered, 4 to 6 membered, 2 to 3 membered, or 4 to 5 membered), $R^{21B}$-substituted or unsubstituted cycloalkyl (e.g., $C_3$-$C_8$, $C_3$-$C_6$, $C_4$-$C_6$, or $C_5$-$C_6$), $R^{21B}$-substituted or unsubstituted heterocycloalkyl (e.g., 3 to 8 membered, 3 to 6 membered, 4 to 6 membered, 4 to 5 membered, or 5 to 6 membered), $R^{21B}$-substituted or unsubstituted aryl (e.g., $C_6$-$C_{10}$ or phenyl), or $R^{21B}$-substituted or unsubstituted heteroaryl (e.g., 5 to 10 membered, 5 to 9 membered, or 5 to 6 membered). In embodiments, $R^{20B}$ is independently oxo, halogen, —$CX^{20B}_3$, —$CHX^{20B}_2$, —$CH_2X^{20B}$, —$OCX^{20B}_3$, —$OCH_2X^{20B}$, —$OCHX^{20B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC=(O)NHNH_2$, —$NHC=(O)NH_2$, —$NHSO_2H$, —$NHC=(O)H$, —$NHC(O)$—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{20B}$ is independently —F, —Cl, —Br, or —I.

In embodiments, $R^{20B}$ is independently unsubstituted methyl. In embodiments, $R^{20B}$ is independently unsubstituted ethyl.

$R^{21B}$ is independently oxo, halogen, —$CX^{21B}_3$, —$CHX^{21B}_2$, —$CH_2X^{21B}$, —$OCX^{21B}_3$, —$OCH_2X2^{1B}$, —$OCHX^{21B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC=(O)NHNH_2$, —$NHC=(O)NH_2$, —$NHSO_2H$, —$NHC=(O)H$, —$NHC(O)$—OH, —NHOH, —$N_3$, Re-substituted or unsubstituted alkyl (e.g., $C_1$-$C_8$, $C_1$-$C_6$, $C_1$-$C_4$, or $C_1$-$C_2$), $R^{22B}$-substituted or unsubstituted heteroalkyl (e.g., 2 to 8 membered, 2 to 6 membered, 4 to 6 membered, 2 to 3 membered, or 4 to 5 membered), $R^{22B}$-substituted or unsubstituted cycloalkyl (e.g., $C_3$-$C_8$, $C_3$-$C_6$, $C_4$-$C_6$, or $C_5$-$C_6$), $R^{22B}$-substituted or unsubstituted heterocycloalkyl (e.g., 3 to 8 membered, 3 to 6 membered, 4 to 6 membered, 4 to 5 membered, or 5 to 6 membered), $R^{22B}$-substituted or unsubstituted aryl (e.g., $C_6$-$C_{10}$ or phenyl), or $R^{22B}$-substituted or unsubstituted heteroaryl (e.g., 5 to 10 membered, 5 to 9 membered, or 5 to 6 membered). In embodiments, $R^{21B}$ is independently oxo, halogen, —$CX^{21B}_3$, —$CHX^{21B}_2$, —$CH_2X^{21B}$, —$OCX^{21B}_3$, —$OCH_2X^{21B}$, —$OCHX^{21B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC=(O)NHNH_2$, —$NHC=(O)NH_2$, —$NHSO_2H$, —$NHC=(O)H$, —$NHC(O)$—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{21B}$ is independently —F, —Cl, —Br, or —I.

In embodiments, $R^{21B}$ is independently unsubstituted methyl. In embodiments, $R^{21B}$ is independently unsubstituted ethyl.

$R^{22B}$ is independently oxo, halogen, $-CX^{22B}_3$, $-CHX^{22B}_2$, $-CH_2X^{22B}$, $-OCX^{22B}_3$, $-OCH_2X^{22B}$, $-OCHX^{22B}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_0$ or phenyl), or unsubstituted heteroaryl (e.g., 5 to 10 membered, 5 to 9 membered, or 5 to 6 membered). $X^{22B}$ is independently $-F$, $-Cl$, $-Br$, or $-I$.

In embodiments, $R^{22B}$ is independently unsubstituted methyl. In embodiments, $R^{22B}$ is independently unsubstituted ethyl.

In embodiments, $R^{1C}$ is independently hydrogen, $-CX^{1C}_3$, $-CHX^{1C}_2$, $-CH_2X^{1C}$, $-CN$, $-COOH$, $-CONH_2$, $R^2$-substituted or unsubstituted alkyl (e.g., $C_1$-$C_8$, $C_1$-$C_6$, $C_1$-$C_4$, or $C_1$-$C_2$), $R^2$-substituted or unsubstituted heteroalkyl (e.g., 2 to 8 membered, 2 to 6 membered, 4 to 6 membered, 2 to 3 membered, or 4 to 5 membered), $R^{20C}$-substituted or unsubstituted cycloalkyl (e.g., $C_3$-$C_8$, $C_3$-$C_6$, $C_4$-$C_6$, or $C_5$-$C_6$), $R^{20C}$-substituted or unsubstituted heterocycloalkyl (e.g., 3 to 8 membered, 3 to 6 membered, 4 to 6 membered, 4 to 5 membered, or 5 to 6 membered), $R^{20C}$-substituted or unsubstituted aryl (e.g., $C_6$-$C_{10}$ or phenyl), or $R^2$-substituted or unsubstituted heteroaryl (e.g., 5 to 10 membered, 5 to 9 membered, or 5 to 6 membered). In embodiments, $R^{1C}$ is independently hydrogen, $-CX^{1C}_3$, $-CHX^{1C}_2$, $-CH_2X^{1C}$, $-CN$, $-COOH$, $-CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{1C}$ is independently $-F$, $-Cl$, $-Br$, or $-I$.

In embodiments, $R^{1C}$ is independently hydrogen. In embodiments, $R^{1C}$ is independently unsubstituted methyl. In embodiments, $R^{1C}$ is independently unsubstituted ethyl.

$R^{2C}$ is independently oxo, halogen, $-CX^{20C}_3$, $-CHX^{20C}_2$, $-CH_2X^{20C}$, $-OCX^{20C}_3$, $-OCH_2X^{20C}$, $-OCHX^{20C}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, $R^{21C}$-substituted or unsubstituted alkyl (e.g., $C_1$-$C_8$, $C_1$-$C_6$, $C_1$-$C_4$, or $C_1$-$C_2$), $R^{21C}$-substituted or unsubstituted heteroalkyl (e.g., 2 to 8 membered, 2 to 6 membered, 4 to 6 membered, 2 to 3 membered, or 4 to 5 membered), $R^{21C}$-substituted or unsubstituted cycloalkyl (e.g., $C_3$-$C_8$, $C_3$-$C_6$, $C_4$-$C_6$, or $C_5$-$C_6$), $R^{21C}$-substituted or unsubstituted heterocycloalkyl (e.g., 3 to 8 membered, 3 to 6 membered, 4 to 6 membered, 4 to 5 membered, or 5 to 6 membered), $R^{21C}$-substituted or unsubstituted aryl (e.g., $C_6$-$C_{10}$ or phenyl), or $R^{21C}$-substituted or unsubstituted heteroaryl (e.g., 5 to 10 membered, 5 to 9 membered, or 5 to 6 membered). In embodiments, $R^{20C}$ is independently oxo, halogen, $-CX^{20C}_3$, $-CHX^{20C}_2$, $-CH_2X^{20C}$, $-OCX^{20C}_3$, $-OCH_2X^{20C}$, $-OCHX^{20C}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{20C}$ is independently $-F$, $-Cl$, $-Br$, or $-I$.

In embodiments, $R^{20C}$ is independently unsubstituted methyl. In embodiments, $R^{20C}$ is independently unsubstituted ethyl.

$R^{21C}$ is independently oxo, halogen, $-CX^{21C}_3$, $-CHX^{21C}_2$, $-CH_2X^{21C}$, $-OCX^{21C}_3$, $-OCH_2X^{21C}$, $-OCHX^{21C}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, $R^{22C}$-substituted or unsubstituted alkyl (e.g., $C_1$-$C_8$, $C_1$-$C_6$, $C_1$-$C_4$, or $C_1$-$C_2$), $R^{22C}$-substituted or unsubstituted heteroalkyl (e.g., 2 to 8 membered, 2 to 6 membered, 4 to 6 membered, 2 to 3 membered, or 4 to 5 membered), $R^{22C}$-substituted or unsubstituted cycloalkyl (e.g., $C_3$-$C_8$, $C_3$-$C_6$, $C_4$-$C_6$, or $C_5$-$C_6$), $R^{22C}$-substituted or unsubstituted heterocycloalkyl (e.g., 3 to 8 membered, 3 to 6 membered, 4 to 6 membered, 4 to 5 membered, or 5 to 6 membered), $R^{22C}$-substituted or unsubstituted aryl (e.g., $C_6$-$C_{10}$ or phenyl), or $R^{22C}$-substituted or unsubstituted heteroaryl (e.g., 5 to 10 membered, 5 to 9 membered, or 5 to 6 membered). In embodiments, $R^{21C}$ is independently oxo, halogen, $-CX^{21C}_3$, $-CHX^{21C}_2$, $-CH_2X^{21C}$, $-OCX^{20C}_3$, $-OCH_2X^{20C}$, $-OCHX^{20C}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{21C}$ is independently $-F$, $-Cl$, $-Br$, or $-I$.

In embodiments, $R^{21C}$ is independently unsubstituted methyl. In embodiments, $R^{21C}$ is independently unsubstituted ethyl.

$R^{22C}$ is independently oxo, halogen, $-CX^{22C}_3$, $-CHX^{22C}_2$, $-CH_2X^{22C}$, $-OCX^{22C}_3$, $-OCH_2X^{22C}$, $-OCHX^{22C}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{22C}$ is independently —F, —Cl, —Br, or —I.

In embodiments, $R^{22C}$ is independently unsubstituted methyl. In embodiments, $R^{22C}$ is independently unsubstituted ethyl.

In embodiments, $R^{1D}$ is independently hydrogen, —$CX^{1D}{}_3$, —$CHX^{1D}{}_2$, —$CH_2X^{1D}$, —CN, —COOH, —$CONH_2$, $R^{20D}$-substituted or unsubstituted alkyl (e.g., $C_1$-$C_8$, $C_1$-$C_6$, $C_1$-$C_4$, or $C_1$-$C_2$), $R^{20D}$-substituted or unsubstituted heteroalkyl (e.g., 2 to 8 membered, 2 to 6 membered, 4 to 6 membered, 2 to 3 membered, or 4 to 5 membered), $R^{20D}$-substituted or unsubstituted cycloalkyl (e.g., $C_3$-$C_8$, $C_3$-$C_6$, $C_4$-$C_6$, or $C_5$-$C_6$), $R^{20D}$-substituted or unsubstituted heterocycloalkyl (e.g., 3 to 8 membered, 3 to 6 membered, 4 to 6 membered, 4 to 5 membered, or 5 to 6 membered), $R^{20D}$-substituted or unsubstituted aryl (e.g., $C_6$-$C_{10}$ or phenyl), or $R^{20D}$-substituted or unsubstituted heteroaryl (e.g., 5 to 10 membered, 5 to 9 membered, or 5 to 6 membered). In embodiments, $R^{1D}$ is independently hydrogen, —$CX^{1D}{}_3$, —$CHX^{1D}{}_2$, —$CH_2X^{1D}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{1D}$ is independently —F, —Cl, —Br, or —I.

In embodiments, $R^{1D}$ is independently hydrogen. In embodiments, $R^{1D}$ is independently unsubstituted methyl. In embodiments, $R^{1D}$ is independently unsubstituted ethyl.

$R^{20D}$ is independently oxo, halogen, —$CX^{20D}{}_3$, —$CHX^{20D}{}_2$, —$CH_2X^{20D}$, —$OCX^{20D}{}_3$, —$OCH_2X^{20D}$, —$OCHX^{20D}{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, $R^{21D}$-substituted or unsubstituted alkyl (e.g., $C_1$-$C_8$, $C_1$-$C_6$, $C_1$-$C_4$, or $C_1$-$C_2$), $R^{21D}$-substituted or unsubstituted heteroalkyl (e.g., 2 to 8 membered, 2 to 6 membered, 4 to 6 membered, 2 to 3 membered, or 4 to 5 membered), $R^{21D}$-substituted or unsubstituted cycloalkyl (e.g., $C_3$-$C_8$, $C_3$-$C_6$, $C_4$-$C_6$, or $C_5$-$C_6$), $R^{21D}$-substituted or unsubstituted heterocycloalkyl (e.g., 3 to 8 membered, 3 to 6 membered, 4 to 6 membered, 4 to 5 membered, or 5 to 6 membered), $R^{21D}$-substituted or unsubstituted aryl (e.g., $C_6$-$C_{10}$ or phenyl), or $R^{21D}$-substituted or unsubstituted heteroaryl (e.g., 5 to 10 membered, 5 to 9 membered, or 5 to 6 membered). In embodiments, $R^{20D}$ is independently oxo, halogen, —$CX^{20D}{}_3$, —$CHX^{20D}{}_2$, —$CH_2X^{20D}$, —$OCX^{20D}{}_3$, —$OCH_2X^{20D}$, —$OCHX^{20D}{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{20D}$ is independently —F, —Cl, —Br, or —I.

In embodiments, $R^{20D}$ is independently unsubstituted methyl. In embodiments, $R^{20D}$ is independently unsubstituted ethyl.

$R^{21D}$ is independently oxo, halogen, —$CX^{21D}{}_3$, —$CHX^{21D}{}_2$, —$CH_2X^{21D}$, —$OCX^{21D}{}_3$, —$OCH_2X^{21D}$, —$OCHX^{21D}{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, $R^{22D}$-substituted or unsubstituted alkyl (e.g., $C_1$-$C_8$, $C_1$-$C_6$, $C_1$-$C_4$, or $C_1$-$C_2$), $R^{22D}$-substituted or unsubstituted heteroalkyl (e.g., 2 to 8 membered, 2 to 6 membered, 4 to 6 membered, 2 to 3 membered, or 4 to 5 membered), $R^{22D}$-substituted or unsubstituted cycloalkyl (e.g., $C_3$-$C_8$, $C_3$-$C_6$, $C_4$-$C_6$, or $C_5$-$C_6$), $R^2$-substituted or unsubstituted heterocycloalkyl (e.g., 3 to 8 membered, 3 to 6 membered, 4 to 6 membered, 4 to 5 membered, or 5 to 6 membered), $R^{22D}$-substituted or unsubstituted aryl (e.g., $C_6$-$C_{10}$ or phenyl), or $R^{22D}$-substituted or unsubstituted heteroaryl (e.g., 5 to 10 membered, 5 to 9 membered, or 5 to 6 membered). In embodiments, $R^{21D}$ is independently oxo, halogen, —$CX^{21D}{}_3$, —$CHX^{21D}{}_2$, —$CH_2X^{21D}$, —$OCX^{21D}{}_3$, —$OCH_2X^{21D}$, —$OCHX^{21D}{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{21D}$ is independently —F, —Cl, —Br, or —I.

In embodiments, $R^{21D}$ is independently unsubstituted methyl. In embodiments, $R^{21D}$ is independently unsubstituted ethyl.

$R^{22D}$ is independently oxo, halogen, —$CX^{22D}{}_3$, —$CHX^{22D}{}_2$, —$CH_2X^{22D}$, —$OCX^{22D}{}_3$, —$OCH_2X^{22D}$, —$OCHX^{22D}{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{22D}$ is independently —F, —Cl, —Br, or —I.

In embodiments, $R^{22D}$ is independently unsubstituted methyl. In embodiments, $R^{22D}$ is independently unsubstituted ethyl.

In embodiments, $R^2$ is independently hydrogen, halogen, —$CX^2{}_3$, —$CHX^2{}_2$, —$CH_2X^2$, —$OCX^2{}_3$, —$OCH_2X^2$, —$OCHX^2{}_2$, —CN, —$SO_{n2}R^{2D}$, —$SO_{v2}NR^{2A}R^{2B}$, —NHC(O)$NR^{2A}R^{2B}$, —$N(O)_{m2}$, —$NR^{2A}R^{2B}$, —C(O)R, —C(O)—$OR^{2C}$, —C(O)$NR^{2A}R^{2B}$, —$OR^{2D}$, —$NR^{2A}SO_2R^{2D}$, —$NR^{2A}C(O)R^{2D}$, —$NR^{2A}C(O)OR^{2C}$, —$NR^{2A}OR^{2C}$, —$N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^2$ is independently hydrogen, halogen, $-CX^2_3$, $-CN$, $-OH$, $-NH_2$, $-SH$, $-OCX^2_3$, $-OCHX^2_2$, $-OCH_2X^2$, $-CHX^2_2$, $-CH_2X^2$, substituted or unsubstituted $C_1$-$C_4$ alkyl, or substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^2$ is independently hydrogen, halogen, $-CX^2_3$, $-CN$, $-OH$, $-NH_2$, $-SH$, $-OCX^2_3$, $-OCHX^2_2$, $-OCH_2X^2$, $-CHX^2_2$, $-CH_2X^2$, unsubstituted $C_1$-$C_4$ alkyl, or unsubstituted 2 to 4 membered heteroalkyl.

In embodiments, $R^2$ is independently hydrogen, halogen, $-CX^2_3$, $-CHX^2_2$, $-CH_2X^2$, $-OCX^2_3$, $-OCH_2X^2$, $-OCHX^2_2$, $-NR^{2A}R^{2B}$, $-C(O)R^{2C}$, $-C(O)-OR^{2C}$, $-C(O)NR^{2A}R^{2B}$, $-OR^{2D}$, $-NR^{2A}C(O)R^{2C}$, $-NR^{2A}C(O)OR^{2C}$, $-NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^2$ is independently hydrogen, halogen, $-NR^{2A}R^{2B}$, $-C(O)R^{2C}$, $-C(O)-OR^{2C}$, $-C(O)NR^{2A}R^{2B}$, $-OR^{2D}$, $-NR^{2A}C(O)R^{2C}$, $-NR^{2A}C(O)OR^{2C}$, $-NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^2$ is independently hydrogen, halogen, $-NR^{2A}R^{2B}$, $-OR^{2D}$, or substituted or unsubstituted heteroaryl. In embodiments, $R^2$ is substituted or unsubstituted aryl. In embodiments, $R^2$ is substituted or unsubstituted phenyl. In embodiments, $R^2$ is hydrogen. In embodiments, $R^2$ is halogen. In embodiments, $R^2$ is $-NR^{2A}R^{2B}$. In embodiments, $R^2$ is $-OR^{2D}$. In embodiments, $R^2$ is substituted or unsubstituted heteroaryl. In embodiments, $R^2$ is substituted heteroaryl. In embodiments, $R^2$ is substituted 5 to 6 membered heteroaryl. In embodiments, $R^2$ is $-NH_2$. In embodiments, $R^2$ is $-OH$. In embodiments, $R^2$ is $-Cl$. In embodiments, $R^2$ is $-F$. In embodiments, $R^2$ is halogen.

In embodiments, $R^2$ is substituted or unsubstituted ($C_3$-$C_{10}$) cycloalkyl, substituted or unsubstituted 3 to 10 membered heterocycloalkyl, substituted or unsubstituted ($C_6$-$C_{10}$) aryl, or substituted or unsubstituted 5 to 10 membered heteroaryl. In embodiments, $R^2$ is a substituted or unsubstituted heteroaryl. In embodiments, $R^2$ is a substituted or unsubstituted 5 to 6 membered heteroaryl. In embodiments, $R^2$ is a substituted or unsubstituted 5 membered heteroaryl.

In embodiments, $R^2$ is a substituted or unsubstituted ($C_3$-$C_{10}$) cycloalkyl, a substituted or unsubstituted 3 to 10 membered heterocycloalkyl, a substituted or unsubstituted ($C_6$-$C_{10}$) aryl, or a substituted or unsubstituted 5 to 10 membered heteroaryl. In embodiments, $R^2$ is a substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^2$ is a substituted or unsubstituted $C_3$-$C_8$ cycloalkyl. In embodiments, $R^2$ is a substituted or unsubstituted $C_3$-$C_6$ cycloalkyl. In embodiments, $R^2$ is a substituted or unsubstituted $C_5$-$C_6$ cycloalkyl. In embodiments, $R^2$ is a substituted or unsubstituted $C_6$ cycloalkyl. In embodiments, $R^2$ is a substituted or unsubstituted $C_5$ cycloalkyl. In embodiments, $R^2$ is a substituted or unsubstituted ($C_6$-$C_{10}$) aryl. In embodiments, $R^2$ is substituted or unsubstituted phenyl. In embodiments, $R^2$ is substituted or unsubstituted naphthyl. In embodiments, $R^2$ is substituted or unsubstituted aziridinyl, substituted or unsubstituted oxiranyl, substituted or unsubstituted thiiranyl, substituted or unsubstituted azetidinyl, substituted or unsubstituted oxetanyl, substituted or unsubstituted thietanyl, substituted or unsubstituted pyrrolidinyl, substituted or unsubstituted pyrrolyl, substituted or unsubstituted imidazolyl, substituted or unsubstituted imidazolinyl, substituted or unsubstituted pyrazolinyl, substituted or unsubstituted tetrahydrofuranyl, substituted or unsubstituted thiolanyl, substituted or unsubstituted piperidinyl, substituted or unsubstituted piperazinyl, substituted or unsubstituted pyranyl, substituted or unsubstituted morpholinyl, substituted or unsubstituted 1,4-dioxanyl, substituted or unsubstituted tetrahydro-2H-pyranyl, substituted or unsubstituted thianyl, or substituted or unsubstituted dithianyl. In embodiments, $R^2$ is substituted or unsubstituted phenyl, substituted or unsubstituted thiofuranyl, substituted or unsubstituted imidazolyl, substituted or unsubstituted pyrazolyl, substituted or unsubstituted triazolyl, substituted or unsubstituted tetrazolyl, substituted or unsubstituted furanyl, substituted or unsubstituted oxazolyl, substituted or unsubstituted isooxazolyl, substituted or unsubstituted oxadiazolyl, substituted or unsubstituted oxatriazolyl, substituted or unsubstituted thienyl, substituted or unsubstituted thiazolyl, substituted or unsubstituted isothiazolyl, substituted or unsubstituted pyridinyl, substituted or unsubstituted pyrazinyl, substituted or unsubstituted pyrimidinyl, substituted or unsubstituted pyridazinyl, or substituted or unsubstituted triazinyl (e.g., 1,3,5-triazinyl, 1,2,3-triazinyl, or 1,2,4-triazinyl). In embodiments, $R^2$ is substituted or unsubstituted indolyl, substituted or unsubstituted benzimidazolyl, substituted or unsubstituted indazolyl, substituted or unsubstituted benzotriazolyl, substituted or unsubstituted pyrrolopyrimidinyl, substituted or unsubstituted purinyl, substituted or unsubstituted indolizinyl, substituted or unsubstituted pyrrolopyriazinyl, substituted or unsubstituted pyrrolopyrimidinyl, substituted or unsubstituted imidazopyridazinyl, substituted or unsubstituted imidazopyridinyl, substituted or unsubstituted imidazopyrimidinyl, substituted or unsubstituted cinnolinyl, substituted or unsubstituted quinazolinyl, substituted or unsubstituted quinoxalinyl, substituted or unsubstituted phthalazinyl, substituted or unsubstituted pyridopyrazinyl, substituted or unsubstituted pteridinyl, substituted or unsubstituted pyrazolopyridinyl, substituted or unsubstituted quinolinyl, substituted or unsubstituted isoquinolinyl, substituted or unsubstituted naphthyridinyl, or substituted or unsubstituted carbazolyl. In embodiments, $R^2$ is substituted aziridinyl, substituted oxiranyl, substituted thiiranyl, substituted azetidinyl, substituted oxetanyl, substituted thietanyl, substituted pyrrolidinyl, substituted pyrrolyl, substituted imidazolyl, substituted imidazolinyl, substituted pyrazolinyl, substituted tetrahydrofuranyl, substituted thiolanyl, substituted piperidinyl, substituted piperazinyl, substituted pyranyl, substituted morpholinyl, substituted 1,4-dioxanyl, substituted tetrahydro-2H-pyranyl, substituted thianyl, or substituted dithianyl. In embodiments, $R^2$ is substituted phenyl, substituted thiofuranyl, substituted imidazolyl, substituted pyrazolyl, substituted triazolyl, substituted tetrazolyl, substituted furanyl, substituted oxazolyl, substituted isooxazolyl, substituted oxadiazolyl, substituted oxatriazolyl, substituted thienyl, substituted thiazolyl, substituted isothiazolyl, substituted pyridinyl, substituted pyrazinyl, substituted pyrimidinyl, substituted pyridazinyl, or substituted triazinyl (e.g., 1,3,5-triazinyl, 1,2,3-triazinyl, or 1,2,4-triazinyl). In embodiments, $R^2$ is substituted indolyl, substituted benzimidazolyl, substituted indazolyl, substituted benzotriazolyl, substituted pyrrolopyrimidinyl, substituted purinyl, substituted indolizinyl, substituted pyrrolopyriazinyl, substituted pyrrolopyrimidinyl, substituted imidazopyridazinyl, substituted imidazopyridinyl, substituted imidazopyrimidinyl, substituted cinnolinyl, substituted quinazolinyl, substituted quinoxalinyl, substituted phthalazinyl, substituted pyridopyrazinyl, substituted pteridinyl, substituted pyrazolopyridinyl, substituted quinolinyl, substituted isoquinolinyl, substituted naphthyridinyl, or substituted carbazolyl. In embodiments, $R^2$ is unsubstituted aziridinyl, unsubstituted oxiranyl, unsubstituted thiiranyl, unsubstituted azetidinyl, unsubstituted oxetanyl, unsubstituted thietanyl, unsubstituted pyrrolidinyl, unsubstituted pyrrolyl, unsubstituted imidazolyl, unsubstituted imidazolinyl, unsubstituted pyrazolinyl, unsubstituted tetrahydrofuranyl, unsubstituted thiolanyl, unsubstituted piperidinyl, unsubstituted piperazinyl, unsubstituted pyranyl, unsubstituted morpholinyl, unsubstituted 1,4-dioxanyl, unsubstituted tetrahydro-2H-pyranyl, unsubstituted thianyl, or unsubstituted dithianyl. In embodiments, $R^2$ is unsubstituted phenyl, unsubstituted thiofuranyl, unsubstituted imidazolyl, unsubstituted pyrazolyl, unsubstituted triazolyl, unsubstituted tetrazolyl, unsubstituted furanyl, unsubstituted oxazolyl, unsubstituted isooxazolyl, unsubstituted oxadiazolyl, unsubstituted oxatriazolyl, unsubstituted thienyl, unsubstituted thiazolyl, unsubstituted isothiazolyl, unsubstituted pyridinyl, unsubstituted pyrazinyl, unsubstituted pyrimidinyl, unsubstituted pyridazinyl, or unsubstituted triazinyl (e.g., 1,3,5-triazinyl, 1,2,3-triazinyl, or 1,2,4-triazinyl). In embodiments, $R^2$ is unsubstituted indolyl, unsubstituted benzimidazolyl, unsubstituted indazolyl, unsubstituted benzotriazolyl, unsubstituted pyrrolopyrimidinyl, unsubstituted purinyl, unsubstituted indolizinyl, unsubstituted pyrrolopyriazinyl, unsubstituted pyrrolopyrimidinyl, unsubstituted imidazopyridazinyl, unsubstituted imidazopyridinyl, unsubstituted imidazopyrimidinyl, unsubstituted cinnolinyl, unsubstituted quinazolinyl, unsubstituted quinoxalinyl, unsubstituted phthalazinyl, unsubstituted pyridopyrazinyl, unsubstituted pteridinyl, unsubstituted pyrazolopyridinyl, unsubstituted quinolinyl, unsubstituted isoquinolinyl, unsubstituted naphthyridinyl, or unsubstituted carbazolyl.

In embodiments, —($R^2$)—($R^{23}$)$_{z23}$ is:

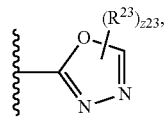

wherein $R^{23}$ and z23 are as described herein including embodiments.

In embodiments, —($R^2$)—($R^{23}$)$_{z23}$ is:

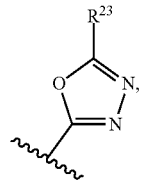

wherein $R^{23}$ is as described herein, including embodiments.

In embodiments, $R^2$ is $R^2$-substituted phenyl. In embodiments, $R^2$ is $R^{23}$-substituted 5 to 6 membered heteroaryl. $R^{23}$ is independently halogen, —$CX^{23}_3$, —$CHX^{23}_2$, —$CH_2X^{23}$, —$OCX^{23}_3$, —$OCH_2X^{23}$, —$OCHX^{23}_2$, —CN, —$SO_{n23}R^{100D}$, —$SO_{v23}NR^{100A}R^{100B}$, —NHC(O) $NR^{100A}R^{100B}$, —N(O)$_{m23}$, —$NR^{100A}R^{100B}$, —C(O)$R^{100C}$, —C(O)—$OR^{100C}$, —C(O)$NR^{100A}R^{100B}$, —$OR^{100D}$, —$NR^{100A}SO_2R^{100D}$, —$NR^{100A}C(O)R^{100C}$, —$NR^{100A}C(O)$ $OR^{100C}$, —$NR^{100A}OR^{100C}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Two adjacent $R^{23}$ substituents may optionally be joined to form a substituted or unsubstituted cycloalkyl, substituted or unsubstituted heterocycloalkyl, substituted or unsubstituted aryl, or substituted or unsubstituted heteroaryl. $R^{100A}$, $R^{100B}$ $R^{100C}$, and $R^{100D}$ are independently hydrogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{100A}$ and $R^{100B}$ substituents bonded to the same nitrogen atom may optionally be joined to form a substituted or unsubstituted heterocycloalkyl or substituted or unsubstituted heteroaryl; X and $X^{23}$ are independently —F, —Cl, —Br, or —I. The symbol n23 is independently an integer from 0 to 4. The symbols m23 and v23 are independently 1 or 2.

In embodiments, $R^{2A}$ is independently substituted or unsubstituted alkyl (e.g., $C_1$-$C_8$, $C_1$-$C_6$, $C_1$-$C_4$, or $C_1$-$C_2$). In embodiments, $R^{2A}$ is independently substituted alkyl (e.g., $C_1$-$C_8$, $C_1$-$C_6$, $C_1$-$C_4$, or $C_1$-$C_2$). In embodiments, $R^{2A}$ is independently unsubstituted alkyl (e.g., $C_1$-$C_8$, $C_1$-$C_6$, $C_1$-$C_4$, or $C_1$-$C_2$). In embodiments, $R^2$ is independently unsubstituted methyl. In embodiments, $R^{2A}$ is independently unsubstituted ethyl. In embodiments, $R^{2A}$ is independently unsubstituted propyl. In embodiments, $R^{2A}$ is independently unsubstituted isopropyl. In embodiments, $R^{2A}$ is independently unsubstituted tert-butyl. In embodiments, $R^{2A}$ is independently substituted or unsubstituted heteroalkyl (e.g., 2 to 8 membered, 2 to 6 membered, 4 to 6 membered, 2 to 3 membered, or 4 to 5 membered). In embodiments, $R^{2A}$ is independently substituted heteroalkyl (e.g., 2 to 8 membered, 2 to 6 membered, 4 to 6 membered, 2 to 3 membered, or 4 to 5 membered). In embodiments, $R^{2A}$ is independently unsubstituted heteroalkyl (e.g., 2 to 8 membered, 2 to 6 membered, 4 to 6 membered, 2 to 3 membered, or 4 to 5 membered). In embodiments, $R^2$ is independently substituted or unsubstituted cycloalkyl (e.g., $C_3$-$C_8$, $C_3$-$C_6$, $C_4$-$C_6$, or $C_5$-$C_6$). In embodiments, $R^{2A}$ is independently substituted cycloalkyl (e.g., $C_3$-$C_8$, $C_3$-$C_6$, $C_4$-$C_6$, or $C_5$-$C_6$). In embodiments, $R^{2A}$ is independently unsubstituted cycloalkyl (e.g., $C_3$-$C_8$, $C_3$-$C_6$, $C_4$-$C_6$, or $C_5$-$C_6$). In embodiments, $R^2$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{2A}$ is independently substituted heterocycloalkyl (e.g., 3 to 8 membered, 3 to 6 membered, 4 to 6 membered, 4 to 5 membered, or 5 to 6 membered). In embodiments, $R^{2A}$ is independently unsubstituted heterocycloalkyl (e.g., 3 to 8 membered, 3 to 6 membered, 4 to 6 membered, 4 to 5 membered, or 5 to 6 membered). In embodiments, $R^{2A}$ is independently substituted or unsubstituted aryl (e.g., $C_6$-$C_{10}$ or phenyl). In embodiments, $R^{2A}$ is independently substituted aryl (e.g., $C_6$-$C_{10}$ or phenyl). In embodiments, $R^{2A}$ is independently unsubstituted aryl (e.g., $C_6$-$C_{10}$ or phenyl). In embodiments, $R^{2A}$ is independently substituted or unsubstituted heteroaryl (e.g., 5 to 10 membered, 5 to 9 membered, or 5 to 6 membered).

In embodiments, $R^2$ is independently substituted heteroaryl (e.g., 5 to 10 membered, 5 to 9 membered, or 5 to 6 membered). In embodiments, $R^{2A}$ is independently unsubstituted heteroaryl (e.g., 5 to 10 membered, 5 to 9 membered, or 5 to 6 membered).

In embodiments, $R^{2A}$ is substituted or unsubstituted aryl (e.g., $C_6$-$C_{10}$ aryl, $C_{10}$ aryl, or phenyl). In embodiments, $R^{2A}$ is substituted aryl (e.g., $C_6$-$C_{10}$ aryl, $C_{10}$ aryl, or phenyl). In embodiments, $R^2$ is an unsubstituted aryl (e.g., $C_6$-$C_{10}$ aryl, $C_{10}$ aryl, or phenyl).

In embodiments, $R^{2B}$ is independently substituted or unsubstituted alkyl (e.g., $C_1$-$C_8$, $C_1$-$C_6$, $C_1$-$C_4$, or $C_1$-$C_2$). In embodiments, $R^{2B}$ is independently substituted alkyl (e.g., $C_1$-$C_8$, $C_1$-$C_6$, $C_1$-$C_4$, or $C_1$-$C_2$). In embodiments, $R^{2B}$ is independently unsubstituted alkyl (e.g., $C_1$-$C_8$, $C_1$-$C_6$, $C_1$-$C_4$, or $C_1$-$C_2$). In embodiments, $R^{2B}$ is independently unsubstituted methyl. In embodiments, $R^{2B}$ is independently unsubstituted ethyl. In embodiments, $R^{2B}$ is independently unsubstituted propyl. In embodiments, $R^{2B}$ is independently unsubstituted isopropyl. In embodiments, $R^{2B}$ is independently unsubstituted tert-butyl. In embodiments, $R^{2B}$ is independently substituted or unsubstituted heteroalkyl (e.g., 2 to 8 membered, 2 to 6 membered, 4 to 6 membered, 2 to 3 membered, or 4 to 5 membered). In embodiments, $R^{2B}$ is independently substituted heteroalkyl (e.g., 2 to 8 membered, 2 to 6 membered, 4 to 6 membered, 2 to 3 membered, or 4 to 5 membered). In embodiments, $R^{2B}$ is independently unsubstituted heteroalkyl (e.g., 2 to 8 membered, 2 to 6 membered, 4 to 6 membered, 2 to 3 membered, or 4 to 5 membered). In embodiments, $R^{2B}$ is independently substituted or unsubstituted cycloalkyl (e.g., $C_3$-$C_8$, $C_3$-$C_6$, $C_4$-$C_6$, or $C_5$-$C_6$). In embodiments, $R^{2B}$ is independently substituted cycloalkyl (e.g., $C_3$-$C_8$, $C_3$-$C_6$, $C_4$-$C_6$, or $C_5$-$C_6$). In embodiments, $R^{2B}$ is independently unsubstituted cycloalkyl (e.g., $C_3$-$C_8$, $C_3$-$C_6$, $C_4$-$C_6$, or $C_5$-$C_6$). In embodiments, $R^{2B}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{2B}$ is independently substituted heterocycloalkyl (e.g., 3 to 8 membered, 3 to 6 membered, 4 to 6 membered, 4 to 5 membered, or 5 to 6 membered). In embodiments, $R^{2B}$ is independently unsubstituted heterocycloalkyl (e.g., 3 to 8 membered, 3 to 6 membered, 4 to 6 membered, 4 to 5 membered, or 5 to 6 membered). In embodiments, $R^{2B}$ is independently substituted or unsubstituted aryl (e.g., $C_6$-$C_{10}$ or phenyl). In embodiments, $R^{2B}$ is independently substituted aryl (e.g., $C_6$-$C_{10}$ or phenyl). In embodiments, $R^{2B}$ is independently unsubstituted aryl (e.g., $C_6$-$C_{10}$ or phenyl). In embodiments, $R^{2B}$ is independently substituted or unsubstituted heteroaryl (e.g., 5 to 10 membered, 5 to 9 membered, or 5 to 6 membered). In embodiments, $R^{2B}$ is independently substituted heteroaryl (e.g., 5 to 10 membered, 5 to 9 membered, or 5 to 6 membered). In embodiments, $R^{2B}$ is independently unsubstituted heteroaryl (e.g., 5 to 10 membered, 5 to 9 membered, or 5 to 6 membered).

In embodiments, $R^{2A}$ and $R^{2B}$ substituents bonded to the same nitrogen atom may be joined to form a substituted or unsubstituted heterocycloalkyl (e.g., 3 to 8 membered, 3 to 6 membered, 4 to 6 membered, 4 to 5 membered, or 5 to 6 membered). In embodiments, $R^{2A}$ and $R^{2B}$ substituents bonded to the same nitrogen atom may be joined to form a substituted heterocycloalkyl (e.g., 3 to 8 membered, 3 to 6 membered, 4 to 6 membered, 4 to 5 membered, or 5 to 6 membered). In embodiments, $R^{2A}$ and $R^{2B}$ substituents bonded to the same nitrogen atom may be joined to form an unsubstituted heterocycloalkyl (e.g., 3 to 8 membered, 3 to 6 membered, 4 to 6 membered, 4 to 5 membered, or 5 to 6 membered).

In embodiments, $R^{2A}$ and $R^{2B}$ substituents bonded to the same nitrogen atom may be joined to form a substituted or unsubstituted heteroaryl (e.g., 5 to 10 membered, 5 to 9 membered, or 5 to 6 membered). In embodiments, $R^{2A}$ and $R^{2B}$ substituents bonded to the same nitrogen atom may be joined to form a substituted heteroaryl (e.g., 5 to 10 membered, 5 to 9 membered, or 5 to 6 membered). In embodiments, $R^{2A}$ and $R^{2B}$ substituents bonded to the same nitrogen atom may be joined to form an unsubstituted heteroaryl (e.g., 5 to 10 membered, 5 to 9 membered, or 5 to 6 membered).

In embodiments, $R^{2C}$ is independently substituted or unsubstituted alkyl (e.g., $C_1$-$C_8$, $C_1$-$C_6$, $C_1$-$C_4$, or $C_1$-$C_2$). In embodiments, $R^{2C}$ is independently substituted alkyl (e.g., $C_1$-$C_8$, $C_1$-$C_6$, $C_1$-$C_4$, or $C_1$-$C_2$). In embodiments, $R^{2C}$ is independently unsubstituted alkyl (e.g., $C_1$-$C_8$, $C_1$-$C_6$, $C_1$-$C_4$, or $C_1$-$C_2$). In embodiments, $R^{2C}$ is independently unsubstituted methyl. In embodiments, $R^{2C}$ is independently unsubstituted ethyl. In embodiments, $R^{2C}$ is independently unsubstituted propyl. In embodiments, $R^{2C}$ is independently unsubstituted isopropyl. In embodiments, $R^{2C}$ is independently unsubstituted tert-butyl. In embodiments, $R^{2C}$ is independently substituted or unsubstituted heteroalkyl (e.g., 2 to 8 membered, 2 to 6 membered, 4 to 6 membered, 2 to 3 membered, or 4 to 5 membered). In embodiments, $R^{2C}$ is independently substituted heteroalkyl (e.g., 2 to 8 membered, 2 to 6 membered, 4 to 6 membered, 2 to 3 membered, or 4 to 5 membered). In embodiments, $R^{2C}$ is independently unsubstituted heteroalkyl (e.g., 2 to 8 membered, 2 to 6 membered, 4 to 6 membered, 2 to 3 membered, or 4 to 5 membered). In embodiments, $R^{2C}$ is independently substituted or unsubstituted cycloalkyl (e.g., $C_3$-$C_8$, $C_3$-$C_6$, $C_4$-$C_6$, or $C_5$-$C_6$). In embodiments, $R^{2C}$ is independently substituted cycloalkyl (e.g., $C_3$-$C_8$, $C_3$-$C_6$, $C_4$-$C_6$, or $C_5$-$C_6$). In embodiments, $R^{2C}$ is independently unsubstituted cycloalkyl (e.g., $C_3$-$C_8$, $C_3$-$C_6$, $C_4$-$C_6$, or $C_5$-$C_6$). In embodiments, $R^{2C}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{2C}$ is independently substituted heterocycloalkyl (e.g., 3 to 8 membered, 3 to 6 membered, 4 to 6 membered, 4 to 5 membered, or 5 to 6 membered). In embodiments, $R^{2C}$ is independently unsubstituted heterocycloalkyl (e.g., 3 to 8 membered, 3 to 6 membered, 4 to 6 membered, 4 to 5 membered, or 5 to 6 membered). In embodiments, $R^{2C}$ is independently substituted or unsubstituted aryl (e.g., $C_6$-$C_{10}$ or phenyl). In embodiments, $R^{2C}$ is independently substituted aryl (e.g., $C_6$-$C_{10}$ or phenyl). In embodiments, $R^{2C}$ is independently unsubstituted aryl (e.g., $C_6$-$C_{10}$ or phenyl). In embodiments, $R^{2C}$ is independently substituted or unsubstituted heteroaryl (e.g., 5 to 10 membered, 5 to 9 membered, or 5 to 6 membered). In embodiments, $R^{2C}$ is independently substituted heteroaryl (e.g., 5 to 10 membered, 5 to 9 membered, or 5 to 6 membered). In embodiments, $R^{2C}$ is independently unsubstituted heteroaryl (e.g., 5 to 10 membered, 5 to 9 membered, or 5 to 6 membered).

In embodiments, $R^{2D}$ is independently substituted or unsubstituted alkyl (e.g., $C_1$-$C_8$, $C_1$-$C_6$, $C_1$-$C_4$, or $C_1$-$C_2$). In embodiments, $R^{2D}$ is independently substituted alkyl (e.g., $C_1$-$C_8$, $C_1$-$C_6$, $C_1$-$C_4$, or $C_1$-$C_2$). In embodiments, $R^{2D}$ is independently unsubstituted alkyl (e.g., $C_1$-$C_8$, $C_1$-$C_6$, $C_1$-$C_4$, or $C_1$-$C_2$). In embodiments, $R^{2D}$ is independently unsubstituted methyl. In embodiments, $R^{2D}$ is independently unsubstituted ethyl. In embodiments, $R^{2D}$ is independently unsubstituted propyl. In embodiments, $R^{2D}$ is independently unsubstituted isopropyl. In embodiments, $R^{2D}$ is independently unsubstituted tert-butyl. In embodiments, $R^{2D}$ is independently substituted or unsubstituted heteroalkyl (e.g., 2 to 8 membered, 2 to 6 membered, 4 to 6 membered, 2 to 3 membered, or 4 to 5 membered). In embodiments, $R^{2D}$ is independently substituted heteroalkyl (e.g., 2 to 8 membered, 2 to 6 membered, 4 to 6 membered, 2 to 3 membered, or 4 to 5 membered). In embodiments, $R^{2D}$ is independently unsubstituted heteroalkyl (e.g., 2 to 8 membered, 2 to 6 membered, 4 to 6 membered, 2 to 3 membered, or 4 to 5 membered). In embodiments, $R^{2D}$ is independently substituted or unsubstituted cycloalkyl (e.g., $C_3$-$C_8$, $C_3$-$C_6$, $C_4$-$C_6$, or $C_5$-$C_6$). In embodiments, $R^{2D}$ is independently substituted cycloalkyl (e.g., $C_3$-$C_8$, $C_3$-$C_6$, $C_4$-$C_6$, or $C_5$-$C_6$). In embodiments, $R^{2D}$ is independently unsubstituted cycloalkyl (e.g., $C_3$-$C_8$, $C_3$-$C_6$, $C_4$-$C_6$, or $C_5$-$C_6$). In embodiments, $R^{2D}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{2D}$ is independently substituted heterocycloalkyl (e.g., 3 to 8 membered, 3 to 6 membered, 4 to 6 membered, 4 to 5 membered, or 5 to 6 membered). In embodiments, $R^{2D}$ is independently unsubstituted heterocycloalkyl (e.g., 3 to 8 membered, 3 to 6 membered, 4 to 6 membered, 4 to 5 membered, or 5 to 6 membered). In embodiments, $R^{2D}$ is independently substituted or unsubstituted aryl (e.g., $C_6$-$C_{10}$ or phenyl). In embodiments, $R^{2D}$ is independently substituted aryl (e.g., $C_6$-$C_{10}$ or phenyl). In embodiments, $R^{2D}$ is independently unsubstituted aryl (e.g., $C_6$-$C_{10}$ or phenyl). In embodiments, $R^{2D}$ is independently substituted or unsubstituted heteroaryl (e.g., 5 to 10 membered, 5 to 9 membered, or 5 to 6 membered). In embodiments, $R^{2D}$ is independently substituted heteroaryl (e.g., 5 to 10 membered, 5 to 9 membered, or 5 to 6 membered). In embodiments, $R^{2D}$ is independently unsubstituted heteroaryl (e.g., 5 to 10 membered, 5 to 9 membered, or 5 to 6 membered).

In embodiments, $R^2$ is independently hydrogen, halogen, $-CX^2_3$, $-CHX^2_2$, $-CH_2X^2$, $-OCX^2_3$, $-OCH_2X^2$, $-OCHX^2_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, $R^2$-substituted or unsubstituted alkyl (e.g., $C_1$-$C_8$, $C_1$-$C_6$, $C_1$-$C_4$, or $C_1$-$C_2$), $R^{23}$-substituted or unsubstituted heteroalkyl (e.g., 2 to 8 membered, 2 to 6 membered, 4 to 6 membered, 2 to 3 membered, or 4 to 5 membered), $R^{23}$-substituted or unsubstituted cycloalkyl (e.g., $C_3$-$C_8$, $C_3$-$C_6$, $C_4$-$C_6$, or $C_5$-$C_6$), $R^{23}$-substituted or unsubstituted heterocycloalkyl (e.g., 3 to 8 membered, 3 to 6 membered, 4 to 6 membered, 4 to 5 membered, or 5 to 6 membered), $R^{23}$-substituted or unsubstituted aryl (e.g., $C_6$-$C_{10}$ or phenyl), or $R^{23}$-substituted or unsubstituted heteroaryl (e.g., 5 to 10 membered, 5 to 9 membered, or 5 to 6 membered). In embodiments, $R^2$ is independently hydrogen, halogen, $-CX^2_3$, $-CHX^2_2$, $-CH_2X^2$, $-OCX^2_3$, $-OCH_2X^2$, $-OCHX^2_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^2$ is independently $-F$, $-Cl$, $-Br$, or $-I$.

In embodiments, $R^2$ is independently hydrogen. In embodiments, $R^2$ is independently $R^{23}$-substituted methyl. In embodiments, $R^2$ is independently $R^{23}$-substituted ethyl. In embodiments, $R^2$ is independently unsubstituted methyl. In embodiments, $R^2$ is independently unsubstituted ethyl.

$R^{23}$ is independently oxo, halogen, $-CX^{23}_3$, $-CHX^{23}_2$, $-CH_2X^2$, $-OCX^{23}_3$, $-OCH_2X^{23}$, $-OCHX^{23}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, $R^{24}$-substituted or unsubstituted alkyl (e.g., $C_1$-$C_8$, $C_1$-$C_6$, $C_1$-$C_4$, or $C_1$-$C_2$), $R^{24}$-substituted or unsubstituted heteroalkyl (e.g., 2 to 8 membered, 2 to 6 membered, 4 to 6 membered, 2 to 3 membered, or 4 to 5 membered), $R^{24}$-substituted or unsubstituted cycloalkyl (e.g., $C_3$-$C_8$, $C_3$-$C_6$, $C_4$-$C_6$, or $C_5$-$C_6$), $R^{24}$-substituted or unsubstituted heterocycloalkyl (e.g., 3 to 8 membered, 3 to 6 membered, 4 to 6 membered, 4 to 5 membered, or 5 to 6 membered), $R^{24}$-substituted or unsubstituted aryl (e.g., $C_6$-$C_{10}$ or phenyl), or $R^2$-substituted or unsubstituted heteroaryl (e.g., 5 to 10 membered, 5 to 9 membered, or 5 to 6 membered). In embodiments, $R^2$ is independently oxo, halogen, $-CX^{23}_3$, $-CHX^{23}_2$, $-CH_2X^3$, $-OCX^{23}_3$, $-OCH_2X^{23}$, $-OCHX^{23}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{23}$ is independently $-F$, $-Cl$, $-Br$, or $-I$.

In embodiments, $R^{23}$ is halogen or $-CX^{23}_3$. In embodiments, $R^{23}$ is independently unsubstituted methyl. In embodiments, $R^{23}$ is independently unsubstituted ethyl. In embodiments, $R^{23}$ is hydrogen. In embodiments, $R^{23}$ is unsubstituted phenyl. In embodiments, $R^{23}$ is unsubstituted thiophenyl. In embodiments, $R^{23}$ is $R^{24}$-substituted aryl. In embodiments, $R^{23}$ is unsubstituted thienyl. In embodiments, $R^{23}$ is substituted phenyl. In embodiments, $R^{23}$ is $R^{24}$-substituted phenyl.

$R^{24}$ is independently oxo, halogen, $-CX^{24}_3$, $-CHX^{24}_2$, $-CH_2X^{24}$, $-OCX^{24}_3$, $-OCH_2X^{24}$, $-OCHX^{24}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, —NHC=(O)NH$_2$, —NHSO$_2$H, —NHC=(O)H, —NHC(O)—OH, —NHOH, —N$_3$, R$^{25}$-substituted or unsubstituted alkyl (e.g., C$_1$-C$_8$, C$_1$-C$_6$, C$_1$-C$_4$, or C$_1$-C$_2$), R$^{25}$-substituted or unsubstituted heteroalkyl (e.g., 2 to 8 membered, 2 to 6 membered, 4 to 6 membered, 2 to 3 membered, or 4 to 5 membered), R$^{25}$-substituted or unsubstituted cycloalkyl (e.g., C$_3$-C$_8$, C$_3$-C$_6$, C$_4$-C$_6$, or C$_5$-C$_6$), R$^{25}$-substituted or unsubstituted heterocycloalkyl (e.g., 3 to 8 membered, 3 to 6 membered, 4 to 6 membered, 4 to 5 membered, or 5 to 6 membered), R$^{25}$-substituted or unsubstituted aryl (e.g., C$_6$-C$_{10}$ or phenyl), or R$^{25}$-substituted or unsubstituted heteroaryl (e.g., 5 to 10 membered, 5 to 9 membered, or 5 to 6 membered). In embodiments, R$^{24}$ is independently oxo, halogen, —CX$^{24}$$_3$, —CHX$^{24}$$_2$, —CH$_2$X$^{24}$, —OCX$^{24}$$_3$, —OCH$_2$X$^{24}$, —OCHX$^{24}$$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered). X$^{24}$ is independently —F, —Cl, —Br, or —I.

In embodiments, R$^{24}$ is hydrogen. In embodiments, R$^{24}$ is —OCH$_3$. In embodiments, R$^{24}$ is halogen. In embodiments, R$^{24}$ is —CF$_3$. In embodiments, R$^{24}$ is —Br. In embodiments, R$^{24}$ is —I. In embodiments, R$^{24}$ is unsubstituted 2 to 4 membered heteroalkyl. In embodiments, R$^{24}$ is unsubstituted C$_1$-C$_4$ alkoxy.

R$^{25}$ is independently oxo, halogen, —CX$^{25}$$_3$, —CHX$^{25}$$_2$, —CH$_2$X$^{25}$, —OCX$^{25}$$_3$, —OCH$_2$X$^{25}$, —OCHX$^{25}$$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered). X$^{25}$ is independently —F, —Cl, —Br, or —I.

In embodiments, R$^{25}$ is independently unsubstituted methyl. In embodiments, R$^{25}$ is independently unsubstituted ethyl.

In embodiments, R$^{2A}$ is independently hydrogen, —CX$^{2A}$$_3$, —CHX$^{2A}$$_2$, —CH$_2$X$^{2A}$, —CN, —COOH, —CONH$_2$, R$^{23A}$-substituted or unsubstituted alkyl (e.g., C$_1$-C$_8$, C$_1$-C$_6$, C$_1$-C$_4$, or C$_1$-C$_2$), R$^{23A}$-substituted or unsubstituted heteroalkyl (e.g., 2 to 8 membered, 2 to 6 membered, 4 to 6 membered, 2 to 3 membered, or 4 to 5 membered), R$^{23A}$-substituted or unsubstituted cycloalkyl (e.g., C$_3$-C$_8$, C$_3$-C$_6$, C$_4$-C$_6$, or C$_5$-C$_6$), R$^{23A}$-substituted or unsubstituted heterocycloalkyl (e.g., 3 to 8 membered, 3 to 6 membered, 4 to 6 membered, 4 to 5 membered, or 5 to 6 membered), R$^{23A}$-substituted or unsubstituted aryl (e.g., C$_6$-C$_{10}$ or phenyl), or R$^{23A}$-substituted or unsubstituted heteroaryl (e.g., 5 to 10 membered, 5 to 9 membered, or 5 to 6 membered). In embodiments, R$^{2A}$ is independently hydrogen, —CX$^{2A}$$_3$, —CHX$^{2A}$$_2$, —CH$_2$X$^{2A}$, —CN, —COOH, —CONH$_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered). X2 is independently —F, —Cl, —Br, or —I.

In embodiments, R$^{2A}$ is independently hydrogen. In embodiments, R$^{2A}$ is independently unsubstituted methyl. In embodiments, R$^{2A}$ is independently unsubstituted ethyl.

In embodiments, R$^{2A}$ and R$^{2B}$ substituents bonded to the same nitrogen atom may optionally be joined to form a R$^{23A}$-substituted or unsubstituted heterocycloalkyl (e.g., 3 to 8 membered, 3 to 6 membered, 4 to 6 membered, 4 to 5 membered, or 5 to 6 membered) or R$^{23A}$-substituted or unsubstituted heteroaryl (e.g., 5 to 10 membered, 5 to 9 membered, or 5 to 6 membered). In embodiments, R$^{2A}$ and R$^{2B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 10 membered, 5 to 9 membered, or 5 to 6 membered). In embodiments, R$^{2A}$ and R$^{2B}$ substituents bonded to the same nitrogen atom may optionally be joined to form a R$^{23A}$-substituted or unsubstituted heterocycloalkyl (e.g., 3 to 8 membered, 3 to 6 membered, 4 to 6 membered, 4 to 5 membered, or 5 to 6 membered). In embodiments, R$^{2A}$ and R$^{2B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

R$^{23A}$ is independently oxo, halogen, —CX$^{23A}$$_3$, —CHX$^{23A}$$_2$, —CH$_2$X$^{23A}$, —OCX$^{23A}$$_3$, —OCH$_2$X$^{23A}$, —OCHX$^{23A}$$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, R$^{24A}$-substituted or unsubstituted alkyl (e.g., C$_1$-C$_8$, C$_1$-C$_5$, C$_1$-C$_4$, or C$_1$-C$_2$), R$^{24A}$-substituted or unsubstituted heteroalkyl (e.g., 2 to 8 membered, 2 to 6 membered, 4 to 6 membered, 2 to 3 membered, or 4 to 5 membered), R$^{24A}$-substituted or unsubstituted cycloalkyl (e.g., C$_3$-C$_8$, C$_3$-C$_6$, C$_4$-C$_6$, or C$_5$-C$_6$), R$^{24A}$-substituted or unsubstituted heterocycloalkyl (e.g., 3 to 8 membered, 3 to 6 membered, 4 to 6 membered, 4 to 5 membered, or 5 to 6 membered), R$^{24}$-substituted or unsubstituted aryl (e.g., C$_6$-C$_0$ or phenyl), or R$^{24A}$-substituted or unsubstituted heteroaryl (e.g., 5 to 10 membered, 5 to 9 membered, or 5 to 6 membered). In embodiments, R$^{23A}$ is independently oxo, halogen, —CX$^{23A}$$_3$, —CHX$^{23A}$$_2$, —CH$_2$X$^{23A}$, —OCX$^{23A}$$_3$, —OCH$_2$X$^{23A}$, —OCHX$^{23A}$$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC—(O)NHNH$_2$, —NHC=(O)NH$_2$, —NHSO$_2$H, —NHC=(O)H, —NHC(O)—OH, —NHOH, —N$_3$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{23A}$ is independently —F, —Cl, —Br, or —I.

In embodiments, $R^{23A}$ is independently unsubstituted methyl. In embodiments, $R^{23A}$ is independently unsubstituted ethyl.

$R^{24A}$ is independently oxo, halogen, —$CX^{24A}_3$, —$CHX^{24A}_2$, —$CH_2X^{24A}$, —$OCX^{24A}_3$, —$OCH_2X^{24A}$, —$OCHX^{24A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, $R^{25A}$-substituted or unsubstituted alkyl (e.g., $C_1$-$C_8$, $C_1$-$C_6$, $C_1$-$C_4$, or $C_1$-$C_2$), $R^{25A}$-substituted or unsubstituted heteroalkyl (e.g., 2 to 8 membered, 2 to 6 membered, 4 to 6 membered, 2 to 3 membered, or 4 to 5 membered), $R^{25A}$-substituted or unsubstituted cycloalkyl (e.g., $C_3$-$C_8$, $C_3$-$C_6$, $C_4$-$C_6$, or $C_5$-$C_6$), $R^{25A}$-substituted or unsubstituted heterocycloalkyl (e.g., 3 to 8 membered, 3 to 6 membered, 4 to 6 membered, 4 to 5 membered, or 5 to 6 membered), $R^{25A}$-substituted or unsubstituted aryl (e.g., $C_6$-$C_{10}$ or phenyl), or $R^{25A}$-substituted or unsubstituted heteroaryl (e.g., 5 to 10 membered, 5 to 9 membered, or 5 to 6 membered). In embodiments, $R^{24A}$ is independently oxo, halogen, —$CX^{24A}_3$, —$CHX^{24A}_2$, —$CH_2X^{24A}$, —$OCX^{24A}_3$, —$OCH_2X^{24A}$, —$OCHX^{24A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{24A}$ is independently —F, —Cl, —Br, or —I.

$R^{25A}$ is independently oxo, halogen, —$CX^{25A}_3$, —$CHX^{25A}_2$, —$CH_2X^{25A}$, —$OCX^{25A}_3$, —$OCH_2X^{25A}$, —$OCHX^{25A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{25A}$ is independently —F, —Cl, —Br, or —I.

In embodiments, $R^{2B}$ is independently hydrogen, —$CX^{2B}_3$, —$CHX^{2B}_2$, —$CH_2X^B$, —CN, —COOH, —$CONH_2$, $R^{23B}$-substituted or unsubstituted alkyl (e.g., $C_1$-$C_8$, $C_1$-$C_6$, $C_1$-$C_4$, or $C_1$-$C_2$), $R^{23B}$-substituted or unsubstituted heteroalkyl (e.g., 2 to 8 membered, 2 to 6 membered, 4 to 6 membered, 2 to 3 membered, or 4 to 5 membered), $R^{23B}$-substituted or unsubstituted cycloalkyl (e.g., $C_3$-$C_8$, $C_3$-$C_6$, $C_4$-$C_6$, or $C_5$-$C_6$), $R^{23B}$-substituted or unsubstituted heterocycloalkyl (e.g., 3 to 8 membered, 3 to 6 membered, 4 to 6 membered, 4 to 5 membered, or 5 to 6 membered), $R^{23B}$-substituted or unsubstituted aryl (e.g., $C_6$-$C_{10}$ or phenyl), or $R^{23B}$-substituted or unsubstituted heteroaryl (e.g., 5 to 10 membered, 5 to 9 membered, or 5 to 6 membered). In embodiments, $R^{23B}$ is independently hydrogen, —$CX^{2B}_3$, —$CHX^{2B}_2$, —$CH_2X^{2B}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{2B}$ is independently —F, —Cl, —Br, or —I.

In embodiments, $R^{2B}$ is independently hydrogen. In embodiments, $R^{2B}$ is independently unsubstituted methyl. In embodiments, $R^{2B}$ is independently unsubstituted ethyl.

In embodiments, $R^{2A}$ and $R^{2B}$ substituents bonded to the same nitrogen atom may optionally be joined to form a $R^{23B}$-substituted or unsubstituted heterocycloalkyl (e.g., 3 to 8 membered, 3 to 6 membered, 4 to 6 membered, 4 to 5 membered, or 5 to 6 membered) or $R^{23B}$-substituted or unsubstituted heteroaryl (e.g., 5 to 10 membered, 5 to 9 membered, or 5 to 6 membered). In embodiments, $R^{2A}$ and $R^{2B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 10 membered, 5 to 9 membered, or 5 to 6 membered). In embodiments, $R^{2A}$ and $R^{2B}$ substituents bonded to the same nitrogen atom may optionally be joined to form a $R^{23B}$-substituted or unsubstituted heterocycloalkyl (e.g., 3 to 8 membered, 3 to 6 membered, 4 to 6 membered, 4 to 5 membered, or 5 to 6 membered). In embodiments, $R^{2A}$ and $R^{2B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

$R^{23B}$ is independently oxo, halogen, —$CX^{23B}_3$, —$CHX^{23B}_2$, —$CH_2X^{23B}$, —$OCX^{23B}_3$, —$OCH_2X^{23B}$, —$OCHX^{23B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, $R^{24B}$-substituted or unsubstituted alkyl (e.g., $C_1$-$C_8$, $C_1$-$C_6$, $C_1$-$C_4$, or $C_1$-$C_2$), $R^{24B}$-substituted or unsubstituted heteroalkyl (e.g., 2 to 8 membered, 2 to 6 membered, 4 to 6 membered, 2 to 3 membered, or 4 to 5 membered), $R^{24B}$-substituted or unsubstituted cycloalkyl (e.g., $C_3$-$C_8$, $C_3$-$C_6$, $C_4$-$C_6$, or $C_5$-$C_6$), $R^{24B}$-substituted or unsubstituted heterocycloalkyl (e.g., 3 to 8 membered, 3 to 6 membered, 4 to 6 membered, 4 to 5 membered, or 5 to 6 membered), $R^{24B}$-substituted or unsubstituted aryl (e.g., $C_6$-$C_{10}$ or phenyl), or $R^{24B}$-substituted or unsubstituted heteroaryl (e.g., 5 to 10 membered, 5 to 9 membered, or 5 to 6 membered). In embodiments, $R^{3B}$ is independently oxo, halogen, —$CX^{23B}_3$, —$CHX^{23B}_2$, —$CH_2X^{23B}$, —$OCX^{23B}_3$, —$OCH_2X^{23B}$, —$OCHX^{23B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{23B}$ is independently —F, —Cl, —Br, or —I.

In embodiments, $R^{23B}$ is independently unsubstituted methyl. In embodiments, $R^{23B}$ is independently unsubstituted ethyl.

$R^{24B}$ is independently oxo, halogen, —$CX^{24B}_3$, —$CHX^{24B}_2$, —$CH_2X^{24B}$, —$OCX^{24B}_3$, —$OCH_2X^{24B}$, —$OCHX^{24B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, $R^{25B}$-substituted or unsubstituted alkyl (e.g., $C_1$-$C_8$, $C_1$-$C_6$, $C_1$-$C_4$, or $C_1$-$C_2$), $R^{25B}$-substituted or unsubstituted heteroalkyl (e.g., 2 to 8 membered, 2 to 6 membered, 4 to 6 membered, 2 to 3 membered, or 4 to 5 membered), $R^{25B}$-substituted or unsubstituted cycloalkyl (e.g., $C_3$-$C_8$, $C_3$-$C_6$, $C_4$-$C_6$, or $C_5$-$C_6$), $R^{25B}$-substituted or unsubstituted heterocycloalkyl (e.g., 3 to 8 membered, 3 to 6 membered, 4 to 6 membered, 4 to 5 membered, or 5 to 6 membered), $R^{25B}$-substituted or unsubstituted aryl (e.g., $C_6$-$C_{10}$ or phenyl), or $R^{25B}$-substituted or unsubstituted heteroaryl (e.g., 5 to 10 membered, 5 to 9 membered, or 5 to 6 membered). In embodiments, $R^{24B}$ is independently oxo, halogen, —$CX^{24B}_3$, —$CHX^{24B}_2$, —$CH_2X^{24B}$, —$OCX^{24B}_3$, —$OCH_2X^{24B}$, —$OCHX^{24B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{24B}$ is independently —F, —Cl, —Br, or —I.

$R^{25B}$ is independently oxo, halogen, —$CX^{25B}_3$, —$CHX^{25B}_2$, —$CH_2X^{25B}$, —$OCX^{25B}_3$, —$OCH_2X^{25B}$, —$OCHX^{25B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{25B}$ is independently —F, —Cl, —Br, or —I.

In embodiments, $R^{2C}$ is independently hydrogen, —$CX^{2C}_3$, —$CHX^{2C}_2$, —$CH_2X^{2C}$, —CN, —COOH, —$CONH_2$, $R^{23C}$-substituted or unsubstituted alkyl (e.g., $C_1$-$C_8$, $C_1$-$C_6$, $C_1$-$C_4$, or $C_1$-$C_2$), $R^{23C}$-substituted or unsubstituted heteroalkyl (e.g., 2 to 8 membered, 2 to 6 membered, 4 to 6 membered, 2 to 3 membered, or 4 to 5 membered), $R^{23C}$-substituted or unsubstituted cycloalkyl (e.g., $C_3$-$C_8$, $C_3$-$C_6$, $C_4$-$C_6$, or $C_5$-$C_6$), $R^{23C}$-substituted or unsubstituted heterocycloalkyl (e.g., 3 to 8 membered, 3 to 6 membered, 4 to 6 membered, 4 to 5 membered, or 5 to 6 membered), $R^{23C}$-substituted or unsubstituted aryl (e.g., $C_6$-$C_{10}$ or phenyl), or $R^{23C}$-substituted or unsubstituted heteroaryl (e.g., 5 to 10 membered, 5 to 9 membered, or 5 to 6 membered). In embodiments, $R^{2C}$ is independently hydrogen, —$CX^{2C}_3$, —$CHX^{2C}_2$, —$CH_2X^{2C}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{2C}$ is independently —F, —Cl, —Br, or —I.

In embodiments, $R^{2C}$ is independently hydrogen. In embodiments, $R^{2C}$ is independently unsubstituted methyl. In embodiments, $R^{2C}$ is independently unsubstituted ethyl.

$R^{23C}$ is independently oxo, halogen, —$CX^{23C}_3$, —$CHX^{23C}_2$, —$CH_2X^{23C}$, —$OCX^{23C}_3$, —$OCH_2X^{23C}$, —$OCHX^{23C}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, $R^{24C}$-substituted or unsubstituted alkyl (e.g., $C_1$-$C_8$, $C_1$-$C_6$, $C_1$-$C_4$, or $C_1$-$C_2$), $R^{24C}$-substituted or unsubstituted heteroalkyl (e.g., 2 to 8 membered, 2 to 6 membered, 4 to 6 membered, 2 to 3 membered, or 4 to 5 membered), $R^{24C}$-substituted or unsubstituted cycloalkyl (e.g., $C_3$-$C_8$, $C_3$-$C_6$, $C_4$-$C_6$, or $C_5$-$C_6$), $R^{24C}$-substituted or unsubstituted heterocycloalkyl (e.g., 3 to 8 membered, 3 to 6 membered, 4 to 6 membered, 4 to 5 membered, or 5 to 6 membered), $R^{24C}$-substituted or unsubstituted aryl (e.g., $C_6$-$C_{10}$ or phenyl), or $R^{24C}$-substituted or unsubstituted heteroaryl (e.g., 5 to 10 membered, 5 to 9 membered, or 5 to 6 membered). In embodiments, $R^{23C}$ is independently oxo, halogen, —$CX^{23C}_3$, —$CHX^{23C}_2$, —$CH_2X^{23C}$, —$OCX^{23C}_3$, —$OCH_2X^{23C}$, —$OCHX^{23C}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{23C}$ is independently —F, —Cl, —Br, or —I.

In embodiments, $R^{23C}$ is independently unsubstituted methyl. In embodiments, $R^{23C}$ is independently unsubstituted ethyl.

$R^{24C}$ is independently oxo, halogen, —$CX^{24C}_3$, —$CHX^{24C}_2$, —$CH_2X^{24C}$, —$OCX^{24C}_3$, —$OCH_2X^{24C}$, —$OCHX^{24C}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, $R^{25C}$-substituted or unsubstituted alkyl (e.g., $C_1$-$C_8$, $C_1$-$C_6$, $C_1$-$C_4$, or $C_1$-$C_2$), $R^{25C}$-substituted or unsubstituted heteroalkyl (e.g., 2 to 8 membered, 2 to 6 membered, 4 to 6 membered, 2 to 3 membered, or 4 to 5 membered), $R^{25C}$-substituted or unsubstituted cycloalkyl (e.g., $C_3$-$C_8$, $C_3$-$C_6$, $C_4$-$C_6$, or $C_5$-$C_6$), $R^{25C}$-substituted or unsubstituted heterocycloalkyl (e.g., 3 to 8 membered, 3 to 6 membered, 4 to 6 membered, 4 to 5 membered, or 5 to 6 membered), $R^{25C}$-substituted or unsubstituted aryl (e.g., $C_6$-$C_{10}$ or phenyl), or $R^{25C}$-substituted or unsubstituted heteroaryl (e.g., 5 to 10 membered, 5 to 9 membered, or 5 to 6 membered). In embodiments, $R^{24C}$ is independently oxo,
halogen, —$CX^{24C}_3$, —$CHX^{24C}_2$, —$CH_2X^{24C}$, —$OCX^{24C}_3$, —$OCH_2X^{24C}$, —$OCHX^{24C}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$—C, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{24C}$ is independently —F, —Cl, —Br, or —I.

$R^{25C}$ is independently oxo,
halogen, —$CX^{25C}_3$, —$CHX^{25C}_2$, —$CH_2X^{25C}$, —$OCX^{25C}_3$, —$OCH_2X^{25C}$, —$OCHX^{25C}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_0$ or phenyl), or unsubstituted heteroaryl (e.g., 5 to 10 membered, 5 to 9 membered, or 5 to 6 membered). $X^{25C}$ is independently —F, —Cl, —Br, or —I.

In embodiments, $R^{2D}$ is independently hydrogen, —$CX^{2D}_3$, —$CHX^{2D}_2$, —$CH_2X^{2D}$, —CN, —COOH, —$CONH_2$, $R^{23D}$-substituted or unsubstituted alkyl (e.g., $C_1$-$C_8$, $C_1$-$C_6$, $C_1$-$C_4$, or $C_1$-$C_2$), $R^{23D}$-substituted or unsubstituted heteroalkyl (e.g., 2 to 8 membered, 2 to 6 membered, 4 to 6 membered, 2 to 3 membered, or 4 to 5 membered), $R^{23D}$-substituted or unsubstituted cycloalkyl (e.g., $C_3$-$C_8$, $C_3$-$C_6$, $C_4$-$C_6$, or $C_5$-$C_6$), $R^{23D}$-substituted or unsubstituted heterocycloalkyl (e.g., 3 to 8 membered, 3 to 6 membered, 4 to 6 membered, 4 to 5 membered, or 5 to 6 membered), $R^{23D}$-substituted or unsubstituted aryl (e.g., $C_6$-$C_0$ or phenyl), or $R^{23D}$-substituted or unsubstituted heteroaryl (e.g., 5 to 10 membered, 5 to 9 membered, or 5 to 6 membered). In embodiments, $R^{2D}$ is independently hydrogen, —$CX^{2D}_3$, —$CHX^{2D}_2$, —$CH_2X^{2D}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{2D}$ is independently —F, —Cl, —Br, or —I.

In embodiments, $R^{2D}$ is independently hydrogen. In embodiments, $R^{2D}$ is independently unsubstituted methyl. In embodiments, $R^{2D}$ is independently unsubstituted ethyl.

$R^{23D}$ is independently oxo,
halogen, —$CX^{23D}_3$, —$CHX^{23D}_2$, —$CH_2X^{23D}$, —$OCX^{23D}_3$, —$OCH_2X^{23D}$, —$OCHX^{23D}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, $R^{24D}$-substituted or unsubstituted alkyl (e.g., $C_1$-$C_8$, $C_1$-$C_6$, $C_1$-$C_4$, or $C_1$-$C_2$), $R^{24D}$-substituted or unsubstituted heteroalkyl (e.g., 2 to 8 membered, 2 to 6 membered, 4 to 6 membered, 2 to 3 membered, or 4 to 5 membered), $R^{24D}$-substituted or unsubstituted cycloalkyl (e.g., $C_3$-$C_8$, $C_3$-$C_6$, $C_4$-$C_6$, or $C_5$-$C_6$), $R^{24D}$-substituted or unsubstituted heterocycloalkyl (e.g., 3 to 8 membered, 3 to 6 membered, 4 to 6 membered, 4 to 5 membered, or 5 to 6 membered), $R^{24D}$-substituted or unsubstituted aryl (e.g., $C_6$-$C_{10}$ or phenyl), or $R^{24D}$-substituted or unsubstituted heteroaryl (e.g., 5 to 10 membered, 5 to 9 membered, or 5 to 6 membered). In embodiments, $R^{23D}$ is independently oxo,
halogen, —$CX^{23D}_3$, —$CHX^{23D}_2$, —$CH_2X^{23D}$, —$OCX^{23D}_3$, —$OCH_2X^{23D}$, —$OCHX^{23D}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{23D}$ is independently —F, —Cl, —Br, or —I.

In embodiments, $R^{23D}$ is independently unsubstituted methyl. In embodiments, $R^{23D}$ is independently unsubstituted ethyl.

$R^{24D}$ is independently oxo,
halogen, —$CX^{24D}_3$, —$CHX^{24D}_2$, —$CH_2X^{24D}$, —$OCX^{24D}_3$, —$OCH_2X^{24D}$, —$OCHX^{24D}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC(O)$NH_2$, —$NHSO_2H$, —NHC=(O)H, —NHC(O)—OH, —NHOH, —$N_3$, $R^{25D}$-substituted or unsubstituted alkyl (e.g., $C_1$-$C_8$, $C_1$-$C_6$, $C_1$-$C_4$, or $C_1$-$C_2$), $R^{25D}$-substituted or unsubstituted heteroalkyl (e.g., 2 to 8 membered, 2 to 6 membered, 4 to 6 membered, 2 to 3 membered, or 4 to 5 membered), $R^{25D}$-substituted or unsubstituted cycloalkyl (e.g., $C_3$-$C_8$, $C_3$-$C_6$, $C_4$-$C_6$, or $C_5$-$C_6$), $R^{25D}$-substituted or unsubstituted heterocycloalkyl (e.g., 3 to 8 membered, 3 to 6 membered, 4 to 6 membered, 4 to 5 membered, or 5 to 6 membered), $R^{2D}$-substituted or unsubstituted aryl (e.g., $C_6$-$C_{10}$ or phenyl), or $R^{25D}$-substituted or unsubstituted heteroaryl (e.g., 5 to 10 membered, 5 to 9 membered, or 5 to 6 membered). In embodiments, $R^{24D}$ is independently oxo,
halogen, —$CX^{24D}_3$, —$CHX^{24D}_2$, —$CH_2X^{24D}$, —$OCX^{24D}_3$, —$OCH_2X^{24D}$, —$OCHX^{24D}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{24D}$ is independently —F, —Cl, —Br, or —I.

$R^{25D}$ is independently oxo, halogen, —$CX^{25D}_3$, —$CHX^{25D}_2$, —$CH_2X^{25D}$, —$OCX^{25D}_3$, —$OCH_2X^{25D}$, —$OCHX^{25D}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=$(O)NHNH_2$, —NHC=$(O)NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{25D}$ is independently —F, —Cl, —Br, or —I.

In embodiments, $R^3$ is independently hydrogen, —$CX^3_3$, —$CHX^3_2$, —$CH_2X^3$, —CN, —C(O)$R^{3C}$, —C(O)O$R^{3C}$, —C(O)N$R^{3A}R^{3B}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^3$ is independently hydrogen, —$CX^3_3$, —$CHX^3_2$, —$CH_2X^3$, —CN, —C(O)$R^{3C}$, —C(O)O$R^{3C}$, —C(O)N$R^{3A}R^{3B}$, substituted or unsubstituted $C_1$-$C_4$ alkyl, or substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^3$ is independently hydrogen, —$CX^3_3$, —$CHX^3_2$, —$CH_2X^3$, —CN, —C(O)$R^{3C}$, —C(O)O$R^{3C}$, —C(O)N$R^{3A}R^{3B}$, unsubstituted $C_1$-$C_4$ alkyl, or unsubstituted 2 to 4 membered heteroalkyl.

In embodiments, $R^{3A}$ is independently substituted or unsubstituted alkyl (e.g., $C_1$-$C_8$, $C_1$-$C_6$, $C_1$-$C_4$, or $C_1$-$C_2$). In embodiments, $R^{3A}$ is independently substituted alkyl (e.g., $C_1$-$C_8$, $C_1$-$C_6$, $C_1$-$C_4$, or $C_1$-$C_2$). In embodiments, $R^{3A}$ is independently unsubstituted alkyl (e.g., $C_1$-$C_8$, $C_1$-$C_6$, $C_1$-$C_4$, or $C_1$-$C_2$). In embodiments, $R^{3A}$ is independently unsubstituted methyl. In embodiments, $R^{3A}$ is independently unsubstituted ethyl. In embodiments, $R^{3A}$ is independently unsubstituted propyl. In embodiments, $R^{3A}$ is independently unsubstituted isopropyl. In embodiments, $R^{3A}$ is independently unsubstituted tert-butyl. In embodiments, $R^{3A}$ is independently substituted or unsubstituted heteroalkyl (e.g., 2 to 8 membered, 2 to 6 membered, 4 to 6 membered, 2 to 3 membered, or 4 to 5 membered). In embodiments, $R^{3A}$ is independently substituted heteroalkyl (e.g., 2 to 8 membered, 2 to 6 membered, 4 to 6 membered, 2 to 3 membered, or 4 to 5 membered). In embodiments, $R^{3A}$ is independently unsubstituted heteroalkyl (e.g., 2 to 8 membered, 2 to 6 membered, 4 to 6 membered, 2 to 3 membered, or 4 to 5 membered). In embodiments, $R^{3A}$ is independently substituted or unsubstituted cycloalkyl (e.g., $C_3$-$C_8$, $C_3$-$C_6$, $C_4$-$C_6$, or $C_5$-$C_6$). In embodiments, $R^{3A}$ is independently substituted cycloalkyl (e.g., $C_3$-$C_8$, $C_3$-$C_6$, $C_4$-$C_6$, or $C_5$-$C_6$). In embodiments, $R^{3A}$ is independently unsubstituted cycloalkyl (e.g., $C_3$-$C_8$, $C_3$-$C_6$, $C_4$-$C_6$, or $C_5$-$C_6$). In embodiments, $R^{3A}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^A$ is independently substituted heterocycloalkyl (e.g., 3 to 8 membered, 3 to 6 membered, 4 to 6 membered, 4 to 5 membered, or 5 to 6 membered). In embodiments, $R^{3A}$ is independently unsubstituted heterocycloalkyl (e.g., 3 to 8 membered, 3 to 6 membered, 4 to 6 membered, 4 to 5 membered, or 5 to 6 membered). In embodiments, $R^{3A}$ is independently substituted or unsubstituted aryl (e.g., $C_6$-$C_{10}$ or phenyl). In embodiments, $R^{3A}$ is independently substituted aryl (e.g., $C_6$-$C_{10}$ or phenyl). In embodiments, $R^{3A}$ is independently unsubstituted aryl (e.g., $C_6$-$C_{10}$ or phenyl). In embodiments, $R^{3A}$ is independently substituted or unsubstituted heteroaryl (e.g., 5 to 10 membered, 5 to 9 membered, or 5 to 6 membered). In embodiments, $R^{3A}$ is independently substituted heteroaryl (e.g., 5 to 10 membered, 5 to 9 membered, or 5 to 6 membered). In embodiments, $R^{3A}$ is independently unsubstituted heteroaryl (e.g., 5 to 10 membered, 5 to 9 membered, or 5 to 6 membered).

In embodiments, $R^{3B}$ is independently substituted or unsubstituted alkyl (e.g., $C_1$-$C_8$, $C_1$-$C_6$, $C_1$-$C_4$, or $C_1$-$C_2$). In embodiments, $R^{3B}$ is independently substituted alkyl (e.g., $C_1$-$C_8$, $C_1$-$C_6$, $C_1$-$C_4$, or $C_1$-$C_2$). In embodiments, $R^{3B}$ is independently unsubstituted alkyl (e.g., $C_1$-$C_8$, $C_1$-$C_6$, $C_1$-$C_4$, or $C_1$-$C_2$). In embodiments, $R^{3B}$ is independently unsubstituted methyl. In embodiments, $R^{3B}$ is independently unsubstituted ethyl. In embodiments, $R^{3B}$ is independently unsubstituted propyl. In embodiments, $R^{3B}$ is independently unsubstituted isopropyl. In embodiments, $R^{3B}$ is independently unsubstituted tert-butyl. In embodiments, $R^{3B}$ is independently substituted or unsubstituted heteroalkyl (e.g., 2 to 8 membered, 2 to 6 membered, 4 to 6 membered, 2 to 3 membered, or 4 to 5 membered). In embodiments, $R^{3B}$ is independently substituted heteroalkyl (e.g., 2 to 8 membered, 2 to 6 membered, 4 to 6 membered, 2 to 3 membered, or 4 to 5 membered). In embodiments, $R^{3B}$ is independently unsubstituted heteroalkyl (e.g., 2 to 8 membered, 2 to 6 membered, 4 to 6 membered, 2 to 3 membered, or 4 to 5 membered). In embodiments, $R^{3B}$ is independently substituted or unsubstituted cycloalkyl (e.g., $C_3$-$C_8$, $C_3$-$C_6$, $C_4$-$C_6$, or $C_5$-$C_6$). In embodiments, $R^{3B}$ is independently substituted cycloalkyl (e.g., $C_3$-$C_8$, $C_3$-$C_6$, $C_4$-$C_6$, or $C_5$-$C_6$). In embodiments, $R^{3B}$ is independently unsubstituted cycloalkyl (e.g., $C_3$-$C_8$, $C_3$-$C_6$, $C_4$-$C_6$, or $C_5$-$C_6$). In embodiments, $R^{3B}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{3B}$ is independently substituted heterocycloalkyl (e.g., 3 to 8 membered, 3 to 6 membered, 4 to 6 membered, 4 to 5 membered, or 5 to 6 membered). In embodiments, $R^{3B}$ is independently unsubstituted heterocycloalkyl (e.g., 3 to 8 membered, 3 to 6 membered, 4 to 6 membered, 4 to 5 membered, or 5 to 6 membered). In embodiments, $R^{3B}$ is independently substituted or unsubstituted aryl (e.g., $C_6$-$C_{10}$ or phenyl). In embodiments, $R^{3B}$ is independently substituted aryl (e.g., $C_6$-$C_0$ or phenyl). In embodiments, $R^{3B}$ is independently unsubstituted aryl (e.g., $C_6$-$C_{10}$ or phenyl). In embodiments, $R^{3B}$ is independently substituted or unsubstituted heteroaryl (e.g., 5 to 10 membered, 5 to 9 membered, or 5 to 6 membered). In embodiments, $R^{3B}$ is independently substituted heteroaryl (e.g., 5 to 10 membered, 5 to 9 membered, or 5 to 6 membered). In embodiments, $R^{3B}$ is independently unsubstituted heteroaryl (e.g., 5 to 10 membered, 5 to 9 membered, or 5 to 6 membered).

In embodiments, $R^{3A}$ and $R^{3B}$ substituents bonded to the same nitrogen atom may be joined to form a substituted or unsubstituted heterocycloalkyl (e.g., 3 to 8 membered, 3 to 6 membered, 4 to 6 membered, 4 to 5 membered, or 5 to 6 membered). In embodiments, $R^{3A}$ and $R^{3B}$ substituents bonded to the same nitrogen atom may be joined to form a substituted heterocycloalkyl (e.g., 3 to 8 membered, 3 to 6 membered, 4 to 6 membered, 4 to 5 membered, or 5 to 6 membered). In embodiments, $R^{3A}$ and $R^{3B}$ substituents bonded to the same nitrogen atom may be joined to form an unsubstituted heterocycloalkyl (e.g., 3 to 8 membered, 3 to 6 membered, 4 to 6 membered, 4 to 5 membered, or 5 to 6 membered).

In embodiments, $R^{3A}$ and $R^{3B}$ substituents bonded to the same nitrogen atom may be joined to form a substituted or unsubstituted heteroaryl (e.g., 5 to 10 membered, 5 to 9 membered, or 5 to 6 membered). In embodiments, $R^{3A}$ and $R^{3B}$ substituents bonded to the same nitrogen atom may be joined to form a substituted heteroaryl (e.g., 5 to 10 membered, 5 to 9 membered, or 5 to 6 membered). In embodiments, $R^{3A}$ and $R^{3B}$ substituents bonded to the same nitrogen atom may be joined to form an unsubstituted heteroaryl (e.g., 5 to 10 membered, 5 to 9 membered, or 5 to 6 membered).

In embodiments, $R^3$ is independently substituted or unsubstituted alkyl (e.g., $C_1$-$C_8$, $C_1$-$C_6$, $C_1$-$C_4$, or $C_1$-$C_2$). In embodiments, $R^{3C}$ is independently substituted alkyl (e.g., $C_1$-$C_8$, $C_1$-$C_6$, $C_1$-$C_4$, or $C_1$-$C_2$). In embodiments, $R^{3C}$ is independently unsubstituted alkyl (e.g., $C_1$-$C_8$, $C_1$-$C_6$, $C_1$-$C_4$, or $C_1$-$C_2$). In embodiments, $R^{3C}$ is independently unsubstituted methyl. In embodiments, $R^{3C}$ is independently unsubstituted ethyl. In embodiments, $R^{3C}$ is independently unsubstituted propyl. In embodiments, $R^{3C}$ is independently unsubstituted isopropyl. In embodiments, $R^{3C}$ is independently unsubstituted tert-butyl. In embodiments, $R^{3C}$ is independently substituted or unsubstituted heteroalkyl (e.g., 2 to 8 membered, 2 to 6 membered, 4 to 6 membered, 2 to 3 membered, or 4 to 5 membered). In embodiments, $R^{3C}$ is independently substituted heteroalkyl (e.g., 2 to 8 membered, 2 to 6 membered, 4 to 6 membered, 2 to 3 membered, or 4 to 5 membered). In embodiments, $R^{3C}$ is independently unsubstituted heteroalkyl (e.g., 2 to 8 membered, 2 to 6 membered, 4 to 6 membered, 2 to 3 membered, or 4 to 5 membered). In embodiments, $R^{3C}$ is independently substituted or unsubstituted cycloalkyl (e.g., $C_3$-$C_8$, $C_3$-$C_6$, $C_4$-$C_6$, or $C_5$-$C_6$). In embodiments, $R^{3C}$ is independently substituted cycloalkyl (e.g., $C_3$-$C_8$, $C_3$-$C_6$, $C_4$-$C_6$, or $C_5$-$C_6$). In embodiments, $R^{3C}$ is independently unsubstituted cycloalkyl (e.g., $C_3$-$C_8$, $C_3$-$C_6$, $C_4$-$C_6$, or $C_5$-$C_6$). In embodiments, $R^{3C}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^3$ is independently substituted heterocycloalkyl (e.g., 3 to 8 membered, 3 to 6 membered, 4 to 6 membered, 4 to 5 membered, or 5 to 6 membered). In embodiments, $R^C$ is independently unsubstituted heterocycloalkyl (e.g., 3 to 8 membered, 3 to 6 membered, 4 to 6 membered, 4 to 5 membered, or 5 to 6 membered). In embodiments, $R^{3C}$ is independently substituted or unsubstituted aryl (e.g., $C_6$-$C_{10}$ or phenyl). In embodiments, $R^{3C}$ is independently substituted aryl (e.g., $C_6$-$C_{10}$ or phenyl). In embodiments, $R^{3C}$ is independently unsubstituted aryl (e.g., $C_6$-$C_{10}$ or phenyl). In embodiments, $R^{3C}$ is independently substituted or unsubstituted heteroaryl (e.g., 5 to 10 membered, 5 to 9 membered, or 5 to 6 membered). In embodiments, $R^{3C}$ is independently substituted heteroaryl (e.g., 5 to 10 membered, 5 to 9 membered, or 5 to 6 membered). In embodiments, $R^{3C}$ is independently unsubstituted heteroaryl (e.g., 5 to 10 membered, 5 to 9 membered, or 5 to 6 membered).

In embodiments, $R^3$ is independently hydrogen, $-CX^3_3$, $-CHX^3_2$, $-CH_2X^3$, $-CN$, $C(O)R^{3C}$, $-C(O)OR^{3C}$, $-C(O)NR^{3A}R^{3B}$, $R^{26}$-substituted or unsubstituted alkyl (e.g., $C_1$-$C_8$, $C_1$-$C_6$, $C_1$-$C_4$, or $C_1$-$C_2$), $R^{26}$-substituted or unsubstituted heteroalkyl (e.g., 2 to 8 membered, 2 to 6 membered, 4 to 6 membered, 2 to 3 membered, or 4 to 5 membered), $R^{26}$-substituted or unsubstituted cycloalkyl (e.g., $C_3$-$C_8$, $C_3$-$C_6$, $C_4$-$C_6$, or $C_5$-$C_6$), $R^{26}$-substituted or unsubstituted heterocycloalkyl (e.g., 3 to 8 membered, 3 to 6 membered, 4 to 6 membered, 4 to 5 membered, or 5 to 6 membered), $R^{26}$-substituted or unsubstituted aryl (e.g., $C_6$-$C_{10}$ or phenyl), or $R^{26}$-substituted or unsubstituted heteroaryl (e.g., 5 to 10 membered, 5 to 9 membered, or 5 to 6 membered). In embodiments, $R^3$ is independently hydrogen, $-CX^3_3$, $-CHX^3_2$, $-CH_2X^3$, $-CN$, $-COOH$, $-CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^3$ is independently $-F$, $-Cl$, $-Br$, or $-I$.

In embodiments, $R^3$ is independently hydrogen. In embodiments, $R^3$ is independently unsubstituted methyl. In embodiments, $R^3$ is independently unsubstituted ethyl.

$R^{26}$ is independently oxo, halogen, $-CX^{26}_3$, $-CHX^{26}_2$, $-CH_2X^{26}$, $-OCX^{26}_3$, $-OCH_2X^{26}$, $-OCHX^{26}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, $R^{27}$-substituted or unsubstituted alkyl (e.g., $C_1$-$C_8$, $C_1$-$C_6$, $C_1$-$C_4$, or $C_1$-$C_2$), $R^{27}$-substituted or unsubstituted heteroalkyl (e.g., 2 to 8 membered, 2 to 6 membered, 4 to 6 membered, 2 to 3 membered, or 4 to 5 membered), $R^{27}$-substituted or unsubstituted cycloalkyl (e.g., $C_3$-$C_8$, $C_3$-$C_6$, $C_4$-$C_6$, or $C_5$-$C_6$), $R^{27}$-substituted or unsubstituted heterocycloalkyl (e.g., 3 to 8 membered, 3 to 6 membered, 4 to 6 membered, 4 to 5 membered, or 5 to 6 membered), $R^{27}$-substituted or unsubstituted aryl (e.g., $C_6$-$C_{10}$ or phenyl), or $R^{27}$-substituted or unsubstituted heteroaryl (e.g., 5 to 10 membered, 5 to 9 membered, or 5 to 6 membered). In embodiments, $R^{26}$ is independently oxo, halogen, $-CX^{26}_3$, $-CHX^{26}_2$, $-CH_2X^{26}$, $-OCX^{26}_3$, $-OCH_2X^{26}$, $-OCHX^{26}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{26}$ is independently $-F$, $-Cl$, $-Br$, or $-I$.

In embodiments, $R^{26}$ is independently unsubstituted methyl. In embodiments, $R^{26}$ is independently unsubstituted ethyl.

$R^{27}$ is independently oxo, halogen, $-CX^{27}_3$, $-CHX^{27}_2$, $-CH_2X^{27}$, $-OCX^{27}_3$, $-OCH_2X^{27}$, $-OCHX^{27}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, $R^{28}$-substituted or unsubstituted alkyl (e.g., $C_1$-$C_8$, $C_1$-$C_6$, $C_1$-$C_4$, or $C_1$-$C_2$), $R^{28}$-substituted or unsubstituted heteroalkyl (e.g., 2 to 8 membered, 2 to 6 membered, 4 to 6 membered, 2 to 3 membered, or 4 to 5 membered), $R^{28}$-substituted or unsubstituted cycloalkyl (e.g., $C_3$-$C_8$, $C_3$-$C_6$, $C_4$-$C_6$, or $C_5$-$C_6$), $R^{28}$-substituted or unsubstituted heterocycloalkyl (e.g., 3 to 8 membered, 3 to 6 membered, 4 to 6 membered, 4 to 5 membered, or 5 to 6 membered), $R^{28}$-substituted or unsubstituted aryl (e.g., $C_6$-$C_{10}$ or phenyl), or $R^{28}$-substituted or unsubstituted heteroaryl (e.g., 5 to 10 membered, 5 to 9 membered, or 5 to 6 membered). In embodiments, $R^{27}$ is independently oxo, halogen, $-CX^{27}_3$, $-CHX^{27}_2$, $-CH_2X^{27}$, $-OCX^{27}_3$, $-OCH_2X^{27}$, $-OCHX^{27}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{27}$ is independently $-F$, $-Cl$, $-Br$, or $-I$. In embodiments, $R^{27}$ is independently unsubstituted methyl. In embodiments, $R^{27}$ is independently unsubstituted ethyl.

$R^{28}$ is independently oxo, halogen, $-CX^{28}_3$, $-CHX^{28}_2$, $-CH_2X^{28}$, $-OCX^{28}_3$, $-OCH_2X^{28}$, $-OCHX^{28}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, unsubstituted alkyl (e.g., $C_1$-$C_8$, $C_1$-$C$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{11}$ or phenyl), or unsubstituted heteroaryl (e.g., 5 to 10 membered, 5 to 9 membered, or 5 to 6 membered). $X^{28}$ is independently $-F$, $-Cl$, $-Br$, or $-I$.

In embodiments, $R^{28}$ is independently unsubstituted methyl. In embodiments, $R^{28}$ is independently unsubstituted ethyl.

In embodiments, $R^{3A}$ is independently hydrogen, $-CX^{3A}_3$, $-CHX^{3A}_2$, $-CH_2X^{3A}$, $-CN$, $-COOH$, $-CONH_2$, $R^{26A}$-substituted or unsubstituted alkyl (e.g., $C_1$-$C_8$, $C_1$-$C_6$, $C_1$-$C_4$, or $C_1$-$C_2$), $R^{26A}$-substituted or unsubstituted heteroalkyl (e.g., 2 to 8 membered, 2 to 6 membered, 4 to 6 membered, 2 to 3 membered, or 4 to 5 membered), $R^{26A}$-substituted or unsubstituted cycloalkyl (e.g., $C_3$-$C_8$, $C_3$-$C_6$, $C_4$-$C_6$, or $C_5$-$C_6$), $R^{26A}$-substituted or unsubstituted heterocycloalkyl (e.g., 3 to 8 membered, 3 to 6 membered, 4 to 6 membered, 4 to 5 membered, or 5 to 6 membered), $R^{26A}$-substituted or unsubstituted aryl (e.g., $C_6$-$C_{10}$ or phenyl), or $R^{26A}$-substituted or unsubstituted heteroaryl (e.g., 5 to 10 membered, 5 to 9 membered, or 5 to 6 membered). In embodiments, $R^{3A}$ is independently hydrogen, $-CX^{3A}_3$, $-CHX^{3A}_2$, $-CH_2X^{3A}$, $-CN$, $-COOH$, $-CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{3A}$ is independently $-F$, $-Cl$, $-Br$, or $-I$.

In embodiments, $R^{3A}$ is independently hydrogen. In embodiments, $R^{3A}$ is independently unsubstituted methyl. In embodiments, $R^{3A}$ is independently unsubstituted ethyl.

In embodiments, $R^{3A}$ and $R^{3B}$ substituents bonded to the same nitrogen atom may optionally be joined to form a $R^{26A}$-substituted or unsubstituted heterocycloalkyl (e.g., 3 to 8 membered, 3 to 6 membered, 4 to 6 membered, 4 to 5 membered, or 5 to 6 membered) or $R^{26A}$-substituted or unsubstituted heteroaryl (e.g., 5 to 10 membered, 5 to 9 membered, or 5 to 6 membered). In embodiments, $R^{3A}$ and $R^{3B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 10 membered, 5 to 9 membered, or 5 to 6 membered). In embodiments, $R^{3A}$ and $R^{3B}$ substituents bonded to the same nitrogen atom may optionally be joined to form a $R^{26A}$-substituted or unsubstituted heterocycloalkyl (e.g., 3 to 8 membered, 3 to 6 membered, 4 to 6 membered, 4 to 5 membered, or 5 to 6 membered). In embodiments, $R^{3A}$ and $R^{3B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

$R^{26A}$ is independently oxo, halogen, $-CX^{26A}_3$, $-CHX^{26A}_2$, $-CH_2X^{26A}$, $-OCX^{26A}_3$, $-OCH_2X^{26A}$, $-OCHX^{26A}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, $R^{27A}$-substituted or unsubstituted alkyl (e.g., $C_1$-$C_8$, $C_1$-$C_6$, $C_1$-$C_4$, or $C_1$-$C_2$), $R^{27A}$-substituted or unsubstituted heteroalkyl (e.g., 2 to 8 membered, 2 to 6 membered, 4 to 6 membered, 2 to 3 membered, or 4 to 5 membered), $R^{27A}$-substituted or unsubstituted cycloalkyl (e.g., $C_3$-$C_8$, $C_3$-$C_6$, $C_4$-$C_6$, or $C_5$-$C_6$), $R^{27A}$-substituted or unsubstituted heterocycloalkyl (e.g., 3 to 8 membered, 3 to 6 membered, 4 to 6 membered, 4 to 5 membered, or 5 to 6 membered), $R^{27A}$-substituted or unsubstituted aryl (e.g., $C_6$-$C_{10}$ or phenyl), $R^{27}$-substituted or unsubstituted heteroaryl (e.g., 5 to 10 membered, 5 to 9 membered, or 5 to 6 membered). In embodiments, $R^{26A}$ is independently oxo, halogen, $-CX^{26A}_3$, $-CHX^{26A}_2$, $-CH_2X^{26A}$, $-OCX^{26A}_3$, $-OCH_2X^{26A}$, $-OCHX^{26A}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), unsubstituted heteroaryl (e.g., 5 to 10 membered, 5 to 9 membered, or 5 to 6 membered). $X^{26A}$ is independently —F, —Cl, —Br, or —I.

In embodiments, $R^{26A}$ is independently unsubstituted methyl. In embodiments, $R^{26A}$ is independently unsubstituted ethyl.

$R^{27A}$ is independently oxo, halogen, —$CX^{27A}_3$, —$CHX^{27A}_2$, —$CH_2X^{27A}$, —$OCX^{27A}_3$, —$OCH_2X^{27A}$, —$OCHX^{27A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, $R^{28A}$-substituted or unsubstituted alkyl (e.g., $C_1$-$C_8$, $C_1$-$C_6$, $C_1$-$C_4$, or $C_1$-$C_2$), $R^{28A}$-substituted or unsubstituted heteroalkyl (e.g., 2 to 8 membered, 2 to 6 membered, 4 to 6 membered, 2 to 3 membered, or 4 to 5 membered), $R^{28A}$-substituted or unsubstituted cycloalkyl (e.g., $C_3$-$C_8$, $C_3$-$C_6$, $C_4$-$C_6$, or $C_5$-$C_6$), $R^{28A}$-substituted or unsubstituted heterocycloalkyl (e.g., 3 to 8 membered, 3 to 6 membered, 4 to 6 membered, 4 to 5 membered, or 5 to 6 membered), $R^{28A}$-substituted or unsubstituted aryl (e.g., $C_6$-$C_{10}$ or phenyl), or $R^{28A}$-substituted or unsubstituted heteroaryl (e.g., 5 to 10 membered, 5 to 9 membered, or 5 to 6 membered). In embodiments, $R^{27A}$ is independently oxo, halogen, —$CX^{27A}_3$, —$CHX^{27A}_2$, —$CH_2X^{27A}$, —$OCX^{27A}_3$, —$OCH_2X^{27A}$, —$OCHX^{27A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{27A}$ is independently —F, —Cl, —Br, or —I.

$R^{28A}$ is independently oxo, halogen, —$CX^{28A}_3$, —$CHX^{28A}_2$, —$CH_2X^{28A}$, —$OCX^{28A}_3$, —$OCH_2X^{28A}$, —$OCHX^{28A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{28A}$ is independently —F, —Cl, —Br, or —I.

In embodiments, $R^{3B}$ is independently hydrogen, —$CX^{3B}_3$, —$CHX3^B_2$, —$CH_2X^{3B}$, —CN, —COOH, —$CONH_2$, $R^{26B}$-substituted or unsubstituted alkyl (e.g., $C_1$-$C_8$, $C_1$-$C_6$, $C_1$-$C_4$, or $C_1$-$C_2$), $R^{26B}$-substituted or unsubstituted heteroalkyl (e.g., 2 to 8 membered, 2 to 6 membered, 4 to 6 membered, 2 to 3 membered, or 4 to 5 membered), $R^{26B}$-substituted or unsubstituted cycloalkyl (e.g., $C_3$-$C_8$, $C_3$-$C_6$, $C_4$-$C_6$, or $C_5$-$C_6$), $R^{26B}$-substituted or unsubstituted heterocycloalkyl (e.g., 3 to 8 membered, 3 to 6 membered, 4 to 6 membered, 4 to 5 membered, or 5 to 6 membered), $R^{26B}$-substituted or unsubstituted aryl (e.g., $C_6$-$C_{10}$ or phenyl), or $R^{26B}$-substituted or unsubstituted heteroaryl (e.g., 5 to 10 membered, 5 to 9 membered, or 5 to 6 membered). In embodiments, $R^{3B}$ is independently hydrogen, —$CX^{3B}_3$, —$CHX^{3B}_2$, —$CH_2X^{3B}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{3B}$ is independently —F, —Cl, —Br, or —I.

In embodiments, $R^{3B}$ is independently hydrogen. In embodiments, $R^{3B}$ is independently unsubstituted methyl. In embodiments, $R^{3B}$ is independently unsubstituted ethyl.

In embodiments, $R^{3A}$ and $R^{3B}$ substituents bonded to the same nitrogen atom may optionally be joined to form a $R^{26B}$-substituted or unsubstituted heterocycloalkyl (e.g., 3 to 8 membered, 3 to 6 membered, 4 to 6 membered, 4 to 5 membered, or 5 to 6 membered) or $R^{26B}$-substituted or unsubstituted heteroaryl (e.g., 5 to 10 membered, 5 to 9 membered, or 5 to 6 membered). In embodiments, $R^{3A}$ and $R^{3B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 10 membered, 5 to 9 membered, or 5 to 6 membered). In embodiments, $R^{3A}$ and $R^{3B}$ substituents bonded to the same nitrogen atom may optionally be joined to form a $R^{26B}$-substituted or unsubstituted heterocycloalkyl (e.g., 3 to 8 membered, 3 to 6 membered, 4 to 6 membered, 4 to 5 membered, or 5 to 6 membered). In embodiments, $R^{3A}$ and $R^{3B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

$R^{26B}$ is independently oxo, halogen, —$CX^{26B}_3$, —$CHX^{26B}_2$, —$CH_2X^{26B}$, —$OCX^{26B}_3$, —$OCH_2X^{26B}$, —$OCHX^{26B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, $R^{27}$-substituted or unsubstituted alkyl (e.g., $C_1$-$C_8$, $C_1$-$C_6$, $C_1$-$C_4$, or $C_1$-$C_2$), $R^{27B}$-substituted or unsubstituted heteroalkyl (e.g., 2 to 8 membered, 2 to 6 membered, 4 to 6 membered, 2 to 3 membered, or 4 to 5 membered), $R^{27B}$-substituted or unsubstituted cycloalkyl (e.g., $C_3$-$C_8$, $C_3$-$C_6$, $C_4$-$C_6$, or $C_5$-$C_6$), $R^{27B}$-substituted or unsubstituted heterocycloalkyl (e.g., 3 to 8 membered, 3 to 6 membered, 4 to 6 membered, 4 to 5 membered, or 5 to 6 membered), $R^{27B}$-substituted or unsubstituted aryl (e.g., $C_6$-$C_{10}$ or phenyl), $R^{27B}$-substituted or unsubstituted heteroaryl (e.g., 5 to 10 membered, 5 to 9 membered, or 5 to 6 membered). In embodiments, $R^{26B}$ is independently oxo, halogen, —$CX^{26B}_3$, —$CHX^{26B}_2$, —$CH_2X^{26B}$, —$OCX^{26B}_3$, —$OCH_2X^{26B}$, —$OCHX^{26B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), unsubstituted heteroaryl (e.g., 5 to 10 membered, 5 to 9 membered, or 5 to 6 membered). $X^{26B}$ is independently —F, —Cl, —Br, or —I.

In embodiments, $R^{26B}$ is independently unsubstituted methyl. In embodiments, $R^{26B}$ is independently unsubstituted ethyl.

$R^{27}$ is independently oxo, halogen, —$CX^{27B}_3$, —$CHX^{27B}_2$, —$CH_2X^{27B}$, —$OCX^{27B}_3$, —$OCH_2X^{27B}$, —$OCHX^{27B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, $R^2$-substituted or unsubstituted alkyl (e.g., $C_1$-$C_8$, $C_1$-$C_6$, $C_1$-$C_4$, or $C_1$-$C_2$), $R^{28B}$-substituted or unsubstituted heteroalkyl (e.g., 2 to 8 membered, 2 to 6 membered, 4 to 6 membered, 2 to 3 membered, or 4 to 5 membered), $R^{28B}$-substituted or unsubstituted cycloalkyl (e.g., $C_3$-$C_8$, $C_3$-$C_6$, $C_4$-$C_6$, or $C_5$-$C_6$), $R^2SB$-substituted or unsubstituted heterocycloalkyl (e.g., 3 to 8 membered, 3 to 6 membered, 4 to 6 membered, 4 to 5 membered, or 5 to 6 membered), $R^{28B}$-substituted or unsubstituted aryl (e.g., $C_6$-$C_{10}$ or phenyl), or $R^{28B}$-substituted or unsubstituted heteroaryl (e.g., 5 to 10 membered, 5 to 9 membered, or 5 to 6 membered). In embodiments, $R^{27B}$ is independently oxo, halogen, —$CX^{27B}_3$, —$CHX^{27B}_2$, —$CH_2X^{27B}$, —$OCX^{27B}_3$, —$OCH_2X^{27B}$, —$OCHX^{27B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{27B}$ is independently —F, —Cl, —Br, or —I.

$R^{28B}$ is independently oxo, halogen, —$CX^{28B}_3$, —$CHX^{28B}_2$, —$CH_2X^{28B}$, —$OCX^{28B}_3$, —$OCH_2X^{28B}$, —$OCHX^{28B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{28B}$ is independently —F, —Cl, —Br, or —I.

In embodiments, $R^{3C}$ is independently hydrogen, —$CX^{3C}_3$, —$CHX^{3C}_2$, —$CH_2X^{3C}$, —CN, —COOH, —$CONH_2$, $R^{26C}$-substituted or unsubstituted alkyl (e.g., $C_1$-$C_8$, $C_1$-$C_6$, $C_1$-$C_4$, or $C_1$-$C_2$), $R^{26C}$-substituted or unsubstituted heteroalkyl (e.g., 2 to 8 membered, 2 to 6 membered, 4 to 6 membered, 2 to 3 membered, or 4 to 5 membered), $R^{26C}$-substituted or unsubstituted cycloalkyl (e.g., $C_3$-$C_8$, $C_3$-$C_6$, $C_4$-$C_6$, or $C_5$-$C_6$), $R^{26C}$-substituted or unsubstituted heterocycloalkyl (e.g., 3 to 8 membered, 3 to 6 membered, 4 to 6 membered, 4 to 5 membered, or 5 to 6 membered), $R^{26C}$-substituted or unsubstituted aryl (e.g., $C_6$-$C_{10}$ or phenyl), or $R^{26C}$-substituted or unsubstituted heteroaryl (e.g., 5 to 10 membered, 5 to 9 membered, or 5 to 6 membered). In embodiments, $R^{3C}$ is independently hydrogen, —$CX^{3C}_3$, —$CHX^{3C}_2$, —$CH_2X^{3C}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{3C}$ is independently —F, —Cl, —Br, or —I.

In embodiments, $R^{3C}$ is independently hydrogen. In embodiments, $R^{3C}$ is independently unsubstituted methyl. In embodiments, $R^{3C}$ is independently unsubstituted ethyl.

$R^{26C}$ is independently oxo, halogen, —$CX^{26C}_3$, —$CHX^{26C}_2$, —$CH_2X^{26C}$, —$OCX^{26C}_3$, —$OCH_2X^{26C}$, —$OCHX^{26C}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, $R^{27C}$-substituted unsubstituted alkyl (e.g., $C_1$-$C_8$, $C_1$-$C_6$, $C_1$-$C_4$, or $C_1$-$C_2$), $R^{27C}$-substituted unsubstituted heteroalkyl (e.g., 2 to 8 membered, 2 to 6 membered, 4 to 6 membered, 2 to 3 membered, or 4 to 5 membered), $R^{27C}$-substituted unsubstituted cycloalkyl (e.g., $C_3$-$C_8$, $C_3$-$C_6$, $C_4$-$C_6$, or $C_5$-$C_6$), $R^{27C}$-substituted unsubstituted heterocycloalkyl (e.g., 3 to 8 membered, 3 to 6 membered, 4 to 6 membered, 4 to 5 membered, or 5 to 6 membered), $R^{27C}$-substituted unsubstituted aryl (e.g., $C_6$-$C_{10}$ or phenyl), $R^{27C}$-substituted or unsubstituted heteroaryl (e.g., 5 to 10 membered, 5 to 9 membered, or 5 to 6 membered). In embodiments, $R^{26C}$ is independently oxo, halogen, —$CX^{26C}_3$, —$CHX^{26C}_2$, —$CH_2X^{26C}$, —$OCX^{26C}_3$, —$OCH_2X^{26C}$, —$OCHX^{26C}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), unsubstituted heteroaryl (e.g., 5 to 10 membered, 5 to 9 membered, or 5 to 6 membered). $X^{26C}$ is independently —F, —Cl, —Br, or —I.

In embodiments, $R^{26C}$ is independently unsubstituted methyl. In embodiments, $R^{26C}$ is independently unsubstituted ethyl.

$R^{27C}$ is independently oxo, halogen, —$CX^{27C}_3$, —$CHX^{27C}_2$, —$CH_2X^{27C}$, —$OCX^{27C}_3$, —$OCH_2X^{27C}$, —$OCHX^{27C}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, $R^{28C}$-substituted or unsubstituted alkyl (e.g., $C_1$-$C_8$, $C_1$-$C_6$, $C_1$-$C_4$, or $C_1$-$C_2$), $R^{28C}$- substituted or unsubstituted heteroalkyl (e.g., 2 to 8 membered, 2 to 6 membered, 4 to 6 membered, 2 to 3 membered, or 4 to 5 membered), $R^{28C}$-substituted or unsubstituted cycloalkyl (e.g., $C_3$-$C_8$, $C_3$-$C_6$, $C_4$-$C_6$, or $C_5$-$C_6$), $R^{28C}$-substituted or unsubstituted heterocycloalkyl (e.g., 3 to 8 membered, 3 to 6 membered, 4 to 6 membered, 4 to 5 membered, or 5 to 6 membered), $R^{28C}$-substituted or unsubstituted aryl (e.g., $C_6$-$C_{10}$ or phenyl), or $R^{28C}$-substituted or unsubstituted heteroaryl (e.g., 5 to 10 membered, 5 to 9 membered, or 5 to 6 membered). In embodiments, $R^{27C}$ is independently oxo,
halogen, —$CX^{27C}_3$, —$CHX^{27C}_2$, —$CH_2X^{27C}$, —$OCX^{27C}_3$, —$OCH_2X^{27C}$, —$OCHX^{27C}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{27C}$ is independently —F, —Cl, —Br, or —I.

$R^{28C}$ is independently oxo,
halogen, —$CX^{28C}_3$, —$CHX^{28C}_2$, —$CH_2X^{28C}$, —$OCX^{28C}_3$, —$OCH_2X^{28C}$, —$OCHX^{28C}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{28C}$ is independently —F, —Cl, —Br, or —I.

In embodiments, $R^4$ is independently hydrogen, —$CX^4_3$, —$CHX^4_2$, —$CH_2X^4$, —CN, —C(O)$R^{4C}$, —C(O)O$R^{4C}$, —C(O)N$R^{4A}R^{4B}$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, $R^4$ is independently hydrogen, halogen, —$CX^4_3$, —CN, —$CHX^4_2$, —$CH_2X^4$, —COOH, —$CONH_2$, substituted or unsubstituted $C_1$-$C_4$ alkyl, or substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^4$ is independently hydrogen, halogen, —$CX^4_3$, —CN, —$CHX^4_2$, —$CH_2X^4$, unsubstituted $C_1$-$C_4$ alkyl, or unsubstituted 2 to 4 membered heteroalkyl.

In embodiments, $R^{4A}$ is independently substituted or unsubstituted alkyl (e.g., $C_1$-$C_8$, $C_1$-$C_6$, $C_1$-$C_4$, or $C_1$-$C_2$). In embodiments, $R^{4A}$ is independently substituted alkyl (e.g., $C_1$-$C_8$, $C_1$-$C_6$, $C_1$-$C_4$, or $C_1$-$C_2$). In embodiments, $R^{4A}$ is independently unsubstituted alkyl (e.g., $C_1$-$C_8$, $C_1$-$C_6$, $C_1$-$C_4$, or $C_1$-$C_2$). In embodiments, $R^{4A}$ is independently unsubstituted methyl. In embodiments, $R^{4A}$ is independently unsubstituted ethyl. In embodiments, $R^{4A}$ is independently unsubstituted propyl. In embodiments, $R^{4A}$ is independently unsubstituted isopropyl. In embodiments, $R^{4A}$ is independently unsubstituted tert-butyl. In embodiments, $R^{4A}$ is independently substituted or unsubstituted heteroalkyl (e.g., 2 to 8 membered, 2 to 6 membered, 4 to 6 membered, 2 to 3 membered, or 4 to 5 membered). In embodiments, $R^{4A}$ is independently substituted heteroalkyl (e.g., 2 to 8 membered, 2 to 6 membered, 4 to 6 membered, 2 to 3 membered, or 4 to 5 membered). In embodiments, $R^{4A}$ is independently unsubstituted heteroalkyl (e.g., 2 to 8 membered, 2 to 6 membered, 4 to 6 membered, 2 to 3 membered, or 4 to 5 membered). In embodiments, $R^{4A}$ is independently substituted or unsubstituted cycloalkyl (e.g., $C_3$-$C_8$, $C_3$-$C_6$, $C_4$-$C_6$, or $C_5$-$C_6$). In embodiments, $R^{4A}$ is independently substituted cycloalkyl (e.g., $C_3$-$C_8$, $C_3$-$C_6$, $C_4$-$C_6$, or $C_5$-$C_6$). In embodiments, $R^{4A}$ is independently unsubstituted cycloalkyl (e.g., $C_3$-$C_8$, $C_3$-$C_6$, $C_4$-$C_6$, or $C_5$-$C_6$). In embodiments, $R^{4A}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^A$ is independently substituted heterocycloalkyl (e.g., 3 to 8 membered, 3 to 6 membered, 4 to 6 membered, 4 to 5 membered, or 5 to 6 membered). In embodiments, $R^{4A}$ is independently unsubstituted heterocycloalkyl (e.g., 3 to 8 membered, 3 to 6 membered, 4 to 6 membered, 4 to 5 membered, or 5 to 6 membered). In embodiments, $R^{4A}$ is independently substituted or unsubstituted aryl (e.g., $C_6$-$C_{10}$ or phenyl). In embodiments, $R^{4A}$ is independently substituted aryl (e.g., $C_6$-$C_{10}$ or phenyl). In embodiments, $R^{4A}$ is independently unsubstituted aryl (e.g., $C_6$-$C_{10}$ or phenyl). In embodiments, $R^{4A}$ is independently substituted or unsubstituted heteroaryl (e.g., 5 to 10 membered, 5 to 9 membered, or 5 to 6 membered). In embodiments, $R^{4A}$ is independently substituted heteroaryl (e.g., 5 to 10 membered, 5 to 9 membered, or 5 to 6 membered). In embodiments, $R^{4A}$ is independently unsubstituted heteroaryl (e.g., 5 to 10 membered, 5 to 9 membered, or 5 to 6 membered).

In embodiments, $R^{4B}$ is independently substituted or unsubstituted alkyl (e.g., $C_1$-$C_8$, $C_1$-$C_6$, $C_1$-$C_4$, or $C_1$-$C_2$). In embodiments, $R^{4B}$ is independently substituted alkyl (e.g., $C_1$-$C_8$, $C_1$-$C_6$, $C_1$-$C_4$, or $C_1$-$C_2$). In embodiments, $R^{4B}$ is independently unsubstituted alkyl (e.g., $C_1$-$C_8$, $C_1$-$C_6$, $C_1$-$C_4$, or $C_1$-$C_2$). In embodiments, $R^{4B}$ is independently unsubstituted methyl. In embodiments, $R^{4B}$ is independently unsubstituted ethyl. In embodiments, $R^{4B}$ is independently unsubstituted propyl. In embodiments, $R^{4B}$ is independently unsubstituted isopropyl. In embodiments, $R^{4B}$ is independently unsubstituted tert-butyl. In embodiments, $R^{4B}$ is independently substituted or unsubstituted heteroalkyl (e.g., 2 to 8 membered, 2 to 6 membered, 4 to 6 membered, 2 to 3 membered, or 4 to 5 membered). In embodiments, $R^{4B}$ is independently substituted heteroalkyl (e.g., 2 to 8 membered, 2 to 6 membered, 4 to 6 membered, 2 to 3 membered, or 4 to 5 membered). In embodiments, $R^{4B}$ is independently unsubstituted heteroalkyl (e.g., 2 to 8 membered, 2 to 6 membered, 4 to 6 membered, 2 to 3 membered, or 4 to 5 membered). In embodiments, $R^{4B}$ is independently substituted or unsubstituted cycloalkyl (e.g., $C_3$-$C_8$, $C_3$-$C_6$, $C_4$-$C_6$, or $C_5$-$C_6$). In embodiments, $R^{4B}$ is independently substituted cycloalkyl (e.g., $C_3$-$C_8$, $C_3$-$C_6$, $C_4$-$C_6$, or $C_5$-$C_6$). In embodiments, $R^{4B}$ is independently unsubstituted cycloalkyl (e.g., $C_3$-$C_8$, $C_3$-$C_6$, $C_4$-$C_6$, or $C_5$-$C_6$). In embodiments, $R^{4B}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{4B}$ is independently substituted heterocycloalkyl (e.g., 3 to 8 membered, 3 to 6 membered, 4 to 6 membered, 4 to 5 membered, or 5 to 6 membered). In embodiments, $R^{4B}$ is independently unsubstituted heterocycloalkyl (e.g., 3 to 8 membered, 3 to 6 membered, 4 to 6 membered, 4 to 5 membered, or 5 to 6 membered). In embodiments, $R^{4B}$ is independently substituted or unsubstituted aryl (e.g., $C_6$-$C_{10}$ or phenyl). In embodiments, $R^4$ is independently substituted aryl (e.g., $C_6$-$C_{10}$ or phenyl). In embodiments, $R^{4B}$ is independently unsubstituted aryl (e.g., $C_6$-$C_0$ or phenyl). In embodiments, $R^{4B}$ is independently substituted or unsubstituted heteroaryl (e.g., 5 to 10 membered, 5 to 9 membered, or 5 to 6 membered). In embodiments, $R^{4B}$ is independently substituted heteroaryl (e.g., 5 to 10 membered, 5 to 9 membered, or 5 to 6 membered). In embodiments, $R^{4B}$ is independently unsubstituted heteroaryl (e.g., 5 to 10 membered, 5 to 9 membered, or 5 to 6 membered).

In embodiments, $R^{4A}$ and $R^{4B}$ substituents bonded to the same nitrogen atom may be joined to form a substituted or unsubstituted heterocycloalkyl (e.g., 3 to 8 membered, 3 to 6 membered, 4 to 6 membered, 4 to 5 membered, or 5 to 6 membered). In embodiments, $R^{4A}$ and $R^{4B}$ substituents bonded to the same nitrogen atom may be joined to form a substituted heterocycloalkyl (e.g., 3 to 8 membered, 3 to 6 membered, 4 to 6 membered, 4 to 5 membered, or 5 to 6 membered). In embodiments, $R^{4A}$ and $R^{4B}$ substituents bonded to the same nitrogen atom may be joined to form an unsubstituted heterocycloalkyl (e.g., 3 to 8 membered, 3 to 6 membered, 4 to 6 membered, 4 to 5 membered, or 5 to 6 membered).

In embodiments, $R^{4A}$ and $R^{4B}$ substituents bonded to the same nitrogen atom may be joined to form a substituted or unsubstituted heteroaryl (e.g., 5 to 10 membered, 5 to 9 membered, or 5 to 6 membered). In embodiments, $R^{4A}$ and $R^{4B}$ substituents bonded to the same nitrogen atom may be joined to form a substituted heteroaryl (e.g., 5 to 10 membered, 5 to 9 membered, or 5 to 6 membered). In embodiments, $R^{4A}$ and $R^{4B}$ substituents bonded to the same nitrogen atom may be joined to form an unsubstituted heteroaryl (e.g., 5 to 10 membered, 5 to 9 membered, or 5 to 6 membered).

In embodiments, $R^{4C}$ is independently substituted or unsubstituted alkyl (e.g., $C_1$-$C_8$, $C_1$-$C_6$, $C_1$-$C_4$, or $C_1$-$C_2$). In embodiments, $R^{4C}$ is independently substituted alkyl (e.g., $C_1$-$C_8$, $C_1$-$C_6$, $C_1$-$C_4$, or $C_1$-$C_2$). In embodiments, $R^{4C}$ is independently unsubstituted alkyl (e.g., $C_1$-$C_8$, $C_1$-$C_6$, $C_1$-$C_4$, or $C_1$-$C_2$). In embodiments, $R^{4C}$ is independently unsubstituted methyl. In embodiments, $R^{4C}$ is independently unsubstituted ethyl. In embodiments, $R^{4C}$ is independently unsubstituted propyl. In embodiments, $R^{4C}$ is independently unsubstituted isopropyl. In embodiments, $R^{4C}$ is independently unsubstituted tert-butyl. In embodiments, $R^{4C}$ is independently substituted or unsubstituted heteroalkyl (e.g., 2 to 8 membered, 2 to 6 membered, 4 to 6 membered, 2 to 3 membered, or 4 to 5 membered). In embodiments, $R^{4C}$ is independently substituted heteroalkyl (e.g., 2 to 8 membered, 2 to 6 membered, 4 to 6 membered, 2 to 3 membered, or 4 to 5 membered). In embodiments, $R^{4C}$ is independently unsubstituted heteroalkyl (e.g., 2 to 8 membered, 2 to 6 membered, 4 to 6 membered, 2 to 3 membered, or 4 to 5 membered). In embodiments, $R^{4C}$ is independently substituted or unsubstituted cycloalkyl (e.g., $C_3$-$C_8$, $C_3$-$C_6$, $C_4$-$C_6$, or $C_5$-$C_6$). In embodiments, $R^{4C}$ is independently substituted cycloalkyl (e.g., $C_3$-$C_8$, $C_3$-$C_6$, $C_4$-$C_6$, or $C_5$-$C_6$). In embodiments, $R^{4C}$ is independently unsubstituted cycloalkyl (e.g., $C_3$-$C_8$, $C_3$-$C_6$, $C_4$-$C_6$, or $C_5$-$C_6$). In embodiments, $R^{4C}$ is independently substituted or unsubstituted heterocycloalkyl (e.g., 3 to 8 membered, 3 to 6 membered, 4 to 6 membered, 4 to 5 membered, or 5 to 6 membered). In embodiments, $R^{4C}$ is independently substituted heterocycloalkyl (e.g., 3 to 8 membered, 3 to 6 membered, 4 to 6 membered, 4 to 5 membered, or 5 to 6 membered). In embodiments, $R^{4C}$ is independently unsubstituted heterocycloalkyl (e.g., 3 to 8 membered, 3 to 6 membered, 4 to 6 membered, 4 to 5 membered, or 5 to 6 membered). In embodiments, $R^{4C}$ is independently substituted or unsubstituted aryl (e.g., $C_6$-$C_{10}$ or phenyl). In embodiments, $R^{4C}$ is independently substituted aryl (e.g., $C_6$-$C_{10}$ or phenyl). In embodiments, $R^{4C}$ is independently unsubstituted aryl (e.g., $C_6$-$C_{10}$ or phenyl). In embodiments, $R^{4C}$ is independently substituted or unsubstituted heteroaryl (e.g., 5 to 10 membered, 5 to 9 membered, or 5 to 6 membered). In embodiments, $R^{4C}$ is independently substituted heteroaryl (e.g., 5 to 10 membered, 5 to 9 membered, or 5 to 6 membered). In embodiments, $R^{4C}$ is independently unsubstituted heteroaryl (e.g., 5 to 10 membered, 5 to 9 membered, or 5 to 6 membered).

In embodiments, $R^4$ is independently hydrogen, —$CX^4_3$, —$CHX^4_2$, —$CH_2X^4$, —CN, —C(O)$R^{4C}$, —C(O)O$R^{4C}$, —C(O)N$R^{4A}R^{4B}$, $R^{29}$-substituted or unsubstituted alkyl (e.g., $C_1$-$C_8$, $C_1$-$C_6$, $C_1$-$C_4$, or $C_1$-$C_2$), $R^{29}$-substituted or unsubstituted heteroalkyl (e.g., 2 to 8 membered, 2 to 6 membered, 4 to 6 membered, 2 to 3 membered, or 4 to 5 membered), $R^{29}$-substituted or unsubstituted cycloalkyl (e.g., $C_3$-$C_8$, $C_3$-$C_6$, $C_4$-$C_6$, or $C_5$-$C_6$), $R^{29}$-substituted or unsubstituted heterocycloalkyl (e.g., 3 to 8 membered, 3 to 6 membered, 4 to 6 membered, 4 to 5 membered, or 5 to 6 membered), $R^{29}$-substituted or unsubstituted aryl (e.g., $C_6$-$C_{10}$ or phenyl), or $R^{29}$-substituted or unsubstituted heteroaryl (e.g., 5 to 10 membered, 5 to 9 membered, or 5 to 6 membered). In embodiments, $R^4$ is independently hydrogen, —$CX^4_3$, —$CHX^4_2$, —$CH_2X^4$, —CN, —C(O)$R^{4C}$, —C(O)O$R^{4C}$, —C(O)N$R^{4A}R^{4B}$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^4$ is independently —F, —Cl, —Br, or —I.

In embodiments, $R^4$ is independently hydrogen. In embodiments, $R^4$ is independently unsubstituted methyl. In embodiments, $R^4$ is independently unsubstituted ethyl.

$R^{29}$ is independently oxo, halogen, —$CX^{29}_3$, —$CHX^{29}_2$, —$CH_2X^{29}$, —$OCX^{29}_3$, —$OCH_2X^{29}$, —$OCHX^{29}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)NHNH$_2$, —NHC=(O)NH$_2$, —NHSO$_2$H, —NHC=(O)H, —NHC(O)—OH, —NHOH, —$N_3$, $R^{30}$-substituted or unsubstituted alkyl (e.g., $C_1$-$C_8$, $C_1$-$C_6$, $C_1$-$C_4$, or $C_1$-$C_2$), $R^{30}$-substituted or unsubstituted heteroalkyl (e.g., 2 to 8 membered, 2 to 6 membered, 4 to 6 membered, 2 to 3 membered, or 4 to 5 membered), $R^{30}$-substituted or unsubstituted cycloalkyl (e.g., $C_3$-$C_8$, $C_3$-$C_6$, $C_4$-$C_6$, or $C_5$-$C_6$), $R^{30}$-substituted or unsubstituted heterocycloalkyl (e.g., 3 to 8 membered, 3 to 6 membered, 4 to 6 membered, 4 to 5 membered, or 5 to 6 membered), $R^{30}$-substituted or unsubstituted aryl (e.g., $C_6$-$C_{10}$ or phenyl), or $R^{30}$-substituted or unsubstituted heteroaryl (e.g., 5 to 10 membered, 5 to 9 membered, or 5 to 6 membered). In embodiments, $R^{29}$ is independently oxo, halogen, —$CX^{29}_3$, —$CHX^{29}_2$, —$CH_2X^{29}$, —$OCX^{29}_3$, —$OCH_2X^{29}$, —$OCHX^{29}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC$=(O)$NHNH_2$, —$NHC$=(O)$NH_2$, —$NHSO_2H$, —$NHC$=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_0$ or phenyl), or unsubstituted heteroaryl (e.g., 5 to 10 membered, 5 to 9 membered, or 5 to 6 membered). $X^{29}$ is independently —F, —Cl, —Br, or —I.

In embodiments, $R^{29}$ is independently unsubstituted methyl. In embodiments, $R^{29}$ is independently unsubstituted ethyl.

$R^{30}$ is independently oxo, halogen, —$CX^{30}_3$, —$CHX^{30}_2$, —$CH_2X^{30}$, —$OCX^{30}_3$, —$OCH_2X^{30}$, —$OCHX^{30}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC$=(O)$NHNH_2$, —$NHC$=(O)$NH_2$, —$NHSO_2H$, —$NHC$=(O)H, —NHC(O)—OH, —NHOH, —$N_3$, $R^{31}$-substituted or unsubstituted alkyl (e.g., $C_1$-$C_8$, $C_1$-$C_6$, $C_1$-$C_4$, or $C_1$-$C_2$), $R^{31}$-substituted or unsubstituted heteroalkyl (e.g., 2 to 8 membered, 2 to 6 membered, 4 to 6 membered, 2 to 3 membered, or 4 to 5 membered), $R^{31}$-substituted or unsubstituted cycloalkyl (e.g., $C_3$-$C_8$, $C_3$-$C_6$, $C_4$-$C_6$, or $C_5$-$C_6$), $R^{31}$-substituted or unsubstituted heterocycloalkyl (e.g., 3 to 8 membered, 3 to 6 membered, 4 to 6 membered, 4 to 5 membered, or 5 to 6 membered), $R^{31}$-substituted or unsubstituted aryl (e.g., $C_6$-$C_{10}$ or phenyl), or $R^{31}$-substituted or unsubstituted heteroaryl (e.g., 5 to 10 membered, 5 to 9 membered, or 5 to 6 membered). In embodiments, $R^{30}$ is independently oxo, halogen, —$CX^{30}_3$, —$CHX^{30}_2$, —$CH_2X^{30}$, —$OCX^{30}_3$, —$OCH_2X^{30}$, —$OCHX^{30}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC$=(O)$NHNH_2$, —$NHC$=(O)$NH_2$, —$NHSO_2H$, —$NHC$=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{30}$ is independently —F, —Cl, —Br, or —I. In embodiments, $R^{30}$ is independently unsubstituted methyl. In embodiments, $R^{30}$ is independently unsubstituted ethyl.

$R^{31}$ is independently oxo, halogen, —$CX^{31}_3$, —$CHX^{31}_2$, —$CH_2X^{31}$, —$OCX^{31}_3$, —$OCH_2X^{31}$, —$OCHX^{31}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC$—(O)$NHNH_2$, —$NHC$=(O)$NH_2$, —$NHSO_2H$, —$NHC$—(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{31}$ is independently —F, —Cl, —Br, or —I.

In embodiments, $R^{31}$ is independently unsubstituted methyl. In embodiments, $R^{31}$ is independently unsubstituted ethyl.

In embodiments, $R^{4A}$ is independently hydrogen, —$CX^{4A}_3$, —$CHX^{4A}_2$, —$CH_2X^{4A}$, —CN, —COOH, —$CONH_2$, $R^{29A}$-substituted or unsubstituted alkyl (e.g., $C_1$-$C_8$, $C_1$-$C_6$, $C_1$-$C_4$, or $C_1$-$C_2$), $R^{29A}$-substituted or unsubstituted heteroalkyl (e.g., 2 to 8 membered, 2 to 6 membered, 4 to 6 membered, 2 to 3 membered, or 4 to 5 membered), $R^{29A}$-substituted or unsubstituted cycloalkyl (e.g., $C_3$-$C_8$, $C_3$-$C_6$, $C_4$-$C_6$, or $C_5$-$C_6$), $R^{29A}$-substituted or unsubstituted heterocycloalkyl (e.g., 3 to 8 membered, 3 to 6 membered, 4 to 6 membered, 4 to 5 membered, or 5 to 6 membered), $R^{29A}$-substituted or unsubstituted aryl (e.g., $C_6$-$C_{10}$ or phenyl), or $R^{29A}$-substituted or unsubstituted heteroaryl (e.g., 5 to 10 membered, 5 to 9 membered, or 5 to 6 membered). In embodiments, $R^{4A}$ is independently hydrogen, —$CX^{4A}_3$, —$CHX^{4A}_2$, —$CH_2X^{4A}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{4A}$ is independently —F, —Cl, —Br, or —I. In embodiments, $R^{4A}$ is independently hydrogen. In embodiments, $R^{4A}$ is independently unsubstituted methyl. In embodiments, $R^{4A}$ is independently unsubstituted ethyl.

In embodiments, $R^{4A}$ and $R^{4B}$ substituents bonded to the same nitrogen atom may optionally be joined to form a $R^{29A}$-substituted or unsubstituted heterocycloalkyl (e.g., 3 to 8 membered, 3 to 6 membered, 4 to 6 membered, 4 to 5 membered, or 5 to 6 membered) or $R^{29A}$-substituted or unsubstituted heteroaryl (e.g., 5 to 10 membered, 5 to 9 membered, or 5 to 6 membered). In embodiments, $R^{4A}$ and $R^{4B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 10 membered, 5 to 9 membered, or 5 to 6 membered). In embodiments, $R^{4A}$ and $R^{4B}$ substituents bonded to the same nitrogen atom may optionally be joined to form a $R^{29A}$-substituted or unsubstituted heterocycloalkyl (e.g., 3 to 8 membered, 3 to 6 membered, 4 to 6 membered, 4 to 5 membered, or 5 to 6 membered). In embodiments, $R^{4A}$ and $R^{4B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

$R^{29A}$ is independently oxo, halogen, —$CX^{29A}_3$, $CHX^{29A}_2$, —$CH_2X^{29A}$, —$OCX^{29A}_3$, —$OCH_2X^{29A}$, —$OCHX^{29A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC$=(O)$NHNH_2$, —$NHC$=(O)$NH_2$, —$NHSO_2H$, —$NHC$—(O)H, —NHC(O)—OH, —NHOH, —$N_3$, $R^{30A}$-substituted or unsubstituted alkyl (e.g., $C_1$-$C_8$, $C_1$-$C_6$, $C_1$-$C_4$, or $C_1$-$C_2$), $R^{30A}$- substituted or unsubstituted heteroalkyl (e.g., 2 to 8 membered, 2 to 6 membered, 4 to 6 membered, 2 to 3 membered, or 4 to 5 membered), $R^{30A}$-substituted or unsubstituted cycloalkyl (e.g., $C_3$-$C_8$, $C_3$-$C_6$, $C_4$-$C_6$, or $C_5$-$C_6$), $R^{30A}$-substituted or unsubstituted heterocycloalkyl (e.g., 3 to 8 membered, 3 to 6 membered, 4 to 6 membered, 4 to 5 membered, or 5 to 6 membered), $R^{30A}$-substituted or unsubstituted aryl (e.g., $C_6$-$C_{10}$ or phenyl), or $R^{30A}$-substituted or unsubstituted heteroaryl (e.g., 5 to 10 membered, 5 to 9 membered, or 5 to 6 membered). In embodiments, $R^{29A}$ is independently oxo, halogen, —$CX^{29A}{}_3$, —$CHX^{29A}{}_2$, —$CH_2X^{29A}$, —$OCX^{29A}{}_3$, —$OCH_2X^{29A}$, —$OCHX^{29A}{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{29A}$ is independently —F, —Cl, —Br, or —I.

In embodiments, $R^{29A}$ is independently unsubstituted methyl. In embodiments, $R^{29A}$ is independently unsubstituted ethyl.

$R^{30A}$ is independently oxo, halogen, —$CX^{30A}{}_3$, —$CHX^{30A}{}_2$, —$CH_2X^{30A}$, —$OCX^{30A}{}_3$, —$OCH_2X^{30A}$, —$OCHX^{30A}{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC—(O)$NHNH_2$, —NHC=(O)$NH_2$, —$NHSO_2H$, —NHC=(O)H, —NHC(O)—OH, —NHOH, —$N_3$, $R^{31A}$-substituted or unsubstituted alkyl (e.g., $C_1$-$C_8$, $C_1$-$C_6$, $C_1$-$C_4$, or $C_1$-$C_2$), $R^{31A}$-substituted or unsubstituted heteroalkyl (e.g., 2 to 8 membered, 2 to 6 membered, 4 to 6 membered, 2 to 3 membered, or 4 to 5 membered), $R^{31A}$-substituted or unsubstituted cycloalkyl (e.g., $C_3$-$C_8$, $C_3$-$C_6$, $C_4$-$C_6$, or $C_5$-$C_6$), $R^{31A}$-substituted or unsubstituted heterocycloalkyl (e.g., 3 to 8 membered, 3 to 6 membered, 4 to 6 membered, 4 to 5 membered, or 5 to 6 membered), $R^{31A}$-substituted or unsubstituted aryl (e.g., $C_6$-$C_{10}$ or phenyl), or $R^{31A}$-substituted or unsubstituted heteroaryl (e.g., 5 to 10 membered, 5 to 9 membered, or 5 to 6 membered). In embodiments, $R^{30A}$ is independently oxo, halogen, —$CX^{30A}{}_3$, —$CHX^{30A}{}_2$, —$CH_2X^{30A}$, —$OCX^{30A}{}_3$, —$OCH_2X^{30A}$, —$OCHX^{30A}{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{30A}$ is independently —F, —Cl, —Br, or —I.

$R^{31A}$ is independently oxo, halogen, —$CX^{31A}{}_3$, $CX^{31A}{}_2$, —$CH_2X^{31A}$, —$OCX^{31A}{}_3$, —$OCH_2X^{31A}$, $OCHX^{31A}{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{31A}$ is independently —F, —Cl, —Br, or —I In embodiments, $R^{4B}$ is independently hydrogen, —$CX^{4B}{}_3$, —$CHX^{4B}{}_2$, —$CH_2X^{4B}$, —CN, —COOH, —$CONH_2$, $R^{29B}$-substituted or unsubstituted alkyl (e.g., $C_1$-$C_8$, $C_1$-$C_6$, $C_1$-$C_4$, or $C_1$-$C_2$), $R^{29B}$-substituted or unsubstituted heteroalkyl (e.g., 2 to 8 membered, 2 to 6 membered, 4 to 6 membered, 2 to 3 membered, or 4 to 5 membered), $R^{29B}$-substituted or unsubstituted cycloalkyl (e.g., $C_3$-$C_8$, $C_3$-$C_6$, $C_4$-$C_6$, or $C_5$-$C_6$), $R^{29B}$-substituted or unsubstituted heterocycloalkyl (e.g., 3 to 8 membered, 3 to 6 membered, 4 to 6 membered, 4 to 5 membered, or 5 to 6 membered), $R^{29B}$-substituted or unsubstituted aryl (e.g., $C_6$-$C_0$ or phenyl), or $R^{29B}$-substituted or unsubstituted heteroaryl (e.g., 5 to 10 membered, 5 to 9 membered, or 5 to 6 membered). In embodiments, $R^{4B}$ is independently hydrogen, —$CX^{4B}{}_3$, —$CHX^{4B}{}_2$, —$CH_2X^{4B}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{4B}$ is independently —F, —Cl, —Br, or —I.

In embodiments, $R^{4B}$ is independently hydrogen. In embodiments, $R^{4B}$ is independently unsubstituted methyl. In embodiments, $R^{4B}$ is independently unsubstituted ethyl.

In embodiments, $R^{4A}$ and $R^{4B}$ substituents bonded to the same nitrogen atom may optionally be joined to form a $R^{29B}$-substituted or unsubstituted heterocycloalkyl (e.g., 3 to 8 membered, 3 to 6 membered, 4 to 6 membered, 4 to 5 membered, or 5 to 6 membered) or $R^{29B}$-substituted or unsubstituted heteroaryl (e.g., 5 to 10 membered, 5 to 9 membered, or 5 to 6 membered). In embodiments, $R^{4A}$ and $R^{4B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 10 membered, 5 to 9 membered, or 5 to 6 membered). In embodiments, $R^{4A}$ and $R^{4B}$ substituents bonded to the same nitrogen atom may optionally be joined to form a $R^{29B}$-substituted or unsubstituted heterocycloalkyl (e.g., 3 to 8 membered, 3 to 6 membered, 4 to 6 membered, 4 to 5 membered, or 5 to 6 membered). In embodiments, $R^{4A}$ and $R^{4B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

$R^{29B}$ is independently oxo, halogen, —$CX^{29B}{}_3$, —$CHX^{29}B2$, —$CH_2X^{29B}$, —$OCX^{29B}{}_3$, —$OCH_2X^{29B}$, —$OCHX^{29B}{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)

NHNH$_2$, —NHC=(O)NH$_2$, —NHSO$_2$H, —NHC=(O)H, —NHC(O)—OH, —NHOH, —N$_3$, R$^{30B}$-substituted or unsubstituted alkyl (e.g., C$_1$-C$_8$, C$_1$-C$_6$, C$_1$-C$_4$, or C$_1$-C$_2$), R$^{30B}$-substituted or unsubstituted heteroalkyl (e.g., 2 to 8 membered, 2 to 6 membered, 4 to 6 membered, 2 to 3 membered, or 4 to 5 membered), R$^{30B}$-substituted or unsubstituted cycloalkyl (e.g., C$_3$-C$_8$, C$_3$-C$_6$, C$_4$-C$_6$, or C$_5$-C$_6$), R$^{30B}$-substituted or unsubstituted heterocycloalkyl (e.g., 3 to 8 membered, 3 to 6 membered, 4 to 6 membered, 4 to 5 membered, or 5 to 6 membered), R$^{30B}$-substituted or unsubstituted aryl (e.g., C$_6$-C$_{10}$ or phenyl), or R$^{30B}$-substituted or unsubstituted heteroaryl (e.g., 5 to 10 membered, 5 to 9 membered, or 5 to 6 membered). In embodiments, R$^{29B}$ is independently oxo, halogen, —CX$^{29B}$$_3$, —CHX$^{29B}$$_2$, —CH$_2$X$^{29B}$, —OCX$^{29B}$$_3$, —OCH$_2$X$^{29B}$, —OCHX$^{29B}$$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered). X$^{29B}$ is independently —F, —Cl, —Br, or —I.

In embodiments, R$^{29B}$ is independently unsubstituted methyl. In embodiments, R$^{29B}$ is independently unsubstituted ethyl.

R$^{30B}$ is independently oxo, halogen, —CX$^{30B}$$_3$, —CHX$^{30B}$$_2$, —CH$_2$X$^{30B}$, —OCX$^{30B}$$_3$, —OCH$_2$X$^{30B}$, —OCHX$^{30B}$$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, R$^{31B}$-substituted or unsubstituted alkyl (e.g., C$_1$-C$_8$, C$_1$-C$_6$, C$_1$-C$_4$, or C$_1$-C$_2$), R$^{31B}$-substituted or unsubstituted heteroalkyl (e.g., 2 to 8 membered, 2 to 6 membered, 4 to 6 membered, 2 to 3 membered, or 4 to 5 membered), R$^{31B}$-substituted or unsubstituted cycloalkyl (e.g., C$_3$-C$_8$, C$_3$-C$_6$, C$_4$-C$_6$, or C$_5$-C$_6$), R$^{31B}$-substituted or unsubstituted heterocycloalkyl (e.g., 3 to 8 membered, 3 to 6 membered, 4 to 6 membered, 4 to 5 membered, or 5 to 6 membered), R$^{31B}$-substituted or unsubstituted aryl (e.g., C$_6$-C$_{10}$ or phenyl), or R$^{31B}$-substituted or unsubstituted heteroaryl (e.g., 5 to 10 membered, 5 to 9 membered, or 5 to 6 membered). In embodiments, R$^{30B}$ is independently oxo, halogen, —CX$^{30B}$$_3$, —CHX$^{30B}$$_2$, —CH$_2$X$^{30B}$, —OCX$^{30B}$$_3$, —OCH$_2$X$^{30B}$, —OCHX$^{30B}$$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered). X$^{30B}$ is independently —F, —Cl, —Br, or —I.

R$^{31B}$ is independently oxo, halogen, —CX$^{31B}$$_3$, —CHX$^{31B}$$_2$, —CH$_2$X$^{31B}$, —OCX$^{31B}$$_3$, —OCH$_2$X$^{31B}$, —OCHX$^{31B}$$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_0$ or phenyl), or unsubstituted heteroaryl (e.g., 5 to 10 membered, 5 to 9 membered, or 5 to 6 membered). X$^{31B}$ is independently —F, —Cl, —Br, or —I In embodiments, R$^{4C}$ is independently hydrogen, —CX$^{4C}$$_3$, —CHX$^{4C}$$_2$, —CH$_2$X, —CN, —COOH, —CONH$_2$, R$^{29C}$-substituted or unsubstituted alkyl (e.g., C$_1$-C$_8$, C$_1$-C$_6$, C$_1$-C$_4$, or C$_1$-C$_2$), R$^{29C}$-substituted or unsubstituted heteroalkyl (e.g., 2 to 8 membered, 2 to 6 membered, 4 to 6 membered, 2 to 3 membered, or 4 to 5 membered), R$^{29C}$-substituted or unsubstituted cycloalkyl (e.g., C$_3$-C$_8$, C$_3$-C$_6$, C$_4$-C$_6$, or C$_5$-C$_6$), R$^{29C}$-substituted or unsubstituted heterocycloalkyl (e.g., 3 to 8 membered, 3 to 6 membered, 4 to 6 membered, 4 to 5 membered, or 5 to 6 membered), R$^{29C}$-substituted or unsubstituted aryl (e.g., C$_6$-C$_{10}$ or phenyl), or R$^{29C}$-substituted or unsubstituted heteroaryl (e.g., 5 to 10 membered, 5 to 9 membered, or 5 to 6 membered). In embodiments, R$^{4C}$ is independently hydrogen, —CX$^{4C}$$_3$, —CHX$^{4C}$$_2$, —CH$_2$X$^{4C}$, —CN, —COOH, —CONH$_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered). X$^{4C}$ is independently —F, —Cl, —Br, or —I. In embodiments, R$^{4C}$ is independently hydrogen. In embodiments, R$^{4C}$ is independently unsubstituted methyl. In embodiments, R$^{4C}$ is independently unsubstituted ethyl.

R$^{29}$ is independently oxo, halogen, —CX$^{29C}$$_3$, —CHX$^{29C}$$_2$, —CH$_2$X$^{29C}$, —OCX$^{29C}$$_3$, —OCH$_2$X$^{29C}$, —OCHX$^{29C}$$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, R$^{30C}$-substituted or unsubstituted alkyl (e.g., C$_1$-C$_8$, C$_1$-C$_6$, C$_1$-C$_4$, or C$_1$-C$_2$), R$^{30C}$-substituted or unsubstituted heteroalkyl (e.g., 2 to 8 membered, 2 to 6 membered, 4 to 6 membered, 2 to 3 membered, or 4 to 5 membered), R$^{30C}$-substituted or unsubstituted cycloalkyl (e.g., C$_3$-C$_8$, C$_3$-C$_6$, C$_4$-C$_6$, or C$_5$-C$_6$), R$^{30C}$-substituted or unsubstituted heterocycloalkyl (e.g., 3 to 8 membered, 3 to 6 membered, 4 to 6 membered, 4 to 5 membered, or 5 to 6 membered), R$^{30C}$-substituted or unsubstituted aryl (e.g., C$_6$-C$_{10}$ or phenyl), or R$^{30C}$-substituted or unsubstituted heteroaryl (e.g., 5 to 10 membered, 5 to 9 membered, or 5 to 6 membered). In embodiments, R$^{29C}$ is independently oxo, halogen, —CX$^{29C}$$_3$, —CHX$^{29C}$$_2$, —CH$_2$X$^{29C}$, —OCX$^{29C}$$_3$, —OCH$_2$X$^{29C}$, —OCHX$^{29C}$$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC (O)—OH, —NHOH, —N$_3$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered). X$^{29C}$ is independently —F, —Cl, —Br, or —I.

In embodiments, R$^{29C}$ is independently unsubstituted methyl. In embodiments, R$^{29C}$ is independently unsubstituted ethyl.

R$^{30C}$ is independently oxo, halogen, —CX$^{30C}_3$, —CHX$^{30C}_2$, —CH$_2$X$^{30C}$, —OCX$^{30C}_3$, —OCH$_2$X$^{30C}$, —OCHX$^{30C}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, R$^{31C}$-substituted or unsubstituted alkyl (e.g., C$_1$-C$_8$, C$_1$-C$_6$, C$_1$-C$_4$, or C$_1$-C$_2$), R$^{31C}$-substituted or unsubstituted heteroalkyl (e.g., 2 to 8 membered, 2 to 6 membered, 4 to 6 membered, 2 to 3 membered, or 4 to 5 membered), R$^{31C}$-substituted or unsubstituted cycloalkyl (e.g., C$_3$-C$_8$, C$_3$-C$_6$, C$_4$-C$_6$, or C$_5$-C$_6$), R$^{31C}$-substituted or unsubstituted heterocycloalkyl (e.g., 3 to 8 membered, 3 to 6 membered, 4 to 6 membered, 4 to 5 membered, or 5 to 6 membered), R$^{31C}$-substituted or unsubstituted aryl (e.g., C$_6$-C$_{10}$ or phenyl), or R$^{31C}$-substituted or unsubstituted heteroaryl (e.g., 5 to 10 membered, 5 to 9 membered, or 5 to 6 membered). In embodiments, R$^{30C}$ is independently oxo, halogen, —CX$^{30C}_3$, —CHX$^{30C}_2$, —CH$_2$X$^{30C}$, —OCX$^{30C}_3$, —OCH$_2$X$^{30C}$, —OCHX$^{30C}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered). X$^{30C}$ is independently —F, —Cl, —Br, or —I.

R$^{31C}$ is independently oxo, halogen, —CX$^{31C}_3$, —CHX$^{31C}_2$, —CH$_2$X$^{31C}$, —OCX$^{31C}_3$, —OCH$_2$X$^{31C}$, —OCHX$^{31C}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered). X$^{31C}$ is independently —F, —Cl, —Br, or —I L$^1$ is —O—, —S—, substituted or unsubstituted C$_1$-C$_2$ alkylene (e.g., —CH$_2$—, —CH$_2$CH$_2$—, —C(CH$_3$)H—, or —CH(CH$_3$)CH$_2$—), or substituted or unsubstituted 2 membered heteroalkylene (e.g., —CH$_2$O—, —OCH$_2$—, —CH$_2$S—, —SCH$_2$—, —CH$_2$NH—, —NHCH$_2$—, —CH(CH$_3$)O—, —OCH(CH$_3$)—, —CH(CH$_3$)S—, —SCH(CH$_3$)—, —CH(CH$_3$)NH—, —NHCH(CH$_3$)—, —CH$_2$N(CH$_3$)—, or —N(CH$_3$)CH$_2$—). In embodiments, L$^1$ is —O—, —S—, or substituted or unsubstituted methylene. In embodiments, L$^1$ is —SCH$_2$—. In embodiments, L$^1$ is —O—. In embodiments, L$^1$ is —S—. In embodiments, L$^1$ is —CH(CH$_3$)—.

In embodiments, L$^1$ is a bond, —S(O)$_2$—, —N(R$^3$)—, —O—, —S—, —C(O)—, —C(O)N(R$^3$)—, —N(R$^3$)C(O)—, —N(R$^3$)C(O)NH—, substituted or unsubstituted alkylene, or substituted or unsubstituted heteroalkylene. In embodiments, L$^1$ is a bond, —C(O)N(R$^3$)—, —N(R$^3$)C(O)—, substituted or unsubstituted alkylene, or substituted or unsubstituted heteroalkylene. In embodiments, L$^1$ is —C(O)N(R$^3$)—, unsubstituted alkylene, or unsubstituted heteroalkylene. In embodiments, L$^1$ is —C(O)N(R$^3$)—. In embodiments, L$^1$ is unsubstituted alkylene. In embodiments, L$^1$ is unsubstituted heteroalkylene. In embodiments, L$^1$ is —C(O)NH—.

In embodiments, L$^1$ is

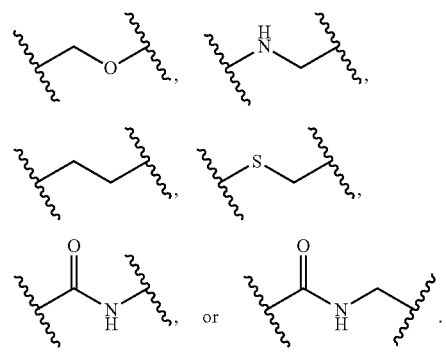

In embodiments, L$^1$ is

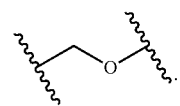 [SMILES: *CO*]

In embodiments, L$^1$ is

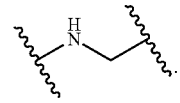 [SMILES: *CN*]

In embodiments, L$^1$ is

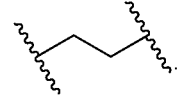

In embodiments, $L^1$ is

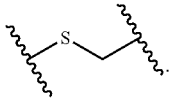 [SMILES: *CS*]

In embodiments, $L^1$ is

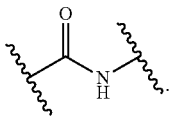 [SMILES: *NC(*)=O]

In embodiments, $L^1$ is

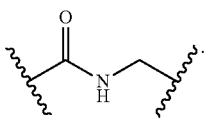

In embodiments, $L^1$ is independently —O—, —S—, $R^{32}$-substituted or unsubstituted $C_1$-$C_2$ alkylene (e.g., $C_1$ or $C_2$) or $R^{32}$-substituted or unsubstituted 2 membered heteroalkylene. In embodiments, $L^1$ is $R^{32}$-substituted or unsubstituted alkylene (e.g., $C_1$-$C_8$ alkylene, $C_1$-$C_6$ alkylene, or $C_1$-$C_4$ alkylene), $R^{32}$-substituted or unsubstituted heteroalkylene (e.g., 2 to 8 membered heteroalkylene, 2 to 6 membered heteroalkylene, or 2 to 4 membered heteroalkylene), $R^{32}$-substituted or unsubstituted cycloalkylene (e.g., $C_3$-$C_8$ cycloalkylene, $C_3$-$C_6$ cycloalkylene, or $C_5$-$C_6$ cycloalkylene), $R^{32}$-substituted or unsubstituted heterocycloalkylene (e.g., 3 to 8 membered heterocycloalkylene, 3 to 6 membered heterocycloalkylene, or 5 to 6 membered heterocycloalkylene), $R^{32}$-substituted or unsubstituted arylene (e.g., $C_6$-$C_{10}$ arylene, $C_{10}$ arylene, or phenylene), or $R^{32}$-substituted or unsubstituted heteroarylene (e.g., 5 to 10 membered heteroarylene, 5 to 9 membered heteroarylene, or 5 to 6 membered heteroarylene). In embodiments, $L^1$ is independently —O—, —S—, unsubstituted $C_1$-$C_2$ alkylene (e.g., $C_1$ or $C_2$) or unsubstituted 2 membered heteroalkylene. In embodiments, $L^1$ is independently unsubstituted methylene. In embodiments, $L^1$ is independently unsubstituted ethylene. In embodiments, $L^1$ is substituted 2 membered heteroalkylene. In embodiments, $L^1$ is substituted 3 membered heteroalkylene. In embodiments, $L^1$ is substituted 4 membered heteroalkylene. In embodiments, $L^1$ is an unsubstituted 2 membered heteroalkylene. In embodiments, $L^1$ is an unsubstituted 3 membered heteroalkylene. In embodiments, $L^1$ is an unsubstituted 4 membered heteroalkylene. In embodiments, $L^1$ is —CONHCH$_2$—.

$R^{32}$ is independently oxo, halogen, —CX$^{32}_3$, —CHX$^{32}_2$, —CH$_2$X$^{32}$, —OCX$^{32}_3$, —OCH$_2$X$^{32}$, —OCHX$^{32}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, $R^{33}$-substituted or unsubstituted alkyl (e.g., $C_1$-$C_8$, $C_1$-$C_6$, $C_1$-$C_4$, or $C_1$-$C_2$), $R^{33}$-substituted or unsubstituted heteroalkyl (e.g., 2 to 8 membered, 2 to 6 membered, 4 to 6 membered, 2 to 3 membered, or 4 to 5 membered), $R^{33}$-substituted or unsubstituted cycloalkyl (e.g., $C_3$-$C_8$, $C_3$-$C_6$, $C_4$-$C_6$, or $C_5$-$C_6$), $R^{33}$-substituted or unsubstituted heterocycloalkyl (e.g., 3 to 8 membered, 3 to 6 membered, 4 to 6 membered, 4 to 5 membered, or 5 to 6 membered), $R^{33}$-substituted or unsubstituted aryl (e.g., $C_6$-$C_{10}$ or phenyl), or $R^{33}$-substituted or unsubstituted heteroaryl (e.g., 5 to 10 membered, 5 to 9 membered, or 5 to 6 membered). In embodiments, $R^{32}$ is independently oxo, halogen, —CX$^{32}_3$, —CHX$^{32}_2$, —CH$_2$X$^{32}$, —OCX$^{32}_3$, —OCH$_2$X$^{32}$, —OCHX$^{32}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_0$ or phenyl), or unsubstituted heteroaryl (e.g., 5 to 10 membered, 5 to 9 membered, or 5 to 6 membered). $X^{32}$ is independently —F, —Cl, —Br, or —I.

In embodiments, $R^{32}$ is independently unsubstituted methyl. In embodiments, $R^{32}$ is independently unsubstituted ethyl.

$R^{33}$ is independently oxo, halogen, —CX$^{33}_3$, —CHX$^{33}_2$, —CH$_2$X$^{33}$, —OCX$^{33}_3$, —OCH$_2$X$^{33}$, —OCHX$^{33}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, $R^{34}$-substituted or unsubstituted alkyl (e.g., $C_1$-$C_8$, $C_1$-$C_6$, $C_1$-$C_4$, or $C_1$-$C_2$), $R^{34}$-substituted or unsubstituted heteroalkyl (e.g., 2 to 8 membered, 2 to 6 membered, 4 to 6 membered, 2 to 3 membered, or 4 to 5 membered), $R^{34}$-substituted or unsubstituted cycloalkyl (e.g., $C_3$-$C_8$, $C_3$-$C_6$, $C_4$-$C_6$, or $C_5$-$C_6$), $R^{34}$-substituted or unsubstituted heterocycloalkyl (e.g., 3 to 8 membered, 3 to 6 membered, 4 to 6 membered, 4 to 5 membered, or 5 to 6 membered), $R^{34}$-substituted or unsubstituted aryl (e.g., $C_6$-$C_0$ or phenyl), or $R^{34}$-substituted or unsubstituted heteroaryl (e.g., 5 to 10 membered, 5 to 9 membered, or 5 to 6 membered). In embodiments, $R^{33}$ is independently oxo, halogen, —CX$^{33}_3$, —CHX$^{33}_2$, —CH$_2$X$^{33}$, —OCX$^{33}_3$, —OCH$_2$X$^{33}$, —OCHX$^{33}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{33}$ is independently —F, —Cl, —Br, or —I.

In embodiments, $R^{33}$ is independently unsubstituted methyl. In embodiments, $R^{33}$ is independently unsubstituted ethyl.

$R^{34}$ is independently oxo, halogen, —CX$^{34}_3$, —CHX$^{34}_2$, —CH$_2$X$^{34}$, —OCX$^{34}_3$, —OCH$_2$X$^{34}$, —OCHX$^{34}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC (O)—OH, —NHOH, —N$_3$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered). X$^{34}$ is independently —F, —Cl, —Br, or —I.

In embodiments, R$^{34}$ is independently unsubstituted methyl. In embodiments, R$^{34}$ is independently unsubstituted ethyl.

In embodiments, L$^2$ is —O—, —S—, substituted or unsubstituted C$_1$-C$_2$ alkylene (e.g., —CH$_2$—, —CH$_2$CH$_2$—, —C(CH$_3$)H—, or —CH(CH$_3$)CH$_2$—), or substituted or unsubstituted 2 membered heteroalkylene (e.g., —CH$_2$O—, —OCH$_2$—, —CH$_2$S—, —SCH$_2$—, —CH$_2$NH—, —NHCH$_2$—, —CH(CH$_3$)O—, —OCH(CH$_3$)—, —CH(CH$_3$)S—, —SCH(CH$_3$)—, —CH(CH$_3$)NH—, —NHCH(CH$_3$)—, —CH$_2$N(CH$_3$)—, or —N(CH$_3$)CH$_2$—). In embodiments, L$^2$ is —O—, —S—, or substituted or unsubstituted methylene. In embodiments, L$^2$ is —SCH$_2$—. In embodiments, L$^2$ is —O—. In embodiments, L$^2$ is —S—. In embodiments, L$^2$ is —CH(CH$_3$)—. In embodiments, L$^2$ is a bond, —S(O)$_2$—, —N(R$^4$)—, —O—, —S—, —C(O)—, —C(O)N(R$^4$)—, —N(R$^4$)C(O)—, —N(R$^4$)C(O)NH—, substituted or unsubstituted alkylene, or substituted or unsubstituted heteroalkylene. In embodiments, L$^2$ is a bond, —N(R$^4$)C(O)—, or substituted heteroalkylene. In embodiments, L$^2$ is a bond. In embodiments, L$^2$ is —N(R$^4$)C(O)—. In embodiments, L$^2$ is substituted heteroalkylene.

In embodiments, L$^2$ is a bond. In embodiments, L$^2$ is —O—. In embodiments, L$^2$ is

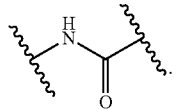

In embodiments, L$^2$ is

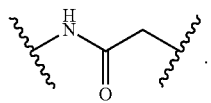

In embodiments, L$^2$ is

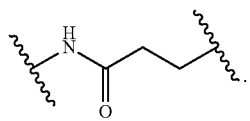 [SMILES: *CCC(=O)N*]

In embodiments, L$^2$ is

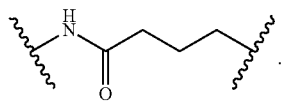 [SMILES: *CCCC(=O)N*]

In embodiments, L$^2$ is

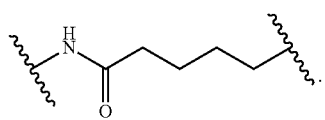 [SMILES: *CCCCC(=O)N*]

In embodiments, L$^2$ is

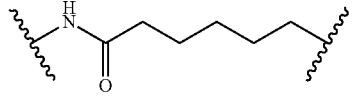

In embodiments, L$^2$ is

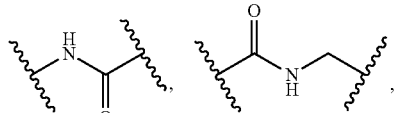

In embodiments, L$^2$ is

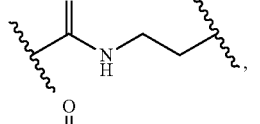

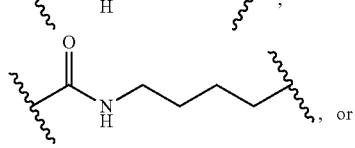

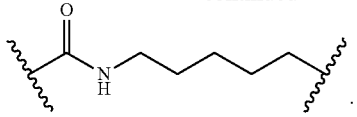

In embodiments, $L^2$ is a bond, —S(O)$_2$—, —NH—, —O—, —S—, —C(O)—, —C(O)NH—, —NHC(O)—, —NHC(O)NH—, substituted or unsubstituted alkylene, or substituted or unsubstituted heteroalkylene. In embodiments, $L^2$ is a bond, —NHC(O)—, or substituted heteroalkylene. In embodiments, $L^2$ is a bond. In embodiments, $L^2$ is —NHC(O)—. In embodiments, L is substituted heteroalkylene.

In embodiments, $L^2$ is substituted 2 to 6 membered heteroalkylene. In embodiments, $L^2$ is substituted 3 to 6 membered heteroalkylene. In embodiments, $L^2$ is substituted 3 to 5 membered heteroalkylene. In embodiments, $L^2$ is substituted 2 membered heteroalkylene. In embodiments, $L^2$ is substituted 3 membered heteroalkylene. In embodiments, $L^2$ is substituted 4 membered heteroalkylene. In embodiments, $L^2$ is substituted 5 membered heteroalkylene. In embodiments, $L^2$ is substituted 6 membered heteroalkylene. In embodiments, $L^2$ is —NHC(O)CH$_2$CH$_2$—. In embodiments, $L^2$ is —NHC(O)CH$_2$—. In embodiments, $L^2$ is a bond.

In embodiments, $L^2$ is independently —O—, —S—, $R^{35}$-substituted or unsubstituted $C_1$-$C_2$ alkylene (e.g., $C_1$ or $C_2$) or $R^{35}$-substituted or unsubstituted 2 membered heteroalkylene. In embodiments, $L^2$ is $R^{35}$-substituted or unsubstituted alkylene (e.g., $C_1$-$C_8$ alkylene, $C_1$-$C_6$ alkylene, or $C_1$-$C_4$ alkylene), $R^{35}$-substituted or unsubstituted heteroalkylene (e.g., 2 to 8 membered heteroalkylene, 2 to 6 membered heteroalkylene, or 2 to 4 membered heteroalkylene), $R^{35}$-substituted or unsubstituted cycloalkylene (e.g., $C_3$-$C_8$ cycloalkylene, $C_3$-$C_6$ cycloalkylene, or $C_5$-$C_6$ cycloalkylene), $R^{35}$-substituted or unsubstituted heterocycloalkylene (e.g., 3 to 8 membered heterocycloalkylene, 3 to 6 membered heterocycloalkylene, or 5 to 6 membered heterocycloalkylene), $R^{35}$-substituted or unsubstituted arylene (e.g., $C_6$-$C_{10}$ arylene, $C_{10}$ arylene, or phenylene), or $R^{35}$-substituted or unsubstituted heteroarylene (e.g., 5 to 10 membered heteroarylene, 5 to 9 membered heteroarylene, or 5 to 6 membered heteroarylene). In embodiments, $L^2$ is independently —O—, —S—, unsubstituted $C_1$-$C_2$ alkylene (e.g., $C_1$ or $C_2$) or unsubstituted 2 membered heteroalkylene. In embodiments, $L^2$ is independently unsubstituted methylene. In embodiments, $L^2$ is independently unsubstituted ethylene.

$R^{35}$ is independently oxo, halogen, —CX$^{35}$$_3$, —CHX$^{35}$$_2$, —CH$_2$X$^{35}$, —OCX$^{35}$$_3$, —OCH$_2$X$^{35}$, —OCHX$^{35}$$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, $R^{36}$-substituted or unsubstituted alkyl (e.g., $C_1$-$C_8$, $C_1$-$C_6$, $C_1$-$C_4$, or $C_1$-$C_2$), $R^{36}$-substituted or unsubstituted heteroalkyl (e.g., 2 to 8 membered, 2 to 6 membered, 4 to 6 membered, 2 to 3 membered, or 4 to 5 membered), $R^{36}$-substituted or unsubstituted cycloalkyl (e.g., $C_3$-$C_8$, $C_3$-$C_6$, $C_4$-$C_6$, or $C_5$-$C_6$), $R^{36}$-substituted or unsubstituted heterocycloalkyl (e.g., 3 to 8 membered, 3 to 6 membered, 4 to 6 membered, 4 to 5 membered, or 5 to 6 membered), $R^{36}$-substituted or unsubstituted aryl (e.g., $C_6$-$C_{10}$ or phenyl), or $R^{36}$-substituted or unsubstituted heteroaryl (e.g., 5 to 10 membered, 5 to 9 membered, or 5 to 6 membered). In embodiments, $R^{35}$ is independently oxo, halogen, —CX$^{35}$$_3$, —CHX$^{35}$$_2$, —CH$_2$X$^{35}$, —OCX$^{35}$$_3$, —OCH$_2$X$^{35}$, —OCHX$^{35}$$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC—(O)NH$_2$, —NHSO$_2$H, —NHC=(O)H, —NHC(O)—OH, —NHOH, —N$_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_0$ or phenyl), or unsubstituted heteroaryl (e.g., 5 to 10 membered, 5 to 9 membered, or 5 to 6 membered). $X^{35}$ is independently —F, —Cl, —Br, or —I.

In embodiments, $R^{35}$ is independently unsubstituted methyl. In embodiments, $R^{35}$ is independently unsubstituted ethyl.

$R^{36}$ is independently oxo, halogen, —CX$^{36}$$_3$, —CHX$^{36}$$_2$, —CH$_2$X$^{36}$, —OCX$^{36}$$_3$, —OCH$_2$X$^{36}$, —OCHX$^{36}$$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, $R^{37}$-substituted or unsubstituted alkyl (e.g., $C_1$-$C_8$, $C_1$-$C_6$, $C_1$-$C_4$, or $C_1$-$C_2$), $R^{37}$-substituted or unsubstituted heteroalkyl (e.g., 2 to 8 membered, 2 to 6 membered, 4 to 6 membered, 2 to 3 membered, or 4 to 5 membered), $R^{37}$-substituted or unsubstituted cycloalkyl (e.g., $C_3$-$C_8$, $C_3$-$C_6$, $C_4$-$C_6$, or $C_5$-$C_6$), $R^{37}$-substituted or unsubstituted heterocycloalkyl (e.g., 3 to 8 membered, 3 to 6 membered, 4 to 6 membered, 4 to 5 membered, or 5 to 6 membered), $R^{37}$-substituted or unsubstituted aryl (e.g., $C_6$-$C_0$ or phenyl), or $R^{37}$-substituted or unsubstituted heteroaryl (e.g., 5 to 10 membered, 5 to 9 membered, or 5 to 6 membered). In embodiments, $R^{36}$ is independently oxo, halogen, —CX$^{36}$$_3$, —CHX$^{36}$$_2$, —CH$_2$X$^{36}$, —OCX$^{36}$$_3$, —OCH$_2$X$^{36}$, —OCHX$^{36}$$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —N$_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{36}$ is independently —F, —Cl, —Br, or —I.

In embodiments, $R^{36}$ is independently unsubstituted methyl. In embodiments, $R^{36}$ is independently unsubstituted ethyl.

$R^{37}$ is independently oxo, halogen, —CX$^{37}$$_3$, —CHX$^{37}$$_2$, —CH$_2$X$^{37}$, —OCX$^{37}$$_3$, —OCH$_2$X$^{37}$, —OCHX$^{37}$$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC—(O)NH$_2$, —NHSO$_2$H, —NHC=(O)H, —NHC(O)—OH, —NHOH, —N$_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{37}$ is independently —F, —Cl, —Br, or —I.

In embodiments, $R^{37}$ is independently unsubstituted methyl. In embodiments, $R^{37}$ is independently unsubstituted ethyl.

In embodiments, the compound as described herein, including embodiments thereof, has the formula:

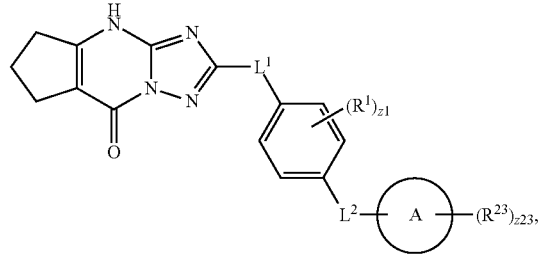

(IIA)

wherein $R^{23}$ is as described herein, including embodiments. Ring A is a cycloalkyl, heterocycloalkyl, aryl, or heteroaryl. The symbol z23 is an integer from 0 to 5.

In embodiments, Ring A is ($C_3$-$C_{10}$) cycloalkyl, 3 to 10 membered heterocycloalkyl, ($C_6$-$C_{10}$) aryl, or 5 to 10 membered heteroaryl. In embodiments, Ring A is a heteroaryl. In embodiments, Ring A is a 5 to 6 membered heteroaryl. In embodiments, Ring A is a 5 membered heteroaryl.

In embodiments, Ring A is a ($C_3$-$C_{10}$) cycloalkyl, a 3 to 10 membered heterocycloalkyl, a ($C_6$-$C_{10}$) aryl, or a 5 to 10 membered heteroaryl. In embodiments, Ring A is a cycloalkyl (e.g., $C_3$-$C_8$ cycloalkyl, $C_3$-$C_6$ cycloalkyl, or $C_5$-$C_6$ cycloalkyl). In embodiments, Ring A is a $C_3$-$C_8$ cycloalkyl. In embodiments, Ring A is a $C_3$-$C_6$ cycloalkyl. In embodiments, Ring A is a $C_5$-$C_6$ cycloalkyl. In embodiments, Ring A is a $C_6$ cycloalkyl. In embodiments, Ring A is a $C_5$ cycloalkyl. In embodiments, Ring A is a ($C_6$-$C_{10}$) aryl. In embodiments, Ring A is phenyl. In embodiments, Ring A is naphthyl. In embodiments, Ring A is aziridinyl, oxiranyl, thiiranyl, azetidinyl, oxetanyl, thietanyl, pyrrolidinyl, pyrrolyl, imidazolyl, imidazolinyl, pyrazolinyl, tetrahydrofuranyl, thiolanyl, piperidinyl, piperazinyl, pyranyl, morpholinyl, 1,4-dioxanyl, tetrahydro-2H-pyranyl, thianyl, or dithianyl. In embodiments, Ring A is a phenyl, thiofuranyl, imidazolyl, pyrazolyl, triazolyl, tetrazolyl, furanyl, oxazolyl, isooxazolyl, oxadiazolyl, oxatriazolyl, thienyl, thiazolyl, isothiazolyl, pyridinyl, pyrazinyl, pyrimidinyl, pyridazinyl, or triazinyl (e.g., 1,3,5-triazinyl, 1,2,3-triazinyl, or 1,2,4-triazinyl). In embodiments, Ring A is indolyl, benzimidazolyl, indazolyl, benzotriazolyl, pyrrolopyrimidinyl, purinyl, indolizinyl, pyrrolopyriazinyl, pyrrolopyrimidinyl, imidazopyridazinyl, imidazopyridinyl, imidazopyrimidinyl, cinnolinyl, quinazolinyl, quinoxalinyl, phthalazinyl, pyridopyrazinyl, pteridinyl, pyrazolopyridinyl, quinolinyl, isoquinolinyl, naphthyridinyl, or carbazolyl.

In embodiments, -(Ring A)-$(R^{23})_{z23}$ is:

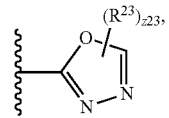

wherein $R^{23}$ and z23 are as described herein including embodiments.

In embodiments, -(ring A)-$(R^{23})_{z23}$ is:

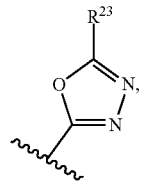

wherein $R^{23}$ is as described herein, including embodiments.

In embodiments, $R^2$ is independently halogen, —$CX^{23}_3$, —$C(O)R^{100C}$, —$C(O)$—$OR^{100C}$, —$C(O)NR^{100A}R^{100B}$, —$OR^{100D}$, —$NR^{100A}SO_2R^{100D}$, —$NR^{100A}C(O)R^{100C}$, —$NR^{100A}C(O)OR^{100C}$, —$NR^{100A}OR^{100C}$, substituted or unsubstituted alkyl, substituted or unsubstituted heteroalkyl, substituted or unsubstituted aryl, or substituted or unsubstituted heteroaryl.

In embodiments, $R^{23}$ is independently halogen, —$CX^{23}_3$, $C(O)R^{100C}$, substituted or unsubstituted heterocycloalkyl, substituted or unsubstituted aryl, or substituted or unsubstituted heteroaryl. In embodiments, $R^{23}$ is substituted or unsubstituted phenyl. In embodiments, $R^{23}$ is substituted phenyl. In embodiments, $R^{23}$ is unsubstituted phenyl.

In embodiments, $R^{23}$ is independently halogen, —$CX^{23}_3$, $C(O)R^{100C}$, $R^{24}$-substituted or unsubstituted heterocycloalkyl, $R^{24}$-substituted or unsubstituted aryl, or $R^{24}$-substituted or unsubstituted heteroaryl. In embodiments, $R^2$ is $R^{24}$-substituted or unsubstituted phenyl. In embodiments, $R^{23}$ is $R^{24}$-substituted phenyl.

In embodiments, $R^{23}$ is $R^{24}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{23}$ is $R^{24}$-substituted cycloalkyl (e.g., $C_3$-$C_8$ cycloalkyl, $C_3$-$C_6$ cycloalkyl, or $C_5$-$C_6$ cycloalkyl). In embodiments, $R^2$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{23}$ is $R^{24}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{23}$ is $R^{24}$-substituted heterocycloalkyl (e.g., 3 to 8 membered heterocycloalkyl, 3 to 6 membered heterocycloalkyl, or 5 to 6 membered heterocycloalkyl). In embodiments, $R^{23}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{23}$ is $R^{24}$-substituted or unsubstituted aryl (e.g., $C_6$-$C_{10}$ aryl, $C_{10}$ aryl, or phenyl). In embodiments, $R^{23}$ is $R^{24}$-substituted aryl (e.g., $C_6$-$C_{10}$ aryl, $C_{10}$ aryl, or phenyl). In embodiments, $R^{23}$ is an unsubstituted aryl (e.g., $C_6$-$C_{10}$ aryl, $C_{10}$ aryl, or phenyl). In embodiments, $R^{23}$ is an unsubstituted phenyl. In embodiments, $R^{23}$ is a $R^{24}$-substituted phenyl.

In embodiments, $R^{23}$ is $R^{24}$-substituted or unsubstituted heteroaryl (e.g., 5 to 10 membered heteroaryl, 5 to 9 membered heteroaryl, or 5 to 6 membered heteroaryl). In embodiments, $R^{23}$ is $R^{24}$-substituted heteroaryl (e.g., 5 to 10 membered heteroaryl, 5 to 9 membered heteroaryl, or 5 to 6 membered heteroaryl). In embodiments, $R^{23}$ is an unsubstituted heteroaryl (e.g., 5 to 10 membered heteroaryl, 5 to 9 membered heteroaryl, or 5 to 6 membered heteroaryl). In embodiments, $R^{23}$ is $R^{24}$-substituted imidazolyl, $R^{24}$-substituted pyrrolyl, $R^{24}$-substituted pyrazolyl, $R^{24}$-substituted triazolyl, $R^{24}$-substituted tetrazolyl, $R^{24}$-substituted furanyl, $R^{24}$-substituted oxazolyl, $R^{24}$-substituted isooxazolyl, $R^{24}$-substituted oxadiazolyl, $R^{24}$-substituted oxatriazolyl, $R^{24}$-substituted thienyl, $R^{24}$-substituted thiazolyl, $R^{24}$-substituted isothiazolyl, $R^{24}$-substituted pyridinyl, RU-substituted pyrazinyl, $R^{24}$-substituted pyrimidinyl, $R^{24}$-substituted pyridazinyl, $R^{24}$-substituted triazinyl (e.g., $R^{24}$-substituted 1,3,5-triazinyl, $R^{24}$-substituted 1,2,3-triazinyl, or $R^{24}$-substituted 1,2,4-triazinyl). In embodiments, $R^{23}$ is an unsubstituted imidazolyl, an unsubstituted pyrrolyl, an unsubstituted pyrazolyl, an unsubstituted triazolyl, an unsubstituted tetrazolyl, an unsubstituted furanyl, an unsubstituted oxazolyl, an unsubstituted isooxazolyl, an unsubstituted oxadiazolyl, an unsubstituted oxatriazolyl, an unsubstituted thienyl, an unsubstituted thiazolyl, an unsubstituted isothiazolyl, an unsubstituted pyridinyl, an unsubstituted pyrazinyl, an unsubstituted pyrimidinyl, an unsubstituted pyridazinyl, an unsubstituted triazinyl (e.g., an unsubstituted 1,3,5-triazinyl, an unsubstituted 1,2,3-triazinyl, or an unsubstituted 1,2,4-triazinyl). In embodiments, $R^{23}$ is an unsubstituted thiofuranyl. In embodiments, $R^{23}$ is unsubstituted thienyl.

In embodiments, $R^{24}$ is —Br. In embodiments, $R^{24}$ is —Cl. In embodiments, $R^{24}$ is -I. In embodiments, $R^{24}$ is —F. In embodiments, $R^{24}$ is —OCH$_3$. In embodiments, $R^{24}$ is —OCH$_2$CH$_3$. In embodiments, $R^{24}$ is substituted or unsubstituted 2 to 3 membered heteroalkyl. In embodiments, $R^{24}$ is substituted or unsubstituted 2 to 4 membered heteroalkyl. In embodiments, $R^{24}$ is substituted or unsubstituted 2 to 6 membered heteroalkyl. In embodiments, $R^{24}$ is —CF$_3$. In embodiments, $R^{24}$ is —CHF$_2$. In embodiments, $R^{24}$ is —CH$_2$F. In embodiments, $R^{24}$ is —CCl$_3$. In embodiments, $R^{24}$ is —CHCl$_2$. In embodiments, $R^{24}$ is —CH$_2$Cl. In embodiments, $R^{24}$ is —CBr$_3$. In embodiments, $R^{24}$ is —CHBr$_2$. In embodiments, $R^{24}$ is —CH$_2$Br. In embodiments, $R^{24}$ is —CI$_3$. In embodiments, $R^{24}$ is —CHI$_2$. In embodiments, $R^2$ is —CH$_2$I. In embodiments, $R^{24}$ is —OCF$_3$. In embodiments, $R^{24}$ is —OCHF$_2$. In embodiments, $R^{24}$ is —OCH$_2$F. In embodiments, $R^{24}$ is —OCCl$_3$. In embodiments, $R^{24}$ is —OCHCl$_2$. In embodiments, $R^{24}$ is —OCH$_2$Cl. In embodiments, $R^{24}$ is —OCBr$_3$. In embodiments, $R^{24}$ is —OCHBr$_2$. In embodiments, $R^{24}$ is —OCH$_2$Br. In embodiments, $R^{24}$ is —OCI$_3$. In embodiments, $R^{24}$ is —OCHI$_2$. In embodiments, $R^{24}$ is —OCH$_2$I.

In embodiments, $R^{24}$ is substituted or unsubstituted $C_1$-$C_6$ alkyl. In embodiments, $R^{24}$ is substituted or unsubstituted 2 to 6 membered heteroalkyl. In embodiments, $R^{24}$ is substituted or unsubstituted $C_3$-$C_8$ cycloalkyl. In embodiments, $R^{24}$ is substituted or unsubstituted 3 to 8 membered heterocycloalkyl. In embodiments, $R^{24}$ is substituted or unsubstituted phenyl. In embodiments, $R^{24}$ is substituted or unsubstituted 5 to 6 membered heteroaryl. In embodiments, $R^{24}$ is independently halogen. In embodiments, $R^2$ is independently —CX$^{24}_3$. In embodiments, $R^{24}$ is independently —CHX$^{24}_2$. In embodiments, $R^{24}$ is independently —CH$_2$X$^{24}$. In embodiments, $R^{24}$ is independently —OCX$^{24}_3$. In embodiments, $R^{24}$ is independently —OCH$_2$X$^{24}$. In embodiments, $R^{24}$ is independently —OCHX$^{24}_2$. In embodiments, $R^{24}$ is independently —OCH$_2$X$^{24}$. In embodiments, $R^{24}$ is independently —CN. In embodiments, $R^{24}$ is independently —CH$_3$. In embodiments, $R^{24}$ is independently —OCH$_3$.

In embodiments, $R^2$ is substituted or unsubstituted alkyl (e.g., $C_1$-$C_8$ alkyl, $C_1$-$C_6$ alkyl, or $C_1$-$C_4$ alkyl). In embodiments, $R^{24}$ is substituted alkyl (e.g., $C_1$-$C_8$ alkyl, $C_1$-$C_6$ alkyl, or $C_1$-$C_4$ alkyl). In embodiments, $R^{24}$ is an unsubstituted alkyl (e.g., $C_1$-$C_8$ alkyl, $C_1$-$C_6$ alkyl, or $C_1$-$C_4$ alkyl). In embodiments, $R^{24}$ is substituted or unsubstituted methyl. In embodiments, $R^{24}$ is substituted or unsubstituted $C_2$ alkyl. In embodiments, $R^{24}$ is substituted or unsubstituted $C_3$ alkyl. In embodiments, $R^{24}$ is substituted or unsubstituted $C_4$ alkyl. In embodiments, $R^{24}$ is substituted or unsubstituted $C_5$ alkyl. In embodiments, $R^{24}$ is substituted or unsubstituted $C_6$ alkyl. In embodiments, $R^{24}$ is substituted or unsubstituted $C_7$ alkyl. In embodiments, $R^{24}$ is substituted or unsubstituted $C_8$ alkyl. In embodiments, $R^{24}$ is substituted methyl. In embodiments, $R^{24}$ is substituted $C_2$ alkyl. In embodiments, $R^{24}$ is substituted $C_3$ alkyl. In embodiments, $R^{24}$ is substituted $C_4$ alkyl. In embodiments, $R^{24}$ is substituted $C_5$ alkyl. In embodiments, $R^{24}$ is substituted $C_6$ alkyl. In embodiments, $R^{24}$ is substituted $C_7$ alkyl. In embodiments, $R^{24}$ is substituted $C_8$ alkyl. In embodiments, $R^{24}$ is an unsubstituted methyl. In embodiments, $R^{24}$ is an unsubstituted $C_2$ alkyl. In embodiments, $R^{24}$ is an unsubstituted $C_3$ alkyl. In embodiments, $R^{24}$ is an unsubstituted $C_4$ alkyl. In embodiments, $R^{24}$ is an unsubstituted $C_5$ alkyl. In embodiments, $R^{24}$ is an unsubstituted $C_6$ alkyl. In embodiments, $R^{24}$ is an unsubstituted $C_7$ alkyl. In embodiments, $R^{24}$ is an unsubstituted $C_8$ alkyl.

$R^{100A}$, $R^{100B}$, $R^{100C}$, and $R^{100D}$ are independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{100A}$ and $R^{100B}$ substituents bonded to the same nitrogen atom may optionally be joined to form a substituted or unsubstituted heterocycloalkyl or substituted or unsubstituted heteroaryl.

In embodiments, $R^{100A}$ is independently hydrogen, —CX$^{100A}_3$, —CHX$^{100A}_2$, —CH$_2$X$^{100A}$, —CN, —COOH, —CONH$_2$, $R^{101A}$-substituted or unsubstituted alkyl (e.g., $C_1$-$C_8$, $C_1$-$C_6$, $C_1$-$C_4$, or $C_1$-$C_2$), $R^{100A}$-substituted or unsubstituted heteroalkyl (e.g., 2 to 8 membered, 2 to 6 membered, 4 to 6 membered, 2 to 3 membered, or 4 to 5 membered), $R^{101A}$-substituted or unsubstituted cycloalkyl (e.g., $C_3$-$C_8$, $C_3$-$C_6$, $C_4$-$C_6$, or $C_5$-$C_6$), $R^{101A}$-substituted or unsubstituted heterocycloalkyl (e.g., 3 to 8 membered, 3 to 6 membered, 4 to 6 membered, 4 to 5 membered, or 5 to 6 membered), $R^{101A}$-substituted or unsubstituted aryl (e.g., $C_6$-$C_{10}$ or phenyl), or $R^{101A}$-substituted or unsubstituted heteroaryl (e.g., 5 to 10 membered, 5 to 9 membered, or 5 to 6 membered). In embodiments, $R^{100A}$ is independently hydrogen, —CX$^{100A}_3$, —CHX$^{100A}_2$, —CH$_2$X$^{100A}$, —CN, —COOH, —CONH$_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{100A}$ is independently —F, —Cl, —Br, or —I.

In embodiments, $R^{100A}$ is independently hydrogen. In embodiments, $R^{100A}$ is independently unsubstituted methyl. In embodiments, $R^{100A}$ is independently unsubstituted ethyl.

In embodiments, $R^{100A}$ and $R^{100B}$ substituents bonded to the same nitrogen atom may optionally be joined to form a $R^{100A}$-substituted or unsubstituted heterocycloalkyl (e.g., 3 to 8 membered, 3 to 6 membered, 4 to 6 membered, 4 to 5 membered, or 5 to 6 membered) or $R^{101A}$-substituted or unsubstituted heteroaryl (e.g., 5 to 10 membered, 5 to 9 membered, or 5 to 6 membered). In embodiments, $R^{100A}$ and $R^{100B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 10 membered, 5 to 9 membered, or 5 to 6 membered). In embodiments, $R^{100A}$ and $R^{100B}$ substituents bonded to the same nitrogen atom may optionally be joined to form a $R^{101A}$-substituted or unsubstituted heterocycloalkyl (e.g., 3 to 8 membered, 3 to 6 membered, 4 to 6 membered, 4 to 5 membered, or 5 to 6 membered). In embodiments, $R^{100A}$ and $R^{100B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

$R^{101A}$ is independently oxo, halogen, —$CX^{101A}_3$, —$CHX^{101A}_2$, —$CH_2X^{100A}$, —$OCX^{101A}_3$, —$OCH_2X^{101A}$, —$OCHX^{101A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O) $NHNH_2$, —NHC═(O)$NH_2$, —$NHSO_2H$, —NHC═(O)H, —NHC(O)—OH, —NHOH, —$N_3$, $R^{102A}$-substituted or unsubstituted alkyl (e.g., $C_1$-$C_8$, $C_1$-$C_6$, $C_1$-$C_4$, or $C_1$-$C_2$), $R^{102A}$-substituted or unsubstituted heteroalkyl (e.g., 2 to 8 membered, 2 to 6 membered, 4 to 6 membered, 2 to 3 membered, or 4 to 5 membered), $R^{102A}$-substituted or unsubstituted cycloalkyl (e.g., $C_3$-$C_8$, $C_3$-$C_6$, $C_4$-$C_6$, or $C_5$-$C_6$), $R^{102A}$-substituted or unsubstituted heterocycloalkyl (e.g., 3 to 8 membered, 3 to 6 membered, 4 to 6 membered, 4 to 5 membered, or 5 to 6 membered), $R^{102A}$-substituted or unsubstituted aryl (e.g., $C_6$-$C_{10}$ or phenyl), or $R^{102A}$-substituted or unsubstituted heteroaryl (e.g., 5 to 10 membered, 5 to 9 membered, or 5 to 6 membered). In embodiments, $R^{101A}$ is independently oxo, halogen, —$CX^{101A}_3$, —$CHX^{101A}_2$, —$CH_2X^{101A}$, —$OCX^{101A}_3$, —$OCH_2X^{101A}$, —$OCHX^{101A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O) $NHNH_2$, —NHC═(O)$NH_2$, —$NHSO_2H$, —NHC═(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$—C, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_0$ or phenyl), or unsubstituted heteroaryl (e.g., 5 to 10 membered, 5 to 9 membered, or 5 to 6 membered). $X^{101A}$ is independently —F, —Cl, —Br, or —I.

In embodiments, $R^{101A}$ is independently unsubstituted methyl. In embodiments, $R^{101A}$ is independently unsubstituted ethyl.

$R^{102A}$ is independently oxo, halogen, —$CX^{102A}_3$, —$CHX^{102A}_2$, —$CH_2X^{102A}$, —$OCX^{102A}_3$, —$OCH_2X^{102A}$, —$OCHX^{102A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O) $NHNH_2$, —NHC═(O)$NH_2$, —$NHSO_2H$, —NHC═(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{102A}$ is independently —F, —Cl, —Br, or —I.

In embodiments, $R^{100B}$ is independently hydrogen, —$CX^{100B}_3$, —$CHX^{100B}_2$, —$CH_2X^{100B}$, —CN, —COOH, —$CONH_2$, $R^{100B}$-substituted or unsubstituted alkyl (e.g., $C_1$-$C_8$, $C_1$-$C_6$, $C_1$-$C_4$, or $C_1$-$C_2$), $R^{101B}$-substituted or unsubstituted heteroalkyl (e.g., 2 to 8 membered, 2 to 6 membered, 4 to 6 membered, 2 to 3 membered, or 4 to 5 membered), $R^{101B}$-substituted or unsubstituted cycloalkyl (e.g., $C_3$-$C_8$, $C_3$-$C_6$, $C_4$-$C_6$, or $C_5$-$C_6$), $R^{101B}$-substituted or unsubstituted heterocycloalkyl (e.g., 3 to 8 membered, 3 to 6 membered, 4 to 6 membered, 4 to 5 membered, or 5 to 6 membered), $R^{101B}$-substituted or unsubstituted aryl (e.g., $C_6$-$C_{10}$ or phenyl), or $R^{101B}$-substituted or unsubstituted heteroaryl (e.g., 5 to 10 membered, 5 to 9 membered, or 5 to 6 membered). In embodiments, $R^{100B}$ is independently hydrogen, —$CX^{100B}_3$, —$CHX^{100B}_2$, —$CH_2X^{100B}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{100B}$ is independently —F, —Cl, —Br, or —I.

In embodiments, $R^{100B}$ is independently hydrogen. In embodiments, $R^{100B}$ is independently unsubstituted methyl. In embodiments, $R^{100B}$ is independently unsubstituted ethyl.

In embodiments, $R^{100A}$ and $R^{100B}$ substituents bonded to the same nitrogen atom may optionally be joined to form a $R^{101B}$-substituted or unsubstituted heterocycloalkyl (e.g., 3 to 8 membered, 3 to 6 membered, 4 to 6 membered, 4 to 5 membered, or 5 to 6 membered) or $R^{101B}$-substituted or unsubstituted heteroaryl (e.g., 5 to 10 membered, 5 to 9 membered, or 5 to 6 membered). In embodiments, $R^{100A}$ and $R^{100B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered) or unsubstituted heteroaryl (e.g., 5 to 10 membered, 5 to 9 membered, or 5 to 6 membered). In embodiments, $R^{100A}$ and $R^{100B}$ substituents bonded to the same nitrogen atom may optionally be joined to form a $R^{101B}$-substituted or unsubstituted heterocycloalkyl (e.g., 3 to 8 membered, 3 to 6 membered, 4 to 6 membered, 4 to 5 membered, or 5 to 6 membered). In embodiments, $R^{100A}$ and $R^{100B}$ substituents bonded to the same nitrogen atom may optionally be joined to form an unsubstituted heterocycloalkyl (e.g., 3 to 8 membered, 3 to 6 membered, 4 to 6 membered, 4 to 5 membered, or 5 to 6 membered).

$R^{101B}$ is independently oxo, halogen, —$CX^{101B}_3$, —$CHX^{101B}_2$, —$CH_2X^{101B}$, —$OCX^{101B}_3$, —$OCH_2X^{101B}$, —$OCHX^{101B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC—(O) $NHNH_2$, —NHC═(O)$NH_2$, —$NHSO_2H$, —NHC═(O)H, —NHC(O)—OH, —NHOH, —$N_3$, $R^{102B}$-substituted or unsubstituted alkyl (e.g., $C_1$-$C_8$, $C_1$-$C_6$, $C_1$-$C_4$, or $C_1$-$C_2$), $R^{102B}$-substituted or unsubstituted heteroalkyl (e.g., 2 to 8 membered, 2 to 6 membered, 4 to 6 membered, 2 to 3 membered, or 4 to 5 membered), $R^{102B}$-substituted or unsubstituted cycloalkyl (e.g., $C_3$-$C_8$, $C_3$-$C_6$, $C_4$-$C_6$, or $C_5$-$C_6$), $R^{102B}$-substituted or unsubstituted heterocycloalkyl (e.g., 3 to 8 membered, 3 to 6 membered, 4 to 6 membered, 4 to 5 membered, or 5 to 6 membered), $R^{102B}$-substituted or unsubstituted aryl (e.g., $C_6$-$C_{10}$ or phenyl), or $R^{102B}$-substituted or unsubstituted heteroaryl (e.g., 5 to 10 membered, 5 to 9 membered, or 5 to 6 membered). In embodiments, $R^{101B}$ is independently oxo, halogen, —$CX^{101B}{}_3$, —$CHX^{101B}{}_2$, —$CH_2X^{101B}$, —$OCX^{101B}{}_3$, —$OCH_2X^{101B}$, —$OCHX^{101B}{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{101B}$ is independently —F, —Cl, —Br, or —I.

In embodiments, $R^{101B}$ is independently unsubstituted methyl. In embodiments, $R^{101B}$ is independently unsubstituted ethyl.

$R^{102B}$ is independently oxo, halogen, —$CX^{102B}{}_3$, —$CHX^{102B}{}_2$, —$CH_2X^{102B}$, —$OCX^{102B}{}_3$, —$OCH_2X^{102B}$, —$OCHX^{102B}{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{102B}$ is independently —F, —Cl, —Br, or —I.

In embodiments, $R^{100C}$ is independently hydrogen, —$CX^{100C}{}_3$, —$CHX^{100C}{}_2$, —$CH_2X^{100C}$, —CN, —COOH, —$CONH_2$, $R^{101C}$-substituted or unsubstituted alkyl (e.g., $C_1$-$C_8$, $C_1$-$C_6$, $C_1$-$C_4$, or $C_1$-$C_2$), $R^{101C}$-substituted or unsubstituted heteroalkyl (e.g., 2 to 8 membered, 2 to 6 membered, 4 to 6 membered, 2 to 3 membered, or 4 to 5 membered), $R^{100C}$-substituted or unsubstituted cycloalkyl (e.g., $C_3$-$C_8$, $C_3$-$C_6$, $C_4$-$C_6$, or $C_5$-$C_6$), $R^{101C}$-substituted or unsubstituted heterocycloalkyl (e.g., 3 to 8 membered, 3 to 6 membered, 4 to 6 membered, 4 to 5 membered, or 5 to 6 membered), $R^{100C}$-substituted or unsubstituted aryl (e.g., $C_6$-$C_{10}$ or phenyl), or $R^{101C}$-substituted or unsubstituted heteroaryl (e.g., 5 to 10 membered, 5 to 9 membered, or 5 to 6 membered). In embodiments, $R^{100C}$ is independently hydrogen, —$CX^{100C}{}_3$, —$CHX^{100C}{}_2$, —$CH_2X^{100C}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{100C}$ is independently —F, —Cl, —Br, or —I.

In embodiments, $R^{100C}$ is independently hydrogen. In embodiments, $R^{100C}$ is independently unsubstituted methyl. In embodiments, $R^{100C}$ is independently unsubstituted ethyl.

$R^{101C}$ is independently oxo, halogen, —$CX^{101C}{}_3$, —$CHX^{101C}{}_2$, —$CH_2X^{101C}$, —$OCX^{101C}{}_3$, —$OCH_2X^{101C}$, —$OCHX^{101C}{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, $R^{102C}$-substituted or unsubstituted alkyl (e.g., $C_1$-$C_8$, $C_1$-$C_6$, $C_1$-$C_4$, or $C_1$-$C_2$), $R^{102C}$-substituted or unsubstituted heteroalkyl (e.g., 2 to 8 membered, 2 to 6 membered, 4 to 6 membered, 2 to 3 membered, or 4 to 5 membered), $R^{102C}$-substituted or unsubstituted cycloalkyl (e.g., $C_3$-$C_8$, $C_3$-$C_6$, $C_4$-$C_6$, or $C_5$-$C_6$), $R^{102C}$-substituted or unsubstituted heterocycloalkyl (e.g., 3 to 8 membered, 3 to 6 membered, 4 to 6 membered, 4 to 5 membered, or 5 to 6 membered), $R^{102C}$-substituted or unsubstituted aryl (e.g., $C_6$-$C_{10}$ or phenyl), or $R^{102C}$-substituted or unsubstituted heteroaryl (e.g., 5 to 10 membered, 5 to 9 membered, or 5 to 6 membered). In embodiments, $R^{100C}$ is independently oxo, halogen, —$CX^{100C}{}_3$, —$CHX^{100C}{}_2$, —$CH_2X^{101C}$, —$OCX^{101C}{}_3$, —$OCH_2X^{101C}$, —$OCHX^{101C}{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{101C}$ is independently —F, —Cl, —Br, or —I.

In embodiments, $R^{101C}$ is independently unsubstituted methyl. In embodiments, $R^{101C}$ is independently unsubstituted ethyl.

$R^{102C}$ is independently oxo, halogen, —$CX^{102C}{}_3$, —$CHX^{102C}{}_2$, —$CH_2X^{102C}$, —$OCX^{102C}{}_3$, —$OCH_2X^{102C}$, —$OCHX^{102C}{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$X^{102C}$ is independently —F, —Cl, —Br, or —I.

In embodiments, $R^{100D}$ is independently hydrogen, —$CX^{100D}{}_3$, —$CHX^{100D}{}_2$, —$CH_2X^{100D}$, —CN, —COOH, —$CONH_2$, $R^{101D}$-substituted or unsubstituted alkyl (e.g., $C_1$-$C_8$, $C_1$-$C_6$, $C_1$-$C_4$, or $C_1$-$C_2$), $R^{101D}$-substituted or unsubstituted heteroalkyl (e.g., 2 to 8 membered, 2 to 6 membered, 4 to 6 membered, 2 to 3 membered, or 4 to 5 membered), $R^{101D}$-substituted or unsubstituted cycloalkyl (e.g., $C_3$-$C_8$, $C_3$-$C_6$, $C_4$-$C_6$, or $C_5$-$C_6$), $R^{101D}$-substituted or unsubstituted heterocycloalkyl (e.g., 3 to 8 membered, 3 to 6 membered, 4 to 6 membered, 4 to 5 membered, or 5 to 6 membered), $R^{101D}$-substituted or unsubstituted aryl (e.g., $C_6$-$C_{10}$ or phenyl), or $R^{101D}$-substituted or unsubstituted heteroaryl (e.g., 5 to 10 membered, 5 to 9 membered, or 5 to 6 membered). In embodiments, $R^{101D}$ is independently hydrogen, —$CX^{100D}_3$, —$CHX^{100D}_2$, —$CH_2X^{100D}$, —CN, —COOH, —$CONH_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{100D}$ is independently —F, —Cl, —Br, or —I.

In embodiments, $R^{100D}$ is independently hydrogen. In embodiments, $R^{100D}$ is independently unsubstituted methyl. In embodiments, $R^{100D}$ is independently unsubstituted ethyl.

$R^{101D}$ is independently oxo, halogen, —$CX^{101D}_3$, —$CHX^{101D}_2$, —$CH_2X^{101D}$, —$OCX^{101D}_3$, —$OCH_2X^{101D}$, —$OCHX^{101D}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, $R^{102D}$-substituted or unsubstituted alkyl (e.g., $C_1$-$C_8$, $C_1$-$C_6$, $C_1$-$C_4$, or $C_1$-$C_2$), $R^{102D}$-substituted or unsubstituted heteroalkyl (e.g., 2 to 8 membered, 2 to 6 membered, 4 to 6 membered, 2 to 3 membered, or 4 to 5 membered), $R^{102D}$-substituted or unsubstituted cycloalkyl (e.g., $C_3$-$C_8$, $C_3$-$C_6$, $C_4$-$C_6$, or $C_5$-$C_6$), $R^{102D}$-substituted or unsubstituted heterocycloalkyl (e.g., 3 to 8 membered, 3 to 6 membered, 4 to 6 membered, 4 to 5 membered, or 5 to 6 membered), $R^{102D}$-substituted or unsubstituted aryl (e.g., $C_6$-$C_{10}$ or phenyl), or $R^{102D}$-substituted or unsubstituted heteroaryl (e.g., 5 to 10 membered, 5 to 9 membered, or 5 to 6 membered). In embodiments, $R^{101D}$ is independently oxo, halogen, —$CX^{101D}_3$, —$CHX^{101D}_2$, —$CH_2X^{101D}$, —$OCX^{101D}_3$, —$OCH_2X^{101D}$, $CHX^{101D}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{101D}$ is independently —F, —Cl, —Br, or —I.

In embodiments, $R^{101D}$ is independently unsubstituted methyl. In embodiments, $R^{101D}$ is independently unsubstituted ethyl.

$R^{102D}$ is independently oxo, halogen, —$CX^{102D}_3$, —$CHX^{102D}_2$, —$CH_2X^{102D}$, $OCX^{102D}_3$, —$OCH_2X^{102D}$, —$OCHX^{101D}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O) $NHNH_2$, —NHC=(O)$NH_2$, —$NHSO_2H$, —NHC=(O)H, —NHC(O)—OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{102D}$ is independently —F, —Cl, —Br, or —I.

In embodiments, the compound has the formula:

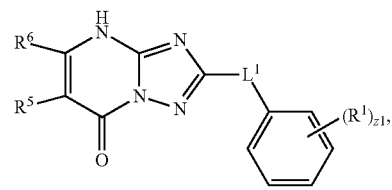

wherein $R^6$, $R^5$, $L^1$, $R^1$, and z1 are as described herein, including embodiments.

In embodiments, the compound has the formula:

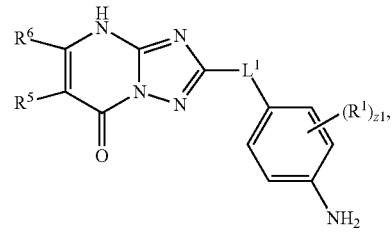

wherein $R^6$, $R^5$, $L^1$, $R^1$, and z1 are as described herein, including embodiments.

In embodiments, the compound has the formula:

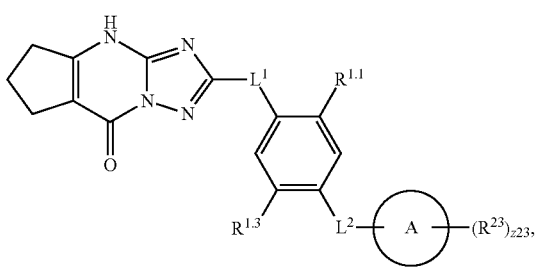

wherein $L^1$, $L^2$, Ring A, R, and z23 are as described herein, including embodiments. $R^{1.1}$ and $R^{1.3}$ are each $R^1$ at a fixed position on the attached ring. $R^{1.1}$ and $R^{1.3}$ may be any substituent of $R^1$ described herein, including in any aspect, embodiment, example, figure, or claim.

In embodiments, $R^{1.1}$ and $R^{1.3}$ are each independently substituted or unsubstituted alkyl (e.g., $C_1$-$C_8$ alkyl, $C_1$-$C_6$ alkyl, or $C_1$-$C_4$ alkyl). In embodiments, $R^{1.1}$ and $R^{1.3}$ are each independently substituted alkyl (e.g., $C_1$-$C_8$ alkyl, $C_1$-$C_6$ alkyl, or $C_1$-$C_4$ alkyl). In embodiments, $R^{1.1}$ and $R^{1.3}$ are each independently an unsubstituted alkyl (e.g., $C_1$-$C_8$ alkyl, $C_1$-$C_6$ alkyl, or $C_1$-$C_4$ alkyl). In embodiments, $R^{1.1}$ and $R^{1.3}$ are each independently substituted or unsubstituted methyl. In embodiments, $R^{1.1}$ and $R^{1.3}$ are each independently substituted or unsubstituted $C_2$ alkyl. In embodiments, $R^{1.1}$ and $R^{1.3}$ are each independently substituted or unsubstituted $C_3$ alkyl. In embodiments, $R^{1.1}$ and $R^{1.3}$ are each independently substituted or unsubstituted $C_4$ alkyl. In embodiments, $R^{1.1}$ and $R^{1.3}$ are each independently substituted or unsubstituted $C_5$ alkyl. In embodiments, $R^{1.1}$ and $R^{1.3}$ are each independently substituted or unsubstituted $C_6$ alkyl. In embodiments, $R^{1.1}$ and $R^{1.3}$ are each independently substituted or unsubstituted $C_7$ alkyl. In embodiments, $R^{1.1}$ and $R^{1.3}$ are each independently substituted or unsubstituted $C_8$ alkyl. In embodiments, $R^{1.1}$ and $R^{1.3}$ are each independently substituted methyl. In embodiments, $R^{1.1}$ and $R^{1.3}$ are each independently substituted $C_2$ alkyl. In embodiments, $R^{1.1}$ and $R^{1.3}$ are each independently substituted $C_3$ alkyl. In embodiments, $R^{1.1}$ and $R^{1.3}$ are each independently substituted $C_4$ alkyl. In embodiments, $R^{1.1}$ and $R^{1.3}$ are each independently substituted $C_5$ alkyl. In embodiments, $R^{1.1}$ and $R^{1.3}$ are each independently substituted $C_6$ alkyl. In embodiments, $R^{1.1}$ and $R^{1.3}$ are each independently substituted $C_7$ alkyl. In embodiments, $R^{1.1}$ and $R^{1.3}$ are each independently substituted $C_8$ alkyl. In embodiments, $R^{1.1}$ and $R^{1.3}$ are each independently an unsubstituted methyl. In embodiments, $R^{1.1}$ and $R^{1.3}$ are each independently an unsubstituted $C_2$ alkyl. In embodiments, $R^{1.1}$ and $R^{1.3}$ are each independently an unsubstituted $C_3$ alkyl. In embodiments, $R^{1.1}$ and $R^{1.3}$ are each independently an unsubstituted $C_4$ alkyl. In embodiments, $R^{1.1}$ and $R^{1.3}$ are each independently an unsubstituted $C_5$ alkyl. In embodiments, $R^{1.1}$ and $R^{1.3}$ are each independently an unsubstituted $C_6$ alkyl. In embodiments, $R^{1.1}$ and $R^{1.3}$ are each independently an unsubstituted $C_7$ alkyl. In embodiments, $R^{1.1}$ and $R^{1.3}$ are each independently an unsubstituted $C_8$ alkyl.

In embodiments, the compound has the formula:

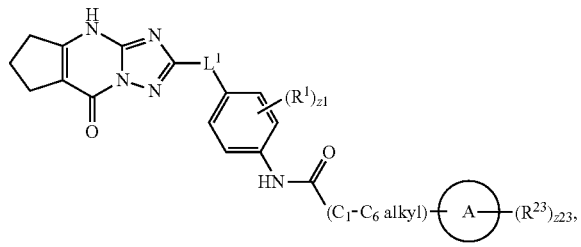

wherein $L^1$, Ring A, $R^{23}$, $R^1$, z1, and z23 are as described herein, including embodiments.

In embodiments, the compound has the formula:

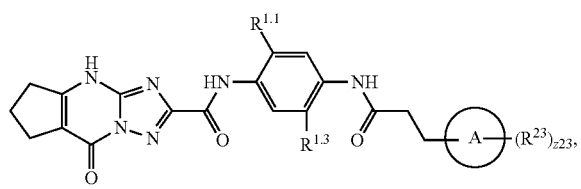

wherein $R^{1.1}$ and $R^{1.3}$. Ring A, $R^{23}$, and z23 are as described herein, including embodiments.

In embodiments, the compound has the formula:

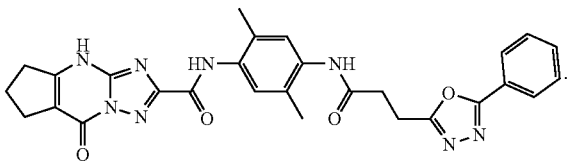

(III)

Formula III is also referred to herein as 113B7, PDZ1 in, and PDZ1i.

Figure 6:
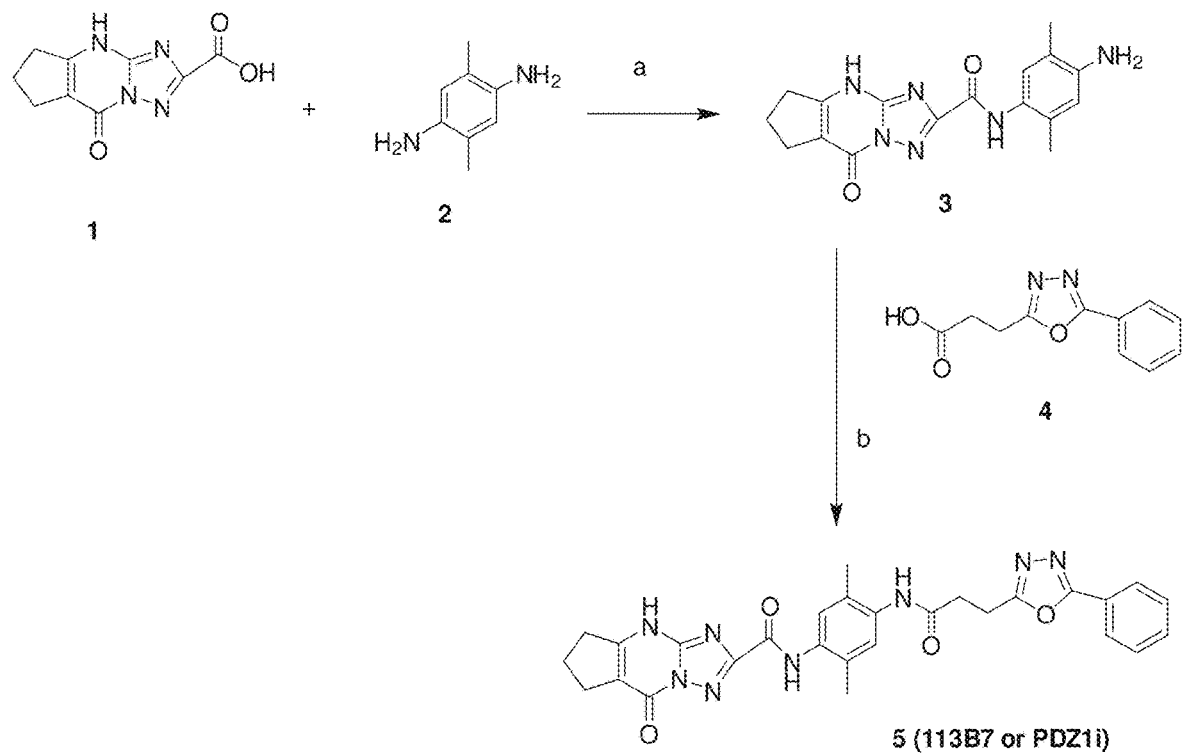
FIG. 6. Synthetic scheme for the preparation of 113B7 (PDZ1i). Reagents and Conditions: (a) HATU, DIEA, DMSO, r.t., 24 h; (b) HATU, DIEA, DMF, r.t., 24 h.

The compounds of Formula I, Formula II, Formula IIA, and Formula III can be synthesized according to procedures described herein, including in FIG. 6.

In some aspects of the invention, the compounds described herein are provided as prodrugs. In this case, one or more than one functional group, and/or one or more than one type of functional group, is covalently attached to reactive group of the molecule, e.g. to an OH, an NH, a carboxyl, etc. In some aspects, the protecting group is removed by enzymatic and/or non-enzymatic reactions, e.g. by hydrolysis, at or near the site of action (e.g. at the site of a tumor). In other aspects, the protecting group remains attached to the drug at the site of action, but does not interfere with the activity of the drug, or at least does not interfere to an extent that make the drug ineffective. In yet other aspects, the protecting groups are selected so as to be gradually removed non-enzymatically as the drug circulates, resulting in a slow release over time of an active drug. Exemplary protecting groups that may be used to make such prodrugs include but are not limited to: amidomethyl esters (for carboxyl groups); acyloxymethyl (for carboxyl groups); monomethoxytrityl (MMT) (for amino groups); carbamoyl moieties (carbamate esters of amino acids); pivaloyloxymethyl (POM, pivoxil, pivoxyl), benzoyl, acetyl, trimethylsilyl, triethylsilyl, or methoxymethyl groups (for hydroxy groups); etc. In some aspects, carboxyl groups of the molecule are protected in this manner and the protecting group is removed in vivo, e.g. the protecting group is a cleavable alkyl of aryl ester at a C-terminal carboxylate.

In embodiments, n1 is 0. In embodiments, n1 is 1. In embodiments, n1 is 2. In embodiments, n1 is 3. In embodiments, n1 is 4. In embodiments, m1 is 1. In embodiments, m1 is 2. In embodiments, v1 is 1. In embodiments, v is 2.

In embodiments, z1 is 0. In embodiments, z1 is 1. In embodiments, z1 is 2. In embodiments, z1 is 3. In embodiments, z1 is 4. In embodiments, z1 is 5. In embodiments, the symbol z1 is an integer from 0 to 4. In embodiments, the symbol z1 is an integer from 0 to 2. In embodiments, z23 is 0. In embodiments, z23 is 1. In embodiments, z23 is 2. In embodiments, z23 is 3. In embodiments, z23 is 4. In embodiments, z23 is 5. In embodiments, the symbol z23 is an integer from 0 to 4.

In embodiments, n2 is 0. In embodiments, n2 is 1. In embodiments, n2 is 2. In embodiments, n2 is 3. In embodiments, n2 is 4. In embodiments, m2 is 1. In embodiments, m2 is 2. In embodiments, v2 is 1. In embodiments, v2 is 2.

In embodiments, n23 is 0. In embodiments, n23 is 1. In embodiments, n23 is 2. In embodiments, n23 is 3. In embodiments, n23 is 4. In embodiments, m23 is 1. In embodiments, m23 is 2. In embodiments, v23 is 1. In embodiments, v23 is 2.

In embodiments, the compound is a compound described herein, for example a compound in Table 1. In embodiments the compound is 113B12, 113B11, 113B9, 113B7, 112H9, 113B8, B112G11, 112G4, 112G3, 112G2, 112G1, 112F12, 112F11, 112F10, 112F1, 112E12, 112E7, 112D11, cmpd14, cmpd13, cmpd12, cmpd11, cmpd10, cmpd9, cmpd8, cmpd7, cmpd6, cmpd5, cmpd4, cmpd3, cmpd2, cmpd1, or 30A9 as identified in Table 1.

In an aspect is provided a pharmaceutical compositions including a compound as described herein, including embodiments thereof, and a pharmaceutically acceptable salt.

III. Method of Treating Cancer

Also provided herein are methods of treating cancer in a subject in need thereof.

In some aspects, the subject who is treated as described herein has, in fact, not been diagnosed with cancer. Rather, the subject is genetically prone to development of cancer (e.g. the subject may be a woman with a harmful mutation in the PALB2, BRCA1 and/or BRCA2, tumor suppressor genes; c-Kit, APC, mutated p53, PTEN deletion, Braf, are some common gene alterations that are currently tested for predicting cancer risk; activation of oncogenes including members of the Ras gene family, AEG-1 (MTDH), myc gene family (C-myc, N-myc, L-myc); deregulated cell cycle genes such as cyclin E1; etc. In these cases, the compounds of the invention are administered prophylactically and prevent or slow and/or lessen the extent of the cancer that develops and/or make the cancer more treatable when is does occur.

In yet other aspects, the compounds disclosed herein are used to treat subjects who are not diagnosed with cancer per se but rather with a pre-cancerous condition. For example, individuals with colon polyps that are benign, individuals with cervical dysplasia, individuals at high risk for cancer based on familial history, individuals exposed to a carcinogen potentially causing cancer (through the skin, respiratory track, gastrointestinal track, or other route of entry into the body), individuals who have been positively diagnosed using a genetic test for cancer (including containing potentially cancerous circulating tumor cells, presence of positive cancer associated biomarkers (proteins in plasma, miRNA in the blood) expressed in body fluids (blood, urine, saliva, etc.), etc.

In embodiments, the subject who is treated as described herein has been diagnosed with early stage cancer. In such cases, the compounds described herein may be used alone or in combination with other therapeutic modes to address the cancer and to prevent its spread or progression. For example, patients with early stage bladder or prostate cancer are treated to prevent invasion and development of metastatic lesions. Patients who underwent surgery to remove primary or metastatic tumor or have undergone treatment with chemotherapy/radiotherapy/immunotherapy for treating cancers. Potential applications of the current anti-invasive and anti-metastatic molecules is to prevent secondary tumor and metastasis development following conventional surgery or therapy (radiation, chemotherapy, immunotherapy) for cancer. Treatment would begin prior to surgery or other therapies (radiation, chemotherapy, immunotherapy) and continue after surgery or therapy.

In another aspect is provided a method of preventing or treating cancer in a subject in need thereof, including administering to the subject a therapeutically effective amount of as compound described herein, including embodiments thereof, wherein the therapeutically effective amount is sufficient to prevent or treat the cancer.

In another aspect is provided a method of sensitizing cancer cells to killing by radiation, including contacting the cancer cells with an effective (e.g., therapeutically effective) amount of a compound described herein, including embodiments thereof, wherein the therapeutically effective amount is sufficient to sensitize the cancer cells to killing by radiation.

In another aspect is provided a method of slowing or preventing metastasis of cancer cells in a subject in need thereof, including administering to the subject an effective (e.g., therapeutically effective) amount of a compound described herein, including embodiments thereof, wherein the therapeutically effective amount is sufficient to slow or prevent the metastasis.

In another aspect is provided a method of treating a glioblastoma multiforme brain tumor in a subject in need thereof, including performing surgery on the subject to debulk the glioblastoma multiforme brain tumor; radiosensitizing remaining tumor cells by administering to the subject a therapeutically effective amount of at least one of the compounds of any of the invention, wherein the therapeutically effective amount is sufficient to sensitize the remaining tumor cells to killing by radiation; and providing radiation therapy to the subject.

In an aspect is provided a method of treating a glioblastoma multiforme brain tumor in a subject in need thereof. In embodiments, the method includes performing surgery on the subject to debulk the glioblastoma multiforme brain tumor. In embodiments, the method includes radiosensitizing the remaining tumor cells by administering to the subject a therapeutically effective amount of at least one of the compounds as described herein, including embodiments. In embodiments, the therapeutically effective amount is sufficient to sensitize the remaining tumor cells to killing by radiation. In embodiments, the method includes providing radiation therapy to the subject.

It is contemplated that inhibiting MDA-9 activity through binding of the MDA-9 PDZ1 domain by a PDZ1 domain binder is useful for the treatment of cancer (e.g., cancers having increased MDA-9 expression). Thus, in an aspect is provided a method of inhibiting MDA-9 protein activity, the method including contacting the MDA-9 protein with an effective amount of a PDZ1 domain binder, thereby inhibiting MDA-9 activity.

As mentioned above, a PDZ1 domain binder as referred to herein is a compound or composition as described herein, including embodiments thereof, (e.g., small molecule, antibody, aptamer, ligand) that selectively binds to a PDZ1 domain of an MDA-9 protein. In embodiments, a PDZ1 domain of an MDA-9 protein includes the sequence of SEQ ID NO:1. In embodiments, a PDZ1 domain of an MDA-9 protein is the sequence of SEQ ID NO: 1. In embodiments, the PDZ1 domain binder binds the PDZ1 domain, thereby inhibiting PDZ1 domain function. In embodiments, the PDZ1 domain binder binds a portion of the PDZ1 domain. In embodiments, the PDZ1 domain binder binds a portion of the PDZ1 domain and an amino acid interface region located between the PDZ1 domain and the PDZ2 domain. A portion of a PDZ1 domain and/or an amino acid interface region refers to less than all of the amino acids that make up the region. For example, in embodiments, PDZ1 domain binder binds to less than 100% of the amino acids included in the PDZ1 domain. In embodiments, PDZ1 domain binder binds to less than 90% of the amino acids included in the PDZ1 domain. In embodiments, PDZ1 domain binder binds to less than 80% of the amino acids included in the PDZ1 domain. In embodiments, PDZ1 domain binder binds to less than 70% of the amino acids included in the PDZ1 domain. In embodiments, PDZ1 domain binder binds to less than 60% of the amino acids included in the PDZ1 domain. In embodiments, PDZ1 domain binder binds to less than 50% of the amino acids included in the PDZ1 domain. In embodiments, PDZ1 domain binder binds to less than 40% of the amino acids included in the PDZ1 domain. In embodiments, PDZ1 domain binder binds to less than 30% of the amino acids included in the PDZ1 domain. In embodiments, PDZ1 domain binder binds to less than 20% of the amino acids included in the PDZ1 domain. In embodiments, PDZ1 domain binder binds to less than 15% of the amino acids included in the PDZ1 domain. In embodiments, PDZ1 domain binder binds to less than 10% of the amino acids included in the PDZ1 domain. In embodiments, PDZ1 domain binder binds to less than 9% of the amino acids included in the PDZ1 domain. In embodiments, PDZ1 domain binder binds to less than 8% of the amino acids included in the PDZ1 domain. In embodiments, PDZ1 domain binder binds to less than 7% of the amino acids included in the PDZ1 domain. In embodiments, PDZ1 domain binder binds to less than 6% of the amino acids included in the PDZ1 domain. In embodiments, PDZ1 domain binder binds to less than 5% of the amino acids included in the PDZ1 domain. In embodiments, PDZ1 domain binder binds to less than 4% of the amino acids included in the PDZ1 domain. In embodiments, PDZ1 domain binder binds to less than 3% of the amino acids included in the PDZ1 domain. In embodiments, PDZ1 domain binder binds to less than 2% of the amino acids included in the PDZ1 domain. In embodiments, PDZ1 domain binder binds to less than 1% of the amino acids included in the PDZ1 domain.

Similarly, in embodiments, PDZ1 domain binder binds to less than 100% of the amino acids included in the interface region. In embodiments, PDZ1 domain binder binds to less than 90% of the amino acids included in the interface region. In embodiments, PDZ1 domain binder binds to less than 80% of the amino acids included in the interface region. In embodiments, PDZ1 domain binder binds to less than 70% of the amino acids included in the interface region. In embodiments, PDZ1 domain binder binds to less than 60% of the amino acids included in the interface region. In embodiments, PDZ1 domain binder binds to less than 50% of the amino acids included in the interface region. In embodiments, PDZ1 domain binder binds to less than 40% of the amino acids included in the interface region. In embodiments, PDZ1 domain binder binds to less than 30% of the amino acids included in the interface region. In embodiments, PDZ1 domain binder binds to less than 20% of the amino acids included in the interface region. In embodiments, PDZ1 domain binder binds to less than 15% of the amino acids included in the interface region. In embodiments, PDZ1 domain binder binds to less than 10% of the amino acids included in the interface region. In embodiments, PDZ1 domain binder binds to less than 9% of the amino acids included in the interface region. In embodiments, PDZ1 domain binder binds to less than 8% of the amino acids included in the interface region. In embodiments, PDZ1 domain binder binds to less than 7% of the amino acids included in the interface region. In embodiments, PDZ1 domain binder binds to less than 6% of the amino acids included in the interface region. In embodiments, PDZ1 domain binder binds to less than 5% of the amino acids included in the interface region. In embodiments, PDZ1 domain binder binds to less than 4% of the amino acids included in the interface region. In embodiments, PDZ1 domain binder binds to less than 3% of the amino acids included in the interface region. In embodiments, PDZ1 domain binder binds to less than 2% of the amino acids included in the interface region. In embodiments, PDZ1 domain binder binds to less than 1% of the amino acids included in the interface region.

In embodiments, the PDZ1 domain binder occludes about 5% of the PDZ1 domain. In embodiments, the PDZ1 domain binder occludes about 10% of the PDZ1 domain. In embodiments, the PDZ1 domain binder occludes about 15% of the PDZ1 domain. In embodiments, the PDZ1 domain binder occludes about 20% of the PDZ1 domain. In embodiments, the PDZ1 domain binder occludes about 25% of the PDZ1 domain. In embodiments, the PDZ1 domain binder occludes about 30% of the PDZ1 domain. In embodiments, the PDZ1 domain binder occludes about 35% of the PDZ1 domain. In embodiments, the PDZ1 domain binder occludes about 40% of the PDZ1 domain. In embodiments, the PDZ1 domain binder occludes about 45% of the PDZ1 domain. In embodiments, the PDZ1 domain binder occludes about 50% of the PDZ1 domain. In embodiments, the PDZ1 domain binder occludes about 55% of the PDZ1 domain. In embodiments, the PDZ1 domain binder occludes about 60% of the PDZ1 domain. In embodiments, the PDZ1 domain binder occludes about 65% of the PDZ1 domain. In embodiments, the PDZ1 domain binder occludes about 70% of the PDZ1 domain. In embodiments, the PDZ1 domain binder occludes about 75% of the PDZ1 domain. In embodiments, the PDZ1 domain binder occludes about 80% of the PDZ1 domain. In embodiments, the PDZ1 domain binder occludes about 85% of the PDZ1 domain. In embodiments, the PDZ1 domain binder occludes about 90% of the PDZ1 domain. In embodiments, the PDZ1 domain binder occludes about 91% of the PDZ1 domain. In embodiments, the PDZ1 domain binder occludes about 92% of the PDZ1 domain. In embodiments, the PDZ1 domain binder occludes about 93% of the PDZ1 domain. In embodiments, the PDZ1 domain binder occludes about 94% of the PDZ1 domain. In embodiments, the PDZ1 domain binder occludes about 95% of the PDZ1 domain. In embodiments, the PDZ1 domain binder occludes about 96% of the PDZ1 domain. In embodiments, the PDZ1 domain binder occludes about 97% of the PDZ1 domain. In embodiments, the PDZ1 domain binder occludes about 98% of the PDZ1 domain. In embodiments, the PDZ1 domain binder occludes about 99% of the PDZ1 domain. In embodiments, the PDZ1 domain binder occludes 100% of the PDZ1 domain.

In embodiments, the PDZ1 domain binder occludes 5% of the PDZ1 domain. In embodiments, the PDZ1 domain binder occludes 10% of the PDZ1 domain. In embodiments, the PDZ1 domain binder occludes 15% of the PDZ1 domain. In embodiments, the PDZ1 domain binder occludes 20% of the PDZ1 domain. In embodiments, the PDZ1 domain binder occludes 25% of the PDZ1 domain. In embodiments, the PDZ1 domain binder occludes 30% of the PDZ1 domain. In embodiments, the PDZ1 domain binder occludes 35% of the PDZ1 domain. In embodiments, the PDZ1 domain binder occludes 40% of the PDZ1 domain. In embodiments, the PDZ1 domain binder occludes 45% of the PDZ1 domain. In embodiments, the PDZ1 domain binder occludes 50% of the PDZ1 domain. In embodiments, the PDZ1 domain binder occludes 55% of the PDZ1 domain. In embodiments, the PDZ1 domain binder occludes 60% of the PDZ1 domain. In embodiments, the PDZ1 domain binder occludes 65% of the PDZ1 domain. In embodiments, the PDZ1 domain binder occludes 70% of the PDZ1 domain. In embodiments, the PDZ1 domain binder occludes 75% of the PDZ1 domain. In embodiments, the PDZ1 domain binder occludes 80% of the PDZ1 domain. In embodiments, the PDZ1 domain binder occludes 85% of the PDZ1 domain. In embodiments, the PDZ1 domain binder occludes 90% of the PDZ1 domain. In embodiments, the PDZ1 domain binder occludes 91% of the PDZ1 domain. In embodiments, the PDZ1 domain binder occludes 92% of the PDZ1 domain. In embodiments, the PDZ1 domain binder occludes 93% of the PDZ1 domain. In embodiments, the PDZ1 domain binder occludes 94% of the PDZ1 domain. In embodiments, the PDZ1 domain binder occludes 95% of the PDZ1 domain. In embodiments, the PDZ1 domain binder occludes 96% of the PDZ1 domain. In embodiments, the PDZ1 domain binder occludes 97% of the PDZ1 domain. In embodiments, the PDZ1 domain binder occludes 98% of the PDZ1 domain. In embodiments, the PDZ1 domain binder occludes 99% of the PDZ1 domain. In embodiments, the PDZ1 domain binder occludes 100% of the PDZ1 domain.

In embodiments, the PDZ1 domain binder occludes at least 5% of the PDZ1 domain. In embodiments, the PDZ1 domain binder occludes at least 10% of the PDZ1 domain. In embodiments, the PDZ1 domain binder occludes at least 15% of the PDZ1 domain. In embodiments, the PDZ1 domain binder occludes at least 20% of the PDZ1 domain. In embodiments, the PDZ1 domain binder occludes at least 25% of the PDZ1 domain. In embodiments, the PDZ1 domain binder occludes at least 30% of the PDZ1 domain. In embodiments, the PDZ1 domain binder occludes at least 35% of the PDZ1 domain. In embodiments, the PDZ1 domain binder occludes at least 40% of the PDZ1 domain. In embodiments, the PDZ1 domain binder occludes at least 45% of the PDZ1 domain. In embodiments, the PDZ1 domain binder occludes at least 50% of the PDZ1 domain. In embodiments, the PDZ1 domain binder occludes at least 55% of the PDZ1 domain. In embodiments, the PDZ1 domain binder occludes at least 60% of the PDZ1 domain. In embodiments, the PDZ1 domain binder occludes at least 65% of the PDZ1 domain. In embodiments, the PDZ1 domain binder occludes at least 70% of the PDZ1 domain. In embodiments, the PDZ1 domain binder occludes at least 75% of the PDZ1 domain. In embodiments, the PDZ1 domain binder occludes at least 80% of the PDZ1 domain. In embodiments, the PDZ1 domain binder occludes at least 85% of the PDZ1 domain. In embodiments, the PDZ1 domain binder occludes at least 90% of the PDZ1 domain. In embodiments, the PDZ1 domain binder occludes at least 91% of the PDZ1 domain. In embodiments, the PDZ1 domain binder occludes at least 92% of the PDZ1 domain. In embodiments, the PDZ1 domain binder occludes at least 93% of the PDZ1 domain. In embodiments, the PDZ1 domain binder occludes at least 94% of the PDZ1 domain. In embodiments, the PDZ1 domain binder occludes at least 95% of the PDZ1 domain. In embodiments, the PDZ1 domain binder occludes at least 96% of the PDZ1 domain. In embodiments, the PDZ1 domain binder occludes at least 97% of the PDZ1 domain. In embodiments, the PDZ1 domain binder occludes at least 98% of the PDZ1 domain. In embodiments, the PDZ1 domain binder occludes at least 99% of the PDZ1 domain. In embodiments, the PDZ1 domain binder occludes at least 100% of the PDZ1 domain.

PDZ1 domain occlusion may be measured using methods known in the art. A Non-limiting example includes measuring the solvent accessible surface area in the presence and absence of the PDZ1 domain binder.

In embodiments, the PDZ1 domain binder is a small molecule (e.g., a compound described herein), an antibody, an aptamer, or a ligand. In embodiments, the PDZ1 domain binder is a small molecule (e.g., a compound as described herein). In embodiments, the PDZ1 domain binder is an antibody. In embodiments, the PDZ1 domain binder is an aptamer. In embodiments, the PDZ1 domain binder is a ligand.

In embodiments, the antibody may be linked (e.g., covalently, non-covalently) to a phosphorothioate nucleic acid, (e.g., wherein the phosphorothioate nucleic acid facilitates intracellular delivery of the antibody). In embodiments, the aptamer may be linked (e.g., covalently, non-covalently) to a phosphorothioate nucleic acid, (e.g., wherein the phosphorothioate nucleic acid facilitates intracellular delivery of the aptamer). In embodiments, the ligand may be linked (e.g., covalently, non-covalently) to a phosphorothioate nucleic acid, (e.g., wherein the phosphorothioate nucleic acid facilitates intracellular delivery of the ligand). Alternative, in embodiments, the antibody may be linked (e.g., covalently, non-covalently) to a ligand that binds a cell-surface receptor, (e.g., thereby promoting intracellular delivery of the antibody). In embodiments, the aptamer may be linked (e.g., covalently, non-covalently) to a ligand that binds a cell-surface receptor, (e.g., thereby promoting intracellular delivery of the aptamer). In embodiments, the ligand may be linked (e.g., covalently, non-covalently) to a ligand that binds a cell-surface receptor, (e.g., thereby promoting intracellular delivery of the ligand).

In embodiments, the small molecule is a compound as described herein, including embodiments thereof.

In embodiments, the PDZ1 domain binder (e.g., compound described herein) binds a PDZ1 domain with a Kd of less than 25 μM. In embodiments, the PDZ1 domain binder (e.g., compound described herein) binds a PDZ1 domain with a Kd of less than 24 μM. In embodiments, the PDZ1 domain binder (e.g., compound described herein) binds a PDZ1 domain with a Kd of less than 23 μM. In embodiments, the PDZ1 domain binder (e.g., compound described herein) binds a PDZ1 domain with a Kd of less than 22 μM. In embodiments, the PDZ1 domain binder (e.g., compound described herein) binds a PDZ1 domain with a Kd of less than 21 μM. In embodiments, the PDZ1 domain binder (e.g., compound described herein) binds a PDZ1 domain with a Kd of less than 20 μM. In embodiments, the PDZ1 domain binder (e.g., compound described herein) binds a PDZ1 domain with a Kd of less than 15 μM. In embodiments, the PDZ1 domain binder (e.g., compound described herein) binds a PDZ1 domain with a Kd of less than 10 μM. In embodiments, the PDZ1 domain binder (e.g., compound described herein) binds a PDZ1 domain with a Kd of less than 9 μM. In embodiments, the PDZ1 domain binder (e.g., compound described herein) binds a PDZ1 domain with a Kd of less than 8 μM. In embodiments, the PDZ1 domain binder (e.g., compound described herein) binds a PDZ1 domain with a Kd of less than 7 μM. In embodiments, the PDZ1 domain binder (e.g., compound described herein) binds a PDZ1 domain with a Kd of less than 6 μM. In embodiments, the PDZ1 domain binder (e.g., compound described herein) binds a PDZ1 domain with a Kd of less than 5 μM. In embodiments, the PDZ1 domain binder (e.g., compound described herein) binds a PDZ1 domain with a Kd of less than 4 μM. In embodiments, the PDZ1 domain binder (e.g., compound described herein) binds a PDZ1 domain with a Kd of less than 3 μM. In embodiments, the PDZ1 domain binder (e.g., compound described herein) binds a PDZ1 domain with a Kd of less than 2 μM. In embodiments, the PDZ1 domain binder (e.g., compound described herein) binds a PDZ1 domain with a Kd of less than 1 μM. In embodiments, the PDZ1 domain binder (e.g., compound described herein) binds a PDZ1 domain with a Kd of less than 500 nM. In embodiments, the PDZ1 domain binder (e.g., compound described herein) binds a PDZ1 domain with a Kd of less than 100 nM. In embodiments, the PDZ1 domain binder (e.g., compound described herein) binds a PDZ1 domain with a Kd of less than 50 nM. In embodiments, the PDZ1 domain binder (e.g., compound described herein) binds a PDZ1 domain with a Kd of less than 20 nM. In embodiments, the PDZ1 domain binder (e.g., compound described herein) binds a PDZ1 domain with a Kd of less than 10 nM. In embodiments, the PDZ1 domain binder (e.g., compound described herein) binds a PDZ1 domain with a Kd of less than 5 nM. In embodiments, the PDZ1 domain binder (e.g., compound described herein) binds a PDZ1 domain with a Kd of less than 1 nM. In embodiments, the PDZ1 domain binder (e.g., compound described herein) binds a PDZ1 domain with a Kd of less than 0.5 nM. In embodiments, the PDZ1 domain binder (e.g., compound described herein) binds a PDZ1 domain with a Kd of less than 0.1 nM. In embodiments, the PDZ1 domain binder (e.g., compound described herein) binds a PDZ1 domain with a Kd of less than 0.05 nM. In embodiments, the PDZ1 domain binder (e.g., compound described herein) binds a PDZ1 domain with a Kd of less than 0.025 nM.

In embodiments, the ligand is a natural ligand of a PDZ1 domain. In embodiments, the ligand is a natural ligand of a PDZ1 domain or a portion thereof. The term "natural ligand" refers to a naturally occurring ligand that binds a PDZ1 domain.

In an aspect is provided a method of treating cancer in a subject in need thereof the method including administering to the subject an effective amount of a PDZ1 domain binder.

In embodiments, the PDZ1 domain binder is a compound described herein, including in embodiments, an aspect, an example, a figure, a claim, a scheme, or a table.

In embodiments, the method further includes administering to the subject an anti-cancer agent. In embodiments, the anti-cancer agent is radiation, 5-FU, sorafenib, taxol, temozolimide, or Mcl-1. In embodiments, the anti-cancer agent is radiation. In embodiments, the anti-cancer agent is 5-FU. In embodiments, the anti-cancer agent is sorafenib. In embodiments, the anti-cancer agent is taxol. In embodiments, the anti-cancer agent is temozolimide. In embodiments, the anti-cancer agent is Mcl-1.

In embodiments, the method further includes administering to the subject a second therapy. In embodiments, the second therapy is radiation. In embodiments, the second therapy may be administered before the PDZ1 domain binder (e.g., compound described herein). In embodiments, the second therapy may be administered after the PDZ1 domain binder (e.g., compound described herein). In embodiments, the second therapy may be administered concurrently with the PDZ1 domain binder (e.g., compound described herein). In embodiments, the second therapy is radiation. In embodiments, the second therapy is administration of a second therapeutic agent. In embodiments, the second therapeutic agent is an anti-cancer agent. In embodiments, the second therapeutic agent is a chemotherapeutic agent. In embodiments, the second therapeutic agent is an agent for treating glioblastoma. In embodiments, the second therapeutic agent is an agent for treating breast cancer. In embodiments, the second therapeutic agent is an agent for treating urothelial cancer. In embodiments, the second therapeutic agent is an agent for treating melanoma. In embodiments, the second therapeutic agent is an agent for treating hepatocellular carcinoma. In embodiments, the second therapeutic agent is an agent for treating colorectal cancer. In embodiments, the second therapeutic agent is an agent for treating neuroblastoma. In embodiments, the second therapeutic agent is an agent for treating colon cancer. In embodiments, the second therapeutic agent is an agent for treating gastric cancer. In embodiments, the second therapeutic agent is an agent for treating bladder cancer. In embodiments, the second therapeutic agent is an agent for treating lung cancer. In embodiments, the second therapeutic agent is an agent for treating pancreatic cancer. In embodiments, the second therapeutic agent is an agent for treating head and neck cancer.

It is further contemplated that the compositions provided herein, including embodiments thereof, are useful for preventing or reducing metastasis of cancer cells. The compositions provided herein, including embodiments thereof, can accomplish prevention or reduction of metastasis of cancer cells by inhibiting cancer cell invasion and attachment of cancer cells and cancer-associated angiogenesis. Cancer cell invasion refers to the ability of cancer cells to become motile and infiltrate neighboring tissue or blood vessels. Cancer cell attachment refers the ability of cancer cells to adhere to blood vessel walls and extravasate, or to adhere to neighboring tissue, thereby forming metastases.

Therefore, in an aspect is provided a method of preventing metastasis of cancer cells in a subject in need thereof, the method including administering to the subject an effective amount of a PDZ1 domain binder.

In an aspect is provided a method of reducing metastasis of cancer cells in a subject in need thereof, the method including administering to the subject an effective amount of a PDZ1 domain binder. In embodiments, the method of reducing is measured relative to a control (e.g., the absence of the PDZ1 domain binder).

In an aspect is provided a method of inhibiting cancer associated angiogenesis in a subject in need thereof, the method including administering to the subject an effective amount of a PDZ1 domain binder. In embodiments, the method of inhibiting is measured relative to a control (e.g., the absence of the PDZ1 domain binder).

In embodiments, the cancer is associated with an increased MDA-9 gene expression. In embodiments, the cancer cells are associated with an increased MDA-9 gene expression. Detection of increased MDA-9 gene expression may be determined, for example, by comparing MDA-9 gene expression from a biological sample (e.g., tumor biopsy, blood) obtained from a patient against a control sample. The control sample may be a biological sample (e.g., healthy tissue) taken from the same patient. Alternatively, the control sample may be a biological sample (e.g., tissue, blood) obtained from a cancer-free subject. In embodiments, an increased MDA-9 gene expression level is at least 1.02, 1.03, 1.04, 1.05, 1.1, 1.2, 1.3, 1.4, 1.5, 1.6, 1.7, 1.8, 1.9, 2, 2.5, 3, 3.5, 4, 4.5, 5, 5.5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 150, 200, 250, or 300 times greater than the expression level observed in the control sample.

Detection of increased MDA-9 gene expression may also be determined by comparing the level of MDA-9 gene expression in a biological sample (e.g., tumor biopsy, blood) obtained from a patient against MDA-9 expression levels from biological samples obtained from a population of patients. Population data may be obtained from public genome-wide expression databases. In embodiments, an increased MDA-9 gene expression level is equal to or greater than the mean of the MDA-9 expression level of the patient population. In embodiments, an increased MDA-9 gene expression level is greater than the median of the MDA-9 expression level of the patient population. In embodiments, an increased expression level of MDA-9 may be a relative expression level of at least 1.02, 1.03, 1.04, 1.05, 1.1, 1.2, 1.3, 1.4, 1.5, 1.6, 1.7, 1.8, 1.9, 2, 2.5, 3, 3.5, 4, 4.5, 5, 5.5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 150, 200, 250, or 300. The relative expression level value (z) can be quantified by the following equation:

$$z=(In-\text{Average}I_{norm})/\text{standard deviation}_{norm},$$

wherein n refers to every sample in the dataset (including tumors) and norm refers to normal samples only.

In embodiments, the cancer is melanoma, glioblastoma, head and neck cancer, urothelial cancer, breast cancer, uveal melanoma, gastric cancer, lung adenocarcinoma, hepatocellular carcinoma, colorectal cancer, prostate cancer, pancreatic cancer, or neuroblastoma. In embodiments, the cancer is melanoma. In embodiments, the cancer is glioblastoma. In embodiments, the cancer is head and neck cancer. In embodiments, the cancer is urothelial cancer. In embodiments, the cancer is breast cancer. In embodiments, the cancer is uveal melanoma. In embodiments, the cancer is gastric cancer. In embodiments, the cancer is lung adenocarcinoma. In embodiments, the cancer is hepatocellular carcinoma. In embodiments, the cancer is colorectal cancer. In embodiments, the cancer is prostate cancer. In embodiments, the cancer is pancreatic cancer. In embodiments, the cancer is neuroblastoma.

In embodiments, the cancer cells are melanoma, glioblastoma, head and neck cancer, urothelial cancer, breast cancer, uveal melanoma, gastric cancer, lung adenocarcinoma, hepatocellular carcinoma, colorectal cancer, prostate cancer, pancreatic cancer, or neuroblastoma cancer cells. In embodiments, the cancer cells are melanoma cancer cells. In embodiments, the cancer cells are glioblastoma cancer cells. In embodiments, the cancer cells are head and neck cancer cells. In embodiments, the cancer cells are urothelial cancer cells. In embodiments, the cancer cells are breast cancer cells. In embodiments, the cancer cells are uveal melanoma cancer cells. In embodiments, the cancer cells are gastric cancer cells. In embodiments, the cancer cells are lung adenocarcinoma cancer cells. In embodiments, the cancer cells are hepatocellular carcinoma cancer cells. In embodiments, the cancer cells are colorectal cancer cells. In embodiments, the cancer cells are prostate cancer cells. In embodiments, the cancer cells are pancreatic cancer cells. In embodiments, the cancer cells are neuroblastoma cancer cells.

In embodiments, the compound (e.g., compound described herein) or method includes reducing the level of activity of NF-kB. In embodiments, the compound (e.g., compound described herein) or method includes reducing the level of activity of c-Src. In embodiments, the compound (e.g., compound described herein) or method includes reducing the level of activity of p38 MAPK. In embodiments, the compound (e.g., compound described herein) or method includes reducing the level of activity of a c-Src/p38 MAPK signaling pathway. In embodiments, the compound (e.g., compound described herein) or method includes reducing the level of activity of MMP2. In embodiments, the compound (e.g., compound described herein) or method includes reducing the level of activity of FAK. In embodiments, the compound (e.g., compound described herein) or method includes reducing the level of activity of EphA2. In embodiments, the compound (e.g., compound described herein) or method includes reducing the level of activity of EGFR. In embodiments, the compound (e.g., compound described herein) or method includes reducing the level of activity of EGFRvII. In embodiments, the compound (e.g., compound described herein) or method includes reducing the level of activity of MMP9. In embodiments, the compound (e.g., compound described herein) or method includes reducing the level of activity of IGF-1R. In embodiments, the compound (e.g., compound described herein) or method includes reducing the level of activity of STAT3. In embodiments, the compound (e.g., compound described herein) or method includes reducing the level of activity of IGFBP-2. In embodiments, the compound (e.g., compound described herein) or method includes reducing the level of activity of RhoA. In embodiments, the compound (e.g., compound described herein) or method includes reducing the level of activity of Cdc42. In embodiments, the compound (e.g., compound described herein) or method includes reducing the level of activity of TGFβ1. In embodiments, the compound (e.g., compound described herein) or method includes reducing the level of activity of Slug. In embodiments, the compound (e.g., compound described herein) or method includes reducing the level of activity of Snail. In embodiments, the compound (e.g., compound described herein) or method includes reducing the level of activity of Zeb1. In embodiments, the compound (e.g., compound described herein) or method includes reducing the level of activity of N-cadherin. In embodiments, the compound (e.g., compound described herein) or method includes reducing the level of activity of IL-8. In embodiments, the compound (e.g., compound described herein) or method includes reducing the level of activity of cyclin D1. In embodiments, the compound (e.g., compound described herein) or method includes reducing the level of activity of CDK4. In embodiments, the compound (e.g., compound described herein) or method includes reducing the level of activity of PI3K. In embodiments, the compound (e.g., compound described herein) or method includes reducing the level of activity of CTNNB1. In embodiments, the compound (e.g., compound described herein) or method includes reducing the level of activity of integrin β1. In embodiments, the compound (e.g., compound described herein) or method includes reducing the level of activity of Akt. In embodiments, the compound (e.g., compound described herein) or method includes reducing the level of activity of HIF-1α. In embodiments, the compound (e.g., compound described herein) or method includes reducing the level of activity of VEGF-A. In embodiments, the compound (e.g., compound described herein) or method includes reducing the level of activity of AEG-1.

In embodiments, the cancer is melanoma. In embodiments, the cancer is gastric cancer. In embodiments, the cancer is bladder cancer. In embodiments, the cancer is glioblastoma. In embodiments, the cancer is lung cancer. In embodiments, the cancer is small cell lung cancer. In embodiments, the cancer is hepatoma. In embodiments, the cancer is head and neck cancer. In embodiments, the cancer is breast cancer. In embodiments, the cancer is triple negative breast cancer. In embodiments, the cancer is prostate cancer. In embodiments, the cancer is hormone refractory prostate cancer. In embodiments, the cancer is hormone sensitive prostate cancer. In embodiments, the cancer is urothelial cancer. In embodiments, the cancer is uveal melanoma. In embodiments, the cancer is adenocarcinoma. In embodiments, the cancer is hepatocellular carcinoma. In embodiments, the cancer is colorectal cancer. In embodiments, the cancer is pancreatic cancer. In embodiments, the cancer is neuroblastoma. In embodiments, the cancer is colon cancer.

IV. Method of Treating Additional Diseases

In yet other aspects, the invention provides methods of treating human diseases other than cancer that are associated with elevated expression of mda-9. Examples of such diseases include but are not limited to: asthma, neurodegenerative diseases and infectious diseases including viral infection (e.g., HIV, SARS, HPV, influenza), virus shedding (HIV), bacterial colonization in the human gastrointestinal tract, etc.

In an aspect is provided a method of treating an inflammatory disease in a subject in need thereof; the method including administering to the subject an effective amount of a PDZ1 domain binder (e.g., compound described herein).

In an aspect is provided a method of treating a neurodegenerative disease in a subject in need thereof, the method including administering to the subject an effective amount of a PDZ1 domain binder (e.g., compound described herein).

In an aspect is provided a method of treating an infectious disease in a subject in need thereof, the method including administering to the subject an effective amount of a PDZ1 domain binder (e.g., compound described herein).

V. Formulations

The compounds described herein are generally delivered (administered) as a pharmaceutical composition. Such pharmaceutical compositions generally include at least one of the disclosed compounds (e.g., in pure form, salt, or prodrugs), and more than one (a plurality) of different compounds (e.g. 2 or more such as 2, 3, 4, 5, 6, 7, 8, 9, 10 or more) may be included in a single formulation. Accordingly, the present invention encompasses such formulations and compositions. The compositions generally include one or more substantially purified compounds as described herein, and a pharmacologically suitable (physiologically compatible) carrier, which may be aqueous or oil-based. In some embodiments, such compositions are prepared as liquid solutions or suspensions. In other embodiments, the compositions are prepared in solid forms such as tablets, pills, powders and the like. Solid forms suitable for solution, dissolution or suspension in liquids prior to administration are also contemplated (e.g. lyophilized forms of the compounds), as are emulsified preparations. In some embodiments, the liquid formulations are aqueous or oil-based suspensions or solutions. In some embodiments, the active ingredients are mixed with excipients which are pharmaceutically acceptable and compatible with the active ingredients, e.g. pharmaceutically acceptable salts. Suitable excipients include, for example, water, saline, dextrose, glycerol, cyclodextrin, ethanol and the like, or combinations thereof. In addition, the composition may contain minor amounts of auxiliary substances such as wetting or emulsifying agents, pH buffering agents, preservatives, and the like. If it is desired to administer an oral form of the composition, various thickeners, flavorings, diluents, emulsifiers, dispersing aids or binders and the like are added. The composition of the present invention may contain any such additional ingredients so as to provide the composition in a form suitable for administration. The final amount of compound in the formulations varies, but is generally from about 1-99%. Still other suitable formulations for use in the present invention are found, for example in Remington's Pharmaceutical Sciences, 22nd ed. (2012; eds. Allen, Adejarem Desselle and Felton).

Some examples of materials which serve as pharmaceutically acceptable carriers include, but are not limited to, ion exchangers, alumina, aluminum stearate, lecithin, serum proteins (such as human serum albumin), buffer substances (such as Tween 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropylene-block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water, isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

"Pharmaceutically acceptable salts" refers to the relatively non-toxic, inorganic and organic acid addition salts, and base addition salts, of compounds (e.g., compound described herein). These: salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulfamates, malonates, salicylates, propionates, methylene-bis-.beta.-hydroxynaphthoates, gentisates, isethionates, di-p-toluoyltartrates, methanesulfonates, ethanesulfonates, benzenesulfonates, p-toluenesulfonates, cyclohexylsulfamates and laurylsulfonate salts, and the like. See, for example S. M. Berge, et al., "Pharmaceutical Salts," J. Pharm. Sci., 66, 1-19 (1977) which is incorporated herein by reference. Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which have sufficient basicity to form a stable salt, and preferably include those amines which are frequently used in medicinal chemistry because of their low toxicity and acceptability for medical use. ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

VI. Administration

In embodiments, the formulation is administered in vivo by any suitable route including but not limited to: inoculation or injection (e.g. intravenous, intraperitoneal, intramuscular, subcutaneous, intra-aural, intraarticular, intramammary, intracranial, and the like), topical application (e.g. on any suitable skin or membrane surface), by absorption through epithelial or mucocutaneous linings (e.g., nasal, oral, vaginal, rectal, gastrointestinal mucosa, etc.) and the like. In embodiments, the compounds may be incorporated into implantable delivery means, e.g. drug permeated wafers, etc. Timed (sustained, extended, controlled) release formulations, e.g. in the form of pills, tablets, capsules, etc. are also contemplated, including various diffusion systems such as reservoir and matrix devices; osmotic, ion exchange, floating, bio-adhesive, and depot systems, etc. In embodiments, the mode of administration is intranasal, orally or parenteral, by intravenous, intraperitoneal, intramuscular, topical or subcutaneous routes, and usually is by intravenous injection.

In addition, in embodiments, the compounds may be administered in conjunction with other treatment modalities. Examples of such additional treatments include but are not limited to: administration of various anti-cancer agents, for example, cytotoxic chemotherapy agents; radiation; hormone therapy; T-cell therapy; various immune checkpoint inhibitors; various forms of targeted therapy (e.g. small molecules such as tyrosine-kinase inhibitors, folate receptor inhibitors, serine/threonine kinase inhibitors monoclonal antibodies, etc.).

In some aspects, the compounds as described herein, including embodiments, administered with or in conjunction with one or more anti-invasive and/or anti-attachment therapies. In some aspects, the compounds of the invention are administered with or in conjunction with one or more anti-cancer agents. Such combinations result in induction of apoptosis and/or toxic autophagy and death of cancer cells. For example, in embodiments, the present drugs can be combined with PDZ inhibitors, with radiation (e.g. for GBM) with sorafenib (for liver cancer), with taxol (for breast cancer), etc.

Administration of other therapies that are not specific for cancer, together with the compounds disclosed herein, is also contemplated, e.g. appetite stimulants, nutritional supplements; pain medication, anti-depressants, etc.

Administering a compound, antibody, aptamer, or ligand, as described herein, including embodiments, "with" or "in conjunction with" another agent may refer to administering a single composition that includes both agents, but more typically refers to administering one or more compounds of the invention to the same subject during a course of treatment with the other agent, e.g. more or less consecutively, or on the same day but several hours apart, or several days (or even weeks) apart. In embodiments, the compound, antibody, aptamer, or ligand, as described herein, including embodiments, and the additional treatment (e.g., anti-cancer agent) are administered consecutively. In embodiments, compound, antibody, aptamer or ligand, as described herein, including embodiments, additional treatment (e.g., anti-cancer agent) are administered simultaneously. In embodiments, compound, antibody, aptamer or ligand, as described herein, including embodiments, are admixed with additional treatment (e.g., anti-cancer agent) prior to administration.

In embodiments, administration is carried out in a coordinated manner at time intervals which are spaced apart by minutes, hours, days or weeks, etc. and the use of the multiple agents is thus integrated into a treatment protocol in which the effects are at least additive (i.e., a combined additive amount), and may be synergistic (i.e., a combined synergistic amount).

A "combined additive amount" as used herein refers to the sum of a first amount of a first agent (e.g., compound as described herein) and a second amount of a second agent (e.g., an anti-cancer agent), that results in an additive effect (i.e. an effect equal to the sum of the effects). Therefore, the terms "additive", "combined additive amount", and "additive therapeutic effect" which are used herein interchangeably, refer to a measured effect of compounds administered in combination where the measured effect is equal to the sum of the individual effects of each of the compounds administered alone as a single agent.

A "combined synergistic amount" as used herein refers to the sum of a first amount of first agent (e.g., compound as described herein) and a second amount of a second agent (e.g., an anti-cancer agent) that results in a synergistic effect (i.e. an effect greater than an additive effect). Therefore, the terms "synergy", "synergism", "synergistic", "combined synergistic amount", and "synergistic therapeutic effect" which are used herein interchangeably, refer to a measured effect of compounds administered in combination where the measured effect is greater than the sum of the individual effects of each of the compounds administered alone as a single agent.

In embodiments, a combined synergistic amount may be about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the amount of the first amount (e.g., PDZ1 domain binder) when used separately from the second amount (e.g., anti-cancer agent). In embodiments, a combined synergistic amount may be about 0, 1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the amount of the second amount (e.g., anti-cancer agent) when used separately from the first amount (e.g., PDZ1 domain binder).

Of particular interest is administration of the present agents together with radiation therapy, which are shown herein, results in a synergistic effect in that more cancer cells are killed by the combination than would be predicted if the effect was purely additive, when based on results obtained by administering each agent alone.

In some embodiments, the compounds of the invention are used to block and/or prevent metastatic seeding of cells in the circulatory system. Such methods are carried out by pretreating the patient with a compound (e.g., compound described herein), i.e. treating the patient before another cancer treatment is begun, and then performing at least one other cancer treatment. The second ("other") cancer treatment may be, for example, surgical removal of the tumor, and may be performed in the presence of any of the compounds described herein. Thereafter, the method may include continuing to treat the patient for a suitable period of time after removing the tumor.

In yet other embodiments, the compounds of the invention are used to block and/or prevent metastatic seeding. In such methods, a patient with early stage cancer is treated with a compound (e.g., compound described herein), thereby preventing invasion and shedding of tumor cells into the bloodstream and preventing secondary seeding (colonization) of tumor cells in a distant site (metastasis).

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

EXAMPLES

The following examples illustrate certain specific embodiments of the invention and are not meant to limit the scope of the invention.

Embodiments herein are further illustrated by the following examples and detailed protocols. However, the examples are merely intended to illustrate embodiments and are not to be construed to limit the scope herein. The contents of all references and published patents and patent applications cited throughout this application are hereby incorporated by reference.

Example 1. Inhibition of Radiation-Induced Glioblastoma Invasion by Genetic and Pharmacological Targeting of MDA-9/Syntenin (SDCBP)

Glioblastoma multiforme (GBM) is an intractable tumor despite therapeutic advances principally because of its invasive properties. Radiation is a staple in modern therapeutic regimens, although cells surviving radiation can become more aggressive and invasive. Subtraction hybridization identified melanoma differentiation associated gene-9 (MDA-9/Syntenin; Syndecan Binding Protein (SDCBP)), as a differentially regulated gene associated with aggressive cancer phenotypes in melanoma. MDA-9/Syntenin, a highly conserved double PDZ domain-containing scaffolding protein, is robustly expressed in human-derived GBM cell lines and patient samples, with expression increasing with tumor grade and correlating with shorter survival times and poorer response to radiotherapy. Knockdown (kd) of MDA-9/Syntenin sensitizes GBM cells to radiation, significantly reducing post-radiation invasion gains. Radiation induces Src and EGFRvIII signaling, which is abrogated through MDA-9/Syntenin downregulation. A novel exemplary inhibitor of MDA-9/Syntenin activity, PDZ1i (113B7), was identified through Nuclear Magnetic resonance (NMR) guided Fragment-Based Drug Design (FBDD). PDZ1 i treatment inhibited MDA-9/Syntenin binding to EGFRvIII, which was increased following radiation. Both genetic (shmda-9) and pharmacological (PDZ1i) targeting of MDA-9/Syntenin reduced invasion gains in GBM cells following radiation. Although not affecting normal astrocyte survival when combined with radiation, PDZ1i radiosensitized GBM cells.

PDZ1i inhibited crucial GBM signaling involving FAK and mutant EGFR, EGFRvII, and abrogated gains in secreted proteases, MMP2 and MMP9, following radiation. In an in vivo glioma model, PDZ1 i treatment resulted in smaller, less invasive tumors and enhanced survival. When combined with radiation, survival gains exceeded radiotherapy alone. Small molecule MDA-9/Syntenin inhibitors, like PDZ1i, hold promise to advance targeted therapy of aggressive cancers like GBM.

GBM invasion into normal brain compounded by an inability to surgically eliminate complete tumor contribute to GBM lethality and recurrence. The "gold standard" for GBM therapy is radiation. Unfortunately, evading radiation toxicity leads to further therapeutic resistance. SDCBP (MDA-9/Syntenin) expression is elevated in patient-derived samples and GBM cell lines, which correlates with decreased survival and poor response to radiation. Genetic suppression of MDA-9 expression sensitizes GBM to radiation by inhibiting radiation-induced invasion gains and signaling changes. Using fragment-based drug-discovery combined with NMR a novel small molecule MDA-9/Syntenin inhibitor, PDZ1i, was identified. PDZ1 i improved survival of brain tumor bearing mice, which was enhanced further when used with radiation supporting the potential of PDZ1i as a novel therapeutic for this deadly disease.

Despite advances in surgical, pharmacological, and radiation therapeutic approaches, GBM remains a particularly aggressive and ultimately an invariably fatal tumor with a median survival less than 15 months and 5-year survival at 5%. The current standard of care includes maximal surgical resection followed by radiation and temozolomide chemotherapy. However, inevitable recurrence occurs near resection margins and within the high-dose radiation field, implying that intrinsic invasiveness and radioresistance contributes significantly to relapse. While highly effective in inducing cytotoxicity in a majority of tumor cells, sub-lethal radiation has repeatedly been shown to induce invasion and migration in surviving tumor cells, enhancing the very property that makes curative treatment so difficult. A contributing factor to tumor relapse and recurrence is the ability of tumor cells to escape from the primary tumor mass, which underscores the importance of developing anti-invasive therapies that complement, and ideally enhance, conventional therapeutic approaches. Therefore, gaining a deeper understanding of the crucial molecular signaling events and regulatory molecules will help identify targets for anti-invasive and radiosensitizing approaches.

Melanoma differentiation associated gene-9 (mda-9), also known as syntenin (Syndecan Binding Protein; SDCBP) has been demonstrated in multiple cancer settings to be involved in invasion and metastatic signaling. MDA-9/Syntenin serves critical roles in signal transduction, as well as in cell-cell, and cell-matrix adhesion. In addition to its well-described roles in melanoma metastasis and tumor progression, MDA-9/Syntenin was shown to be highly expressed and involved in breast, gastric, and urothelial cell cancers. In recent work, we showed that MDA-9/Syntenin is an important regulator of GBM invasion, angiogenesis, and tumor progression, and that inhibiting the expression of MDA-9/Syntenin can decrease GBM invasion, and enhance survival. Gene expression analysis of the TCGA database revealed that patients whose tumors express high levels of MDA-9/Syntenin have a poor prognosis and reduced survival compared to low-expressing MDA-9/Syntenin tumors. mda-9/syntenin expression correlates positively with astrocytoma grade, as analyzed through tissue samples and gene expression databases, and is most highly expressed in GBM. In both melanoma and glioma, MDA-9/Syntenin is involved in NF-kB activation through a c-Src/p38 MAPK signaling pathway. Inhibiting MDA-9/Syntenin expression can lead to a reduction in NF-kB target gene expression such as MMP2, a critical secreted metalloproteinase involved in GBM invasion.

A vital characteristic of MDA-9/syntenin is the inclusion of two tandem PDZ domains, so named for their discovery in PSD95/SAP90, DLGA, and ZO-1. PDZ domains are common to a number of scaffolding proteins, critical for facilitating protein-protein interactions throughout various regions of the cell. MDA-9/Syntenin utilizes these motifs to successfully facilitate the interaction of c-Src/FAK kinase complexes, noted for involvement in pro-invasive signaling in cancer. While inhibiting the interaction between MDA-9/Syntenin and its targets could be fruitful, to date, no molecular inhibitor of the PDZ domain of MDA-9/Syntenin has been developed. Fragment-based lead design or fragment-based drug design (FBDD) is an emerging and useful strategy for the development of biologically active compounds. Using an NMR guided FBDD approach, combined with in silico modeling and synthetic medicinal chemistry, we have now identified first generation PDZ1 MDA-9/Syntenin binding small molecules, represented by compound 113B7 (herein referred to as PDZ1i) that binds with micromolar affinity to the PDZ1 domain of MDA-9/Syntenin (FIG. 4A-4E, FIG. 5, FIG. 6, and Table 1). PDZ1i is long lived in vivo after both IV and IP administration in mice. These data indicated that PDZ1 i was a suitable pharmacological tool to investigate the role of the PDZ1 domain of MDA-9 in cellular mechanistic and in vivo efficacy studies.

TABLE 1

| ID | Compound Structure | Binding affinity ranking * ($K_d$ values) |
|---|---|---|
| 30A9 | 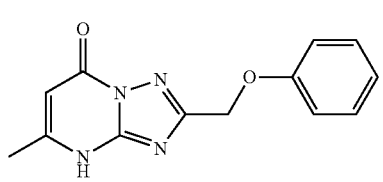 | 4 (197.2 μM) |

TABLE 1-continued

| ID | Compound Structure | Binding affinity ranking * ($K_d$ values) |
|---|---|---|
| cmpd1 | 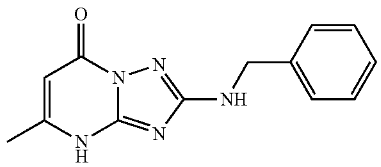 [SMILES: Cc1cc(=O)n2nc(NCc3ccccc3)nc2[nH]1] | 2 |
| cmpd2 | 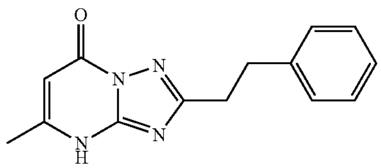 | 3 |
| cmpd3 | 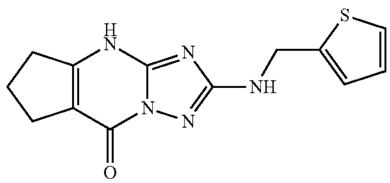 [SMILES: O=c1c2c([nH]c3nc(NCc4cccs4)nn13)CCC2] | 1 |
| cmpd4 | 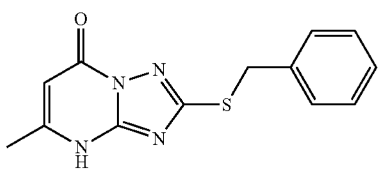 | 4 |
| cmpd5 | 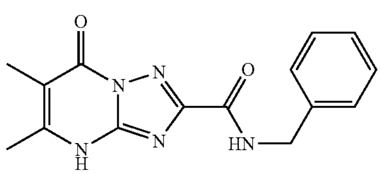 [SMILES: Cc1[nH]c2nc(C(=O)NCc3ccccc3)nn2c(=O)c1C] | 2 |
| cmpd6 | 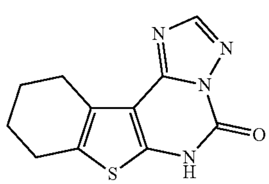 [SMILES: O=c1[nH]c2sc3c(c2c2ncnn12)CCCC3] | 1 |
| cmpd7 | 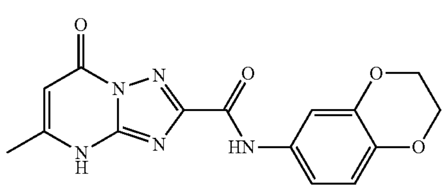 [SMILES: Cc1cc(=O)n2nc(C(=O)Nc3ccc4c(c3)OCCO4)nc2[nH]1] | 2 |
| cmpd8 | 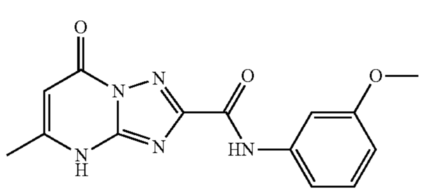 | 3 |

TABLE 1-continued

| ID | Compound Structure | Binding affinity ranking * ($K_d$ values) |
|---|---|---|
| cmpd9 | 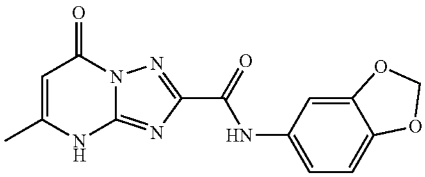 [SMILES: Cc1cc(=O)n2nc(C(=O)Nc3ccc4c(c3)OCO4)nc2[nH]1] | 3 |
| cmpd10 | 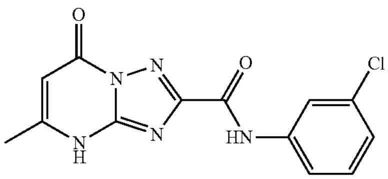 [SMILES: Cc1cc(=O)n2nc(C(=O)Nc3cccc(Cl)c3)nc2[nH]1] | 4 (151.4 µM) |
| cmpd11 | 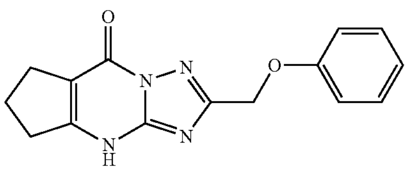 [SMILES: O=c1c2c([nH]c3nc(COc4ccccc4)nn13)CCC2] | 5 (170.6 µM) |
| cmpd12 | 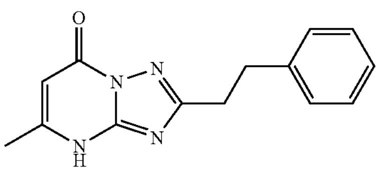 [SMILES: Cc1cc(=O)n2nc(CCc3ccccc3)nc2[nH]1] | 3 |
| cmpd13 | 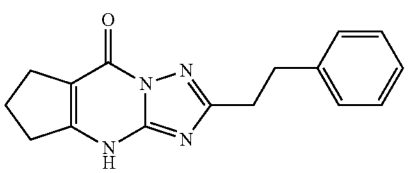 [SMILES: O=c1c2c([nH]c3nc(CCc4ccccc4)nn13)CCC2] | 3 |
| cmpd14 | 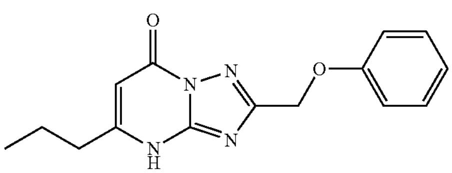 [SMILES: CCCc1cc(=O)n2nc(COc3ccccc3)nc2[nH]1] | 1 |
| 112D11 | 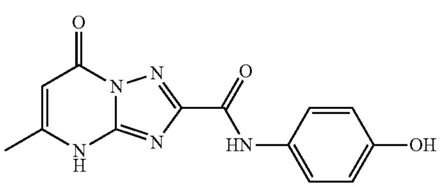 [SMILES: Cc1cc(=O)n2nc(C(=O)Nc3ccc(O)cc3)nc2[nH]1] | 2 (244.7 µM) |
| 112E7 | 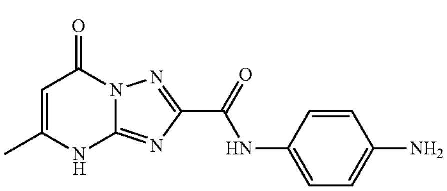 [SMILES: Cc1cc(=O)n2nc(C(=O)Nc3ccc(N)cc3)nc2[nH]1] | 1 (944.2 µM) |

TABLE 1-continued

| ID | Compound Structure | Binding affinity ranking * ($K_d$ values) |
|---|---|---|
| 112E12 | 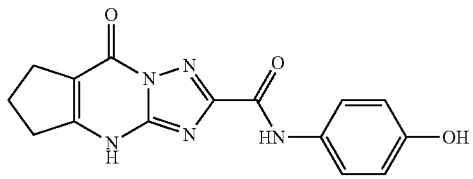 [SMILES: O=C(Nc1ccc(O)cc1)c1nc2[nH]c3c(c(=O)n2n1)CCC3] | 1 (1610 μM) |
| 112F1 | 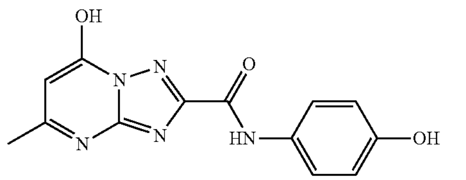 [SMILES: Cc1cc(O)n2nc(C(=O)Nc3ccc(O)cc3)nc2n1] | 1 |
| 112F10 | 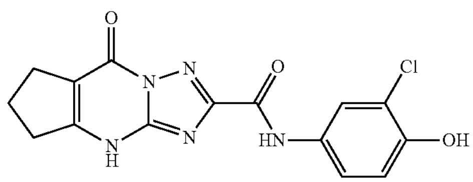 [SMILES: O=C(Nc1ccc(O)c(Cl)c1)c1nc2[nH]c3c(c(=O)n2n1)CCC3] | 4 |
| 112F11 | 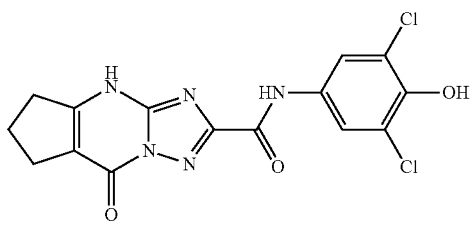 [SMILES: O=C(Nc1cc(Cl)c(O)c(Cl)c1)c1nc2[nH]c3c(c(=O)n2n1)CCC3] | 5 (71.76 μM) |
| 112F12 | 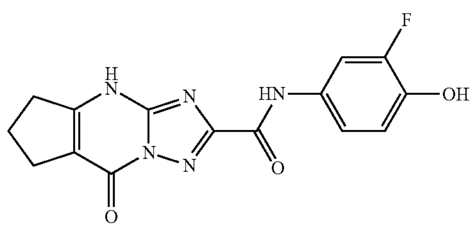 | 2 (165.9 μM) |
| 112G1 | 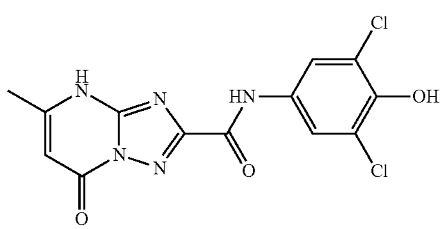 [SMILES: Cc1cc(=O)n2nc(C(=O)Nc3cc(Cl)c(O)c(Cl)c3)nc2[nH]1] | 6 (57.3 μM) |
| 112G2 | 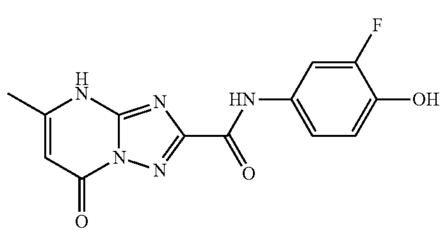 [SMILES: Cc1cc(=O)n2nc(C(=O)Nc3ccc(O)c(F)c3)nc2[nH]1] | 4 (146.8 μM) |

TABLE 1-continued

| ID | Compound Structure | Binding affinity ranking * ($K_d$ values) |
|---|---|---|
| 112G3 | 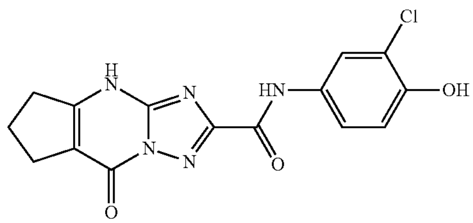 [SMILES: O=C(Nc1ccc(O)c(Cl)c1)c1nc2[nH]c3c(c(=O)n2n1)CCC3] | 4 (119.3 µM) |
| 112G4 | 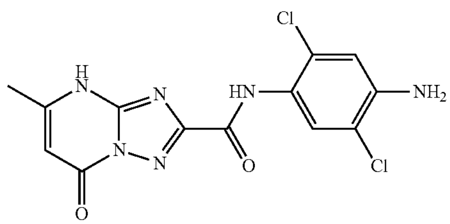 [SMILES: Cc1cc(=O)n2nc(C(=O)Nc3cc(Cl)c(N)cc3Cl)nc2[nH]1] | 6 (34.3 µM) |
| 112G11 | 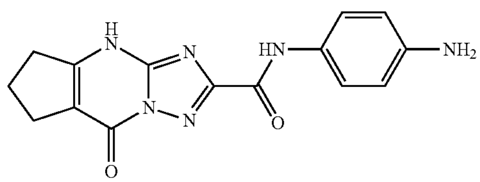 [SMILES: Nc1ccc(NC(=O)c2nc3[nH]c4c(c(=O)n3n2)CCC4)cc1] | 2 (263.1 µM) |
| 113B8 | 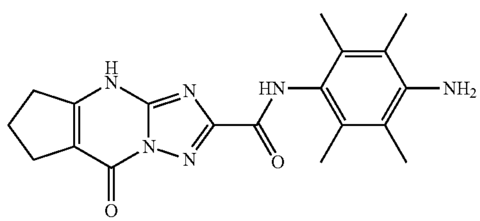 [SMILES: Cc1c(C)c(NC(=O)c2nc3[nH]c4c(c(=O)n3n2)CCC4)c(C)c(C)c1N] | 5 (151.1 µM) |
| 112H9 | 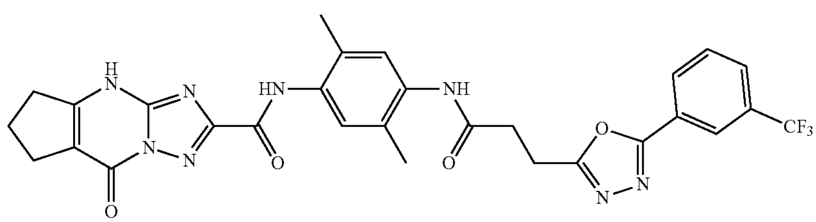 [SMILES: Cc1cc(NC(=O)c2nc3[nH]c4c(c(=O)n3n2)CCC4)c(C)cc1NC(=O)CCc1nnc(-c2cccc(C(F)(F)F)c2)o1] | 2 (38.33 µM) |
| 113B7 (PDZ1i) | 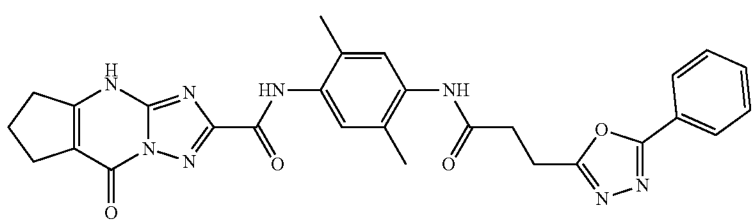 [SMILES: Cc1cc(NC(=O)c2nc3[nH]c4c(c(=O)n3n2)CCC4)c(C)cc1NC(=O)CCc1nnc(-c2ccccc2)o1] | 4 (21.37 µM) |
| 113B9 | 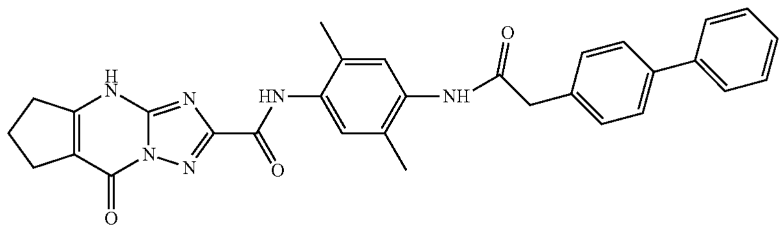 [SMILES: Cc1cc(NC(=O)c2nc3[nH]c4c(c(=O)n3n2)CCC4)c(C)cc1NC(=O)Cc1ccc(-c2ccccc2)cc1] | N.B. |

TABLE 1-continued

| ID | Compound Structure | Binding affinity ranking * ($K_d$ values) |
|---|---|---|
| 113B11 | 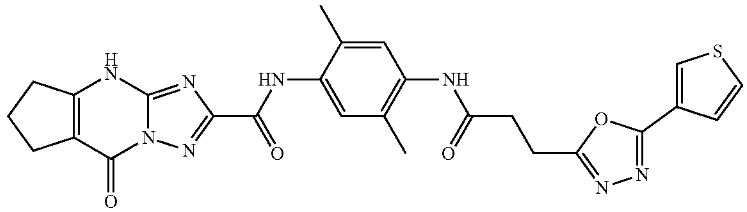 [SMILES: Cc1cc(NC(=O)c2nc3[nH]c4c(c(=O)n3n2)CCC4)c(C)cc1NC(=O)CCc1nnc(-c2ccsc2)o1] | 3 |
| 113B12 | 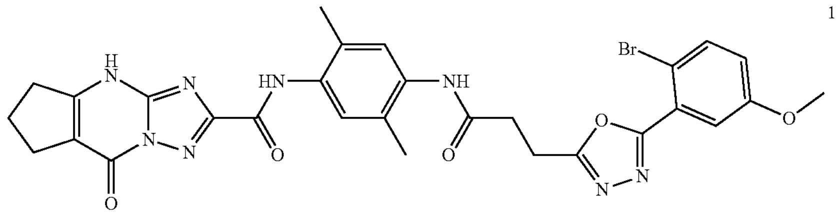 | 1 |

* Rank ordering of compound affinity for PDZ1 were estimated based on chemical shift changes (DPPM) of the backbone amide of residue 147 on the [$^{15}$N,$^1$H] HSQC spectrum of 50 μM PDZ12 caused by compound at 1:1 molar ratio: 1 for DPPM 0.00-0.02; 2 for DPPM 0.02-0.04; 3 for DPPM 0.04-0.06; 4 for DPPM 0.06-0.08; 5 for DPPM 0.08-0.1; 6 for DPPM above 0.1; N.B. no appreciable binding detected. Kd values reported in parentheses were obtained by NMR titration experiments following the chemical shifts of the backbone amide of residue 147 at different ligand concentrations.

Here, the efficacy of supplementing radiotherapy by targeting, both genetically (shmda-9) and pharmacologically (PDZ1i), MDA-9/Syntenin in GBM is demonstrated. By counteracting gains in Src, FAK, and EphA2 signaling, MDA-9/Syntenin inhibition can reduce radiation-induced invasion, as well as radiosensitize GBM cells, ideal properties to complement radiation treatment.

MDA-9/Syntenin inhibition leads to radiosensitization and inhibition of radiation-induced invasion. Prior studies indicate that MDA-9/Syntenin is an important mediator of glioma progression. Specifically, MDA-9/Syntenin was shown to be a valuable target in addressing one of the deadliest aspects of GBM, its propensity to invade. Since radiation therapy has been demonstrated to induce invasion in GBM cells, targeting MDA-9/Syntenin could be a useful approach to complement conventional treatment. Gliomas with higher expression of MDA-9/Syntenin are more likely to be high-grade, and patients whose tumors had high levels of MDA-9/Syntenin had a worse prognosis. With this in mind, possible connections between MDA-9/Syntenin expression and radiotherapy in glioma were explored. using the REpository for Molecular BRAin Neoplasia DaTa (REMBRANDT) database, a publicly available dataset with information on tumor gene expression, treatment history, and survival (21). In glioma patients with no history of radiation who then underwent subsequent radiotherapy, we probed if survival time correlated with MDA-9/Syntenin expression. Patients whose tumors had higher expression of MDA-9/Syntenin had significantly shorter survival (FIG. 1A, p<0.01). Median survival was reduced nearly threefold in patients with gliomas expressing high levels of MDA-9/Syntenin (15.2 months) compared to others (43.6 months).

Figure 1B:
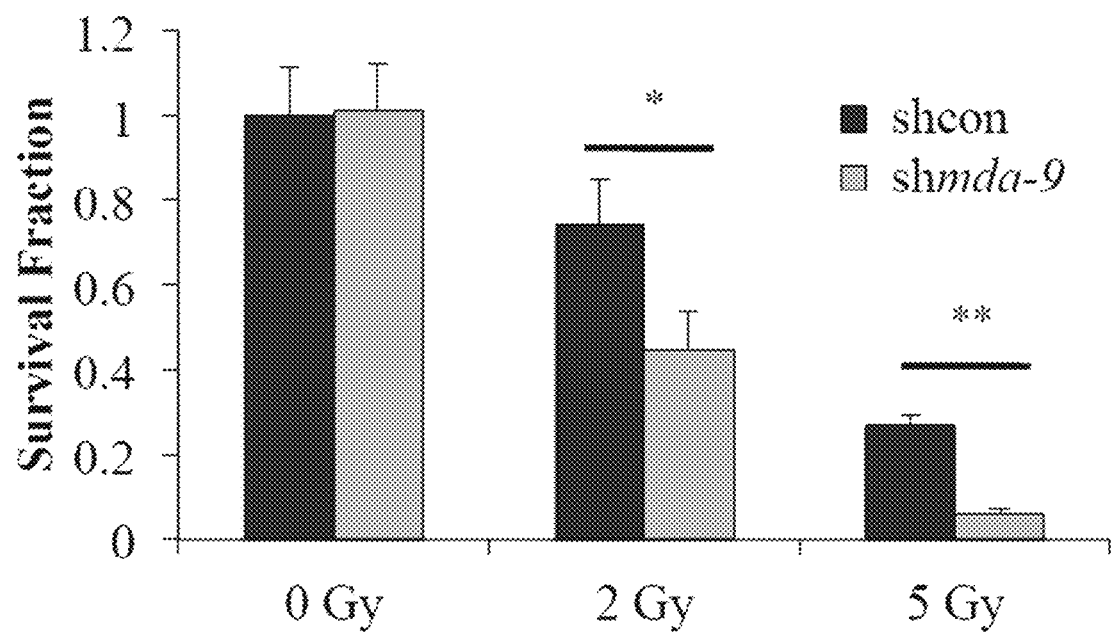
Figure 1C:
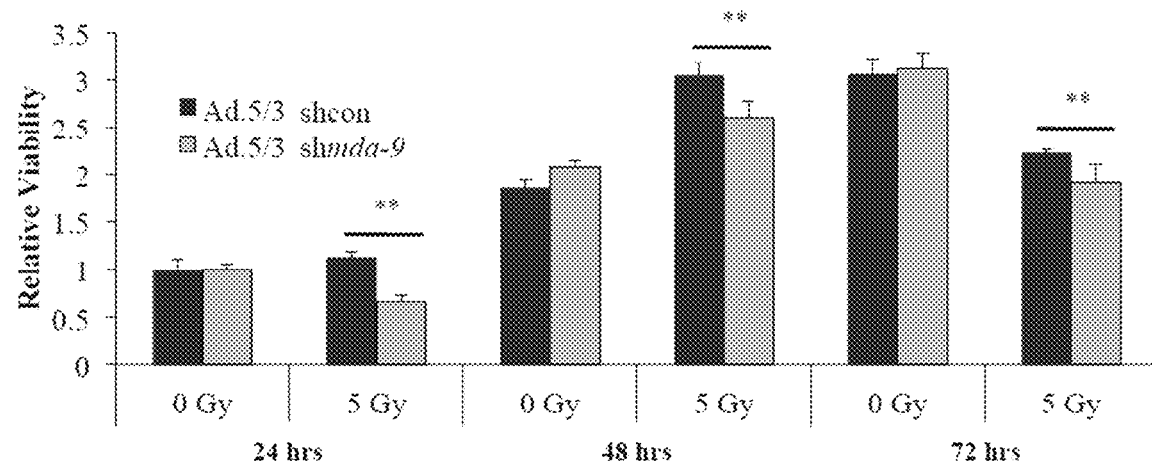

The impact of inhibiting the expression of MDA-9/Syntenin on changes in radiosensitivity was explored in vitro. Using GBM cells expressing a control shRNA, U1242-shcon, or shRNA targeting mda-9/syntenin, U1242-shmda-9/syntenin, it was found that low levels of MDA-9/Syntenin radiosensitized GBM in a colony formation assay (FIG. 1B). Furthermore, proliferation was inhibited in cells transiently reduced in MDA-9/Syntenin expression via adenoviral vector Ad.5/3-shmda-9 (FIG. 1C). This indicates that MDA-9/Syntenin may have a central role in cell survival following radiation exposure.

Figure 2:
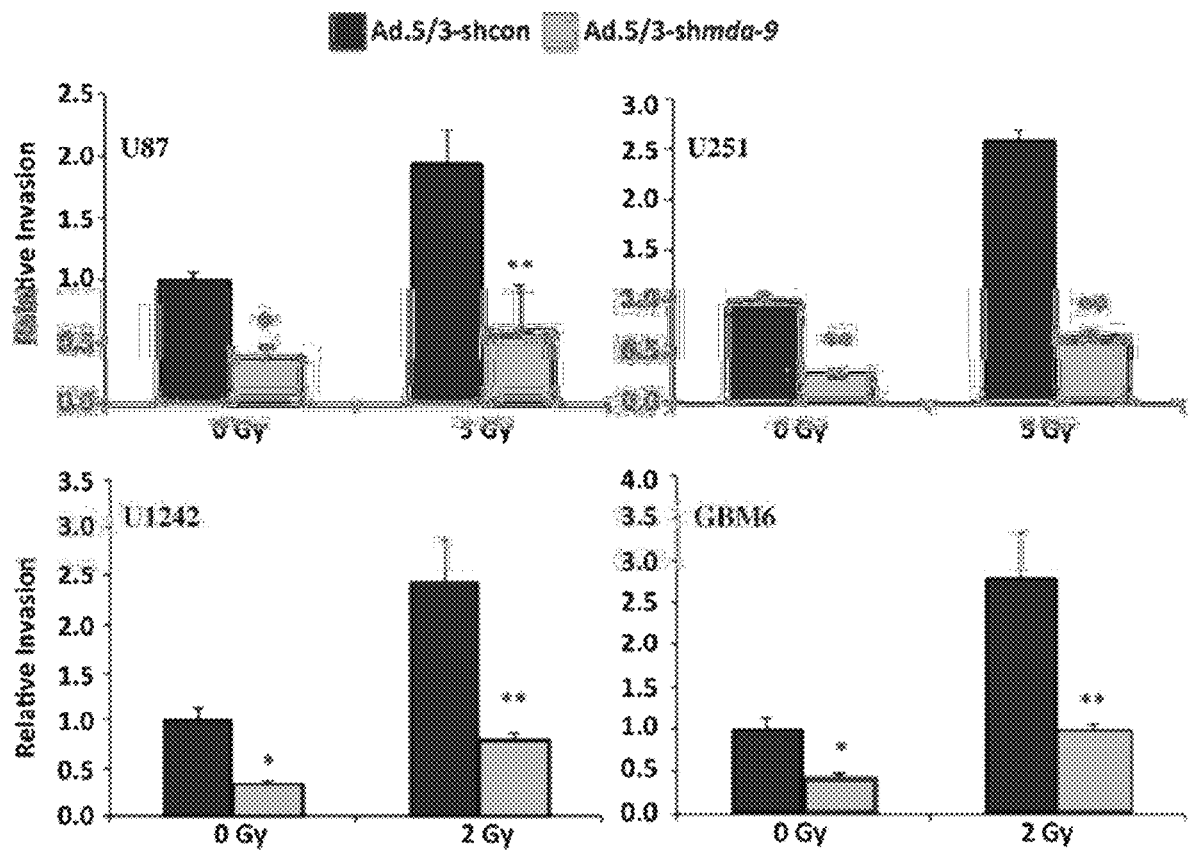
FIG. 2. MDA-9/Syntenin knockdown inhibits radiation-induced invasion. U87, U251, U1242, and GBM6 cells were treated with either Ad.5/3-shcon or Ad.5/3-shmda-9 and irradiated 48 hrs later. These cells were then seeded in a trans-well Matrigel invasion assay and stained after 18 hr. Relative invasion is quantified from 5 random fields. Error bars=s.d. *$p<0.05$, **$p<0.01$.
Figure 3A:
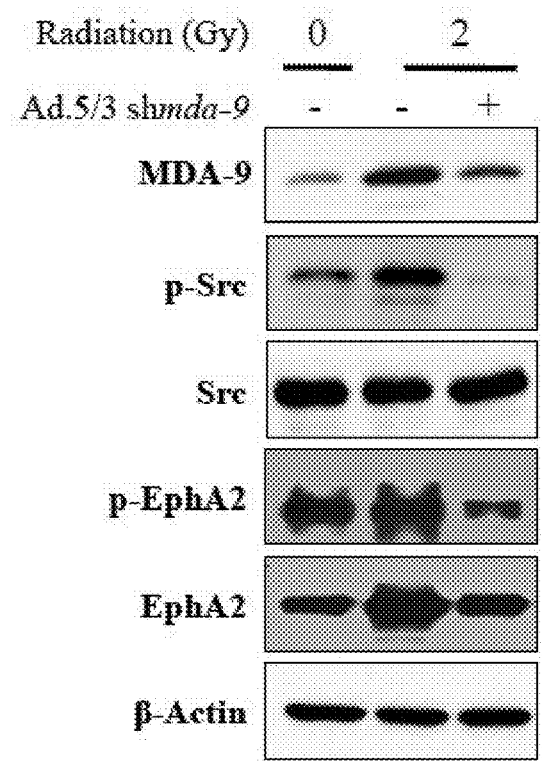
FIGS. 3A-3F. Inhibition of MDA-9/Syntenin impairs Src-EphA2 signaling.
Figure 3B:
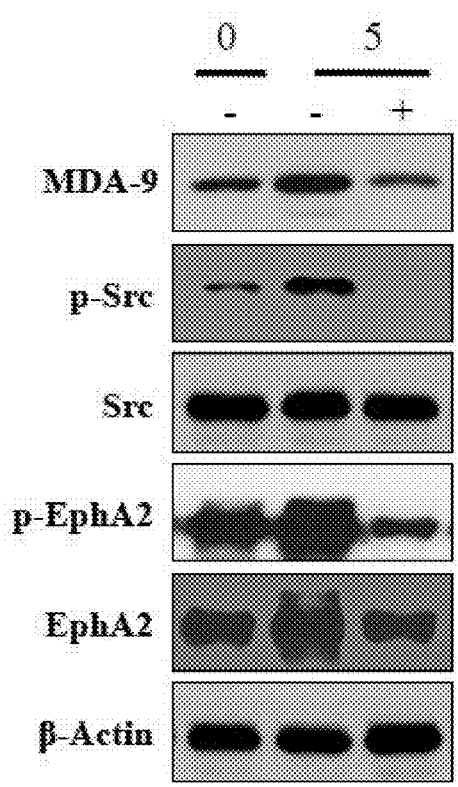
Figure 3C:
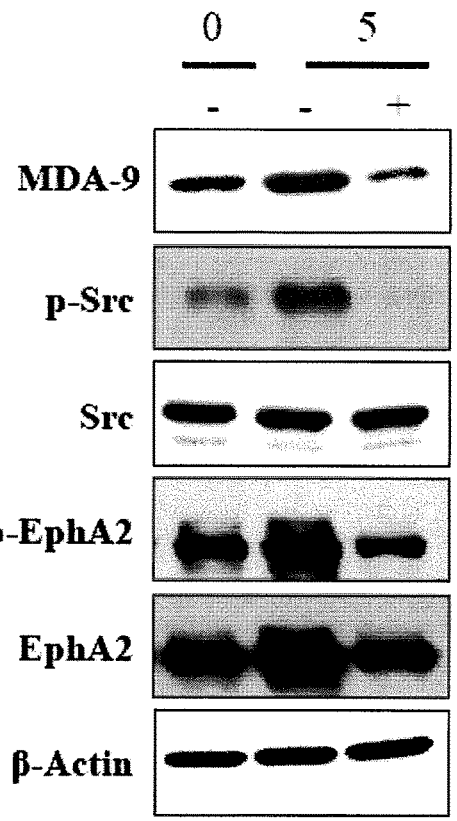
Figure 3D:
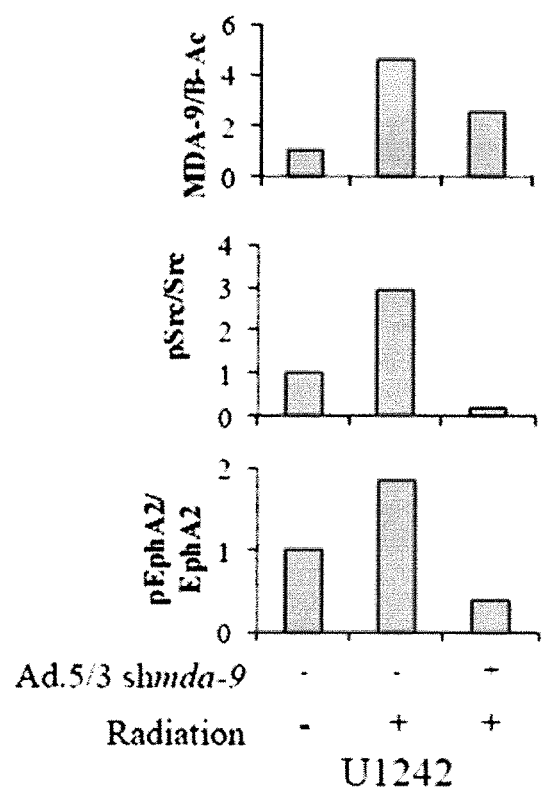
Figure 3E:
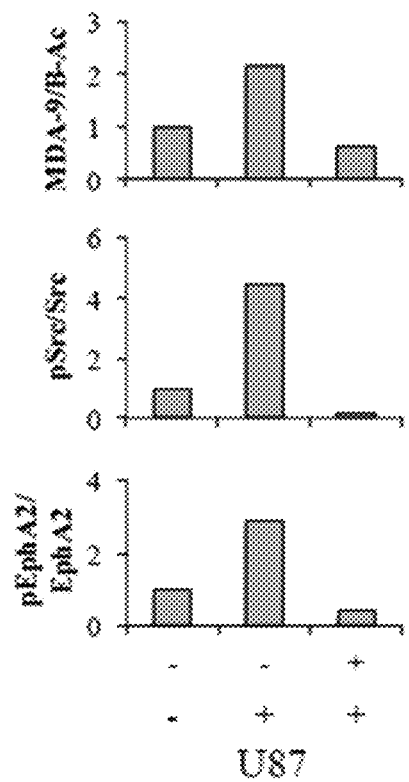
Figure 3F:
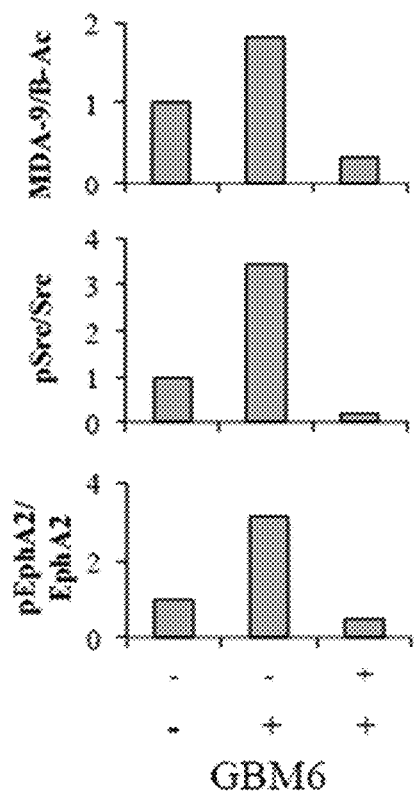
Figure 4A:
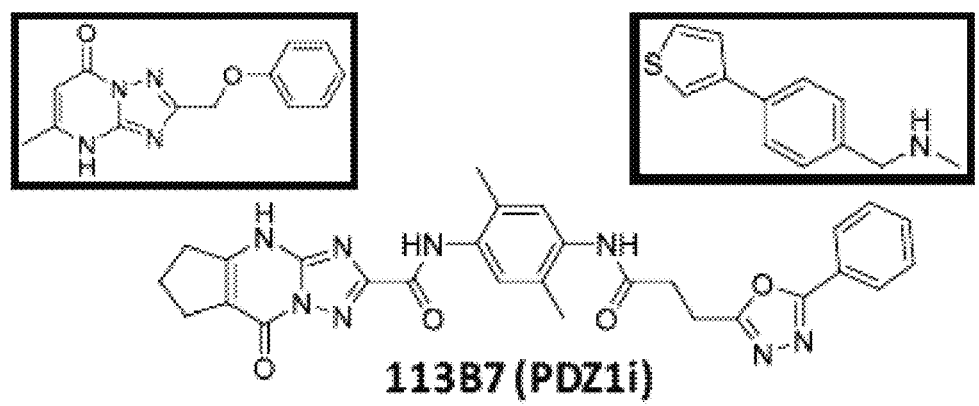
Figure 4B:
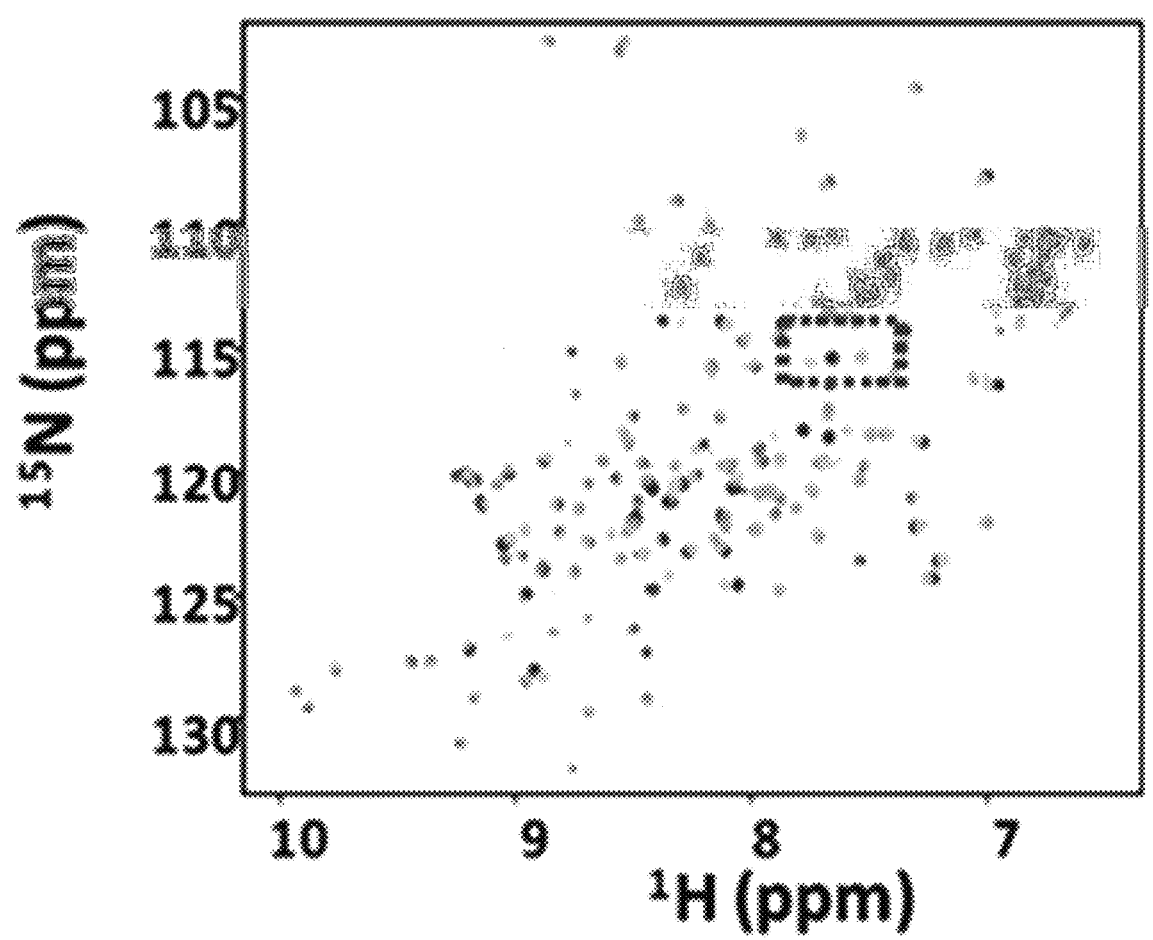
Figure 4C:
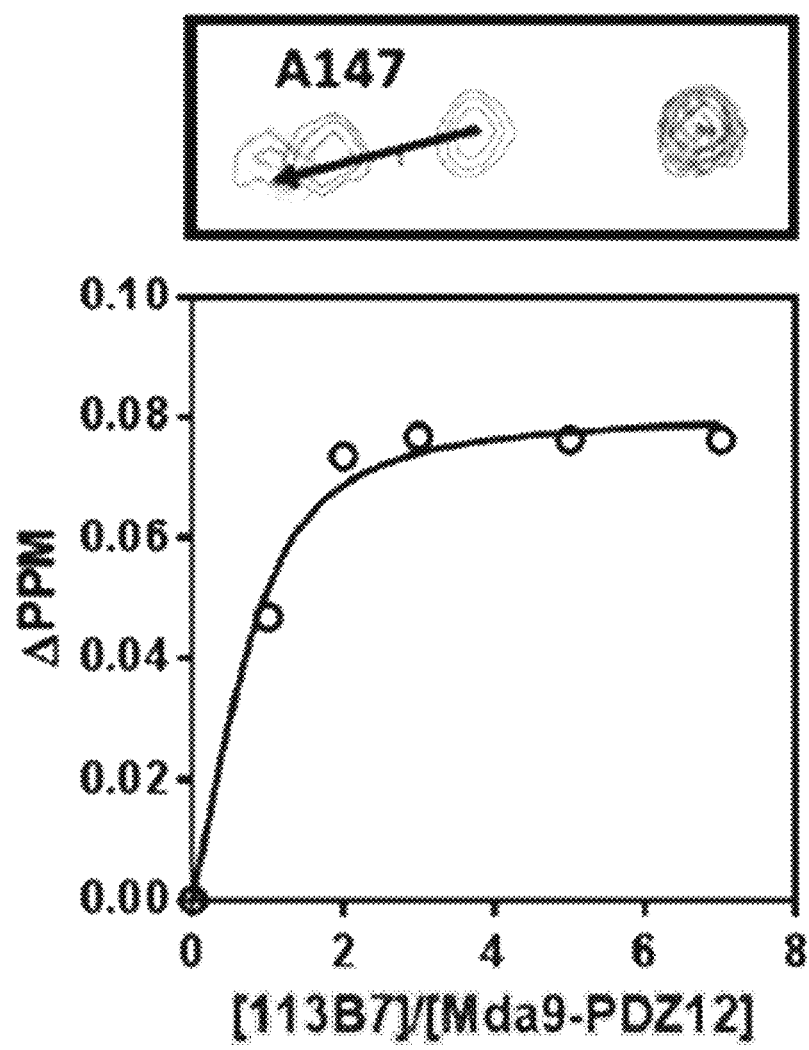
Figure 4D:
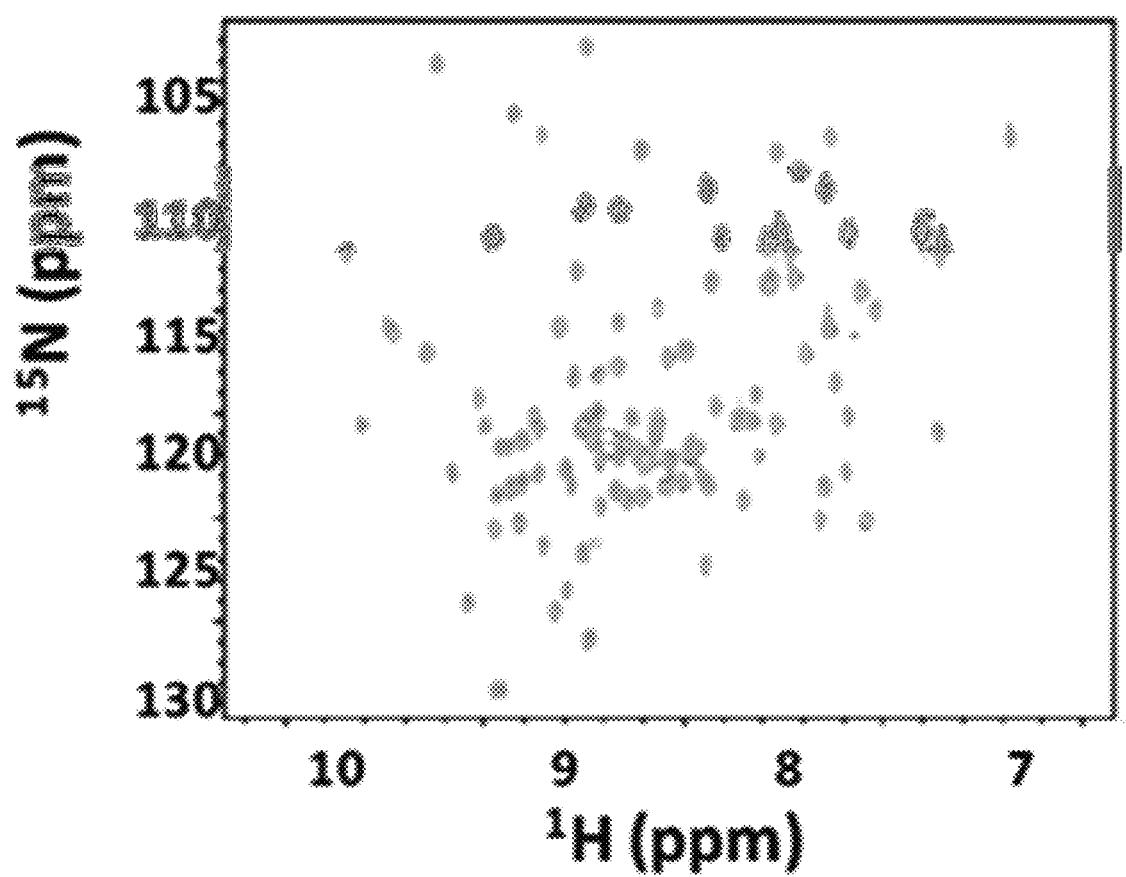

Radiation consistently increases motility and invasion in GBM cells. Four cell lines were exposed to radiation after treatment with control adenovirus, Ad.5/3-shcon, or Ad.5/3-shmda-9. Each of the cell lines received a range of radiation doses, and the dose that demonstrated maximal radiation gains was used for MDA-9/Syntenin knockdown studies. As expected, knockdown of MDA-9/Syntenin levels reduced invasion with no radiation exposure. After irradiation, each GBM cell line exhibited at least a twofold invasion gain, while MDA-9/Syntenin knockdown significantly curtailed these gains (FIG. 2). GBM invasion following radiation was reduced with MDA-9/Syntenin knockdown to about 33% of levels observed in controls. This represents a substantial reduction to an undesirable side effect displayed upon exposure to conventional radiotherapy.

Knockdown of mda-9/syntenin inhibits Src and EphA2 activation post-radiation. MDA-9/Syntenin amplifies Src and NF-κB signaling in melanoma and glioma. Src is a recognized enhancer of invasive signals in cancer settings and has demonstrated involvement in post-radiation signaling. While a modest increase in MDA-9/Syntenin levels 24 h post-radiation was observed, a significant increase in activated levels of Src (FIG. 3) was detected. MDA-9/Syntenin knockdown reduced those activation levels in each of the GBM cell lines tested. EphA2 is a member of the Eph-receptor family, the largest subfamily of receptor tyrosine kinases (RTKs), and are involved in numerous cellular processes including angiogenesis and motility. EphA2 overexpression correlates with poor prognosis and increased metastasis, is implicated in the pathogenesis of numerous tumors, including those of the brain. Importantly, EphA2 has been shown to interact with Src in invasion signaling, is upregulated following radiation, and enhances the malignant phenotype in melanoma. Both total and activated EphA2 levels increased after radiation exposure, yet MDA-9/Syntenin inhibition reduced these gains effectively in each case (FIG. 3). Since MDA-9/Syntenin inhibition negated the gains in Src and EphA2 signaling post-radiation, it can be considered a valuable target in controlling radiation-induced pathogenesis.

A small molecule targeting MDA-9/Syntenin inhibits invasion and radiosensitizes GBM. To develop a deliverable agent that could effectively inhibit the action of MDA-9/Syntenin in cellular and in subsequent in vivo studies, a Fragment-based drug discovery (FBDD) approach was enlisted. FBDD is an important technique that has been used with success in efforts to develop small molecule inhibitors of challenging drug targets including those involved in protein-protein interactions. NMR based screening of an house assembled fragment library of about 5,000 compounds using [$^{15}$N,$^{1}$H] HSQC correlation spectra with $^{15}$N-labeled PDZ1/2 tandem domain from MDA9 resulted in the identification of two hit compounds (FIG. 4). Chemical shift mapping studies with these two classes of hits revealed that these molecules interacted mainly with the PDZ1 domain and in a region at the interface between the domains, while no viable fragment hits were found binding to the PDZ2 domain (FIG. 4). A combination of molecular docking studies and structure-activity relationships (SAR) studies led to the synthesis of the molecule 113B7 (PDZ1i; FIGS. 4A-4E). The proposed docked structure of PDZ1i in the PDZ1 domain and interdomain of MDA-9/Syntenin is shown in FIGS. 4A-4E and FIG. 5, while the chemical structure of PDZ1i is also shown in FIGS. 4A-4E and FIG. 5. In agreement with the data with the individual fragments that compose 113B7, the molecule does not appreciably bind to the PDZ2 domain of MDA-9, indicating selectivity (FIGS. 4A-4E). The synthetic scheme for the preparation of the PDZ1i is reported in FIG. 6. Based on this scheme, relatively large scale amounts of the compound (>500 mg) were synthesized and used in a variety of cellular and in vivo characterizations, including pharmacokinetics (PK) and efficacy studies in mice (Table 2). Other compounds in Table 1 may also be utilized in the practice of compositions and method described herein and PDZ1i is a preferred model of this genus of compounds.

Figure 7A:
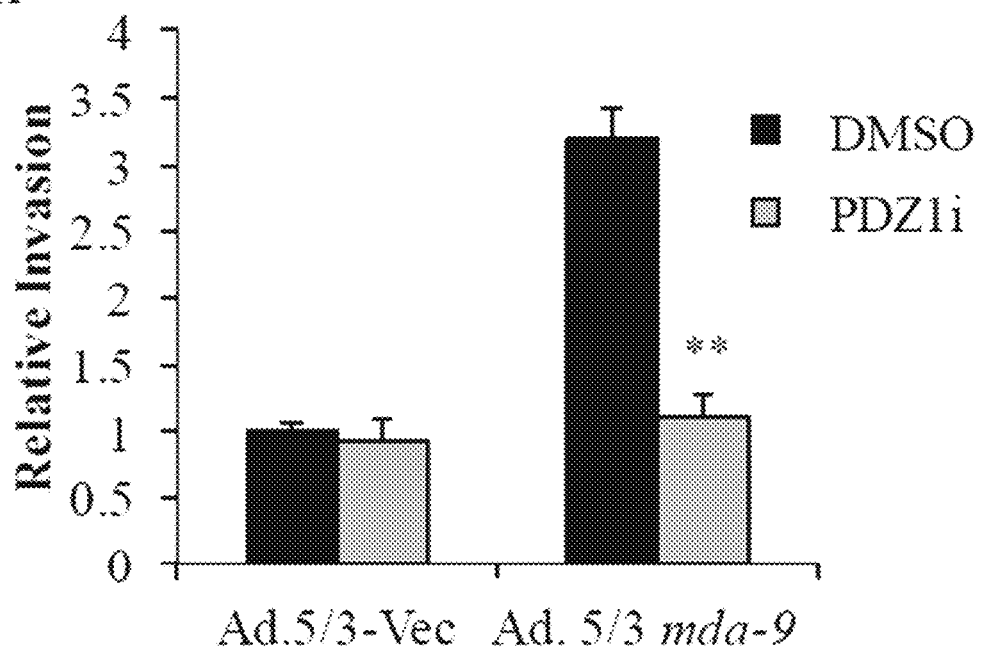
FIGS. 7A-7B.
Figure 7B:
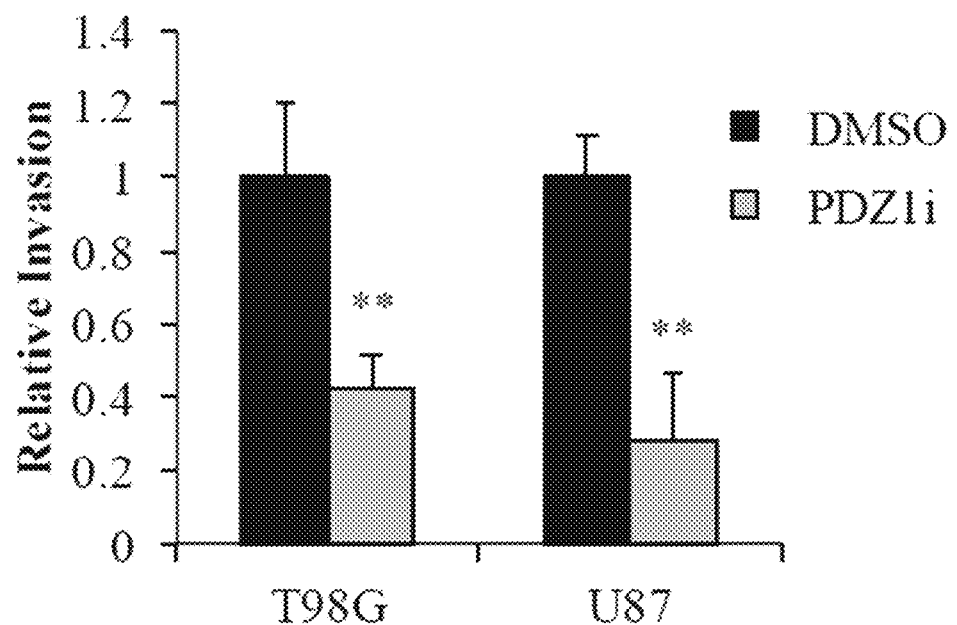
Figure 8A:
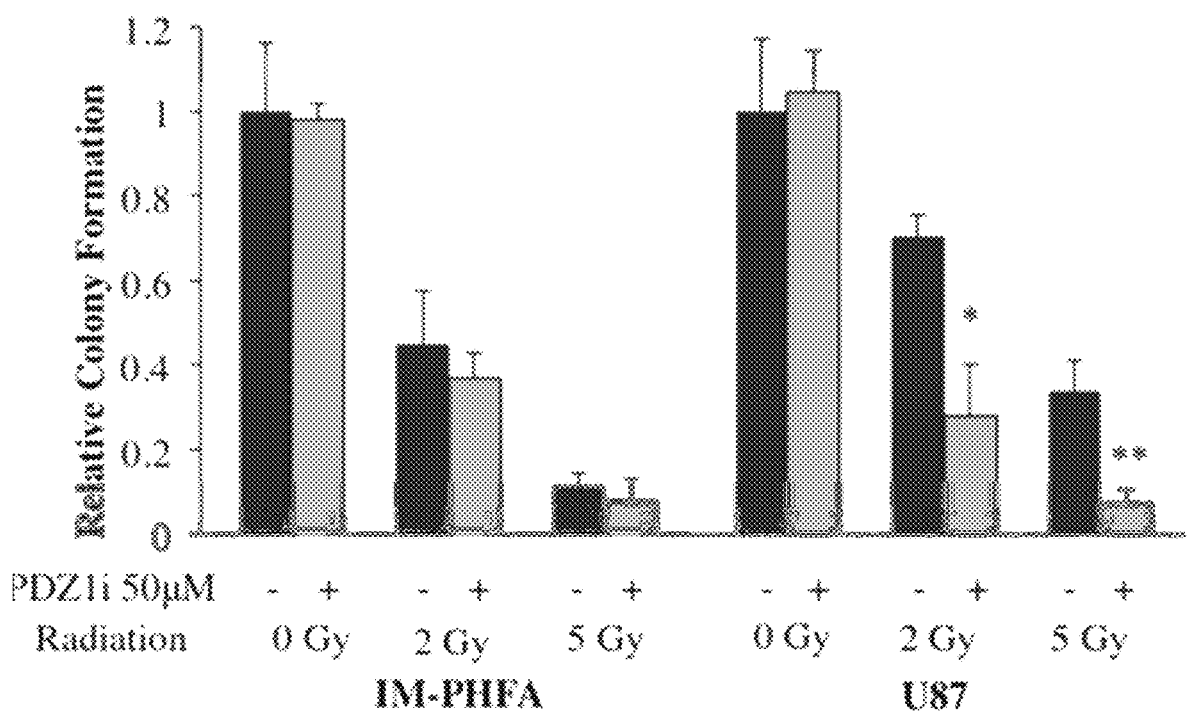
FIGS. 8A-8D. PDZ1i produces similar effects to mda-9/syntenin knockdown post-radiation.
Figure 8B:
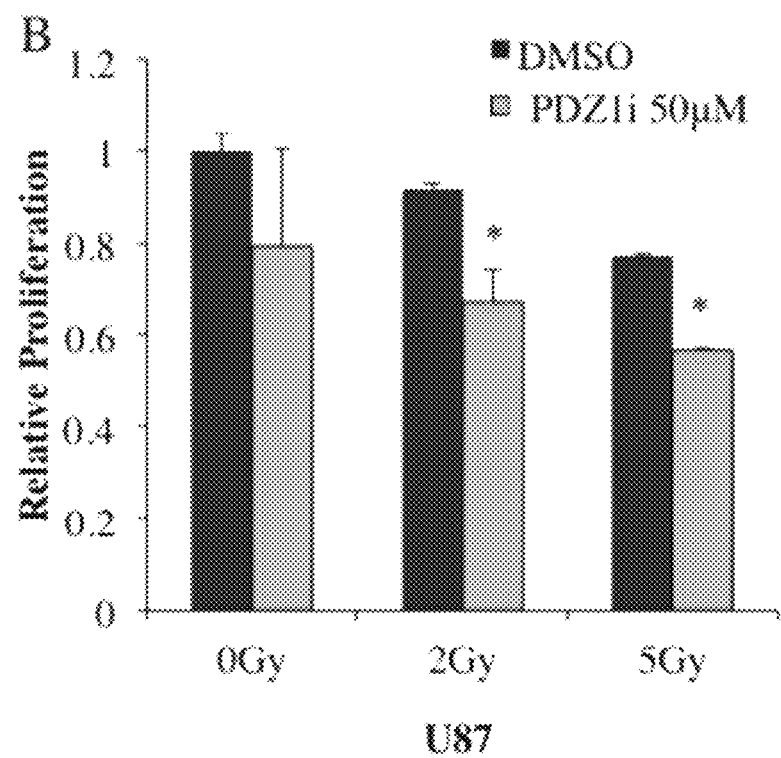
Figure 8C:
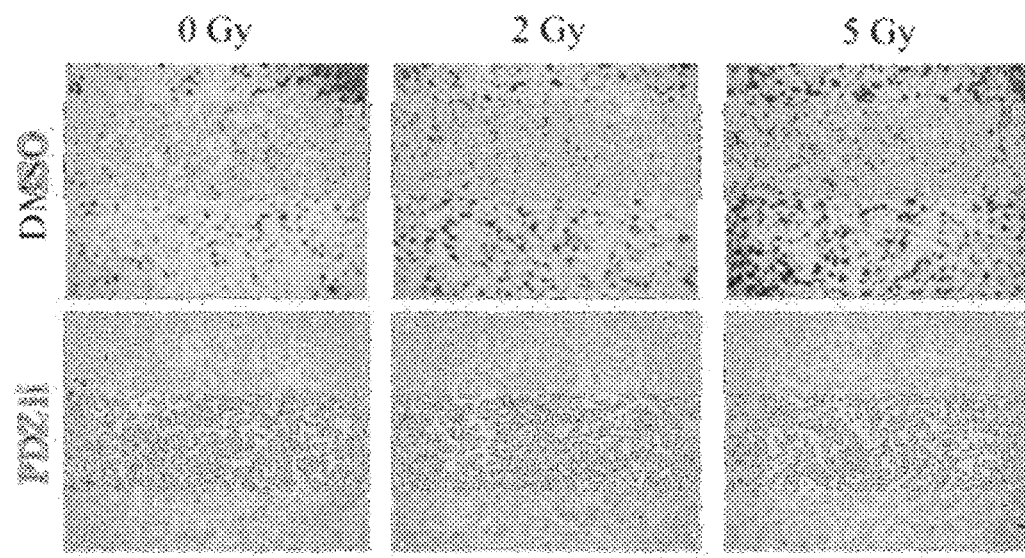
Figure 8D:
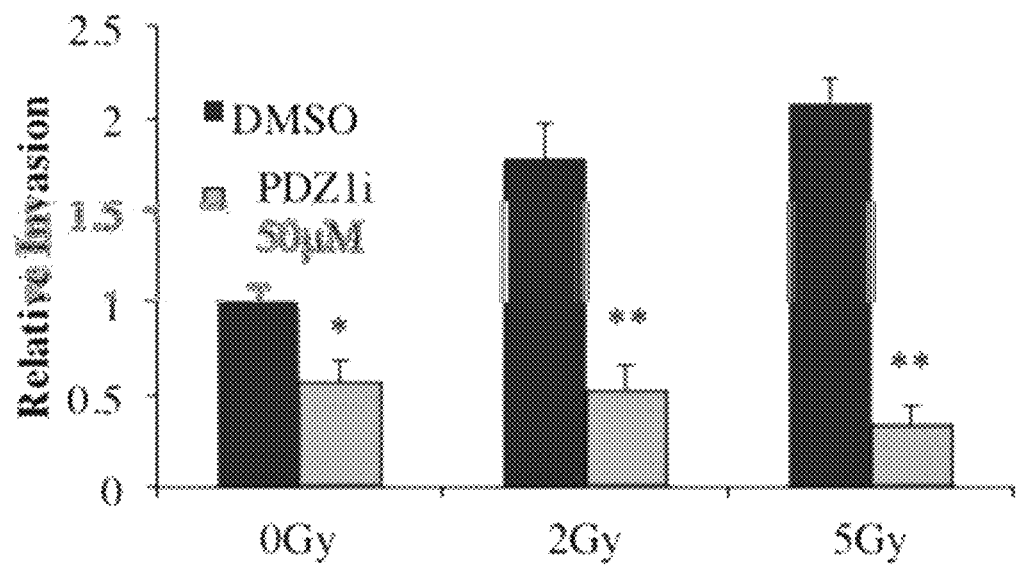

Initial studies with PDZ1i revealed that it effectively inhibited invasion in T98G and U87 cells (FIG. 7). Moreover, it was effective in inhibiting MDA-9/Syntenin-induced invasion following MDA-9/Syntenin overexpression (FIG. 7). The ability of PDZ1i to radiosensitize glioma cells was tested. Immortalized astrocytes, ImPHFA, and the GBM cell line U87 to 0, 2, were exposed to 5 Gy radiation after a two hour pretreatment with PDZ1 i. As expected, normal astrocytes showed significant radiosensitivity following radiation exposure, yet PDZ1i treatment did not further radiosensitize these cells (FIG. 8A). However, U87 cells showed markedly more radiosensitivity when combined with PDZ1i treatment. Proliferation following radiation was also significantly decreased in U87 cells that combined radiation and PDZ1i compared to radiation with control DMSO treatment (FIG. 8B). Finally, U87 cells were exposed to 2 and 5 Gy of radiation, with or without PDZ1i pretreatment, which increased the ability of these cells to invade, while PDZ1 i pretreatment abolished these invasion gains (FIG. 8C and FIG. 8D).

Figure 9A:
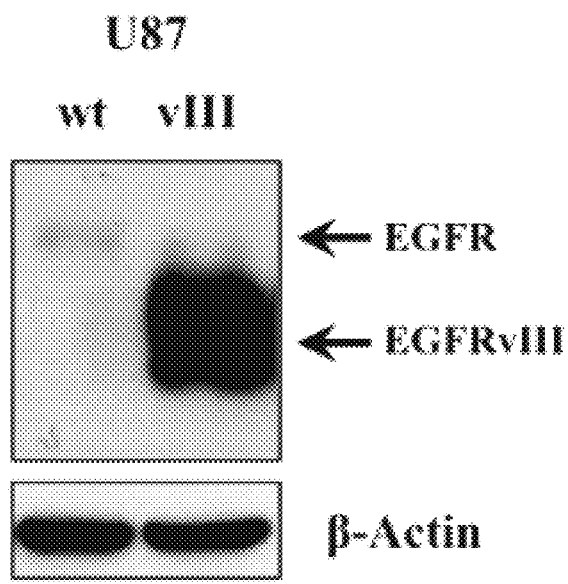
FIGS. 9A-9C. PDZ1i treatment impairs EGFRvIII and FAK signaling, as well as EGFRvIII-MDA-9 interaction.
Figure 9B:
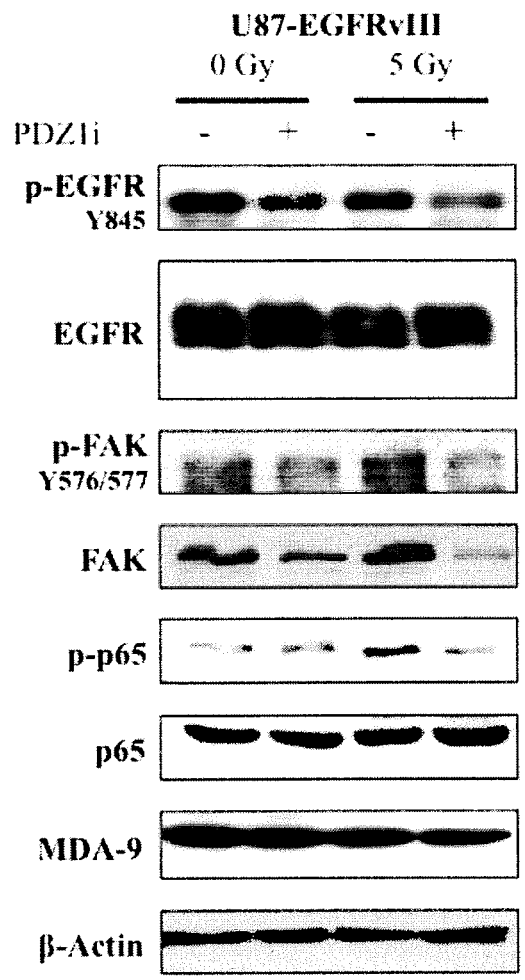
Figure 9C:
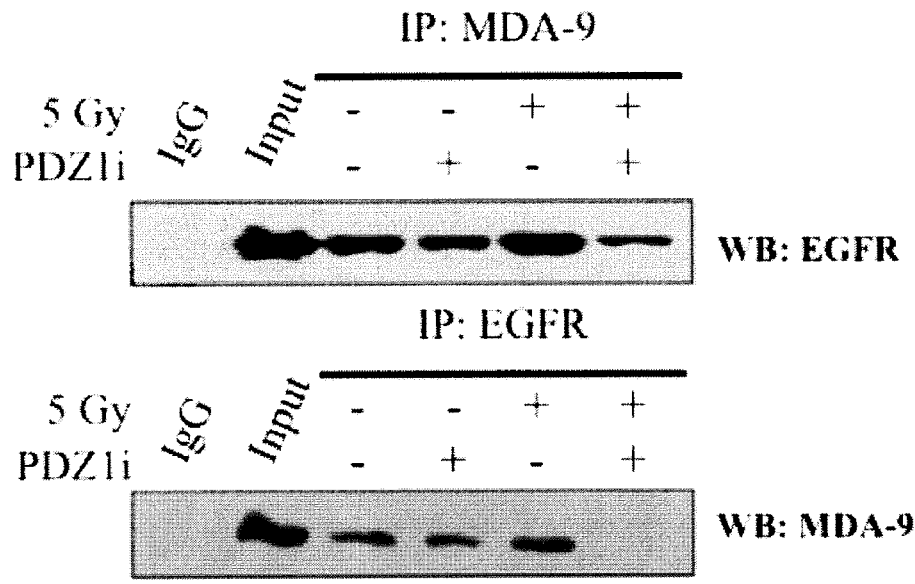
Figure 10A:
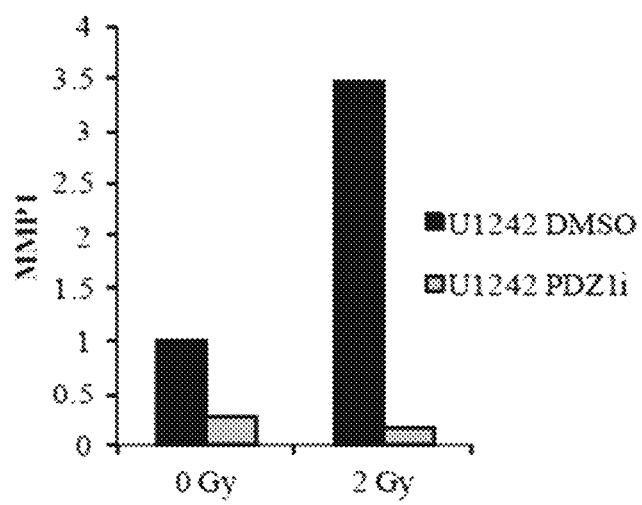
FIGS. 10A-10L, PDZ1i inhibits key invasion proteins. U1242 cells were treated with either DMSO or 50 µM PDZ1i 2 hrs prior to radiation in serum-free media. After 48 hrs, media was collected analyzed via the Proteome Profiler Human Protease Array Kit (R&D Systems). Relative protein amounts of the indicated proteins were quantified via ImageJ.
Figure 10B:
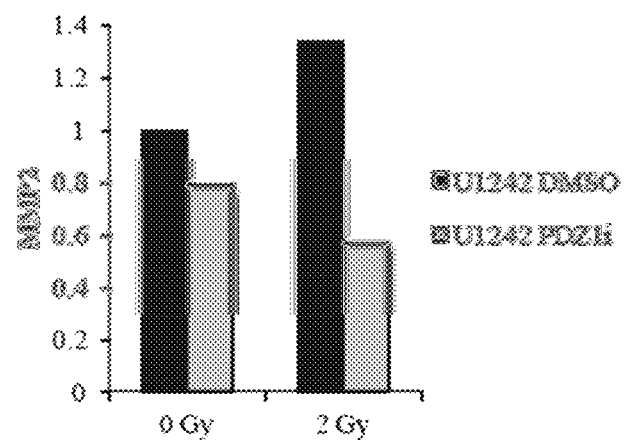
Figure 10C:
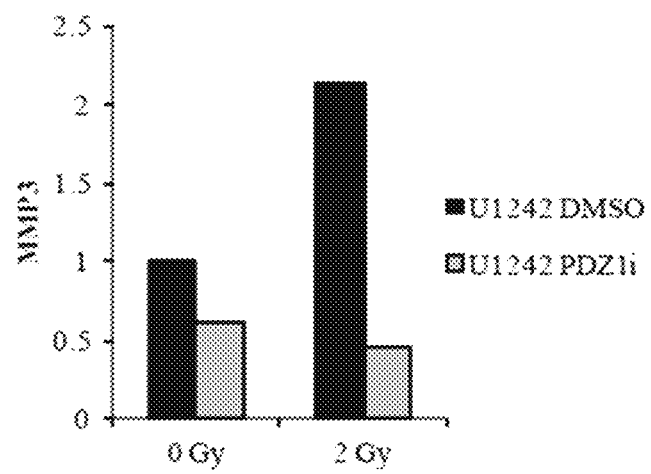
Figure 10D:
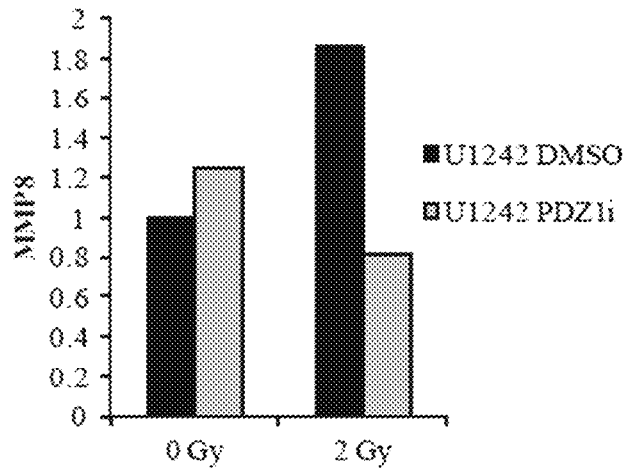
Figure 10E:
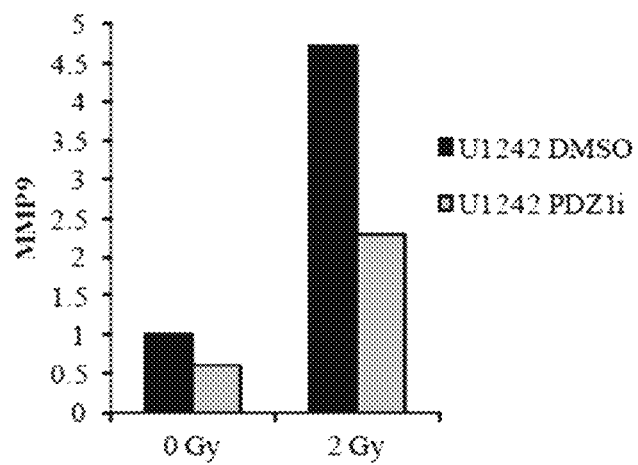
Figure 10F:
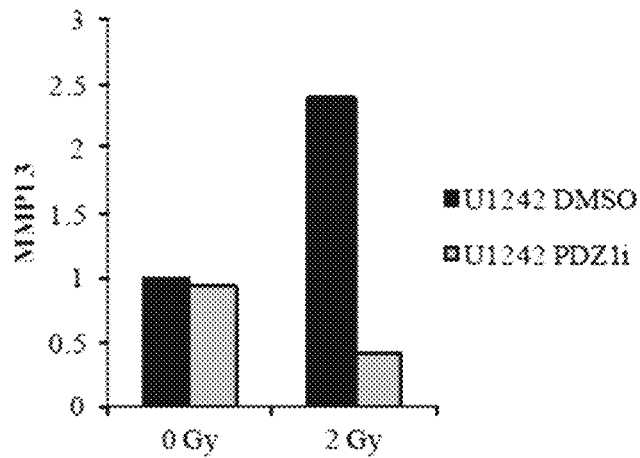
Figure 10G:
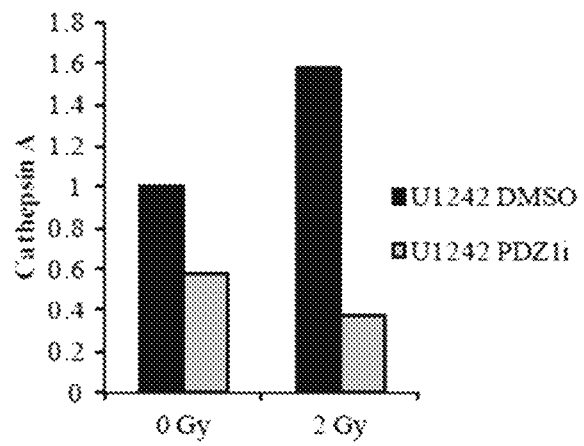
Figure 10H:
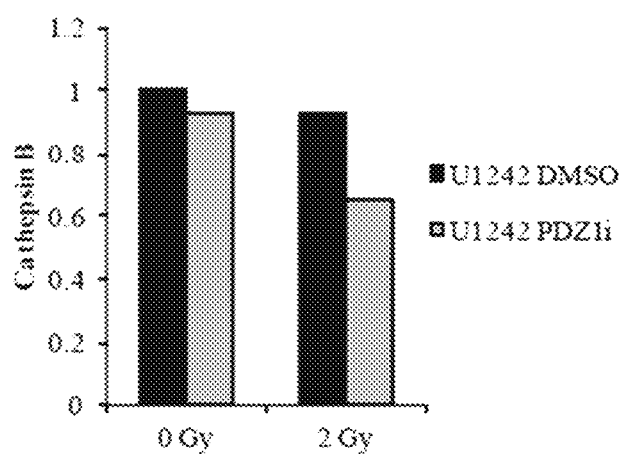
Figure 10I:
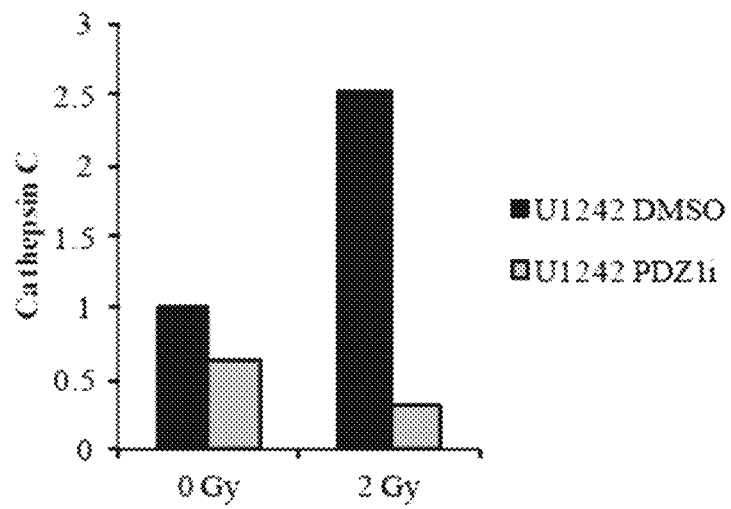
Figure 10J:
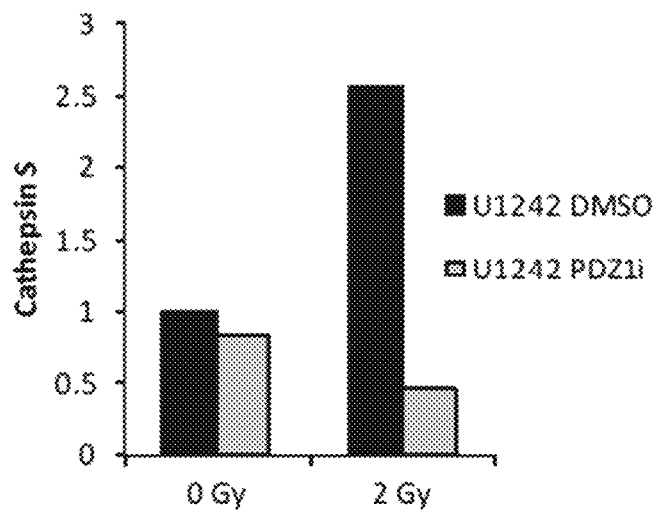
Figure 10K:
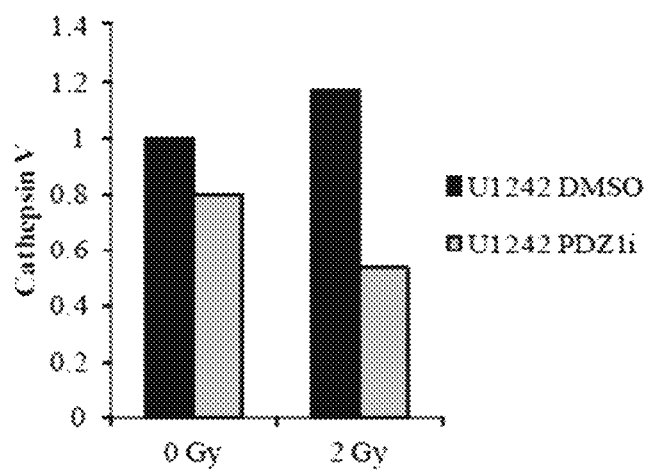
Figure 10L:
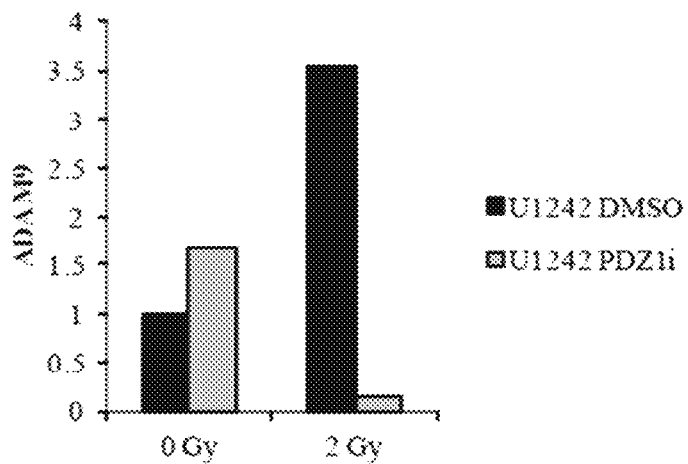

PDZ1i inhibits EGFRvIII-driven signaling in GBM and reduces MMP secretion. EGFR amplification and mutation is both a common and important alteration in GBM. A particular mutation of this receptor, EGFRvIII, is often co-expressed along with EGFR amplification in GBM. Recent data has demonstrated that EGFRvIII and FAK interact as part of a complex to mediate EGFRvIII-mediated MAPK activation. Given the demonstrated role of MDA-9/Syntenin in enhancing downstream signaling of the FAK/Src complex in melanoma, we determined if PDZ1i could inhibit EGFRvIII signaling in GBM. U87 cells stably expressing EGFRvIII, U87-EGFRvIII (FIG. 9), were treated with PDZ1i prior to radiation. In both radiated and non-radiated cells, phospho-EGFR was significantly reduced in the presence of PDZ1i. FAK activation was enhanced after radiation, and this activation was nullified by PDZ1i treatment (FIG. 9). Downstream, it was observed that NF-kB activation, enhanced following radiation, was reduced in the presence of PDZ1i. These results show that PDZ1i disrupts

TABLE 2

Pharmacokinetic data for PDZ1i (113B7). Balb/c mice (n = 3 per group) were injected with 3 mg/Kg and 30 mg/Kg PDZ1i intravenously (IV) or intraperitoneally (IP), respectively, and the average concentration of intact compound in plasma was determined via HPLC at the indicated time points.
Plasma Concentration (ng/mL) in mice (n = 3) after IV (3 mg/kg) and IP (30 mg/kg) administration

| IV Time (h) | Mean IV | | SD | CV (%) | IP Time (h) | Mean IP | | SD | CV (%) |
|---|---|---|---|---|---|---|---|---|---|
| Body Weight (g) | 25.1 | ± | 0.0173 | 0.690 | Body Weight (g) | 24.5 | ± | 0.252 | 1.03 |
| 0 | ND | ± | ND | ND | 0 | ND | ± | ND | ND |
| 0.250 | 29533 | ± | 7387 | 25.0 | 0.250 | 98233 | ± | 10289 | 10.5 |
| 1.00 | 17733 | ± | 3630 | 20.5 | 1.00 | 69233 | ± | 9757 | 14.1 |
| 2.00 | 11600 | ± | 965 | 8.49 | 2.00 | 58967 | ± | 7257 | 12.3 |
| 6.00 | 6113 | ± | 531 | 8.68 | 6.00 | 54600 | ± | 6351 | 11.6 |
| 12.0 | 3360 | ± | 927 | 27.6 | 12.0 | 42833 | ± | 7129 | 16.6 |
| 24.0 | 541 | ± | 79.6 | 14.7 | 24.0 | 15133 | ± | 2754 | 18.2 |
| No. points used for $I_{1/2}$ | | | 3 | | No. points used for $T_{1/2}$ | | | 3 | |
| $C_0$ (ng/mL) | 35033 | ± | 9424 | 26.9 | $C_{max}$ (ng/mL) | 98233 | ± | 10289 | 10.5 |
| $T_{1/2}$ (h) | 5.06 | ± | 0.285 | 5.64 | $T_{max}$ (h) | 0.250 | ± | 0.000 | 0.00 |
| $AUC_{0-int}$ (ng · h/mL) | 120000 | ± | 17692 | 14.7 | $T_{1/2}$ (h) | 9.42 | ± | 0.585 | 6.22 |
| $AUC_{0-int}$ (ng · h/mL) | 124000 | ± | 17349 | 14.0 | $AUC_{0-int}$ (ng · h/mL) | 974667 | ± | 127602 | 13.1 |
| | | | | | $AUC_{0-int}$ (ng · h/mL) | 1183333 | ± | 180093 | 15.2 |
| | | | | | Bioavailability (IP/IV) | 81.2% | ± | 10.6% | |

EGFRvIII-FAK signaling, which ultimately reduces the observed post-radiation gains in NF-kB activation.

Secreted factors can significantly impact cancer cell invasion, and MDA-9/Syntenin can affect the secretion of important factors such as MMP2 and VEGF in glioma. Radiation can enhance the release of important enzymes, including those involved in invasion such as the matrix metalloproteinase family (MMP). We therefore determined if PDZ1i could affect the secretion of invasion-related proteins following radiation therapy. U1242 cells were treated for 2 hours prior to radiation therapy, and their media collected after 48 hours. Several MMP family members showed a significant increase in expression following radiation therapy, including MMP2 and MMP9. PDZ1i treatment reduced the levels of these enzymes following radiation therapy (FIG. 10), an important aspect of reducing radiation-induced invasion gains. Additionally, radiation therapy increased the expression of several Cathepsin family members as well as ADAM9, while PDZ1i eliminated these gains (FIG. 10). Cathepsin family proteases modulate tumor invasion and metastasis in a variety of malignancies including melanoma and breast cancer metastatic to the brain. Notably, the expression of this family is important in microenvironment-mediated chemo- and radioresistance and in facilitating supportive tumor stroma.

Figure 11:
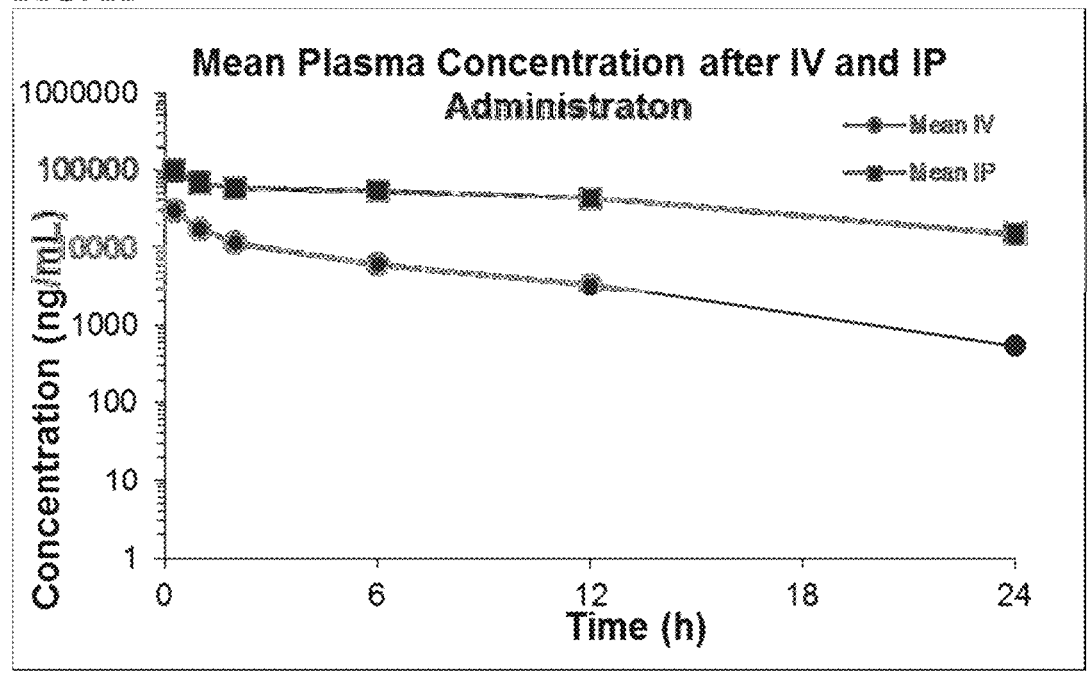
FIG. 11. PK studies with PDZ1i. 3.0 mg/Kg (I.V.) and 30.0 mg/Kg (I.P.) drug were administered in mice (n=3) and compound concentration in serum were measured at the indicated times. Noteworthy are the lack of adverse signs of toxicity during the experiment, the very slow clearance with T½>9 hr in each route and the 80% bioavailability for the compounds administered I.P.
Figure 12:
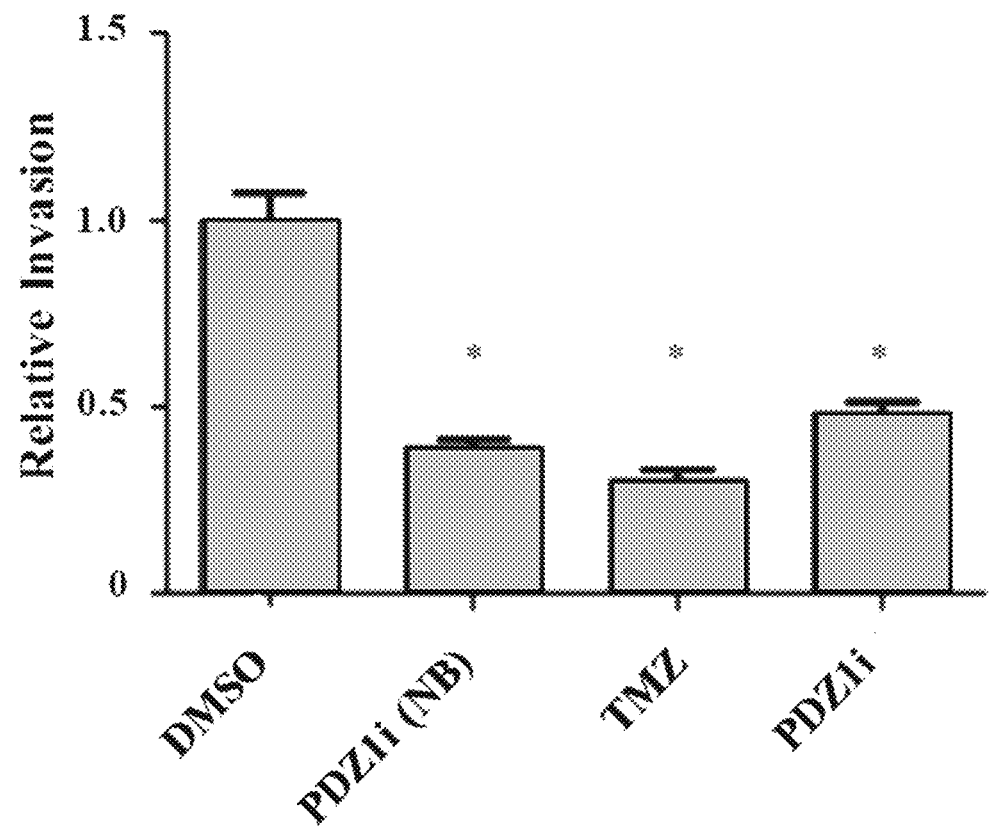
FIG. 12. PDZ1i crosses the blood brain barrier (BBB). Primary human malignant glioma cells (GBM6) were seeded on the bottom well of a transwell chamber. In the top chamber, a monolayer of HBMEC cells separated GBM6 cells from media containing DMSO, 50 µM PDZ1i or Temozolomide (500 µM). After 24 h incubation in these conditions, invasion of GBM6 cells were analyzed by seeding in a trans-well Matrigel invasion assay and stained after 24 h. NB: PDZ1i treatment and invasion assay without HBMEC barrier. Error bars=f s.d.
Figure 13A:
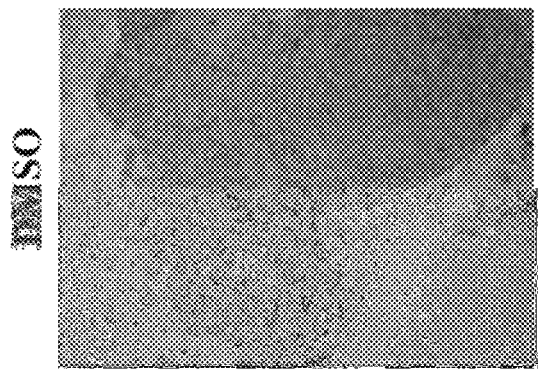
FIGS. 13A-13E. Effect of PDZ1i on survival in an in vivo model of glioma. GBM6 cells were pretreated for 2 hrs prior to intracranial injection with vehicle (DMSO) or PDZ1i and after 7 days, brain tissue was isolated and sectioned at injection site.
Figure 13B:
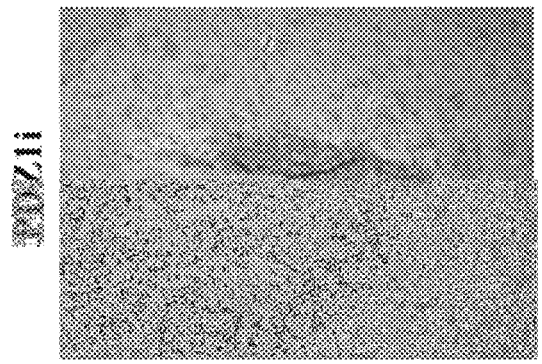
Figure 13C:
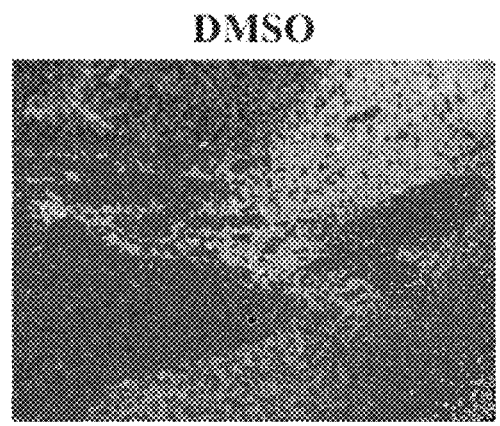
Figure 13D:
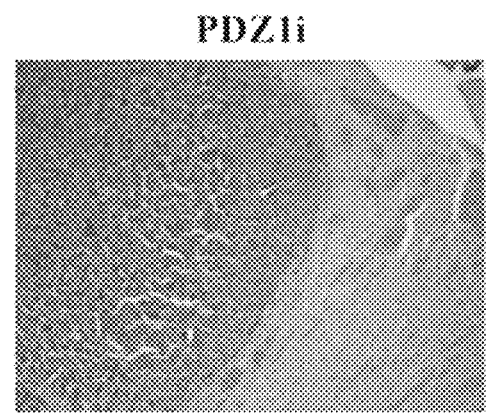
Figure 13E:
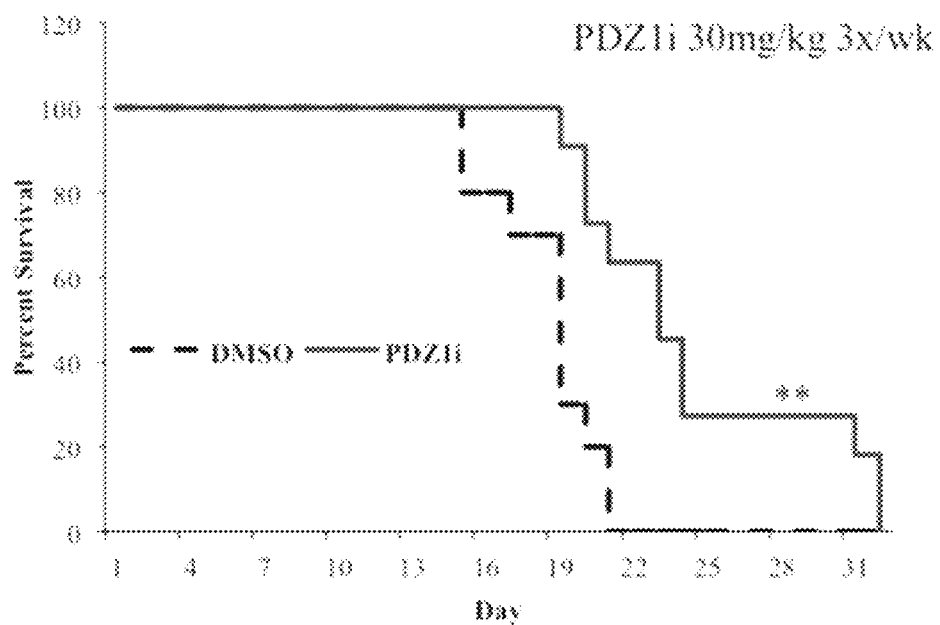

A critical property of a potential therapeutic agent is its stability in the circulation and bioavailability in vivo. Hence, pharmacokinetics (PK) studies were performed administering 3.0 mg/Kg (IV) and 30.0 mg/Kg (IP) in mice (n=3) and compound concentration in serum were measured at various times (15 min to 24 hrs after administration of the drug). Noteworthy were the lack of adverse signs of toxicity during the experiment, the very slow clearance with $T_{1/2}$>9 hr in each route and the 80% bioavailability for the compound administered IP versus IV (FIG. 11). Based on these data, 1-3 weekly doses of the drug I.P at 30 mg/Kg would result in an effective dose for achieving a constant inhibition of the target. Additionally, when treating glioma pharmaceutically, the ability for a compound to cross the blood brain barrier (BBB) is paramount. We did not anticipate issues inhibiting brain exposure as it is known that mice with GBM have a leaky blood brain barrier. Prior to in vivo efficacy studies, we evaluated the ability of the compound to cross the blood brain barrier using a target-based surrogate cellular assay. This method is preferred to direct in vivo measurements of compound concentration in the brain because of low sensitivity of the detection methods, and most importantly because of the presence of drug in various vascular spaces, i.e., the residual blood of the brain. Accordingly, we used human brain microvascular endothelial cells (HBMEC) seeded with PDZ1i in the upper chamber of transwell inserts placed on top of wells containing GBM6 cells. After 24 h, we assessed the invasive ability of the treated GBM6 cells compared to pretreated controls. PDZ1i effectively crossed the HBMEC barrier to inhibit invasion in GBM6 cells comparably to the pretreated control with no barrier (FIG. 12). Taken together, these results suggest that PDZ1i is a potent inhibitor of invasion with radiosensitizing effects and favorable properties for CNS treatment. Thus, we moved our assessment of PDZ1i as a therapeutic agent into in vive models of GBM.

PDZ1i is effective in reducing tumor invasion in an animal model of GBM. To test the efficacy of PDZ1i, we used an orthotopic xenograft model with GBM6 cells that were pretreated with either DMSO or PDZ1i and injected intracranially to form tumors. Seven d post injection tumor and brain tissue were isolated for sectioning. Tumor cells treated with PDZ1i developed noticeably smaller and more demarcated neoplasms at this time point compared to controls (FIG. 13). Separately, untreated cells were injected and tumors established, then mice were treated IP with either DMSO or PDZ1i (30 mg/kg) three times per wk for two wk. Survival was significantly increased in treated mice compared to controls (FIG. 13), and tumors were well circumscribed and less infiltrative on analysis than those of control treated mice (FIG. 13). Similar to previous studies, knocking down MDA-9/Syntenin expression in an in vivo model, PDZ1i was effective in reducing tumor invasion and extending survival in an animal model of GBM.

Figure 14A:
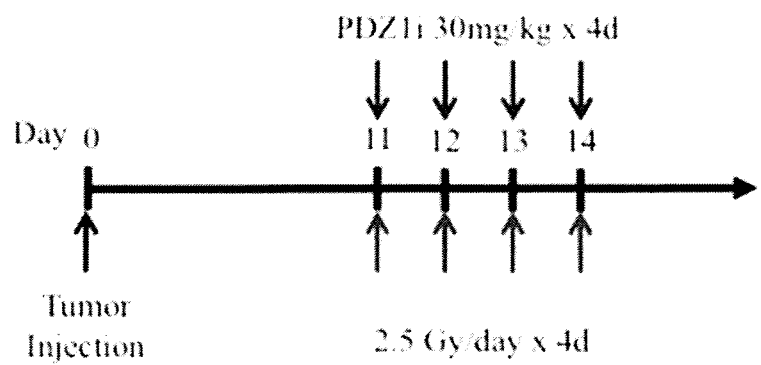
FIGS. 14A-14F. PDZ1i treatment combined with radiation in an in vivo model of GBM.
Figure 14B:
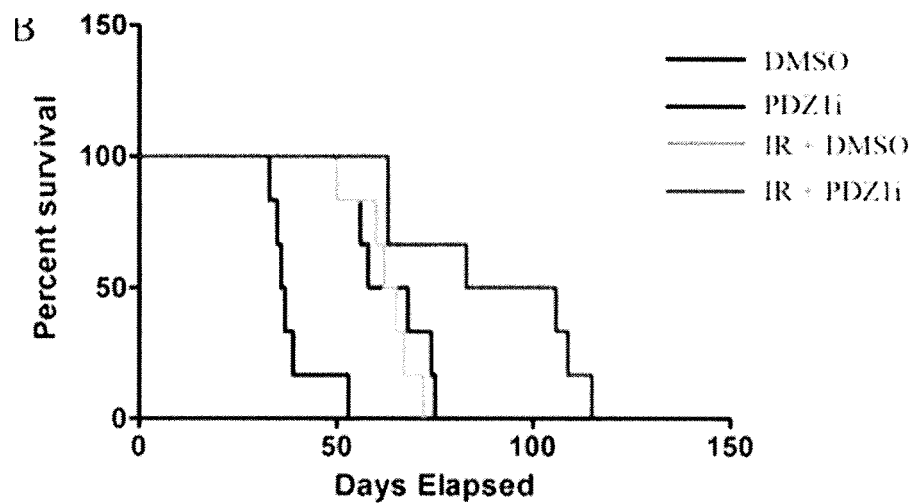
Figure 14C:
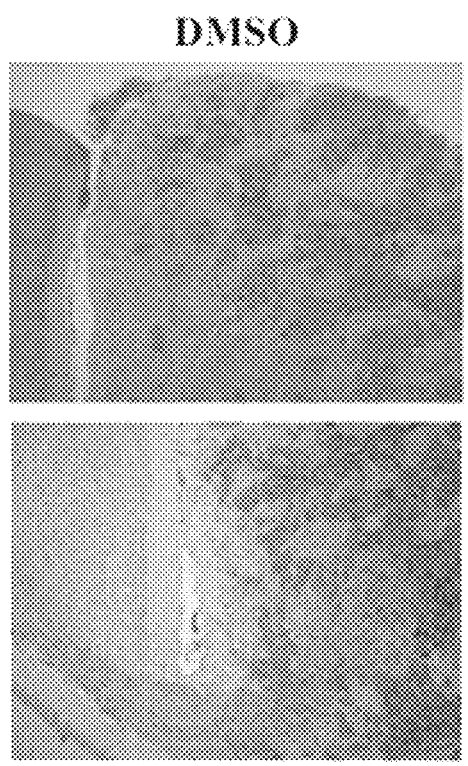
Figure 14D:
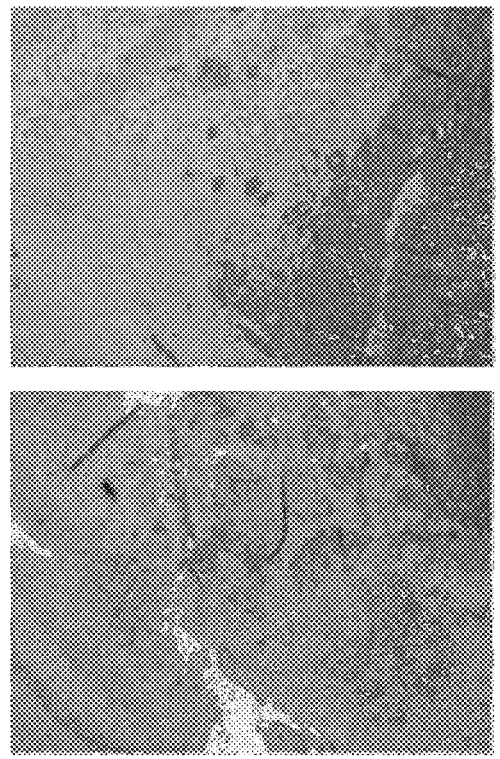
Figure 14E:
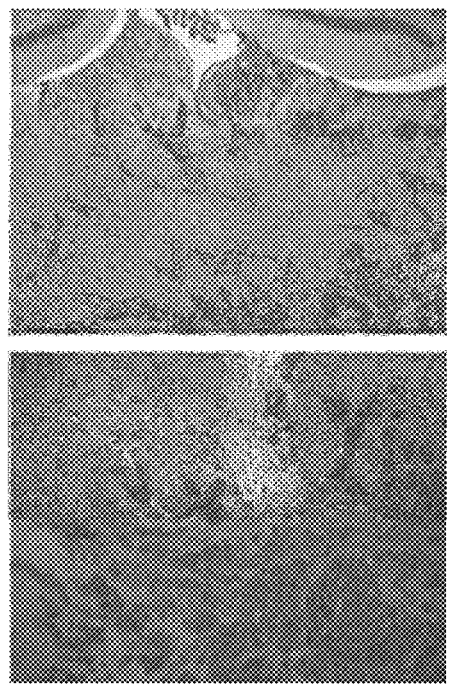
Figure 14F:
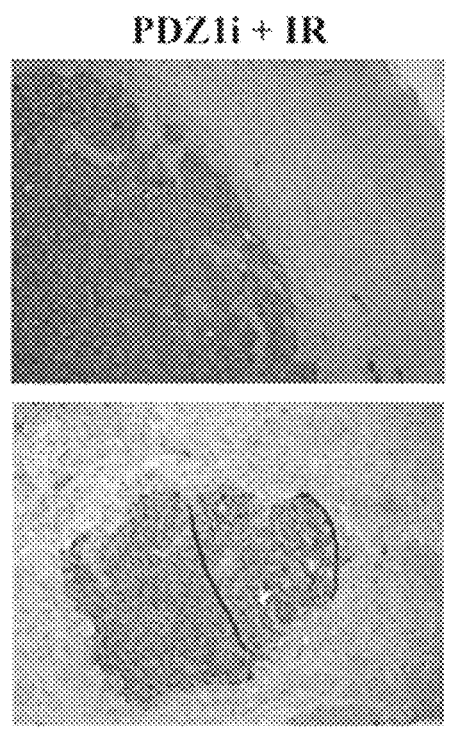

PDZ1i combined with radiation extends survival and reduces GBM invasion in vivo. We next investigated the combination of PDZ1i with radiotherapy in vivo. U1242-Luc cells were injected intracranially under anesthesia and formed tumors, confirmed by imaging at 7 d post-injection. At this point, mice were randomized to 4 groups: DMSO treatment, PDZ1i treatment (30 mg/kg), DMSO+IR, and PDZ1i+IR. Treatment began on 11 d post-injection and mice receiving radiation were treated with 2.5 Gy for 4 consecutive d. PDZ1i was administered 2 h prior to radiation treatment on each of the 4 treatment d (FIG. 14A). Control treated mice had an average survival of 41.3 d, while PDZ1i treatment extended that to 54.7 d. Radiation alone extended survival to 62.8 d, while PDZ1 i treatment+IR therapy led to survival of 78.8 d (FIG. 14B). Finally, we asked if there were changes in tumor morphology and invasion pattern between treatment groups. To investigate this, brain tissue sections were collected and H & E stains were analyzed. Indeed, U1242-Luc cells developed diffusely infiltrating tumors in control groups. Tumor margins were slightly more demarcated in groups treated with PDZ1 i (FIG. 14C). Radiation treatment led to generally smaller, yet still diffuse tumor patterns, which frequently crossed the midline of the brain with invasive outgrowths. The combination of PDZ1i with radiation led to tumors with markedly more circumscribed margins, less invasive outgrowths, and less spread to the leptomeninges (FIG. 14). Analysis of tumor sections from these treatment groups indicated that activated forms of EGFR, FAK, and Src correlated with PDZ1i treatment status. Those mice treated with radiation only showed marked increases in activation of these proteins, while groups that underwent treatment with PDZ1i showed decreased signal intensity compared both to control and radiation-treated groups. Collectively, this data demonstrates that targeting MDA-9/Syntenin is a viable approach to enhancing conventional radiation treatment.

MDA-9/Syntenin is an important mediator of the post-radiation signaling process, eliminating the invasion enhancement induced by radiation. The combination of PDZ1i and radiotherapy in a model of GBM showed evidence of improvement over each method alone. In vivo, important interactions occur within the tumor microenvironment, including extracellular communication between tumor cells, but also between tumor cells and normal cells, such as endothelial cells. Therefore, PDZ1i has positive therapeutic effects on both tumor and normal cells within the tumor microenvironment.

MDA-9/Syntenin targeting is a viable approach for combating radiation-induced invasion by radiosensitizing GBM. Development of a targeted inhibitor leads to a reduction in phenotypes enhanced by MDA-9/Syntenin, and is effective when combined with conventional radiotherapy in vivo. The present study highlights a first in class MDA-9/Syntenin PDZ1 inhibitor with profound anti-invasive effects, good stability without overt toxicity in vivo, an ability to pass the blood brain barrier and the capacity to both radiosensitize and block invasion gains of radiation in aggressive GBM cells in vivo.

Materials and Methods

Reagents, Plasmids, Adenoviruses and Stable Cell Lines.

PDZ1i (113B7) (N-(2,5-dimethyl-4-(3-(5-phenyl-1,3,4-oxadiazol-2-yl)propanamido)phenyl)-8-oxo-5,6,7,8-tetrahydro-4H-cyclopenta[d][1,2,4]triazolo[1,5-a]pyrimidine-2-carboxamide) was synthesized from 3-(5-phenyl-1,3,4-oxadiazol-2-yl)propanoic acid (418 mg, 1.92 mmol), HATU (875 mg, 2.30 mmol), and DIEA (0.83 mL, 4.8 mmol) in DMF (10 mL) (room temperature for 24 h). PDZ1i was purified via a C18 column (Combi-Flash $R_f$, Teledyne ISCO), using acetonitrile-water as an eluent. This compound was used for all subsequent cellular and in vivo studies, including PK and efficacy studies (Table 2).

Small hairpin RNA for mda-9/syntenin (shmda-9), plasmids pAd.5/3-shmda-9 or pAd.5/3-shcon were constructed with pSilencer™ hygro expression vectors according to the manufacturer's protocol (Ambion Inc. TX) as previously described (1), and the resultant plasmids were cleaved with PacI to release the recombinant adenovirus genomes and then transfected to HEK-293 cells to rescue the corresponding Ad.5/3-based vectors. The rescued viruses were upscaled using HEK-293 cells and purified by cesium chloride double ultracentrifugation using standard protocol and the titers of infectious viral particles were determined by plaque assay using HEK-293 cells as described (2).

Cell Lines, Cell Culture, and Treatments.

Human malignant glioma cells U87, U251, and T98G as well as grade III astrocytoma lines Sw1088 and Sw1783 were purchased from the American Type Culture Collection (Manassas, Va.). Human primary GBM6 cells were described previously and were provided (3). These and U1242 cells (4) were cultured in DMEM+F12 supplemented with 10% FCS in a 37° C. incubator supplemented with 5% $CO_2$. Primary human fetal astrocytes (PHFA) were obtained from pre-term abortions as previously described with IRB approval, and h-TERT-immortalized primary human fetal astrocytes (IM-PHFA) were produced and cultured as described (1). All cells were routinely screened for mycoplasma contamination. Cells were treated with PDZ1i at the indicated concentrations 2 h prior to irradiation. Irradiations were done using an MDS Nordion Gammacell 40 research irradiator with a 137-Cs source delivering a dose rate of 0.896 Gy/min.

Antibodies and Reagents.

Antibodies against FAK, phospho-FAK (Tyr 576/577), IGF-1R, phospho-IGF-1R (1135/36), p38MAPK, phospho-p38MAPK (Thr180/Tyr182), p65, and phospho-p65(S536), Src, and phospho-Src (Tyr 416), were obtained from Cell Signaling (Beverly, Mass.). β-actin and α-Tubulin were obtained from Abcam (Cambridge, Mass.), and MDA-9/Syntenin from Abnova (Taipei, Taiwan). Fibronectin was purchased from Sigma-Aldrich (St. Louis, Mo.).

Preparation of Whole-Cell Lysates and Western Blotting Analysis.

Preparation of whole-cell lysates and Western blotting analysis was performed as described (5). For densitometry evaluation, X-ray films were scanned and analyzed with ImageJ software (NIH).

Extraction of Total RNA and Real-Time PCR.

Total RNA was extracted from cells using the QIAGEN miRNAeasy Mini Kit (QIAGEN, Hilden, Germany). cDNA preparation was done using ABI cDNA synthesis kit (Applied Biosystems, Foster City, Calif.). Real-time polymerase chain reaction (RT-PCR) was performed using an ABI ViiA7 fast real-time PCR system and Taqman gene expression assays according to the manufacturer's protocol (Applied Biosystems, Foster City, Calif.).

Immunohistochemistry.

A portion of the frozen tumor specimen was fixed in phosphate-buffered formalin and preserved as paraffin sections following standard procedure for the maintenance of histological structure. Paraffin-embedded sections were dewaxed and rehydrated through incubations in xylene and a gradient series of alcohol. Antigen retrieval was processed in 10 mM citric acid (pH 6.0) with microwave treatment for 20 min. Endogenous hydrogen peroxidase was quenched with 3% $H_2O_2$ for 20 min. After blocking non-specific binding sites with 5% normal sera, the sections were incubated overnight with antibody. The sections were incubated with appropriate biotinylated secondary antibody and subsequently with ABC-peroxidase (Vector Elite, Vector laboratories, Burlingame Calif.). Colorimetric reactions were developed by incubation in DAB substrate (0.02% DAB, 0.005% hydrogen peroxide), and counterstained with 10% Harris' hematoxylin. Hematoxylin & eosin staining was conducted following a standard protocol (6). The images were analyzed under the Olympus BX41 microscope system equipped with DP25 digital camera and software. Tissue microarray CNS2081 was purchased from US Biomax (Rockville, Md.).

Invasion and Migration Assays.

Invasion was measured using 24-well BioCoat cell culture inserts (BD Biosciences, Bedford, Mass.) with an 8-μm-porosity polyethylene terephthalate membrane coated with Matrigel Basement Membrane Matrix (100 μg/cm$^2$). Briefly, the Matrigel was allowed to rehydrate for 2 h at room temperature by adding warm, serum-free DMEM. The wells of the lower chamber were filled with medium containing 10% fetal bovine serum. Cells ($5\times10^4$) were seeded in the upper compartment (6.5-mm membrane size) in serum-free medium. The invasion assay was done at 37° C. in a 5% $CO_2$ humidified incubator for 18 h. At the end of the invasion assay, filters were removed, fixed, and stained with the Diff-Quick Staining kit (IMEB, San Marcos, Calif.). Cells remaining on the upper surface of the filters were removed by wiping with a cotton swab, and invasion was determined by counting the cells that migrated to the lower side of the filter using at least 5 fields per insert at 100× magnification. Wound healing scratch motility assays were done as described previously (6). Data from triplicate experiments were expressed as mean±95% confidence interval (CI).

Survival and Viability Analysis.

Clonogenic radiosurvival experiments were carried out as described previously (4,7). Briefly, cells were diluted, seeded on 6-cm dishes, and after the cells attached, treated with DMSO or PDZ1i (12.5, 25, or 50 μM) in the medium for 2 h before irradiation. Cells were incubated overnight, and the medium changed to nondrug containing medium 16 h postirradiation. Cells were incubated further for 14 days, stained with 2% Giemsa solution, and colonies consisting of 50 or more were counted. Cell viability was assessed through MTT analysis as described previously (8).

Conditioned Media (CM) Isolation and Analysis.

CM was harvested from an overnight culture of plated cells in serum-free DMEM+F12 media, filtered with 0.2 μM filters and further concentrated 10-fold on an Amicon Ultra centrifugal filter—3K (Millipore, Billerica, Mass.). Protein levels were analyzed via the Proteome Profiler Human Protease Array Kit (R&D Systems, Minneapolis, Minn.).

Relative quantification was performed by densitometry evaluation. X-ray films were scanned and analyzed with ImageJ software (NIH).

Virus Infections and Reporter Assays.

Viral infection conditions and protocols were performed as delineated previously (6). Luciferase reporter assays were performed using 2×10$^5$ cells infected with either Ad.5/3-vec or Ad.5/3-mda-9. Twenty-four h post-infection, cells were transfected with a NF-κB-responsive luciferase reporter construct with LipofectAMINE 2000 as described (6,9). Forty-eight h after transfection, cells were trypsinized and plated on fibronectin-coated surfaces (10 μg/mL) in serum-free medium for 1 h. Cell lysates were harvested and luciferase activity was measured using a Dual-Luciferase Reporter Assay system (Promega, Madison, Wis.) according to the manufacturer's instructions. Luciferase activity was normalized by *Renilla* activity and data represent the average of triplicates+S.D.

Intracranial Implant of Cells in Nude Mice.

Athymic female NCr-nu/nu mice (NCI-Fredrick) weighing ~25 gm were used for this study. Mice were maintained under pathogen-free conditions in facilities approved by the American Association for Accreditation of Laboratory Animal Care and in accordance with current regulations and standards of the U.S. Department of Agriculture, Washington, D.C., the U.S. Department of Health and Human Services, Washington, D.C., and the NIH, Bethesda, Md. At least 5 mice per group were utilized with duplicate replications for minimum total of 10 mice per group. Mice were anesthetized through i.p. administration of ketamine (40 mg/kg) and xylazine (3 mg/kg), and immobilized in a stereotactic frame (Stoelting, Wood Dale, Ill.). A 24-gauge needle attached to a Hamilton syringe was inserted into the right basal ganglia to a depth of 3.5-mm and then withdrawn 0.5-mm to make space for tumor cell accumulation. The entry point at the skull was 2-mm lateral and 1-mm dorsal to the bregma. Intracerebral injections of 1.5×10$^4$ cells in 2 L per mouse were completed over 10 min using an automated injector (Stoelting, Wood Dale, Ill.). The skull opening was enclosed with sterile bone wax and the skin incision was closed using sterile surgical staples. Post-sacrifice, the tumors were resected, weighed, and preserved for IHC staining.

Database Mining.

The REpository for Molecular BRAin Neoplasia DaTa (REMBRANDT) (rembrandt.nci.nih.gov) database was accessed and mined for all Astrocytoma and GBM patients (10). These were filtered for those with no previous history of radiation therapy, but had record of undergoing subsequent radiation. This population was stratified for SDCBP (mda-9/syntenin) expression. The survival data for the resulting groups was downloaded and analyzed via GraphPad Prism.

Example 2. Suppression of Prostate Cancer Pathogenesis Using an MDA-9/Syntenin (SDCBP) PDZ1 Small Molecule Inhibitor Metastasis is the primary determinant of death in patients with diverse solid tumors and MDA-9/Syntenin (SDCBP), a pro-metastatic and pro-angiogenic gene, is a primary contributor to this process. Here we show that through physical association with IGF-1R, MDA-9 activates STAT3 regulating prostate cancer pathogenesis. MDA-9 contains two highly homologous PDZ domains, which have been difficult to drug, but are predicted to interact with a plethora of proteins, many of which are central to the cancerous process. Using fragment-based drug discovery (FBDD) guided by NMR spectroscopy, an MDA-9 PDZ1 domain-targeted small molecule antagonist (PDZ1i) has been identified which is well-tolerated in vivo, has significant half-life ($t_{1/2}$=9h) and displays substantial preclinical in vivo activity. PDZ1i blocks tumor cell invasion and migration in vitro, and metastasis in vivo. Hence, MDA-9 PDZ1 target-specific small molecule inhibitors have been developed for therapy of prostate and other cancers expressing elevated levels of MDA-9.

MDA-9 Expression is Elevated in PC and Promotes Invasion.

Figure 15A:
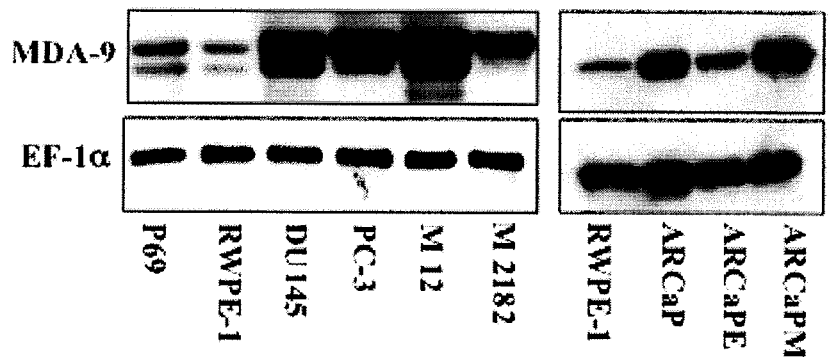
FIGS. 15A-15D. MDA-9 regulates PC progression.
Figure 15B:
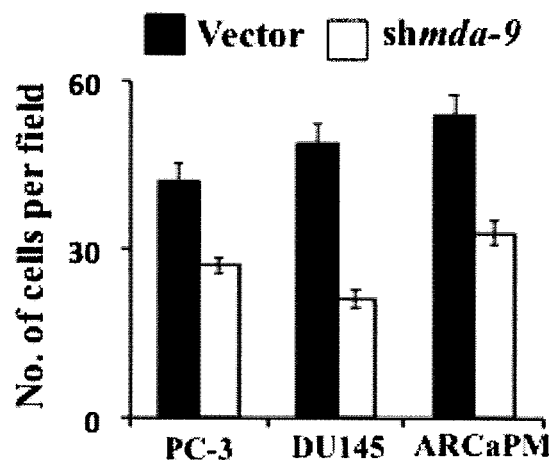
Figure 15C:
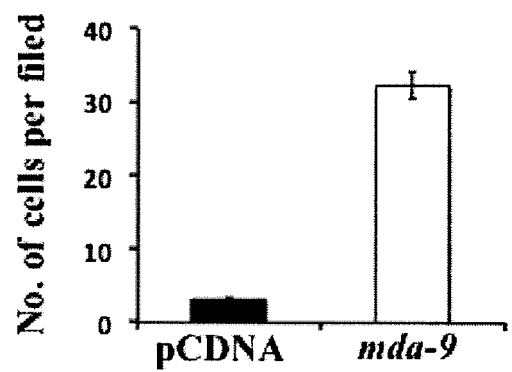
Figure 15D:
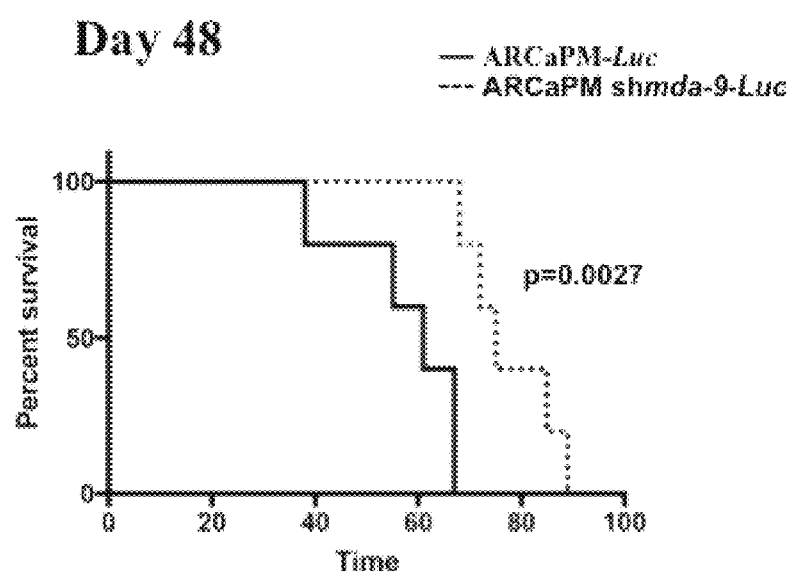

Recent computational analysis identified mda-9 mRNA overexpression in PC compared to normal prostate. Immunohistochemistry (IHC) of MDA-9 protein expression in a tissue microarray (TMA) containing 9 adjacent tumor tissue and 88 human prostate tumor samples of different stages supported the genomic profiling data. Compared to adjacent normal tissue, MDA-9 expression was noticeably increased in PC. mda-9 is elevated at both mRNA and protein levels (E2 FIG. 15A) in different human PC cell lines in comparison with non-tumorigenic prostate epithelial cells. Expression is significantly up-regulated in M12, a metastatic variant of P69 (a normal immortalized prostate epithelial cell line), suggesting an association of MDA-9 with metastasis, which was supported further by in vitro invasion assays using gain and loss of function approaches (FIG. 15B and FIG. 1C). In addition, higher expression of MDA-9 was evident in mesenchymal ARCaPM (metastatic variant) cells in comparison with epithelial variant ARCaPE cells, providing additional confirmation of the potential relevance of MDA-9 in metastasis. MDA-9 is also overexpressed in M2182 cells, which are tumorigenic but non-metastatic P69 variant cells suggesting that in addition to a role in metastasis, MDA-9 might also contribute to tumorigenic phenotypes. A direct role of MDA-9 in PC metastasis was evident in vivo where stable knockdown of mda-9 using shmda-9 in ARCaPM cells decreased metastatic potential and increased survival time, as compared with parental ARCaP-M cells (FIG. 15D). MDA-9 expression was also elevated in prostate adenocarcinomas that developed in 6-month old and older Hi-myc mice, a spontaneous prostate cancer transgenic mouse model.

MDA-9 Regulates PC Invasion Through STAT3 Activation.

Figure 16A:
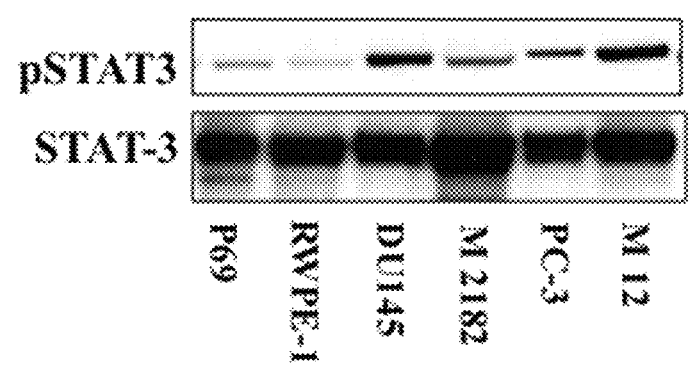
FIG. 16A-16N. IGFBP-2 regulates STAT3 activity in PC cells.
Figure 16B:
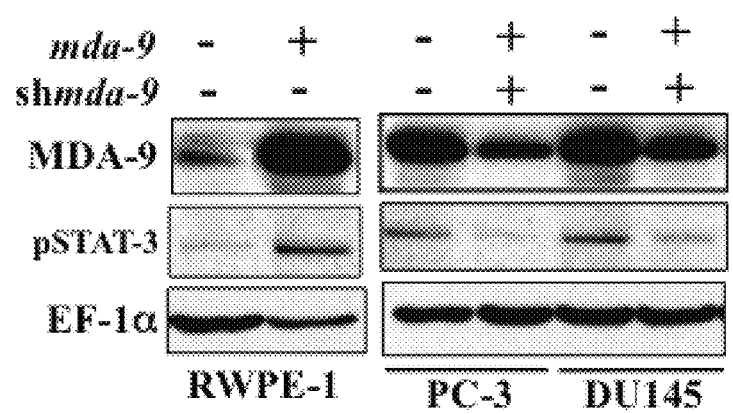
FIG. 16B) Cells were either transfected with control vector, mda-9 expression vector (RWPE-1) or mda-9 shRNA vector (PC-3 and DU145). 48 h after transfection, cells were replaced on fibronectin-coated plates for 1 h. Western blot analysis was conducted with the indicated antibodies.
Figure 16C:
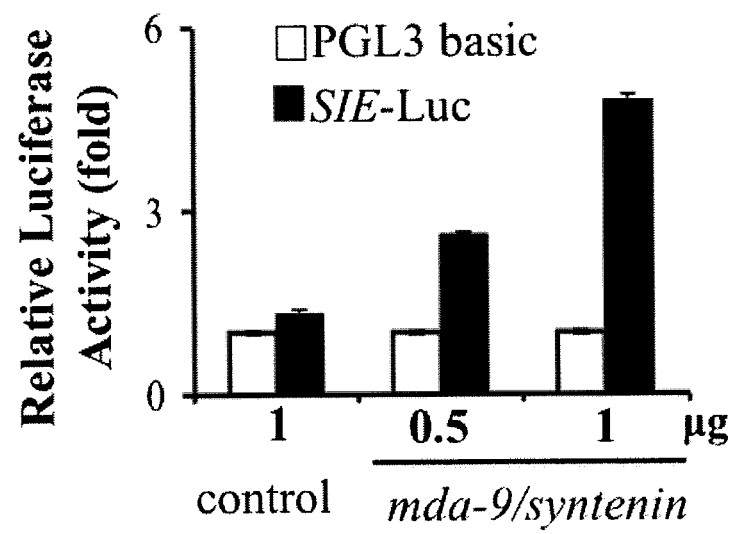
In FIGS. 16C-16E) The indicated cells, FIG. 16C), RWPE-1, FIG. 16D), PC-3 and FIG. 16E), DU145, were co-transfected with a reporter gene and empty vector, mda-9 or shmda-9 as indicated in the figure and after 48 h, luciferase activity was measured. Data presented as fold-change in comparison with the control group (empty vector).
Figure 16D:
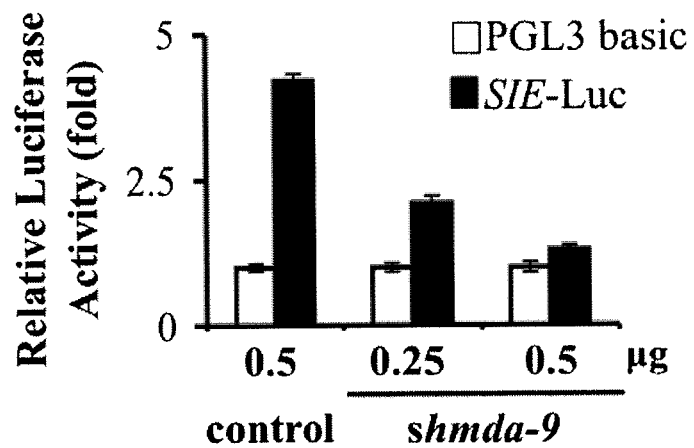
Figure 16E:
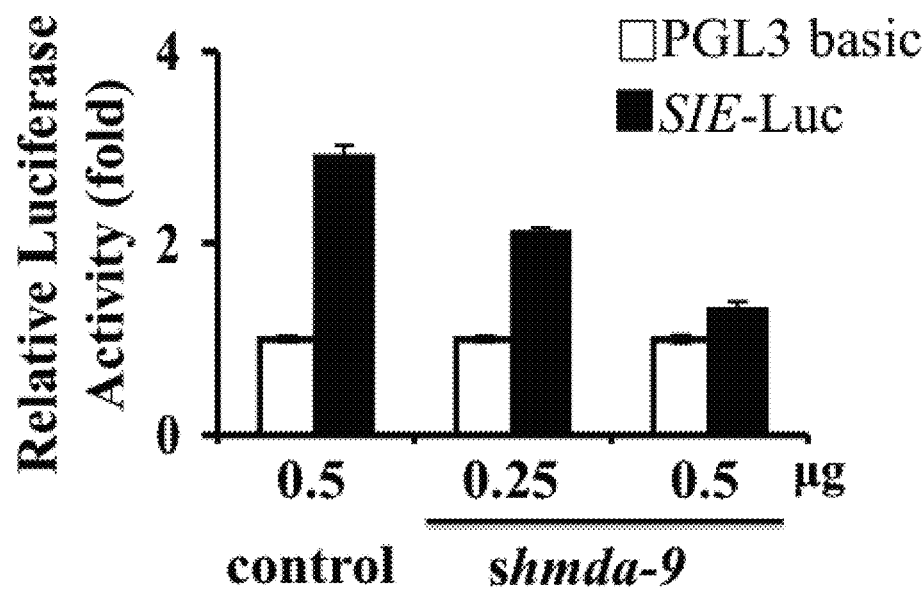
Figure 16F:
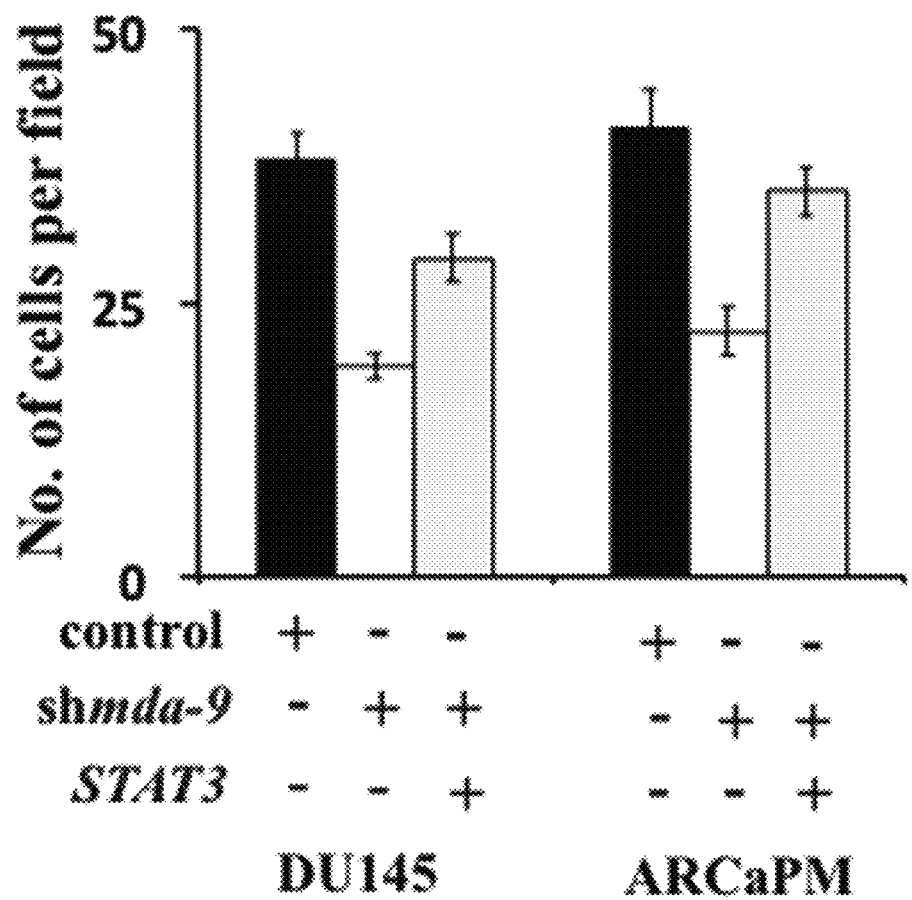
FIG. 16F) Cells were co-transfected with different expression plasmids as indicated. 48 h later, cells were trypsinized and invasion was assayed. Cells were counted using bright field microscopy.
Figure 16G:
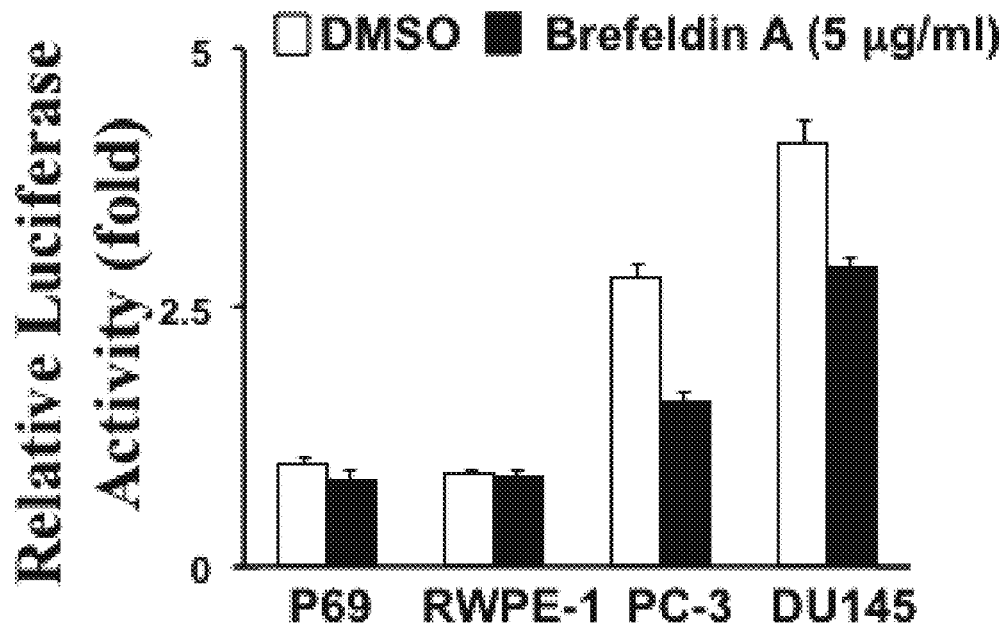
FIG. 16G) Cells were transfected with reporter genes and after 36 h, cells were treated with Brefeldin A for 30 min. Media was removed and cells were cultured for an additional 3 h in serum-free media and luciferase activity was measured.
Figure 16H:
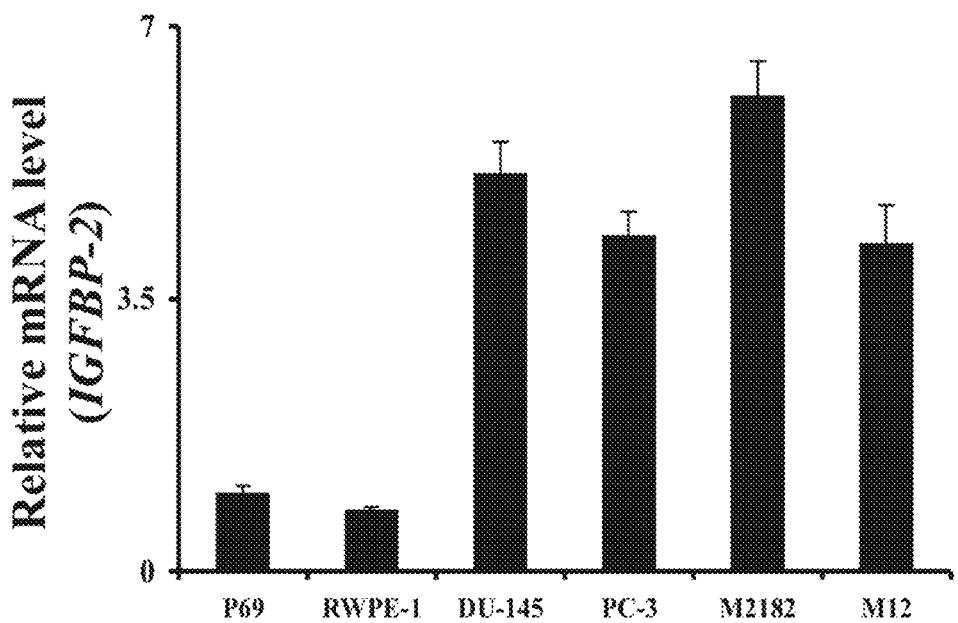
FIG. 16H) expression of IGFBP-2 mRNA in different PC cells as determined by qPCR.
Figure 16I:
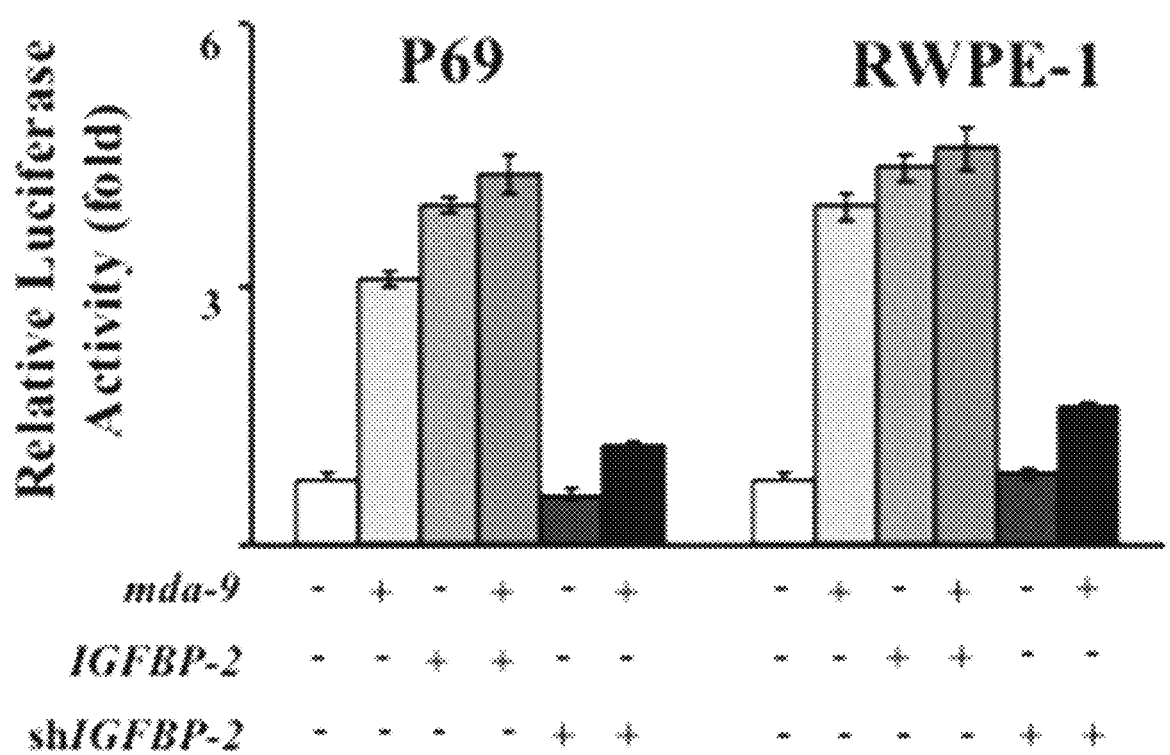
FIGS. 16I-16J) Cells (FIG. 16I, P-69 and RWPE-1, FIG. 16J, PC-3 and DU-145) were co-transfected with reporter genes and different plasmids and after 48 h luciferase activity was measured. Data presented as fold-change after normalizing with renilla luciferase activity.
Figure 16J:
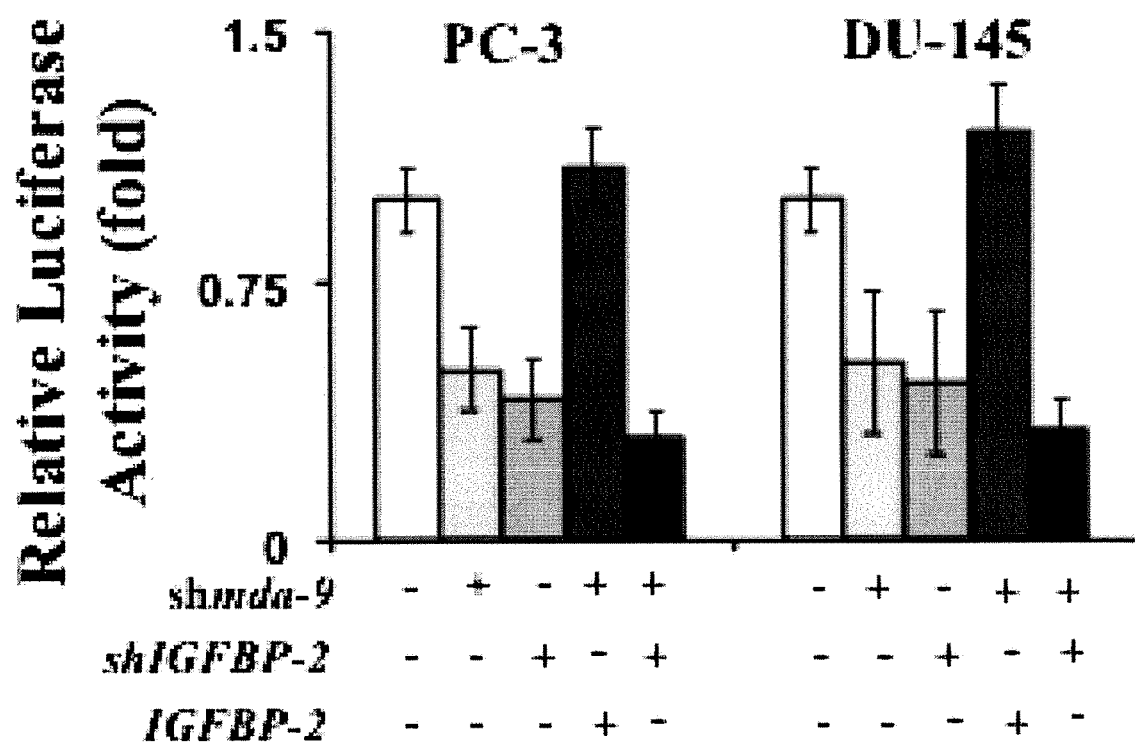

A large percentage of tumor-derived cell lines as well as human tumors, including PC, express a constitutively activated STAT3 protein. To determine the effect of MDA-9 expression on STAT3 activity, STAT3 reporter constructs from SA Bioscience (Valencia, Calif.), which encode a firefly luciferase reporter gene under the control of a minimal CMV promoter and tandem repeats of the SIE transcriptional response element, were utilized. These constructs monitor both increases and decreases in the transcriptional activity of STAT3-containing dimers, and hence the activity of the STAT3 signaling pathway. STAT3 activity (measured by phosphorylated (Tyr705) STAT3) was significantly higher in 4 aggressive PC cells, which correlated with MDA-9 levels (FIG. 16A and FIG. 15A for MDA-9). Further evidence for mda-9-mediated STAT3 activation was documented by phosphorylated STAT-3 levels detected by western blotting analysis (FIG. 16B), and by co-transfection of a STAT3 reporter with mda-9 or shmda-9 in primary immortal normal prostate epithelial (RWPE-1), PC-3 and DU145 cells (FIGS. 16C-16E). Moreover, the anti-invasive activity of MDA-9 was rescued by overexpressing a constitutive active STAT3 in mda-9 knockdown PC cells (FIG. 16F). Blocking secretion, using Brefeldin A, significantly reduced STAT3 activity in PC cells indicating the contribution of a secretory process in activation (FIG. 16G). MDA-9-mediated STAT3 regulation involved IGFBP-2, a downstream target of MDA-9 which was expressed at elevated levels in aggressive PC cells (FIG. 16H) as documented by co-transfection studies with various combination of plasmids (FIG. 16I and FIG. 16J).

MDA-9 Physically Interacts with IGF-1R and Activates STAT3.

Figure 16K:
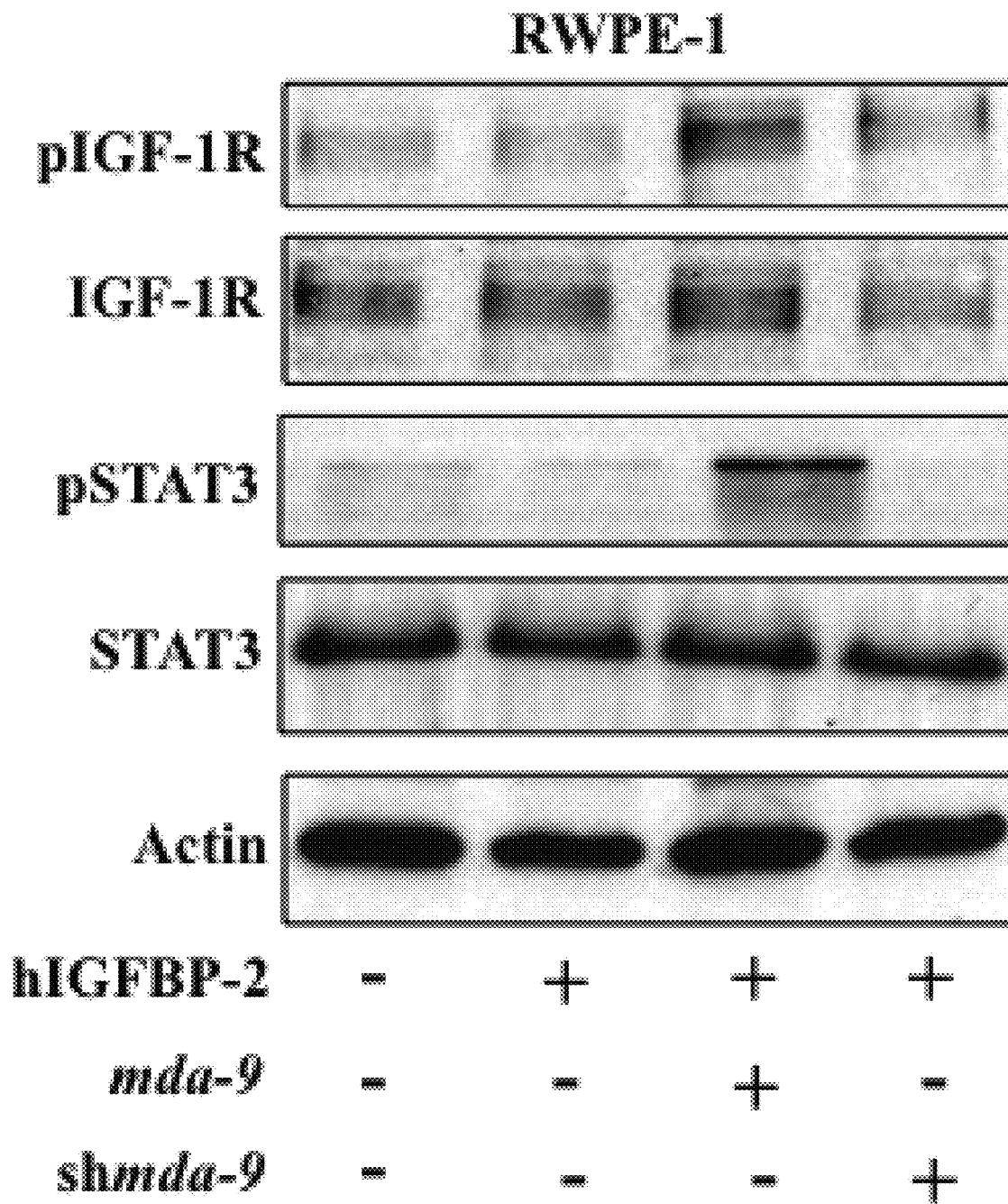
FIG. 16K) RWPE-1 cells were treated with rIGFBP-2 under different conditions as indicated in the figure and phospho-IGF-1R expression was determined by Western blotting.
Figure 16L:
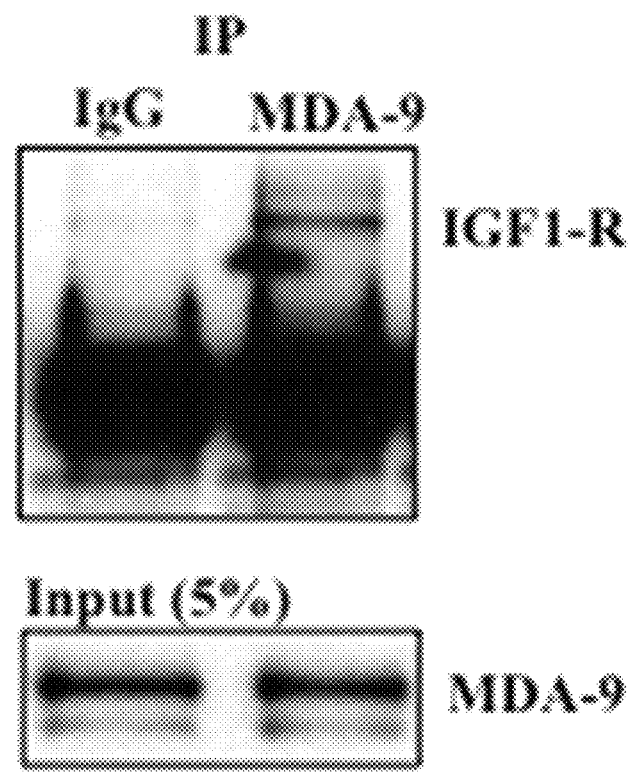
FIG. 16L) 200 µg of total protein from PC-3 cells was incubated with MDA-9 overnight for immunoprecipitation and Western blotting was performed with the anti-IGF-1R antibody to confirm interaction.
Figure 16M:
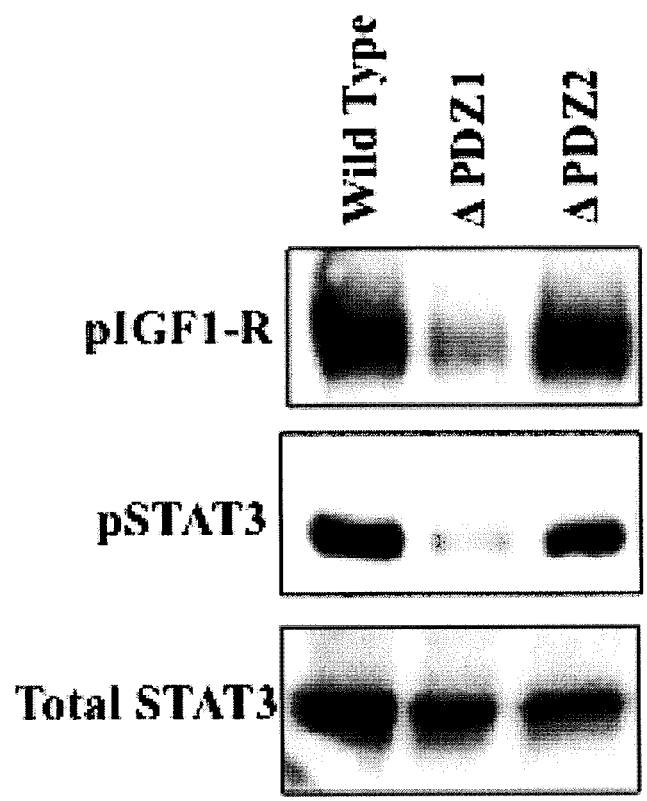
FIG. 16M) RWPE-1 cells were transfected with wild type or mutant mda-9 vectors. 48 h later, cells were replated on fibronectin-coated plates for 1 h and cell lysates were analyzed using the indicated antibodies.
Figure 16N:
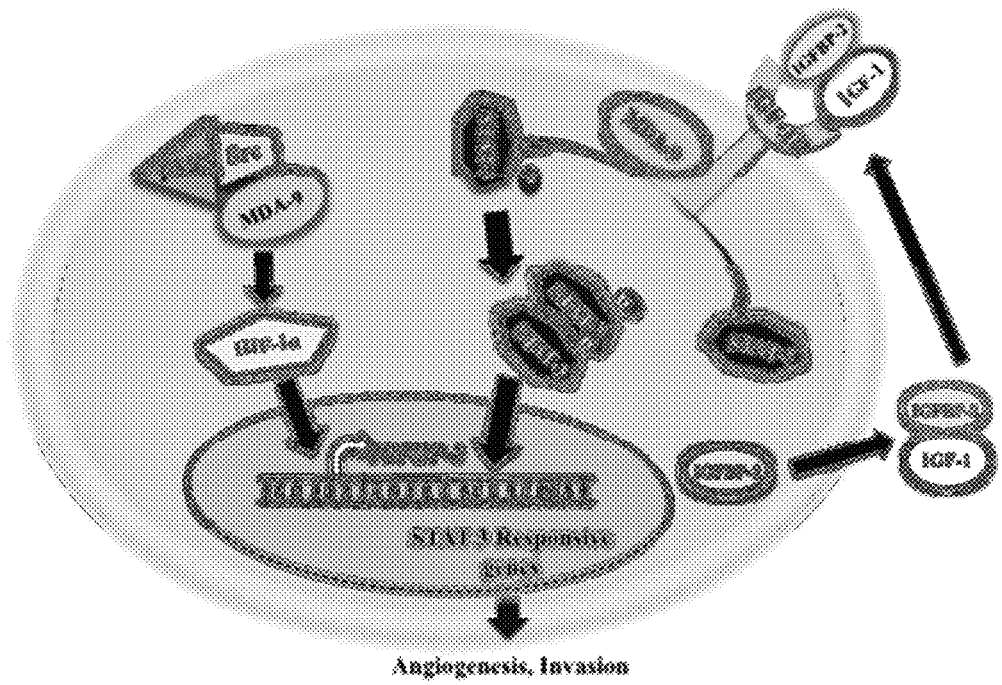

IGF-1R is a tyrosine kinase that can phosphorylate STAT3[48]. IGF-1R, which belongs to the IGF receptor family, is a transmembrane receptor tyrosine kinase (RTK). In response to insulin-like growth factor 1 ligand binding IGF-1R is activated via autophosphorylation (Tyr 980), leading to activation of various signaling cascades including STAT3. Because IGF-1R can also potently activate the STAT3 pathway, one could envision a model in which IGFBP-2 (through binding with IGF-1) might activate STAT3 in an IGF-1R-dependent manner. To explore this possibility, we treated RWPE-1 (immortal normal human prostate epithelial cells) with recombinant IGFBP-2 (hIGFBP-2) in the absence of serum and Western blotting was performed to determine autophosphorylation, representing the activation state of IGF-1R. As anticipated, the presence of IGFBP-2 in the absence of exogenous IGF-1 (not ruling out the possibility of endogenous- or cells-derived IGF-1 in the media) activated IGF-1R, which only occurred in the presence of MDA-9 (FIG. 16K). Enhanced STAT3 activation was also observed in these samples. These findings support the importance of MDA-9 in IGF-1R-mediated STAT3 activation. Further experiments revealed that MDA-9 physically interacts with IGF-1R (FIG. 16L), which might play an essential role in transmitting the activation signal to STAT3. To obtain more insight into the potential binding site(s) and the consequences of this interaction, different deletion mutants of mda-9 were overexpressed in RWPE-1 cells and IGF-1R activation was examined (FIG. 16M). Expression of a PDZ1-deleted fragment (ΔPDZ1) failed to activate IGF-1R (following hIGFBP-2 treatment) indicating that the potential binding site of IGF-1R resides in the PDZ1 domain of MDA-9. As expected, STAT3 activity also correlated with IGF-1R activation further confirming that MDA-9-mediated STAT3 activation is a downstream consequence of MDA-9/IGF-1R interaction. It is likely that MDA-9/Syntenin and IGF-1R physically interact and stabilize the functional unit to activate STAT3 through phosphorylation at tyrosine 705. Phospho-STAT3 forms a dimer and translocates into the nucleus to induce various genes that actively participate in PC progression (FIG. 16N).

PDZ1i Suppresses MDA-9-Mediated Invasion in PC and MDA-9 Overexpressing Normal Prostate Epithelial Cells.

Figure 17A:
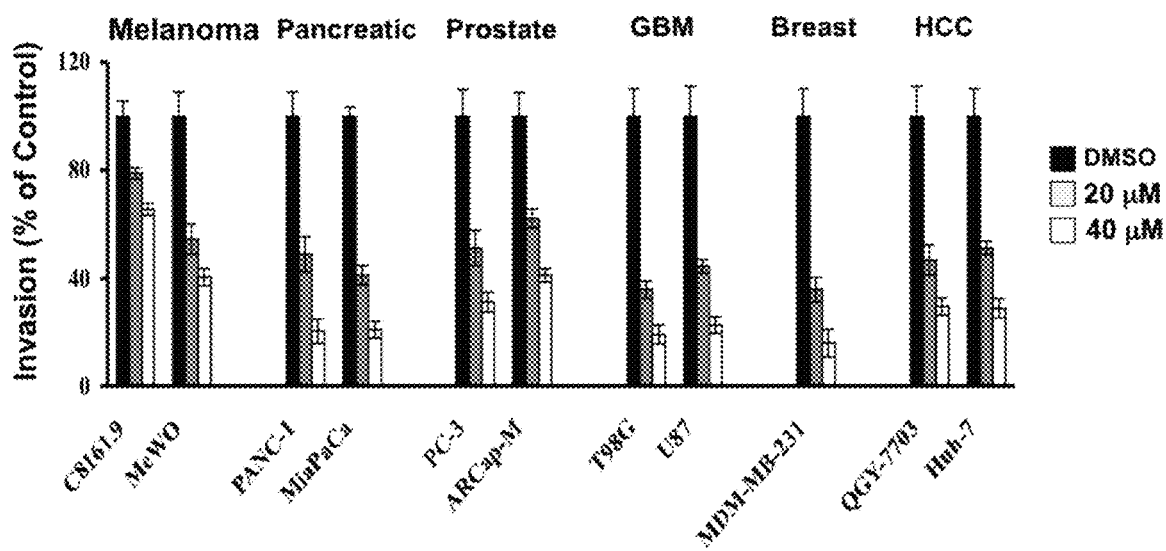
FIGS. 17A-17H. Effect of PDZ1i on invasion, MDA-9/IGF-R1 interaction and IGF-R1, STAT3 and SRC phosphorylation.
Figure 17B:
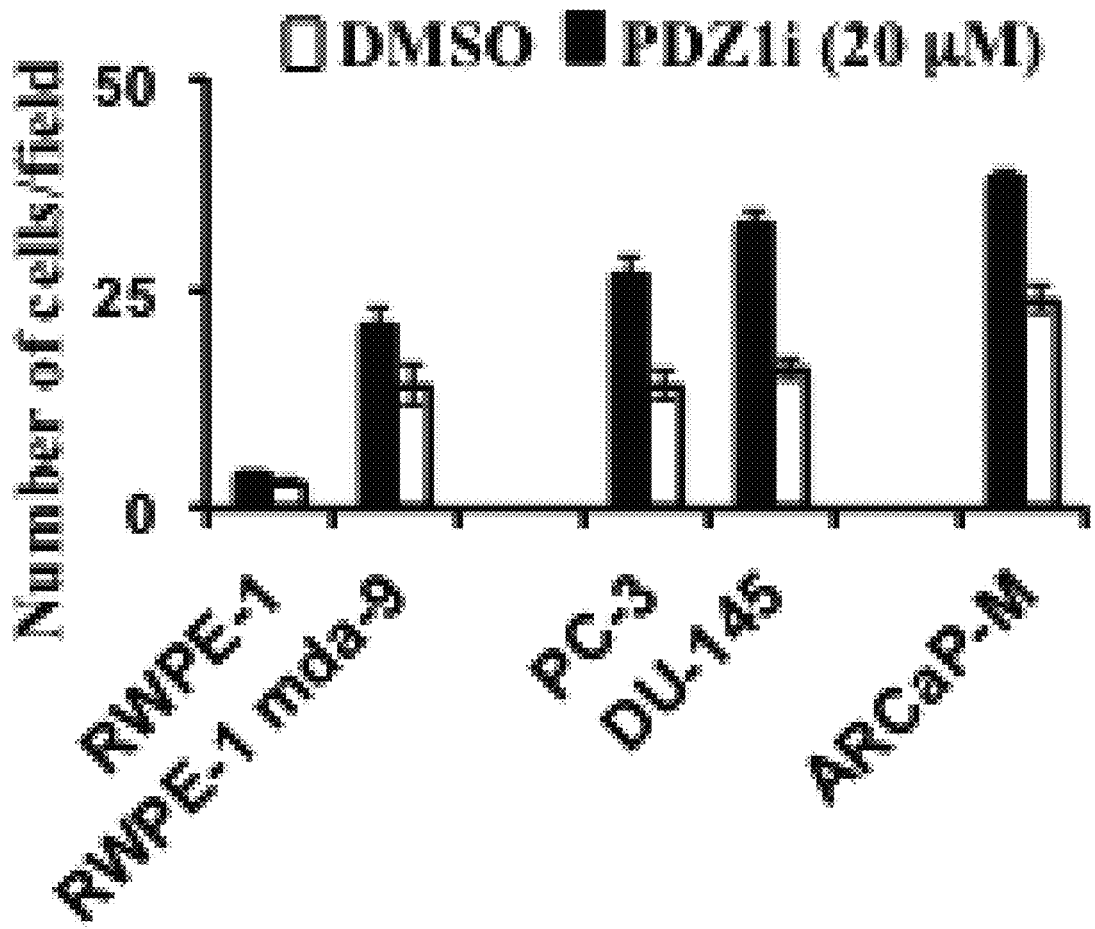

Identification and characterization of a novel PDZ1 antagonist, PDZ1i, was described in Example 1. Initial screening with established cell lines demonstrated that pre-treatment with PDZ1i (20 μM or 40 μM) significantly inhibited the invasion of various types of cancer cells (FIG. 17A) including PC (FIG. 17B). It is worth noting that the compound did not show any toxicity, even when tested at 50 μM. In addition, to assess the direct effect of PDZ1i on mda-9-mediated invasion, normal immortal prostate epithelial (RWPE-1) cells were genetically modified to overexpress mda-9. The parent RWPE-1 cells express minimal levels of MDA-9 and possess minimal invasive ability. However, the cells overexpressing mda-9 displayed increased invasion capability which was significantly attenuated when cells were treated with PDZ1i (FIG. 17B). The anti-invasive effect of PDZ1i was also tested on other PC cells including PC-3, DU145, metastatic variant ARCaPM (FIG. 17B). These findings establish that PDZ1i can inhibit invasion by interrupting mda-9-mediated promotion of transformed (invasive) properties.

Figure 17C:
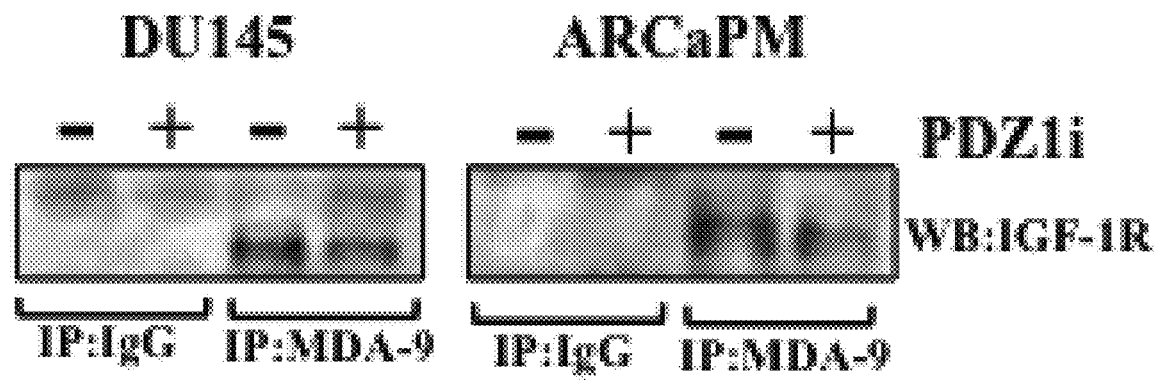
Figure 17D:
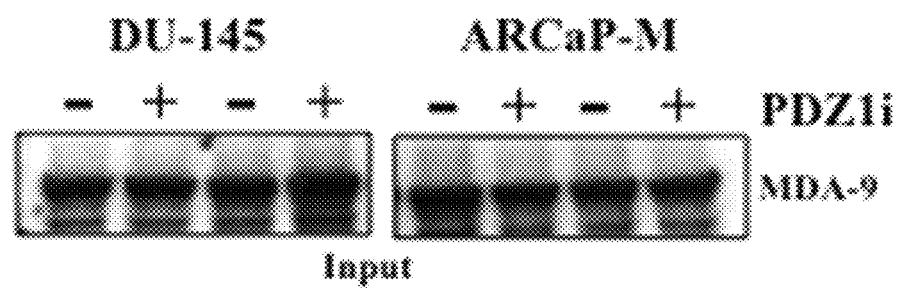

Next, the effect of PDZ1i on MDA-9 and IGF-1R interactions was determined. DU145 and ARCaPM cells were treated with PDZ1i for 6 h and cell lysates were subjected to co-IP analysis to determine potential physical interactions between MDA-9 and IGF-1R (FIG. 17C). The same samples were also analyzed for MDA-9 (FIG. 17D) and Src interactions. The results confirmed that PDZ1i selectively inhibits MDA-9/IGF-1R interactions, but not interactions of MDA-9/Src. These results provide further evidence for the specificity of this PDZ1i.

Figure 17E:
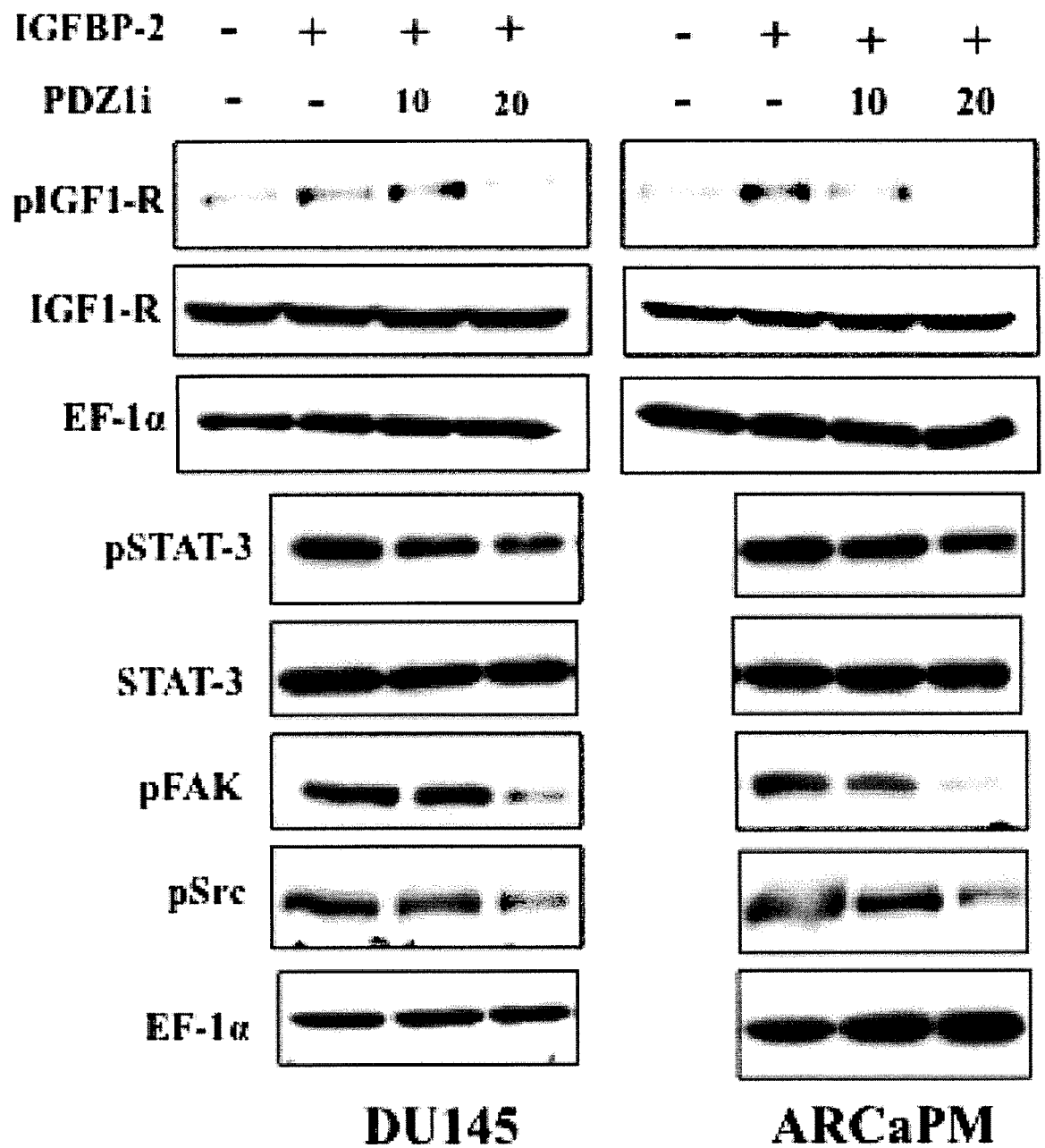
Figure 17F:
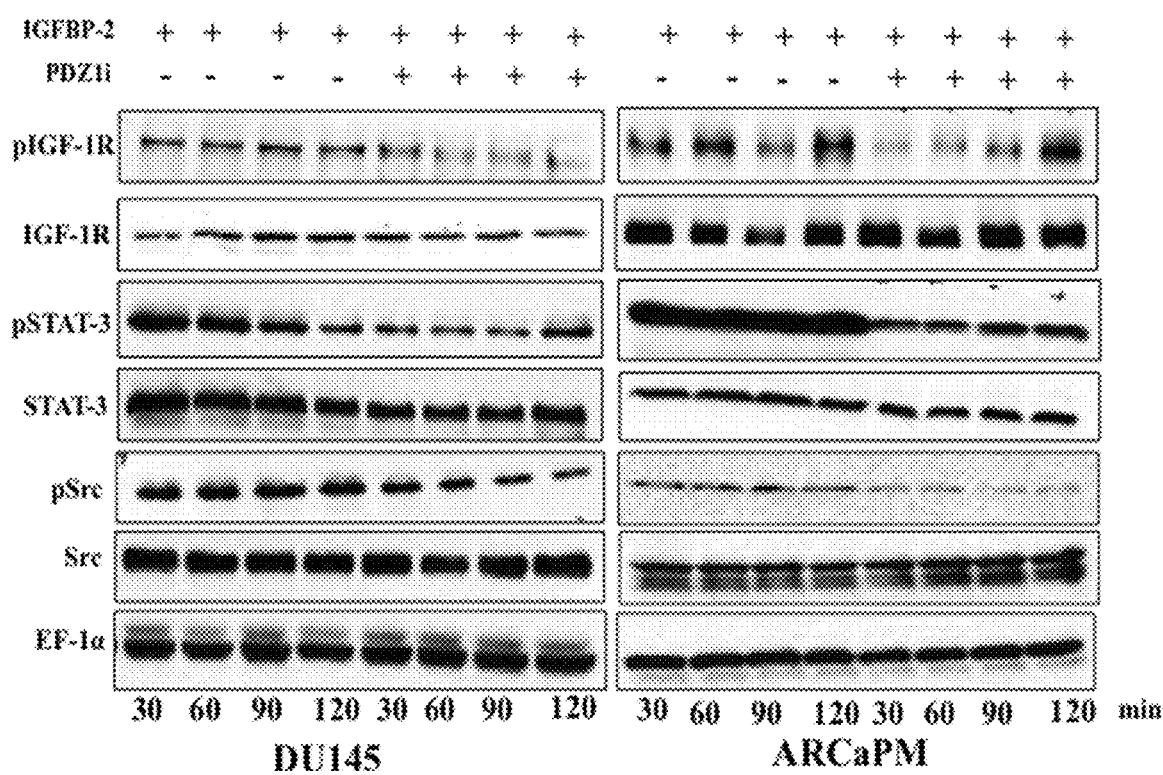
Figure 17G:
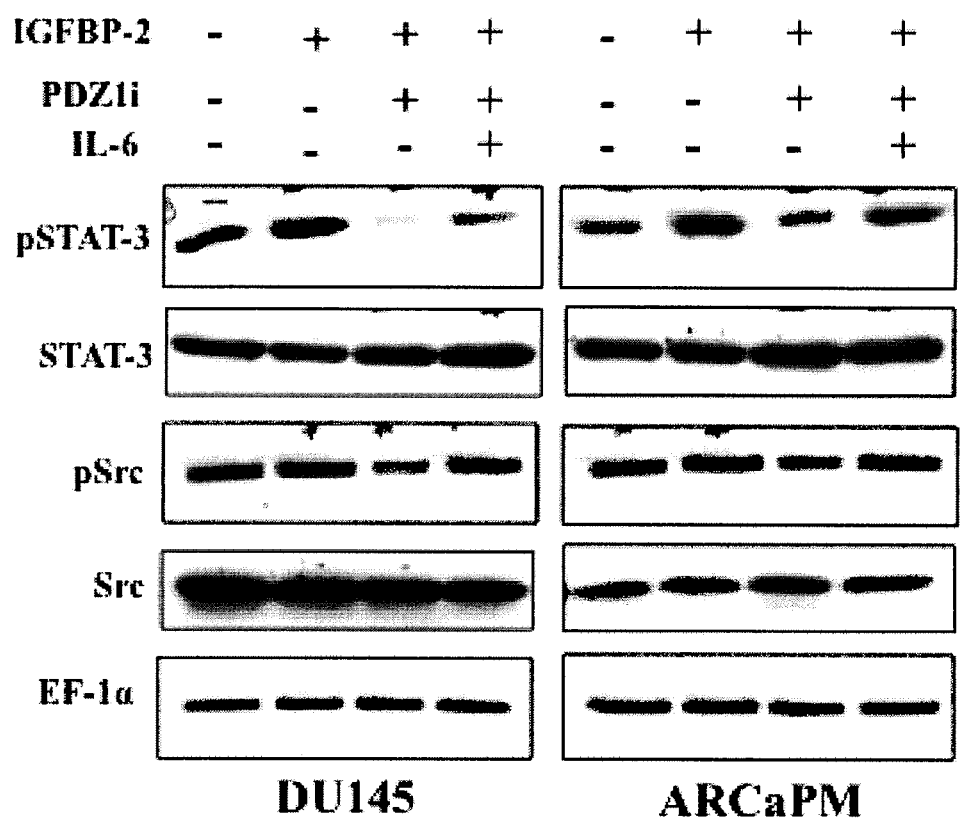
Figure 17H:
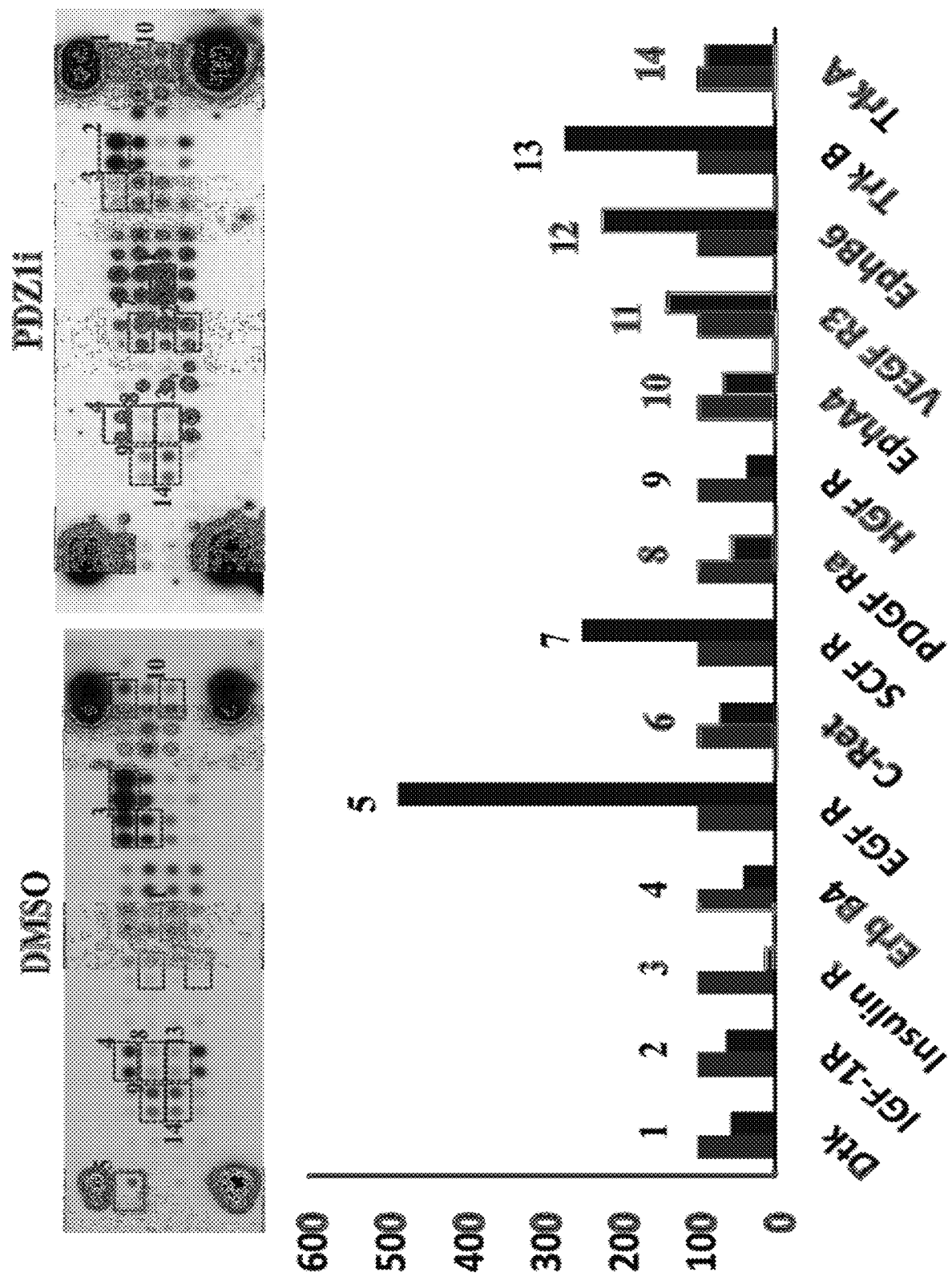

Further studies confirmed that PDZ1i down regulates IGF-1R and STAT3 activity in both a dose- (FIG. 17E) and time-dependent (FIG. 17F) manner. Previous studies indicate that IL-6 can activate STAT3 through IGF-1R in PC[43]. PDZ1i's ability to interrupt IL-6-mediated STAT3 activation was also demonstrated (FIG. 17G). Although PDZ1i did not effect MDA-9/Src interactions, Src activity was reduced (FIG. 17G) suggesting that IGF-1R might play a role in Src activation. PDZ1i might directly or indirectly down regulate multiple receptor tyrosine kinases, which is currently being explored. Finally, consistent with previous observations[16, 51], PDZ1i downregulates both MMP-2 and MMP-9 at both the protein and activity level, documented by western blotting and zymography, respectively (FIG. 17H).

Anti-Angiogenic Role of PDZ1i.

Figure 18A:
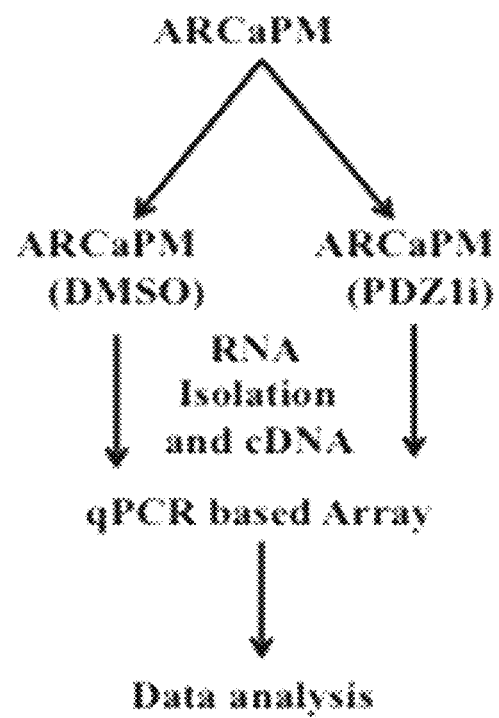
FIGS. 18A-18C. PDZ1i suppresses production of tumor-derived pro-angiogenic factors.
Figure 18B:
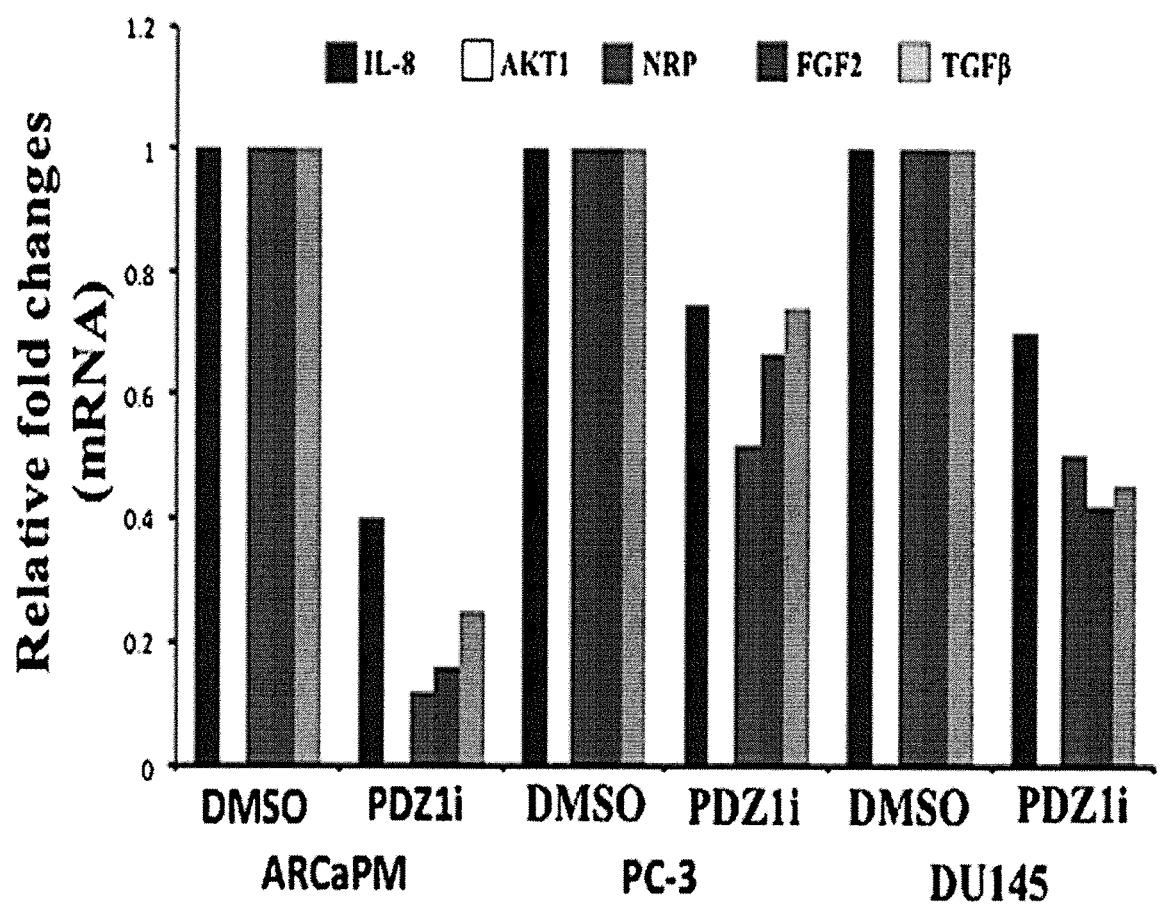
Figure 18C:
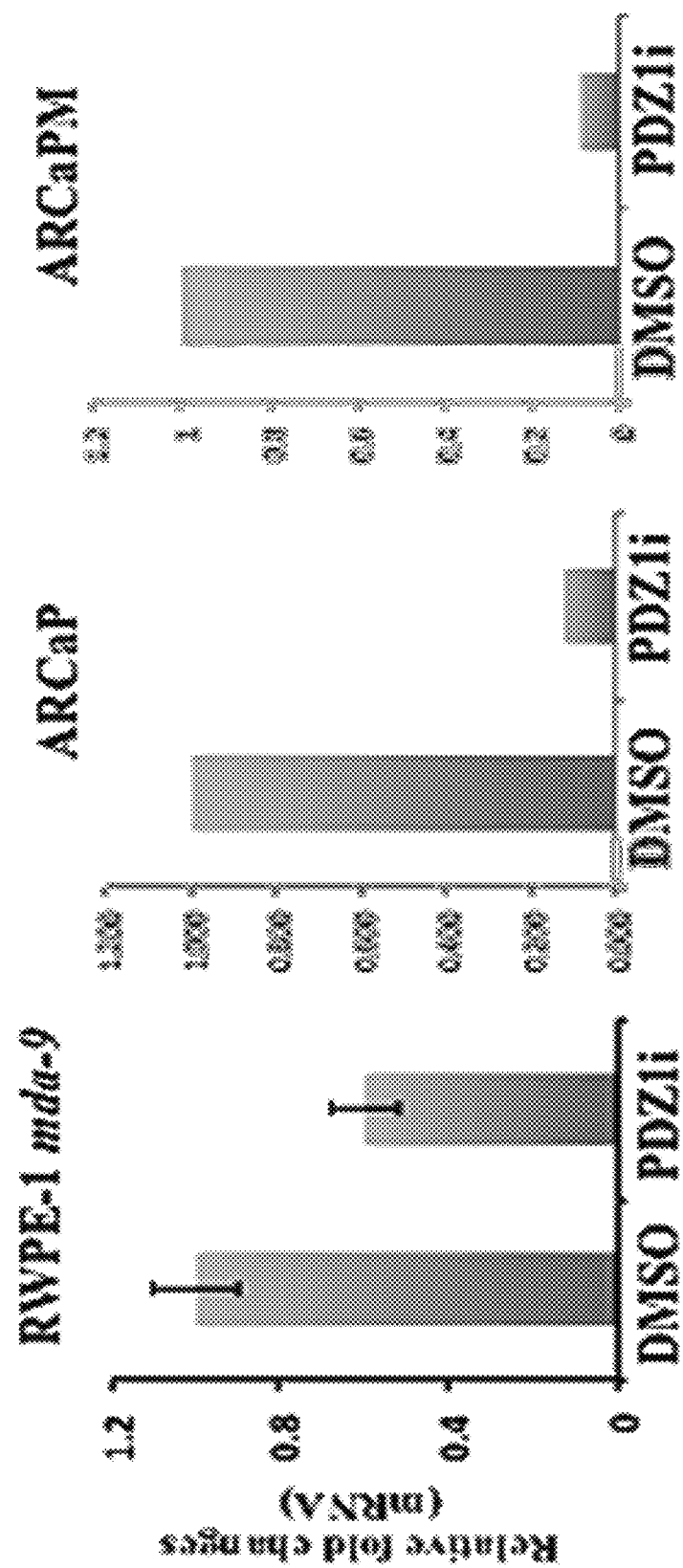

In this study, the potential impact of PDZ1i on tumor-derived angiogenesis in a prostate cancer context was explored. The experimental strategy is outlined in FIG. 18A. Data analysis from a qPCR-based array highlighted a number gene that were downregulated as a consequence of PDZ1i-treatment (FIG. 18B). This observation was also validated in different PC cells by qPCR. Additionally, since VEGF-A is a potent angiogenic factor and a downstream target of STAT3, the expression pattern of VEGF-A at both mRNA and protein levels was also evaluated in different PC cells, including mda-9 stably expressing RWPE-1 cells (FIG. 18C). Finally, both in vitro tube formation and in vivo CAM assays confirmed the anti-angiogenic properties of PDZ1i-treated tumor cell-derived conditioned media (not shown).

PDZ1i Inhibits PC Development In Vivo.

Figure 19A:
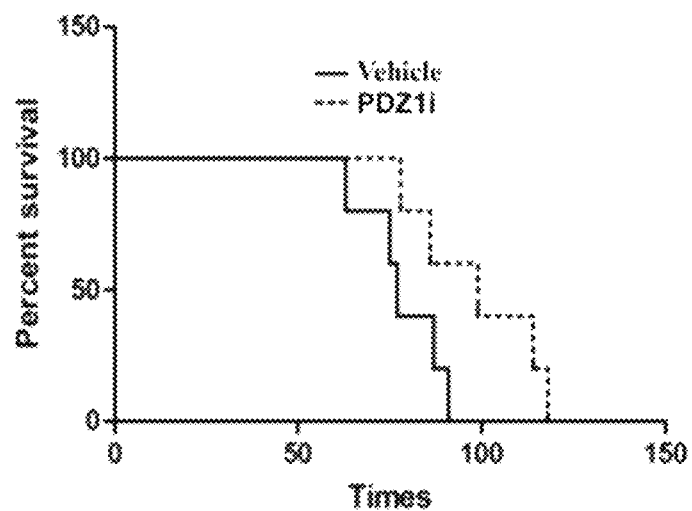
FIG. 19A-19F. PDZ1i suppresses prostate cancer metastasis and tumor progression.
Figure 19B:
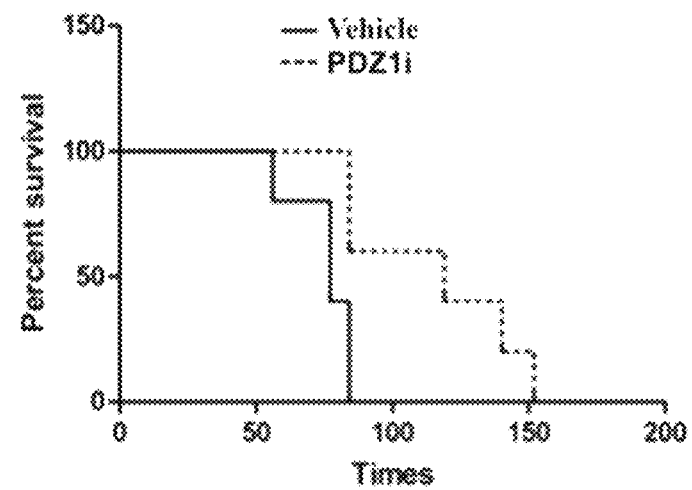
Figure 19C:
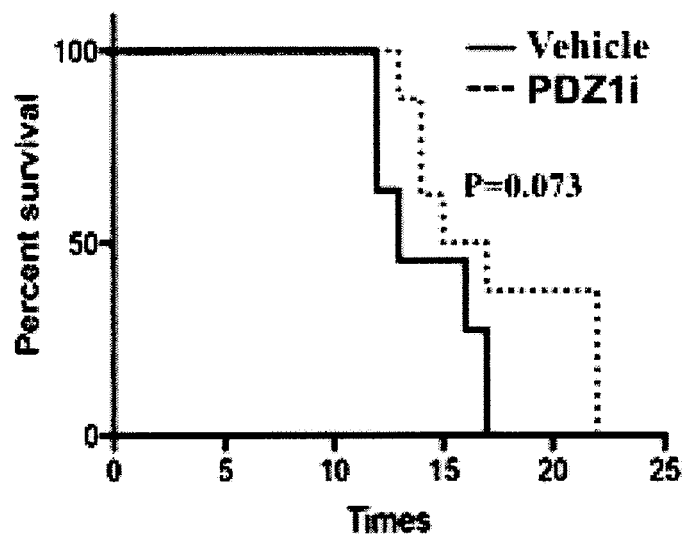
Figure 19D:
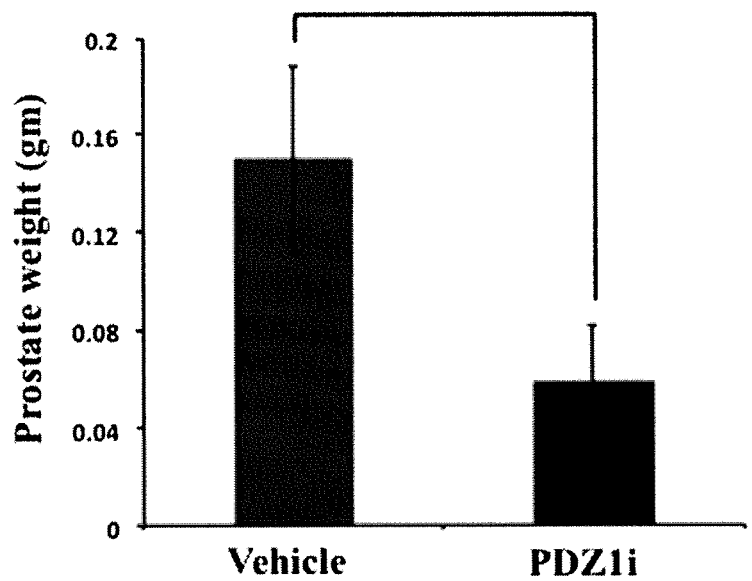
Figure 19E:
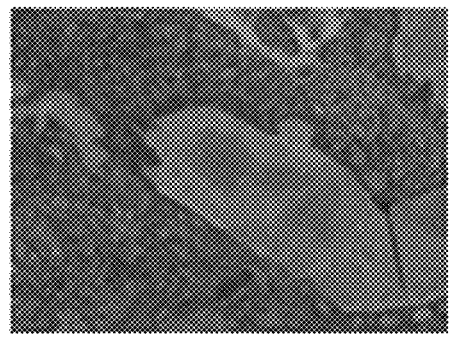
Figure 19F:
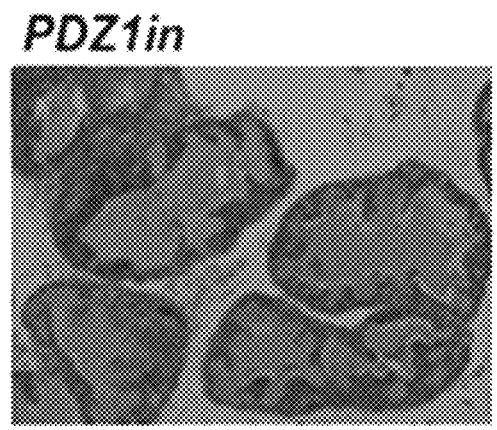

To evaluate potential therapeutic efficacy of PDZ1i four sets of in vivo experiments were conducted. First, stable luciferase expressing ARCaPM (ARCaPM-Luc) cells were pre-treated with PDZ1i and injected intravenously into animals to determine the effect of the MDA-9 inhibitor in modulating retention and adhesion of metastatic tumor cells in the lungs. The results showed that mice inoculated with PDZ1i pre-treated cells had lower cancer cell concentrations in the lungs than did control mice inoculated with non-pretreated cells in mice, and the PDZ1i pre-treated cells were cleared more rapidly from the lungs (within 2 h post-inoculation). This suggests that pre-treatment with PDZ1i alters the adhesion ability of potentially metastatic tumor cells, which would ultimately have a direct effect on development of metastatic lesions at secondary sites. Moreover, animals injected with PDZ1i-treated ARCaPM cells survived longer than control animals treated with vehicle without the small molecule PDZ inhibitor (FIG. 19A). In another set of experiments, an equal number of cells was implanted into animals using an intravenous (i.v.) tail vein route. Experimental groups received 30 mg/kg body weight of PDZ1i LP. As predicted, the treated groups developed significantly fewer lesions compared to control groups, as detected by bioluminescence imaging (BLI) ultimately resulting in prolonged survival (FIG. 19B). In another set of experiments, RM1-Luc cells were injected by the intracardiac route in syngeneic C57BL/6 mice, which were treated with PDZ1i LP. (3 injections/first week). The results were similar to those observed in the nude mice experiments, i.e., PDZ1i significantly reduced the tumor burden in the lungs and prolonged survival (FIG. 19C). In another experiment, 8-week old Hi-myc male mice were injected with tumor cells and then treated I.P. with either PDZ1i (30 mg/kg) or vehicle 9 times for the first three weeks. Mice were then maintained until 6-months of age, when adenocarcinomas fully develop in this transgenic animal model. Additionally, to understand drug-mediated molecular changes, 48 h before sacrifice, a single additional treatment with PDZ1 i was given. Both the size and weight of prostates collected from the PDZ1i-treated groups were significantly less than the control groups (FIG. 19D). H & E staining of prostate sections indicated that histologically the prostate from the control (vehicle-treated) group showed a significant progression to adenocarcinoma (FIG. 19E), which was not evident in the PDZ1i-treated groups (FIG. 19F; representative photomicrographs are presented). Immunostaining for the expression of pIGF-1R and pSTAT3, two downstream effectors of MDA-9, were also significantly reduced in PDZ1i-treated animals, validating the in vitro observations in vivo.

A major component of cancer progression relates to tumor heterogeneity, which may be the driving force in defining why only 10% of PC cases progress to lethality. Based on accumulating data various pathways are being targeted to effect beneficial outcomes in patients with metastatic PC including tumor vasculature, androgen receptors, IGF-1 and IL-6 signaling, and cytoprotective chaperones. However, therapy of advanced PC, particularly when metastasis to bone has occurred, still remains an unattainable objective. This example demonstrates that MDA-9/Syntenin (SDCBP) provides a molecular target for small molecules that intervene in the invasive and metastatic properties of PC both in vitro and in vivo, thus providing a novel approach for managing PC.

The present studies also identify IGF-1R as a new MDA-9 binding partner. Considering this association, experiments focused on the functional significance of this interaction. Once IGF-1R binds to MDA-9 it results in the downstream activation of STAT3. Apart from inflammation, active STAT3 is known to transcriptionally regulate various genes involved in survival, proliferation, invasion and angiogenesis. Since, MDA-9 did not show any direct impact on cell survival or proliferation in PC cells based in vitro experiment, it is likely that MDA-9-mediated up regulation of STAT-3 activity is relevant in regulating cell invasion rather than cell survival, which is experimentally supported in the present study.

Considering the key role of MDA-9/IGF-1R interactions in STAT-3 activation, which has a decisive impact on PC progression, small molecule inhibitors that bind to MDA-9 were tested for their ability to specifically interrupt MDA-9/IGF-1R interactions thereby affecting STAT3 activation and PC invasion. As described in Example 1, a PDZ1-specific binding small molecule, PDZ1i, was identified, and it was found that, in micromolar doses, PDZ1i modifies the ability of IGF-R1 to bind to MDA-9. Previous studies demonstrated that both PDZ domains of MDA-9 are critical for interacting with c-Src and the present studies show that PDZ1i downregulates Src activation, thereby negatively influencing further downstream signaling, including p38 and NF-κB activation in different PC cells. c-Src can be activated in multiple ways, either by autophosphorylation or through various tyrosine kinases including IGF-1R. In PC cells, PDZ1i-mediated downregulation of c-Src activation is partially IGF-1R dependent. Another tyrosine kinase, EGFR, which is also an interacting partner of MDA-9, has been reported to activate c-Src in PC. However, PDZ1i did not have any effect on EGFR activation, at least under the conditions used in this study (data not shown).

Because of the clinical significance of IGF-1R in PC, diverse therapeutic approaches have been tested that target this protein including human monoclonal antibodies and small molecules to inhibit IGF-1R activity through distinct targeting approaches, e.g., IGF-1R ligands, blocking ligand binding, inhibiting enzymatic activity, etc. As documented in the present studies, rather than targeting IGF-1R directly, PDZ1 i advantageously inhibits IGF-1R activity by perturbing MDA-9/IGF-IR interactions, which may be restricted to its' role in cancer cells. Additionally, recent studies demonstrate that MDA-9/Syntenin-1 (SDCBP) knockout mice are viable[69,70] and in these mice tumor-supporting inflammation is inhibited and melanoma metastasis is suppressed[70]. Thus, the activity of MDA-9 is dispensable for normal cellular functions and MDA-9-targeted molecules are more specific to neoplastic cells, an important prerequisite for drug development.

In summary, this study demonstrates that the PDZ1 domain of MDA-9 is "druggable" using small molecule inhibitors that are unique to this domain of MDA-9 and which affect its interactions with specific proteins. Such small molecule MDA-9 inhibitors can be used to treat, prevent or ameliorate cancer development and/or metastasis.

Methods

NMR studies and Synthesis of PDZ1i were performed as described in Example 1.

Human Cell Lines.

M12 and M2182 (progressed prostate cancer cells obtained from VCU School of Medicine, Richmond, Va.). Other cells except ARCaP with its epithelial and metastatic variants, ARCaPE and ARCaPM, respectively were obtained from ATCC (Manassas, Va.) and maintained in culture as per ATCC recommendations. ARCaP, ARCaPE and ARCaPM cells were obtained from Novicure Biotechnology (Birmingham, Ala.) and maintained in media as recommended by the provider. Primary immortal prostate epithelial cells, RWPE-1, were purchased from ATCC. HuVEC (Human Umbilical Vein Endothelial Cells) were obtained from Lonza (Allendale, N.J.). All cell lines were routinely checked for mycoplasma contamination by using commercial kits. Cell lines were purchased from ATCC, an authenticated and reliable source for human cancer cells. In our study most of our experiments carried out in RWPE-1, PC-3, DU145 and ARCaPM cells. All of these cell lines were purchased recently (within the last 3 years) and strictly maintained as per the manufacturer's recommendation. The other cell lines P69, M12 and M2182 were used to as panel of prostate cancer cells and described in our previous publications. Androgen-refractory mouse prostate cancer cell lines RM1, was provided and was maintained in DMEM as previously described. The metastatic capability of stable luciferase-expressing RM (RM1-Luc) was previously reported.

Reagents and Antibodies.

A list of antibodies used in this study are provided in supplemental "Methods". All reagents for cell cultures including media and serum were purchased from Gibco. Recombinant IGFBP-2 was purchased from R & D Biosystems (Minneapolis, Minn.).

Gelatin Zymography.

Gelatin zymography is used to determine the gelatinolytic activity of MMP-2 and MMP-9 in conditioned media collected from in vitro cell cultures. Briefly, the cancer cells were treated with either DMSO or 113B7 (PDZ1i), cultured for 48 h, and then the media was replaced with fresh serum-free media and cultured for an additional 24 h. The conditioned media was then collected. Equal amounts of protein containing conditioned media was electrophoresed in 8% SDS-polyacrylamide gels containing 1.5 mg/mL gelatin. The gels were washed three times for 30 min each with 2.5% Triton X-100 solution to remove SDS. The gels were then incubated at 37° C. overnight in incubation buffer [50 mmol/L Tris-HCl (pH 7.5), 0.05% $NaN_3$, 5 mmol/L $CaCl_2$, and 1 µmol/L $ZnCl_2$]. After incubation the gels were stained with 0.1% Amido black staining solution and subsequently destained with destaining solution to visualize the gelatinolytic activities that were identified as clear zones of lysis against (clear band) a blue background.

Tissue Microarray.

A prostate cancer tissue microarray along with matched adjacent normal tissues was purchased from Imgenx Corp (Currently part of Novus Biologicals (Littleton, Colo.)) and stained with MDA-9 antibody (anti rabbit) from Sigma Aldrich (St. Louis).

Real Time PCR.

For qPCR, total RNA were extracted using miRNeasy kits (Qiagen, Valencia, Calif.) as recommended by the manufacturer and cDNA was prepared as previously described[27]. Quantitative qPCR was performed using an ABI ViiA7 fast real-time PCR system and Taqman gene expression assays according to the manufacturer's protocol (Applied Biosystems, Foster City, Calif.).

Constructs and Stable Cell Clones.

Various vector constructs used in this study were either cloned by our group (mda-9, shmda-9) n or purchased from Adgene (Cambridge, Mass.) (pRc.CMV.Stat3Y705F). For developing stable luciferase-expressing clones, cells were transfected with expression vectors and selected with neomycin for approximately 2 weeks. Individual colonies were picked and analyzed for luciferase expression.

In Vivo Experiments.

All in vivo experiments were performed in accordance with IACUC approved protocols. To determine the effect of PDZ1i on tumor cell retention in the lungs, we inoculated cohorts of mice (n=5, each group) via tail vein injection with either vehicle (DMSO) or test compound (50 µM) pretreated ARCaPM-Luc (1×10⁶ cells in 100 µl saline) metastatic PC cells. Luciferase activity was monitored for differential cellular clearance from the lungs between 15 min and 5 h by Bio luminescence imaging (Xenogen in vivo imaging (IVIS) system) (Caliper Life Sciences, Inc., Hopkinton, Mass.). For the lung experimental metastasis model, a total of 5×10⁵ ARCaPM-Luc cells were injected (in 100 µL PBS) by intravenous tail vein injection. Treatment began 12 days after PC cell injection. PDZ1i was given at a dose of 30 mg/kg body weight in solution containing DMSO, Tween 20 and PBS (10:10:80). Drug was delivered every alternate day for the first three weeks (total 9 injections). Mice were periodically observed for any signs of toxicity. Mice were kept until euthanized as recommended by IACUC. In other experiments C57BL/6, 1×10⁵ RM1-Luc cells (TRAMP-derived prostate cancer cells[76]).

Animals were injected by the intracardiac route to develop lung metastases. Similar to athymic nude mice studies, experimental mice received only three doses of PDZ1i within the first week of treatment. Mice were kept until they required euthanasia. In an additional experiment, Hi-myc mice (prostate cancer spontaneous transgenic mouse model)[38] were injected with PDZ1i i.p. starting at 2 months of age and continued for subsequent three weeks (total 9 injections). Mice were kept until they reached 6 months of age. Prostates were removed, photographed, weighed and processed for paraffin sectioning. Immunohistochemistry was done as previously described[27] with the antibodies as indicated.

Co-Immunoprecipitation.

Co-Immunoprecipitation was performed as described previously[27] using kit from Pierce (Pierce Biotechnology, Rockford, Ill.).

Invasion Assay.

Boyden chamber assays were done to investigate the invasive properties of cancer cells[26, 27]. Briefly, cells were pretreated with PDZ1i or DMSO and plated on the upper chamber. After 18 h, invasive cells were photographed and analyzed.

In Vitro Tube Formation and Chorioallantoic Membrane (CAM) Assays.

Tube formation and CAM assays were performed as described previously[27]. Briefly, tumor-derived conditioned media were collected after 24 h of treatment (either DMSO or PDZ1i) and concentrated. Equal amounts of protein (50 µg) containing conditioned media were mixed with basal media and incubated with HuVEC cells on Matrigel layers. Photographs were taken after 6 h. In CAM assays, DMSO- or PDZ1 i-treated tumor cell-derived conditioned media were implanted on the CAM of 8 day-old fertilized eggs. Photographs were taken on day 12, 4 days after applying conditioned media.

Example 3: MDA-9/Syntenin (SDCBP) Enhances Epithelial Mesenchymal Transition in Breast Cancer MDA-9/Syntenin (SDCBP) is a scaffold protein that plays a key role in tumor progression and metastasis in several cancer indications. We have uncovered a novel mechanism by which MDA-9 enhances metastasis in breast cancer. Epithelial mesenchymal transition (EMT) is a key step in the process of metastasis and we have uncovered the mechanism by which MDA-9 mediates EMT in breast cancer. When the expression of MDA-9 was suppressed in metastatic mesenchymal breast cancer cell lines, an obvious change in cell morphology was observed where the cells appeared epithelial like. Conversely, when MDA-9 was overexpressed in non metastatic epithelial breast cancer cells, the cell morphology appeared mesenchymal like. Consistent with these findings, several EMT markers were altered following modulation of MDA-9 expression. Additionally, changes in cytoskeletal organization and invasive abilities were also observed. At the mechanistic level, we found that MDA-9 upregulated active levels of known EMT modulators—the small GTPases RhoA and Cdc42 via TGFβ1. Further we determined that MDA-9 interacts with TGFβ1 and the PDZ1 domain of MDA-9 is key for this interaction. Finally we verified our observations using in vive studies. In an in vivo lung metastasis model, suppressing the expression of MDA-9 resulted in a decrease in lung metastasis that could be partially restored by re-expression of TGFβ1. Our findings uncover the importance of MDA-9 in EMT in breast cancer and identify MDA-9 as a therapeutic target against metastatic breast cancer.

Our studies demonstrate for the first time that MDA-9 enhances epithelial mesenchymal transition (EMT) in breast cancer via interaction with TGFβ1. MDA-9 has been reported to regulate cancer metastasis, however, this is the first time that we report the role of MDA-9 in EMT in breast cancer. The novel mechanisms of action that we uncover in our study also serve to identify therapeutic targets against metastatic breast cancer.

Considering the pivotal role of MDA-9 in regulating metastasis, directly targeting MDA-9 expression or its interaction with TGFβ1 using genetic or pharmacological approaches may provide a unique opportunity to develop targeted therapies against metastatic disease.

Most available technology has been unsuccessful in effectively targeting tumor metastases and hence our findings provide an important therapeutic intervention option for metastatic breast cancer.

Developing a targeted approach or specifically inhibiting MDA-9 interaction with TGFβ1 might overcome this problem. Since an MDA-9 knockout mouse (lacking mda-9 expression in all tissues) is viable, targeting MDA-9, which is syntenin-1, would not be predicted to be toxic. Indeed, we have generated inhibitors of MDA-9 that target the PDZ1 domain of MDA-9 and alter protein-protein interactions which results in suppression of tumor invasion, tumor cell attachment, tumor angiogenesis and metastasis.

Metastatic breast cancer therapy remains a challenge in the clinic. We identified MDA-9/Syntenin (syndecan binding protein, SDCBP) as a key player in enhancing metastasis and identified its detailed molecular mechanism of action. This understanding of the role of MDA-9 as well as its mechanism of action has uncovered several therapeutic options to specifically target metastatic breast cancer.

MDA-9/Syntenin (SDCBP) modulates small GTPases RhoA and Cdc42 via transforming growth factor β1 to enhance epithelial-mesenchymal transition in breast cancer. Epithelial-mesenchymal transition (EMT) is one of the decisive steps regulating cancer invasion and metastasis. However, the molecular mechanisms underlying this transition require further clarification. MDA-9/syntenin (SDCBP) expression is elevated in breast cancer patient samples as well as cultured breast cancer cells. Silencing expression of MDA-9 in mesenchymal metastatic breast cancer cells triggered a change in cell morphology in both 2D- and 3D-cultures to a more epithelial-like phenotype, along with changes in EMT markers, cytoskeletal rearrangement and decreased invasion. Conversely, over expressing MDA-9 in epithelial non-metastatic breast cancer cells instigated a change in morphology to a more mesenchymal phenotype with corresponding changes in EMT markers, cytoskeletal rearrangement and an increase in invasion. We also found that MDA-9 upregulated active levels of known modulators of EMT, the small GTPases RhoA and Cdc42, via TGFβ1. Reintroducing TGFβ1 in MDA-9 silenced cells restored active RhoA and cdc42 levels, modulated cytoskeletal rearrangement and increased invasion. We further determined that MDA-9 interacts with TGFβ1 via its PDZ1 domain. Finally, in vivo studies demonstrated that silencing the expression of MDA-9 resulted in decreased lung metastasis and TGFβ1 re-expression partially restored lung metastases. Our findings provide evidence for the relevance of MDA-9 in mediating EMT in breast cancer and support the use of MDA-9 as a therapeutic target against metastatic disease.

The American Cancer Society estimates that in 2016, about 246,660 women will be diagnosed with breast cancer and approximately 40,450 women will die of the disease in the United States (American Cancer Society, Cancer Facts & Figures, 2016). Despite enhanced early detection, breast cancer is the second leading cause of cancer-related death among women in the United States. One of the reasons for this discrepancy is that treatment options are limited once primary tumors metastasize to distant areas in the body. Overall prognosis and patient survival are also adversely affected in metastatic disease. Consequently, it is imperative to identify relevant therapeutic targets that can inhibit metastasis of breast cancer. At the molecular level, epithelial-mesenchymal transition (EMT) enhances invasion and metastasis of cancer cells. EMT is a well conserved cellular process during which polarized, non-motile epithelial cells lose their polarized organization and cell-cell junctions and transition into motile mesenchymal cells [1, 2]. EMT is now widely accepted as a mechanism utilized by cancer cells to gain access to distant areas in the body [2-5]. Identifying distinctive molecules that regulate EMT and are "druggable" are thus critical to gain control of metastatic disease.

Melanoma differentiation associated gene-9 (MDA-9), also known as syntenin-1 (SDCBP; syndecan binding protein), is a member of the PDZ-domain containing family and is located on chromosome 8q12 [6]. Initially identified in our laboratory while screening for genes that were differentially expressed in human melanoma cells reprogrammed to terminally differentiate [7], MDA-9 has now been identified as a multifunctional protein involved in diverse physiological and pathological processes [8, 9]. MDA-9/syntenin plays an important role in several cellular functions including regulating cell-cell and cell-matrix adhesion, signal transduction from the cell surface to the interior through interaction with a number of proteins, intracellular and secreted lipid trafficking, and cell surface targeting [6, 9]. Recent studies also implicate MDA-9 as a key gene involved in cancer stem cell growth and survival [6, 9]. MDA-9 was also found to play a causative role in the progression of several different cancer types including melanoma [10-12], gastric cancer [13], bladder cancer [14], glioblastoma [15], small cell lung cancer [16], hepatoma [17] and head and neck cancers [18]. Recently, a study analyzing clinical patient samples found that MDA-9 expression was higher in patients with breast cancer and was associated with poor overall patient outcome [19]. Another study showed that MDA-9 regulates tumor cell growth in breast cancer [20]. However, the molecular mechanisms underlying the functional relevance and consequences of MDA-9 in breast cancer remains largely unexplored.

In the present study, we evaluated the role of MDA-9 in the invasive, metastatic and EMT abilities of breast cancer cells. We assessed the expression pattern of MDA-9 in breast cancer patient samples and breast cancer cell lines, and examined the impact of loss-of-function and gain-of-function of MDA-9 expression on metastatic and non-metastatic breast cancer cells. We further elucidated the molecular mechanism by which MDA-9 regulates EMT and metastasis in breast cancer. This is the first study that identifies the detailed molecular mechanism by which MDA-9 regulates EMT in breast cancer. Overall, our findings show that MDA-9 could provide a useful therapeutic and diagnostic target for breast cancer metastasis.

MDA-9 Expression is Elevated in Human Breast Cancer.

Figure 20A:
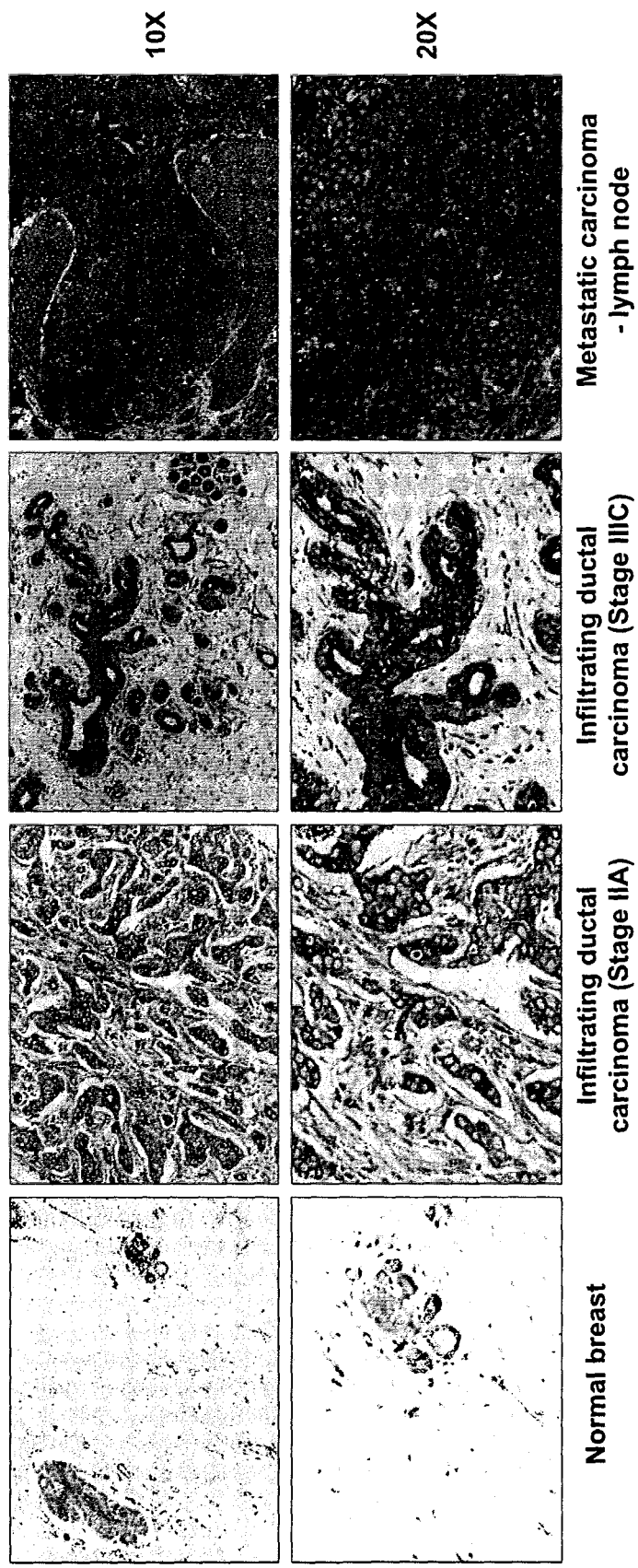
FIGS. 20A-20C. MDA-9 expression is elevated in breast cancer.
Figure 20B:
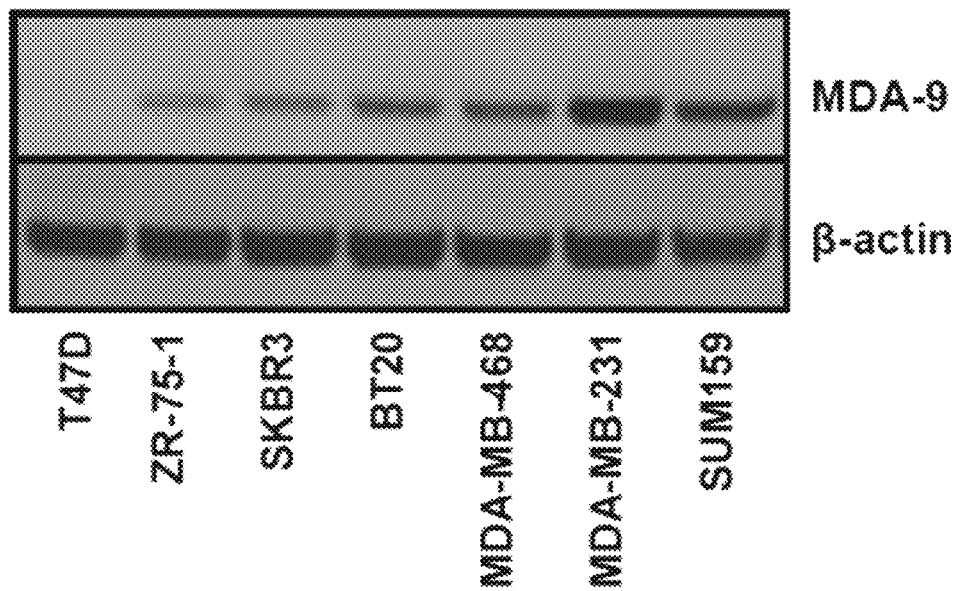
Figure 20C:
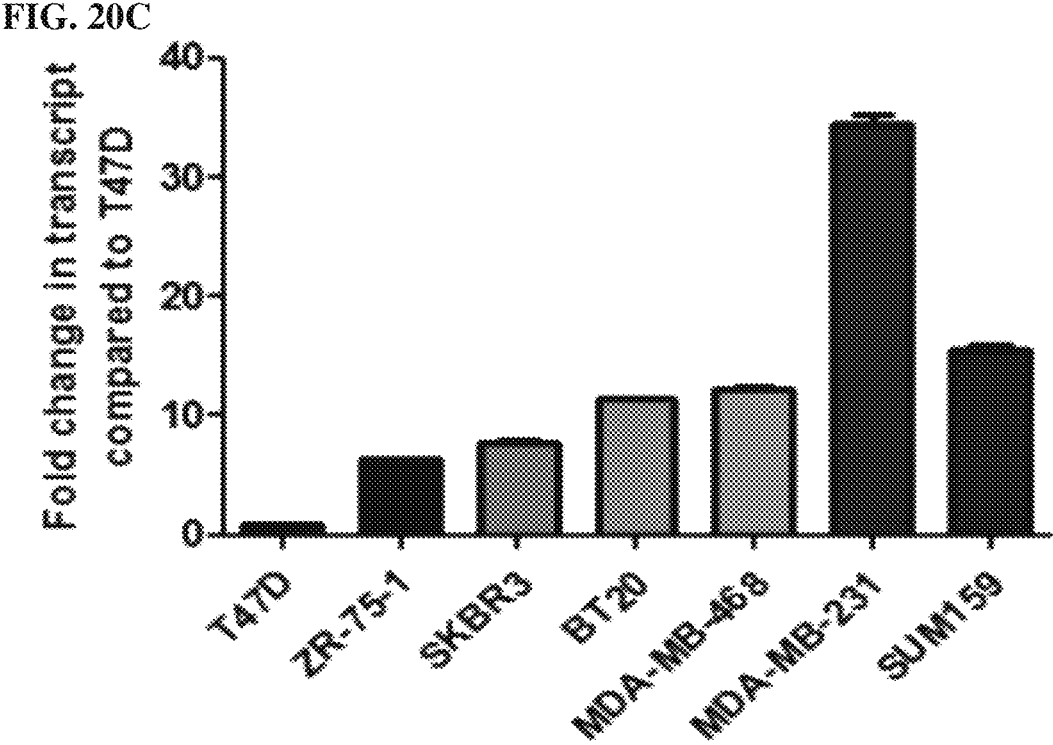

Metastatic breast cancer continues to pose a formidable problem for favorable patient outcome [21]. We recently demonstrated that MDA-9 plays a causative role in tumor progression and metastasis in melanoma [10, 11], urothelial [14], glioblastoma [15], and head and neck cancers [18]. To determine the role of MDA-9 in progression and metastasis of breast cancer, we assessed the expression of MDA-9 in patient samples and cell lines. A commercially available tissue microarray of breast cancer patient samples comprising adjacent normal breast tissue, breast tumor tissue and metastatic lesions was probed for MDA-9 expression by immunohistochemistry. Breast tumor tissue and metastatic lesions showed an increased expression of MDA-9 as compared to normal breast tissue (FIG. 20A). This finding is in agreement with previous studies and was performed to verify previously published research to confirm that MDA-9/syntenin expression was elevated in breast cancer tissues and metastatic breast cancer cell lines [13, 19, 20]. A clinical study also found that elevated expression of MDA-9 correlated with increased metastasis and tumor recurrence in breast cancer patients [19]. This study showed that both overall survival and disease-free survival were reduced when MDA-9 expression was elevated [19]. We also assessed the DNA copy number of MDA-9 in the TCGA database to assess MDA-9 in a larger cohort of breast cancer patients (FIG. 27). MDA-9 DNA copy number was elevated in breast cancer patients as compared to normal controls in this larger cohort as well. Next, we assessed the expression of MDA-9 in a number of non-metastatic and metastatic human breast cancer cell lines and found that MDA-9 expression was elevated in metastatic cells at both the protein (FIG. 20B) and transcript level (FIG. 20C). Having validated that MDA-9 was indeed upregulated in breast cancer and was associated with increased metastatic incidence, we performed studies to understand the role of MDA-9 in the metastatic process in breast cancer.

Modulating the Expression of MDA-9 in Breast Cancer Cells Correlates with Changes in Invasive Abilities and Actin Cytoskeletal Rearrangement.

Figure 21B:
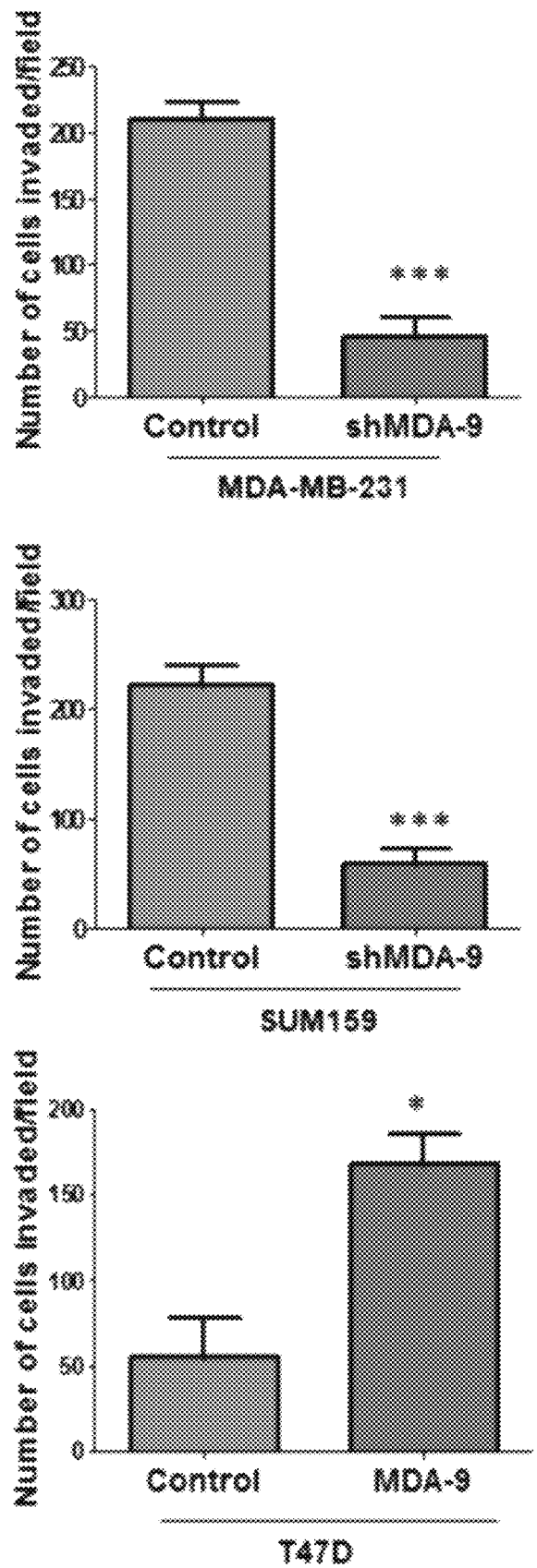
Figure 21C:
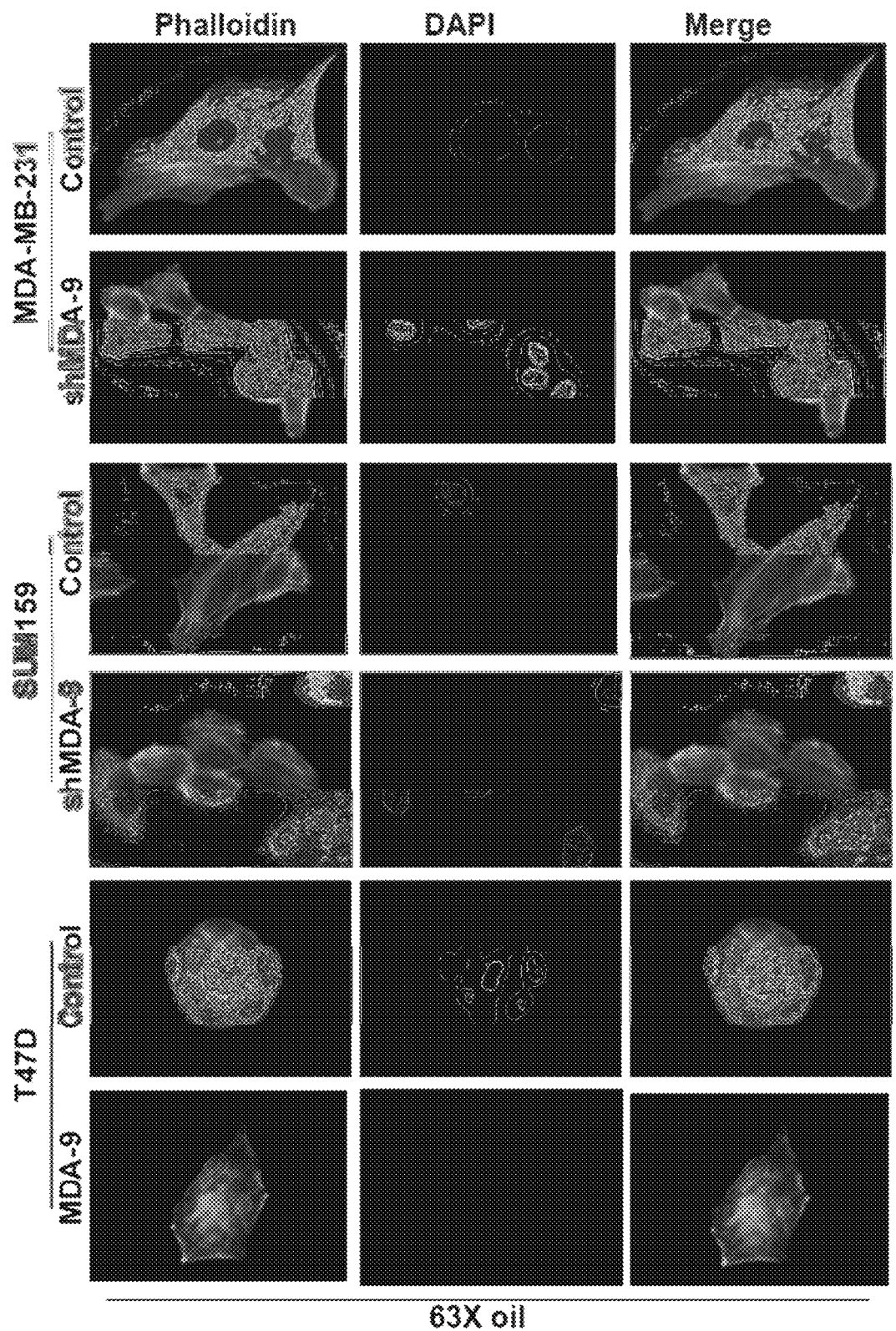

One of the hallmarks of cancer and particularly of metastasis, is the ability to invade into the surrounding basement membrane [4]. To investigate the importance of MDA-9 in metastatic breast cancer cells, we silenced MDA-9 expression in metastatic breast cancer cells, MDA-MB-231 and SUM159, using shRNA targeted to MDA-9 and non-targeted control (FIG. 21A). Silencing the expression of MDA-9 caused a dramatic reduction in invasion in both MDA-MB-231 and SUM159 cells (FIG. 21B). Next, we over expressed MDA-9 in non-metastatic breast cancer cells T47D using an adenovirus expressing MDA-9 and vector control. Overexpressing MDA-9 in T47D cells caused an increase in invasive abilities of these cells (FIG. 21B). Reorganization of the cytoskeleton via polymerization and depolymerization of filamentous actin (F-actin) leads to changes in cell shape and assists in cell motility [1, 22]. We determined whether MDA-9 was able to regulate cytoskeletal rearrangement in breast cancer cells by staining for F-actin using phalloidin. Silencing the expression of MDA-9 in MDA-MB-231 and SUM159 cells caused a decrease in stress fibers, while overexpressing MDA-9 in T47D cells caused an increase in stress fiber formation (FIG. 21C).

Modulating the Expression of MDA-9 in Breast Cancer Cells Correlates with Changes in Cell Shape in 2D- and 3D-Culture.

Figure 28A:
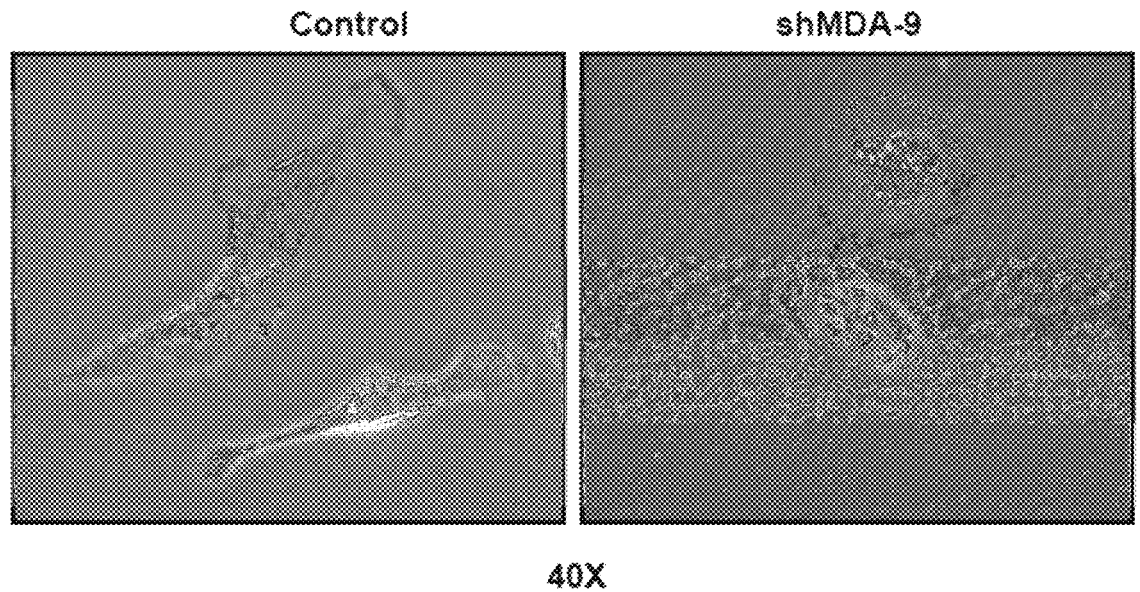
FIGS. 28A-28C. Modulation of MDA-9 expression causes changes in cell shape. Representative images showing change in morphology in 2-dimensional culture on plastic plates following silencing MDA-9 expression in (FIG. 28A) MDA-MB-231 and (FIG. 28B) SUM159 and overexpressing MDA-9 in (FIG. 28C) T47D cells.
Figure 28B:
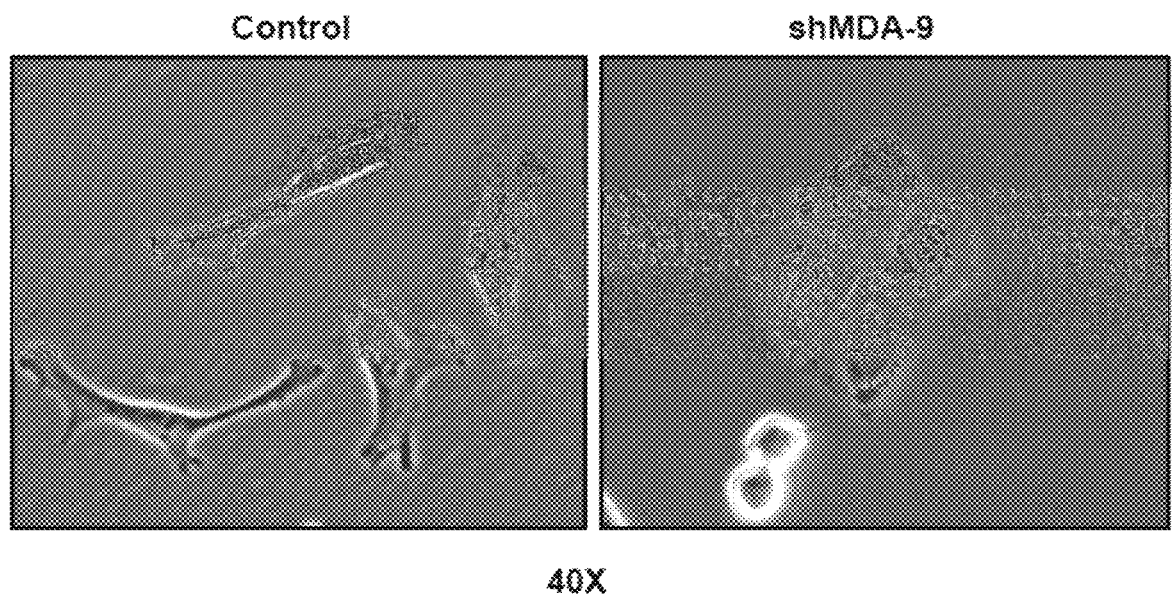
Figure 28C:
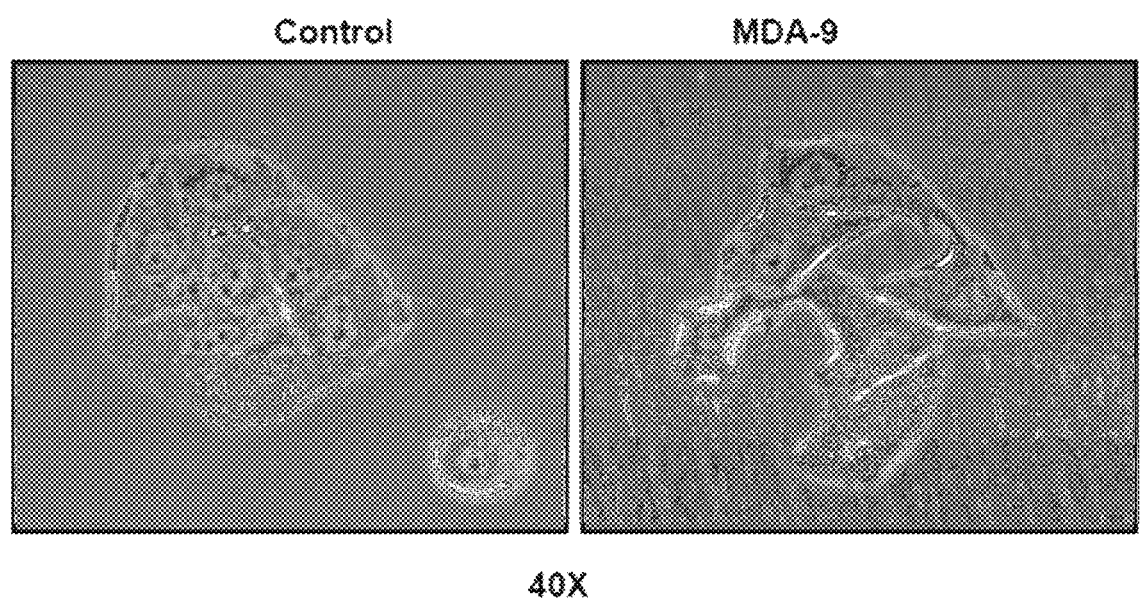

Modulating MDA-9 expression caused changes in cell shape in 2-dimensional (2D) culture conditions on plastic plates. Silencing the expression of MDA-9 in mesenchymal metastatic cells MDA-MB-231 and SUM159 caused the cells to appear epithelial-like (FIG. 28). Conversely, the epithelial T47D cells transitioned to a more mesenchymal phenotype following over expression of MDA-9 in 2D-culture. Next, the effects of modulating MDA-9 in cells grown in 3-dimensional (3D) culture conditions were assessed. Growing mammary epithelial cells in 3D-culture on a reconstituted basement membrane causes the cells to form spheroids that recapitulate several aspects of glandular architecture in vivo [23]. MDA-9 silenced cells formed compact spherical structures (spheroids) and lacked the invasive structures produced by the non-targeted control cells (FIG. 22A). This indicates that MDA-9 silenced cells lose their ability to invade into the basement membrane and surrounding matrix. Conversely, when grown in 3D-culture conditions, unlike the compact spheroids observed in T47D control cells, T47D cells overexpressing MDA-9 produced projections, indicative of an increased ability to invade the basement membrane and surrounding matrix (FIG. 22A).

Modulating the Expression of MDA-9 in Breast Cancer Cells Correlates with Changes in EMT.

Figure 22B:
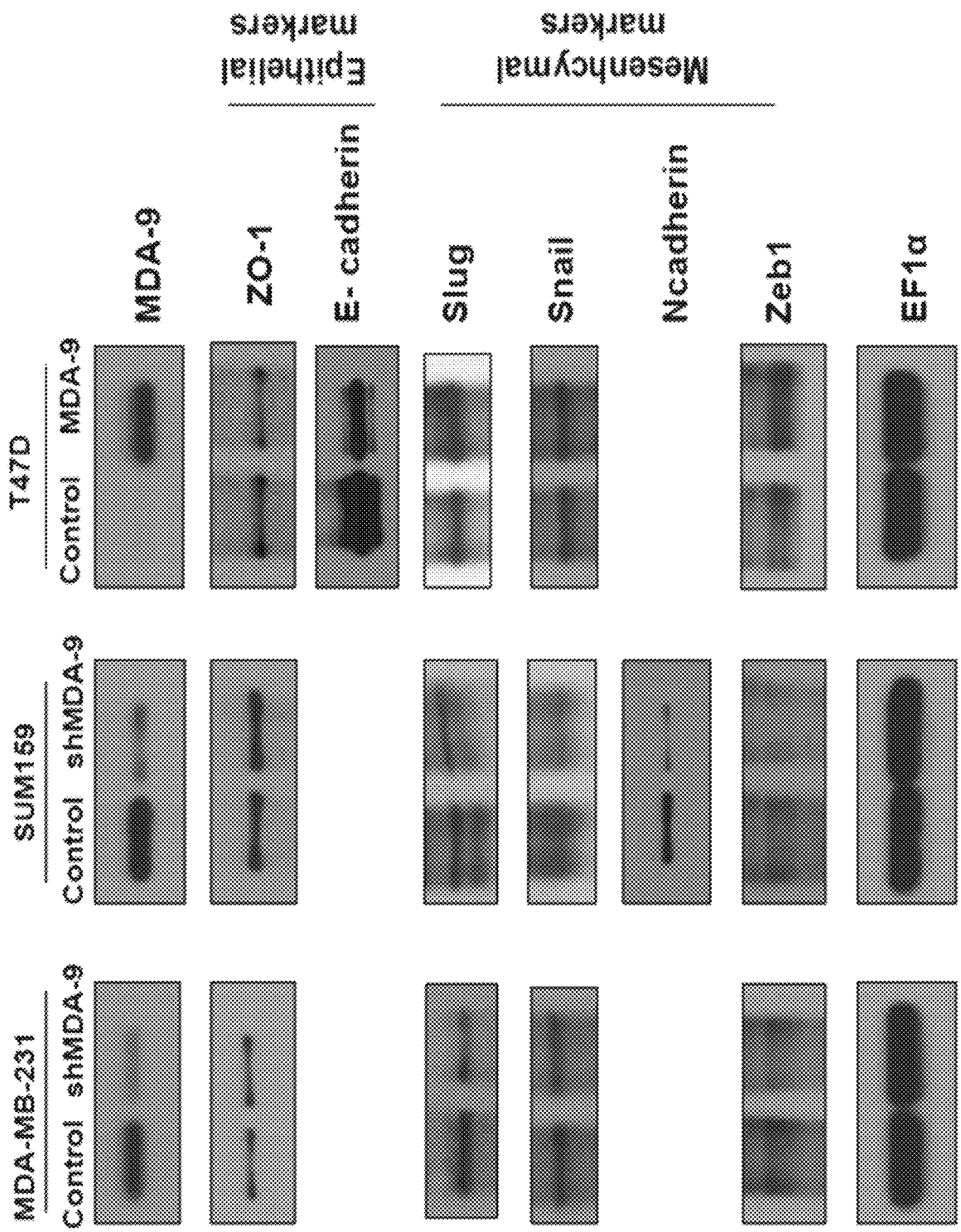

Recent studies have identified EMT as the mechanism by which non-motile epithelial cancer cells progress towards more aggressive motile and invasive mesenchymal cells [1, 4]. Since MDA-9 enhanced invasive abilities and we observed a change in cell morphology both in 2D- and 3D-culture upon modulating the expression of MDA-9, which is indicative of EMT, we evaluated the role of MDA-9 in EMT and assessed the expression of several EMT markers in MDA-9 silenced metastatic breast cancer cells and MDA-9 overexpressing non-metastatic breast cancer cells (FIG. 22B). Silencing the expression of MDA-9 caused a reduction in mesenchymal markers Slug, Snail and Zeb1 in both MDA-MB-231 and SUM159 cells. N-cadherin was also decreased in SUM159 cells. MDA-MB-231 cells are N-cadherin negative [24]. There was a slight increase in the epithelial marker ZO-1. Both SUM159 and MDA-MB-231 cells are E-cadherin negative [24]. Conversely, overexpressing MDA-9 in T47D cells resulted in a decrease in epithelial markers E-cadherin and ZO-1 and an increase in mesenchymal markers Slug, Snail and Zeb1. T47D cells are N-cadherin negative [25].

MDA-9 Modulates the Small Rho GTPases RhoA and Cdc42 and Enhances Invasion and Cyloskeletal Rearrangement Via TGFβ1.

Since the Rho family GTPases, RhoA and Cdc42, are known modulators of the actin cytoskeleton and play a vital role in EMT and metastasis in breast cancer [1, 26-28], we assessed the activity of these GTPases following MDA-9 modulation. We found that the active levels of RhoA and Cdc42 were downregulated when MDA-9 expression was silenced, while the active levels of RhoA and cdc42 were upregulated when MDA-9 was over expressed (FIGS. 23A-23C—first two bars on each of the graphs).

Figure 23D:
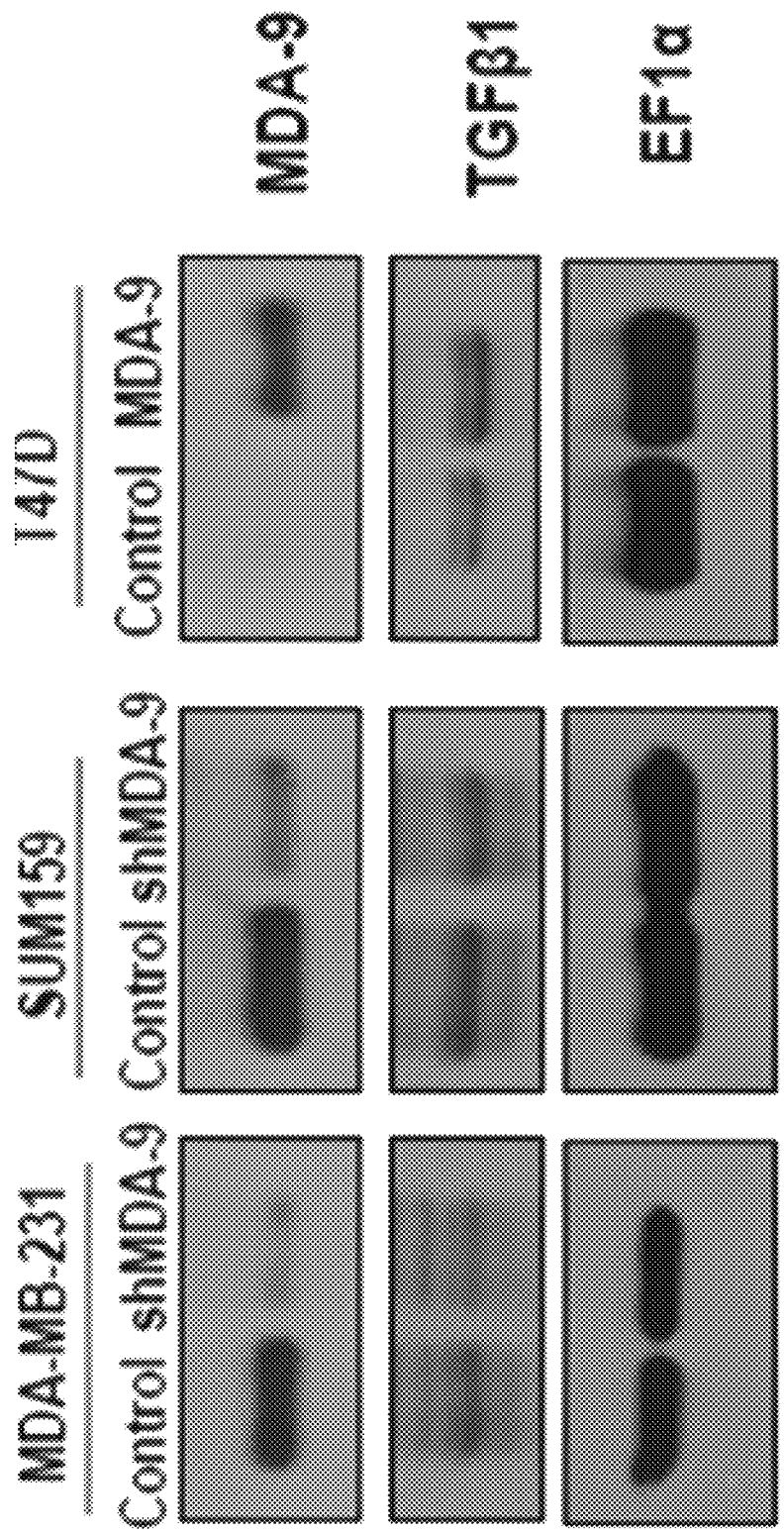
Figure 24A:
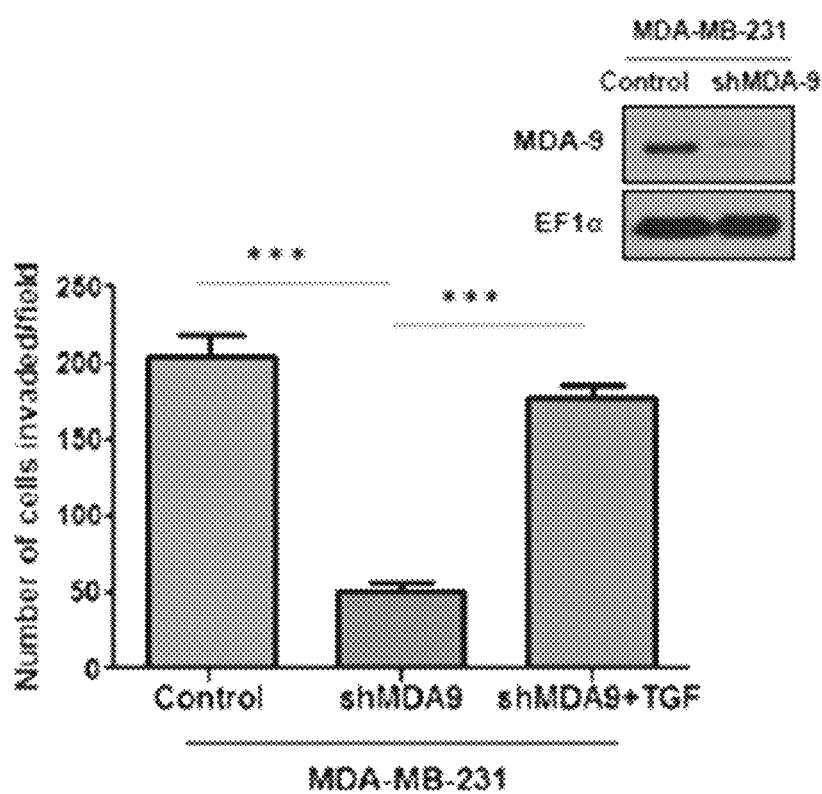
FIGS. 24A-24C. TGFβ1 modulation in MDA-9 modulated cells regulates invasion and cytoskeletal rearrangement. Graphical representation of the invasion assay results and representative images showing cytoskeletal rearrangement upon re-introduction of TGFβ1 in MDA-9 silenced MDA-MB-231 (FIG. 24A) and SUM159 (FIG. 24B) cells. Inset: western blots showing efficient silencing of MDA-9.
Figure 24B:
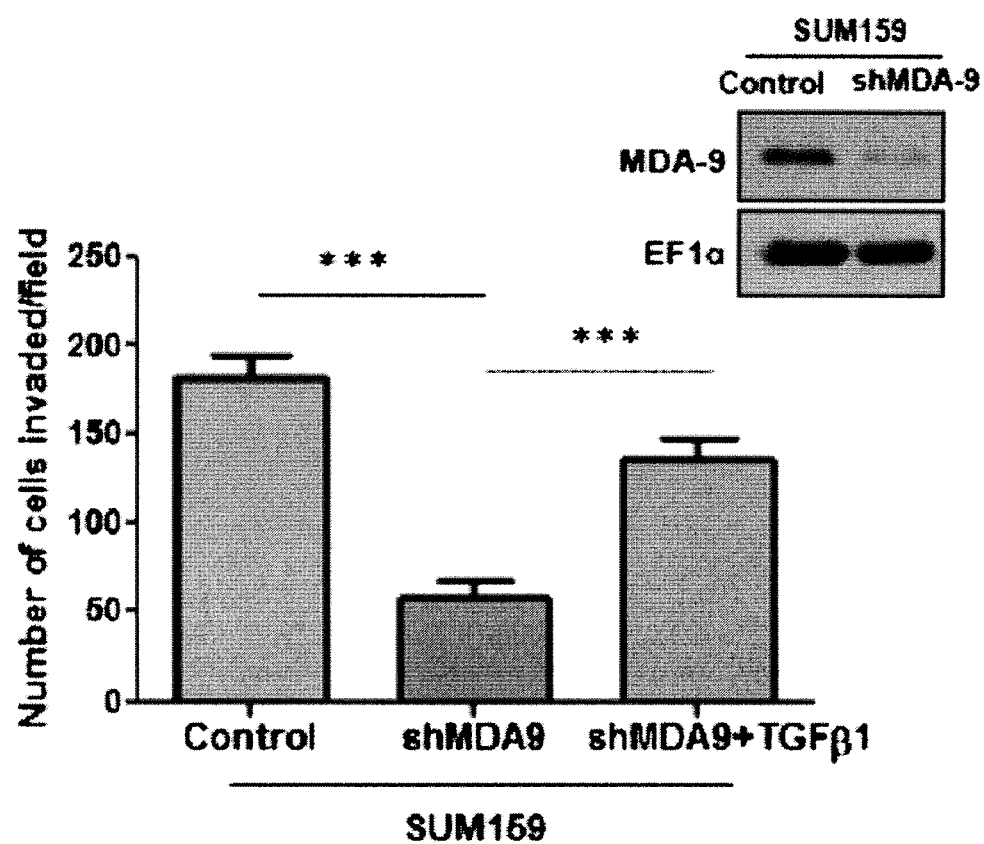
Figure 24C:
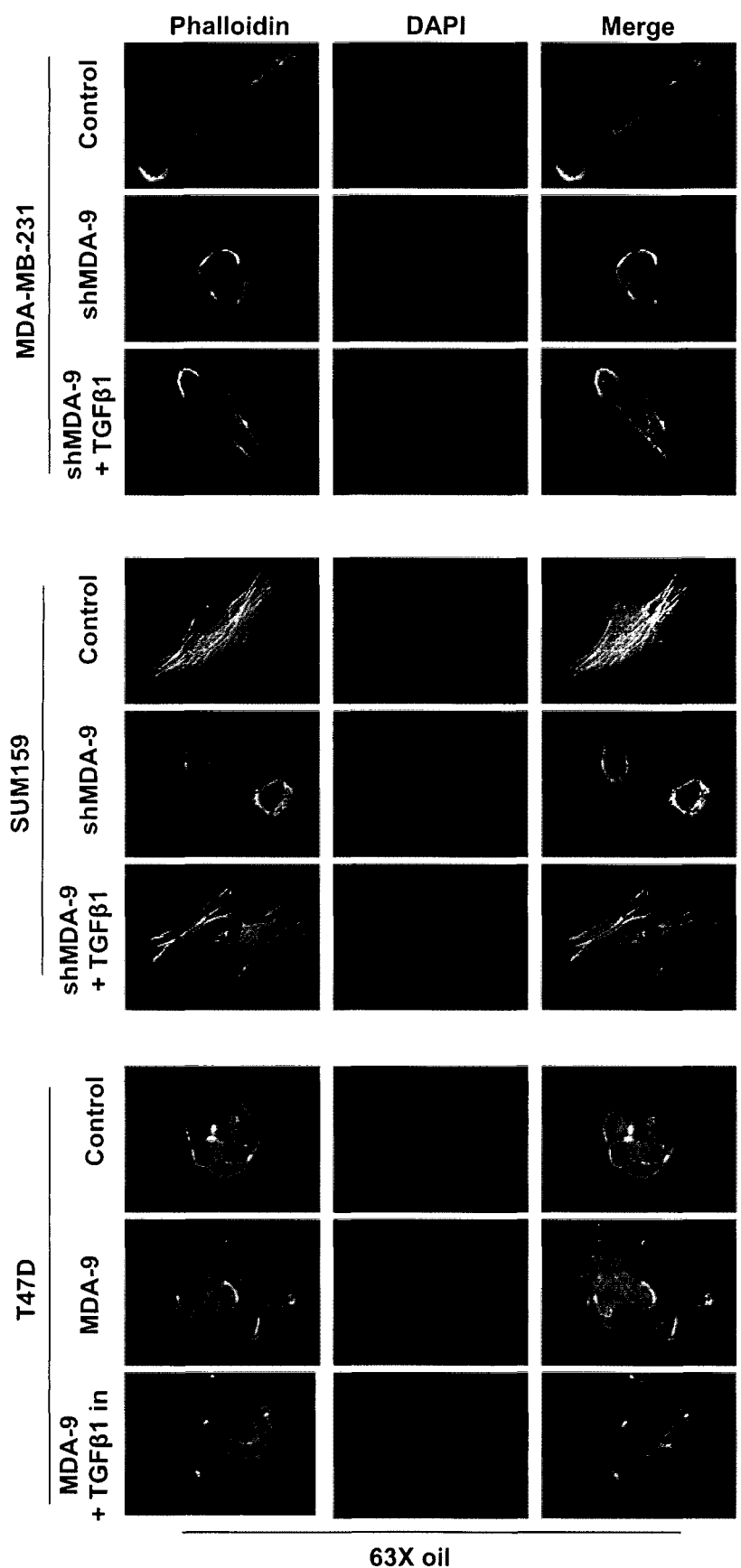

One of the key modulators of RhoA and Cdc42 is TGFβ1 [29, 30]. To determine whether MDA-9/syntenin might regulate TGFβ1 to modulate RhoA and Cdc42 expression we assessed the expression levels of TGFβ1. We found that TGFβ1 levels were downregulated when MDA-9 expression was silenced while TGFβ1 levels were upregulated when MDA-9 was overexpressed (FIG. 23D). To determine whether MDA-9 mediates its effects on RhoA and Cdc42 via TGFβ1, we re-introduced TGFβ1 in MDA-9 silenced cells and assessed active RhoA and Cdc42 levels (FIGS. 23A-23B). Similarly, we inhibited TGFβ1 in T47D cells overexpressing MDA-9 and assessed the expression of RhoA and Cdc42 (FIG. 23C). To further validate these findings in relation to the role of MDA-9 in invasion, we found that re-introducing TGFβ1 in MDA-9 silenced cells restored the invasive abilities of MDA-MB-231 and SUM159 cells and caused cytoskeletal rearrangement (FIGS. 24A-24B). Conversely, inhibiting TGFβ1 expression in MDA-9 overexpressing cells resulted in a decrease in invasive abilities and cytoskeletal rearrangement (FIG. 24C).

PDZ1 Domain of MDA-9 Interacts with TGFβ1.

Figure 29:
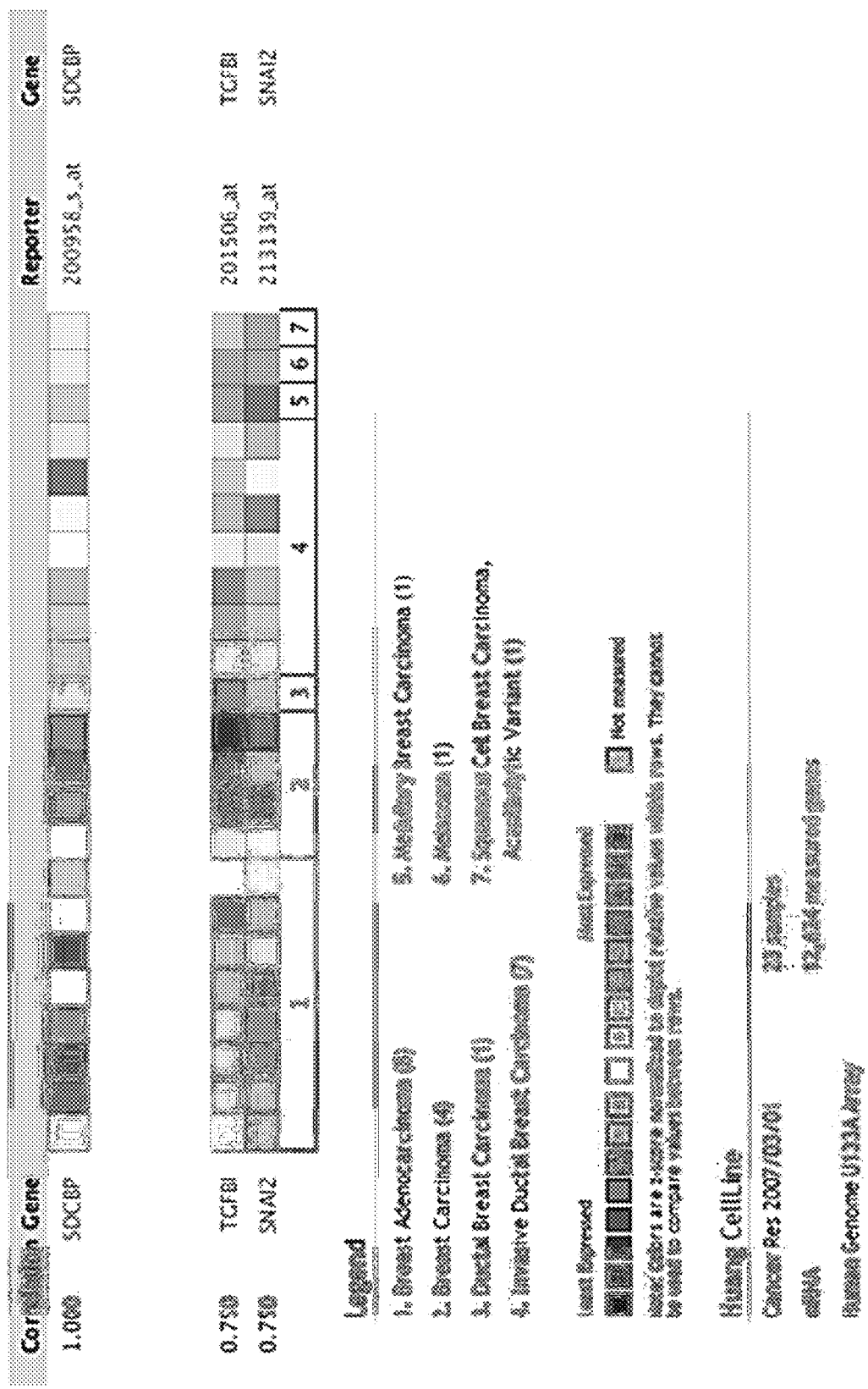
FIG. 29. MDA-9 and TGFβ1 are co-expressed in breast cancer patient samples. Correlation data from TCGA database in Oncomine demonstrating that MDA-9, TGFβ1 and SNAI2 (also known as Slug, a key EMT marker) genes are coexpressed in breast cancer patient samples.

Next, we endeavored to determine how MDA-9 regulates TGFβ1. To assess whether MDA-9 regulates the transcription of TGFβ1, we performed luciferase reporter assays using TGFβ1 promoter luciferase constructs, but did not find an increase in luciferase reporter activity. This indicates that MDA-9 did not regulate TGFβ1 at the transcriptional level. We searched the Oncomine database to determine any association between MDA-9 and TGFβ1 in breast cancer patient populations. Interestingly, we found a dataset that showed that MDA-9 and TGFβ1 were co-expressed in a set of breast cancer patients (FIG. 29). We also found that Slug (SNAI2), a well-known EMT-inducing transcription factor, was also co-expressed with MDA-9 and TGFβ13, further supporting our overall hypothesis. Next we determined the DNA copy number of TGFβ1 in the same breast cancer patient cohort that was assessed for MDA-9 DNA copy number in FIG. 27 (FIG. 30). We observed an association between the DNA copy numbers of MDA-9 and TGFβ1 in the breast cancer patient samples.

Figure 25A:
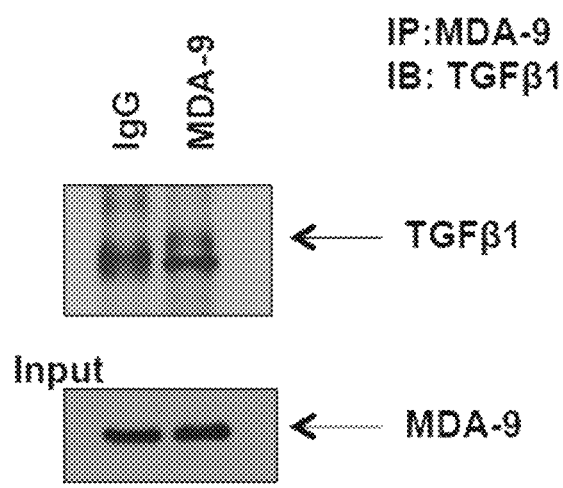
FIGS. 25A-25D. MDA-9 interacts with TGFβ1.
Figure 25B:
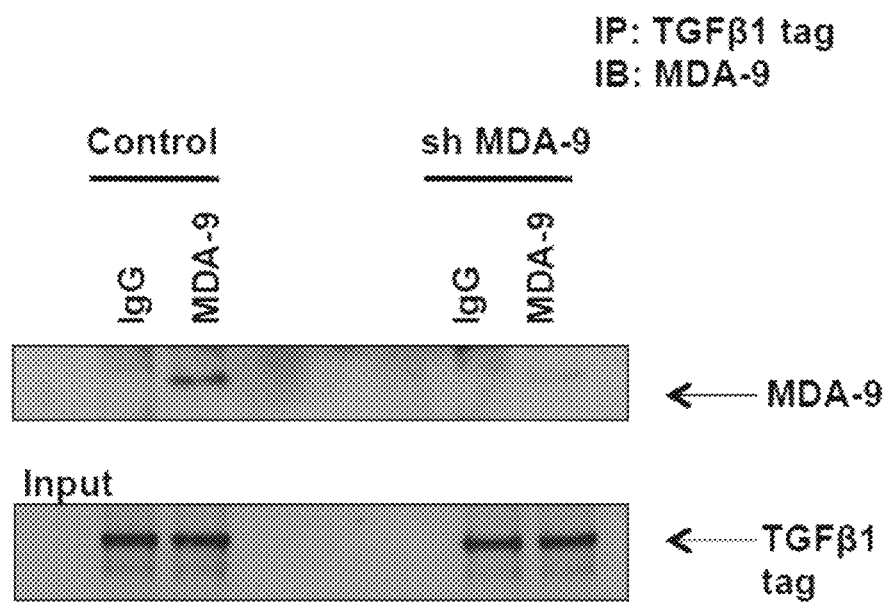
Figure 25C:
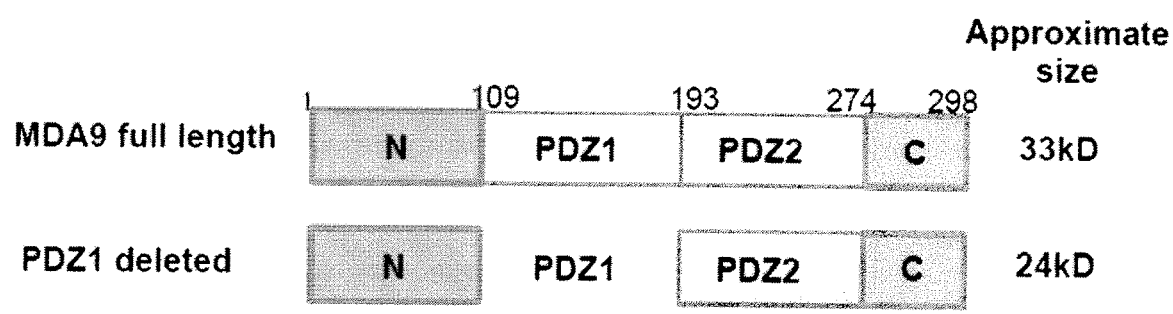
Figure 25D:
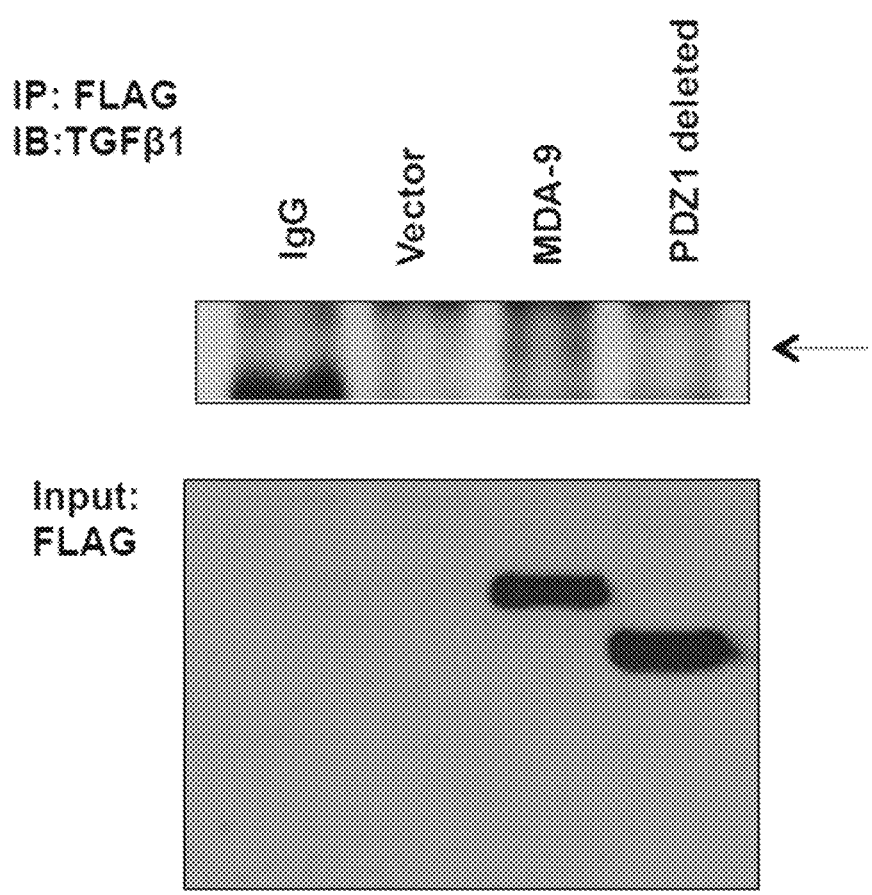

To validate these findings, we performed coimmunoprecipitation assays and determined that MDA-9 physically interacted with TGFβ1. First, we performed immunoprecipitation in SUM159 cells using the MDA-9 antibody and immunoblotted with the TGFβ1 antibody and found that MDA-9 interacts with TGFβ1 (FIG. 25A). Next we performed immunoprecipitation in SUM159 control cells overexpressing TGFβ1 and SUM159 cells silenced for MDA-9 expression and overexpressing TGFβ1 in order to easily pull down TGFβ1 using the TGFβ3 tag and immunoblotted using the MDA-9 antibody and found that MDA-9 interacted with TGFβ1 (FIG. 25B). The MDA-9-TGFβ1 interaction was decreased in MDA-9 silenced cells, further validating our observations. Next, we determined the region of MDA-9 that was involved in the interaction with TGFβ1. FIG. 25C shows the full length MDA-9 construct and a PDZ1 deleted version of MDA-9. Deletion of the PDZ1 domain disrupts the interaction between MDA-9 and TGFβ1 (FIG. 25D). This indicates that the PDZ1 domain is essential for its interaction with TGFβ1.

Figure 26A:
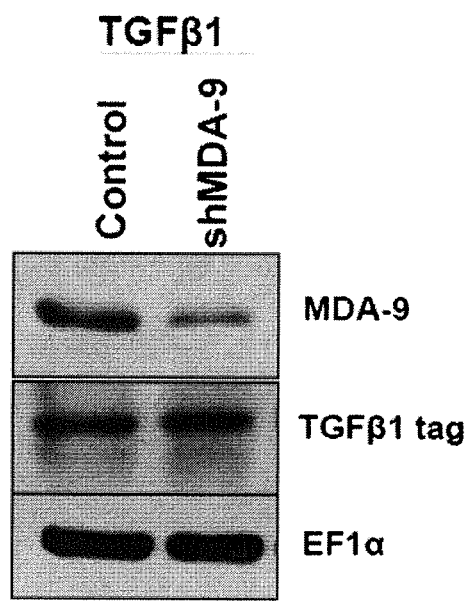
FIGS. 26A-26G. Silencing MDA-9 causes a reduction in lung metastasis, which can be rescued by restoration of TGFβ1 expression.
Figure 26B:
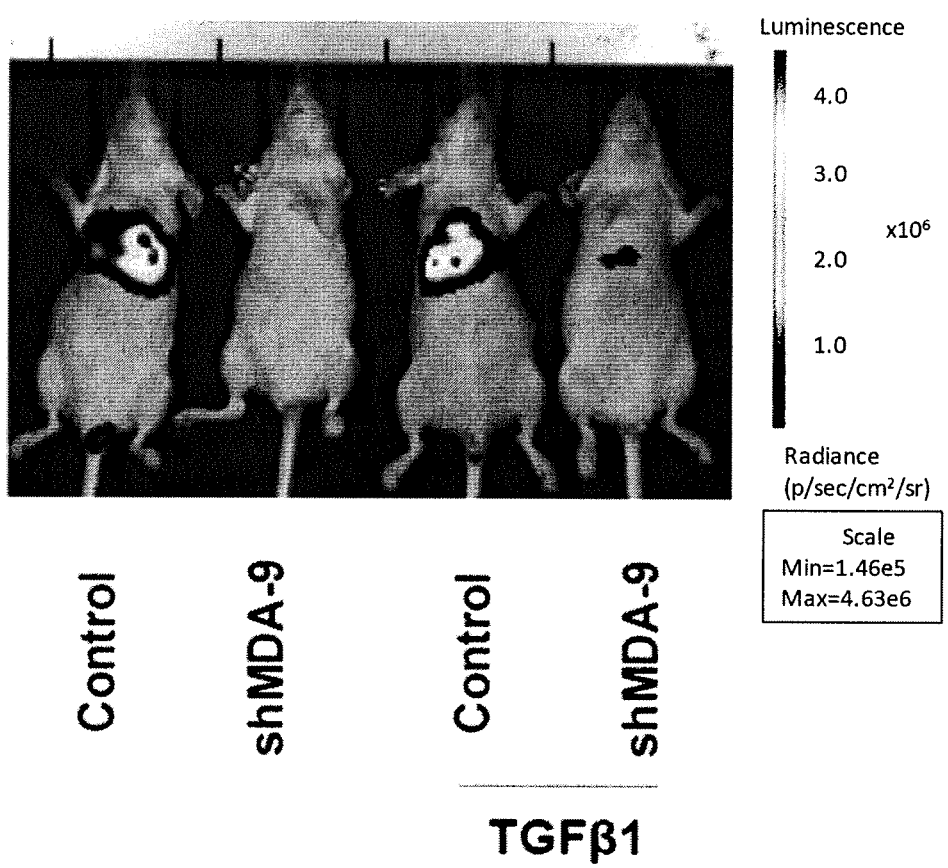
Figure 26C:
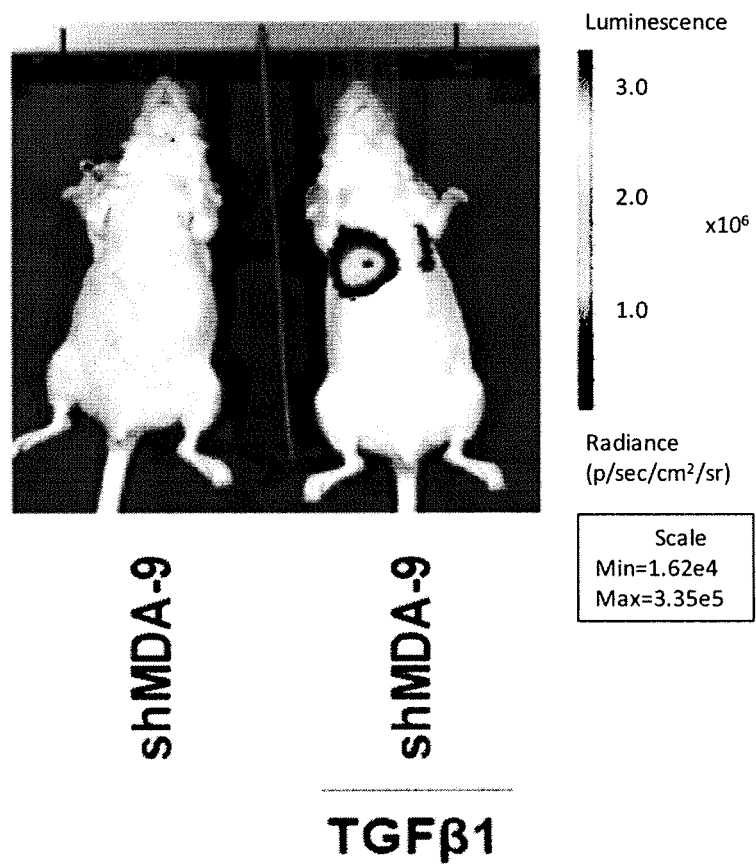
Figure 26D:
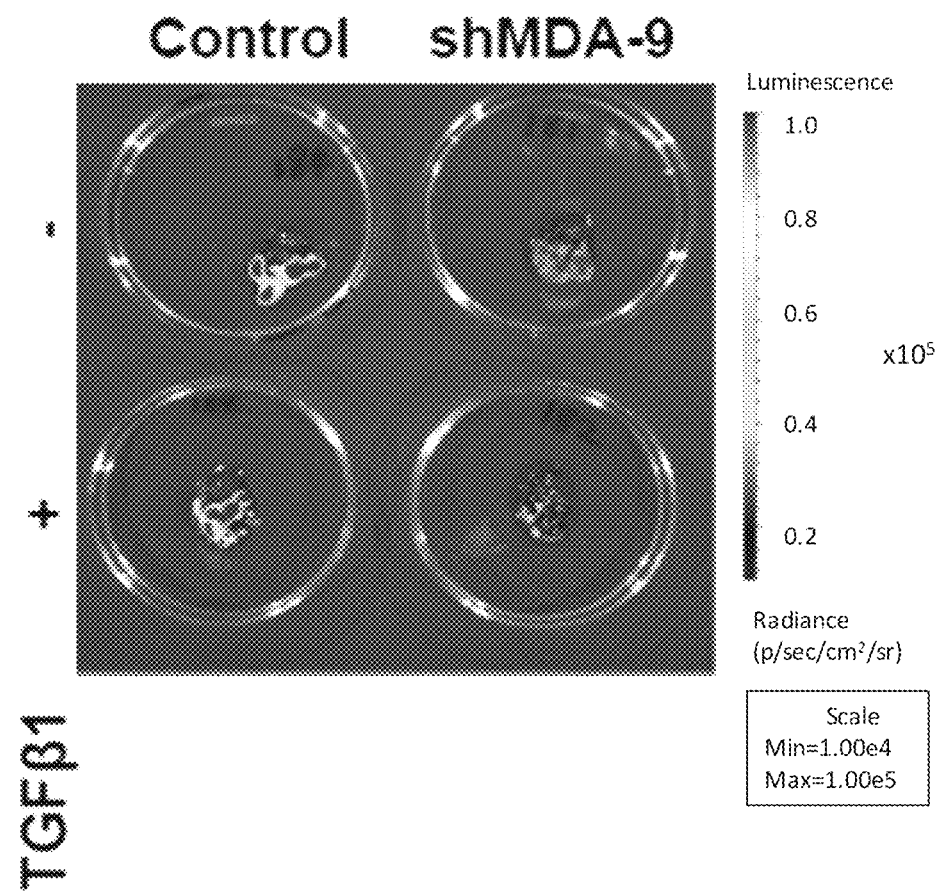
Figure 26E:
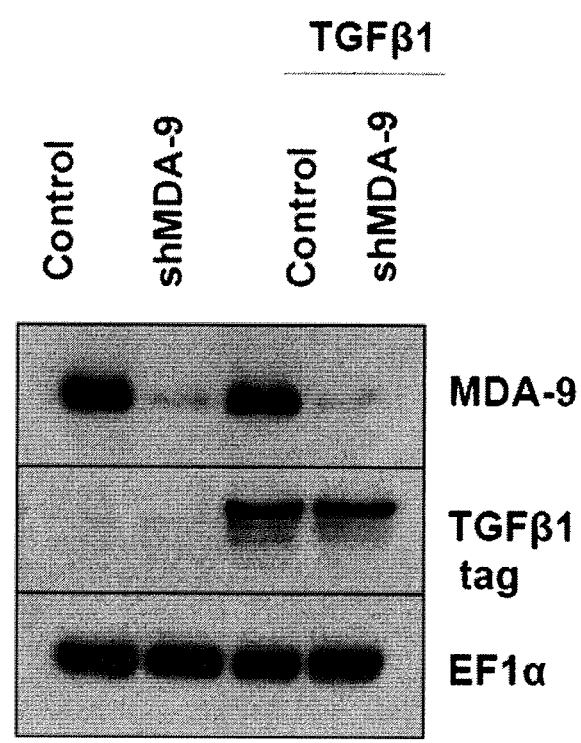
Figure 26F:
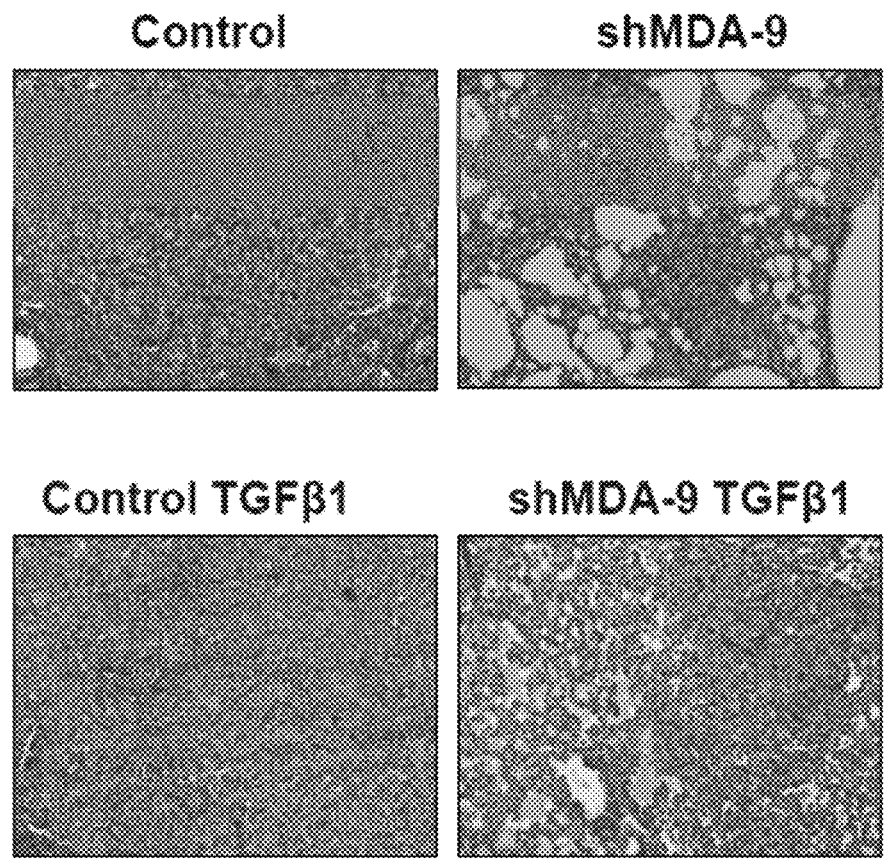

Silencing the expression of MDA-9 in metastatic breast cancer cells causes a decrease in lung metastases in vivo, which could be partially reversed by TGFβ1 restoration. To further validate our findings that MDA-9 was able to enhance the metastatic potential of breast cancer, we performed in vivo lung metastasis studies. We developed MDA-MB-231 control, MDA-MB-231 shMDA-9, MDA-MB-231 control TGFβ1 and MDA-MB-231 shMDA-9 TGFβ11 cells stably expressing luciferase (FIG. 26A). By incorporating luciferase into these MDA-MB-231 cell lines we were able to monitor development of lung metastasis via bioluminescent imaging (BLI). MDA-MB-231 control luciferase cells were able to colonize the lungs and establish metastases following introduction into athymic mice intravenously via the tail vein (FIG. 26B). MDA-MB-231 shMDA-9 luciferase cells however showed a dramatic reduction in the ability to colonize and establish metastases in the lungs. As would be expected, MDA-MB-231 control TGFβ1 luciferase cells were also able to colonize the lungs and establish lung metastases. Importantly, re-expressing TGFβ1 in MDA-MB-231 cells silenced for the expression of MDA-9 caused a partial restoration of lung metastases (FIGS. 26C-26D). Further, tumor cells were harvested from the lung metastases that developed in the athymic mice and re-grown in culture. These cells were evaluated for expression of MDA-9 and TGFβ11. MDA-MB-231 cells that were silenced for MDA-9 expression continued to show very low MDA-9 expression and TGFβ1 expressing cells showed TGFβ11 expression (FIG. 26E). FIG. 26F shows H&E staining of the tumor sections showing presence of lung metastases. The entire lungs were colonized by both MDA-MB-231 control luciferase cells and MDA-MB-231 control TGFβ1 luciferase cells. However only a few small lung metastases were observed in the H&E sections of the lungs injected with MDA-MB-231 shMDA-9 cells. Re-expressing TGFβ1 in MDA-MB-231 cells allowed these cells to form larger lung metastatic lesions as observed in the H&E section.

While widespread awareness regarding breast cancer has facilitated early detection and improved overall patient outcomes, patient prognosis is adversely affected when breast cancer metastasizes to distant areas in the body. Hence, identifying novel therapeutic targets that inhibit EMT and metastasis are key elements in effectively targeting metastatic breast cancer. We report here that MDA-9 is upregulated in breast cancer as well as metastases and plays a key role in EMT induction in breast cancer cells. We further provide detailed mechanistic insights into the signaling mediated by MDA-9 to enhance EMT.

MDA-9 is a scaffold protein with multiple diverse roles in tumorigenesis, particularly, in tumor invasion and metastasis. MDA-9 was found to be over expressed in a number of human cancers including melanoma [10-12], gastric cancer [13], bladder cancer [14], glioblastoma [15], small cell lung cancer [16], hepatoma [17], head and neck cancers [18] and breast cancer [19]. Due to its seminal role in several cancers, researchers have focused on dissecting the signaling mechanisms regulated by MDA-9. In the various cancer types evaluated, MDA-9 orchestrates cancer attributes via its interaction with key binding partners including several oncogenic proteins [9, 31]. In melanoma cells, MDA-9 colocalizes with focal adhesion kinase (FAK), a key component of integrin-mediated signaling pathways, and increased phosphorylation of FAK, c-Jun-NH2-kinase (JNK) and p38 MAPK [10]. MDA-9 was also shown to interact with c-Src, which enhanced FAK/c-Src complex formation and activated c-Src [11]. Studies using glioblastoma cells also showed that MDA-9 increased the activation of c-Src, p38 MAPK and nuclear factor kappa B (NF-□B), which enhanced expression of matrix metalloproteinase 2 (MMP2) and the secretion of interleukin-8 (IL-8) [15]. In urothelial cancer cells, MDA-9 interacts with EGFR and enhanced the expression of EGFR, AKT, phosphoinositide 3-kinase (PI3K) and c-Src [14]. In head and neck squamous cell carcinoma, MDA-9 colocalized with VEGFR1 and regulated the expression of SPRR1B and VEGFR1. Growth regulatory molecules including Cyclin D1, CDK4, STAT3, PI3K and CTNNB1 were also modulated by MDA-9 [18].

The detailed mechanism by which MDA-9 regulates invasion and metastasis of breast cancer remains largely unknown. The findings from our study provide insights into the signaling mechanisms regulated by MDA-9 in breast cancer. We show that MDA-9 expression correlated with invasiveness and metastatic capabilities of breast cancer cells. Loss-of-function and gain-of-function studies confirmed the relevance of MDA-9 in EMT, invasion and cytoskeletal rearrangement and helped elucidate the molecular mechanisms of action of MDA-9. We demonstrate that MDA-9 regulates the small GTPases RhoA and Cdc42 via TGFβ1. Researchers have shown that treating prostate cancer cells with TGFβ1 induced rapid formation of lamellipodia and cytoskeletal rearrangements [32]. Importantly, this response to TGFβ1 was independent of canonical Smad signaling and required the activity of small Rho GTPases Cdc42 and RhoA [32]. This study, albeit in a different cancer indication, supports our findings and suggest that MDA-9 could act upstream of TGFβ1 to mediate cytoskeletal rearrangements.

We further show that MDA-9 could interact with TGFβ1. We also observed that MDA-9 and TGFβ1 were co-expressed in breast cancer patient samples in the TCGA database using Oncomine (FIG. 29). Re-introducing TGFβ1 in MDA-9-silenced cells caused a partial restoration of invasive abilities. Similarly, restoring TGFβ1 expression in MDA-9-silenced cells caused a partial restoration of lung metastases in vivo. Interestingly, a study in A549 lung carcinoma cells showed that MDA-9 might also prevent caveolin-1-mediated internalization of TGFβ1 leading to enhanced canonical TGFβ1 signaling [33]. These findings provide evidence for another layer of regulation of TGFβ1 signaling by MDA-9 supporting our overall hypothesis. MDA-9 is a known scaffold protein and the MDA-9-TGFβ1 interaction might also serve to stabilize the TGFβ1 protein. Further investigation into the mechanism by which MDA-9 regulates TGFβ1 is ongoing. We also observed that MDA-9 and Slug (SNAI2) were co-expressed in breast cancer patient samples in the TCGA database using Oncomine (FIG. 29). A very recent study in lung adenocarcinoma showed that MDA-9 interacts with Slug and regulates invasion and metastasis, further validating our findings [34]. Further, studies have identified a link between triple negative breast tumors and the occurrence of EMT [35, 36]. From the observations in FIG. 20B and FIG. 20C and the understanding we have gained regarding the role of MDA-9 in breast cancer in this paper, one can speculate that there might be an association between the expression of MDA-9 and triple negative breast cancer.

Figure 26G:
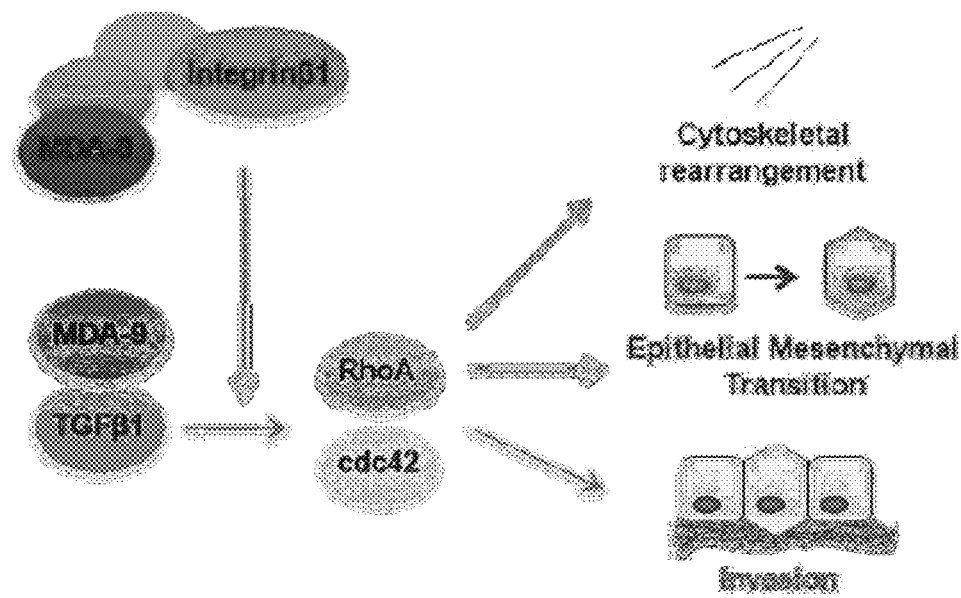
Figure 31A:
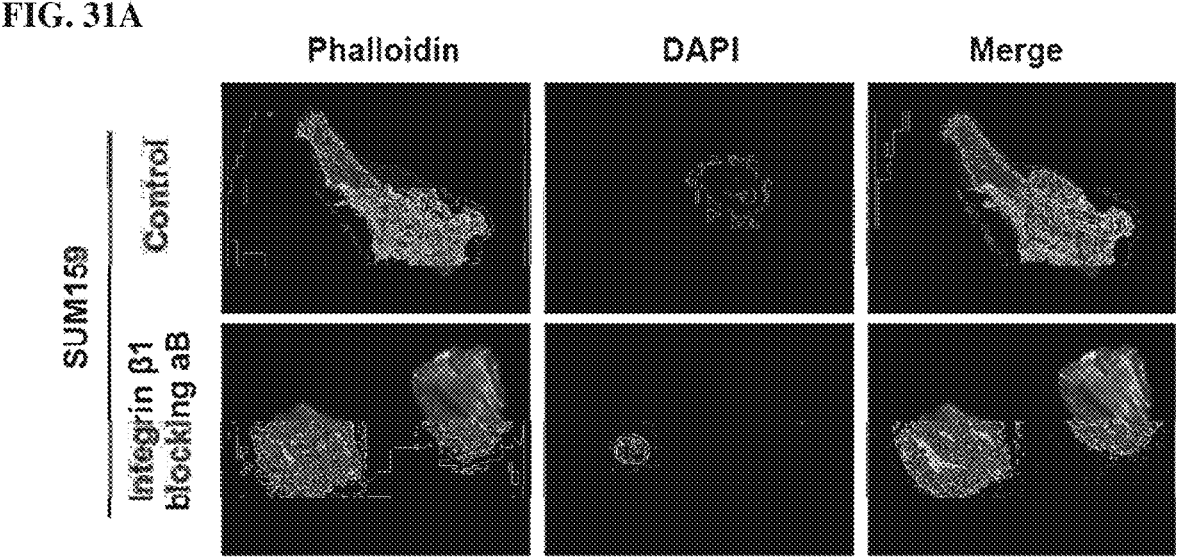
FIGS. 31A-31B. Integrin β1 regulates cytoskeletal reorganization.
Figure 31B:
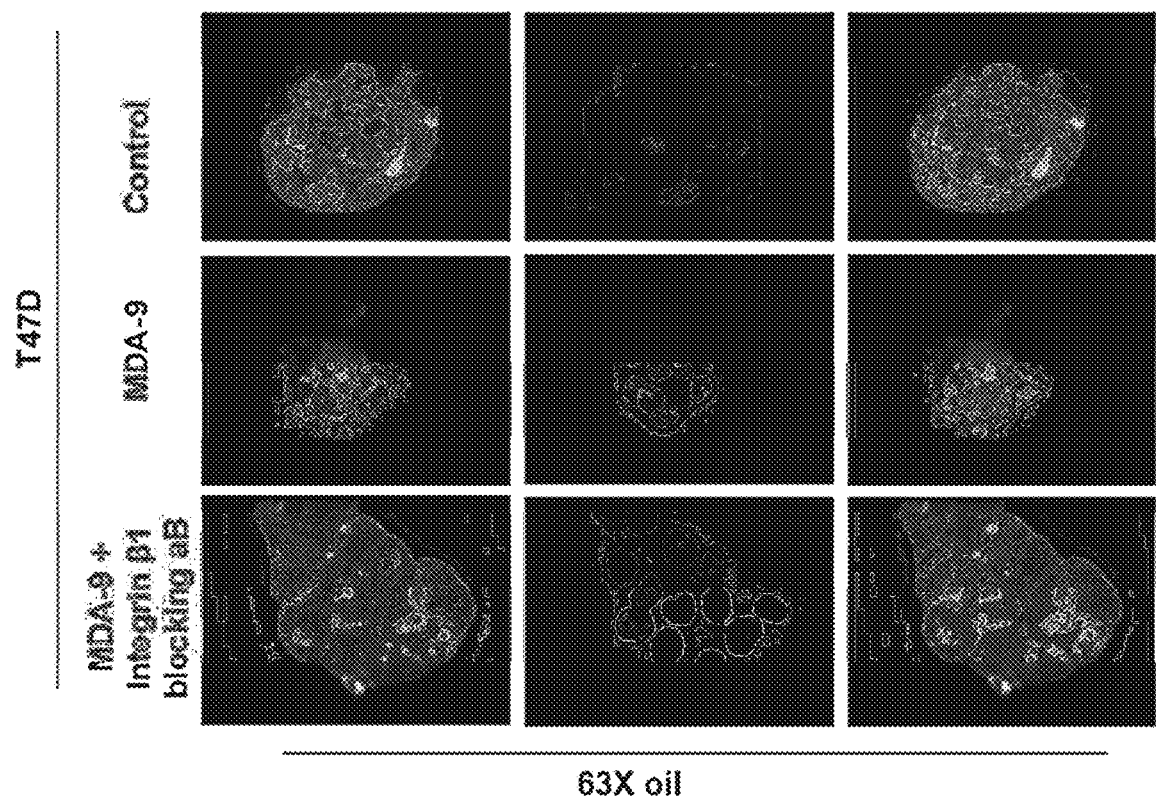

Interestingly, integrin β1 has been shown to play a role in aiding TGFβ1-mediated non-canonical signaling including downstream RhoA and Cdc42 signaling [37]. Additionally, MDA-9 was shown to play a key role in stabilizing integrin β1 signaling complexes [38]. Hence, we wondered whether integrin β1 might also be involved in this MDA-9-TGFβ1 signaling axis. The role of the extracellular matrix, comprised of integrins, cannot be ignored when trying to understand tumor attributes such as invasion [39]. In fact, integrins are key players that enhance breast cancer invasion and metastasis [40, 41] and integrin β1 plays a key role in metastatic progression of breast cancer [42-44]. Hence we added an integrin β1 blocking antibody to SUM159 cells and assessed cytoskeletal rearrangement (FIG. 31A). Addition of integrin β1 blocking antibody caused a change in cytoskeletal organization. Next, we added an integrin β1 blocking antibody to T47D cells overexpressing MDA-9 and observed a change in cytoskeletal organization (FIG. 31B). Our observations and previous studies indicate that integrin β1 might also be involved in MDA-9 mediated regulation of the small GTPases RhoA and Cdc42. This finding is consistent with published reports that show that MDA-9 plays a key role in the assembly of integrin β1 signaling complexes and that silencing the expression of MDA-9 impaired assembly/formation of several integrin β1 signaling complexes [38, 45]. Additionally, silencing the expression MDA-9 also resulted in inhibition of active integrin β1 expression (and downstream phosphorylation of ERK1/2) in breast cancer cells [19]. Thus, the overall signaling mechanism mediated by MDA-9 in breast cancer is illustrated in FIG. 26G.

In summary, our study has identified a novel role of MDA-9 in mediating EMT and enhancing invasive abilities in breast cancer cells. Additionally, our findings provide preclinical evidence that MDA-9 is an effective therapeutic target against breast cancer including metastatic breast cancer.

Materials and Methods

Cell lines and cell culture. Human breast cancer cells T47D, ZR-75-1, SKBR3, BT-20, MDA-MB-468 and MDA-MB-231 were purchased from the American Type Culture Collection (ATCC) (Manassas, Va.) and cultured as recommended by ATCC. T47D, ZR-75-1 and SKBR3 are epithelial cells with low invasive and metastatic ability. BT-20 and MDA-MB-468 are moderately invasive and metastatic. MDA-MB-231 is a highly invasive and metastatic triple negative mesenchymal breast cancer cell line [46, 47]. Human breast cancer cells SUM159PT (labeled SUM159 throughout) were purchased from Asterand, Inc. (Detroit, Mich.). These cells were cultured in F-12 media supplemented with 5% fetal bovine serum, 10 mM HEPES buffer, 5 µg/ml insulin, 1 µg/ml hydrocortisone and 1% Penicillin/Streptomycin. SUM159 cells are triple negative with strong abilities to invade and metastasize [48]. ATCC authenticates these cell lines using short tandem repeat analysis. All the cell lines were expanded and frozen immediately after receipt. The cumulative culture length of the cells was less than 6 months after recovery. Early passage cells were used for all experiments. All the cell lines were frequently tested for mycoplasma contamination using a mycoplasma detection kit from Sigma. All of the cells were maintained at 37° C. with 5% $CO_2$ in a humidified atmosphere.

Breast Cancer Tissue Microarray.

Tissue microarray comprised of breast cancer samples along with metastatic and normal counterpart tissue samples was purchased from Imgenex (San Diego, Calif.). Immunohistochemistry was performed according to standard protocols. Briefly, tumor sections were deparaffinized at 60° C. for 1 hour, followed by rehydration, and antigen retrieval using citrate buffer and heating. Avidin and biotin blocking kits and Vectastain ABC complex kits were obtained from Vector Laboratories (Burlingame, Calif.). IHC-grade Prestige MDA-9 antibody was purchased from Sigma (St. Louis, Mo.). Secondary antibodies were obtained from Jackson Immunoresearch (West Grove, Pa.). The slides were counter-stained using hematoxylin. Following staining, slides were dehydrated and mounted using Vectashield mounting media (Vector Laboratories).

Preparation of Whole-Cell Lysates and Western Blotting Analysis.

Cells were washed twice with ice-cold PBS and lysed in 1× Cell Lysis buffer (Cell Signaling Technology, Danvers, Mass.) with protease and phosphatase inhibitors. The lysates were kept on ice for 1 hour and centrifuged at 10,000 rpm for 30 minutes at 4° C. Protein concentration was measured using BioRad protein assay reagent (Hercules, Calif.). Lysates corresponding to equal amounts of protein were subjected to SDS-PAGE and transferred on to PVDF membrane (0.2 µm). The membranes were blocked with 5% non-fat dried milk or bovine serum albumin (BSA) in TBST (Tris-buffered saline with 0.1% Tween 20) and incubated with primary antibodies overnight at 4° C. The membranes were then washed three times with TBST, incubated with respective secondary antibodies for 1 hour at room temperature, washed three times with TBST and then developed using ECL reagent (GE Healthcare, UK). MDA-9/syntenin antibody was from Abnova (Taiwan), β-actin was from Sigma-Aldrich (St. Louis, Mo.), EMT marker antibodies were from Cell Signaling Technologies and TGFβ1 tag antibody was from Origene (Rockville, Md.). EF 1α was used as a loading control and was obtained from EMD Millipore (Billerica, Mass.).

RNA Extraction and qRT-PCR (Quantitative Real-Time PCR).

Cells were washed with PBS and then harvested using Qiazol. RNAeasy kit (Qiagen, Germany) was used for RNA extraction according to the manufacturer's protocol. RNA was converted to cDNA using the cDNA synthesis kit (Applied Biosystems, Foster City, Calif.). The PCR primers and probes were purchased from Applied Biosystems. qRT-PCR was performed using the Applied Biosystems machine. The gene expression $\Delta C_T$ values of mRNAs from each sample were calculated by normalizing with GAPDH and relative quantification values were plotted using GraphPad Prism®.

Viruses, Plasmids and Reagents.

MDA-9 was silenced using Ad.5/3 shMDA-9 and overexpressed using Ad.5/3 MDA-9. The construction of these viruses has been described in detail previously [49]. For stably silencing the expressing of MDA-9, lentiviruses targeting MDA-9 were purchased from Sigma (St. Louis, Mo.). FLAG-tagged full length and PDZ-1 deleted constructs were obtained from TransOMIC (Huntsville, Ala.). TGFβ1 construct was obtained from Origene. Human TGFβ1 protein was obtained from BioLegend (San Diego, Calif.) and the TGFβ1 inhibitor (A83-01) was obtained from (Stemgent, San Diego, Calif.).

Invasion Assay.

Invasion assays were performed using 24-well BioCoat Matrigel™ invasion chambers (BD Biosciences, San Jose, Calif.) in triplicates according to the manufacturer's instructions. Briefly, the chambers were equilibrated to room temperature and then rehydrated using warm serum-free cell culture media for 2 hours at 37° C. Cells were seeded in serum-free media in the upper chamber and serum-containing media was used as an attractant in the lower chamber. Cells were allowed to invade through the Matrigel™ overnight. The inserts were fixed with methanol, non-invaded cells were wiped off using a cotton swab and the inserts along with the invaded cells were stained with the Diff-Quick staining kit. Cells that invaded were enumerated using at least 8 fields per insert. Data is presented as mean±S.E.M.

Phalloidin Staining.

Cells were seeded in 4-well chambered glass slides and allowed to attach overnight. The next day, the cells were fixed with 4% paraformaldehyde for 1 hour, and permeabilized with 0.01% Triton-X and 1% sodium citrate for 3 minutes on ice. The cells were blocked with 1% bovine serum albumin for 30 minutes. The actin cytoskeleton was stained using Alexa Fluor 488 Phalloidin (Life Technologies, Carlsbad, Calif.) for 30 minutes. The wells were detached from the glass slide and the slide was mounted using mounting media containing DAPI (to label cell nuclei) (Vector Laboratories).

3D (Three-Dimensional) Culture.

Glass slides (eight-well chambered; Nunc, Rochester, N.Y.) were coated with 3D Culture Matrix™ Basement Membrane Extract Reduced Growth Factor (Phenol Red-free) (Trevigen, Gaithersburg, Md.). A total of 5000 cells/well were seeded into the wells in complete medium containing 2% 3D Matrix and the media was replenished every 4 days. The slides were incubated at 37° C., humidified with 5% $CO_2$ atmosphere [23, 50].

GTPase Activity Assay.

The RhoA G-LISA and Cdc42 G-LISA activation assay biochem kits were obtained from Cytoskeleton Inc (Denver, Colo.) and GTPase activity was measured according to the manufacturer's instructions. Briefly, cells were cultured in serum-free media for 48 hours and lysates were prepared using the appropriate G-LISA buffers. The required number of G-LISA wells were rehydrated with ice-cold water, and then lysates, lysis buffer (negative control) and RhoA/Cdc42 control protein (positive control) were added to the wells. The plate was incubated at 4° C., followed by incubation with antigen presenting buffer, primary antibody, secondary antibody and then the HRP detection reagents. After adding the HRP stop buffer, absorbance was measured at 490 nm.

Immunoprecipitation.

Immunoprecipitation was performed using the immunoprecipitation kit with Dynabeads® Protein G (Life Technologies) according to the manufacturer's instructions. Briefly, MDA-9, TGFβ11, FLAG tag or IgG control antibody was incubated with Dynabeads® and allowed to bind. Next, protein lysates were incubated with the antigen bound Dynabeads®. Finally, the antibody-antigen complexes were eluted from the Dynabeads®, run on an SDS-PAGE gel and probed using the appropriate antibody.

In Vivo Metastasis Study.

MDA-MB-231 control cells were stably transfected with the luciferase expression plasmid pGL4.50 (Promega, Madison, Wis.) specifically engineered to aid in vivo imaging. MDA-MB-231 control cells stably expressing luciferase were selected using hygromycin. MDA-9 stably silenced cells were similarly stably transfected with the luciferase expressing plasmid. Both MDA-MB-231 control luciferase and MDA-MB-231 shMDA-9 luciferase cells were stably transfected with TGFβ1. 6-week old female athymic mice (Charles River Laboratories, Wilmington, Mass.) were injected with $1.5 \times 10^6$ cells of the above four cell lines through the tail-vein. Five female athymic mice were injected per cell line. The mice were monitored and luciferase expression was assessed by bioluminescent imaging. The mice were sacrificed after 6 weeks. A section of the lung was collected in DMEM/F-12 media supplemented with Penicillin/Streptomycin. Tumor cells were harvested from the lung metastasis by digesting the lung tissue using trypsin-EDTA. Tumor cells were collected and cultured as per normal procedures. Another section of the lungs was fixed in paraffin, sectioned and H&E stained. Animals were maintained under the guidelines of the National Institute of Health and under evaluation and approval of the Institutional Animal Care and Use Committee (Virginia Commonwealth University). Food and water were provided ad libitum.

Statistical Analysis.

Results are presented as the mean±S.E.M. for at least three individual experiments. Statistical analyses were performed using GraphPad Prism 5. Student's t-test was applied based on the statistical mandates or suggestions of each analysis. $p<0.05$ was considered statistically significant.

Example 4. Rationally Designed Small Molecule Inhibitors for Preventing & Treating Cancer Metastasis Disease complexity is a current barrier to progress in metastasis drug development. Over 400+ cancer types with genotypic heterogeneity. A 1° Genetic lesions can lead to 1000s 2° changes. Selective targeting of cancer-specific lesions is problematic. Limited drug candidates that are efficacious against advanced cancers.

Figure 32:
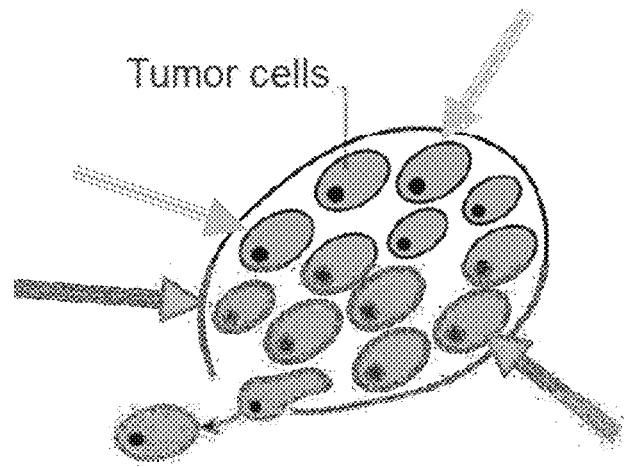
FIG. 32. Cartoon illustration of tumor cells in microenvironment navigating away from tumor microenvironment.

Hundreds of drugs are targeting tumor cells, but none are metastasis-specific. It seems like it should be easy to kill metastatic tumor cells with the current knowledge of cancer mechanisms, but it's not (FIG. 32). Cancer subtypes: 400+ and each subtype exhibits molecular and biological heterogeneity. Evolution through distinctive stages, culminating in lymph node and distant metastasis. Lesional stages can evolve through genomic rearrangement and reprogramming. Relapse and resistance are common.

Figure 33:
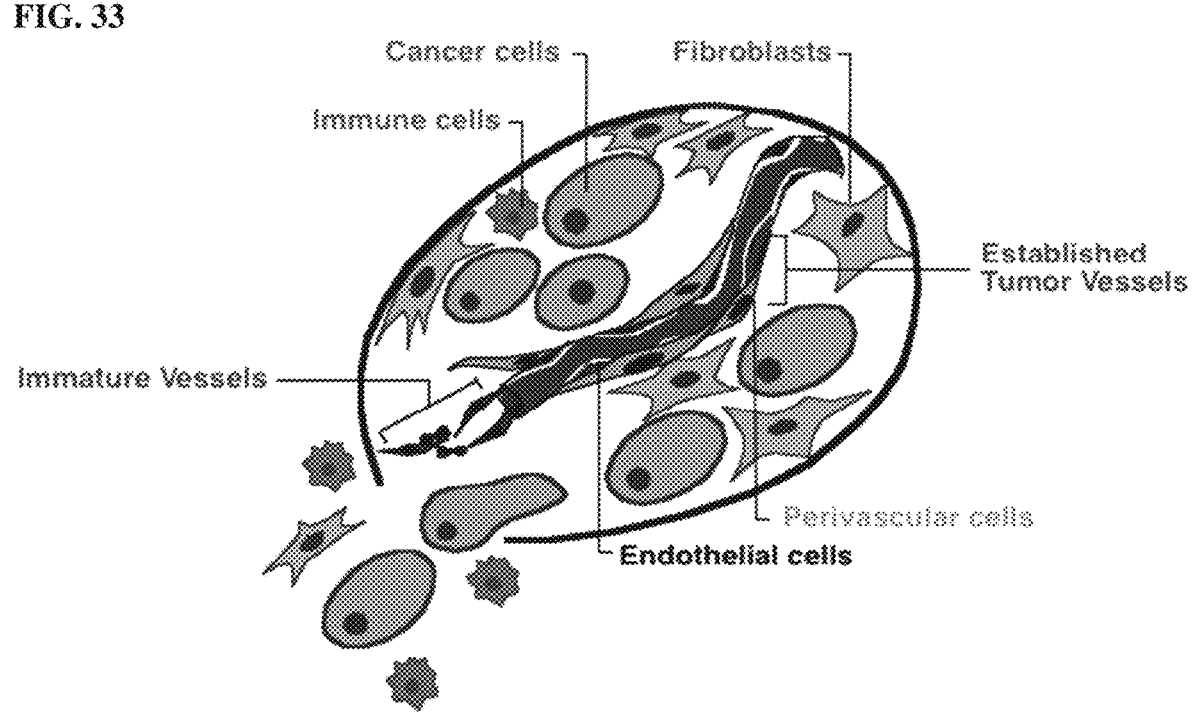
FIG. 33. Detailed cartoon illustration of the tumor microenvironment.

Opportunities for achieving durable responses against metastasis include (1.) Single and Combinatorial therapies targeting metastatic tumor cells (FIG. 33A) and (2.) Combinatorial therapies aimed at the renegade organ, targeting the tumor and its environment (FIG. 33B).

Metastatic tumors do not exist alone, they interact and coexist with multiple cell types in the microenvironment. Metastatic tumors represent complex (renegade) organ systems (FIG. 34).

There are, however, unique opportunities in cancer therapy, including targeting multiple critical steps in metastasis such as cancer cell attachment, invasion, and tumor angiogenesis. Therapies aimed at multiple cell types and steps contributing to metastasis have the greatest potential for success.

Therapies can target an essential gene mediating metastasis, MDA-9/Syntenin/SDCBP, which is a pro-metastatic gene. Targeted small molecule MDA-9 inhibitor (PDZ1i) can act to inhibit invasion, attachment, and angiogenesis. Combined with other therapies, the approach can be lethal to metastases. This represents a new therapeutic approach "Anti-Invasion Therapy."

Figure 34:
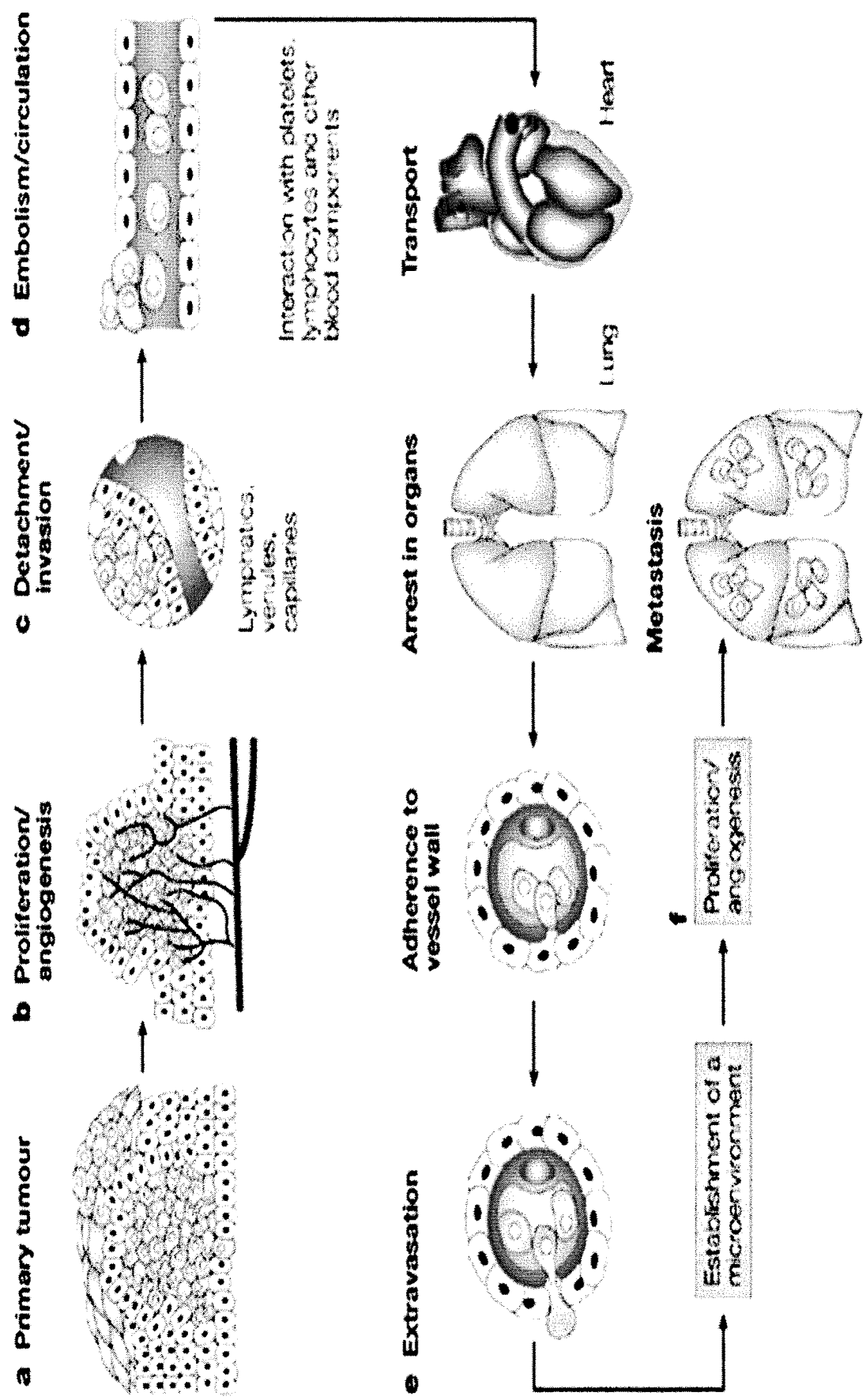
FIG. 34. Flow chart showing MDA-9 and the metastatic cascade.

Tageting multiple steps in the metastatic cascade is critical for effective therapy (FIG. 34).

We have harnessed a unique therapeutic opportunity targeting MDA-9/Syntenin/SDCBP. MDA-9/Syntenin/SDCBP is a key gene regulating multiple steps in metastasis. This gene provides a universal target for therapy in diverse cancer settings. We have developed a first in class small molecule inhibitor of MDA-9, PDZ1i. PDZ1i exhibits good PK and exciting pre-clinical data. It is contemplated that PDZ1i can also be used in combinatorial therapy, thereby creating an anti-invasion therapy converted to cytotoxic therapy in multiple cancers.

Figure 35A:
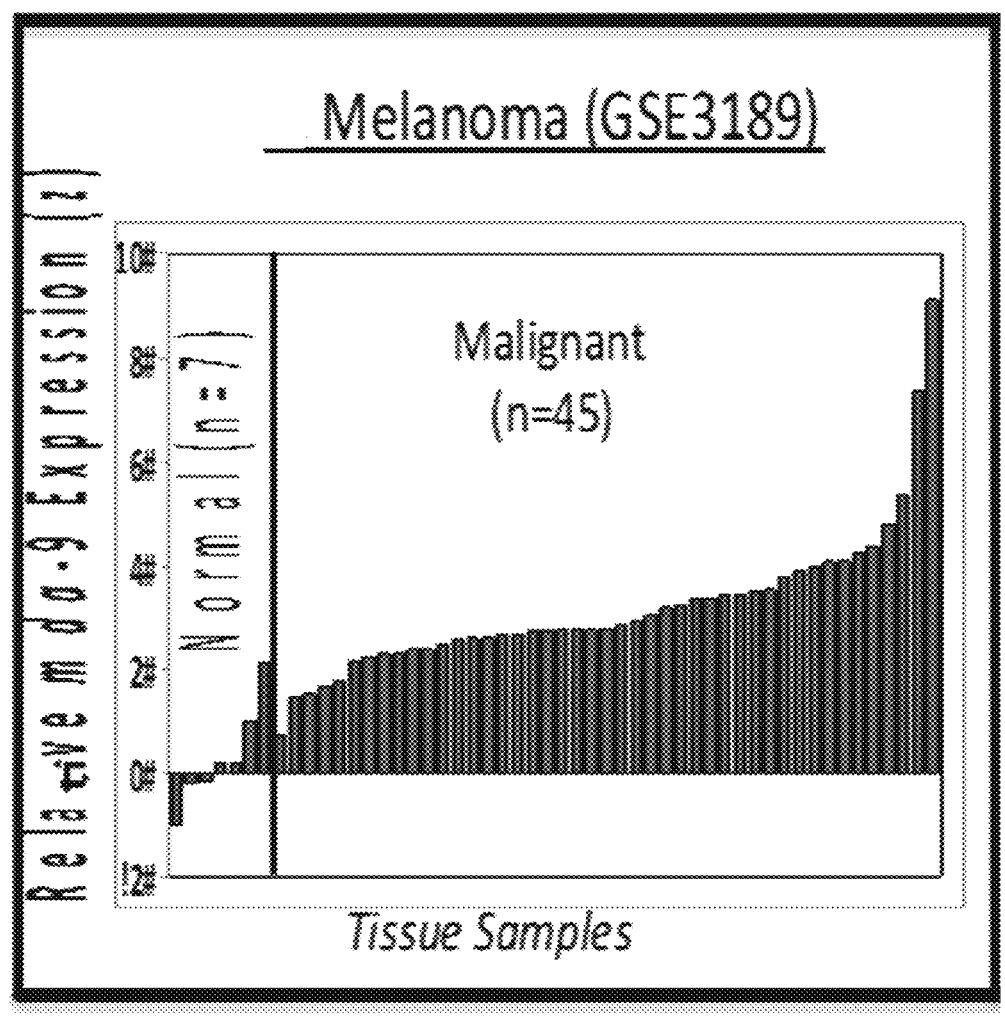
FIGS. 35A-35C. The expression of mda-9/Syntenin (SDCBP) (relative to normal samples) in melanoma (FIG. 35A), prostate cancer (FIG. 35B), and liver cancer (FIG. 35C). The expression values were derived from public genome-wide expression datasets. The relative expression (z) is equal to (In−Average Inorm)/standard dev norm, where n refers to every sample in the dataset (including tumors), while norm refers to normal samples only.
Figure 35B:
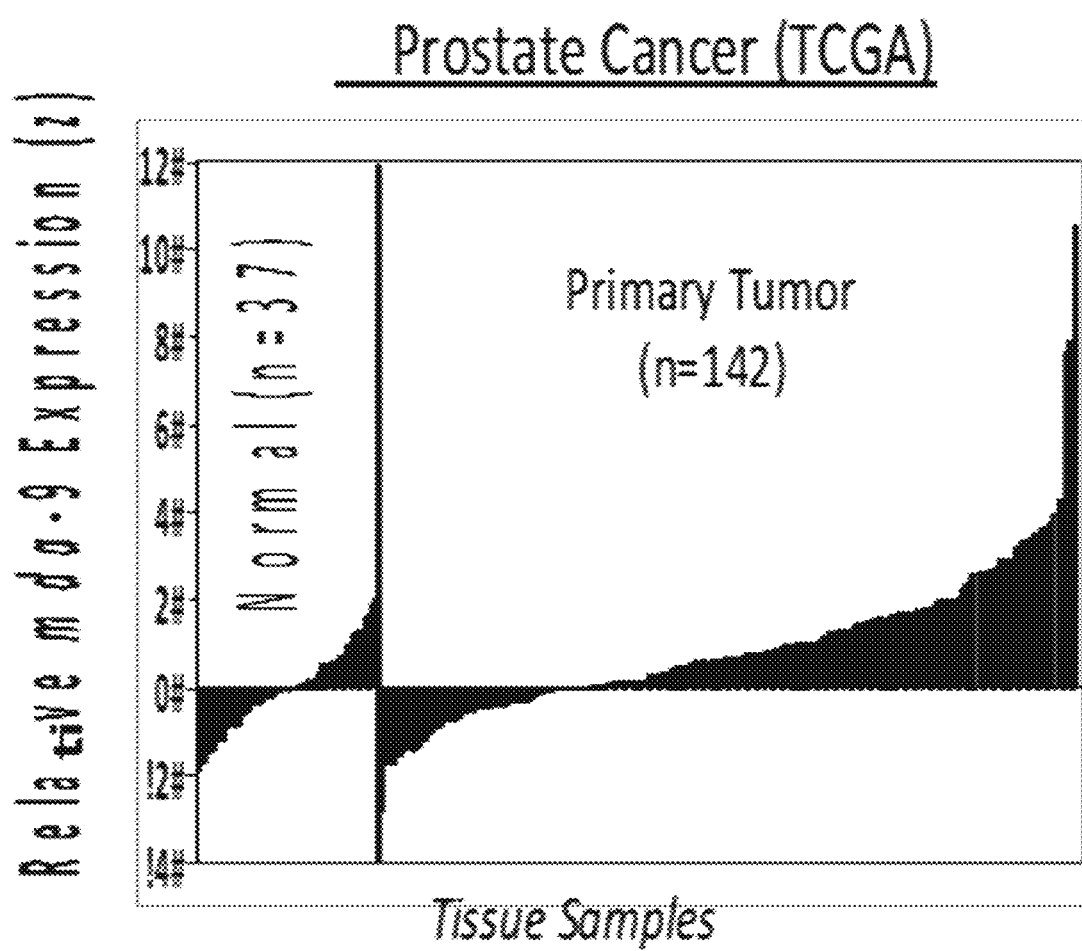
Figure 35C:
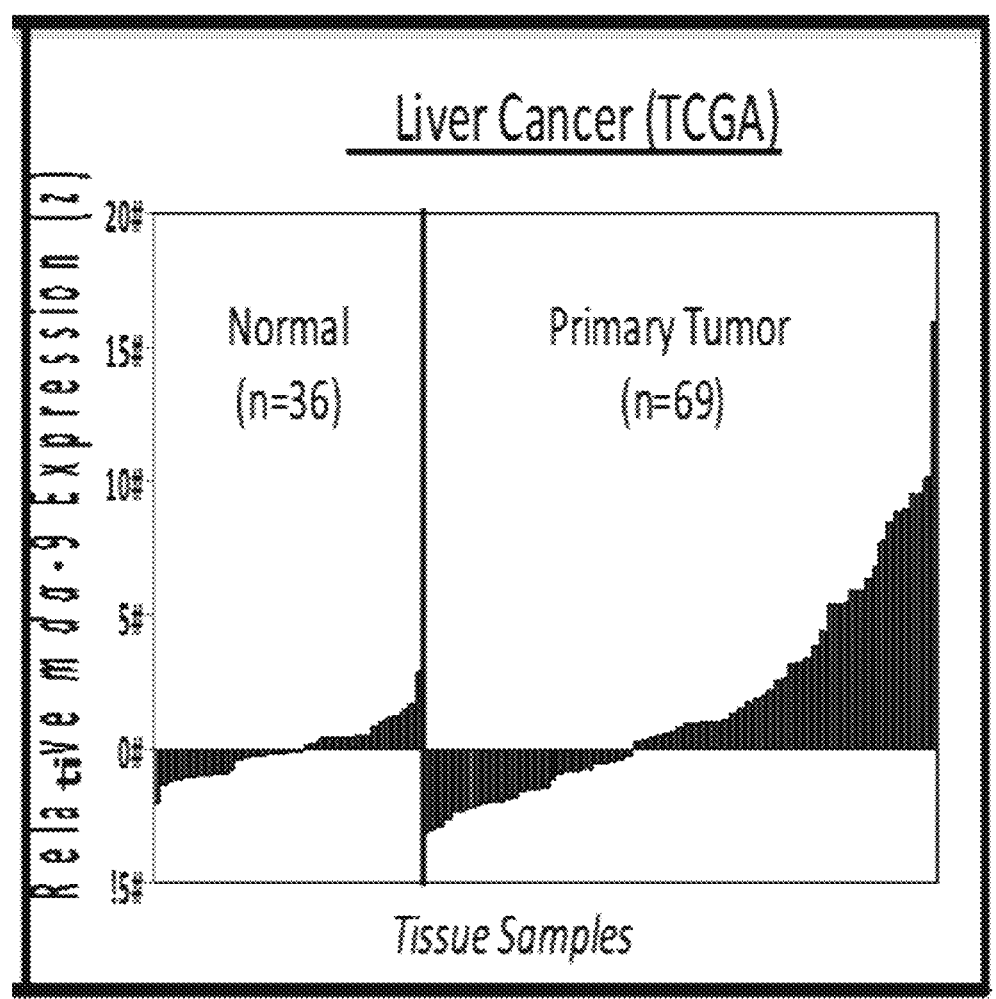
Figure 36:
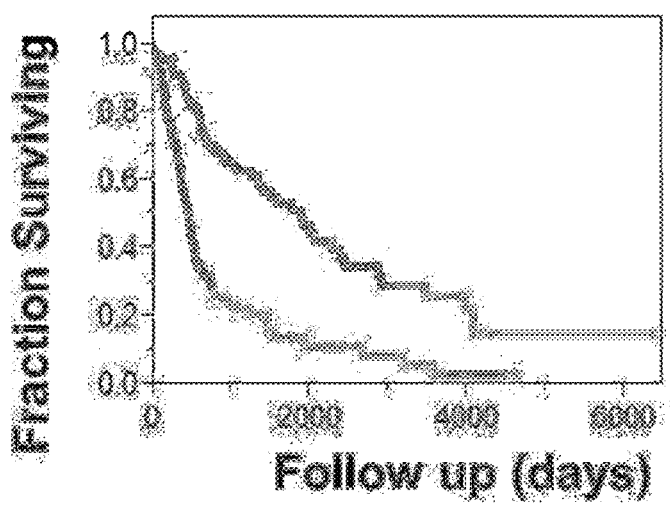
FIG. 36. Graph showing survival fraction as a function of days for patients with MDA-9 expression in the lower half and upper half.
Figure 37:
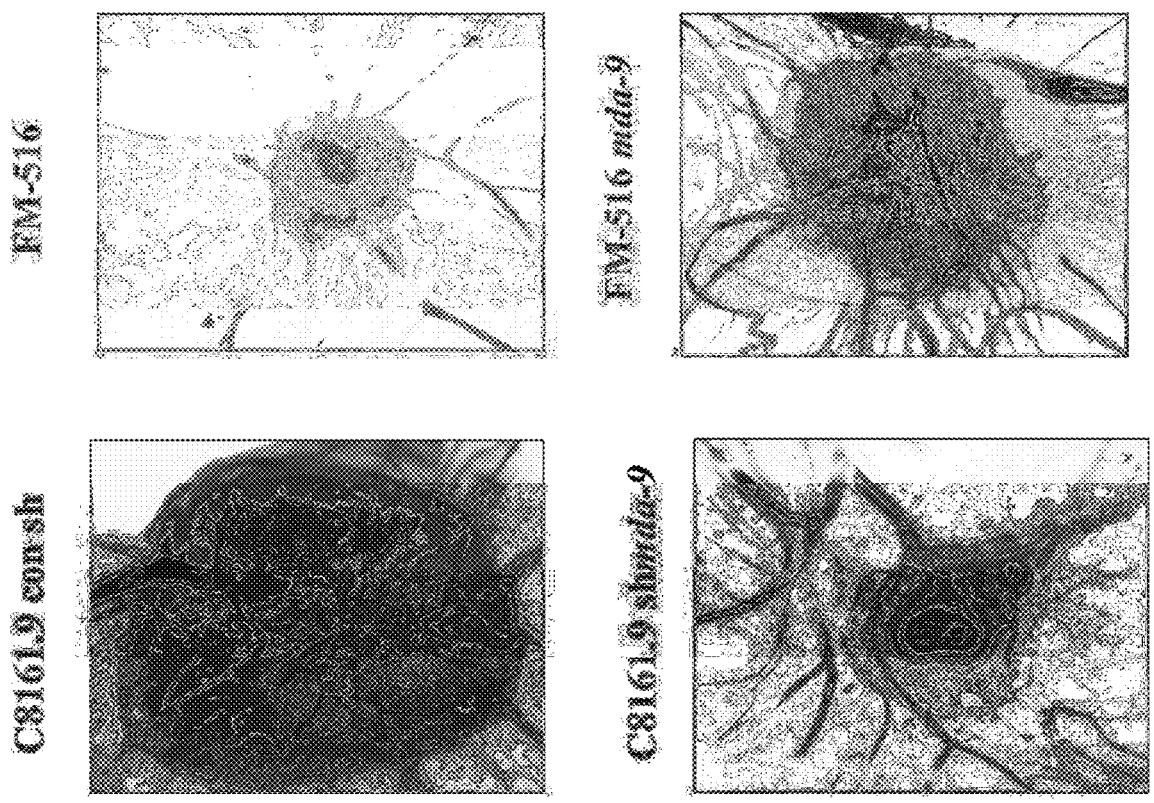
FIG. 37. MDA-9 promotes tumor angiogenesis. Knockdown of MDA-9 with shRNAs reduced angiogenesis while over expression of MDA-9 increased angiogenesis.
Figure 38:
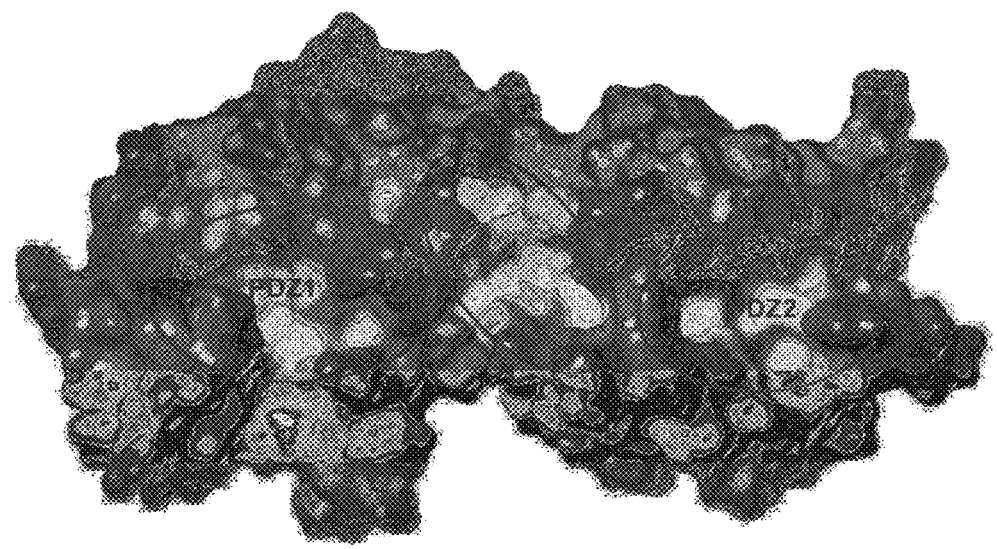
FIG. 38. Crystal structure of MDA-9/Syntenin showing both PDZ domains and the intermediate (e.g., interface) region between the domains.
Figure 39:
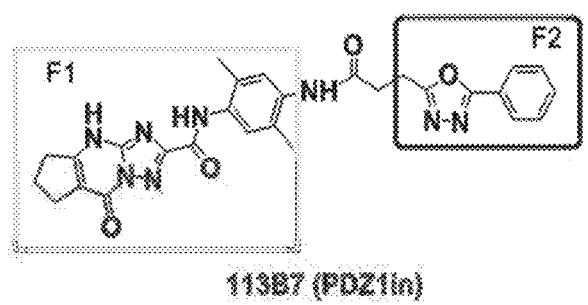
FIG. 39. Structure of 113B7, also referred to as PDZ1i and PDZ1in.
Figure 40:
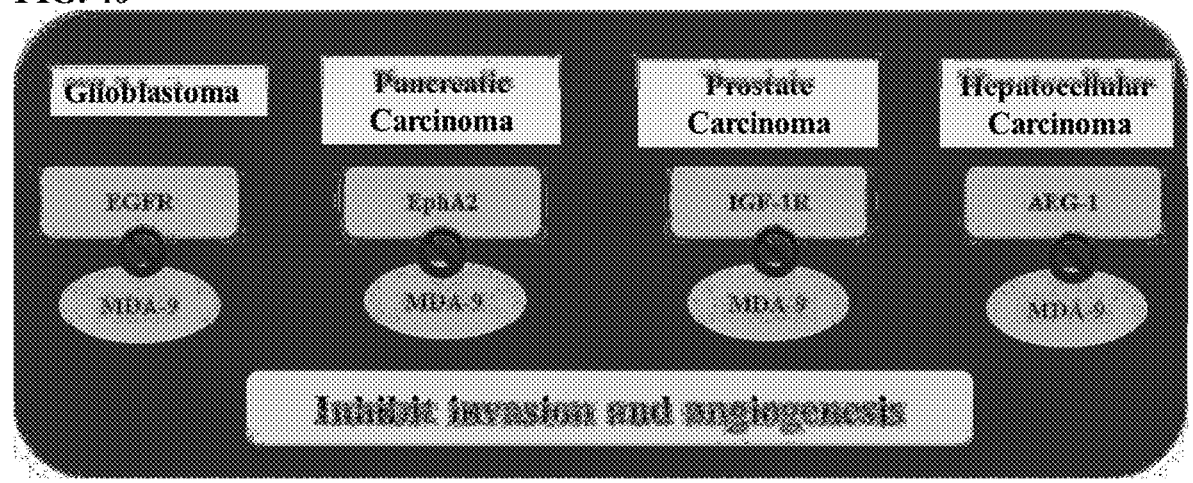
FIG. 40. Cartoon illustration of block of MDA-9 interactions with downstream proteins upon treatment with PDZ1i.
Figure 41:
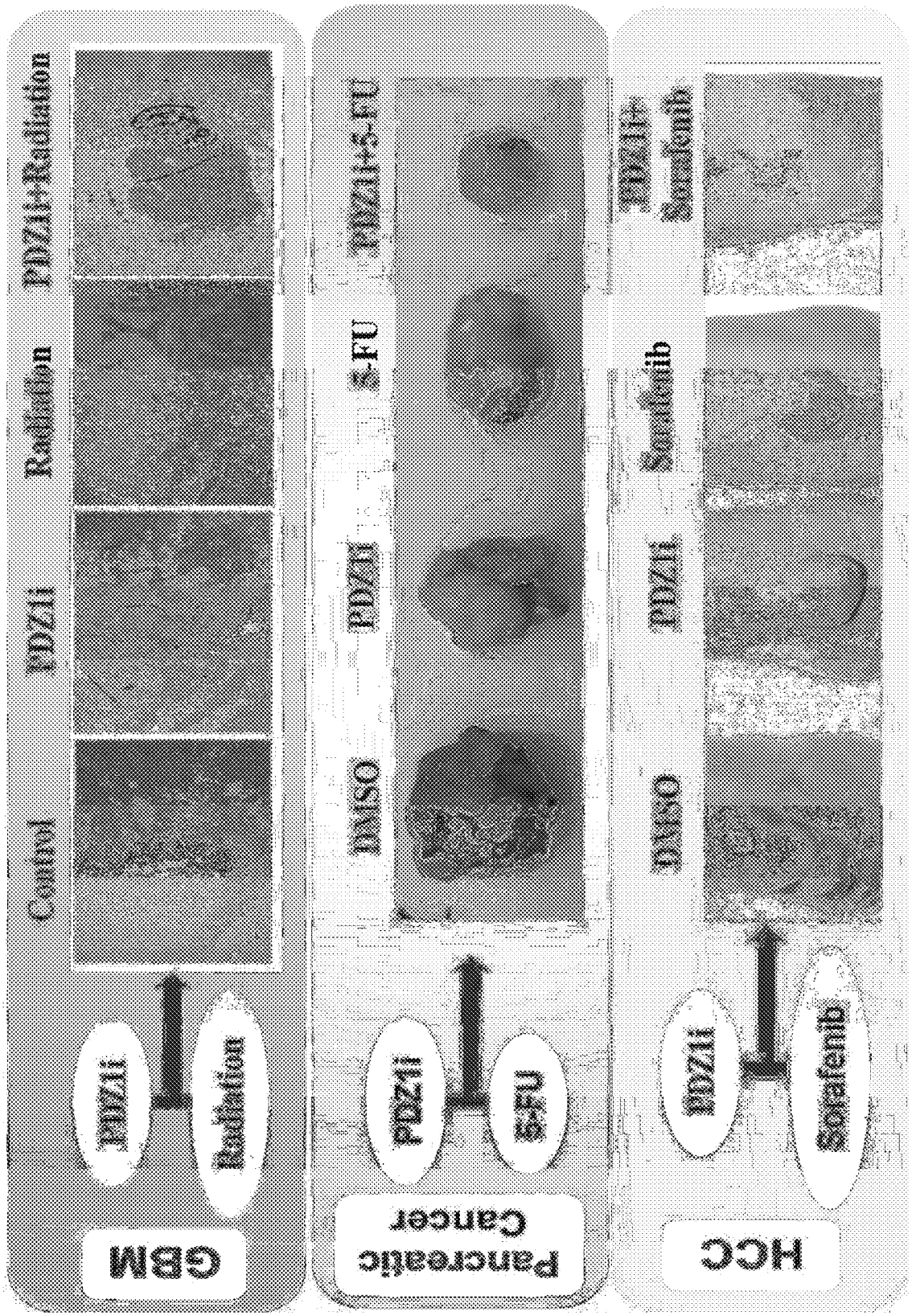
FIG. 41. Results of combination treatment (PDZ1i and anti-cancer agent) in different cancers (GBM, pancreatic cancer, and HCC).
Figure 42:
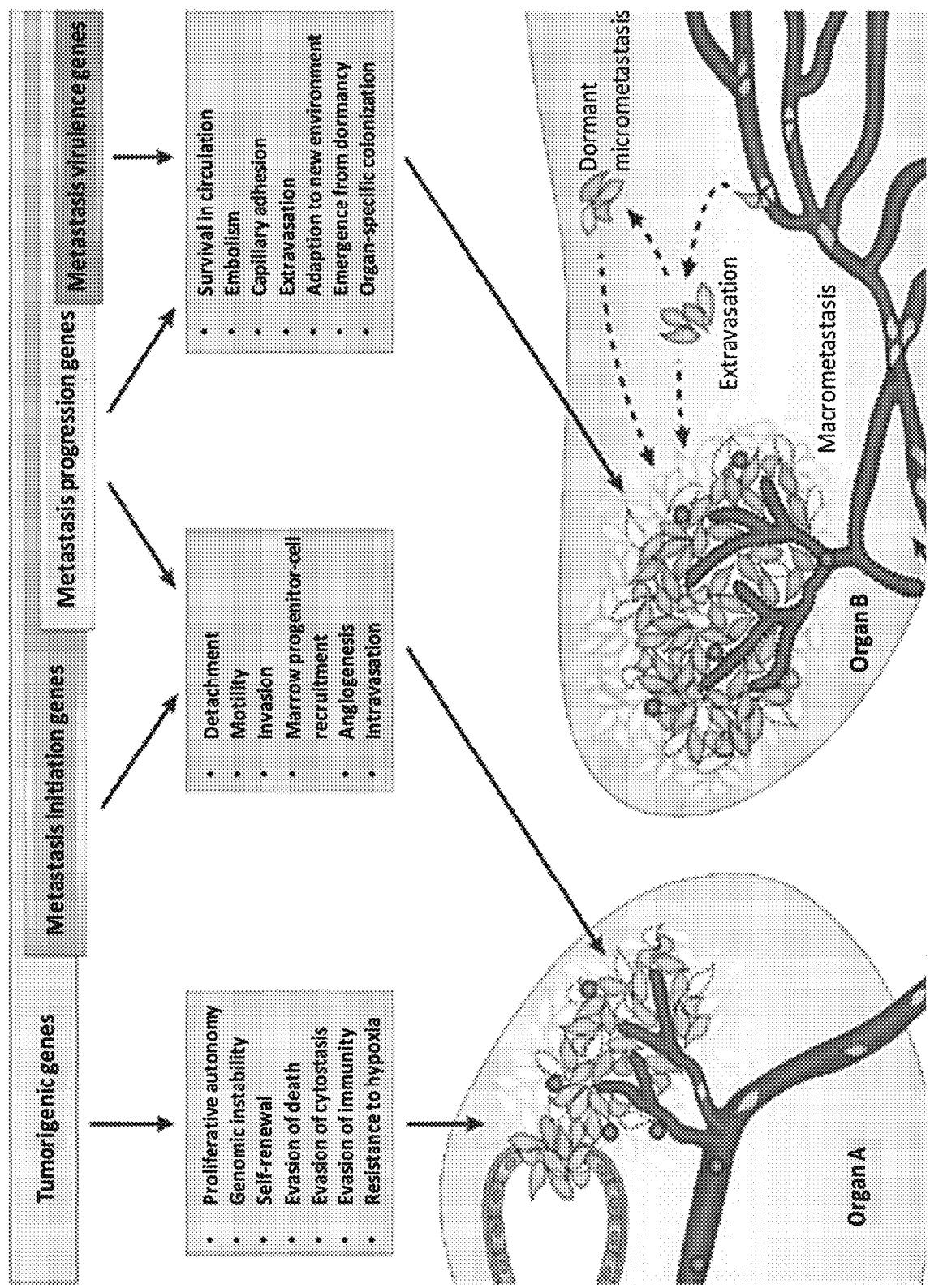
FIG. 42. Cancer progression to metastasis: a temporal process mediated by multiple initiating, progressing and virulence-mediating genes. This model highlights the properties elicited by tumorigenic genes vs. the three classes of metastasis genes (initiation, progression and virulence).

Bioinformatics confirms that mda-9 is a relevant gene in multiple cancer indications, including melanoma, prostate cancer and liver cancer (FIG. 35). MDA-9 expression correlates with cancer progression in patient samples (samples taken from Melanoma, Glioblastoma, Head and Neck Cancer, Urothelial cancer, Breast Cancer, Uveal Melanoma, Gastric Cancer, Lung Adenocarcinoma, Hepatocellular Carcinoma, Colorectal Cancer, Prostate Cancer, Pancreatic Cancer, and Neuroblastoma) (FIG. 36). MDA-9 also promotes tumor angiogenesis (FIG. 37). The crystal structure of MDA-9/Syntenin shows two PDZ domains, PDZ1 and PDZ2 with an interface between the PDZ domains. Applying FBDD and NMR applied to purified PDZ1 and PDZ2 proteins identified PDZ1i (113B7) (FIG. 39). PDZ1i efficiently binds with the PDZ1 domain of MDA-9 (Kd<10 µM), shows low clearance from serum ($T_{1/2}$>9 hrs), and has 80% bioavailability when administered I.P. PDZ1i showed no apparent toxicity in vivo in multiple pre-clinical animal models and was non-toxic to both primary normal cells and cancer cells. PDZ1i is an anti-invasive, anti-angiogenic small molecule that can synergize with conventional therapies in primary tumor and metastatic tumor cells. PDZ1i alters protein-protein interactions thereby inhibiting MDA-9 signaling functions: blocking invasion, attachment and angiogenesis (FIG. 40). PDZ1i "anti-invasion" therapy can be successfully combined with "cytotoxic therapy" to treat primary tumor and metastatic tumor cells (FIG. 41). FIG. 42 shows mechanisms of metastasis prevention through the use of PDZ1i. PDZ1i can inhibit invasion of primary tumors including melanoma, bladder cancer, prostate cancer, GBM, pancreatic, colon, etc. The following are examples of combinatorial approaches to treating cancer using anti-Invasive therapy cytotoxic therapy; PDZ1i+Sorafineb to treat liver cancer; PDZ1i+Radiation to treat glioblastoma; PDZ1i+Temozolomide to treat glioblastoma; PDZ1 i+MCL-1 Inhibitor to treat prostate cancer, breast cancer, and melanoma. PDZ1i alone or in combination prior to or after surgical removal of cancer tissue to prevent secondary metastases.

Example 5. Effective Pharmacological In Vivo Inhibitors of Cancer Invasion and Metastasis Cancer is a progressive disease that can culminate in tumor cell populations that have acquired the capacity to invade surrounding tissue or enter the bloodstream, attach at distant sites in the body and form metastases. If diagnosed early, recent advances in diagnosis and therapy may permit management and even cures for many solid tumors. However, cancer frequently becomes an intractable disease when tumor cells migrate beyond their primary site into adjoining tissue or to distant regions in the body. Although extensively examined, leading to the identification of many critical signal transduction pathways, the fundamental genetic/epigenetic causes of cancer invasiveness and metastasis remain complex and require further clarification. Defining the pivotal genomic changes occurring in diverse cancer cells that control invasion and metastasis holds significant potential for developing rationally based anti-invasive and antimetastatic therapies for these invariably fatal components of the cancerous phenotype.

The central goal is to develop effective pharmacological in vivo inhibitors of cancer invasion and metastasis. Our innovation centers around a novel gene discovered by subtraction hybridization, melanoma differentiation associated gene-9 (mda-9)/syntenin, that based on bioinformatics and direct experimentation represents a key contributor to cancer cell invasion and metastasis in multiple cancer types. Using innovative fragment- and structure-based approaches with NMR, small molecule inhibitors of the critical protein-interacting PDZ1 domain of the MDA-9/Sytenin protein have been identified and shown to inhibit in vivo tumor cell invasion, circulating tumor cell attachment and metastasis formation.

PDZ inhibitory molecules can be refined to enhance potency, selectivity and pharmacological properties. Mechanistic studies will focus on precisely how these inhibitors prevent melanoma cell adhesion and metastasis. The role of mda-9/syntenin in development of hepatocellular carcinoma (HCC) will be determined as well as the utility of this gene or protein as a therapeutic target for inhibiting HCC pathogenesis. Experiments will investigate the therapeutic potential of MDA-9/Syntenin inhibitors in HCC; define precisely how MDA-9/Syntenin promotes hepatocarcinogenesis; and the molecular basis of mda-9/syntenin overexpression in HCC.

The role of mda-9/syntenin in prostate cancer (PC) development and progression will also be interrogated. Studies will elucidate the biological significance and mechanism of over expression of mda-9/syntenin in PC; the involvement of the MDA-9/IGF-1R/STAT-3 axis in PC metastasis; and the therapeutic efficacy of MDA-9/Syntenin inhibitors in PC pathogenesis.

This research will provide biologically active cancer inhibitory MDA-9/Syntenin PDZ specific small molecules that can obstruct tumor cell invasion and metastasis (both cell adhesion and subsequent colonization in secondary sites in the body). Additionally, by combining PDZ-inhibitors with other conventional therapeutic agents, such as chemotherapy, radiation therapy and immunotherapy, future opportunities for developing efficacious combinatorial therapies for preventing cancer invasion and metastasis, thereby enhancing patient survival, may be an achievable goal.

Although the main cause of death from cancer is metastasis, the majority of research has focused on comprehending tumor development and progression at the primary tumor site (1). In principle, there are two defined modes of tumor dissemination, i.e., invasion and metastasis, which employ both common and unique strategies to accomplish movement from a primary tumor, colonization at a new site in the body and survival and expansion at the new site (2,3). The multistep nature of tumor dissemination, particularly metastasis, provides significant obstacles to effective therapy (4,5-8). In these contexts, understanding the molecular determinants, signaling pathways and biology of tumor cell invasion and metastasis will be pivotal if one hopes to develop efficacious therapies for these invariably fatal consequences of cancer (5,6,9).

Overarching Problems and Barriers to Progress in the Field.

A fundamental question is, "why is cancer dissemination (invasion and metastasis) so difficult to treat?" Many factors contribute to the failure of current therapies to impact on this invariably fatal component of the carcinogenic process. Tumor cells from the same and different organ sites are heterogeneous with numerous genetic and epigenetic changes that are exacerbated as cancers progress (7,8). Additionally, the sensitivity for detecting metastatic tumors has current limitations (10-13) and therapeutic approaches frequently encounter tumor-resistance mechanisms engendering opposition to therapy-induced apoptosis and toxic autophagy with enhanced tumor survival in suboptimal environments (14-18). Localized invasion, which is the mode of pathogenesis in glioblastoma multiforme (19-21), bladder cancer (22,23) and the initial stages of melanoma (9,24), involves as a minimum partial separation from the primary tumor, movement through tissue barrier matrices and survival in contiguous tissues (2,3). In these contexts, an invasive tumor is in fact an extension of the primary tumor mass and progresses in a syncytial manner as it expands in size. In this context, agents that provide effective therapies for tumors depending on this mode of pathogenesis would benefit from anti-invasive approaches (2). Metastasis is often viewed as a temporal process, where different genes and signal transduction pathway changes may regulate specific components of this process, i.e., escape from the primary tumor and invasion of tumor cells from a primary tumor mass into the circulation ("intravasation"); survival in the circulatory system; secondary attachment and seeding in a new site in the body involving adherence to endothelial cells and penetration through the basement membrane to enter the tissue parenchyma ("extravasation"); and colonization and development of the secondary tumors with a new blood supply (metastases) (3, 5, 6, 9, 25). Metastasis has also been viewed as a multistep process involving a series of gene and signal transduction pathway changes referred to as: metastasis initiating genes; metastasis progression genes; and metastasis virulence genes (6, 9) (FIG. 42). A key would be to define common genomic changes and pathway(s) that may mediate both invasion and metastasis in multiple cancers, which are necessary for cancer cells but dispensable for expression in normal cells, that could be targeted by drugs to effectively inhibit specific stages in invasion and metastasis (6,9,26). A primary objective is to develop small molecule drugs to effectively inhibit cancer invasion and metastasis.

Figure 43:
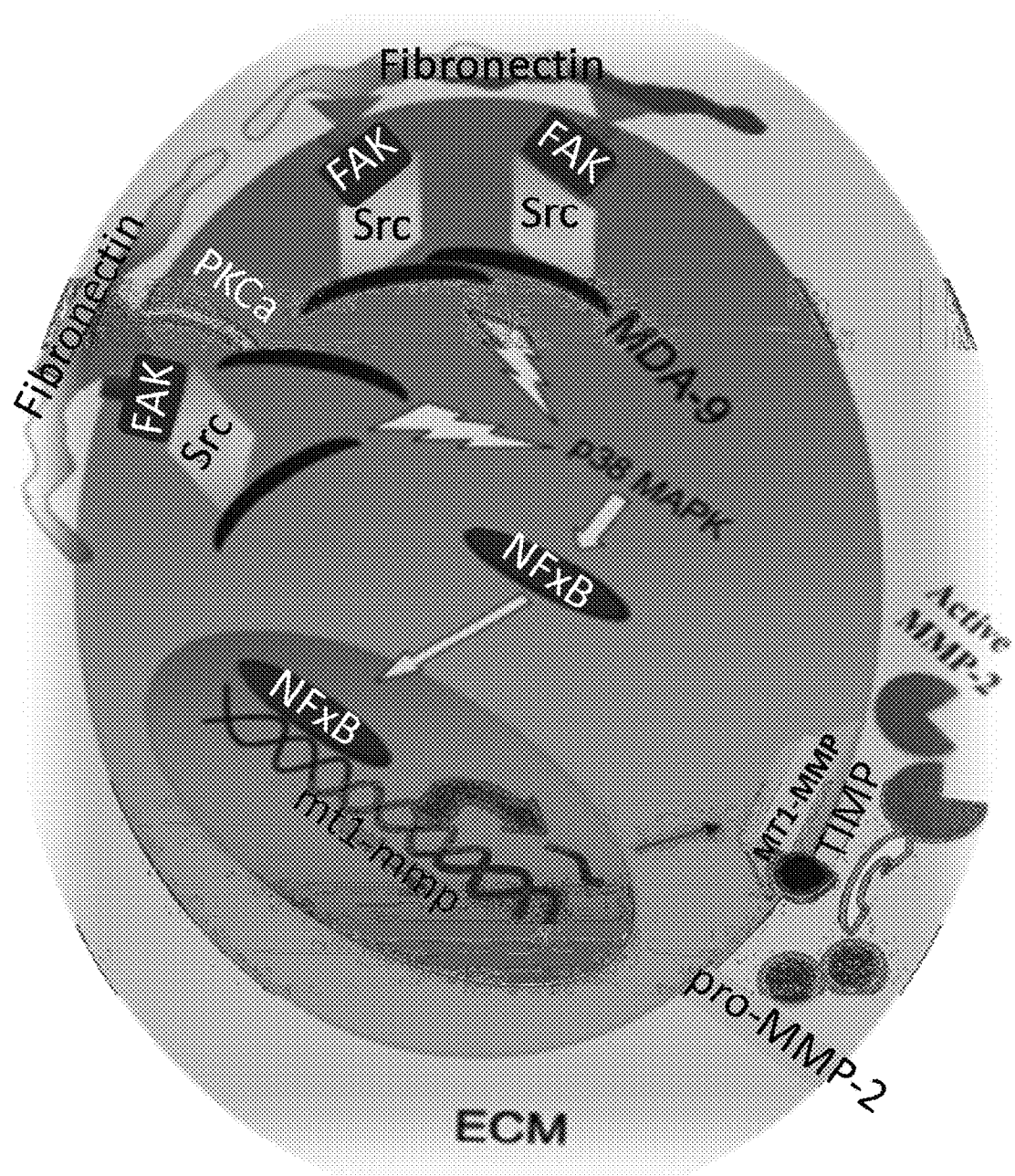
FIG. 43. Model of mda-9/syntenin mediated induction of NF-κB and its downstream genes and processes through its interaction with c-Src. MDA-9/syntenin interactions with c-Src assemble c-Src/FAK signaling complexes and leads to activation of the p38 MAPK/NF-κB pathway that regulates expression of genes involved in cell motility and invasion.

MDA-9/Syntenin: novel pro-metastatic gene/protein with potential as a therapeutic target. Using subtraction hybridization, a novel temporally expressed gene was cloned, melanoma differentiation associated gene-9/syntenin (mda-9/syntenin) from human melanoma cells induced to undergo terminal differentiation (27,28). MDA-9/Syntenin is a protein, which contains two PDZ domains, PDZ1 (aa, 110-193) and PDZ2 (aa, 194-274), that have potential to interact with a plethora of proteins, many of which are relevant to the cancer phenotype (9,29,30). Studies in melanoma indicate that MDA-9/Syntenin functions as an adapter protein interacting with multiple partners and provides a central role in regulating cell-cell and cell-matrix interactions (9,29-33). MDA-9/Syntenin transduces signals from the cell-surface to the cell's interior through its physical communications with a broad spectrum of additional proteins (9, 29, 30). Recent studies provide compelling evidence that MDA-9/Syntenin plays a central role in cancer cell motility, invasion and metastasis (9, 21, 22, 29-39), and functions as a positive regulator of tumor angiogenesis (40). In the context of human melanoma, MDA-9/Syntenin serves as a positive regulator of progression and metastasis through interactions with c-Src and promotes the formation of an active FAK/c-Src signaling complex leading to NF-κB and matrix metalloproteinase (MMP) activation (FIG. 43) (36-39). Additionally, through interaction with the extracellular matrix, MDA-9/Syntenin induces a cascade of molecular/biochemical changes culminating in tumor angiogenesis (40).

MDA-9/Syntenin through c-Src and FAK promotes activation by phosphorylation of Akt inducing HIF-la resulting in the transcription of insulin growth factor-binding protein-2 (IGFBP-2) which upon secretion promotes angiogenesis and also induces endothelial cells to produce and secrete VEGF-A augmenting further tumor angiogenesis (FIG. 44) (40). With respect to the model delineating multiple types of metastasis regulating genes as shown in FIG. 42, evidence is available that MDA-9/Syntenin displays properties of all three components in this multistep and multifactor process, i.e., metastasis initiation and metastasis progression (motility, invasion, angiogenesis, intravasation) and metastasis progression and metastasis virulence (survival in the circulation, capillary adhesion, extravasation) (9, 21, 22, 29, 30, 33, 37-41). Moreover, as emphasized ectopic expression of MDA-9/Syntenin in a normal immortal melanocyte promotes all of the properties necessary for induction of metastasis in an experimental metastasis model following injection into the bloodstream (39).

MDA-9/Syntenin, Syndecan-Binding Protein (SDCBP), is Upregulated in Multiple Cancers:

There is now significant bioinformatics evidence that MDA-9/Syntenin (syndecan binding protein; SDCBP) is a relevant gene in multiple cancer indications. Our comprehensive analyses of various genome-wide expression data-sets (such as those from The Cancer Genome Atlas and NCBI's Gene Expression Omnibus) indicate that MDA-9/Syntenin is commonly upregulated in numerous cancer types. The positive correlation between MDA-9/Syntenin expression and tumor grade is readily observed in glioma, upon analyses of both the TCGA (Glioblastoma Multiforme plus Lower Grade Glioma, Illumina HiSeq 2000 platform) and GSE4290 (from NCBI-GEO; Affymetrix U133 Plus 2 platform) datasets (21). Other tumors exhibiting elevated MDA-9/Syntenin expression (relative to normal tissues) are kidney renal papillary carcinoma (TCGA; Illumina HiSeq 2000), melanoma (GSE3189; Affymetrix U133A),prostate adenocarcinoma (TCGA; Illumina HiSeq 2000), and hepatocellular carcinoma (TCGA; Illumina HiSeq 2000) (FIG. 35).

Novel Chemical Biological Approach Identifies MDA-9/Syntenin PDZ Domain Inhibitors:

Targeting the interaction between MDA-9/syntenin's PDZ1 domain and its targets through novel small molecular inhibitors and developing suitable pharmacologically acceptable drugs using innovative fragment- and structure-based approaches holds significant potential for producing effective therapeutics for inhibiting metastatic disease progression in a broad-spectrum of human cancers. Using an innovative modular approach, a series of inhibitors targeting the PDZ1 domain and the interface between the domains were derived These initial chemical probes were used to further our understanding of the role of MDA-9/Syntenin in mediating invasive behavior of tumors using animal models. Additionally, we intend to obtain the structural determinants that are the basis of the binding of these molecules using solution NMR spectroscopy and to use the resulting structures to refine the molecules for potency, selectivity and also pharmacological properties as needed. This chemical biology approach will likely provide new insights into metastasis mediated by mda-9/syntenin in melanoma, liver, and prostate cancer.

Development of MDA-9/Syntenin Targeted Small Molecules:

The prime objective is to develop small molecules that can selectively inhibit the interactions between the PDZ1 domain of MDA-9/Syntenin with critical interacting proteins. Molecules capable of specifically targeting the PDZ1 and interdomain (e.g., interface region) of MDA-9/Syntenin, such as 113B7 (PDZ1in), are effective inhibitors of the subsequent biological properties induced by MDA-9/Syntenin. Existing PDZ1 inhibitory molecules will be refined in an effort to enhance potency, selectivity and pharmacological properties. The biological and molecular properties of specific inhibitors, including effects on normal cell survival, cancer cell invasion, protein-protein interactions, retention of tumor cells in the lungs and generation of metastatic lesions in vivo, will be ascertained. Mechanistic studies will define the pathways and critical genes associated with enhanced invasion, attachment and metastasis that are manipulated by overexpressing or inhibiting MDA-9/Syntenin expression in human melanoma cells. This combination of medicinal chemistry and preliminary biological characterization (to define appropriate functional and mechanism of action studies in the context of metastatic B16 mouse and human MeWo and C8161 melanoma cells will provide essential insights for studies in HCC and prostate carcinoma. Further refinement and testing of clinical efficacy will also be performed.

Targeting MDA-9/Syntenin to Treat Hepatocellular Carcinoma:

Although the overall incidence and mortality of the majority of cancers is decreasing HCC is one of the few cancers where the incidence and mortality is alarmingly increasing for several decades (49,50). HCC, detected in early stages, might be remedied by surgical resection, radio-embolization and liver transplantation (49,51). However, most patients present at an advanced stage with intra-hepatic and distant metastasis, which is not malleable by standard modalities of treatment. The only FDA-approved drug, sorafenib, for non-resectable HCC provides a survival advantage of only 2.8 months (52,53). Understanding the molecular mechanism of hepatocarcinogenesis and developing targeted therapies are thus mandatory to effectively counteract this fatal disease. 113B7 (PDZ1in) will be evaluated as a therapeutic targeted towards inhibition of invasion and metastasis. We propose to combine PDZ1in with sorafenib for the following rationale: (1) Even though 113B7 (PDZ1in) is a potent inhibitor of invasion, it may not affect proliferation of human HCC cells. PDZ1in may benefit from being combined with a drug that inhibits proliferation of cancer cells and induces apoptosis and sorafenib provides those functions (54,55). (2) Sorafenib is a relatively non-specific kinase inhibitor. However, it targets Raf-1 and VEGFR, and downstream signaling from these kinases has been shown to be active in HCC (56-58). We anticipate that the anti-proliferative and anti-angiogenic functions of sorafenib will complement anti-invasive and antimetastatic function of 113B7 providing a greater synergistic effect. (3) Since sorafenib is already used in the clinic, if our proposed strategy is proven successful, it will allow fast-track translation into the clinic to provide immediate benefits to scores of HCC patients.

Targeting MDA-9/Syntenin to Treat Prostate Cancer:

Although there have been improvements in radiotherapy, chemotherapy and hormone therapy, this has not translated into overall long-term survival benefits in patients, particularly in the context of advanced prostate cancer (PC) (metastatic stage). Consequently, defining the crucial molecules controlling progression of adenocarcinoma of the prostate and defining rationally targeted and more efficacious therapies based on precise mechanisms of pathogenesis are mandatory for developing treatments that are potentially curative. We focus on critically evaluating the role of mda-9/syntenin in PC etiology and progression, with particular emphasis on the invasive phenotype (using the Hi-Myc transgenicmouse model) and metastasis. This will test the prevailing hypothesis underlying the mechanism of action of MDA-9/Syntenin that by physically interacting with specific subsets of proteins in different cancer cells, MDA-9/Syntenin regulates crucial signaling pathways that enable cancer cell invasion and metastasis. Our focus will be on PC with potential to identify unique small molecules that through disruption of MDA-9/Syntenin interactions with relevant partners will impact on final cancer phenotypes in PC cells, with specific attention on invasion and metastasis. Our emphasis in PC will be on defining the outcome of interactions between MDA-9/Syntenin and insulin like growth factor receptor-1 (IGF-R1) and ensuing STAT-3 signaling. The impact of disrupting this complex with existing PDZ1 inhibitor 113B7 (PDZ1in) will be further investigated. We will test further potential MDA-9/Syntenin PDZ1in suppressing tumor growth, invasion and progression to metastasis.

Based on genomic relevance of MDA-9/Syntenin in multiple types of cancer (TCGA, Oncomine, GEO) and experimental evidences indicating a pivotal role of this scaffold protein in promoting tumor cell motility, invasion, metastasis and angiogenesis (9, 21, 22, 29-40), targeting MDA-9/Syntenin or its downstream regulated molecules may provide a means of simultaneously blocking invasion and metastasis. This antiinvasive/anti-metastatic activity of blocking MDA-9/Syntenin could occur by directly inhibiting tumor cell transformed properties (autonomous) and indirectly by blocking angiogenesis (nonautonomous). This multi-pronged attack on a pivotal gene that directly impacts on cancer aggressiveness provides significant potential to develop effective anti-invasive and anti-metastatic drugs, which is a primary objective of cancer treatment.

We have shown that targeting MDA-9/Syntenin protein through inhibiting interaction of its PDZ1 domain with critical effector proteins provides a viable approach for developing small molecules that can affect cancer progression both in vitro and in vivo in animal models. These results could translate into a paradigm shift of how cancer invasion and metastasis are treated. The approach of using a single inhibitor that combines anti-invasive, anti-metastatic and anti-angiogenic activity in the same molecule in conjunction with therapies that inhibit cancer cell growth and survival, is innovative and provides a new Multi-Modality Gene-Specific (MMGS) cancer therapeutic approach to inhibit and potentially prevent cancer pathogenesis mediated through cancer invasion and metastasis.

Elevated MDA-9/Syntenin Expression Correlates with Disease Progression in Multiple Cancers:

Through bioinformatics interrogating various cancer data bases we confirm a correlation between elevated expression of mda-9/syntenin and advanced stages of multiple cancers, including melanoma, HCC and PC (FIG. 35). A direct relationship between MDA-9/Syntenin expression and progression of human melanoma has been documented using tissue sections representing normal and various stages of superficial spreading and uveal melanoma (35,39). In the context of urothelial cell carcinomas, a significantly higher expression of MDA-9/Syntenin was observed in 64% (28 of 44) of primary UCC tumors and an association was evident with stage, grade and invasion status (22). In this study, a direct physical interaction and colocalization of MDA-9/Syntenin and EGFR was evident in UCC cell lines and primary tumors. These studies support MDA-9/Syntenin as an attractive target for developing detection, monitoring and therapeutic strategies for managing UCC (22). In the context of astrocytoma development and progression to GBM, a correlation also exists between expression of mda-9/syntenin and disease progression. In GBM patients, there is a direct relationship between elevated mda-9/syntenin expression and poor patient prognosis with decreased survival. Using both gain and loss of function studies, mda-9/syntenin was shown to positively regulate astrocytoma motility and invasion, in vitro and in vivo (21). The studies in UCC and GBM are particularly relevant in the context of tumor cell invasion, which is a primary mode of pathogenicity of these cancers. A correlation between migration and metastatic human breast and gastric cancer cell lines has also been reported (41). These studies demonstrate that mda-9/syntenin is a highly relevant gene in progression of multiple cancers, including regulation of processes including invasion and metastasis.

MDA-9/Syntenin Expression Directly Correlates with Tumor Progression in Patient Samples and Invasive and Metastatic Phenotypes in Cancer Cells:

Although bioinformatics data is important in providing potential leads and tentative associations between specific gene expression changes and cancer phenotypes, experimental documentation of these changes in primary tumors, cell culture and animal models is compulsory to verify these relationships.

Detailed studies in normal melanocytes and various stages of melanoma (including metastatic cells) (35,39), normal bladder cells and urothelial cell carcinoma (UCC) (22), normal hepatocytes and HCC, normal prostate and PC and astrocytes, low grade astrocytomas and GBM (21) demonstrate a direct correlation between MDA-9/Syntenin expression and tumor histological grade. Using genetic gain and loss of function others (31,32,34,35) and we (21, 22, 36-40) confirmed a direct relationship between MDA-9/Syntenin levels and in vitro and in vivo (animal models) expression of transformed properties, including tumor cell dissemination (motility, invasion, metastases). In the context of UCC and GBM, inhibiting mda-9/syntenin suppressed invasion, whereas overexpression of mda-9/syntenin in normal or less aggressive tumor cells facilitated motility and invasion (21,22). Direct in vivo injection into mouse brains of genetically modified grade III astrocytoma (elevated MDA-9/Syntenin) and GBM (inhibition of MDA-9/Syntenin) confirm a direct relationship between expression of mda-9/syntenin and tumor spread, lethality (21). In metastatic melanoma, inhibiting mda-9/syntenin expression blocks tumor cell retention in lungs and metastasis. Overall, these studies highlight the importance of MDA-9/Syntenin as a positive regulator of cancer dissemination and confirm that inhibiting expression impedes tumor cell invasion and metastasis.

Application of FBDD, NMR and structure-based design identifies MDA-9/Syntenin specific small molecule inhibitors: Recent years have witnessed a growing interest in targeting PDZ domains with relatively high success using small peptides, natural products and small molecules. These initial accomplishments are quite exciting and suggest that the PDZ domains are "druggable" (59-65). There are over 150 PDZ domains in the human genome discovered thus far (66,67). However, while these proteins share similar global folds, their binding surfaces are quite distinct. For this reason, developing small-molecule inhibitors targeting specific PDZ/target interactions is an attainable objective. Here we propose to use a combination of structure- and NMR-guided Drug Discovery approaches (68-70) to derive focused libraries of MDA-9/Syntenin PDZ targeting ligands. Our preliminary data documents that these strategies have enabled the identification and initial optimization of small molecules capable of antagonizing MDA-9/Syntenin in vitro and in cells targeting its PDZ1 domain.

Biological efficacy of small molecules targeting the PDZ1 domain of MDA-9/Syntenin in suppressing cancer dissemination-invasion and metastasis: As briefly described above, using innovative approaches a structurally distinct small molecule inhibitor of MDA-9/Syntenin PDZ1 domain has been produced, 113B7 (interacts with PDZ1 and the interdomain (e.g., interface region) of MDA-9/Syntenin; PDZ1in). Bioinformatics suggest that MDA-9/Syntenin expression is elevated in a large panel of human tumors, which was confirmed by Western blotting (39). Based on these findings, we determined the effect of 113B7 (PDZ1in) on invasion of multiple cancer cell types including melanoma, prostate, HCC, GBM, pancreatic and breast (FIG. 46). 113B7 inhibited invasion in a dose-dependent manner in various cancer cell types, including melanoma, prostate and HCC.

Figure 47:
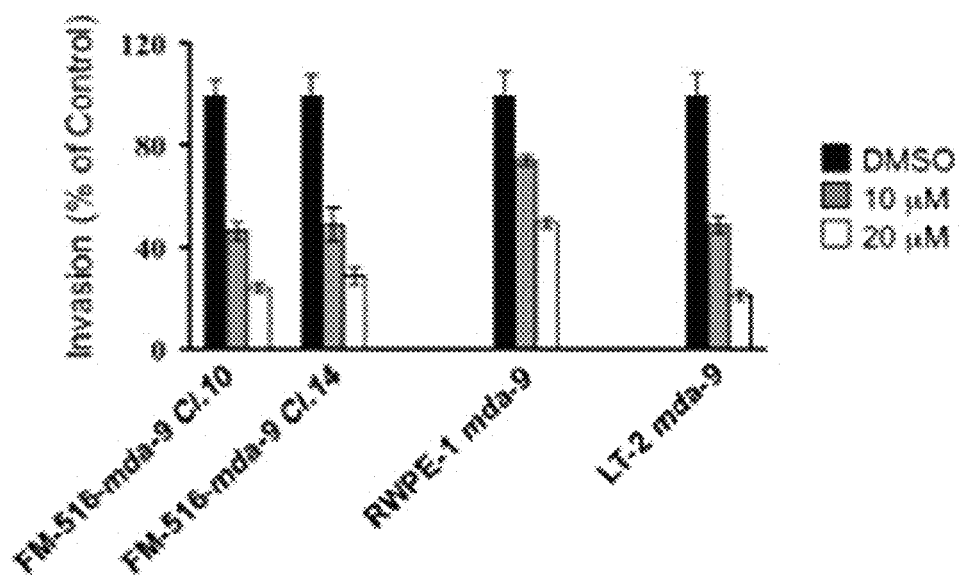
FIG. 47. mda-9/syntenin induces an invasive phenotype in normal immortal melanocytes (FM516), prostate epithelial (RWPE-1) and pancreatic mesenchymal (LT-2) cells, which is inhibited by 113B7. Invasion assay as performed in FIG. 46.

To confirm specificity of this effect, we genetically modified normal immortal human melanocytes (FM516), normal human prostate epithelial cells (RWPE) and normal human mesenchymal pancreatic cells to stably express elevated levels of MDA-9/Syntenin. These MDA-9/Syntenin over-expressing cells displayed elevated levels of invasion, which was inhibited when treated with 113B7 (FIG. 47). In metastatic human melanoma and PC cells, respectively, 113B7 effectively reduced retention time of tumor cells in the lungs, possibly by preventing attachment, and 113B7 inhibited development of metastases in animal models (FIG. 48). A direct anti-invasive effect of 113B7 in the context of Hi-Myc mice was also documented (FIG. 48). Additionally, the combination of 113B7 and sorafenib synergistically inhibited HCC growth in nude mice (FIG. 48). These experiments show the invasive suppressing and anti-metastatic properties of PDZ1in (113B7), suggesting the potential of this molecule to serve as scaffolds for developing novel therapeutics against a broad spectrum of human cancers.

Figure 50:
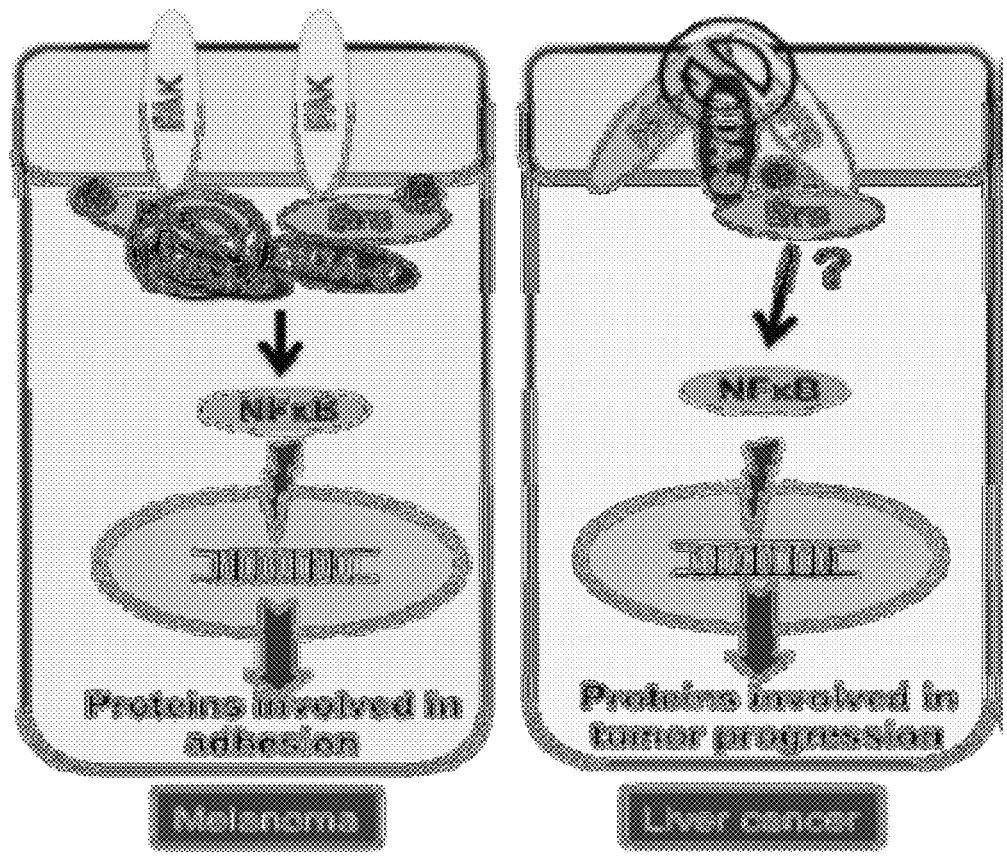
FIG. 50. Major MDA-9/Syntenin-mediated signaling pathways that contribute to tumor progression/invasion/metastasis in multiple cancers. In Melanoma (Left Panel), upon ECM engagement, FAK and Src complex is recruited in the plasma membrane to initiate the initial signaling. MDA-9/Syntenin physically interacts with Src resulting in the formation of multimeric complexes that activate the NF-κB pathway and consequently induce downstream proteins essential for metastasis. In hepatocellular carcinoma (RightPanel), MDA-9/Syntenin interacts in the plasma membrane with AEG-1 and EGFR to form a functional unit, which possibly activates NFκB pathway through the phosphorylation of Src to stimulate/initiate tumor progression signaling cascades.

Novel Molecular Mechanism of Hepatocarcinogenesis Involving Interaction of MDA-9/Syntenin, AEG-1 and EGFR on the Cell Membrane of Human HCC Cells:

Overexpression of the oncogene Astrocyte elevated gene-1 (AEG-1), also known as metadherin (MTDH), has been documented in all cancers studied so far, including HCC (71-73). AEG-1 expression level correlates with poor disease prognosis, decreased overall survival and disease recurrence (71-73). AEG-1 positively regulates all hallmarks of cancer but its more pronounced effect is observed on invasion, metastasis and angiogenesis (71-73). The cell membrane located AEG-1 has been ascribed to promote metastasis of breast cancer cells to the lungs (74). Overexpression of EGFR has been documented in HCC patients and contributes to invasion and metastasis by activating c-Src and c-Met (75,76). We now document a novel interaction among MDA-9/Syntenin, AEG-1 and EGFR on the cell membrane of human HCC cells that might contribute to aggressive progression of hepatocarcinogenesis (FIGS. 49 and 50). Detailed analysis of the consequence of these interactions will provide novel insights into regulation of growth factor signaling, as well as mechanism of regulation of invasion and metastasis by MDA-9/Syntenin and AEG-1. These studies complement mechanistic studies in melanoma.

Unique link between MDA-9/Syntenin/IGF-R1/STAT3 in prostate cancer development and progression: Progression of prostate cancer (PC) to hormone resistance and metastasis are major problems in clinical management, which negatively impact survival. Accordingly, identifying the molecular changes that lead to invasion and distant metastases is critical for developing improved approaches to delimit these processes and enhance patient outcome. Based on genomic databases and pre-clinical studies using patient samples, we have demonstrated that MDA-9/Syntenin expression is associated with high histological grade and advanced cancer stage. At a molecular level, MDA-9/Syntenin activates the transcription factor STAT3, whose aberrant activation is associated with advanced stages of PC (79,80) through interacting with Insulin Growth Factor-1 Receptor (IGF-IR) and may contribute to metastatic progression (81) (FIGS. 49 and 50). Furthermore, a unique link involving this signaling cascade (MDA-9/Syntenin/IGF-R1/STAT3) with metastatic growth is established through experimental evidences indicating that inhibition of metastasis is achievable by selectively disrupting the interaction between MDA-9/Syntenin and IGF-1R (FIG. 50).

mda-9/syntenin was cloned in 1995 (26,27) and has been shown through recent bioinformatics and direct experimentation to be a critical component in cancer progression, serving as a direct regulator of cancer cell invasion and metastasis (21, 22, 29-41). The discovery that MDA-9/Syntenin is a major player in defining tumor dissemination in multiple cancer contexts represents an innovative observation that we are exploiting to develop novel anti-invasive and anti-metastatic therapies. Using state-of-the-art chemical approaches that employ fragment-based drug-discovery (FBDD) approaches in combination with NMR unique small molecules that can interface with the PDZ1 domain (PDZ1in; 113B7) of MDA-9/Syntenin have been identified. These inhibitors have been shown to have remarkable activity in suppressing invasion of a broad spectrum of cancer cells that overexpress MDA-9/Syntenin in vitro (FIGS. 46 and 47), and invasion and metastasis in vivo in animal model systems (FIG. 48).

Protein-protein interaction databases suggest that the PDZ1 motif of MDA-9/Syntenin can interact with a spectrum of proteins (66), including a predicted 151 of 250 proteins associated with the cancerous phenotype (67). Using the creative approaches, molecules unique to the interface of the PDZ1 domain of MDA-9/Syntenin have been generated confirming the power of the FBDD approach plus NMR for identifying small molecule inhibitors specific to this molecule. In the context of HCC, an important interaction at the cell surface of HCC cells between MDA-9/Syntenin, an oncogene AEG-1 (19,20,72,73,82), and EGFR has been demonstrated and characterized (83) (FIGS. 49 and 50) that will provide novel insights into hepatocarcinogenesis. Treatment with 113B7 in combination with sorafenib was also shown to inhibit HCC tumor growth in athymic nude mice, supporting the potential application of this anti-invasive and anti-metastatic agent in combination with other therapeutic agents in potentially treating liver cancer (FIG. 48).

An innovative discovery indicates that MDA-9/Syntenin can interact with IGF-R1 and this interaction is pivotal for activating STAT3 (FIGS. 49, 50, and 51) and this interaction is pivotal in PC development and progression. This discovery suggests potential ways of using PDZ inhibitors to treat PC.

Figure 45:
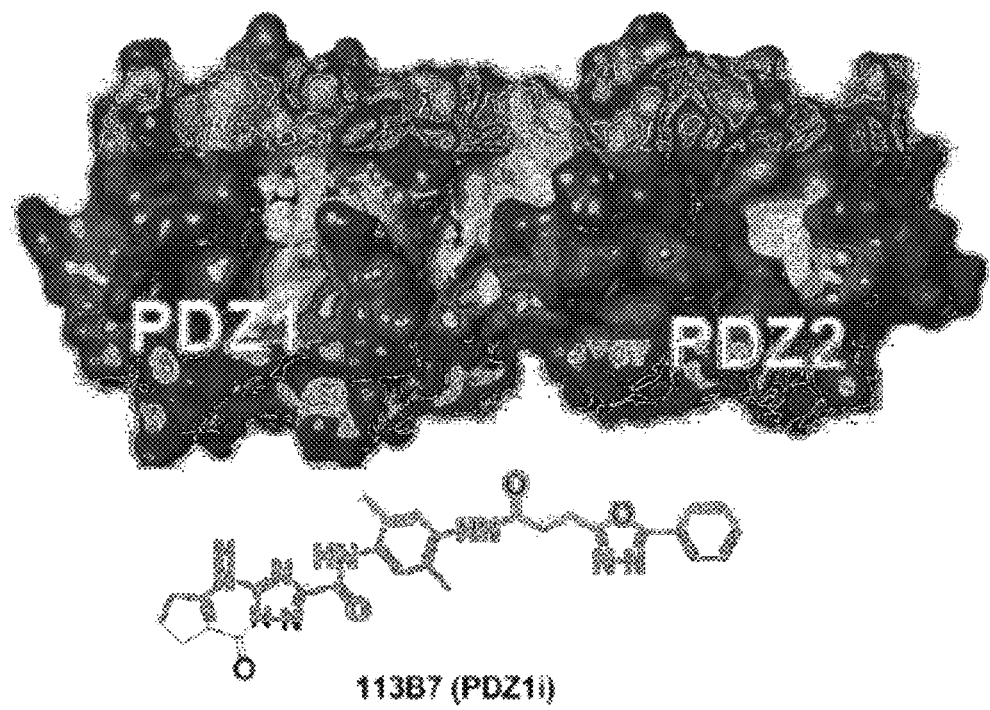
FIG. 45. Docked structure of compound 113B7 (PDZ1 in) on the surface of MDA-9/Syntenin. The docked structure is supported by NMR chemical shift mapping data. The titration allows for the calculation on an upper limit for the dissociation constant of the complex, Kd<10 μM. 113B7 does not bind appreciably to PDZ2 from MDA-9/Syntenin. or other PDZs used as counter screens.

The present program benefited from state-of-art approaches, FBDD and NMR guided structure based design, to identify small molecules that selectively bind to the PDZ1 domain of MDA-9/Syntenin, 113B7(PDZ1in) (FIG. 45). Once initial hits are verified (non-toxic to normal cells, suppress invasion in cancer cells and block specific protein-protein interactions), new variants will be prepared using medicinal chemistry approaches. These new small molecules will undergo a series of evaluations to define appropriate molecules to ultimately be tested for in vivo activity, using lung retention assays and metastasis development. The overall strategy to be used will involve: 1) initial evaluation for a lack of growth inhibitory or toxic properties in normal immortal melanocytes, hepatocytes and prostate epithelial cells using MTT assays; 2) screening of non-toxic compounds for effects on proliferation (MTT assays) and invasion (96-well invasion assays) of human melanoma, HCC and PC cells; 3) confirming the effect of biologically active potential lead compounds as inhibitors of specific protein-protein interactions between the PDZ1 domain and defined interacting molecules (including src, EGFR and IGF-R1) using co-immunoprecipitation and colocalization analyses (FIGS. 49 and 50); and 4) define safety and efficacy in melanoma, HCC and PC animal models when injected IP and IV. Since small molecule development is an iterative process, compounds showing desired activity will then be used as scaffolds for developing new small molecules by appropriate chemical biological approaches. Compounds will be tested in the context of melanoma, HCC, PC, and for defining efficacy against specific metastases (including those induced by melanoma, HCC and PC).

Figure 46:
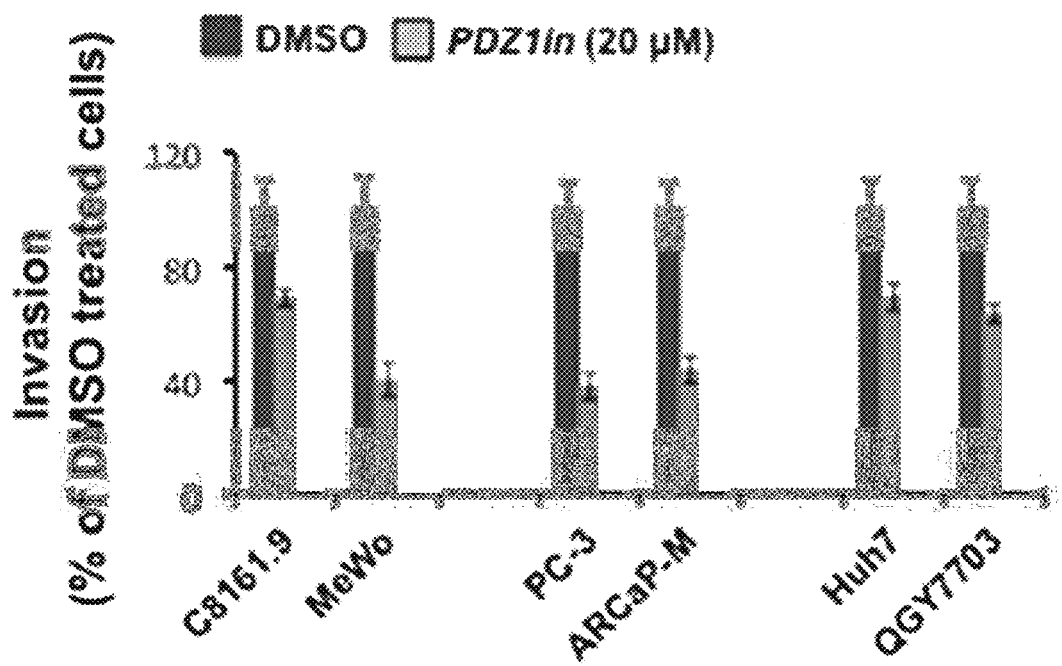
FIG. 46. Small molecule MDA-9/Syntenin PDZ1in (113B7) inhibits invasion in melanoma, HCC and prostate carcinoma cells. Tumor cells were pre-treated with either DMSO (vehicle) or PDZ1in (113B7) (dose indicated) and invasion ability was assayed using a modified Boyden Chamber. Results of three independent experiments is provided in the graphs S.D. Melanoma: C8161.9, MeWo; PC: PC-3, ARCaP; HCC: Huh7, QGY7703.

Preliminary results include the design and characterization of a first series of compounds targeting PDZ1 using a combination of FBDD techniques guided by structure and NMR-based design. Fragment hits were found that bind to the PDZ1 domain (F1 in FIG. 45) and at the interface between the domains (F2 in FIG. 45). An initial F1 PDZ1 fragment hit (FIG. 45) was selected among these based on affinity by NMR and ITC (Kds ranging between 30 and 300 µM for about 30 compounds analogues of this class tested) and by the fact that the fragment hit appears non-cytotoxic (<50 µM) to both primary immortal melanocytes and aggressive melanoma cells. Guided by NMR structural studies and docking, have generated novel and effective bi-dentate PDZ1 inhibitory compounds spanning both the PDZ1 and an interface pocket (FIG. 45). The bi-dentate compound of this series represented by 113B7 has been characterized using NMR techniques and it displays dissociation constant in the low micromolar range according to NMR-titration binding assays. PK studies with 113B7 indicate that the compound is stable and long-lived ($T\frac{1}{2}>9$ hr) with nearly 80% bio-availability when administered I.P. Interestingly, this compound spans both the first PDZ domain and the interface between the two domains (experimentally verified by NMR), but it does not appreciably bind to the second PDZ domain, further corroborating our central hypothesis that it possible to obtain high affinity, selective PDZ antagonists. The effect of 113B7 on invasion was tested using a panel of 25 human cancer cells derived from different sites, including melanoma, pancreas, prostate, breast, liver (HCC) and brain (GBM) (FIGS. 46 and 47). These cancer cell types were chosen because they display a high basal level of mda-9/syntenin expression at both mRNA and protein levels compared with corresponding primary normal cell counterparts.

Pretreatment with 113B7 (PDZ1in) significantly inhibited the invasion of all of these cancer cells (FIG. 46) and invasion and metastasis in vivo (FIG. 48). Similar to the F fragment, the bi-dentate compound did not show any significant cytotoxicity, when tested up to 20 µM.

Another goal is to comprehend the mechanism by which mda-9/syntenin expression is upregulated in human HCC, unravel the molecular mechanism by which protein-protein interactions mediate pro-invasive and pro-metastatic functions of MDA-9/Syntenin, and evaluate a novel MDA-9/Syntenin inhibitor as a potential therapeutic for HCC. Thus, the overall approach is to understand the fundamental molecular mechanism regulating development and progression of HCC and exploit the garnered knowledge to develop novel therapeutics. The analysis of molecular mechanism of mda-9/syntenin upregulation might facilitate employment of strategies to block mda-9/syntenin expression as potential HCC therapeutics. Mapping of the protein-protein interaction domains between MDA-9/Syntenin and its interacting partners will pave the way for developing small molecule or peptidomimetics interrupting these interactions thereby inhibiting HCC. Finally, the evaluation of 113B7 next generation inhibitors, with sorafenib combinatorial treatment might facilitate immediate implementation of this strategy to treat HCC patients. Thus, our approach provides immediate translational significance and will accrue important insights to develop future targeted therapies.

Another goal is to comprehend the molecular mechanism by which mda-9/syntenin expression is upregulated in human PC, define the role of mda-9/syntenin in regulating PC stem/progenitor cell phenotypes, evaluate the MDA-9/Syntenin/IGF-1R/STAT-3 axis in PC metastasis and investigate novel MDA-9/Syntenin PDZ-inhibitors as potential modulators of PC pathogenesis. We will interrogate transcriptional regulation of mda-9/syntenin in PC cells as modulators of enhanced expression using appropriate molecular biological techniques. The role of mda-9/syntenin in maintenance of stemness, tumor evolution, angiogenesis and metastasis will be evaluated using both in vitro 3-dimensional culture systems and in vivo nude mouse models. We will explore the relevance of the observation that MDA-9/Syntenin physically interacts with insulin growth factor-1 receptor (IGF-R1) (FIG. 49), which activates STAT-3. Deletion analysis will be used to define the regions of MDA-9/Syntenin and IGF-R1 that interact and their functions and the downstream signaling pathways affected by these interactions. Studies will focus on the role of specific MDA-9/Syntenin PDZ inhibitors in modulating PC invasion using the Hi-myc mouse (FIG. 48). This inhibitor could also be evaluated in combination with cytotoxic drugs or immune mediators to define further enhancement in clinical activity.

Figure 48A:
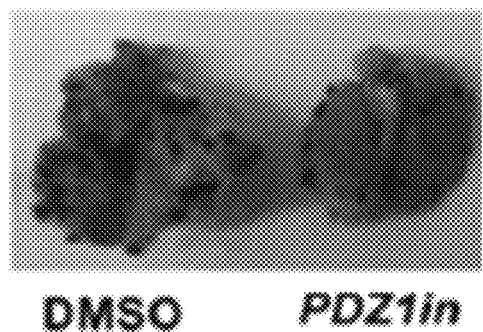
FIGS. 48A-48C. Biological effects of PDZ1i in vivo in melanoma, HCC and PC.
Figure 48B:
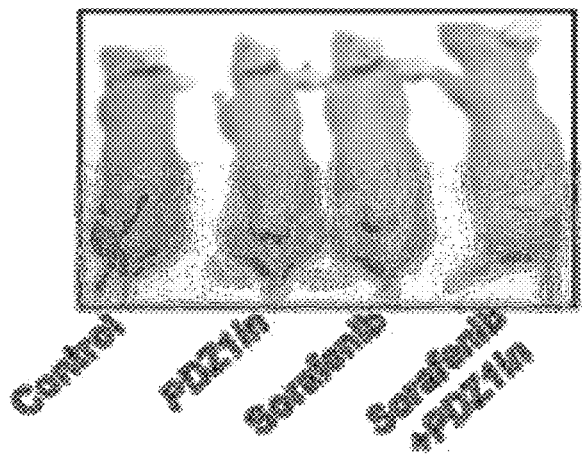

Based on primary screening (invasion assays) using a series of compounds developed using a combination of FBDD techniques guided by in silico docking and NMR-based design a small molecule PDZ inhibitor (PDZ1in) was selected for further validation. Initial validation of PDZ1in compound inhibited the invasive properties of cancer cells from multiple anatomic origins (FIGS. 46 and 47). Consistent with in vitro studies, in in vivo models the compounds demonstrated anti-metastatic efficacy in invasion after inhibitor treatment (FIGS. 46 and 47) and in immunocompetent C57BU6 mice (FIG. 48A).

Figure 48C:
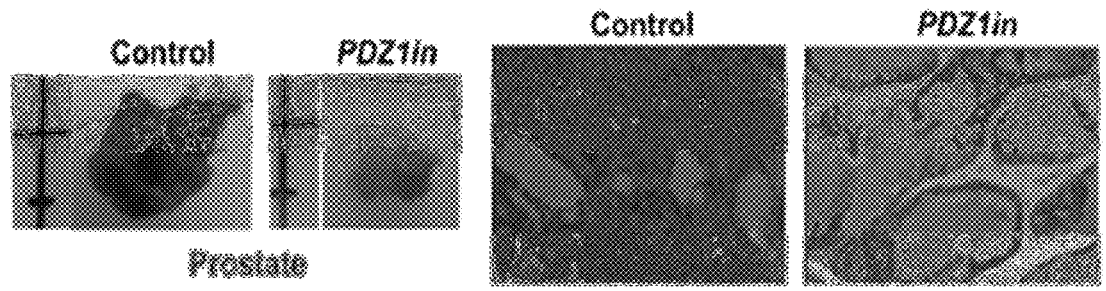
Figure 49A:
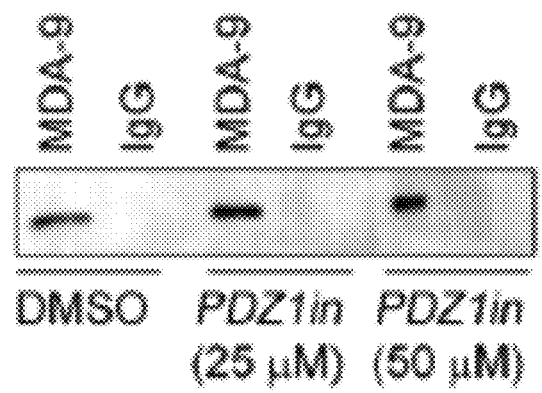
FIGS. 49A-49D. Effects of PDZ1in on interactions between MDA-9/Syntenin and its various interacting painters.
Figure 49B:
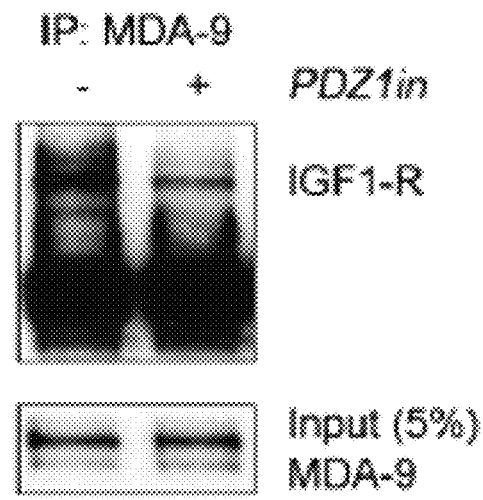
Figure 49C:
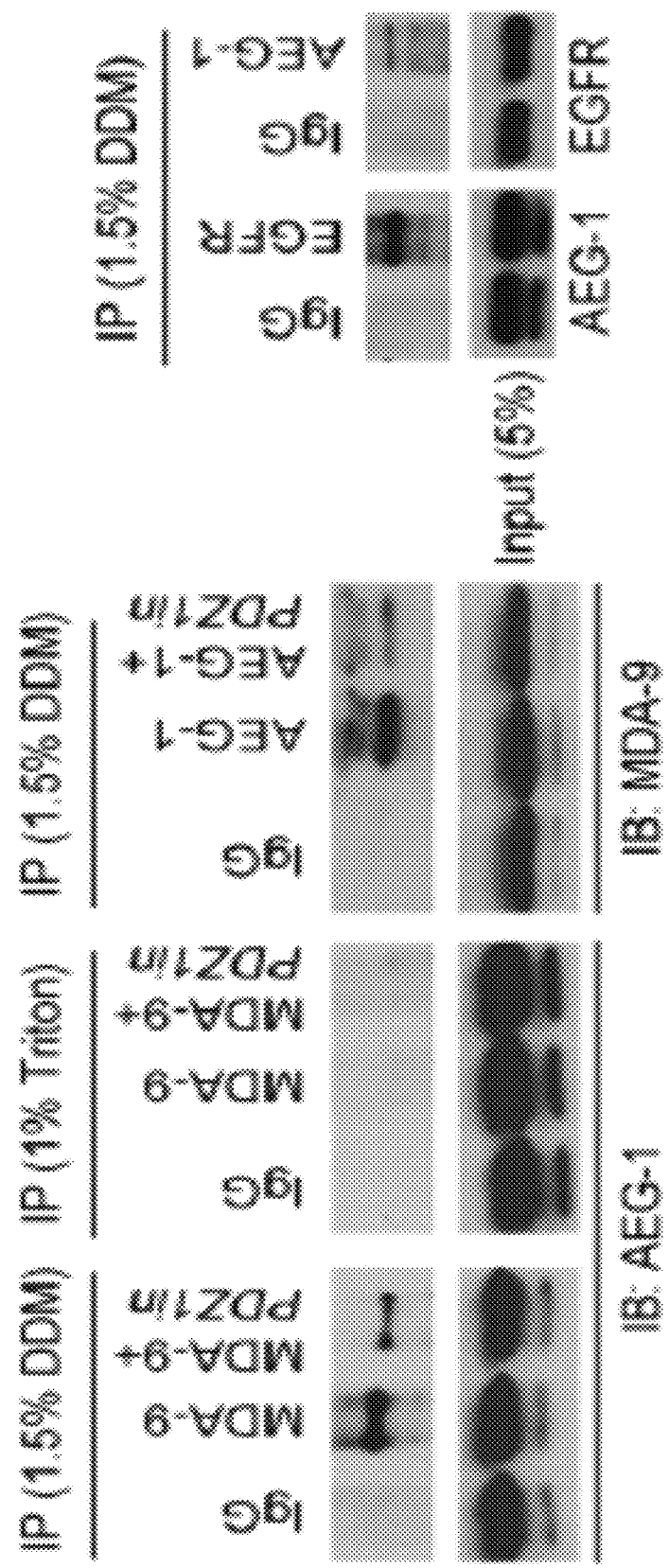
Figure 49D:
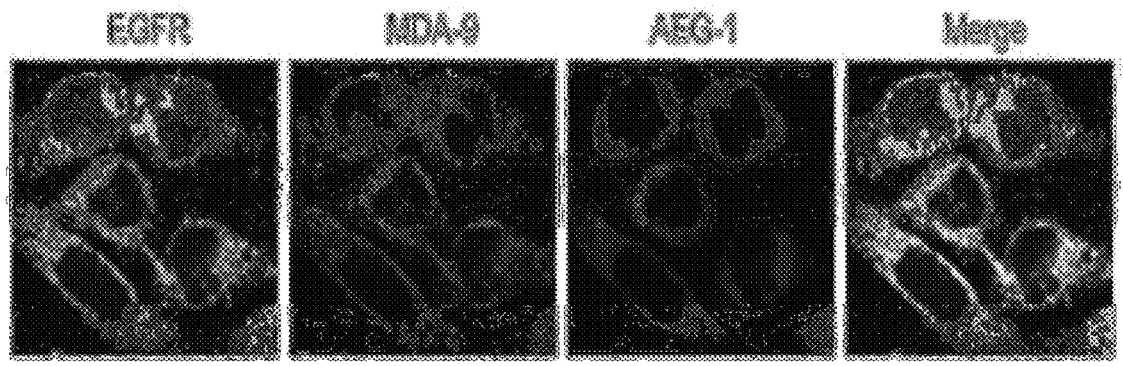
Figure 51:
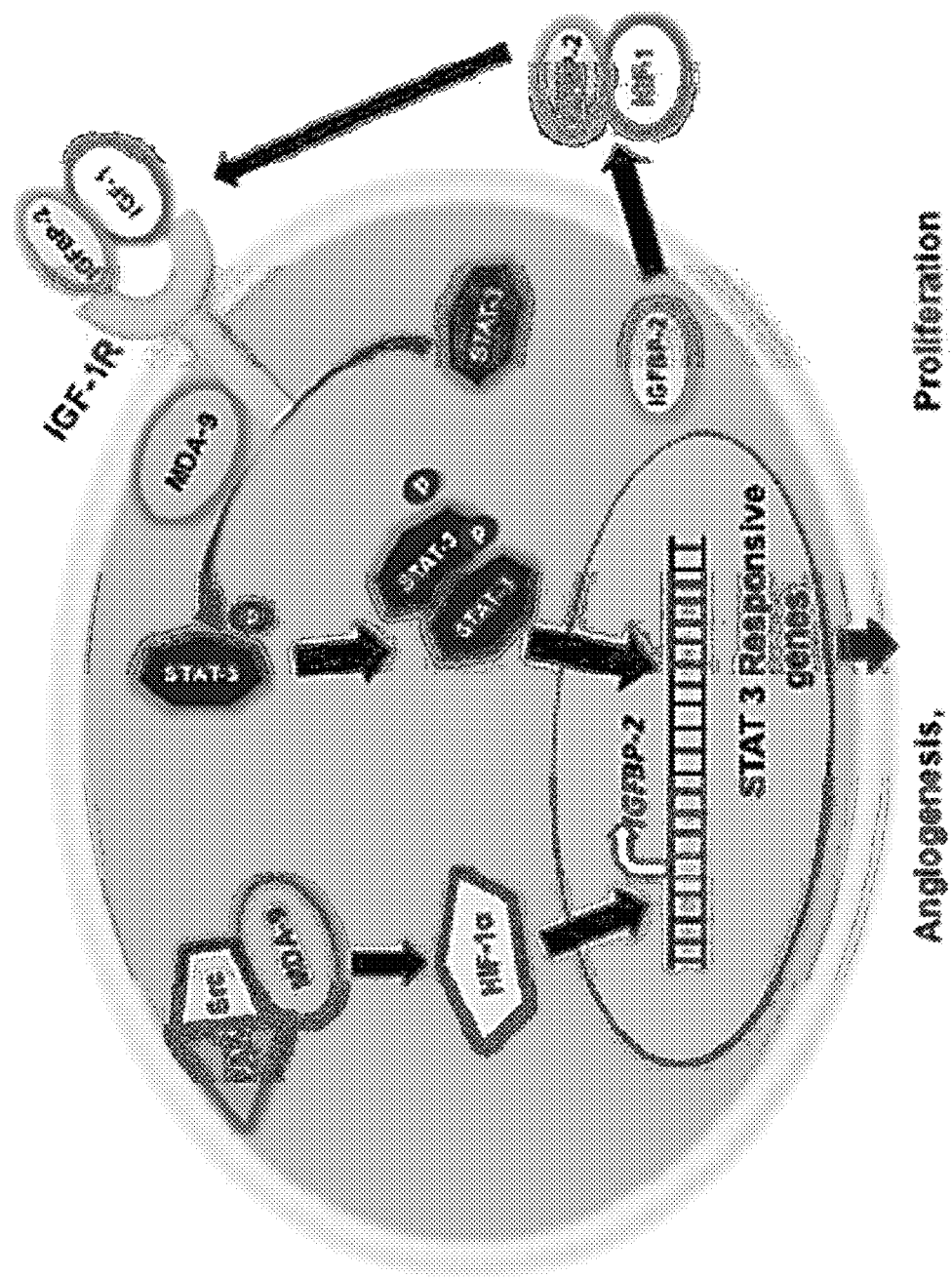
FIG. 51. Hypothetical model for MDA-9/Syntenin mediated prostate cancer progression. Initial supportive evidences were documented that MDA-9/Syntenin and IGF-1R physically interacts and stabilizes the functional unit to activate the STAT3 through phopshorylation at the tyrosine 705 position. Phospho-STAT3 forming a dimer and translocate to nucleus to induce various genes that actively participate in prostate cancer progression.

In addition, the anti-tumorigenic (through inhibition of angiogenesis) and anti-invasive role of PDZ1in was also confirmed in HCC derived xenograft model (FIG. 48B) and spontaneous prostate cancer transgenic model, respectively (FIG. 48C). Further studies showing that MDA-9/Syntenin as an adaptor protein can also interact with multiple protein(s), e.g., AEG-1 (in HCC), IGF-1R (FIG. 49) (in PC) and affect tumor progression, which was blocked by PDZ1in (FIG. 50). Novel observations in PC identify an MDA-9/IGF-R1/STAT3 link in PC development and progression (FIG. 51). Pharmacokinetics studies were performed to obtain insights about the druggable characteristics demonstrating that PDZ1in is stable ($T\frac{1}{2}>9$ hr) and bio-available (80%) (injected I.P. or I.V.).

Example 6. Pharmacological Tools to Inhibit PDZ Domains of MDA-9

Figure 44:
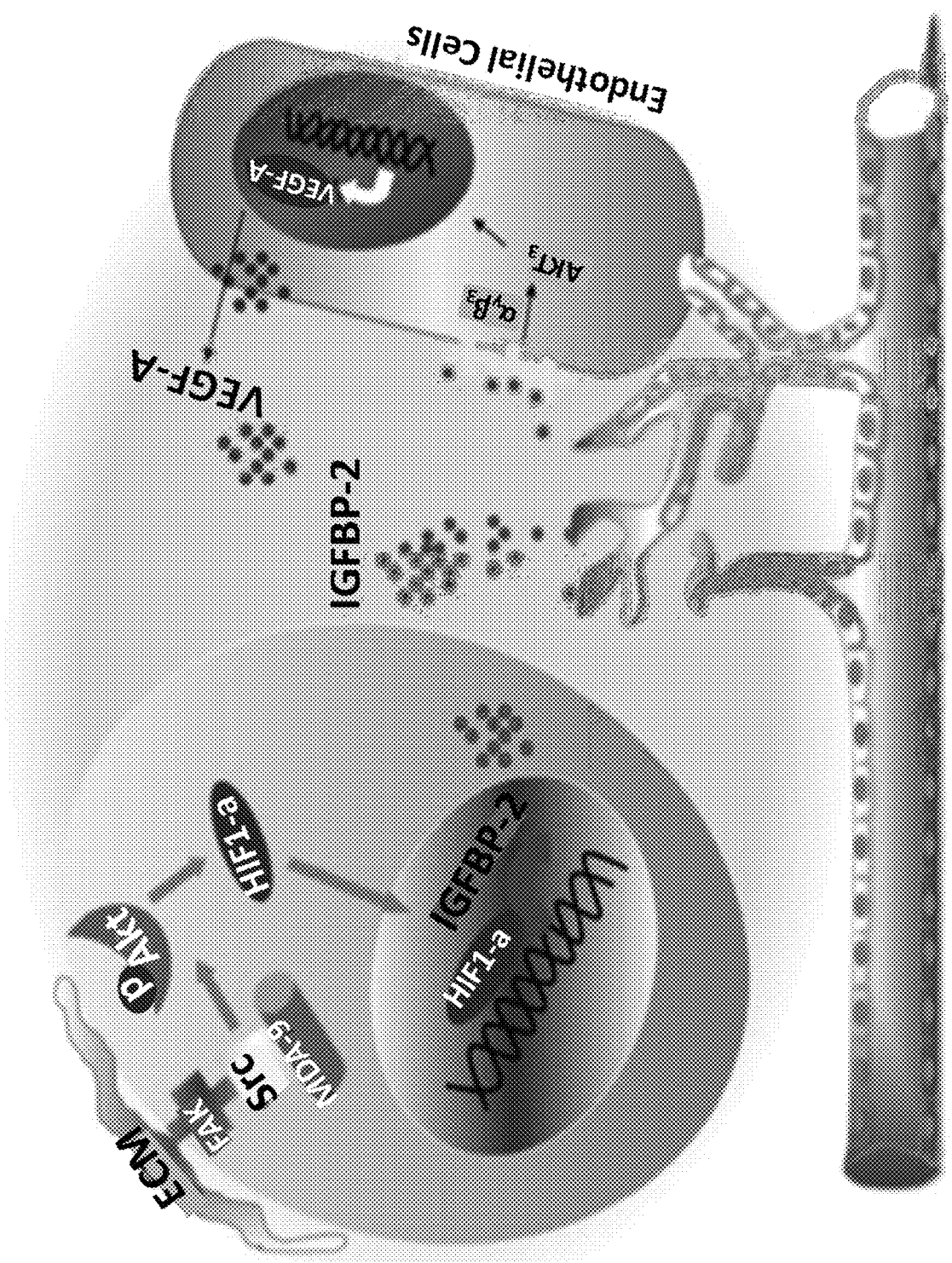
FIG. 44. Hypothetical model of MDA-9/Syntenin-mediated angiogenesis. MDA-9/Syntenin upon interaction with c-Src, activates HIF-1α in an AKT-dependent pathway and induces IGFBP-2 expression. IGFBP2 acts as a chemoattractant for endothelial cells and induces VEGF-A secretion resulting in angiogenic phenotypes.

Recent observations delineate a pivotal role of MDA-9/Syntenin and its PDZ domains (1) in melanoma progression/invasion/metastasis (2-5) (FIG. 44). Intriguingly, this gene is overexpressed in several additional cancers (6, 7) and it has been hypothesized as being potentially associated with tumor evolution and metastatic disease progression in multiple human neoplasms including melanoma, glioblastoma, liver, bladder, head and neck, pancreatic and prostate, thereby establishing MDA-9/Syntenin as a genuine potential global target for developing cancer therapeutics blocking tumor invasion and metastasis. mda-9/syntenin was cloned and shown to be an interaction hub regulating through its PDZ domains (8-10) (FIG. 44), multiple signal transduction pathways, including Src activation, FAK phosphorylation, p38 activation and JNK activation, all of which are involved in tumor progression, invasion and metastasis. Additionally, mda-9/syntenin induces enhanced expression of a number of secreted proteins that contribute to the cancer phenotype. Based on the considerations described above, targeting the interaction between MDA-9/Syntenin's PDZ1 domain and its targets through novel small molecular inhibitors and developing suitable pharmacologically acceptable drugs using innovative fragment- and structure-based approaches holds significant potential for producing effective therapeutics for inhibiting metastatic disease progression in a broad-spectrum of human cancers. Using a modular approach, we have derived inhibitors targeting PDZ1 and the interface between the domains, MDA-9/Syntenin. We intend to use these initial chemical probes to further our understanding of the role of MDA-9/Syntenin in the invasive and metastatic behavior of tumors using animal models. Furthermore, we intend to obtain the structural determinants as the basis of the binding of these molecules using solution NMR spectroscopy and to use the resulting structures to refine the molecules for potency, selectivity and also pharmacological properties as needed. In addition to evaluating these new small molecules in metastatic melanoma it will further be investigated in hepatocellular carcinoma (HCC), and prostate cancer. Our studies will provide new insights into metastasis mediated by a pro-metastatic gene, mda-9/syntenin in a variety of human cancers. As indicated, lead compounds will be evaluated in a variety of models and if successful our studies will provide critical validation. Based on these exciting findings and solid foundations, we propose the following.

To Develop Innovative Pharmacological Tools Targeting PDZ Domains of MDA-9/Syntenin.

Our chemical biology approach consists of parallel optimizations/evaluation including performing structural studies and structure-guided SAR on our initial PDZ inhibitor (PDZin) compounds in complex with MDA-9/Syntenin to iteratively optimize the compounds not only for affinity, but also for their pharmacological properties (ADME-Tox), to increase the likelihood that these resulting compounds will have cellular and in vivo efficacy (Aim 2). Three parallel strategies are proposed in an attempt to obtain specific ligands for the first PDZ domain of MDA-9/syntenin.

Mechanistically Evaluate Current MDA-9/Syntenin PDZ Inhibitors (PDZin) in Preventing Melanoma Cell Adhesion, Invasion and Metastasis, and Identify/Characterize the Next Generation of PDZin.

The biological and molecular properties of specific PDZ inhibitors (PDZin), including effects on normal cell survival, cancer cell invasion, protein-protein interactions, retention of tumor cells in the lungs and generation of metastatic lesions in vivo, will be performed. Mechanistic studies will focus on defining the pathways and critical genes associated with enhancing invasion, attachment and metastasis that are manipulated by overexpressing or inhibiting MDA-9/Syntenin expression in human melanoma cells. This combination of medicinal chemistry and preliminary biological characterization, to define appropriate small molecules and mechanistic studies in the context of metastatic B16 mouse and human MeWo and C8161 melanoma cells, will provide necessary insights for further studies, particularly in vive experiments, proposed in HCC and prostate carcinoma.

Metastasis: the ultimate challenge for effective cancer therapy: Metastasis, is a multistep process involving migration of cancer cells from their origin in a primary tumor to colonization at distant sites, thereby posing significant challenges to drug discovery (11).

Although 90% of cancer-associated mortality is due to metastasis and this process has been extensively studied, it remains one of the most enigmatic aspects of the disease and mandates an in-depth understanding of the sequence of events orchestrating the metastatic cascade (11, 12). From a therapeutic standpoint, elucidating the mechanisms leading to successful physical translocation and colonization of tumor cells from primary sites to loco-regional or distant sites holds promise for developing effective therapeutics for preventing and treating metastases (13-16). In principle, effective antimetastatic drugs could be developed that target intravasation: initial detachment and release from the primary tumor followed by mobilization through the extracellular matrix of surrounding tissues, and survival in the bloodstream; and/or extravasation at secondary sites, followed by production of new blood vessels (angiogenesis) and survival/growth of micro-metastatic lesions (11, 13, 15). The global process is extremely complex involving interplay of multiple signaling pathways, including sequential alterations of genetic and epigenetic components. Consequently, elucidating the molecular targets involved in tumor metastasis is mandatory if one is to develop novel and clinically effective inhibitors for cancer therapy (11, 12, 14-16).

Melanoma differentiation associated gene-9 (mda-9/syntenin): a positive regulator of melanoma metastasis: mda-9, also known as syntenin (1) (mda-9/syntenin), was cloned using subtraction hybridization as a gene displaying differential expression as a consequence of induction of irreversible growth arrest, terminal differentiation and loss of tumorigenic potential in HO-1 human metastatic melanoma cells following treatment with fibroblast interferon (IFN) and the protein kinase C activator mezerein (17). Bioinformatics data employing genome-wide expression datasets (such as TCGA and GEO) indicate that mda-9/syntenin (syndecan binding protein; SDCBP) is elevated in numerous cancer types and expression is enhanced as these cancers progress to a more invasive and metastatic state. This includes glioblastoma multiforme (GBM) (18), urothelial carcinomas (19), melanoma (2-4, 20-22), prostate carcinoma, and hepatocellular carcinoma (HCC). Although both bioinformatics analysis and our preliminary observations indicate a positive correlation of mda-9/syntenin expression with multiple cancers, its exact role(s) in many of these neoplasms have not been established. Suppression subtractive hybridization between poorly invasive/nonmetastatic and an invasive/metastatic breast cancer cell line identified mda-9/syntenin overexpression in metastatic cells (6). Forced expression of mda-9/syntenin resulted in increased migration and invasion by normal and non-metastatic cancer cells, and correlated with a more polarized distribution of F-actin and increased pseudopodia formation (1, 2, 23). Additionally, immunohistochemical analysis revealed a statistically significant gradual increase in MDA-9/syntenin protein expression from acquired melanocytic nevi to primary melanoma without or with progression to metastatic melanomas. Thus, the accumulated data strongly support the hypothesis that mda-9/syntenin functions as a positive regulator for melanoma metastasis as well as aggressiveness in melanoma, GBM, HCC, prostate, breast and gastric cancers, and might be involved in metastasis in multiple additional cancers.

The PDZ domains of MDA-9/Syntenin: prevalence and significance in metastasis: PDZ domains (an acronym for three proteins-postsynaptic density protein PSD95/SAP90, drosophila tumor suppressor DLGA, and tight junction protein ZO-1 containing proteins) are a diverse group of over 150 proteins that control diverse and central physiologic processes (24-26). One of the best-studied proteins from this group MDA-9/Syntenin (8-10, 19, 22, 27, 28), has a surprising variety and diversity of interacting partners and through its specific localization, controls a variety of molecular events. Structurally, MDA-9/Syntenin has two PDZ domains: PDZ1 (a.a. 110-193) and PDZ2 (a.a.194-274) and in the context of melanoma metastasis, both PDZ domains are critically involved, since deletion mutants (either one of the two PDZ domains) of MDA-9/Syntenin significantly reduced lung metastases compared with the cells transfected with wild type MDA-9/Syntenin (4). Mechanistically, MDA-9/Syntenin was shown to interact with c-Src, a member of the Src family tyrosine kinases involved in numerous biological processes associated with cytoskeletal organization, including increased cell motility, invasiveness, and survival (29) through the carboxylate-binding loop of PDZ2. However, PDZ1 also plays a critical role in binding by promoting the proper folding of PDZ2 that assembles MDA-9/Syntenin into a multimeric complex resulting in a more stable functional unit. Accordingly, MDA-9/Syntenin through its interaction with itself and with c-Src enables c-Src/FAK signaling complexes clustered at high concentrations on the plasma membrane to amplify signaling through FAK intermolecular autophosphorylation. These events lead to enhanced cell motility, invasion, and metastasis. Accordingly, loss-of-function (LOF) studies, using genetic and pharmacological approaches, indicate that inhibiting MDA-9/Syntenin or c-Src and thereby decreasing the interaction between MDA-9/Syntenin and c-Src, block metastasis in human melanoma cells (5).

Clinical Relevance of MDA-9/Syntenin Overexpression:

Previous studies have shown a statistically significant increase in MDA-9/syntenin expression in advanced stages of melanoma, GBM, breast, urothelial, HCC and prostate cancer (6, 7, 9, 19)

Targeting PDZ domains of MDA-9/Syntenin for pharmacological intervention. Recent years have witnessed a growing interest in targeting this class of proteins with some initial success (Table 3) using small peptides, natural products and small molecules. These initial accomplishments are quite exciting and suggest that the PDZ domains are "druggable". However, there are several challenges associated with targeting PDZ domains for therapeutic purposes (35-42), since they are involved in many protein-protein interactions. While there are over 150 PDZ domains in the human genome discovered thus far, their binding surfaces are likely distinct. Bioinformatics analysis of The Cancer Genome Atlas (TCGA, cancergenome.nih.gov/) indicates that from at least 151 PDZ-containing proteins present in the human genome, many are overexpressed in multiple cancers, and many of these cancers also have elevated mda-9/syntenin expression. In turn, each of these genes has potential interaction partners that can be identified using protein-protein interaction databases. Peptide-based inhibitors might suffer from bioavailability limitations, such as metabolic stability and unfavorable physiochemical properties, which could reduce their therapeutic benefit. To overcome such limitations, modifications of peptide inhibitors, such as f-strand peptide-mimetic and cyclic peptides, for PDZ protein-protein interactions were suggested (38, 43). Nevertheless, the development of small organic molecules remains the most promising approach (31). For this reason, we propose to use a combination of powerful Fragment- and NMR-Based Drug Discovery (FBDD) approaches (44-47) to derive focused libraries of MDA-9/Syntenin PDZ1-targeting ligands. Our preliminary data demonstrates that these strategies enabled the identification and initial optimization of small molecules capable of targeting and antagonizing MDA-9/Syntenin in vitro in cell cultures through its PDZ1 domain (PDZ1in). Interestingly, these small molecules do not target the PDZ2 domain of MDA-9/Syntenin, demonstrating that despite the similar global fold, these domains tend to have fairly distinct binding surfaces.

TABLE 3

PDZ domains targeted for pharmacological use.

| TARGET | ANTAGONIST | | PHASE OF DEVELOPMENT | FUNCTIONS |
|---|---|---|---|---|
| PSD-95 PDZ2/NMDA or nNOS | NA-1 Lead | | Phase 1 | Treatment of ischemic brain damage; Na-1 showed safety and tolerability after IV administration (30). |
| Dishevelled PDZ/Fz7 Wnt receptor | 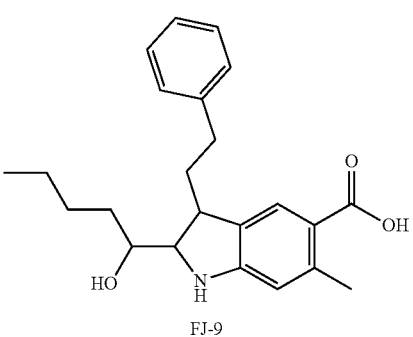 [SMILES: CCCCC(O)C1Nc2cc(C)c(C(=O)O)cc2C1CCc1ccccc1] FJ-9 | | Lead compound | Induction of apoptosis in human cancer cell lines and tumor growth inhibition in a mouse xenograft model (31). |
| PSD-95 PDZ2/NMDA or nNOS | Flavonoids | | Natural product | Flavonoids bind to the PSD-95 PDZ2 (32). |
| Dishevelled PDZ/Fz7 Wnt receptor | Fz7 peptide (GSKTLQSWRRYH) Dapper peptide (SGKLKLMTTV) | | Pre-clinical | In Xenopus embryos, Fz7 (or Dapper) peptide attenuates Wnt3A-induced canonical Wnt signaling (33). |

TABLE 3-continued

PDZ domains targeted for pharmacological use.

| TARGET | ANTAGONIST | PHASE OF DEVELOPMENT | FUNCTIONS |
|---|---|---|---|
| Dishevelled PDZ/Fz7 Wnt receptor | 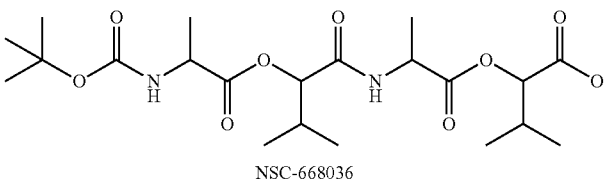 [SMILES: CC(NC(=O)C(OC(=O)C(C)NC(=O)OC(C)(C)C)C(C)C)C(=O)OC(C(=O)O)C(C)C]<br>NSC-668036 | Pre-clinical | In Xenopus embryos, NSC-668036 inhibits the canonical Wnt signaling induced by Wnt3A (34). |

PDZ1in:

small molecules targeting the PDZ1 domain of MDA-9/Syntenin. A series of compounds have been developed targeting PDZ1 using a combination of FBDD techniques guided by in silico docking and NMR-based design. Application of these approaches generated PDZ1 inhibitory compounds (PDZ in).

The bi-dentate compound of this series represented by 113B7 has been characterized using NMR techniques and it displays a dissociation constant in the low micromolar range according to NMR-titration binding assays and ITC. Interestingly, this compound spans both the first PDZ domain and the interface between the two domains (FIG. 52), but it does not appreciably bind to the second PDZ domain or other PDZs, thereby showing selectivity (see FIG. 52) and further corroborating our central hypothesis that it is possible to obtain high affinity, selective PDZ antagonists. The effect of 113B7 on invasion was tested using a panel of human cancer cells derived from different sites, including melanoma, pancreas, prostate, brain (glioblastoma (GBM)), breast, and hepatocellular carcinoma (HCC). These cancer cell types were chosen because they display a high basal level of MDA-9/Syntenin expression at both mRNA and protein levels compared with corresponding primary normal cell counterparts. Pre-treatment with 113B7 (PDZ1in) significantly inhibited the invasion of all of these cancer cells. It is worth noting that the compound did not show any significant toxicity, to melanocytes when tested up to 100 μM.

The immediate objectives are to comprehend how a novel metastasis-associated adapter protein, MDA-9/Syntenin, induces tumor progression culminating in acquisition of metastatic competence and to develop novel targeted therapeutic agents through exploitation of elegant approaches using fragment- and structural-based strategies combined with in silico drug design and medicinal chemistry. The central hypothesis is that through its two PDZ domains, MDA-9/Syntenin facilitates tumor progression by augmenting several distinct but complementary components of the tumorigenic process, including invasion/migration (2) and angiogenesis (3), through its ability to activate multiple signal transduction pathways.

We propose to derive novel, focused compound libraries targeting MDA-9/Syntenin using a combination of FBDD techniques guided by in silico docking and NMR-based design. We will use initial scaffold fragments and subsequent NMR studies to design and prioritize compounds to be synthesized and tested iteratively. The main objective is identify compounds that specifically bind to the PDZ1 domain.

In all binding assays, the MDA-9/Syntenin construct used for the screen contains both PDZ domains. Constructs uniformly labeled with $^{15}$N and $^{13}$C or $^{13}$C-Met selectively labeled are used for binding, mapping and structural studies. These same proteins are used for ITC binding studies.

As anticipated, our fragment-screen of 5,000 compounds resulted in only a few binding hits (tested at 500 μM against PDZ1/2 at 10 μM using ID $^1$H NMR aliphatic screen followed by 2D [$^{15}$N,$^1$H] HSQCs titration and ITC measurements). Interestingly, we found that these hits bind only to the PDZ1 domain or to the space between the domains, while no binders for the PDZ2 were identified.

Based on these studies and NMR guided initial docking calculations, >50 bi-dentate compounds were synthesized and tested, leading to compound 113B7 (FIG. 52). These initial higher-affinity bi-dentate compounds represented by 113B7 (FIG. 52) do not significantly bind to the second domain up to 100 μM, suggesting that it is indeed possible to obtain high affinity and selective ligands with the proposed approach, (4). Moreover, as a way to further address specificity of our ligands, we also tested the most promising compounds against two closely related domains to the PDZs of MDA-9/Syntenin, such as the PDZ tandem protein Harmonin (36% identity to PDZ2 of MDA-9/Syntenin and 31% to PDZ1 of MDA-9/syntenin) or PDZ domain from X11/mint scaffold protein (33% identity with PDZ1), and no significant binding to these counter-screen proteins was observed (FIG. 52).

Figure 53:
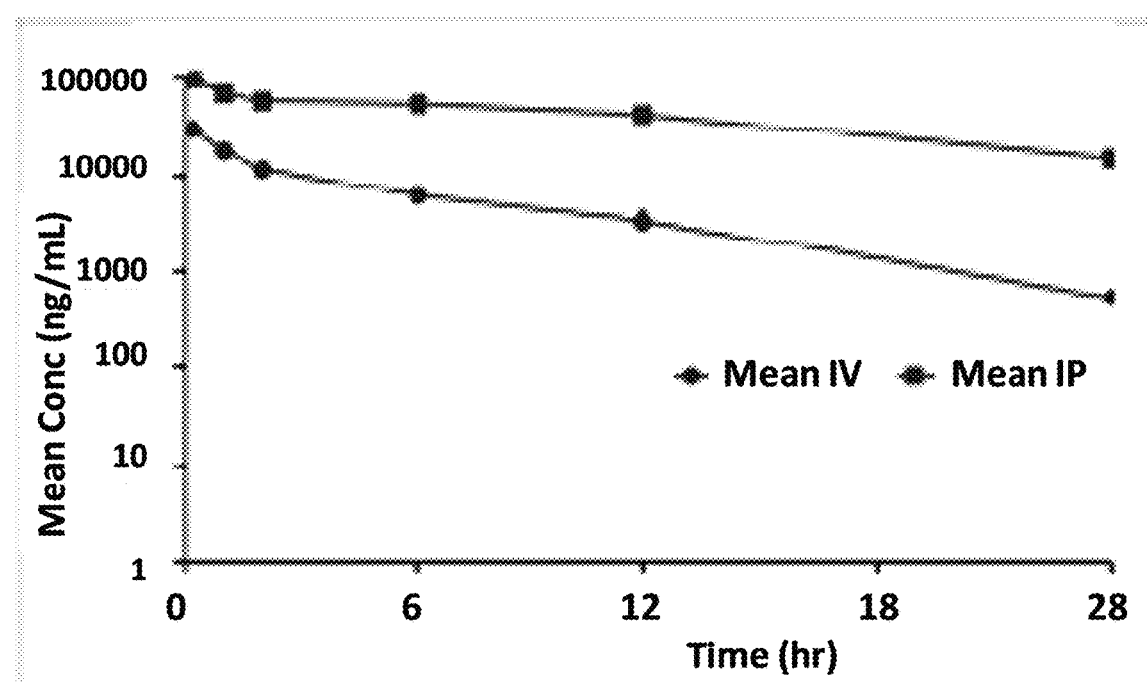
FIG. 53. PK studies with 113B7. 3.0 mg/Kg (IV) and 30.0 mg/Kg (IP) drug were administered in mice (n=3) and compound concentration in serum were measured at the indicated times. Noteworthy are the lack of adverse signs of toxicity during the experiment, the very slow clearance with $T_{1/2}$>9 hr in each route and the 80% bioavailability for the compounds administered IP. Based on these data, we anticipate that 1-3 weekly doses of the drug I.P in 30 mg/Kg would result in an effective dose for achieving a constant inhibition of the target.

In addition, the molecules are tested against a series of proteins available in the laboratory involved in protein-protein interactions including Mcl-1, Bcl-xL, Bid, MT1-MMP-PEX domain, IL20R, RKIP, Jnk2 (JIP-binding site Met labeled), Ubc13, SIAH1, and Ship2-SAM. Preliminary studies with several of these protein domains and 113B7 revealed no appreciable binding at 50 μM with 1:1 ligand/protein ratio. Based on these data, we propose to derive a small library of 113B7 analogues, guided by NMR structural data and test these resulting compounds iteratively against MDA-9/Syntenin by NMR and ITC. In designing compounds using elements of the libraries, particular emphasis will be put on drug-like properties of the compounds. In order to prioritize the compounds for further cellular and efficacy studies, in vitro ADME-tox studies will be performed to select those candidates with the highest likelihood to possess necessary stability, solubility and cell permeability to be meaningfully tested in cells and in vivo. Additionally, the MTD and PK properties on selected compounds prior to their eventual evaluations in vivo in will be addressed. Preliminarily, PK studies with 113B7 indicate that the compound is stable and long-lived with nearly 100% bioavailability when administered IP (FIG. 53).

Synthetic Chemistry and Design:

In designing the compounds to be tested and/or synthesized, particular attention will be given to the chemical properties of the selected compounds in an attempt to address "drug-likeness" on empirical grounds. The goal in using these empirical drug-like property filters is to predict favorable outcome in ADME-Tox (adsorption, distribution, metabolism, excretion, toxicity) studies, as well as final success as drugs in humans. In performing small-scale synthesis of the initially proposed linked compounds, we will make extensive use of either solid-phase synthesis or solution-phase synthesis aided by resin-bound reagents and scavengers. For example, basic reducing reactions including reductions of carbonyl compounds, azides and oximes, reductive amination, reduction of conjugated enones to unsaturated alcohols, will be performed with MP-Borohydride resin (Argonaut). Similarly, our typical synthesis of acyl or sulfonyl derivatives, including esters, amides, and sulfonamides will be performed by using PS-DMAP for "Catch and Release" reactions, (Argonaut).

Likewise, we have successfully performed several reactions in homogenous media including Knoevenagel condensations, Diels-Alder, Claisen rearrangements, etc. For compounds' purification, we will make extensive use of precision packed RediSep columns and our CombiFlash Companion flash-chromatography systems. All final compounds are generally purified to >95% purity, as determined by a HPLC Breeze from Waters Co. using an Atlantis T3 3 µM 4.6 mm×150 mm reverse phase column. Compounds for in vivo studies are purified to ≥95% purity using preparative HPLC. Based on our initial SAR studies on compound 113B7 (Table 4) we propose a number of possible derivatizations.

TABLE 4

Examples of SAR studies (out of >50 compounds synthesized and tested thus far). Dissociation constants are estimated by NMR titration in 2D HSCQ experiments.

| Comp | R1 | $K_d$, µM$^a$ | % migr.$^b$ |
|---|---|---|---|
| 113B7 | (phenyl-oxadiazole) | ~10 | 62 |
| 112H9 | (3-CF$_3$-phenyl-oxadiazole) | 38 | 24 |

TABLE 4-continued

Examples of SAR studies (out of >50 compounds synthesized and tested thus far). Dissociation constants are estimated by NMR titration in 2D HSCQ experiments.

| Comp | R1 | $K_d$, µM$^a$ | % migr.$^b$ |
|---|---|---|---|
| 112H10 | (3-Cl-phenyl-oxadiazole) | ~40 | 35 |

Structural Studies on MDA-9/Syntenin Inhibitor Complexes:

While molecular docking studies in conjunction with chemical shift mapping will provide valuable insights on the mode of binding of compounds, we plan to obtain a high-resolution NMR structure of the most promising compound in complex with MDA9/syntenin, which may provide critical information for proper positioning of a chemical linker or further optimizations and scaffold hopping. This potentially time consuming task is largely facilitated by our current knowledge of the NMR solution structure of the PDZ1 domain of MDA-9/Syntenin and the availability of the complete resonance assignments. In order to obtain high-resolution structural information on MDA-9/Syntenin-inhibitor complexes, the combination of 3D $^{15}$N, $^{13}$C-edited NOESY [$^1$H-$^1$H] and 3D $^{15}$N, $^{13}$C-filtered [$^1$H-$^1$H] NOESY experiment supported by two-dimensional (2D) [$^1$H-$^1$H] NOESY experiments in D$_2$O, should provide necessary intra- and inter-molecular NOE constraints for structure calculation. Structure calculation will be obtained using a modified CYANA (80) and energy minimizations and structure-based docking and analyses will be performed using Sybyl-X (Cetera, NC) and GOLD (CCDC).

SARs of Small Molecule Lead Inhibitors of MDA-9/Syntenin Using Cellular Assays:

A critical step in assessing the properties of the compounds and to support iterative optimization will consist of a number of cellular assays that are relevant to MDA-9/Syntenin activity. For example, 113B7 targeting only PDZ1 domains shows very strong anti-invasive properties against human melanoma and genetically modified (mda-9/syntenin overexpressing) immortal human melanocytes (FM-516-mda-9) according to the manufacturer's instruction.

Three different concentrations will be used for each compound and the small molecule that displays reproducible, dose-dependent reduction of invasion in both cell lines will be further validated using different in vitro approaches including Boyden Chamber assays, anchorage-independent growth in soft agar and migration assays. The molecular mechanism(s) of anti-invasive properties, in particular the effects on MDA-9/Syntenin downstream signaling pathways such as c-Src phosphorylation and FAK. P38 MAPK and NF-κB activation will be scrutinized using our previously described approaches (2-5, 110, 111).

Figure 54:
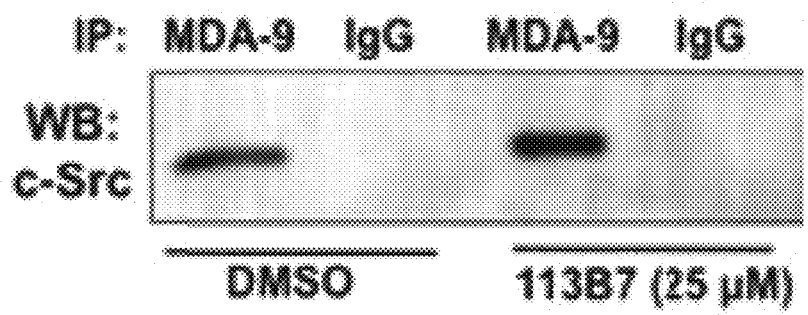
FIG. 54. Effects of PDZ1in (113B7) on MDA-9/Syntenin and c-Src interactions. C8161.9 cells were pre-treated with either DMSO or a dose of 113B7 (as indicated) and re-plated onto fibronectin-coated plates. After 30 minutes, cell lysates were immunoprecipitated and immunoblotted with the indicated antibodies. IgG, immunoglobulin.
Figure 55A:
FIGS. 55A-55D.
Figure 55B:
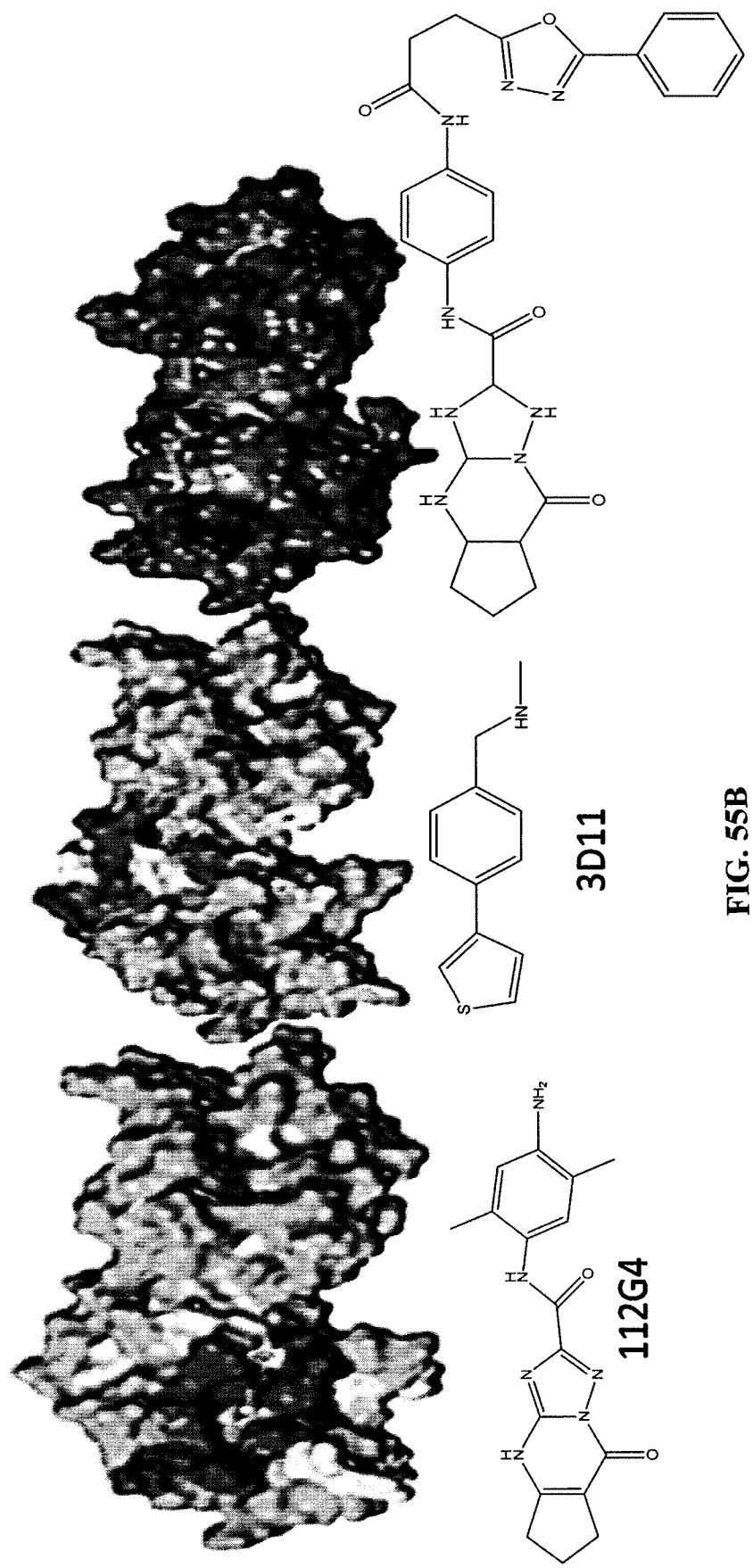
Figure 55C:
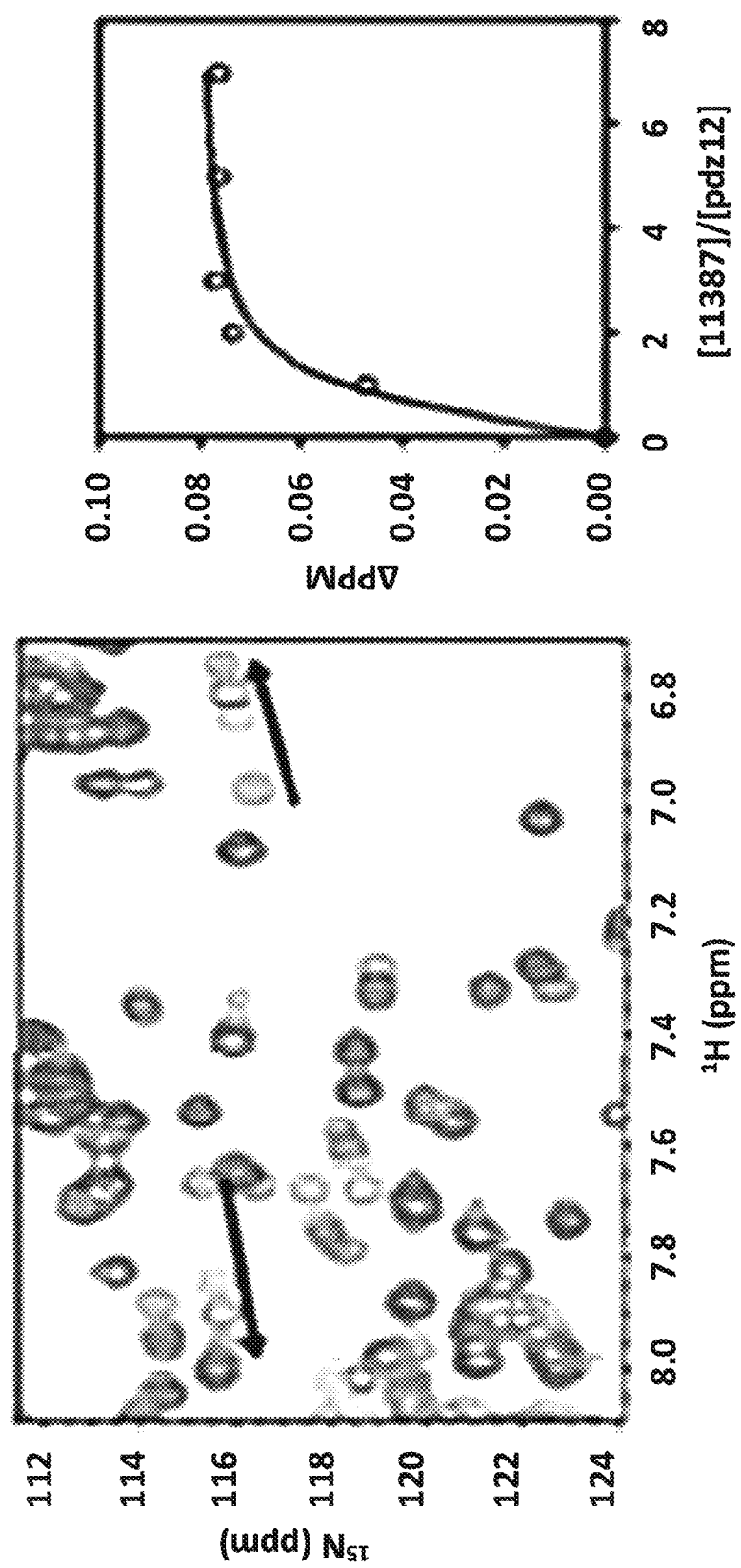
Figure 55D:
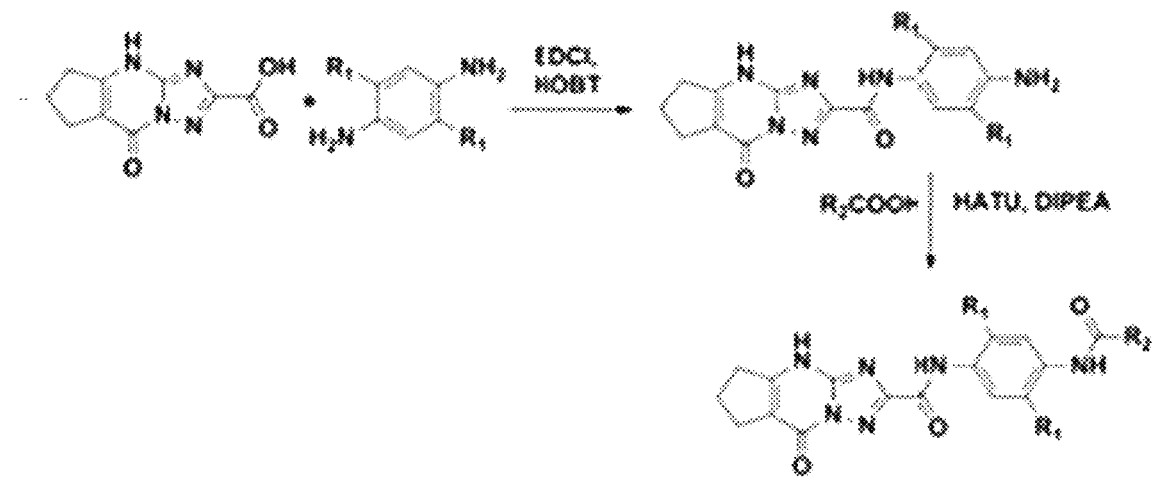

Effect of PDZ1In on c-Src Binding to MDA-9/Syntenin:

Another fundamental issue that we will address as part of the proposed hit-to-lead optimization process is the specificity of the binding of 113B7 to the PDZ1 domain of MDA-9/Syntenin. Previous studies demonstrate that c-SRC initially binds to MDA-9/Syntenin through the PDZ2 domain followed by recruitment of the PDZ1 domain (4, 5). Deletion analysis indicated that both PDZ1 and PDZ2 domains of MDA-9/Syntenin are necessary for retention of binding and downstream signaling and deletion of either or both of the PDZs results in a loss of MDA-9/c-SRC interaction and inhibition of transformation-associated properties (invasion, growth in agar) in vitro and metastasis of melanoma cells to the lungs of mice in vivo (4, 5). To determine if the PDZin molecule alters physical binding we performed co-immunoprecipitation analysis with c-Src and MDA-9/Syntenin in the presence or absence of 113B7 (FIG. 54). In the case of 113B7, which binds to PDZ1 and the interdomain of MDA-9/Syntenin, no inhibition of c-Src binding was evident. This results suggests that other pathways are regulated by MDA-9/Syntenin that contribute to metastasis when PDZ1 is inhibited by 113B7 (FIG. 54).

In Vitro ADME-Tox Properties and Pharmacokinetks Studies:

Studies will be conducted for measurements of plasma and microsomal stability, and protein binding. Usign two API Sciex-4000 quadrupole mass spectrometers, each with a linear ion trap and coupled to a Waters Aquity ultra-performance liquid chromatograph. Initial rapid assessment of compound exposure in a series of candidates will be conducted by using the RACE protocols adapted by the facility (see also Vertebrate Animals). Subsequently, most promising compounds will be subjected to a full bioavailability/distribution analysis. Tissue penetration of compounds will be determined in a non-quantitative manner by LC/MS. These data will give us a rough idea of the concentration of intact compound that reaches the blood stream and the lungs, allowing us to compare that result with the concentration proven to be effective in culture experiments and the preliminary in vivo studies where the drugs are administered IV, IP or orally, and thus informing us whether we are achieving sufficient levels of compound in the desired target tissue. For example, preliminary PK studies with 113B7 were conducted (FIG. 53) suggesting that IP administration (a route of administration for repeated doses for initial efficacy studies) is a viable route of administration for PDZ1in.

To demonstrate in vivo activity and efficacy, compounds must meet certain minimum ADME criteria. As part of this grant application, we will select and iteratively refine the structure of compounds with favorable ADME profiles. Ultimately, these activities will guide the choice of possible antagonists as pharmacological tools for further in vitro cell and in vivo pharmacology and efficacy studies thus minimizing side reactions and liabilities that may be intrinsic with the derived molecules and not related with inhibition of the target. Possible problems that will be identified in any particular series of compounds will be addressed and possibly eliminated iteratively in designing additional compounds. The iterative process of optimizations and evaluation will include our well established and straightforward go-no-go decision tree in which potency, selectivity and drug likeness (e.g., Kit<500 nM: high solubility in buffer S>10×$K_d$) as determined by an NMR method; selectivity against the counter screen PDZs and other PPIs listed above when tested at 10×$K_d$; measured favorable ADME-T properties with T1,2 in plasma and microsomes>30 minutes; cell permeability) are iteratively confronted with cellular mechanism based activity, favorable pharmacological properties and ultimately, in vivo efficacy. These studies will include measuring cytotoxicity against normal cells (melanocytes, hepatocytes, prostate epithelial cells. HUVEC cells), determining inhibition of invasion and cellular interaction with defined partners, PK studies followed by in vivo efficacy with animal models.

Mechanistically Evaluate Current MDA-9/Syntenin PDZ1in in Preventing Melanoma Cell Adhesion, Invasion and Metastasis and Identify/Characterize the Next Generation of PDZ1in.

As emphasized, mda-9/syntenin is a pro-metastatic gene and genetic or pharmacological inhibition of this gene, its interacting partners or its downstream regulated pathways suppress the cancer phenotype in vitro and in vivo in animal models. Additionally, through regulation of several pro-angiogenic factors. MDA-9/syntenin promotes angiogenesis thereby facilitating metastasis (111). These pre-clinical observations strongly support a fundamental role of MDA-9/Syntenin in various stages of tumor cell spreading (migration and invasion) and metastasis, which is a major cause of cancer-associated death. Metastasis is a complex process (112) involving intravasation of tumor cells from the primary tumor site (involving degradation and passage through the basement membrane), survival in the systemic circulation, adherence at a secondary target site, extravasation at the secondary site and creation of a favorable environment for expansion (which also involves angiogenesis (113)). In this multistep process, adherence is essential and directly correlates with the metastatic capacity of tumor cells. In our studies (FIG. 44), we demonstrate that MDA-9/Syntenin regulates the adhesion and invasion phenotypes of tumor cells, which are blocked by 113B7 (PDZ1ln).

PDZ1In Inhibits B16 Experimental Metastasis.

Preliminary studies were performed to determine if administering PDZ1ln (113B7) would affect experimental metastasis. B16, a highly aggressive metastatic mouse melanoma, was intravenously injected resulting in lung nodules within 3 weeks. In this model, repeated treatment I.P. with small molecule PDZ1in significantly reduced the number of lung nodules (FIG. 57) in comparison with the control group. which received vehicle. This experiment confirms that treatment with PDZ1in targeting MDA-9/Syntenin can directly prevent formation of lung metastases in vivo.

Figure 58:
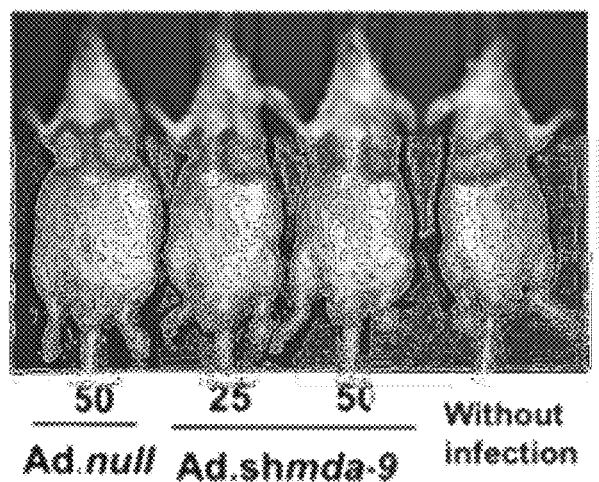
FIG. 58. MDA-9/Syntenin expression facilitates the adhesion phenotype of cancer cells. MeWO-Luc cells (an aggressive melanoma cell line that stably expresses luciferase) were pre-infected (in vitro infection was conducted 48-hr prior to injection) with either Ad.5/3-null or Ad.5/3-shmda-9 at different and then injected I.V. into mice, BLI was performed to determine the levels of circulating metastatic cells in the lungs after 45 min of cell inoculation.
Figure 59:
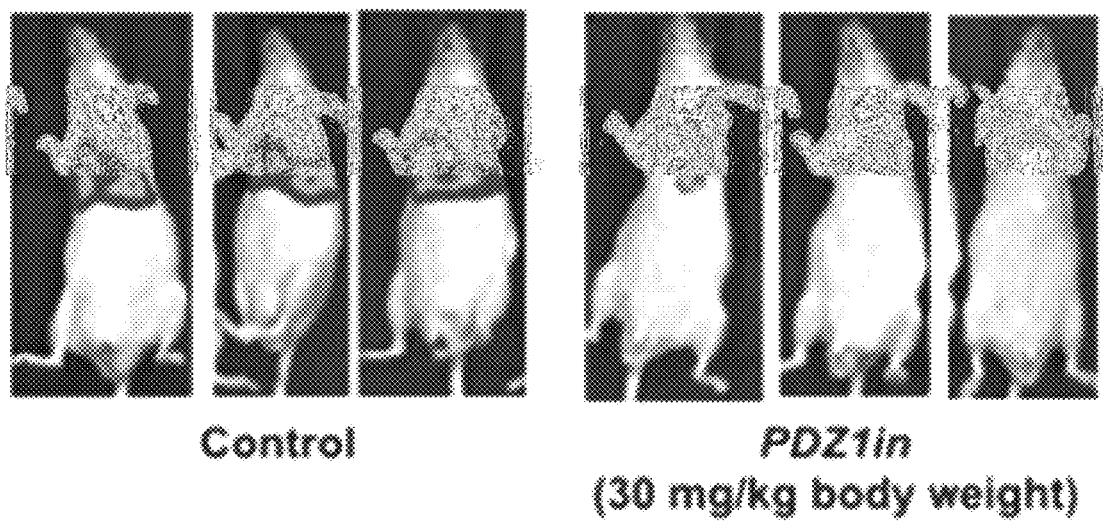
FIG. 59. Inhibition of human melanoma metastasis to the lungs by PDZ1in. MeWo-Luc cells were injected I.V. to establish experimental lung metastases. Mice received DMSO or drug (3× per week for first two weeks and 2×/week for next two weeks, total 8 injections per mice in a 4-week period). BLI images of whole animals from representative control and experimental groups are shown.

Expression of MDA-9/Syntenin Modulates the Adhesion Ability of Metastatic Tumor Cells in the Lungs:

To establish that MDA-9/Syntenin modulates cancer cell homing and adhesion to secondary sites such as the lungs, an early event that correlates with lung metastatic potential, we suppressed MDA-9/Syntenin expression (using an adenovirus expressing an shmda-9 construct (111)) in aggressive metastatic human MeWo melanoma cells (expressing luciferase; MeWo-Luc) and directly injected cells I.V. into mice and visualized tumor cell homing/adhesion to the lungs by bioluminescence (BLI) imaging (FIG. 58). Mice inoculated with Ad.shmda-9 pre-infected cells were present at lower levels than control groups in the lungs immediately after injection (within 45 min post-inoculation), suggesting that MDA-9/Syntenin expression might be critical for adhesion ability of potentially metastatic melanoma (and potentially other circulating tumor) cells, which in principle, could ultimately have a direct effect on development of metastatic lesions at secondary sites. To evaluate the antimetastatic efficiency of 113B7 (PDZ1in) we inoculated metastatic MeWo-Luc cells I.V. and treated animals with either DMSO (compound solvent) or test compound for four weeks by IP injection. After 40 days lung metastases were imaged BLI (FIG. 59).

Figure 56:
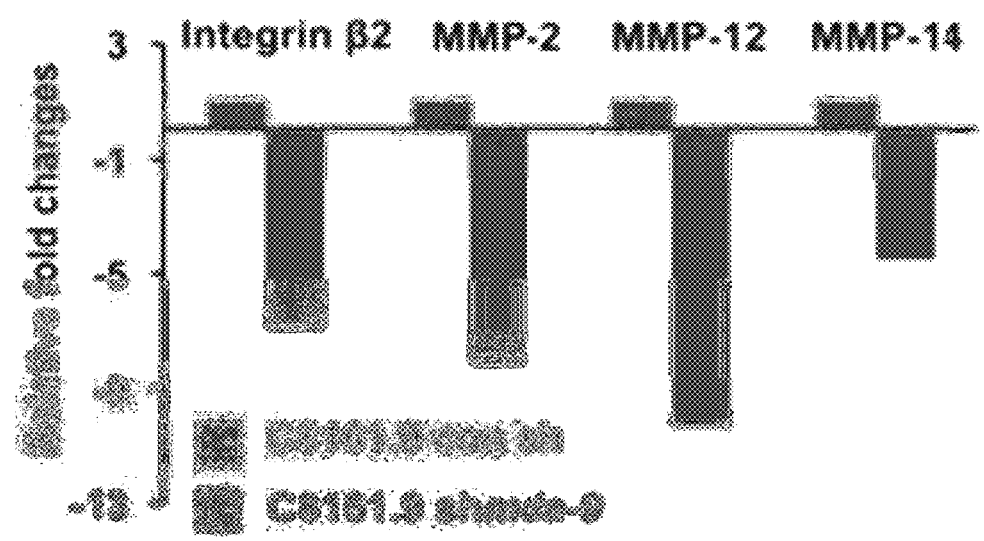
FIG. 56. PCR array for specific adhesion-related molecules. Aggressive melanoma cell line C8161.9 either expressing control shRNA or shmda-9 were seeded on fibronectin-coated plates for 6 hr in growth-starved condition. Total RNA was isolated and subjected to PCR array according to manufacturer's instruction (SA Bioscience). Data was analyzed by the software as provided by SA Bioscience. Select proteins shown.

MDA-9/Syntenin Modulates Adhesion-Related Gene Expression in Human Melanoma:

Our initial experiments confirmed that interruption of MDA-9/Syntenin-mediated signaling pathways significantly reduced the ability of melanoma cells to adhere in the lungs of animals (FIG. 58). To begin to understand the molecular basis of this phenomenon we conducted a PCR-based array containing adhesion-related genes (SA Bioscience) (FIG. 56). RNA profiling between parental aggressive C8161.9 human melanoma cells and its shmda-9 expressing clones identified changes in the levels of several important adhesion-associated genes including Integrin 12, MMP-2. MMP-12 and MMP-14 (FIG. 56). The relevance of these changes to melanoma metastasis as mediated by MDA-9/Syntenin and the possible effect of our proof-of-concept small molecule PDZ1in (113B7) will be explored.

Validation of Genes Involved in MDA-9/Syntenin-Mediated Adhesion:

As shown in FIG. 56, an adhesion array was screened using C8161.9 human melanoma cells and its shmda-9 expressing clone (111) documenting changes in expression of specific signature genes associated with adhesion. This will first be validated be validated in melanoma cell lines and melanocytes expressing MDA-9/Syntenin to establish a direct correlation between MDA-9/syntenin expression and adhesion molecule expression. To define potential clinical relevance, we will perform immunohistochemistry for these genes in patient-derived melanoma samples, which are commercially available through Imgenex Corp. (San Diego, Calif.) Correlations between the expression levels of MDA-9/Syntenin and the analyzed candidate proteins will be established by a two-sided Mann-Whitney test.

Figure 57:
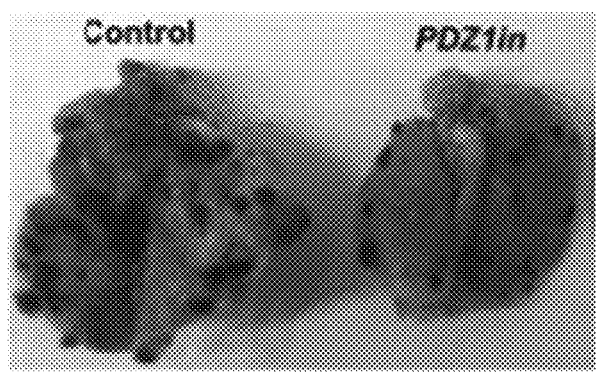
FIG. 57. PDZ1in (113B7) treatment results in marked reduction of B16 experimental lung metastases. C57BU6 mice were inoculated I.V. with B16 cells (5×10) to generate experimental lung metastases. One day after I.V. injection, mice received 30 and 50 mg/kg b.w. PDZ1i I.P. 3× a week for the first two weeks (total 6 injections). After 21 days, mice were sacrificed and lungs were collected, fixed with formalin and examined for nodules. Representative lungs with tumor metastases are shown.

Confirming the Involvement of Specific Candidate Genes in MDA-9/Syntenin-Augmented Adhesion:

Through gain-of-function (GOF) and loss-of function (LOF) analysis as described (111), we will develop a series of cell lines expressing different candidate genes or shRNAs to these genes in luciferase expressing primary immortal melanocytes and aggressive melanoma cells, respectively. The adhesion ability of cells in which target genes have been manipulated will be investigated using our in vivo lung retention model (FIG. 57).

Identify the signal transduction pathways downstream of MDA-9/Syntenin regulating adhesion-related genes: Once validated, the next step will be to define the signaling cascade that regulates the expression of appropriately altered adhesion gene(s). The generation of these molecules may involve activation of a signaling cascade(s) we have already identified (i.e., NF-κB, Akt, HIF-1α) or it might involve additional signaling pathways, such as Ephrin/IGF1/STAT3 and their receptors. Using signal pathway-specific arrays as previously described (2-5). we will define appropriate signaling pathways modified as a consequence of MDA-9/Syntenin regulation and then mechanistically define their role in regulating adhesion of melanoma cells.

Figure 60:
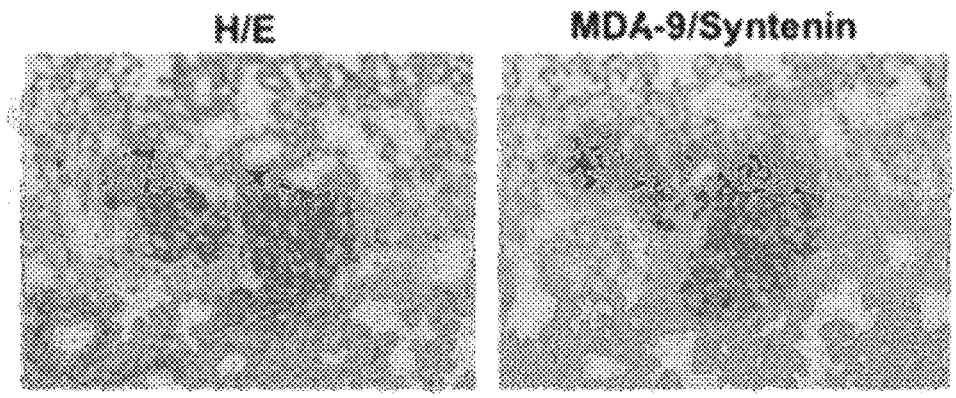
FIG. 60. Mice were treated topically with 4-HT and lungs were collected after 28 days. After confirming the metastatic foci in lungs (H/E stain, Left panel), sections were subjected to immunostaining with MDA-9/Syntenin antibody (Right panel). Representative photo-micrographs are presented.
Figure 61:
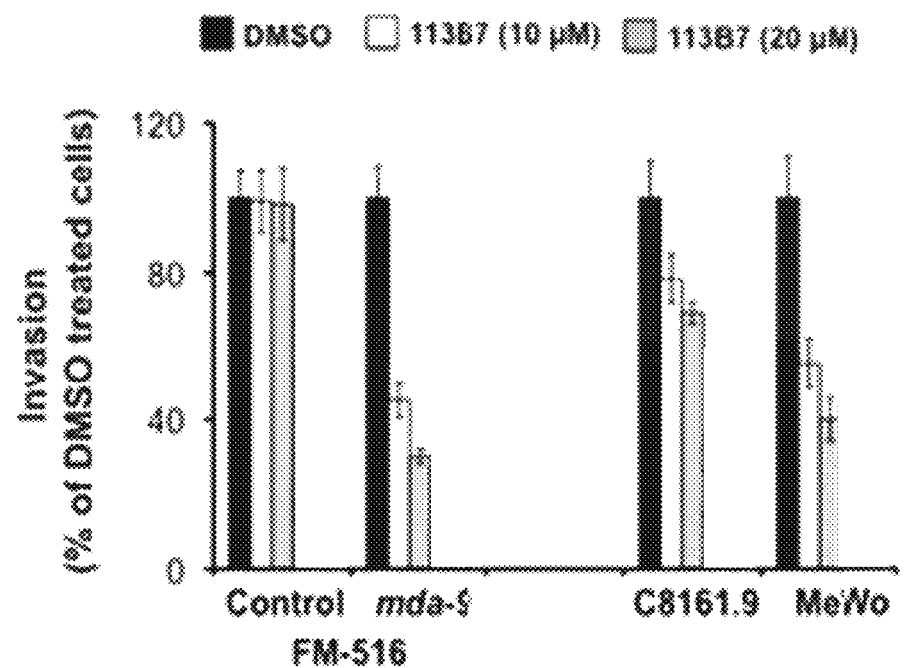
FIG. 61. Small molecule PDZ1 in (113B7) suppresses melanoma invasion. MDA-9/Syntenin overexpressed clone of primary immortal melanocytes (FM-516) and different aggressive melanoma (C8161.9 and MeWo) cells were pre-treated with either DMSO (vehicle) or compound at the dose indicated and invasion ability was assayed using a modified Boyden Chamber according to the manufacturer's instructions. Photomicrographs were taken at 10× magnification and quantification of the results of three independent experiments is provided in the graphs+S.D.

Evaluate the Therapeutic Efficacy of PDZ1in to Inhibit Lung Metastasis Development in a Transgenic Melanoma Metastasis Mouse Model:

A conditional mouse model, Braf$^{V600E}$-induced/Pten deficient (114), which recapitulates the key pathophysiological aspects of human melanoma and shows short latency with metastases in lymph nodes and lungs will be evaluated with our lead small molecule. The utility of this model in pre-clinical experimental therapeutics has been demonstrated (114). We have also confirmed that tumors developing in this animal express MDA-9/Syntenin (FIG. 60). Founder animals for generating this model were acquired from Jackson Laboratories and colonies have been expanded. Studies will confirm that specific PDZ1in have therapeutic activity in this mouse model. For these experiments, a group of 5 mice will be treated with our test compounds before melanoma initiation in adults by topical administration with 4-hydroxytamoxifen (4-HT). In the absence of 4-HT, mice display no discernible phenotype. However, topical or systematic administration with 4-HT results in the rapid development of melanoma with lung metastasis and animals require euthanasia within 3-6 weeks. In other experiments, melanoma will be initiated first and after one week, when the invasive properties are generally observed, they will be treated (IP, 6 injections, 3× a week, for 2-week) with our test compounds. In both cases, Kaplan Meier survival curves will be used to compare the efficacy of our test materials. In addition, we will also collect the lungs for pathological evaluation.

Go-No-go Decision for the Next Generation MDA-9/Syntenin PDZ1in:

We have defined a specific path for moving forward for in vivo testing of newer PDZ1in in melanoma in and then for in vivo testing. Initial hits will first be screened for chemical binding properties to the PDZ1 domain of MDA-9/syntenin. Potentially promising molecules (e.g., with $K_d$<500 nM), will be stratified based on drug-like properties, e.g., i) high solubility in buffer (S>10×Kd as determined by NMR); ii) favorable ADME-T properties ($T_{1/2}$ in plasma and microsomes>30 minutes); iii) selectivity against counter-PDZs and additional proteins from the protein-protein interactions panel when tested at 10×$K_d$ The chemicals will be screened for toxicity using various normal cells including primary melanocyte NHEM (From ATCC), immortal melanocytes FM-516 cells, RWPE-1 prostate epithelial cells (ATCC), hepatocytes, IM-PHFA immortal astrocytes and human endothelial cells (ATCC)). MTT and trypan blue dye exclusion assays will be performed using a concentration>10× of the $K_d$. Any compound displaying toxicity below this range will be excluded from further evaluation. Next, we will confirm the specificity of candidate compounds. MDA-9/Syntenin overexpressing tumor cells or engineered normal cells will be treated with compound followed immunoprecipitation and confocal microscopy to monitor interactions between MDA-9/Syntenin with specific proteins (e.g., c-Src, AEG-1 and IGF-1R for melanoma, liver and prostate cancer cells, respectively). In vitro invasion assays will also be done to determine the anti-invasive properties of candidate PDZ1in molecules. First, we will inject test PDZ1in-pre-treated MeWo-Luc cells I.V. and follow lung retention over time by BLI (115-117). We will also compare the metastatic potency of non-treated cells vs. pre-treated cells. These experiments will be very informative for defining and establishing the molecular mechanism of drug action in the context of adhesion, an early and compulsory step in metastasis, invasion and colonization, later events in metastasis. In addition, we are also proposing to investigate the efficacy of our small molecules in two different contexts, a) protection of animals from developing metastasis resulting from circulating metastatic melanoma cells; and b) clinical benefits against established metastases. To define the protective role of lead compounds in preventing metastases (a) mice will be pre-treated with drugs before IV injection of MeWo-luc cells. After injection of cancer cells, mice will be randomly separated into two experimental groups and one group will continue without any post treatment while the other set will receive experimental drugs via intraperitoneal injection (I.P.) for a total of 9 injections (dose will be determined on the basis of MTD and pharmacokinetics data). BLI imaging will be performed periodically to track metastasis development and to determine therapeutic efficacy. Kaplan Meier survival curves will be generated to determine the efficacy of the therapeutic in protecting animals from developing metastases. In the second experimental protocol (b), we will first inject the cells and allow time for metastases to develop, which will be detected by BLI, before initiating treatment. Once lung metastases are detected by BLI imaging, animals will be treated with test compound or untreated for control animals. Anti-metastatic potential of lead compounds against established metastases will be monitored by BLI, and quantified using Kaplan Meier survival curves. In addition to immunocompromised mice, we would like to address similar questions regarding the efficiency of our molecules in syngeneic animal models or spontaneous metastatic model in melanoma. HCC and prostate cancer. Therapeutic efficacy of the PDZ1 in will also be evaluated using imaging approaches, BLI and SPECT, for these three cancer indications.

The observation that MDA-9/Syntenin augments multiple known genes involved in adhesion implies that one or multiple genes are essential in mda-9/syntenin-mediated melanoma cell adhesion. Using GOF and LOF approaches we will confirm the role of candidate genes in mediating in vivo adherence as defined by reduced lung retention and metastatic nodule formation in vivo. In addition, by employing different chemical and genetic inhibitors of various signaling molecules we will be able to untangle the molecular mechanism(s) underlying these gene regulation changes. As shown in our data, we confirm that MDA-9/Syntenin is directly involved in invasion and metastasis and represents a viable target for inhibiting this process. We predicted and subsequently confirmed that MDA-9/Syntenin PDZ1-targeted small molecule inhibitors (e.g., PDZ1in) can reduce melanoma cell invasion in vitro, alter retention of metastatic cells in the lungs and inhibit the development of lung metastases.

REFERENCES

Example 1 References

1. Kegelman T P, et al. (2014) MDA-9/syntenin is a key regulator of glioma pathogenesis. *Neuro-oncology* 16(1): 50-61.
2. Mittereder N, March K L, & Trapnell B C (1996) Evaluation of the concentration and bioactivity of adenovirus vectors for gene therapy. *Journal of virology* 70(11): 7498-7509.
3. Yacoub A. et al. (2008) MDA-7/IL-24 plus radiation enhance survival in animals with intracranial primary human GBM tumors. *Cancer biology therapy* 7(6):917-933.
4. Golding S E, et al. (2009) Improved ATM kinase inhibitor KU-60019 radiosensitizes glioma cells, compromises insulin, AKT and ERK prosurvival signaling, and inhibits migration and invasion. *Molecular Cancer Therapeutics* 8(10):2894-2902.
5. Emdad L, et al. (2009) Astrocyte elevated gene-1 (AEG-1) functions as an oncogene and regulates angiogenesis. *Proc Natl Acad Sci USA* 106(50):21300-21305.
6. Boukerche H, et al. (2005) mda-9/Syntenin: a positive regulator of melanoma metastasis. *Cancer research* 65(23):10901-10911.
7. Biddlestone-Thorpe L, et al. (2013) ATM kinase inhibition preferentially sensitizes p53-mutant glioma to ionizing radiation. *Clin Cancer Res* 19(12):3189-3200.
8. Bhutia S K, et al. (2010) Astrocyte elevated gene-1 induces protective autophagy. *Proc Natl Acad Sci USA* 107(51):22243-22248.
9. Boukerche H, Su Z-z, Prvot C, Sarkar D, & Fisher P B (2008) mda-9/Syntenin promotes metastasis in human melanoma cells by activating c-Src. *Proc Natl Acad Sci USA* 105(41):15914-15919.
10. National Cancer I (2005) Rembrandt: Home Page.

Example 2 References

1. American Cancer Socitey. Cancer facts and figures 2016. Atlanta: American Cancer Society; 2009. http://www.cancer.org, 1-70.
2. Joshi G, Singh P K, Negi A, Rana A, Singh S, Kumar R. Growth factors mediated cell signalling in prostate cancer progression: Implications in discovery of anti-prostate cancer agents. *Chemico-biological interactions*, (2015), 240:120-33.
3. Shen M M, Abate-Shen C. Molecular genetics of prostate cancer: new prospects for old challenges. *Genes Dev* 24, 1967-2000 (2010).
4. Ouban A, Muraca P, Yeatman T, Coppola D. Expression and distribution of insulin-like growth factor-1 receptor in human carcinomas. *Human pathology* 34, 803-808 (2003).
5. Khandwala H M, McCutcheon I E, Flyvbjerg A, Friend K E. The effects of insulin-like growth factors on tumorigenesis and neoplastic growth. *Endocrine reviews* 21, 215-244 (2000).
6. Chan J M, et al. Plasma insulin-like growth factor-I and prostate cancer risk: a prospective study. *Science* 279, 563-566 (1998).
7. Kaplan-Lefko P J, et al. Enforced epithelial expression of IGF-1 causes hyperplastic prostate growth while negative selection is requisite for spontaneous metastogenesis. *Oncogene* 27, 2868-2876 (2008).
8. DiGiovanni J, et al. Deregulated expression of insulin-like growth factor 1 in prostate epithelium leads to neoplasia in transgenic mice. *Proceedings of the National Academy of Sciences of the United States of America* 97, 3455-3460 (2000).
9. Heidegger 1, Massoner P, Sampson N, Klocker H. The insulin-like growth factor (IGF) axis as an anticancer target in prostate cancer. *Cancer Lett* 367, 113-121 (2015).
10. Playford M P, Bicknell D, Bodmer W F, Macaulay V M. Insulin-like growth factor 1 regulates the location, stability, and transcriptional activity of beta-catenin. *Proceedings of the National Academy of Sciences of the United States of America* 97, 12103-12108 (2000).
11. Zhang D, Samani A A, Brodt P. The role of the IGF-I receptor in the regulation of matrix metalloproteinases, tumor invasion and metastasis. *Hormone and metabolic research Hormon-und Stoffwechselforschung Hormones et metabolisme* 35, 802-808 (2003).
12. Tao Y, Pinzi V, Bourhis J, Deutsch E. Mechanisms of disease: signaling of the insulin-like growth factor 1 receptor pathway—therapeutic perspectives in cancer. *Nature clinical practice Oncology* 4, 591-602 (2007).

13. Lin J J, Jiang H, Fisher P B. Melanoma differentiation associated gene-9, mda-9, is a human gamma interferon responsive gene. *Gene* 207, 105-110 (1998).
14. Lin J J, Jiang H P, Fisher P B. Characterization of a novel melanoma differentiation-associated gene, mda-9, that is down-regulated during terminal cell differentiation. *Molecular and Cellular Differentiation* 4, 317-333 (1996).
15. Grootjans J J, et al. Syntenin, a PDZ protein that binds syndecan cytoplasmic domains. *Proceedings of the National Academy of Sciences of the United States of America* 94, 13683-13688 (1997).
16. Boukerche H, et al. mda-9/Syntenin: a positive regulator of melanoma metastasis. *Cancer Res* 65, 10901-10911 (2005).
17. Kegelman T P D S, Hu B, Bacolod M D, Fuller C E, Menezes M E, Emdad L, Dasgupta S, Baldwin A S, Bruce J N, Dent P, Pellecchia M, Sarkar D, Fisher P B. MDA-9/syntenin is a key regulator of glioma pathogenesis. *Neuro Oncol* 16, 11 (Submitted).
18. Koo T H, Lee J J, Kim E M, Kim K W, Kim H D, Lee J H. Syntenin is overexpressed and promotes cell migration in metastatic human breast and gastric cancer cell lines. *Oncogene* 21, 4080-4088 (2002).
19. Oyesanya R A, et al. MDA-9/Syntenin regulates differentiation and angiogenesis programs in head and neck squamous cell carcinoma. *Oncoscience* 1, 725-737 (2014).
20. Dasgupta S, et al. Novel role of MDA-9/syntenin in regulating urothelial cell proliferation by modulating EGFR signaling. *Clin Cancer Res* 19, 4621-4633 (2013).
21. Liu X, Zhang X, Lv Y, Xiang J, Shi J. Overexpression of syntenin enhances hepatoma cell proliferation and invasion: potential roles in human hepatoma. *Oncol Rep* 32, 2810-2816 (2014).
22. Kim W Y, Jang J Y, Jeon Y K, Chung D H, Kim Y G, Kim C W. Syntenin increases the invasiveness of small cell lung cancer cells by activating p38, AKT, focal adhesion kinase and SP1. *Experimental and Molecular Medicine* 46, (2014).
23. Bacolod M D D S, Sokhi U K, Bradley S, Fenstermacher D A, Pellecchia M, Emdad L, Sarkar D, Fisher P B. Examination of Epigenetic and other Molecular Factors Associated with mda-9/Syntenin Dysregulation in Cancer Through Integrated Analyses of Public Genomic Datasets. *Adv Cancer Res* 127, 49-121 (2015).
24. Boukerche H, Su Z Z, Prevot C, Sarkar D, Fisher P B. mda-9/Syntenin promotes metastasis in human melanoma cells by activating c-Src. *Proceedings of the National Academy of Sciences of the United States of America* 105, 15914-15919 (2008).
25. Hwangbo C, et al. Syntenin regulates TGF-beta1-induced Smad activation and the epithelial-to-mesenchymal transition by inhibiting caveolin-mediated TGF-beta type I receptor internalization. *Oncogene,* 2016 Jan. 21; 35(3): 389-401
26. Das S K, et al. Rafkinase inhibitor RKIP inhibits MDA-9/syntenin-mediated metastasis in melanoma. *Cancer Res,* 2012 Dec. 1; 72(23):6217-26.
27. Das S K, et al. MDA-9/Syntenin and IGFBP-2 Promote Angiogenesis in Human Melanoma. *Cancer Res* 73, 844-854 (2013).
28. Das S K, et al. MDA-9/syntenin: a positive gatekeeper of melanoma metastasis. *Front Biosci* 17, 1-15 (2012).
29. Kegelman T P, et al. Targeting tumor invasion: the roles of MDA-9/Syntenin. *Expert opinion on therapeutic targets* 19, 97-112 (2015).
30. Ghossoub R, et al. Syntenin-ALIX exosome biogenesis and budding into multivesicular bodies are controlled by ARF6 and PLD2. *Nature communications* 5, (2014). 2014 Mar. 18; 5:3477.
31. Gordon-Alonso M, et al. The PDZ-adaptor protein syntenin-1 regulates HIV-1 entry. *Mol Biol Cell* 23, 2253-2263 (2012).
32. Sala-Valdes M, et al. Association of syntenin-1 with M-RIP polarizes Rac-1 activation during chemotaxis and immune interactions. *J Cell Sci* 125, 1235-1246 (2012).
33. Rajesh S, et al. Binding to syntenin-1 protein defines a new mode of ubiquitin-based interactions regulated by phosphorylation. *The Journal of biological chemistry* 286, 39606-39614 (2011).
34. Okumura F, Yoshida K, Liang F, Hatakeyama S. MDA-9/syntenin interacts with ubiquitin via a novel ubiquitin-binding motif. *Mol Cell Biochem* 352, 163-172 (2011).
35. Piserchio A, Salinas G D, Li T, Marshall J, Spaller M R, Mierke D F. Targeting specific PDZ domains of PSD-95; structural basis for enhanced affinity and enzymatic stability of a cyclic peptide. *Chem Biol* 11, 469-473 (2004).
36. Hammond M C, Harris B Z, Lim W A, Bartlett P A. Beta strand peptidomimetics as potent PDZ domain ligands. *Chem Biol* 13, 1247-1251 (2006).
37. Fujii N, et al. An antagonist of dishevelled protein-protein interaction suppresses beta-catenin-dependent tumor cell growth. *Cancer Res* 67, 573-579 (2007).
38. Ellwood-Yen K, et al. Myc-driven murine prostate cancer shares molecular features with human prostate tumors. *Cancer cell* 4, 223-238 (2003).
39. Xie T X, et al. Stat3 activation regulates the expression of matrix metalloproteinase-2 and tumor invasion and metastasis. *Oncogene* 23, 3550-3560 (2004).
40. Agarwal C, Tyagi A, Kaur M, Agarwal R. Silibinin inhibits constitutive activation of Stat3, and causes caspase activation and apoptotic death of human prostate carcinoma DU145 cells. *Carcinogenesis* 28, 1463-1470 (2007).
41. Dhir R, Ni Z, Lou W, DeMiguel F, Grandis J R, Gao A C. Stat3 activation in prostatic carcinomas. *Prostate* 51, 241-246 (2002).
42. Spiotto M T, Chung T D. STAT3 mediates IL-6-induced neuroendocrine differentiation in prostate cancer cells. *Prostate* 42, 186-195 (2000).
43. Rojas A, et al. IL-6 promotes prostate tumorigenesis and progression through autocrine cross-activation of IGF-I R. *Oncogene* 30, 2345-2355 (2011).
44. Nakashima J, et al. Serum interleukin 6 as a prognostic factor in patients with prostate cancer. *Clin Cancer Res* 6, 2702-2706 (2000).
45. Tam L, McGlynn L M, Traynor P, Mukherjee R, Bartlett J M, Edwards J. Expression levels of the JAK/STAT pathway in the transition from hormone-sensitive to hormone-refractory prostate cancer. *Br J Cancer* 97, 378-383 (2007).
46. Kimura G, et al. Insulin-like growth factor (IGF) system components in human prostatic cancer cell-lines: LNCaP, DU145, and PC-3 cells. *International journal of urology: official journal of the Japanese Urological Association* 3, 39-46 (1996).
47. Ho P J, Baxter R C. Insulin-like growth factor-binding protein-2 in patients with prostate carcinoma and benign prostatic hyperplasia. *Clinical endocrinology* 46, 333-342 (1997).
48. Zong C S, Chan J, Levy D E, Horvath C, Sadowski H B, Wang L H. Mechanism of STAT3 activation by insulin-like growth factor 1 receptor. *The Journal of biological chemistry* 275, 15099-15105 (2000).
49. Barile E, Pellecchia M. NMR-based approaches for the identification and optimization of inhibitors of protein-protein interactions. *Chemical reviews* 114, 4749-4763 (2014).
50. Kalyoncu S, Keskin O, Gursoy A. Interaction prediction and classification of PDZ domains. *BMC bioinformatics* 11, 357 (2010).
51. Boukerche H, Su Z Z, Emdad L, Sarkar D, Fisher P B. mda-9/Syntenin regulates the metastatic phenotype in human melanoma cells by activating nuclear factor-kappaB. *Cancer Res* 67, 1812-1822 (2007).
52. Berger M F, et al. The genomic complexity of primary human prostate cancer. *Nature* 470, 214-220 (2011).
53. Taylor B S, et al. Integrative genomic profiling of human prostate cancer. *Cancer cell* 18, 11-22 (2010).
54. Weischenfeldt J, et al. Integrative genomic analyses reveal an androgen-driven somatic alteration landscape in early-onset prostate cancer. *Cancer cell* 23, 159-170 (2013).
55. Kumar A. et al. Exome sequencing identifies a spectrum of mutation frequencies in advanced and lethal prostate cancers. *Proceedings of the National Academy of Sciences of the United States of America* 108, 17087-17092 (2011).
56. Grasso C S, et al. The mutational landscape of lethal castration-resistant prostate cancer. *Nature* 487, 239-243 (2012).
57. Baca S C, et al. Punctuated evolution of prostate cancer genomes. *Cell* 153, 666-677 (2013).
58. Gundem G. et al. The evolutionary history of lethal metastatic prostate cancer. *Nature* 520, 353-357 (2015).
59. Hong M K, et al. Tracking the origins and drivers of subclonal metastatic expansion in prostate cancer. *Nature communications* 6, 6605 (2015).
60. Sarkar D, Boukerche H, Su Z Z, Fisher P B. mda-9/syntenin: More than just a simple adapter protein when it comes to cancer metastasis. *Cancer Research* 68, 3087-3093 (2008).
61. Tanja Ligensa‡, Sonia Krauss‡, Dirk Demuth‡, Ralf Schumacher‡, Jacques Camonis¶, Gabriele Jaques§ and K. Michael Weidner‡∥. A PDZ Domain Protein Interacts with the C-terminal Tail of the Insulin-like Growth Factor-1 Receptor but Not with the Insulin Receptor. *J Biol Chem* 2001 Sep. 7; 276(36):33419-27, (2003).
62. Jarnicki A, Putoczki T, Ernst M. Stat3: linking inflammation to epithelial cancer—more than a "gut" feeling? *Cell Div* 5, 2010 May 17; 5:14.
63. Sekharam M, Nasir A, Kaiser H E, Coppola D. Insulin-like growth factor 1 receptor activates c-SRC and modifies transformation and motility of colon cancer in vitro. *Anticancer Res* 23, 1517-1524 (2003).
64. Sanabria-Figueroa E, et al. Insulin-like growth factor-1 receptor signaling increases the invasive potential of human epidermal growth factor receptor 2-overexpressing breast cancer cells via Src-focal adhesion kinase and forkhead box protein M1. *Molecular pharmacology* 87, 150-161 (2015).
65. Shin D H, et al. Combating resistance to anti-IGFR antibody by targeting the integrin beta3-Src pathway. *J Natl Cancer Inst* 105, 1558-1570 (2013).
66. Nakamura H, Wang Y, Kurita T, Adomat H, Cunha G R, Wang Y. Genistein increases epidermal growth factor receptor signaling and promotes tumor progression in advanced human prostate cancer. *PloS one* 6, e20034 (2011).
67. Wu J, Yu E. Insulin-like growth factor receptor-1 (IGF-IR) as a target for prostate cancer therapy. *Cancer and Metastasis Reviews* 33, 607-617 (2014).
68. Reiss K, et al. IGF-I receptor signaling in a prostatic cancer cell line with a PTEN mutation. *Oncogene* 19, 2687-2694 (2000).
69. Tamura K, et al. Increased production of intestinal immunoglobulins in Syntenin-1-deficient mice. *Immunobiology* 220, 597-604 (2015).
70. Das S K, et al. Knockout of MDA-9/Syntenin (SDCBP) expression in the microenvironment dampens tumor-supporting inflammation and inhibits melanoma metastasis. *Oncotarget* in press (2016).
71. Friand V, David G, Zimmermann P. Syntenin and syndecan in the biogenesis of exosomes. *Biology of the cell/under the auspices of the European Cell Biology Organization* 107, 331-341 (2015).
72. McClelland A C, Sheffler-Collins S I, Kayser M S, Dalva M B. Ephrin-B1 and ephrin-B2 mediate EphB-dependent presynaptic development via syntenin-1. *Proceedings of the National Academy of Sciences of the United States of America* 106, 20487-20492 (2009).
73. Lee H J, Zheng J J. PDZ domains and their binding partners: structure, specificity, and modification. *Cell Communication and Signaling* 8, (2010).
74. Rees D C, Congreve M, Murray C W, Carr R. Fragment-based lead discovery. *Nature reviews Drug discovery* 3, 660-672 (2004).
76. Guo C, et al. In situ vaccination with CD204 gene-silenced dendritic cell, not unmodified dendritic cell, enhances radiation therapy of prostate cancer. *Molecular cancer therapeutics* 11, 2331-2341 (2012).

Example 3 References

1. Lamouille S, Xu J and Derynck R. Molecular mechanisms of epithelial-mesenchymal transition. Nature reviews Molecular cell biology. 2014; 15(3):178-196.
2. Kalluri R and Weinberg R A. The basics of epithelial-mesenchymal transition. J Clin Invest. 2009; 119(6): 1420-1428.
3. Yang J and Weinberg R A. Epithelial-mesenchymal transition: at the crossroads of development and tumor metastasis. Developmental cell. 2008; 14(6):818-829.
4. Hanahan D and Weinberg R A. Hallmarks of cancer: the next generation. Cell. 2011; 144(5):646-674.
5. Ye X and Weinberg R A. Epithelial-Mesenchymal Plasticity: A Central Regulator of Cancer Progression. Trends in cell biology. 2015; 25(11):675-686.
6. Sarkar D, Boukerche H, Su Z Z and Fisher P B. mda-9/Syntenin: more than just a simple adapter protein when it comes to cancer metastasis. Cancer research. 2008; 68(9): 3087-3093.
7. Lin J J, Jiang H and Fisher P B. Melanoma differentiation associated gene-9, mda-9, is a human gamma interferon responsive gene. Gene. 1998; 207(2):105-110.
8. Kegelman T P, Das S K, Emdad L, Hu B, Menezes M E, Bhoopathi P, Wang X Y, Pellecchia M, Sarkar D and Fisher P B. Targeting tumor invasion: the roles of MDA-9/Syntenin. Expert Opin Ther Targets. 2014:1-16.
9. Das S K, Bhutia S K, Kegelman T P, Peachy L, Oyesanya R A, Dasgupta S, Sokhi U K, Azab B, Dash R, Quinn B A, Kim K, Barral P M, Su Z Z, Boukerche H, Sarkar D and Fisher P B. MDA-9/syntenin: a positive gatekeeper of melanoma metastasis. Front Biosci (Landmark Ed). 2012; 17:1-15.

10. Boukerche H, Su Z Z, Emdad L, Baril P, Balme B, Thomas L, Randolph A, Valerie K, Sarkar D and Fisher P B. mda-9/Syntenin: a positive regulator of melanoma metastasis. Cancer research. 2005; 65(23):10901-10911.
11. Boukerche H, Su Z Z, Prevot C, Sarkar D and Fisher P B. mda-9/Syntenin promotes metastasis in human melanoma cells by activating c-Src. Proceedings of the National Academy of Sciences of the United States of America. 2008; 105(41):15914-15919.
12. Gangemi R, Mirisola V, Barisione G, Fabbi M, Brizzolara A, Lanza F, Mosci C, Salvi S, Gualco M, Truini M, Angelini G, Boccardo S, Cilli M, Airoldi I, Queirolo P, Jager M J, et al. Mda-9/syntenin is expressed in uveal melanoma and correlates with metastatic progression. PLoS One. 2012; 7(1):e29989.
13. Koo T H, Lee J J, Kim E M, Kim K W, Kim H D and Lee J H. Syntenin is overexpressed and promotes cell migration in metastatic human breast and gastric cancer cell lines. Oncogene. 2002; 21(26):4080-4088.
14. Dasgupta S, Menezes M E, Das S K, Emdad L, Janjic A, Bhatia S, Mukhopadhyay N D, Shao C, Sarkar D and Fisher P B. Novel role of MDA-9/syntenin in regulating urothelial cell proliferation by modulating EGFR signaling. Clinical cancer research: an official journal of the American Association for Cancer Research. 2013; 19(17): 4621-4633.
15. Kegelman T P, Das S K, Hu B, Bacolod M D, Fuller C E, Menezes M E, Emdad L, Dasgupta S, Baldwin A S, Bruce J N, Dent P, Pellecchia M, Sarkar D and Fisher P B. MDA-9/syntenin is a key regulator of glioma pathogenesis. Neuro-oncology. 2014; 16(1):50-61.
16. Kim W Y, Jang J Y, Jeon Y K, Chung D H, Kim Y G and Kim C W. Syntenin increases the invasiveness of small cell lung cancer cells by activating p38, AKT, focal adhesion kinase and SP1. Exp Mol Med. 2014; 46:e90.
17. Liu X, Zhang X, Lv Y, Xiang J and Shi J. Overexpression of syntenin enhances hepatoma cell proliferation and invasion: Potential roles in human hepatoma. Oncol Rep. 2014; 32(6):2810-2816.
18. Oyesanya R A, Bhatia S, Menezes M E, Dumur C I, Singh K P, Bae S, Troyer D A, Wells R B, Sauter E R, Sidransky D, Fisher P B, Semmes O J and Dasgupta S. MDA-9/Syntenin regulates differentiation and angiogenesis programs in head and neck squamous cell carcinoma. Oncoscience. 2014; 1(11):725-737.
19. Yang Y, Hong Q, Shi P, Liu Z, Luo J and Shao Z. Elevated expression of syntenin in breast cancer is correlated with lymph node metastasis and poor patient survival. Breast cancer research: BCR. 2013; 15(3):R50.
20. Qian X L, Li Y Q, Yu B, Gu F, Liu F F, Li W D, Zhang X M and Fu L. Syndecan binding protein (SDCBP) is overexpressed in estrogen receptor negative breast cancers, and is a potential promoter for tumor proliferation. PLoS One. 2013; 8(3):e60046.
21. Zardavas D, Baselga J and Piccart M. Emerging targeted agents in metastatic breast cancer. Nat Rev Clin Oncol. 2013; 10(4):191-210.
22. Yamazaki D, Kurisu S and Takenawa T. Regulation of cancer cell motility through actin reorganization. Cancer science. 2005; 96(7):379-386.
23. Debnath J, Muthuswamy S K and Brugge J S. Morphogenesis and oncogenesis of MCF-10A mammary epithelial acini grown in three-dimensional basement membrane cultures. Methods. 2003; 30(3):256-268.
24. Nieman M T, Prudoff RS, Johnson K R and Wheelock M J. N-cadherin promotes motility in human breast cancer cells regardless of their E-cadherin expression. J Cell Biol. 1999; 147(3):631-644.
25. Suyama K, Shapiro I, Guttman M and Hazan R B. A signaling pathway leading to metastasis is controlled by N-cadherin and the FGF receptor. Cancer cell. 2002; 2(4):301-314.
26. Zhang Z, Yang M, Chen R, Su W, Li P, Chen S, Chen Z, Chen A, Li S and Hu C. IBP regulates epithelial-to-mesenchymal transition and the motility of breast cancer cells via Rac1, RhoA and Cdc42 signaling pathways. Oncogene. 2014; 33(26):3374-3382.
27. Sit S T and Manser E. Rho GTPases and their role in organizing the actin cytoskeleton. Journal of cell science. 2011; 124(Pt 5):679-683.
28. Tapon N and Hall A. Rho, Rac and Cdc42 GTPases regulate the organization of the actin cytoskeleton. Current opinion in cell biology. 1997; 9(1):86-92.
29. Bhowmick N A, Ghiassi M, Bakin A, Aakre M, Lundquist C A, Engel M E, Arteaga C L and Moses H L. Transforming growth factor-beta1 mediates epithelial to mesenchymal transdifferentiation through a RhoA-dependent mechanism. Molecular biology of the cell. 2001; 12(1):27-36.
30. Zhang Y E. Non-Smad pathways in TGF-beta signaling. Cell research. 2009; 19(1):128-139.
31. Grootjans J J, Zimmermann P, Reekmans G, Smets A, Degeest G, Durr J and David G. Syntenin, a PDZ protein that binds syndecan cytoplasmic domains. Proc Natl Acad Sci USA. 1997; 94(25):13683-13688.
32. Edlund S, Landstrom M, Heldin C H and Aspenstrom P. Transforming growth factor-beta-induced mobilization of actin cytoskeleton requires signaling by small GTPases Cdc42 and RhoA. Molecular biology of the cell. 2002; 13(3):902-914.
33. Hwangbo C, Tae N, Lee S, Kim O, Park O K, Kim J, Kwon S H and Lee J H. Syntenin regulates TGF-beta1-induced Smad activation and the epithelial-to-mesenchymal transition by inhibiting caveolin-mediated TGF-beta type I receptor internalization. Oncogene. 2016; 35(3): 389-401.
34. Wang L K, Pan S H, Chang Y L, Hung P F, Kao S H, Wang W L, Lin C W, Yang S C, Liang C H, Wu C T, Hsiao T H, Hong™ and Yang P C. MDA-9/Syntenin-Slug transcriptional complex promote epithelial-mesenchymal transition and invasion/metastasis in lung adenocarcinoma. Oncotarget. 2016; 7(1):386-401.
35. Cheung S Y, Boey Y J, Koh V C, Thike A A, Lim J C, Iqbal J and Tan P H. Role of epithelial-mesenchymal transition markers in triple-negative breast cancer. Breast cancer research and treatment. 2015; 152(3):489-498.
36. Zeng Q, Li W, Lu D, Wu Z, Duan H, Luo Y, Feng J, Yang D, Fu L and Yan X. C D 146, an epithelial-mesenchymal transition inducer, is associated with triple-negative breast cancer. Proceedings of the National Academy of Sciences of the United States of America. 2012; 109(4):1127-1132.
37. Bhowmick N A, Zent R, Ghiassi M, McDonnell M and Moses H L. Integrin beta I signaling is necessary for transforming growth factor-beta activation ofp38MAPK and epithelial plasticity. J Biol Chem. 2001; 276(50): 46707-46713.
38. Hwangbo C, Kim J, Lee J J and Lee J H. Activation of the integrin effector kinase focal adhesion kinase in cancer cells is regulated by crosstalk between protein kinase Calpha and the PDZ adapter protein mda-9/Syntenin. Cancer research. 2010; 70(4): 1645-1655.

39. Lu P, Weaver V M and Werb Z. The extracellular matrix: a dynamic niche in cancer progression. The Journal of cell biology. 2012; 196(4):395-406.
40. Pontier S M and Muller W J. Integrins in mammary-stem-cell biology and breast-cancer progression—a role in cancer stem cells? Journal of cell science. 2009; 122(Pt 2):207-214.
41. Felding-Habermann B, OToole T E, Smith J W, Fransvea E, Ruggeri Z M, Ginsberg M H, Hughes P E, Pampori N, Shattil S J, Saven A and Mueller B M. Integrin activation controls metastasis in human breast cancer. Proc Natl Acad Sci USA. 2001; 98(4):1853-1858.
42. Huck L, Pontier S M, Zuo D M and Muller W J. beta1-integrin is dispensable for the induction of ErbB2 mammary tumors but plays a critical role in the metastatic phase of tumor progression. Proc Natl Acad Sci USA. 2010; 107(35):15559-15564.
43. White D E and Muller W J. Multifaceted roles of integrins in breast cancer metastasis. Journal of mammary gland biology and neoplasia. 2007; 12(2-3):135-142.
44. Lahlou H and Muller W J. beta1-integrins signaling and mammary tumor progression in transgenic mouse models: implications for human breast cancer. Breast Cancer Res. 2011; 13(6):229.
45. Hwangbo C, Park J and Lee J H. mda-9/Syntenin protein positively regulates the activation of Akt protein by facilitating integrin-linked kinase adaptor function during adhesion to type I collagen. The Journal of biological chemistry. 2011; 286(38):33601-33612.
46. Holliday D L and Speirs V. Choosing the right cell line for breast cancer research. Breast cancer research: BCR. 2011; 13(4):215.
47. Price J E. Metastasis from human breast cancer cell lines. Breast cancer research and treatment. 1996; 39(1): 93-102.
48. Chavez K J, Garimella S V and Lipkowitz S. Triple negative breast cancer cell lines: one tool in the search for better treatment of triple negative breast cancer. Breast disease. 2010; 32(1-2):35-48.
49. Das S K, Bhutia S K, Azab B, Kegelman T P, Peachy L, Santhekadur P K, Dasgupta S, Dash R, Dent P, Grant S, Emdad L, Pellecchia M, Sarkar D and Fisher P B. MDA-9/syntenin and IGFBP-2 promote angiogenesis in human melanoma. Cancer research. 2013; 73(2):844-854.
50. Menezes M E, Mitra A, Shevde L A and Samant R S. DNAJB6 governs a novel regulatory loop determining Wnt/beta-catenin signalling activity. Biochem J. 2012; 444(3):573-580.

Example 5 References

1. Coghlin C, Murray G I. Current and emerging concepts in tumor metastasis. *J Pathol* 2010; 222:1-15. PMID: 20681009.
2. Wells A, Grahovac J, Wheeler S, Ma B, Lauffenburger D. Targeting tumor cell motility as astrategy against invasion and metastasis. *Trends Pharmacological Sciences* 2013; 34: 283-289. PMCID: PMC3640670.
3. Nguyen D X, Bos P D, Massague J. Metastasis: from dissemination to organ-specific colonization. *Nature Rev* 2009: 274-284. PMID:19308067.
4. Fisher R, Pusztai L, Swanton C. Cancer heterogeneity: implications for targeted therapeutics. *Br J Cancer* 2013 108:479-85. PMCID:PMC3593543.
5. Chang A C, Massague J. Molecular basis of metastasis. *N Engl J Med* 2008; 359: 2814-2823. PMID: 19109576.
6. Nguyen D X, Massague J. Genetic determinants of cancer metastasis. *Nature Rev Genet* 2007; 8: 341-352. PMID: 17440531.
7. De Sousa E, Melo F, Vermeulen L, Fessler E, Medema J P. Cancer heterogeneity-a multifaceted view. *EMBO Rep* 2013; 14: 686-695. PMCID:PMC3736134.
8. Marusyk A, Almendro V, Polyak K. Intra-tumour heterogeneity: a looking glass for cancer? *Nat Rev Cancer.* 2012; 12: 323-334. PMID:22513401.
9. Das S K, Bhutia S K, Kegelman T P, Peachy L, Oyesanya R A, Dasgupta S, Sokhi U K, Azab B,Dash R, Quinn B A, Kim K, Barral P M, Su Z-z, Boukerche H, Sarkar D, Fisher P B. MDA-9/syntenin: a positive gatekeeper of melanoma metastasis. *Front Bios* 2012; 17: 1-15. PMID: 22201728.
10. Joosse S A, Pantel K. Biologic challenges in the detection of circulating tumor cells. *Cancer Res* 2013; 73: 8-11. PMID:23271724.
11. Pouliot F, Johnson M, Wu L. Non-invasive molecular imaging of prostate cancer lymph node metastasis. *Trends Mol Med* 2009; 15: 254-262. PMCID:PMC2798142.
12. Bayer C L, Joshi P P, Emelianov S Y. Photoacoustic imaging: a potential tool to detect early indicators of metastasis. *Expert Rev Med Devices* 2013; 10: 125-134. PMCID:PMC3563674.
13. Krause B J, Schwarzenböck S, Souvatzoglou M. FDG PET and PET/C T. *Recent Results Cancer Res* 2013; 187: 351-369. PMID:23179888.
14. Bhutia S K, Mukhopadhyay S, Sinha N, Das D N, Panda P K, Patra S K, Maiti T K, Mandal M, Dent P, Wang X Y, Das S K, Sarkar D, Fisher P B. Autophagy: cancer's friend or foe? *Adv Cancer Res* 2013; 118: 61-95. PMID: 23768510.
15. Rebucci M, Michiels C. Molecular aspects of cancer cell resistance to chemotherapy. *Biochem Pharmacol* 2013; 85: 1219-1226. PMID:23435357.
16. Thomas S, Quinn B A, Das S K, Dash R, Emdad L, Dasgupta S, Wang X Y, Dent P, Reed J C, Pellecchla M, Sarkar D, Fisher P B. Targeting the Bcl-2 family for cancer therapy. *Expert Opin Ther Targets* 2013; 17: 61-75. PMID: 23173842.
17. Maiese K, Chong Z Z, Shang Y C, Wang S. Targeting disease through novel pathways of apoptosis and autophagy. *Expert Opin Ther Targets* 2012; 16: 1203-1214.PMCID:PMC3500415.
18. Quinn B A, Dash R, Azab B, Sarkar S, Das S K, Kumar S, Oyesanya R A, Dasgupta S, Dent P,Grant S, Rahmani M, Curiel D T, Dmitriev I, Hedvat M, Wei J, Wu B, Stebbins J L, Reed J C, Pellecchla M, Sarkar D, Fisher P B. Targeting Mcl-1 for the therapy of cancer. *Expert Opin Investig Drugs* 2011; 20: 1397-1411. PMID: 21851287, PMCID:PMC3205956.
19. Emdad L, Dent P, Sarkar D, Fisher P B. Future approaches for the therapy of malignant glioma: targeting genes mediating invasion. *Future Oncol* 2012; 8: 343-346. PMID:22515436.
20. Emdad L, Sarkar D, Lee S G, Su Z Z, Yoo B K, Dash R, Yacoub A, Fuller C E, Shah K, Dent P, Bruce J N, Fisher P B. Astrocyte elevated gene-1: a novel target for human glioma therapy. *Mol Cancer Ther* 2010; 9: 79-88. PMCID:PMC3165052.
21. Kegelman T P, Das S K, Hu B, Menezes M E, Emdad L, Dasgupta S, Bruce J N, Dent P, Pellecchia M, Sarkar D, Fisher P B. MDA-9/syntenin is a key regulator of glioma pathogenesis. *Neuro-Oncol.* 2013; in press.
22. Dasgupta S, Menezes M, Das S K, Emdad L, Janjic A, Bhatia S, Mukhopadhyay N, Shao C, Sarkar D, Fisher P B. Novel role of MDA-9/Syntenin in regulating urothelial cell proliferation by modulating EGFR signaling. Clin Cancer Res. 2013; 19:4621-4633. PMID:23873690.
23. Ghoneim M A, Abol-Enein H. Management of muscle-invasive bladder cancer: an update. *Nat Clin Pract Urol* 2008; 5: 501-508. PMID:18769377.
24. Orgaz J L, Sanz-Moreno V. Emerging molecular targets in melanoma invasion and metastasis. *Pigment Cell Melanoma Res* 2013; 26: 39-57. PMID:23095214.
25. Langley R R, Fidler I J. The seed and soil hypothesis revisited—the role of tumor-stroma interactions in metastasis to different organs. *Int J Cancer* 2011; 128: 2527-2535. PMCID:PMC3075088.
26. Hedvat M, Emdad L, Das S K, Kim K, Dasgupta S, Thomas S, Hu B, Zhu S, Dash R, Quinn B A, Oyesanya R A, Kegelman T P, Sokhi U K, Sarkar S, Erdogan E, Menezes M E, Bhoopathi P, Wang X Y, Pomper M G, Wei J, Wu B, Stebbins J L, Diaz P W, Reed J C, Pellecchia M, Sarkar D, Fisher P B. Selected approaches for rational drug design and high throughput screening to identify anti-cancer molecules. *Anticancer Agents Med Chem* 2012; 12: 1143-1155. PMID: 22931411, PMCID: PMC3763986.
27. Lin J J, Jiang H P, Fisher P B. Characterization of a novel melanoma differentiation-associated gene, mda-9, that is down-regulated during terminal cell differentiation. Mol Cell Differ 1996; 4: 317-333.
28. Lin J J, Jiang H, Fisher P B. Melanoma differentiation associated gene-9, mda-9, is a human gamma interferon responsive gene. *Gene* 1998; 207: 105-110. PMID: 9511750.
29. Sarkar D, Boukerche H, Su Z Z, Fisher P B. mda-9/Syntenin: more than just a simple adapter protein when it comes to cancer metastasis. *Cancer Res* 2008; 68: 3087-3093. PMID:18451132.
30. Sarkar D, Boukerche H, Su Z Z, Fisher P B. mda-9/syntenin: recent insights into a novel cell signaling and metastasis-associated gene. *Pharmacol Ther* 2004; 104: 101-15. PMID:15518882.
31. Hwangbo C, Park J, Lee J H. mda-9/Syntenin protein positively regulates the activation of Akt protein by facilitating integrin-linked kinase adaptor function during adhesion to type I collagen. *J Biol Chem* 2011; 286: 33601-33612. PMCID:PMC3190898.
32. Hwangbo C, Kim J, Lee I J, Lee J H. Activation of the integrin effector kinase focal adhesion kinase in cancer cells is regulated by crosstalk between protein kinase Calpha and the PDZ adapter protein mda-9/Syntenin. *Cancer Res* 2010; 70: 1645-1655. PMID:20145126.
33. Das S K, Bhutia S K, Sokhi U K, Azab B, Su Z Z, Boukerche H, Anwar T, Moen E L, Chatterjee D, Pellecchia M, Sarkar D, Fisher P B. Raf kinase inhibitor RKIP inhibits MDA-9/synteninmediated metastasis in melanoma. *Cancer Res* 2012; 72: 6217-6226. PMID: 23066033.
34. Zhong D, Ran J H, Tang W Y, Zhang X D, Tan Y, Chen G J, Li X S, Yan Y. Mda-9/syntenin promotes human brain glioma migration through focal adhesion kinase (FAK)-JNK and FAKAKT signaling. *Asian Pac J Cancer Prev* 2012; 13: 2897-2901. PMID: 22938480.
35. Gangemi R, Mirisola V, Barisione G, Fabbi M, Brizzolara A, Lanza F, Mosci C, Salvi S, Gualco M, Truini M, Angelini G, Boccardo S, Cilli M, Airoldi I, Queirolo P, Jager M J, Daga A, Pfeffer U, Ferrini S. Mda-9/syntenin is expressed in uveal melanoma and correlates with metastatic progression. PLoS One. 2012; 7(1): e29989. PMCID: PMC3258266.
36. Boukerche H, Aissaoui H, Prévost C, Hirbec H, Das S K, Su Z Z, Sarkar D, Fisher P B. Src kinase activation is mandatory for MDA-9/syntenin-mediated activation of nuclear factor-kappaB. *Oncogene* 2010; 29: 3054-3066. PMCID: PMC2878370.
37. Boukerche H, Su Z Z, Prévot C, Sarkar D, Fisher P B. mda-9/Syntenin promotes metastasis in human melanoma cells by activating c-Src. *Proc Natl Acad Sci USA* 2008; 105: 15914-15919.PMCID:PMC2572986.
38. Boukerche H, Su Z Z, Emdad L, Sarkar D, Fisher P B. mda-9/Syntenin regulates the metastatic phenotype in human melanoma cells by activating nuclear factor-kappaB. *Cancer Res* 2007; 67: 1812-1822. PMID: 17308124.
39. Boukerche H, Su Z Z, Emdad L, Baril P, Balme B, Thomas L, Randolph A, Valerie K, Sarkar D, Fisher P B. mda-9/Syntenin: a positive regulator of melanoma metastasis. *Cancer Res* 2005; 65: 10901-10911. PMID: 16322237.
40. Das S K, Bhutia S K, Azab B, Kegelman T P, Peachy L, Santhekadur P K, Dasgupta S, Dash R, Dent P, Grant S, Emdad L, Pellechia M, Sarkar D, Fisher P B. MDA-9/syntenin and IGFBP-2 promote angiogenesis in human melanoma. *Cancer Res* 2013; 73: 844-854. PMCID: PMC3548987.
41. Koo T H, Lee J J, Kim E M, Kim K W, Kim H D, Lee J H. Syntenin is overexpressed and promotes cell migration in metastatic human breast and gastric cancer cell lines. Oncogene 2002; 21: 4080-4088. PMID:12037664.
41. Bhang H E, Gabrielson K L, Laterra J, Fisher P B, Pomper M G. Tumor-specific imaging through progression elevated gene-3 promoter-driven gene expression. *Nat Med* 2011; 17: 123-129. PMCID:PMC3057477.
42. Su Z Z, Shi Y, Fisher P B. Subtraction hybridization identifies a transformation progression associated gene PEG-3 with sequence homology to a growth arrest and DNA damage inducible gene. *Proc Natl Acad Sci USA* 1997; 94, 9125-9130. PMCID:PMC23067.
43. Su Z Z, Sarkar D, Emdad L, Duigou G J, Young C S, Ware J, Randolph A, Valerie K, Fisher P B. Targeting gene expression selectively in cancer cells by using the progression-elevated gene-3 promoter. *Proc Natl Acad Sci USA* 2005; 102, 1059-1064. PMCID:PMC545837.
44. Chan I, Lebedeva I V, Su Z Z, Sarkar D, Valerie K, Fisher P B. Progression elevated gene-3 promoter (PEG-Prom) confers cancer cell selectivity to human polynucleotide phosphorylase (hPNPase(old-35))-mediated growth suppression. *J Cell Physiol* 2008; 215, 401-409. PMID: 17960560.
45. Sarkar D, Park E S, Emdad L, Lee S G, Su Z Z, Fisher P B. Molecular basis of nuclear factorkappaB activation by astrocyte elevated gene-1. *Cancer Res* 2008; 68, 1478-1484. PMID:18316612.
46. Lee S G, Kim K, Kegelman T P, Dash R, Das S K, Choi J K, Emdad L, Howlett E L, Jeon H Y, Su Z Z, Yoo B K, Sarkar D, Kim S H, Kang D C, Fisher P B. Oncogene AEG-1 promotes gliomainduced neurodegeneration by increasing glutamate excitotoxicity. *Cancer Res* 2011; 71, 6514-6523. PMCID:PMC3193553.
48. El-Serag H B. Hepatocellular carcinoma. *N Engl J Med* 2011; 365: 1118-1127. PMID:21992124.
49. Siegel R, Naishadham D, Jemal A. Cancer statistics, 2012. *C A Cancer J Clin* 2012; 62: 10-29.PMID: 22237781.
50. Llovet J M, Bruix J. Molecular targeted therapies in hepatocellular carcinoma. *Hepatology* 2008; 48: 1312-1327. PMCID:PMC2597642.

51. Llovet J M, Ricci S, Mazzaferro V, Hilgard P, Gane E, Blanc J F, de Oliveira A C, et al. Sorafenib in advanced hepatocellular carcinoma. *N Engl J Med* 2008; 359: 378-390. PMID: 18650514.
52. Kane R C, Farrell A T, Madabushi R, Booth B, Chattopadhyay S, Sridhara R, Justice R, Pazdur R. Sorafenib for the treatment of unresectable hepatocellular carcinoma. *Oncologist* 2009; 14:95-100. PMID:19144678.
53. Wilhelm S M, Carter C, Tang L, Wilkie D, McNabola A, Rong H, Chen C, Zhang X, Vincent P, McHugh M, Cao Y, Shujath J, Gawlak S, Eveleigh D, Rowley B, Liu L, Adnane L, Lynch M, Auclair D, Taylor I, Gedrich R, Voznesensky A, Riedl B, Post L E, Bollag G, Trail P A. BAY 43-9006 exhibits broad spectrum oral antitumor activity and targets the RAF/MEK/ERK pathway and receptor tyrosine kinases involved in tumor progression and angiogenesis. *Cancer Res* 2004; 64: 7099-7109. PMID: 15466206.
54. Chang Y S, Adnane J, Trail P A, Levy J, Henderson A, Xue D, Bortolon E, Ichetovkin M, Chen C, McNabola A, Wilkie D, Carter C A, Taylor I C, Lynch M, Wilhelm S. Sorafenib (BAY 43-9006) inhibits tumor growth and vascularization and induces tumor apoptosis and hypoxia in RCC xenograft models. *Cancer Chemother Pharmacol* 2007; 59: 561-574. PMID:17160391.
55. Ito Y, Sasaki Y, Horimoto M, Wada S, Tanaka Y, Kasahara A, Ueki T, Hirano T, Yamamoto H, Fujimoto J, Okamoto E, Hayashi N, Hori M. Activation of mitogen-activated protein kinases/extracellular signal-regulated kinases in human hepatocellular carcinoma. *Hepatology* 1990; 27: 951-958. PMID:9537433.
56. Villanueva A, Newell P, Chiang D Y, Friedman S L, Llovet J M. Genomics and signaling pathways in hepatocellular carcinoma. *Semin Liver Dis* 2007; 27: 55-76. PMID:17295177.
57. Calvisi D F, Ladu S, Gorden A, Farina M, Conner E A, Lee J S, Factor V M, Thorgeirsson S S. Ubiquitous activation of Ras and Jak/Stat pathways in human HCC. *Gastroenterology* 2006; 130: 1117-1128. PMID: 16618406.
59. Dev K K. Making protein interactions druggable: targeting PDZ domains. *Nat Rev Drug Discov* 2004; 3: 1047-1056. PMID:15573103.
60. Giansanti F, Di Leandro L, Koutris I, Pitari G, Fabbrini M S, Lombardi A, Flavell D J, Flavell S U, Gianni S, Ippoliti R. Engineering a switchable toxin: the potential use of PDZ domains in the expression, targeting and activation of modified saporin variants. Protein Eng Des Sel 2010; 23: 61-68. PMID:19933699.
61. Ikonomidou C, Turski L. Why did NMDA receptor antagonists fail clinical trials for stroke and traumatic brain injury? Lancet Neurol 2002; 1: 383-386. PMID: 12849400.
62. Piserchio A, Salinas G D, Li T, Marshall J, Spaller M R, Mierke D F. Targeting specific PDZ domains of PSD-95; structural basis for enhanced affinity and enzymatic stability of a cyclic peptide. Chem Biol 2004; 11: 469-473. PMID:15123241.
63. Piserchio A, Spaller M, Mierke D F. Targeting the PDZ domains of molecular scaffolds of transmembrane ion channels. AAPS J 2006; 8: E396-401. PMCID: PMC3231575.
64. Ponting C P, Phillips C, Davies K E, Blake D J. PDZ domains: targeting signalling molecules to sub-membranous sites. Bioessays 1997; 19: 469-479. PMID:9204764.
65. Stricker N L, Huganir R L. The PDZ domains of mLin-10 regulate its trans-Golgi network targeting and the surface expression of AMPA receptors. Neuropharmacology 2003; 45: 837-848. PMID: 14529721.
66. lvarsson Y. Plasticity of PDZ domains in ligand recognition and signaling. *FEBS Lett* 2012; 586: 2638-2647. PMID:22576124.
67. Subbaiah V K, Kranjec C, Thomas M, Banks L. PDZ domains: the building blocks regulating tumorigenesis. *Biochem J* 2011; 439: 195-205. PMID:21954943.
68. Pellecchia M, Bertini I, Cowburn D, Dalvit C, Giralt E, Jahnke W, James T L, Homans S W, Kessler H, Luchinat C, Meyer B, Oschkinat H, Peng J, Schwalbe H, Siegal G. Perspectives on NMR in drug discovery: a technique comes of age. Nat Rev Drug Discov 2008; 7: 738-745. PMCID: PMC2891904.
69. Wu B, Zhang Z, Noberini R, Barile E, Giulianotti M, Pinilla C, Houghten R A, Pasquale E B, Pellecchla M. HTS by NMR of combinatorial libraries: a fragment-based approach to ligand discovery. Chem Biol 2013; 20: 19-33. PMID:23352136.
70. Rega M F, Wu B, Wei J, Zhang Z, Cellitti J F, Pellecchla M. SAR by Interligand Nuclear Overhauser Effects (ILOEs) Based Discovery of Acylsulfonamide Compounds Active against Bcl-x(L) and Mcl-1. J Med Chem 2011; 54: 6000-6013. PMCID: PMC3165075.
71. Yoo B K, Emdad L, Lee S-G, Su Z-Z, Santhekadur P, Chen D, Gredler R, Fisher P B, Sarkar D. Astrocyte elevated gene-1 (AEG-1): a multifunctional regulator of normal and abnormal physiology. Pharmacol Ther 2011; 130: 1-8. PMCID:PMC3043119.
72. Sarkar D, Fisher P B. AEG-1/MTDH/LYRIC implicated in many cancers. *Adv Cancer Res* 2013; 120: 1 to 238. PMID:23889993.
73. Sarkar D, Fisher P B. AEG-1/MTDH/LYRIC: clinical significance. In: AEG-1/MTDH/LYRIC implicated in multiple human cancers. Sarkar D, Fisher P B Eds. *Adv Cancer Res* 2013; 120:39-74. PMID:23889987.
74. Brown D M, Ruoslahti E. Metadhrin, a cell surface protein in breast tumors that mediates lung metastasis. *Cancer Cell* 2004; 5: 365-374. PMID:15093543.
75. Villanueva A, Newell P, Chiang D Y, Friedman S L, Llovet J M. Genomics and signaling pathways in hepatocellular carcinoma. *Semin Liver Dis* 2007; 27: 55-76. PMID:17295177.
76. Breindel J L, Haskins J W, Cowell E P, Zhao M, Nguyen D X, Stern D F. EGF receptor activates MET through MAPK to enhance non-small cell lung carcinoma invasion and brain metastasis. *Cancer Res* 2013; 73: 5053-5065. PMCID:PMC3745527.
77. Sharifi N, Gulley J L, Dahut W L. Androgen deprivation therapy for prostate cancer. JAMA 2005; 294: 238-44. PMID:16014598.
78. Armstrong A J, Carducci M A. Advanced prostate cancer: the future. Can J Urol 2005; 12 Suppl 2: 42-7. PMID:16018833.
79. Tam L, McGlynn L M, Traynor P, Mukherjee R, Bartlett J M, Edwards J. Expression levels of the JAK/STAT pathway in the transition from hormone-sensitive to hormone-refractory prostate cancer. Br J Cancer 2007; 97: 378-83. PMCID:PMC2360337.
80. Dhir R, Ni Z, Lou W, DeMiguel F, Grandis J R, Gao A C. Stat3 activation in prostatic carcinomas. Prostate 2002; 51: 241-6. PMID:11987152.
81. Rojas A, Liu G, Coleman I, Nelson P S, Zhang M, Dash R, Fisher P B, Plymate S R, Wu J D. IL-6 promotes prostate tumorigenesis and progression through autocrine cross-activation of IGF-I R. Oncogene 2011; 30: 2345-55. PMCID: PMC3112005.

82. Emdad L, Lee S G, Su Z Z, Jeon H Y, Boukerche H, Sarkar D, Fisher P B. Astrocyte elevated gene-1 (AEG-1) functions as an oncogene and regulates angiogenesis. Proc Natl Acad Sci USA. 2009; 106: 21300-21305. PMCID: PMC2795510.

83. Sarkar D. AEG-1/MTDHILYRIC in liver cancer. Adv Cancer Res. 2013; 120: 193-221. PMID:23889992.

84. Tonikian R, Zhang Y, Sazinsky S L, Currell B, Yeh J H, Reva B, Held H A, Appleton B A, Evangelista M, Wu Y, Xin X, Chan A C, Seshagiri S, Lasky L A, Sander C, Boone C, Bader G D, Sidhu S S. A specificity map for the PDZ domain family. PLoS Biol. 2008; 6(9):e239. PMCID:PMC2553845.

Example 6 References

Grootjans J J, Zimmermann P, Reekmans G, Smets A, Degeest G, Durr J, David G. Syntenin, a PDZprotein that binds syndecan cytoplasmic domains. Proceedings of the National Academy of Sciences of the United States of America. 1997; 94(25): 13683-8. PMCID: PMC28366.

2. Boukerche H, Su Z Z, Emdad L, Baril P, Balme B, Thomas L, Randolph A, Valerie K, Sarkar D, Fisher P B. mda-9/Syntenin: a positive regulator of melanoma metastasis. *Cancer Res* 2005; 65(23):10901-11. PMID: 16322237.

3. Boukerche H, Su Z Z, Emdad L, Sarkar D, Fisher P B. mda-9/Syntenin regulates the metastatic phenotype in human melanoma cells by activating nuclear factor-kappaB. Cancer Res. 2007; 67(4):1812-22. PMID: 17308124.

4. Boukerche H, Su Z Z, Prevot C, Sarkar D, Fisher P B. mda-9/Syntenin promotes metastasis in human melanoma cells by activating c-Src. Proc Natl Acad Sci USA. 2008; 105(41):15914-9. PMCID:PMC2572986.

5. Boukerche H, Aissaoui H, Prevost C, Hirbec H, Das S K, Su Z Z, Sarkar D, Fisher P B. Src kinase activation is mandatory for MDA-9/syntenin-mediated activation of nuclear factor-kappaB. Oncogene. 2010; 29(21):3054-66. PMCID: PMC2878370.

6. Koo T H, Lee J J, Kim E M, Kim K W, Do Kim H, Lee J H. Syntenin is overexpressed and promotes cell migration in metastatic human breast and gastric cancer cell lines. Oncogene. 2002; 21(26):4080-8. PMID: 12037664.

7. Helmke B M, Polychronidis M, Benner A, Thome M, Arribas J, Deichmann M. Melanoma metastasis is associated with enhanced expression of the syntenin gene. Oncology Reports. 2004; 12(2):221-8. PMID: 15254681.

8. Sarkar D, Boukerche H, Su Z Z, Fisher P B. mda-9/syntenin: recent insights into a novel cell signaling and metastasis-associated gene. Pharmacology & Therapeutics. 2004; 104(2):101-15. PMID:15518882.

9. Sarkar D, Boukerche H, Su Z Z, Fisher P B. mda-9/syntenin: More than just a simple adapter protein when it comes to cancer metastasis. Cancer Research. 2008; 68(9):3087-93. PMID: 18451132.

10. Beekman J M, Coffer P J. The ins and outs of syntenin, a multifunctional intracellular adaptor protein. J Cell Sci. 2008; 121(Pt 9):1349-55. PMID: 18434645.

11. Coghlin C, Murray G I. Current and emerging concepts in tumour metastasis. J Pathol. 2010; 222(1):1-15. PMID: 20681009.

12. Wells A, Grahovac J, Wheeler S, Ma B, Lauffenburger D. Targeting tumor cell motility as a strategyagainst invasion and metastasis. *Trends Pharmacol Sci.* 2013; 34(5):283-9. PMCID: PMC3640670.

13. Nguyen D X, Bos P D, Massague J. Metastasis: from dissemination to organ-specific colonization. Nature reviews Cancer. 2009; 9(4):274-84. PMID: 19308067.

14. Fisher R, Pusztai L, Swanton C. Cancer heterogeneity: implications for targeted therapeutics. Br J Cancer. 2013; 108(3):479-85. PMCID: PMC3593543.

15. Chiang A C, Massague J. Molecular basis of metastasis. N Engl J Med. 2008; 359(26):2814-23. PMID: 19109576.

16. Nguyen D X, Massague J. Genetic determinants of cancer metastasis. Nat Rev Genet. 2007; 8(5):341-52. PMID: 17440531.

17. Lin J J, Jiang H P, Fisher P B. Characterization of a novel melanoma differentiation-associated gene, mda-9, that is down-regulated during terminal cell differentiation. Molecular and Cellular Differentiation. 1996; 4(4):317-33.

18. Kegelman T P, Das S K, Hu B, Menezes M E, Emdad L, Dasgupta S, Bruce J N, Dent P, Pellecchla M, Sarkar D, Fisher P B. MDA-9/syntenin is a key regulator of glioma pathogenesis. Journal of Neuro-Oncol. 2013; In press.

19. Dasgupta S, Menezes M E, Das S K, Emdad L, Janjic A, Bhatia S, Mukhopadhyay N D, Shao C, Sarkar D, Fisher P B. Novel role of MDA-9/Syntenin in regulating urothelial cell proliferation by modulating EGFR signaling. Clinical Cancer Res. 2013; 19(17):4621-33. PMID: 23873690.

20. Boukerche H, Aissaoui H, Prevost C, Hirbec H, Das S K, Su Z Z, Sarkar D, Fisher P B. Src kinase activation is mandatory for MDA-9/syntenin-mediated activation of nuclear factor-kappa B. Oncogene. 2010; 29(21):3054-66. PMCID: PMC2878370.

21. Boukerche H, Su Z Z, Kang D C, Fisher P B. Identification and cloning of genes displaying elevated expression as a consequence of metastatic progression in human melanoma cells by rapid subtraction hybridization. Gene. 2004; 343(1):191-201. PMID: 15563845.

22. Hwangbo C, Park J, Lee J H. mda-9/Syntenin protein positively regulates the activation of Akt protein by facilitating integrin-linked kinase adaptor function during adhesion to type I collagen. *J Biol Chem.*2011; 286(38): 33601-12. PMCID: PMC3190898.

23. Henley J M, Hirbec H, Martin S. Syntenin is involved in the developmental regulation of neuronal membrane architecture. Molecular and Cellular Neuroscience. 2005; 28(4):737-46. PMID: 15797720.

24. Zimmermann P, Zhang Z, Degeest G, Mortier E, Leenaerts I, Coomans C, Schulz J, N'Kuli F, Courtoy P J, David G. Syndecan recycling is controlled by syntenin-PIP2 interaction and Arf6. Developmental Cell. 2005; 9(5):377-88. PMID: 16139226.

25. Ivarsson Y. Plasticity of PDZ domains in ligand recognition and signaling. FEBS Lett.2012; 586(17):2638-47. PMID: 22576124.

26. Subbaiah V K, Kranjec C, Thomas M, Banks L. PDZ domains: the building blocks regulating tumorigenesis. *Biochem J.* 2011; 439(2):195-205. PMID: 21954943.

27. Hwangbo C, Kim J, Lee J J, Lee J H. Activation of the integrin effector kinase focal adhesion kinase in cancer cells is regulated by crosstalk between protein kinase Calpha and the PDZ adapter protein mda-9/Syntenin. Cancer Res. 2010; 70(4):1645-55. PMID: 20145126.

28. Gangemi R, Mirisola V, Barisione G, Fabbi M, Brizzolara A, Lanza F, Mosci C, Salvi S, Gualco M, Truini M, Angelini G, Boccardo S, Cilli M, Airoldi 1, Queirolo P, Jager M J, Daga A, Pfeffer U, Ferrini S. Mda-9/syntenin is expressed in uveal melanoma and correlates with metastatic progression. PLoS One. 2012; 7(1):e29989. PMCID: PMC3258266.
29. Ishizawar R, Parsons S J. c-Src and cooperating partners in human cancer. Cancer Cell.2004; 6(3):209-14. PMID: 15380511.
30. Cui H, Hayashi A, Sun H S, Belmares M P, Cobey C, Phan T, Schweizer J, Salter M W, Wang Y T, Tasker R A, Garman D, Rabinowitz J, Lu P S, Tymianski M. PDZ protein interactions underlying NMDA receptor-mediated excitotoxicity and neuroprotection by PSD-95 inhibitors. *J Neurosci.* 2007; 27(37):9901-15. PMID: 17855605.
31. Fujii N, You L, Xu Z, Uematsu K, Shan J, He B, Mikami I, Edmondson L R, Neale G, Zheng J, Guy R K, Jablons D M. An antagonist of dishevelled protein-protein interaction suppresses beta-catenindependent tumor cell growth. Cancer Res. 2007; 67(2):573-9. PMID: 17234765.
32. Tang W, Sun X, Fang J S, Zhang M, Sucher N J. Flavonoids from Radix Scutellariae as potential stroke therapeutic agents by targeting the second postsynaptic density 95 (PSD-95)/disc large/zonula occludens-1 (PDZ) domain of PSD-95. Phytomedicine. 2004; 11(4):277-84. PMID: 15185839.
33. Wong H C, Bourdelas A, Krauss A, Lee H J, Shao Y, Wu D, Mlodzik M, Shi D L, Zheng J. Direct binding of the PDZ domain of Dishevelled to a conserved internal sequence in the C-terminal region of Frizzled. *Mol Cell.* 2003; 12(5):1251-60. PMID: 14636582.
34. Shan J, Shi D L, Wang J, Zheng J. Identification of a specific inhibitor of the dishevelled PDZ domain. Biochemistry. 2005; 44(47):15495-503. PMID: 16300398.
35. Dev K K. Making protein interactions druggable: targeting PDZ domains. Nat Rev Drug Discov.2004; 3(12): 1047-56. PMID: 15573103.
36. Giansanti F, Di Leandro L, Koutris I, Pitari G, Fabbrini M S, Lombardi A, Flavell D J, Flavell S U, Gianni S, Ippoliti R. Engineering a switchable toxin: the potential use of PDZ domains in the expression, targeting and activation of modified saporin variants. Protein Eng Des Sel. 2010; 23(2):61-8. PMID: 19933699.
37. Ikonomidou C, Turski L Why did NMDA receptor antagonists fail clinical trials for stroke and traumatic brain injury? Lancet Neurol. 2002; 1(6):383-6. PMID: 12849400.
38. Piserchio A, Salinas G D, Li T, Marshall J, Spaller M R, Mierke D F. Targeting specific PDZ domains of PSD-95; structural basis for enhanced affinity and enzymatic stability of a cyclic peptide. Chem Biol. 2004; 11(4):469-73. PMID: 15123241.
39. Piserchio A, Spaller M, Mierke D F. Targeting the PDZ domains of molecular scaffolds of transmembrane ion channels. AAPS J. 2006; 8(2):E396-401. PMID: 16796391, PMC3231575.
40. Ponting C P, Phillips C, Davies K E, Blake D J. PDZ domains: targeting signalling molecules to submembranous sites. Bioessays. 1997; 19(6):469-79. PMID: 9204764.
41. Stricker N L, Huganir R L. The PDZ domains of mLin-10 regulate its trans-Golgi network targeting and the surface expression of AMPA receptors. Neuropharmacology. 2003; 45(6):837-48. PMID: 14529721.
42. Wen W, Wang W, Zhang M. Targeting PDZ domain proteins for treating NMDA receptor-mediated excitotoxicity. Curr Top Med Chem. 2006; 6(7):711-21. PMID: 16719811.
43. Hammond M C, Harris B Z, Lim W A, Bartlett P A. Beta strand peptidomimetics as potent PDZ domain ligands. Chem Biol. 2006; 13(12):1247-51. PMID: 17185220.
44. Hajduk P J, Greer J. A decade of fragment-based drug design: strategic advances and lessons learned. Nat Rev Drug Discov. 2007; 6(3):211-9. PMID: 17290284.
45. Hajduk P J. Fragment-based drug design: how big is too big? J Med Chem. 2006; 49(24):6972-6. PMID: 17125250
46. Hajduk P J. Puzzling through fragment-based drug design. Nat Chem Biol. 2006; 2(12):658-9. PMID: 17108979
47. Pellecchia M, Bertini 1, Cowburn D, Dalvit C, Giralt E, Jahnke W, James T L, Homans S W, Kessler H, Luchinat C, Meyer B, Oschkinat H, Peng J, Schwalbe H, Siegal G. Perspectives on NMR in drug discovery: a technique comes of age. Nat Rev Drug Discov. 2008; 7(9):738-45. PMCID: PMC2891904.
48. Wu B, Zhang Z, Noberini R, Barile E, Giulianotti M, Pinilla C, Houghten R A, Pasquale E B, Pellecchla M. HTS by NMR of combinatorial libraries: a fragment-based approach to ligand discovery. Chem Biol. 2013; 20(1):19-33. PMID: 23352136.
49. Dash R, Azab B, Quinn B A, Shen X, Wang X Y, Das S K, Rahmani M, Wei J, Hedvat M, Dent P, Dmitriev I P, Curiel D T, Grant S, Wu B, Stebbins J L, Pellecchia M, Reed J C, Sarkar D, Fisher P B. Apogossypol derivative BI-97C1 (Sabutoclax) targeting Mcl-1 sensitizes prostate cancer cells to mda-7/IL-24-mediated toxicity. Proc Natl Acad Sci USA. 2011; 108(21):8785-90. PMCID: PMC3102401.
50. Wei J, Kitada S, Stebbins J L, Placzek W, Zhai D, Wu B, Rega M F, Zhang Z, Cellitti J, Yang L, Dahl R, Reed J C, Pellecchia M. Synthesis and biological evaluation of Apogossypolone derivatives as pan-active inhibitors of antiapoptotic B-cell lymphoma/leukemia-2 (Bcl-2) family proteins. J Med Chem. 2010; 53(22):8000-11. PMCID: PMC3059195.
51. Wei J, Stebbins J L, Kitada S, Dash R, Placzek W, Rega M F, Wu B, Cellitti J, Zhai D, Yang L, Dahl R, Fisher P B, Reed J C, Pellecchia M. BI-97C1, an optically pure Apogossypol derivative as pan-active inhibitor of antiapoptotic B-cell lymphoma/leukemia-2 (Bcl-2) family proteins. J Med Chem. 2010; 53(10):4166-76. PMCID: PMC2880850.
52. Wei J, Kitada S, Rega M F, Stebbins J L, Zhai D, Cellitti J, Yuan H, Emdadi A, Dahl R, Zhang Z, Yang L, Reed J C, Pellecchia M. Apogossypol derivatives as pan-active inhibitors of antiapoptotic B-cell lymphoma/leukemia-2 (Bcl-2) family proteins. J Med Chem. 2009; 52(14):4511-23. PMCID: PMC2747480.
53. Wei J, Kitada S, Rega M F, Emdadi A, Yuan H, Cellitti J, Stebbins J L, Zhai D, Sun J, Yang L, Dahl R, Zhang Z, Wu B, Wang S, Reed T A, Wang H G, Lawrence N, Sebti S, Reed J C, Pellecchla M. Apogossypol derivatives as antagonists of antiapoptotic Bel-2 family proteins. Mol Cancer Ther. 2009; 8(4):904-13. PMCID: PMC2750823.
54. Wei J, Rega M F, Kitada S, Yuan H, Zhai D, Risbood P, Seltzman H H, Twine C E, Reed J C, Pellecchia M. Synthesis and evaluation of Apogossypol atropisomers as potential Bcl-xL antagonists. Cancer Lett. 2009; 273(1): 107-13. PMCID: PMC2653056.
55. Rega M F, Wu B, Wei J, Zhang Z, Cellitti J F, Pellecchia M. SAR by Interligand Nuclear Overhauser Effects (ILOEs) Based Discovery of Acylsulfonamide Compounds Active against Bcl-x(L) and Mcl-1. J Med Chem. 2011. PMCID: PMC3165075.

56. Feng Y, Barile E, De S K, Stebbins J L, Cortez A, Aza-Blanc P, Villanueva J, Heryln M, Krajewski S, Pellecchia M, Ronai Z A, Chiang G G. Effective inhibition of melanoma by BI-69A11 is mediated by dual targeting of the AKT and N F-kappaB pathways. Pigment Cell Melanoma Res. 2011. PMCID:PMC3158838.

57. Johnson S, Barile E, Farina B, Purves A, Wei J, Chen L H, Shiryaev S, Zhang Z, Rodionova I, Agmwal A, Cohen S M, Osterman A, Strongin A, Pellecchla M. Targeting metalloproteins by fragment-based lead discovery. Chem Biol Drug Des. 2011; 78(2):211-23. PMCID: PMC3135788.

58. De S K, Barile E, Chen V, Stebbins J L, Cellitti J F, Machleidt T, Carlson C B, Yang L, Dahl R, Pellecchia M. Design, synthesis, and structure-activity relationship studies of thiophene-3-carboxamide derivatives as dual inhibitors of the c-Jun N-terminal kinase. Bioorg Med Chem. 2011; 19(8):2582-8. PMCID: PMC3089059.

59. Leone M, Barile E, Dahl R, Pellecchia M. Design and NMR studies of cyclic peptides targeting the Nterminal domain of the protein tyrosine phosphatase YopH. Chem Biol Drug Des. 2011; 77(1):12-9. PMCID: PMC3149900.

60. Barile E, De S K, Carlson C B, Chen V, Knutzen C, Riel-Mehan M, Yang L, Dahl R, Chiang G, PeUecchia M. Design, Synthesis, and Structure-Activity Relationships of 3-Ethynyl-1H-indazoles as Inhibitors of the Phosphatidylinositol 3-Kinase Signaling Pathway. J Med Chem. 2010. PMCID:PMC3131451.

61. Leone M, Barile E, Vazquez J, Mei A, Guiney D, Dahl R, Pellecchla M. NMR-based design and evaluation of novel bidentate inhibitors of the protein tyrosine phosphatase YopH. *Chem Biol* Drug Des. 2010; 76(1):10-6. PMCID: PMC2905849.

62. De S K, Chen V, Stebbins J L, Chen L H, Cellitti J F, Machleidt T, Barile E, Riel-Mehan M, Dahl R, Yang L, Emdadi A, Murphy R, Pellecchla M. Synthesis and optimization of thiadiazole derivatives as a novel class of substrate competitive c-Jun N-terminal kinase inhibitors. Bioorg Med Chem. 2010; 18(2):590-6. PMCID: PMC2818674.

63. Wu S, Vossius S, Rahmouni S, Miletic A V, Vang T, Vazquez-Rodriguez J, Cerignoli F, Arimura Y, Williams S, Hayes T, Moutschen M, Vasile S, Pellecchia M, Mustelin T, Tautz L. Multidentate smallmolecule inhibitors of vaccinia H I-related (VHR) phosphatase decrease proliferation of cervix cancer cells. J Med Chem. 2009; 52(21): 6716-23. PMCID: PMC2790023.

64. Cellitti J, Zhang Z, Wang S, Wu B, Yuan H, Hasegawa P, Guiney D G, Pellecchla M. Small molecule DnaK modulators targeting the beta-domain. Chem Biol Drug Des. 2009; 74(4):349-57. PMCID: PMC2858402.

65. De S K, Chen L H, Stebbins J L, Machleidt T, Riel-Mehan M, Dahl R, Chen V, Yuan H, Barile E, Emdadi A, Murphy R, Pellecchla M. Discovery of 2-(5-nitrothiazol-2-ylthio)benzo[d]thiazoles as novel c-Jun N-terminal kinase inhibitors. Bioorg Med Chem. 2009; 17(7):2712-7. PMCID: PMC2828351.

66. De S K, Stebbins J L, Chen L H, Riel-Mehan M, Machleidt T, Dahl R, Yuan H, Emdadi A, Barile E, Chen V, Murphy R, Pellecchla M. Design, synthesis, and structure-activity relationship of substrate competitive, selective, and in vivo active triazole and thiadiazole inhibitors of the c-Jun N-terminal kinase. J Med Chem. 2009; 52(7):1943-52. PMCID: PMC2667321.

67. Stebbins J L, De S K, Machleidt T, Becattini B, Vazquez J, Kuntzen C, Chen L H, Cellitti J F, Riel-Mehan M, Emdadi A, Solinas G, Karin M, Pellecchia M. Identification of a new JNK inhibitor targeting the JNK-JIP interaction site. Proc Natl Acad Sci USA. 2008; 105(43): 16809-13. PMCID:PMC2567907.

68. Vazquez J, De S K, Chen L H, Riel-Mehan M, Emdadi A, Cellitti J, Stebbins J L, Rega M F, Pellecchia M. Development of paramagnetic probes for molecular recognition studies in protein kinases. *J Med Chem.* 2008; 51(12):3460-5. PMCID: PMC2825083.

69. Chen J, Zhang Z, Stebbins J L, Zhang X, Hoffman R, Moore A, Pellecchia M. A fragment-based approach for the discovery of isoform-specific p38alpha inhibitors. ACS Chem Biol. 2007; 2(5):329-36.PMID: 17465519.

70. Vazquez J, Tautz L, Ryan J J, Vuori K, Mustelin T, Pellecchia M. Development of molecular probes for second-site screening and design of protein tyrosine phosphatase inhibitors. J Med Chem. 2007; 50(9):2137-43. PMCID: PMC2615387.

71. Johnson S L, Chen L H, Pellecchia M. A high-throughput screening approach to anthrax lethal factor inhibition. Bioorg Chem. 2007; 35(4):306-12. PMCID: PMC2020844.

72. Rega M F, Reed J C, Pellecchla M. Robust lanthanide-based assays for the detection of antiapoptotic Bcl-2-family protein antagonists. Bioorg Chem. 2007; 35(2): 113-20. PMID: 16996562.

73. Becattini B, Culmsee C, Leone M, Zhai D, Zhang X, Crowell K J, Rega M F, Landshamer S, Reed J C, Plesnila N, Pellechla M. Structure-activity relationships by inter-ligand NOE-based design and synthesis of antiapoptotic compounds targeting Bid. Proc Natl Acad Sci USA. 2006; 103(33): 12602-6. PMCID: PMC1567925.

74. Kim K, Lee S G, Kegelman T P, Su Z Z, Das S K, Dash R, Dasgupta S, Barral P M, Hedvat M, Diaz P, Reed J C, Stebbins J L, Pellecchia M, Sarkar D, Fisher P B. Role of Excitatory Amino Acid Transporter-2 (EAAT2) and glutamate in neurodegeneration: Opportunities for developing novel therapeutics. J Cell Physiol. 2011; 226(10): 2484-93. PMCID: PMC3130100.

75. Azab B, Dash R, Das S K, Bhutia S K, Shen X N, Quinn B A, Sarkar S, Wang X Y, Hedvat M, Dmitriev I P, Curiel D T, Grant S, Dent P, Reed J C, Pellecchia M, Sarkar D, Fisher P B. Enhanced delivery of mda-7/IL-24 using a serotype chimeric adenovirus (Ad.5/3) in combination with the Apogossypol derivative BI-97C1 (Sabutoclax) improves therapeutic efficacy in low CAR colorectal cancer cells. J Cell Physiol. 2012; 227(5):2145-53. PMCID: PMC3228880.

76. Kim K, Lee S G, Kegelman T P, Su Z Z, Das S K, Dash R, Dasgupta S, Barral P M, Hedvat M, Diaz P, Reed J C, Stebbins J L, Pellecchia M, Sarkar D, Fisher P B. Role of excitatory amino acid transporter-2 (EAAT2) and glutamate in neurodegeneration: Opportunities for developing novel therapeutics. J Cell Physiol. 2011; 226(10):2484-93. PMCID: PMC3130100.

77. Dash R, Richards J E, Su Z Z, Bhutia S K, Azab B, Rahmani M, Dasmahapatra G, Yacoub A, Dent P, Dmitriev I P, Curiel D T, Grant S, Pellecchia M, Reed J C, Sarkar D, Fisher P B. Mechanism by which Mcl-1 regulates cancer-specific apoptosis triggered by mda-7/IL-24, an IL-10-related cytokine. Cancer Res. 2010; 70(12): 5034-45. PMCID: PMC3171699.

78. Tonikian R, Zhang Y, Sazinsky S L, Currell B, Yeh J H, Reva B, Held H A, Appleton B A, Evangelista M, Wu Y, Xin X, Chan A C, Seshagiri S, Lasky L A, Sander C, Boone C, Bader G D, Sidhu S S. A specificity map for the PDZ domain family. PLoS Biol. 2008; 6(9):e239. PMCID: PMC2553845.

79. Grembecka J, Cierpicki T, Devedjiev Y, Derewenda U, Kang B S, Bushweller J H, Derewenda Z S. The binding of the PDZ tandem of syntenin to target proteins. Biochemistry. 2006; 45(11):3674-83. PMID: 16533050.
80. Guntert P. Automated NMR structure calculation with CYANA. Methods in molecular biology. 2004; 278:353-78. PMID: 18007625.
81. Stebbins J L, Santelli E, Feng Y, De S K, Purves A, Motamedchaboki K, Wu B, Ronai Z A, Liddington R C, Pellecchia M. Structure-based design of covalent siah inhibitors. Chem Biol. 2013; 20(8):973-82. PMCID: PMC3763817.
82. Pellecchia M. Antagonists of protein-protein interactions made easy? Journal of medicinal chemistry. 2013; 56(1): 13-4. PMID: 23265190.
83. Farina B, Fattorusso R, Pellecchia M. Targeting zinc finger domains with small molecules: solution structure and binding studies of the RanBP2-type zinc finger of RBM5. Chembiochem. 2011; 12(18):2837-45. PMCID: PMC3408030.
84. Placzek W J, Sturlese M, Wu B, Cellitti J F, Wei J, Pellecchia M. Identification of a novel Mcl-1 protein binding motif. J Biol Chem. 2011; 286(46):39829-35. PMCID:PMC3220561.
85. Rega M F, Wu B, Wei J, Zhang Z, Cellitti J F, Pellecchia M. SAR by interligand nuclear overhauser effects (ILOEs) based discovery of acylsulfonamide compounds active against Bcl-x(L) and Mcl-1. Journal of medicinal chemistry. 2011; 54(17):6000-13. PMCID: PMC3165075.
86. Leone M, Barile E, Dahl R, Pellecchia M. Design and NMR studies of cyclic peptides targeting the Nterminal domain of the protein tyrosine phosphatase YopH. Chem Biol Drug Des. 2011; 77(1):12-9. PMCID: PMC3149900.
87. Leone M, Barile E, Vazquez J, Mei A, Guiney D, Dahl R, Pellecchia M. NMR-based design and evaluation of novel bidentate inhibitors of the protein tyrosine phosphatase YopH. Chem Biol Drug Des. 2010; 76(1):10-6. PMCID: PMC2905849.
88. Leone M, Cellitti J, Pellecchia M. The Sam domain of the lipid phosphatase Ship2 adopts a common model to interact with Arap3-Sam and EphA2-Sam. BMC Struct Biol. 2009; 9:59. PMCID: PMC2755476.
89. Cellitti J, Zhang Z, Wang S, Wu B, Yuan H, Hasegawa P, Guiney D G, Pellecchia M. Small molecule DnaK modulators targeting the beta-domain. Chem Biol Drug Des. 2009; 74(4):349-57. PMCID: PMC2858402.
90. Wu B, Rega M F, Wei J, Yuan H, Dahl R, Zhang Z, Pellecchia M. Discovery and binding studies on a series of novel Pinl ligands. Chem Biol Drug Des. 2009; 73(4): 369-79. PMCID: PMC2810120.
91. Pellecchia M, Bertini I, Cowbum D, Dalvit C, Giralt E, Jahnke W, James T L, Homans S W, Kessler H, Luchinat C, Meyer B, Oschkinat H, Peng J, Schwalbe H, Siegal G. Perspectives on NMR in drug discovery: a technique comes of age. Nat Rev Drug Discov. 2008; 7(9):738-45. PMCID: PMC2891904.
92. Leone M, Cellitti J, Pellecchia M. NMR studies of a heterotypic Sam-Sam domain association: the interaction between the lipid phosphatase Ship2 and the EphA2 receptor. Biochemistry. 2008; 47(48):12721-8. PMCID: PMC2674315.
93. Huang J W, Zhang Z, Wu B, Cellitti J F, Zhang X, Dahl R, Shiau C W, Welsh K, Emdadi A, Stebbins J L, Reed J C, Pellecchia M. Fragment-based design of small molecule X-linked inhibitor of apoptosis protein inhibitors. Journal of medicinal chemistry. 2008; 51(22):7111-8. PMCID: PMC2692895.
94. Stebbins J L, De S K, Machleidt T, Becattini B, Vazquez J, Kuntzen C, Chen L H, Cellitti J F, Riel-Mehan M, Emdadi A, Solinas G, Karin M, Pellecchia M. Identification of a new JNK inhibitor targeting the JNK-JIP interaction site. P Natl Acad Sci USA. 2008; 105(43): 16809-13. PMCID: PMC2567907.
95. Vazquez J, De S K, Chen L H, Riel-Mehan M, Emdadi A, Cellitti J, Stebbins J L, Rega M F, Pellecchla M. Development of paramagnetic probes for molecular recognition studies in protein kinases. Journal of medicinal chemistry. 2008; 51(12):3460-5. PMCID: PMC2825083.
96. Stebbins J L, Zhang Z, Chen J, Wu B, Emdadi A, Williams M E, Cashman J, Pellecchia M. Nuclear magnetic resonance fragment-based identification of novel FKBP12 inhibitors. Journal of medicinal chemistry. 2007; 50(26):6607-17. PMID: 18038971.
97. Leone M, Yu E C, Liddington R C, Pasquale E B, Pellecchia M. The PTB domain of tensin: NMR solution structure and phosphoinositides binding studies. Biopolymers. 2008; 89(1):86-92. PMID: 17922498.
98. Rega M F, Leone M, Jung D, Cotton N J, Stebbins J L, Pellecchia M. Structure-based discovery of a new class of Bcl-xL antagonists. *Bioorg* Chem. 2007; 35(4):344-53. PMCID: PMC2023964.
99. Leone M, Crowell K J, Chen J, Jung D, Chiang G G, Sareth S, Abraham R T, Pellecchla M. The FRB domain of mTOR: NMR solution structure and inhibitor design. Biochemistry. 2006; 45(34): 10294-302. PMID: 16922504.
100. Leone M, Yu E C, Liddington R, Pellecchia M. NMR assignment of the phosphotyrosine binding (PTB) domain of tensin. J Biomol NMR. 2006; 36 Suppl 1:40. PMID: 16705357.
101. Johnson S L, Pellecchia M. Structure- and fragment-based approaches to protease inhibition. Curr Top Med Chem. 2006; 6(4):317-29. PMID: 16611145.
102. Stebbins J L, Jung D, Leone M, Zhang X K, Pellecchla M. A structure-based approach to retinoid X receptor-alpha inhibition. J Biol Chem. 2006; 281(24):16643-8. PMID: 16606625.
103. Santelli E, Leone M, Li C, Fukushima T, Preece N E, Olson A J, Ely K R, Reed J C, Pellecchia M, Liddington R C, Matsuzawa S. Structural analysis of Siah1-Siah-interacting protein interactions and insights into the assembly of an E3 ligase multiprotein complex. J Biol Chem. 2005; 280(40):34278-87. PMID: 16085652.
104. Forino M, Johnson S, Wong T Y, Rozanov D V, Savinov A Y, Li W, Fattorusso R, Becattini B, Orry A J, Jung D, Abagyan R A, Smith J W, Alibek K, Liddington R C, Strongin A Y, Pellecchia M. Efficient synthetic inhibitors of anthrax lethal factor. P Natl Acad Sci USA. 2005; 102(27):9499-504. PMCID: PMC 1160517.
105. Forino M, Jung D, Easton J B, Houghton P J, Pellecchla M. Virtual docking approaches to protein kinase B inhibition. Journal of medicinal chemistry. 2005; 48(7):2278-81. PMID: 15801821.
106. Fattorusso R, Jung D, Crowell K J, Forino M, Pellecchia M. Discovery of a novel class of reversible nonpeptide caspase inhibitors via a structure-based approach. Journal of medicinal chemistry.2005; 48(5): 1649-56. PMID: 15743206.
107. Tautz L, Bruckner S, Sareth S, Alonso A, Bogetz J, Bottini N, Pellecchia M, Mustelin T. Inhibition of Yersinia tyrosine phosphatase by furanyl salicylate compounds. J Biol Chem. 2005; 280(10):9400-8. PMID: 15615724.
108. Pellecchia M, Becattini B, Crowell K J, Fattorusso R, Forino M, Fragai M, Jung D, Mustelin T, Tautz L.

NMR-based techniques in the hit identification and optimisation processes. Expert Opin Ther Targets. 2004; 8(6):597-611. PMID: 15584865.
109. Becattini B, Sareth S, Zhai D, Crowell K J, Leone M, Reed J C, Pellecchia M. Targeting apoptosis via chemical design: inhibition of bid-induced cell death by small organic molecules. Chem Biol. 2004; 11 (8):1107-17. PMID: 15324812.
110. Das S K, Bhutia S K, Sokhi U K, Azab B, Su Z Z, Boukerche H, Anwar T, Moen E L, Chatterjee D, Pellecchia M, Sarkar D, Fisher P B. Raf kinase inhibitor RKIP inhibits MDA-9/syntenin-mediated metastasis in melanoma. Cancer Res. 2012; 72:6217-26. PMID: 23066033.
111. Das S K, Bhutia S K, Azab B, Kegelman T P, Peachy L, Santhekadur P K, Dasgupta S, Dash R, Dent P, Grant S, Emdad L, Pellecchla M, Sarkar D, Fisher P B. MDA-9/Syntenin and IGFBP-2 Promote Angiogenesis in Human Melanoma. Cancer Res. 2013; 73(2):844-54. PMCID: PMC3548987.
112. Sarkar D, Fisher, P.B. Cancer metastasis: biologic basis and therapeutics. Welch D R L D, Psaila C, editor. New York: Cambridge University Press; 2011.
113. Fidler IJ, Ellis L M. The implications of angiogenesis for the biology and therapy of cancer metastasis. Cell. 1994; 79(2):185-8. PMID: 7525076.
114. Dankort D, Curley D P, Cartlidge R A, Nelson B, Karnezis A N, Damsky W E, Jr., You M J, DePinho R A, McMahon M, Bosenberg M. Braf(V600E) cooperates with Pten loss to induce metastatic melanoma. Nat Genet. 2009; 41(5):544-52. PMCID: PMC2705918.
115. Dash R, Azab B, Quinn B A, Shen X N, Wang X Y, Das S K, Rahmani M, Wei J, Hedvat M, Dent P, Dmitriev I P, Curiel D T, Grant S, Wu B N, Stebbins J L, Pellecchla M, Reed J C, Sarkar D, Fisher P B. Apogossypol derivative BI-97C1 (Sabutoclax) targeting Mcl-1 sensitizes prostate cancer cells to mda-7/IL-24-mediated toxicity. Proceedings of the National Academy of Sciences of the United States of America. 2011; 108(21):8785-90. PMCID: PMC3102401.
116. Azab B M, Dash R, Das S K, Bhutia S K, Sarkar S, Shen X N, Quinn B A, Dent P, Dmitriev I P, Wang X Y, Curiel D T, Pellecchla M, Reed J C, Sarkar D, Fisher P B. Enhanced prostate cancer gene transfer and therapy using a novel serotype chimera cancer terminator virus (Ad.5/3-CTV). J Cell Physiol. 2013 in press. PMID: PMC23868767
117. Bhang HEC, Gabrielson K L, Laterra J, Fisher P B, Pomper M G. Tumor-specific imaging through progression elevated gene-3 promoter-driven gene expression. Nature Medicine. 2011; 17(1):123-29. PMCID: PMC3057477.
118. Bhutia S K, Das S K, Kegelman T P, Azab B, Dash R, Su Z Z, Wang X Y, Rizzi F, Bettuzzi S, Lee S G, Dent P, Grant S, Curiel D T, Sarkar D, Fisher P B. mda-7/IL-24 differentially regulates soluble and nuclear clusterin in prostate cancer. J Cell Physiol. 2012; 227(5): 1805-13. PMCID: PMC3228882.
119. Bhutia S K, Kegelman T P, Das S K, Azab B, Su Z Z, Lee S G, Sarkar D, Fisher P B. Astrocyte elevated gene-1 induces protective autophagy. Proc Natl Acad Sci USA. 2010; 107(51):22243-8. PMCID: PMC3009793.
120. Dash R, Dmitriev I, Su Z Z, Bhutia S K, Azab B, Vozhilla N, Yacoub A, Dent P, Curiel D T, Sarkar D, Fisher P B. Enhanced delivery of mda-7/IL-24 using a serotype chimeric adenovirus (Ad.5/3) improves therapeutic efficacy in low CAR prostate cancer cells. Cancer Gene Therapy. 2010; 17(7):447-56. PMID: 20150932.
121. Emdad L, Lee S G, Su Z Z, Jeon H Y, Boukerche H, Sarkar D, Fisher P B. Astrocyte elevated gene-1 (AEG-1) functions as an oncogene and regulates angiogenesis. Proc Natl Acad Sci USA. 2009; 106(50):21300-5. PMCID: PMC2795510.
122. Emdad L, Sarkar D, Lee S G, Su Z Z, Yoo B K, Dash R, Yacoub A, Fuller C E, Shah K, Dent P, Bruce J N, Fisher P B. Astrocyte Elevated Gene-1: a novel target for human glioma therapy. Mol Cancer Therapeutics. 2010; 9(1):79-88. PMCID: PMC3165052.
123. Wang S, Noberini R, Stebbins J L, Das S, Zhang Z, Wu B, Mitra S, Billet S, Fernandez A, Bhowmick N A, Kitada S, Pasquale E B, Fisher P B, Pellecchia M. Targeted delivery of paclitaxel to EphA2-expressing cancer cells. Clin Cancer Res. 2013; 19(1):128-37. PMCID: PMC3537892.

Informal Sequence Listing (PDZ1 domain)
SEQ ID NO: 1
QGIREVILCKDQDGKIGLRLKSIDNGIFVQLVQANSPASLVG

LRFGDQVLQINGENCAGWSSDKAHKVLKQAFGEKITMTIRDR

PROVISIONAL EMBODIMENTS

Embodiments contemplated herein include the following.
The following definitions pertain exclusively to Provisional (i.e. P) embodiments.

The term "alkyl" refers to linear (unbranched) or branched chain unsubstituted hydrocarbon groups of about 1 to 20 carbon atoms, for example. The term "substituted alkyl" refers to an alkyl group substituted by, for example, about one, two three or four substituents, examples of which include but are not limited to: halo, hydroxy, alkoxy, oxo, alkanoyl, aryloxy, alkanoyloxy, amino, alkylamino, substituted alkylamino, cycloalkylamino, substituted cycloalkylamino, arylamino, substituted arylamino, aralkylamino, substituted aralkyamino, disubstituted amines in which the 2 amino substituents are selected from alkyl, aryl or aralkyl; alkanoylamino, aroylamino, aralkanoylamino, substituted alkanoylamino, substituted arylamino, substituted aralkanoylamino, thiol, alkylthio, arylthio, aralkylthio, alkylthiono, arylthiono, aralkylthiono, alkylsulfonyl, arylsulfonyl, aralkylsulfonyl, sulfonamido, e.g. $SO_2NH_2$, substituted sulfonamido, nitro, cyano, carboxy, carbamyl, e.g. $CONH_2$, substituted carbamyl e.g. CONHalkyl, CONHaryl, CONHaralkyl or cases where there are two substituents on the nitrogen selected from alkyl, aryl or aralkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl. These substituents may be further substituted, e.g. with alkyl, alkoxy, aryl, aralkyl, etc.

The term "aryl" refers to compounds which contain an aromatic group, e.g. a monocyclic or polycyclic aromatic compound. Monocyclic aryls generally have about 4 to about 7 carbon atoms, bicyclic aryls may have e.g. from about 7 to about 11 carbon atoms, and tricyclic aryls may contain from about 10 to about 15 or more carbon atoms. Exemplary aryls are or comprise groups that include but are not limited to: phenyl, naphthyl, biphenyl (diphenyl), thienyl, indolyl, etc. Aryls may be substituted or unsubstituted, and may or may not include one or more heteroatoms (e.g. S, N, O, etc.) in one or more ring structures (heteroaryls).

The term "arylalkyl" refers to an aryl or a substituted aryl group bonded directly to an alkyl group, such as benzyl.

The term "substituted aryl" refers to an aryl group substituted by, for example, about one to about four (e.g. 1, 2, 3, or 4) substituents such as alkyl, substituted alkyl, alkenyl, substituted alkenyl, alkynyl, substituted alkynyl, aryl, substituted aryl, aralkyl, halo, trifluoromethoxy, trifluoromethyl, hydroxy, alkoxy, alkanoyl, alkanoyloxy, aryloxy, aralkyloxy, amino, alkylamino, arylamino, aralkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, aryloxy and the like. The substituent may be further substituted by hydroxy, halo, alkyl, alkoxy, alkenyl, alkynyl, aryl or aralkyl.

Embodiment P1

A compound of Formula I

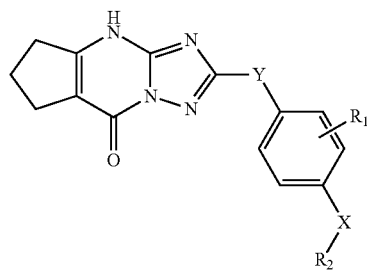

Formula I wherein Y and X are independently selected from the group consisting of: —CONH—, —NHCO—, —SO$_2$NH—, —O—, —CH2-, —S—, —SO$_2$—, —NH—, —N(CH$_3$)—, —COSO$_2$NH—, —OCH$_2$—, and —CH$_2$O—; R1 is —H or independently mono, di-, tri- or tetra-substituted with any of the following: —F, —Cl, —Br, —CF$_3$, —OCF$_3$, —OCH$_3$, —CH3, —CH$_2$CH$_3$, —CONH$_2$, —NHCOH, —SO$_2$NH$_2$, —OH, —NH$_2$, —NH(CH$_3$), —N(CH3)2-COSO$_2$NH$_2$, —CH$_2$OH, —CH$_7$CH1OH; and R2 is a substituted or un-substituted aryl or a substituted or un-substituted alkyl-aryl.

Embodiment P2

The compound of embodiment P1, wherein said compound is Formula II

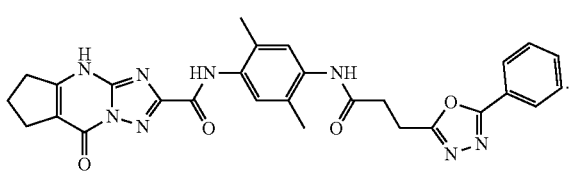

Formula II

Embodiment P3

A salt or prodrug of any of the compounds of embodiments P1-P2.

Embodiment P4

A method of preventing or treating cancer in a subject in need thereof, comprising administering to the subject a therapeutically effective amount of any of the compounds of embodiments P1-P3, wherein the therapeutically effective amount is sufficient to prevent or treat the cancer.

Embodiment P5

A method of sensitizing cancer cells to killing by radiation, comprising contacting the cancer cells with a therapeutically effective amount of any of the compounds of embodiments P1-P3, wherein the therapeutically effective amount is sufficient to sensitize the cancer cells to killing by radiation.

Embodiment P6

A method of slowing or preventing metastasis of cancer cells in a subject in need thereof, comprising administering to the subject a therapeutically effective amount of any of the compounds of embodiments P1-P3, wherein the therapeutically effective amount is sufficient to slow or prevent the metastasis.

Embodiment P7

The method of embodiment P6, wherein the therapeutically effective amount is sufficient to slow or prevent at least one of invasion, migration, and angiogenesis.

Embodiment P8

The method of any of embodiments P4-P6, wherein the cancer is selected from the group consisting of glioblastoma multiforme, melanoma, prostate, breast, and liver cancer.

Embodiment P9

A method of treating a glioblastoma multiforme brain tumor in a subject in need thereof, comprising performing surgery on the subject to debulk the glioblastoma multiforme brain tumor; radiosensitizing remaining tumor cells by administering to the subject a therapeutically effective amount of at least one of the compounds of any of embodiments P1-P3, wherein the therapeutically effective amount is sufficient to sensitize the remaining tumor cells to killing by radiation; and providing radiation therapy to the subject.

Embodiment P10

A method of slowing or preventing prostate cancer metastasis to secondary sites in a subject in need thereof, comprising administering to the subject a therapeutically effective amount of any of the compounds of embodiments P1-P3, wherein the therapeutically effective amount is sufficient to slow or prevent the metastasis.

Embodiment P11

The method of embodiment P10, wherein the therapeutically effective amount is sufficient to slow or prevent at least one of invasion, migration, and angiogenesis.

EMBODIMENTS

Embodiments further contemplated herein include the following:

Embodiment 1

A compound, or pharmaceutically acceptable salt thereof, having the formula:

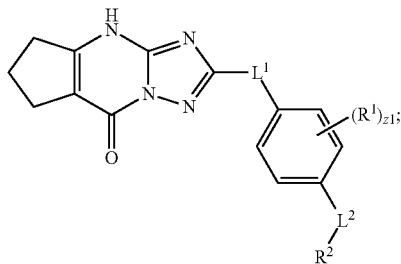

(I)

wherein
$R^1$ is independently halogen, $-CX^1_3$, $-CHX^1_2$, $-CH_2X^1$, $-OCX^1_3$, $-OCH_2X^1$, $-OCHX^1_2$, $-CN$, $-SO_{n1}R^{1D}$, $-SO_{v1}NR^{1A}R^{1B}$, $-NHC(O)NR^{1A}R^{1B}$, $-N(O)_{m1}$, $-NR^{1A}R^{1B}$, $-C(O)R^{1C}$, $-C(O)-OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl;
$R^2$ is independently hydrogen, halogen, $-CX^2_3$, $-CHX^2_2$, $-CH_2X^2$, $-OCX^2_3$, $-OCH_2X^2$, $-OCHX^2_2$, $-CN$, $-SO_{n2}R^{2D}$, $-SO_{v2}NR^{2A}R^{2B}$, $-NHC(O)NR^{2A}R^{2B}$, $-N(O)_{m2}$, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$L^1$ is a bond, $-S(O)_2-$, $-N(R^3)-$, $-O-$, $-S-$, $-C(O)-$, $-C(O)N(R^3)-$, $-N(R^3)C(O)-$, $-N(R^3)C(O)NH-$, $-NHC(O)N(R^3)-$, $-S(O)_2N(R^3)-$, $-N(R^3)S(O)_2-$, $-C(O)S(O)_2N(R^3)-$, $-N(R^3)S(O)_2C(O)-$, $-C(O)O-$, $-OC(O)-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
$R^3$ is independently hydrogen, $-CX^3_3$, $-CHX^3_2$, $-CH_2X^3$, $-CN$, $-C(O)R^{3C}$, $-C(O)OR^{3C}$, $-C(O)NR^{3A}R^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$L^2$ is a bond, $-S(O)_2-$, $-N(R^4)-$, $-O-$, $-S-$, $-C(O)-$, $-C(O)N(R^4)-$, $-N(R^4)C(O)-$, $-N(R^4)C(O)NH-$, $-NHC(O)N(R^4)-$, $-S(O)_2N(R^4)-$, $-N(R^4)S(O)_2-$, $-C(O)S(O)_2N(R^4)-$, $-N(R^4)S(O)_2C(O)-$, $-C(O)O-$, $-OC(O)-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
$R^4$ is independently hydrogen, $-CX^4_3$, $-CHX^4_2$, $-CH_2X^4$, $-CN$, $-C(O)R^{4C}$, $-C(O)OR^{4C}$, $-C(O)NR^{4A}R^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{1A}, R^{1B}, R^{1C}, R^{1D}, R^{2A}, R^{2B}, R^{2C}, R^{2D}, R^{3A}, R^{3B}, R^{3C}, R^{4A}, R^{4B}$, and $R^{4C}$ are independently hydrogen, $-CX_3$, $-CN$, $-COOH$, $-CONH_2$, $-CHX_2$, $-CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; $R^{4A}$ and $R^{4B}$ substituents bonded to the same nitrogen atom may optionally be joined to form a substituted or unsubstituted heterocycloalkyl or substituted or unsubstituted heteroaryl;
$X, X^1, X^2, X^3$, and $X^4$ are independently $-F$, $-Cl$, $-Br$, or $-I$;
n and n2 are independently an integer from 0 to 4;
m1, m2, v1, and v2 are independently 1 or 2; and
z1 is an integer from 0 to 4.

Embodiment 2

The compound of embodiment 1, wherein $R^1$ is independently halogen, $-CX^1_3$, $-CHX^1_2$, $-CH_2X^1$, $-OCX^1_3$, $-OR^{2D}$, $-CN$, $-NR^{1A}R^{1B}$, substituted or unsubstituted alkyl or two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl.

Embodiment 3

The compound of embodiment 1, wherein $R^1$ is independently halogen, $-CX^1_3$, $-CHX^1_2$, $-CH_2X^1$, $-OCX^1_3$, $-OR^{2D}$, $-CN$, $-NR^{1A}R^{1B}$, or substituted or unsubstituted alkyl.

Embodiment 4

The compound of embodiment 1, wherein $R^1$ is independently halogen, $-OR^{2D}$, or $-CH_3$.

Embodiment 5

The compound of embodiment 1, wherein $R^1$ is independently halogen or $-CH_3$.

Embodiment 6

The compound of embodiment 1, wherein $R^1$ is $-CH_3$.

Embodiment 7

The compound of any one of embodiments 1-6, wherein $L^1$ is a bond, $-S(O)_2-$, $-N(R^3)-$, $-O-$, $-S-$, $-C(O)-$, $-C(O)N(R^3)-$, $-N(R^3)C(O)-$, $-N(R^3)C(O)$

237

NH—, substituted or unsubstituted alkylene, or substituted or unsubstituted heteroalkylene.

Embodiment 8

The compound of any one of embodiments 1-6, wherein $L^1$ is a bond, —C(O)N($R^3$)—, —N($R^3$)C(O)—, substituted or unsubstituted alkylene, or substituted or unsubstituted heteroalkylene.

Embodiment 9

The compound of any one of embodiments 1-6, wherein $L^1$ is —C(O)N($R^3$)—, unsubstituted alkylene, or unsubstituted heteroalkylene.

Embodiment 10

The compound of any one of embodiments 1-6, wherein $L^1$ is —C(O)N($R^3$)—.

Embodiment 11

The compound of any one of embodiments 1-6, wherein $L^1$ is —C(O)NH—.

Embodiment 12

The compound of any one of embodiments 1-11, wherein $L^2$ is a bond, —S(O)$_2$—, —N($R^4$)—, —O—, —S—, —C(O)—, —C(O)N(R')—, —N($R^4$)C(O)—, —N($R^4$)C(O)NH—, substituted or unsubstituted alkylene, or substituted or unsubstituted heteroalkylene.

Embodiment 13

The compound of any one of embodiments 1-11, wherein $L^2$ is a bond, —N($R^4$)C(O)—, or substituted heteroalkylene.

Embodiment 14

The compound of any one of embodiments 1-11, wherein $L^2$ is a bond or substituted heteroalkylene.

Embodiment 15

The compound of any one of embodiments 1-11, wherein $L^2$ is substituted heteroalkylene.

Embodiment 16

The compound of any one of embodiments 1-11, wherein $L^2$ is substituted 2 to 6 membered heteroalkylene.

Embodiment 17

The compound of any one of embodiments 1-11, wherein $L^2$ is —NHC(O)CH$_2$CH$_2$—.

Embodiment 18

The compound of any one of embodiments 1-17, wherein $R^2$ is independently hydrogen, halogen, —CX$^2_3$, —CHX$^2_2$, —CH$_2$X$^2$, —OCX$^2_3$, —OCH$_2$X$^2$, —OCHX$^2_2$, —NR$^{2A}$R$^{2B}$, —C(O)R$^{2C}$, —C(O)—OR$^{2C}$, —C(O)NR$^{2A}$R$^{2B}$, —OR$^{2D}$, —NR$^{2A}$C(O)R$^{2C}$, —NR$^{2A}$C(O)OR$^{2C}$, —NR$^{2A}$OR$^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 19

The compound of any one of embodiments 1-17, wherein $R^2$ is independently hydrogen, halogen, —NR$^{2A}$R$^{2B}$, —C(O)R$^{2C}$, —C(O)—OR$^{2C}$, —C(O)NR$^{2A}$R$^{2B}$, —OR$^{2D}$, —NR$^{2A}$C(O)R$^{2C}$, —NR$^{2A}$C(O)OR$^{2C}$, —NR$^{2A}$OR$^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 20

The compound of any one of embodiments 1-17, wherein $R^2$ is independently hydrogen, halogen, —NR$^{2A}$R$^{2B}$, —OR$^{2D}$, or substituted or unsubstituted heteroaryl.

Embodiment 21

The compound of any one of embodiments 1-17, wherein $R^2$ is substituted or unsubstituted heteroaryl.

Embodiment 22

The compound of any one of embodiments 1-17, wherein $R^2$ is substituted heteroaryl.

Embodiment 23

The compound of any one of embodiments 1-17, wherein $R^2$ is substituted 5 to 6 membered heteroaryl.

Embodiment 24

The compound of any one of embodiments 1-17, wherein $R^2$ is $R^{23}$-substituted 5 to 6 membered heteroaryl; and
$R^{23}$ is independently halogen, —CX$^{23}_3$, —CHX$^{23}_2$, —CH$_2$X$^{23}$, —OCX$^{23}_3$, —OCH$_2$X$^{23}$, —OCHX$^{23}_2$, —CN, —SO$_{n23}$R$^{100D}$, —SO$_{v23}$NR$^{100A}$R$^{100B}$, —NHC(O)NR$^{100A}$R$^{100B}$, —N(O)$_{m23}$, —NR$^{100A}$R$^{100B}$, —C(O)R$^{100C}$, —C(O)—OR$^{100C}$, —C(O)NR$^{100A}$R$^{100B}$, —OR$^{100D}$, —NR$^{100A}$SO$_2$R$^{100D}$, —NR$^{100A}$C(O)R$^{100C}$, —NR$^{100A}$C(O)OR$^{100C}$, —NR$^{100A}$OR$^{100C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^{23}$ substituents may optionally be joined to form a substituted or unsubstituted cycloalkyl, substituted or unsubstituted heterocycloalkyl, substituted or unsubstituted aryl, or substituted or unsubstituted heteroaryl;
$R^{100A}$, $R^{100B}$, $R^{100C}$, and $R^{100D}$ are independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{100A}$ and $R^{100B}$ substituents bonded to the same nitrogen atom may optionally be joined to form a substituted or unsubstituted heterocycloalkyl or substituted or unsubstituted heteroaryl;
X and $X^{23}$ are independently —F, —Cl, —Br, or —I;
n23 is independently an integer from 0 to 4;
m23 and v23 are independently 1 or 2; and
z23 is an integer from 0 to 5.

Embodiment 25

The compound of any one of embodiments 1-17 having the formula:

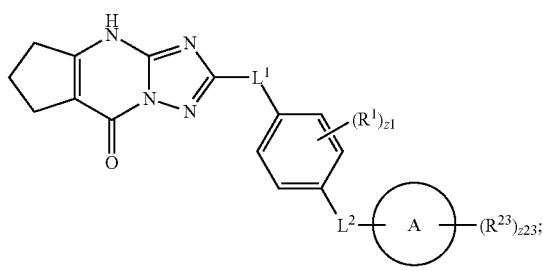

(II)

wherein ring A is a cycloalkyl, heterocycloalkyl, aryl, or heteroaryl;

$R^3$ is independently halogen, $-CX^{23}_3$, $-CHX^{23}_2$, $-CH_2X^{23}$, $-OCX^{23}_3$, $-OCH_2X^{23}$, $-OCHX^{23}_2$, $-CN$, $-SO_{n23}R^{100D}$, $-SO_{v23}NR^{100A}R^{100B}$, $-NHC(O)NR^{100A}R^{100B}$, $-N(O)_{m23}$, $-NR^{100A}R^{100B}$, $-C(O)R^{100C}$, $-C(O)-OR^{100C}$, $-C(O)NR^{100A}R^{100B}$, $-OR^{100D}$, $-NR^{100A}SO_2R^{100D}$, $-NR^{100A}C(O)R^{100C}$, $-NR^{100A}C(O)OR^{100C}$, $-NR^{100A}OR^{100C}$; substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^{23}$ substituents may optionally be joined to form a substituted or unsubstituted cycloalkyl, substituted or unsubstituted heterocycloalkyl, substituted or unsubstituted aryl, or substituted or unsubstituted heteroaryl;

$R^{100A}$, $R^{100B}$, $R^{100C}$, and $R^{100D}$ are independently hydrogen, $-CX_3$, $-CN$, $-COOH$, $-CONH_2$, $-CHX_2$, $-CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{100A}$ and $R^{100B}$ substituents bonded to the same nitrogen atom may optionally be joined to form a substituted or unsubstituted heterocycloalkyl or substituted or unsubstituted heteroaryl;

X and $X^{23}$ are independently $-F$, $-Cl$, $-Br$, or $-I$;

n23 is independently an integer from 0 to 4;

m23 and v23 are independently 1 or 2; and z23 is an integer from 0 to 5.

Embodiment 26

The compound of embodiment 25, wherein ring A is a heteroaryl.

Embodiment 27

The compound of embodiment 25, wherein ring A is a 5 to 6 membered heteroaryl.

Embodiment 28

The compound of embodiment 25, wherein ring A is a 5 membered heteroaryl.

Embodiment 29

The compound of embodiment 25, wherein -(ring A)-$(R^{23})_{z23}$ is

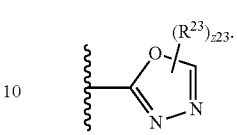

Embodiment 30

The compound of embodiment 25, wherein -(ring A)-$(R^{23})_{z23}$ is

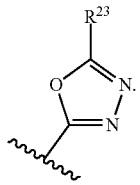

Embodiment 31

The compound of any one of embodiments 25-30, wherein $R^{23}$ is independently halogen, $-CX^{23}_3$, $-C(O)R^{100C}$, $-C(O)-OR^{100C}$, $-C(O)NR^{100A}R^{100B}$, $-OR^{100D}$, $-NR^{100A}SO_2R^{100D}$, $-NR^{100A}C(O)R^{100C}$, $-NR^{100A}C(O)OR^{100C}$, $-NR^{100A}OR^{100C}$, substituted or unsubstituted alkyl, substituted or unsubstituted heteroalkyl, substituted or unsubstituted aryl, or substituted or unsubstituted heteroaryl; two adjacent $R^{23}$ substituents may optionally be joined to form a substituted or unsubstituted cycloalkyl, substituted or unsubstituted heterocycloalkyl, substituted or unsubstituted aryl, or substituted or unsubstituted heteroaryl.

Embodiment 32

The compound of any one of embodiments 25-30, wherein $R^{23}$ is independently halogen, $-CX^{23}_3$, $C(O)R^{100C}$, substituted or unsubstituted heterocycloalkyl, substituted or unsubstituted aryl, or substituted or unsubstituted heteroaryl.

Embodiment 33

The compound of any one of embodiments 25-30, wherein $R^{23}$ is substituted or unsubstituted phenyl.

Embodiment 34

The compound of any one of embodiments 25-30, wherein $R^{23}$ is unsubstituted phenyl.

Embodiment 35

The compound of any one of embodiments 1-34 having the formula:

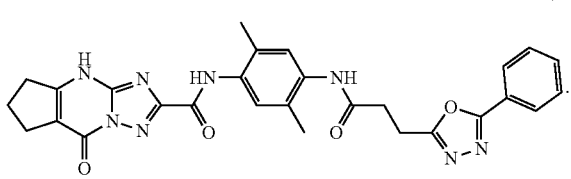

(III)

Embodiment 36

A pharmaceutical composition comprising the compound of any one of embodiments 1 to 35 and a pharmaceutically acceptable excipient.

Embodiment 37

A method of inhibiting MDA-9 protein activity, said method comprising contacting the MDA-9 protein with an effective amount of a PDZ1 domain binder, thereby inhibiting MDA-9 activity.

Embodiment 38

The method of embodiment 37, wherein said PDZ1 domain binder is a small molecule, an antibody, an aptamer, or a ligand.

Embodiment 39

The method of embodiment 38, wherein said small molecule is a compound of any one of embodiments 1-35.

Embodiment 40

The method of embodiment 39, wherein said compound binds a PDZ1 domain with a Kd of less than 25 μM.

Embodiment 41

The method of embodiment 39, wherein said compound binds a PDZ1 domain with a Kd of less than 10 μM.

Embodiment 42

The method of embodiment 38, wherein said ligand is a natural ligand of a PDZ1 domain.

Embodiment 43

A method of treating cancer in a subject in need thereof, said method comprising administering to said subject an effective amount of a PDZ1 domain binder.

Embodiment 44

The method of embodiment 43, wherein said PDZ1 domain binder is a small molecule, an antibody, an aptamer, or a ligand.

Embodiment 45

The method of embodiment 44, wherein said small molecule is a compound of any one of embodiments 1-35.

Embodiment 46

The method of embodiment 45, wherein said compound binds a PDZ1 domain with a Kd of less than 25 μM.

Embodiment 47

The method of embodiment 45, wherein said compound binds a PDZ1 domain with a Kd of less than 10 μM.

Embodiment 48

The method of embodiment 44, wherein said ligand is a natural ligand of a PDZ1 domain.

Embodiment 49

The method of any one of embodiments 43-48, further comprising administering to said subject an anti-cancer agent.

Embodiment 50

The method of embodiment 43, wherein said cancer is associated with increased MDA-9 gene expression.

Embodiment 51

The method of any one of embodiments 43 to 50, wherein said cancer is melanoma, glioblastoma, head and neck cancer, urothelial cancer, breast cancer, uveal melanoma, gastric cancer, lung adenocarcinoma, hepatocellular carcinoma, colorectal cancer, prostate cancer, pancreatic cancer, or neuroblastoma.

Embodiment 52

A method of preventing metastasis of cancer cells in a subject in need thereof, said method comprising administering to said subject an effective amount of a PDZ1 domain binder.

Embodiment 53

The method of embodiment 52, wherein said PDZ1 domain binder is a small molecule, an antibody, an aptamer, or a ligand.

Embodiment 54

The method of embodiment 53, wherein said small molecule is a compound of any one of embodiments 1-35.

Embodiment 55

The method of embodiment 54, wherein said compound binds a PDZ1 domain with a Kd of less than 25 μM.

Embodiment 56

The method of embodiment 54, wherein said compound binds a PDZ1 domain with a Kd of less than 10 μM.

Embodiment 57

The method of embodiment 53, wherein said ligand is a natural ligand of a PDZ1 domain.

Embodiment 58

The method of embodiment 52, wherein said cancer cells are associated with increased MDA-9 gene expression.

Embodiment 59

The method of any one of embodiments 52 to 58, wherein said cancer cells are melanoma, glioblastoma, head and neck, urothelial, breast, uveal melanoma, gastric, lung adenocarcinoma, hepatocellular carcinoma, colorectal, prostate, pancreatic, or neuroblastoma cancer cells.

Embodiment 60

A method of inhibiting cancer associated angiogenesis in a subject in need thereof, said method comprising administering to said subject an effective amount of a PDZ1 domain binder.

Embodiment 61

The method of embodiment 60, wherein said PDZ1 domain binder is a small molecule, an antibody, an aptamer, or a ligand.

Embodiment 62

The method of embodiment 61, wherein said small molecule is a compound of any one of embodiments 1-35.

Embodiment 63

The method of embodiment 62, wherein said compound binds a PDZ1 domain with a Kd of less than 25 µM.

Embodiment 64

The method of embodiment 62, wherein said compound binds a PDZ1 domain with a Kd of less than 10 µM.

Embodiment 65

The method of embodiment 61, wherein said ligand is a natural ligand of a PDZ1 domain or a portion thereof.

Embodiment 66

The method of embodiment 60, wherein said cancer is associated with increased MDA-9 gene expression.

Embodiment 67

The method of any one of embodiments 60 to 66, wherein said cancer is melanoma, glioblastoma, head and neck cancer, urothelial cancer, breast cancer, uveal melanoma, gastric cancer, lung adenocarcinoma, hepatocellular carcinoma, colorectal cancer, prostate cancer, pancreatic cancer, or neuroblastoma.

---

What is claimed is:

1. A compound, or pharmaceutically acceptable salt thereof, having the formula:

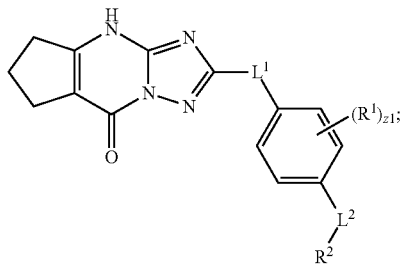

(I)

wherein

R$^1$ is independently halogen, —CX$^1_3$, —CHX$^1_2$, —CH$_2$X$^1$, —OCX$^1_3$, —OCH$_2$X$^1$, —OCHX$^1_2$, —CN, —SO$_{n1}$R$^{1D}$, —SO$_{v1}$NR$^{1A}$R$^{1B}$, —NHC(O)NR$^{1A}$R$^{1B}$, —N(O)$_{m1}$, —NR$^{1A}$R$^{1B}$, —C(O)R$^{1C}$, —C(O)—OR$^{1C}$, —C(O)NR$^{1A}$R$^{1B}$, —OR$^{1D}$, —NR$^{1A}$SO$_2$R$^{1D}$, —NR$^{1A}$C(O)R$^{1C}$, —NR$^{1A}$C(O)OR$^{1C}$, —NR$^{1A}$OR$^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent R$^1$ substituents may optionally be joined to form a substituted or unsubstituted cycloalkyl, substituted or unsubstituted heterocycloalkyl, substituted or unsubstituted aryl, or substituted or unsubstituted heteroaryl;

R$^2$ is

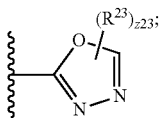

R$^{23}$ is independently halogen, —CX$^{23}_3$, —CHX$^{23}_2$, —CH$_2$X$^{23}$, —OCX$^{23}_3$, —OCH$_2$X$^{23}$, —OCHX$^{23}_2$, —CN, —SO$_{n23}$R$^{100D}$, —SO$_{v23}$NR$^{100A}$R$^{100B}$, —NHC(O)NR$^{100A}$R$^{100B}$, —N(O)$_{m23}$, —N R$^{100A}$R$^{100B}$, —C(O)R$^{100C}$, —C(O)—OR$^{100C}$, —C(O)NR$^{100A}$R$^{100B}$, —OR$^{100D}$, —NR$^{100A}$SO$_2$R$^{100D}$, —NR$^{100A}$C(O)R$^{100C}$, —NR$^{100A}$C(O)OR$^{100C}$, —NR$^{100A}$OR$^{100C}$, N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent R$^{23}$ substituents may optionally be Joined to form a substituted or unsubstituted cycloalkyl, substituted or unsubstituted heterocycloalkyl, substituted or unsubstituted aryl, or substituted or unsubstituted heteroaryl;

L$^1$ is a bond, —S(O)$_2$—, —N(R$^3$)—, —O—, —S—, —C(O)—, —C(O)N(R$^3$)—, —N(R$^3$)C(O)—, —N(R$^3$)C(O)NH—, —NHC(O)N(R$^3$)—, —S(O)$_2$N(R$^3$)—, —N(R$^3$)S(O)$_2$—, —C(O)S(O)$_2$N(R$^3$)—, —N(R$^3$)S(O)$_2$C(O)—, —C(O)O—, -OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

R$^3$ is independently hydrogen, —CX$^3_3$, —CHX$^3_2$, —CH$_2$X$^3$, —CN, —C(O)R$^{3C}$, —C(O)OR$^{3C}$, —C(O)NR$^{3A}$R$^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

L$^2$ is a bond, —S(O)$_2$—, —N(R$^4$)—, —O—, —S—, —C(O)—, —C(O)N(R$^4$)—, —N(R$^4$)C(O)—, —N(R$^4$)C(O)NH—, —NHC(O)N(R$^4$)—, —S(O)$_2$N(R$^4$)—, —N(R$^4$)S(O)$_2$—, —C(O)S(O)$_2$N(R$^4$)—, —N(R$^4$)S(O)$_2$C(O)—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

R$^4$ is independently hydrogen, —CX$^4_3$, —CHX$^4_2$, —CH$_2$X$^4$, —CN, —C(O)R$^{4C}$, —C(O)OR$^{4C}$, —C(O)NR$^{4A}$R$^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{1A}$, R$^{1B}$, R$^{1C}$, R$^{1D}$, R$^{3A}$, R$^{3B}$, R$^{3C}$, R$^{4A}$, R$^{4B}$, R$^{4C}$, R$^{100A}$, R$^{100B}$, R$^{100C}$, and R$^{100D}$ are independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{1A}$ and R$^{1B}$ substituents bonded to the same nitrogen atom may optionally be joined to form a substituted or unsubstituted heterocycloalkyl or substituted or unsubstituted heteroaryl; R$^{2A}$ and R$^{2B}$ substituents bonded to the same nitrogen atom may optionally be joined to form a substituted or unsubstituted heterocycloalkyl or substituted or unsubstituted heteroaryl; R$^{3A}$ and R$^{3B}$ substituents bonded to the same nitrogen atom may optionally be joined to form a substituted or unsubstituted heterocycloalkyl or substituted or unsubstituted heteroaryl; R$^{4A}$ and R$^{4B}$ substituents bonded to the same nitrogen atom may optionally be joined to form a substituted or unsubstituted heterocycloalkyl or substituted or unsubstituted heteroaryl; R$^{100A}$ and R$^{100B}$ substituents bonded to the same nitrogen atom may optionally be Joined to form a substituted or unsubstituted heterocycloalkyl or substituted or unsubstituted heteroaryl;

X, X$^1$, X$^3$, X$^4$, and X$^{23}$ are independently —F, —Cl, —Br, or —I;

n1 and n23 are independently an integer from 0 to 4;

m1, m23, v1, and v23 are independently 1 or 2;

z1 is an integer from 0 to 4; and z23 is an integer from 0 to 2.

2. The compound of claim 1, wherein R$^1$ is independently halogen, —CX$^1_3$, —CHX$^1_2$, —CH$_2$X$^1$, —OCX$^1_3$, —OR$^{1D}$, —CN, —NR$^{1A}$R$^{1B}$, substituted or unsubstituted alkyl or two adjacent R$^1$ substituents may optionally be joined to form a substituted or unsubstituted cycloalkyl, substituted or unsubstituted heterocycloalkyl, substituted or unsubstituted aryl, or substituted or unsubstituted heteroaryl.

3. The compound of claim 1, wherein R$^1$ is independently halogen, —CX$^1_3$, —CHX$^1_2$, —CH$_2$X$^1$, —OCX$^1_3$, —OR$^{1D}$, —CN, —NR$^{1A}$R$^{1B}$, or substituted or unsubstituted alkyl.

4. The compound of claim 1, wherein $R^1$ is independently halogen, —$OR^{1D}$, or —$CH_3$.

5. The compound of claim 1, wherein $R^1$ is independently halogen or —$CH_3$.

6. The compound of claim 1, wherein $R^1$ is -$CH_3$.

7. The compound of claim 1, wherein $L^1$ is a bond, —$S(O)_2$—, —$N(R^3)$—, —O—, —S—, —C(O)—, —C(O)N(R^3)$—, —$N(R^3)C(O)$—, —$N(R^3)C(O)NH$—, substituted or unsubstituted alkylene, or substituted or unsubstituted heteroalkylene.

8. The compound of claim 1, wherein $L^1$ is a bond, —$C(O)N(R^3)$—, —$N(R^3)C(O)$—, substituted or unsubstituted alkylene, or substituted or unsubstituted heteroalkylene.

9. The compound of claim 1, wherein $L^1$ is —C(O)N($R^3$)—, unsubstituted alkylene, or unsubstituted heteroalkylene.

10. The compound of claim 1, wherein $L^1$ is —C(O)N($R^3$)-.

11. The compound of claim 1, wherein $L^1$ is —C(O)NH—.

12. The compound of claim 1, wherein $L^2$ is a bond, —$S(O)_2$—, —$N(R^4)$—, —O—, —S—, —C(O)—, —C(O)N(R^4)$—, —$N(R^4)C(O)$—, —$N(R^4)C(O)NH$—, substituted or unsubstituted alkylene, or substituted or unsubstituted heteroalkylene.

13. The compound of claim 1, wherein $L^2$ is a bond, —$N(R^4)C(O)$—, or substituted heteroalkylene.

14. The compound of claim 1, wherein $L^2$ is a bond or substituted heteroalkylene.

15. The compound of claim 1, wherein $L^2$ is substituted heteroalkylene.

16. The compound of claim 1, wherein $L^2$ is substituted 2 to 6 membered heteroalkylene.

17. The compound of claim 1, wherein $L^2$ is —NHC(O)CH_2CH_2$—.

18. The compound of claim 1 having the formula:

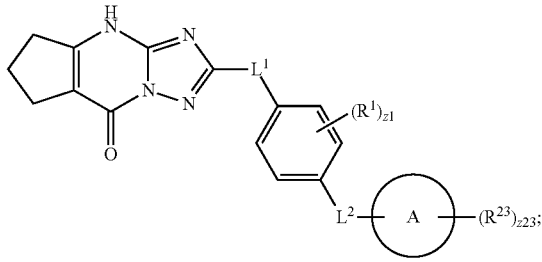

(II)

wherein;
(ring A)-($R^{23}$)$_{z23}$ is

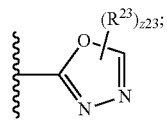

and
$R^{23}$ is independently halogen, —$CX^{23}_3$, —$CHX^{23}_2$, —$CH_2X^2$, —$OCX^{23}_3$, —$OCH_2X^{23}$, —$OCHX^{23}_2$, —CN, —$SO_{n23}R^{1D}$, —$SO_{v23}NR^{100A}R^{100B}$, —NHC(O)NR$^{100A}R^{100B}$, —N(O)$_{m23}$, —NR$^{100A}R^{100B}$, —C(O)R$^{100C}$, —C(O)—OR$^{100C}$, —C(O)NR$^{100A}R^{100B}$, —OR$^{100D}$, —NR$^{100A}SO_2R^{100D}$, —NR$^{100A}C(O)R^{100C}$, —NR$^{100A}C(O)OR^{100C}$, —NR$^{100A}R^{100C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^{23}$ substituents may optionally be joined to form a substituted or unsubstituted cycloalkyl, substituted or unsubstituted heterocycloalkyl, substituted or unsubstituted aryl, or substituted or unsubstituted heteroaryl.

19. The compound of claim 18, wherein -(ring A)-($R^{22}$)$_{z23}$ is

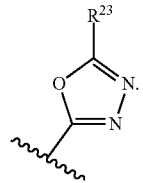

20. The compound of claim 18, wherein $R^{23}$ is independently halogen, —$CX^{23}_3$, —C(O)R$^{100C}$, —C(O)—OR$^{100C}$, —C(O)NR$^{100A}R^{100B}$, —OR$^{100D}$, —NR$^{100A}SO_2R^{100D}$, —NR$^{100A}C(O)R^{100C}$, —NR$^{100A}C(O)OR^{100C}$, —NR$^{100A}OR^{100C}$, substituted or unsubstituted alkyl, substituted or unsubstituted heteroalkyl, substituted or unsubstituted aryl, or substituted or unsubstituted heteroaryl; two adjacent $R^{23}$ substituents may optionally be joined to form a substituted or unsubstituted cycloalkyl, substituted or unsubstituted heterocycloalkyl, substituted or unsubstituted aryl, or substituted or unsubstituted heteroaryl.

21. The compound of claim 18, wherein $R^{23}$ is independently halogen, —$CX^{23}_3$, C(O)R$^{100C}$, substituted or unsubstituted heterocycloalkyl, substituted or unsubstituted aryl, or substituted or unsubstituted heteroaryl.

22. The compound of claim 18, wherein $R^{23}$ is substituted or unsubstituted phenyl.

23. The compound of claim 18, wherein $R^{23}$ is unsubstituted phenyl.

24. The compound of claim 1 having the formula:

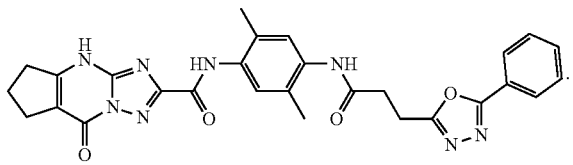

(III)

25. A pharmaceutical composition comprising the compound of claim 1 and a pharmaceutically acceptable excipient.

26. A method of inhibiting MDA-9 protein activity, said method comprising contacting the MDA-9 protein with an effective amount of a PDZ1 domain binder, thereby inhibiting MDA-9 activity, wherein the PDZ1 domain binder is a compound of claim 1.

27. The method of claim 26, wherein said compound binds a PDZ1 domain with a Kd of less than 25 μM.

28. The method of claim 26, wherein said compound binds a PDZ1 domain with a Kd of less than 10 µM.

29. A method of treating cancer in a subject in need thereof, said method comprising administering to said subject an effective amount of a PDZ domain binder, wherein the PDZ1 domain binder is a compound of claim 1.

30. The method of claim 29, wherein said compound binds a PDZ1 domain with a Kd of less than 25 µM.

31. The method of claim 29, wherein said compound binds a PDZ1 domain with a Kd of less than 10 µM.

32. The method of claim 29, further comprising administering to said subject an anti-cancer agent.

33. The method of claim 29, wherein said cancer is associated with increased MDA-9 gene expression.

34. The method of claim 29, wherein said cancer is melanoma, glioblastoma, head and neck cancer, urothelial cancer, breast cancer, uveal melanoma, gastric cancer, lung adenocarcinoma, hepatocellular carcinoma, colorectal cancer, prostate cancer, pancreatic cancer, or neuroblastoma.

35. A method of inhibiting metastasis of cancer cells in a subject in need thereof, said method comprising administering to said subject an effective amount of a PDZ domain binder, wherein the PDZ1 domain binder is a compound of claim 1.

36. A method of inhibiting metastasis of cancer cells in a subject, said method comprising administering to said subject an effective amount of a compound of claim 1.

37. The method of claim 36, wherein said compound binds a PDZ1 domain with a Kd of less than 25 µM.

38. The method of claim 36, wherein said compound binds a PDZ1 domain with a Kd of less than 10 µM.

39. The method of claim 36, wherein said cancer cells are associated with increased MDA-9 gene expression.

40. The method of claim 36, wherein said cancer cells are melanoma, glioblastoma, head and neck, urothelial, breast, uveal melanoma, gastric, lung adenocarcinoma, hepatocellular carcinoma, colorectal, prostate, pancreatic, or neuroblastoma cancer cells.

41. A method of inhibiting cancer associated angiogenesis in a subject in need thereof, said method comprising administering to said subject an effective amount of a PDZ1 domain binder, wherein the PDZ1 domain binder is a compound of claim 1.

42. The method of claim 41, wherein said compound binds a PDZ1 domain with a Kd of less than 25 µM.

43. The method of claim 41, wherein said compound binds a PDZ1 domain with a Kd of less than 10 µM.

44. The method of claim 41, wherein said cancer is associated with increased MDA-9 gene expression.

45. The method of claim 41, wherein said cancer is melanoma, glioblastoma, head and neck cancer, urothelial cancer, breast cancer, uveal melanoma, gastric cancer, lung adenocarcinoma, hepatocellular carcinoma, colorectal cancer, prostate cancer, pancreatic cancer, or neuroblastoma.

46. The compound of claim 18, wherein $R^{23}$ is $R^{24}$-substituted or unsubstituted phenyl;

$R^{24}$ is independently oxo, halogen, $—CX^{24}_3$, $—CHX^{24}_2$, $—CH_2X^{24}$, $—OCX^{24}_3$, $—OCH_2X^{24}$, $—OCHX^{24}_2$, $—CN$, $—OH$, $—NH_2$, $—COOH$, $—CONH_2$, $—NO_2$, $—SH$, $—SO_3H$, $—SO_4H$, $—SO_2NH_2$, $—NHNH_2$, $—ONH_2$, $—NHC=(O)NHNH_2$, $—NHC=(O)NH_2$, $—NHSO_2H$, $—NHC=(O)H$, $—NHC(O)$-$OH$, $—NHOH$, $—N_3$, $R^{25}$-substituted or unsubstituted alkyl, $R^{25}$-substituted or unsubstituted heteroalkyl, $R^{25}$-substituted or unsubstituted cycloalkyl, $R^{25}$-substituted or unsubstituted heterocycloalkyl, $R^{25}$-substituted or unsubstituted aryl, or $R^{25}$-substituted or unsubstituted heteroaryl;

$R^{2}$ is independently oxo, halogen, $—CX^{25}_3$, $—CHX^{25}_2$, $—CH_2X^{25}$, $—OCX^{25}_3$, $—OCH_2X^{25}$, $—OCHX^{25}_2$, $—CN$, $—OH$, $—NH_2$, $—COOH$, $—CONH_2$, $—NO_2$, $—SH$, $—SO_3H$, $—SO_4H$, $—SO_2NH_2$, $—NHNH_2$, $—ONH_2$, $—NHC=(O)NHNH_2$, $—NHC=(O)NH_2$, $—NHSO_2H$, $—NHC=(O)H$, $—NHC(O)$—$OH$, $—NHOH$, $—N_3$, unsubstituted alkyl, unsubstituted heteroalkyl, unsubstituted cycloalkyl, unsubstituted heterocycloalkyl, unsubstituted aryl, or unsubstituted heteroaryl; and $X^{24}$ and $X^{25}$ are independently $—F$, $—Cl$, $—Br$, or $—I$.

47. The compound of claim 46, wherein $R^{23}$ is $R^{24}$-substituted or unsubstituted phenyl; and $R^{24}$ is independently oxo, halogen, $—CX^{24}_3$, $—CHX^{24}_2$, $—CH_2X^{24}$, $—OCX^{24}_3$, $—OCH_2X^{24}$, $—OCHX^{24}_2$, $—CN$, $—OH$, $—NH_2$, $—COOH$, $—CONH_2$, $—NO_2$, $—SH$, $—SO_3H$, $—SO_4H$, $—SO_2NH_2$, $—NHNH_2$, $—ONH_2$, $—NHC=(O)NHNH_2$, $—NHC=(O)NH_2$, $—NHSO_2H$, $—NHC=(O)H$, $—NHC(O)$—$OH$, $—NHOH$, $—N_3$, unsubstituted alkyl, unsubstituted heteroalkyl, unsubstituted cycloalkyl, unsubstituted heterocycloalkyl, unsubstituted aryl, or unsubstituted heteroaryl.

48. The compound of claim 46, wherein $R^{24}$ is $R^{24}$-substituted or unsubstituted phenyl; and $R^{24}$ is independently hydrogen, $—OCH_3$, halogen, $—CF_3$, unsubstituted 2 to 4 membered heteroalkyl, or unsubstituted C1-C4 alkoxy.

49. The compound of claim 46, wherein $R^{23}$ is $R^{24}$-substituted or unsubstituted phenyl; and $R^{24}$ is independently hydrogen, $—F$, $—Br$, $—Cl$, $—I$, substituted or unsubstituted $C_1$-$C_6$ alkyl; or substituted or unsubstituted 2 to 6 membered heteroalkyl.

50. The compound of claim 46, wherein $R^{23}$ is $R^{24}$-substituted or unsubstituted phenyl; and $R^{24}$ is independently hydrogen, $—F$, $—Br$, $—Cl$, $—I$, unsubstituted methyl, unsubstituted ethyl, unsubstituted propyl, $—CF_3$, $—CHF_2$, $—CH_2F$, $—CHCl_2$, $—CH_2Cl$, $—CBr_3$, $—CHBr_2$, $—CH_2Br$, $—CI_3$, $—CHI_2$, $—CH_2I$, $—OCH_3$, $—OCH_2CH_3$, $—OCH_2CH_2CH_3$, $—OCF_3$, $—OCHF_2$, $—OCH_2F$, $—OCCl_3$, $—OCHCl_2$, $—OCH_2Cl$, $—OCBr_3$, $—OCHBr_2$, $—OCH_2Br$, $—OCI_3$, $—OCHI_2$, or $—OCH_2I$.

* * * * *

SEQUENCE LISTING

```
<160> NUMBER OF SEQ ID NOS: 1

<210> SEQ ID NO 1
<211> LENGTH: 84
<212> TYPE: PRT
<213> ORGANISM: Artificial Sequence
<220> FEATURE:
<223> OTHER INFORMATION: Synthetic Polypeptide

<400> SEQUENCE: 1

Gln Gly Ile Arg Glu Val Ile Leu Cys Lys Asp Gln Asp Gly Lys Ile
1               5                   10                  15

Gly Leu Arg Leu Lys Ser Ile Asp Asn Gly Ile Phe Val Gln Leu Val
            20                  25                  30

Gln Ala Asn Ser Pro Ala Ser Leu Val Gly Leu Arg Phe Gly Asp Gln
        35                  40                  45

Val Leu Gln Ile Asn Gly Glu Asn Cys Ala Gly Trp Ser Ser Asp Lys
    50                  55                  60

Ala His Lys Val Leu Lys Gln Ala Phe Gly Glu Lys Ile Thr Met Thr
65                  70                  75                  80

Ile Arg Asp Arg
```